(12) United States Patent
Chandran et al.

(10) Patent No.: US 12,187,969 B2
(45) Date of Patent: *Jan. 7, 2025

(54) SYSTEM AND METHOD FOR LIQUID FUEL PRODUCTION FROM CARBONACEOUS MATERIALS USING RECYCLED CONDITIONED SYNGAS

(71) Applicant: ThermoChem Recovery International, Inc., Baltimore, MD (US)

(72) Inventors: Ravi Chandran, Ellicott City, MD (US); Dave G. Newport, Cumberland, ME (US); Daniel A. Burciaga, Manchester, MD (US); Daniel Michael Leo, Baltimore, MD (US); Justin Kevin Miller, Durham, NC (US); Brian Christopher Attwood, Cary, NC (US)

(73) Assignee: ThermoChem Recovery International, Inc., Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 18/151,095

(22) Filed: Jan. 6, 2023

(65) Prior Publication Data

US 2023/0159837 A1 May 25, 2023

Related U.S. Application Data

(63) Continuation of application No. 16/814,892, filed on Mar. 10, 2020, now Pat. No. 11,555,157.

(51) Int. Cl.
*C01B 3/34* (2006.01)
*B01J 19/00* (2006.01)
(Continued)

(52) U.S. Cl.
CPC .......... *C10J 3/84* (2013.01); *B01J 19/0013* (2013.01); *B01J 19/245* (2013.01); *C01B 3/346* (2013.01);
(Continued)

(58) Field of Classification Search
CPC ...... C10G 2300/104; C10G 2300/1051; C10G 2300/1055; C10G 2400/02;
(Continued)

(56) References Cited

U.S. PATENT DOCUMENTS

| 2,603,608 A | 7/1952 | Lewis et al. |
| 2,619,124 A | 11/1952 | Bertin et al. |

(Continued)

FOREIGN PATENT DOCUMENTS

| AU | 2014236647 | 9/2015 |
| CA | 975643 | 10/1975 |

(Continued)

OTHER PUBLICATIONS

[No Author], "Current MSW Industry Position and State-of-the-Practice on LFG Collection Efficiency, Methane Oxidation, and Carbon Sequestration in Landfills," SCS Engineers, Jan. 2009, 60 pages.

(Continued)

*Primary Examiner* — David W Berke-Schlessel
*Assistant Examiner* — Trent R Clarke
(74) *Attorney, Agent, or Firm* — Fish & Richardson P.C.

(57) ABSTRACT

A method of producing liquid fuel and/or chemicals from a carbonaceous material entails combusting a conditioned syngas in pulse combustion heat exchangers of a steam reformer to help convert carbonaceous material into first reactor product gas which includes carbon monoxide, hydrogen, carbon dioxide and other gases. A portion of the first reactor product gas is transferred to a hydrogen reformer (Continued)

into which additional conditioned syngas is added and a reaction carried out to produce an improved syngas. The improved syngas is then subject to one or more gas clean-up steps to form a new conditioned syngas. A portion of the new conditioned syngas is recycled to be used as the conditioned syngas in the pulse combustion heat exchangers and in the hydrocarbon reformer. A system for carrying out the method include, a steam reformer, a hydrocarbon reformer, first and second gas-cleanup systems, a synthesis system and an upgrading system.

26 Claims, 75 Drawing Sheets

(51) Int. Cl.
*B01J 19/24* (2006.01)
*C01B 3/50* (2006.01)
*C07C 29/151* (2006.01)
*C07C 41/01* (2006.01)
*C10G 2/00* (2006.01)
*C10J 3/84* (2006.01)
*C10K 1/00* (2006.01)
*C10K 3/06* (2006.01)
*C10L 1/02* (2006.01)
*C10L 1/06* (2006.01)
*C10L 1/08* (2006.01)
*C12P 7/06* (2006.01)

(52) U.S. Cl.
CPC ............ *C01B 3/50* (2013.01); *C07C 29/1518* (2013.01); *C07C 41/01* (2013.01); *C10G 2/344* (2013.01); *C10K 1/004* (2013.01); *C10K 1/007* (2013.01); *C10K 3/06* (2013.01); *C10L 1/023* (2013.01); *C10L 1/026* (2013.01); *C10L 1/06* (2013.01); *C10L 1/08* (2013.01); *C12P 7/06* (2013.01); *B01J 2219/0004* (2013.01); *B01J 2219/00157* (2013.01); *C01B 2203/0233* (2013.01); *C01B 2203/04* (2013.01); *C01B 2203/06* (2013.01); *C01B 2203/062* (2013.01); *C01B 2203/0822* (2013.01); *C01B 2203/1235* (2013.01); *C01B 2203/84* (2013.01); *C10G 2300/1022* (2013.01); *C10G 2300/104* (2013.01); *C10G 2300/1051* (2013.01); *C10G 2300/1055* (2013.01); *C10G 2300/4081* (2013.01); *C10G 2400/02* (2013.01); *C10G 2400/04* (2013.01); *C10G 2400/08* (2013.01); *C10J 2300/1628* (2013.01); *C10J 2300/1643* (2013.01); *C10J 2300/1656* (2013.01); *C10J 2300/1659* (2013.01); *C10J 2300/1665* (2013.01); *C10J 2300/1671* (2013.01); *C10J 2300/1823* (2013.01); *C10J 2300/1853* (2013.01); *C10J 2300/1884* (2013.01); *C10L 2200/0423* (2013.01); *C10L 2200/043* (2013.01); *C10L 2200/0446* (2013.01); *C10L 2270/023* (2013.01); *C10L 2270/026* (2013.01); *C10L 2270/04* (2013.01)

(58) Field of Classification Search
CPC ............ C10G 2400/04; C10G 2400/08; C10G 2300/1022; C10G 2/344; C10G 2300/4081; C10J 2300/1659; C10J 2300/1656; C10J 2300/1665; C10J 2300/1643; C10J 2300/1671; C10J 2300/1853; C10J 3/84; C10J 2300/1628; C10J 2300/1823; C10J 2300/1884; C10L 1/023; C10L 1/026; C10L 1/06; C10L 1/08; C10L 2200/0423; C10L 2200/043; C10L 2200/0446; C10L 2270/023; C10L 2270/026; C10L 2270/04; C01B 2203/06; C01B 2203/062; C01B 2203/84; C01B 3/346; C01B 2203/0233; C01B 2203/0822; C01B 3/50; C01B 2203/04; C01B 2203/1235; C07C 41/01; C07C 29/1518; C12P 7/06; B01J 19/0013; B01J 2219/00157; B01J 19/245; B01J 2219/0004; C10K 1/004; C10K 1/007; C10K 3/06

See application file for complete search history.

(56) References Cited

U.S. PATENT DOCUMENTS

| | | |
|---|---|---|
| 2,642,895 A | 6/1953 | Bertin et al. |
| 2,670,011 A | 2/1954 | Bertin et al. |
| 2,680,065 A | 6/1954 | Atwell |
| 2,727,535 A | 12/1955 | Lindeworth |
| 2,795,931 A | 6/1957 | Foll |
| 2,812,635 A | 11/1957 | Foll et al. |
| 2,825,203 A | 3/1958 | Bertin et al. |
| 2,903,416 A | 9/1959 | Metrailer |
| 2,912,821 A | 11/1959 | Horak |
| 2,929,774 A | 3/1960 | Smith |
| 3,039,955 A | 6/1962 | Honnold, Jr. |
| 3,355,249 A | 11/1967 | Squires |
| 3,375,175 A | 3/1968 | Eddinger et al. |
| 3,674,409 A | 7/1972 | Desty et al. |
| 3,687,646 A | 8/1972 | Brent et al. |
| 3,840,354 A | 10/1974 | Donath |
| 3,844,733 A | 10/1974 | Donath |
| 3,853,498 A | 12/1974 | Bailie |
| 3,894,562 A | 7/1975 | Moseley, Jr. et al. |
| 3,910,494 A | 10/1975 | Melton, Jr. |
| 3,927,996 A | 12/1975 | Knudsen et al. |
| 3,954,380 A | 5/1976 | Valaev et al. |
| 3,957,458 A | 5/1976 | Squires |
| 3,966,633 A | 6/1976 | Friedman |
| 3,966,634 A | 6/1976 | Sacks |
| 3,976,592 A | 8/1976 | Lacey et al. |
| 4,002,438 A | 1/1977 | Fleming |
| 4,017,271 A | 4/1977 | Barclay et al. |
| 4,044,904 A | 8/1977 | Trumbull et al. |
| 4,052,172 A | 10/1977 | Shirakawa et al. |
| 4,061,562 A | 12/1977 | McKinney et al. |
| 4,069,024 A | 1/1978 | Fernandes |
| 4,078,973 A | 3/1978 | Choi et al. |
| 4,080,149 A | 3/1978 | Wolfe |
| 4,097,361 A | 6/1978 | Ashworth |
| 4,105,545 A | 8/1978 | Muller et al. |
| 4,133,259 A | 1/1979 | Pelton |
| 4,157,245 A | 6/1979 | Mitchell et al. |
| 4,161,393 A | 7/1979 | Rudolph et al. |
| 4,180,353 A | 12/1979 | Geidies |
| 4,199,327 A | 4/1980 | Hempill et al. |
| 4,219,402 A | 8/1980 | DeGeorge |
| 4,279,710 A | 7/1981 | Coughlin |
| 4,300,916 A | 11/1981 | Frewer et al. |
| 4,347,064 A | 8/1982 | Reh et al. |
| 4,356,151 A | 10/1982 | Woebcke et al. |
| 4,359,326 A | 11/1982 | Hoffert et al. |
| 4,364,745 A | 12/1982 | Weil |
| 4,370,858 A | 2/1983 | Awerbuch et al. |
| 4,372,940 A | 2/1983 | Brandenburg et al. |
| 4,389,391 A | 6/1983 | Dunn, Jr. |
| 4,400,181 A | 8/1983 | Snell et al. |
| 4,421,523 A | 12/1983 | Mehta et al. |
| 4,426,810 A | 1/1984 | Rudolph et al. |
| 4,484,885 A | 11/1984 | Machii et al. |
| 4,508,542 A | 4/1985 | Langhoff et al. |
| 4,519,810 A | 5/1985 | Haas |
| 4,522,685 A | 6/1985 | Feldmann |
| 4,523,986 A | 6/1985 | Seufert |

(56) References Cited

U.S. PATENT DOCUMENTS

| | | |
|---|---|---|
| 4,532,024 A | 7/1985 | Haschke et al. |
| 4,556,402 A | 12/1985 | Rudolph et al. |
| 4,569,310 A | 2/1986 | Davis |
| 4,569,682 A | 2/1986 | Baker, Jr. et al. |
| 4,639,208 A | 1/1987 | Inui et al. |
| 4,650,546 A | 3/1987 | Le Jeune |
| 4,688,521 A | 8/1987 | Korenberg |
| 4,697,358 A | 10/1987 | Kitchen |
| 4,699,632 A | 10/1987 | Babu et al. |
| 4,857,084 A | 8/1989 | Robbins et al. |
| 4,879,021 A | 11/1989 | Hippo et al. |
| 4,909,914 A | 3/1990 | Chiba et al. |
| 4,919,686 A | 4/1990 | Edwards |
| 4,959,009 A | 9/1990 | Hemsath |
| 5,059,404 A * | 10/1991 | Mansour ............. C10K 1/026 48/77 |
| 5,064,444 A | 11/1991 | Kubiak et al. |
| 5,125,965 A | 6/1992 | Sebenik |
| 5,133,297 A | 7/1992 | Mansour |
| 5,134,944 A | 8/1992 | Keller et al. |
| 5,156,099 A | 10/1992 | Ohshita et al. |
| 5,168,835 A | 12/1992 | Last |
| 5,197,399 A | 3/1993 | Mansour |
| 5,205,728 A | 4/1993 | Mansour |
| 5,211,704 A | 5/1993 | Mansour |
| 5,255,634 A | 10/1993 | Mansour |
| 5,306,481 A | 4/1994 | Mansour et al. |
| 5,353,721 A | 10/1994 | Mansour et al. |
| 5,366,371 A | 11/1994 | Mansour et al. |
| 5,439,491 A | 8/1995 | Kubiak et al. |
| 5,473,885 A | 12/1995 | Hunter, Jr. et al. |
| 5,536,488 A | 7/1996 | Mansour et al. |
| 5,560,550 A | 10/1996 | Krawczyk |
| 5,624,470 A | 4/1997 | Tanca |
| 5,635,147 A | 6/1997 | Herbert et al. |
| 5,637,192 A | 6/1997 | Mansour et al. |
| 5,638,609 A | 6/1997 | Chandran et al. |
| 5,667,560 A | 9/1997 | Dunne |
| 5,696,203 A | 12/1997 | Hummel et al. |
| 5,700,310 A | 12/1997 | Bowman et al. |
| 5,752,994 A | 5/1998 | Monacelli et al. |
| 5,800,153 A | 9/1998 | DeRoche |
| 5,807,722 A * | 9/1998 | Gaddy ............... C12M 29/04 435/163 |
| 5,842,289 A | 12/1998 | Chandran et al. |
| 5,853,548 A | 12/1998 | Piskorz et al. |
| 5,861,046 A | 1/1999 | Andersson |
| 5,937,635 A | 8/1999 | Winfree et al. |
| 5,948,378 A | 9/1999 | Koveal et al. |
| 6,067,915 A | 5/2000 | Sharpe |
| 6,084,147 A | 7/2000 | Mason |
| 6,114,399 A | 9/2000 | Roberts et al. |
| 6,133,499 A | 10/2000 | Horizoe et al. |
| 6,149,765 A | 11/2000 | Mansour et al. |
| 6,216,446 B1 | 4/2001 | Stram |
| 6,248,297 B1 | 6/2001 | Stine et al. |
| 6,248,796 B1 | 6/2001 | Jackson et al. |
| 6,298,579 B1 | 10/2001 | Ichitani et al. |
| 6,446,428 B1 | 9/2002 | Kaemming et al. |
| 6,494,034 B2 | 12/2002 | Kaemming et al. |
| 6,495,610 B1 | 12/2002 | Brown |
| 6,548,197 B1 | 4/2003 | Chandran et al. |
| 6,584,765 B1 | 7/2003 | Tew et al. |
| 6,662,550 B2 | 12/2003 | Eidelman et al. |
| 6,667,022 B2 | 12/2003 | Cole |
| 6,680,137 B2 | 1/2004 | Paisley |
| 6,753,353 B2 | 6/2004 | Jackson et al. |
| 6,758,032 B2 | 7/2004 | Hunter et al. |
| 6,793,174 B2 | 9/2004 | Ouellette et al. |
| 6,824,383 B2 | 11/2004 | Cain |
| 6,863,878 B2 | 3/2005 | Klepper |
| 6,883,543 B2 | 4/2005 | Tew et al. |
| 6,923,004 B2 | 8/2005 | Chandran et al. |
| 6,931,833 B2 | 8/2005 | Lupkes |
| 6,938,588 B2 | 9/2005 | Jacobsen et al. |
| 6,997,118 B2 | 2/2006 | Chandran et al. |
| 7,047,724 B2 | 5/2006 | Nordeen et al. |
| 7,214,720 B2 | 5/2007 | Bayle et al. |
| 7,220,390 B2 | 5/2007 | Tonkovich et al. |
| 7,309,378 B2 | 12/2007 | Bancon et al. |
| 7,434,401 B2 | 10/2008 | Hayashi |
| 7,526,912 B2 | 5/2009 | Tangirala et al. |
| 7,531,014 B2 | 5/2009 | Chandran |
| 7,569,086 B2 | 8/2009 | Chandran |
| 7,572,362 B2 | 8/2009 | Freel et al. |
| 7,601,303 B1 | 10/2009 | Karer et al. |
| 7,637,096 B2 | 12/2009 | Razzell et al. |
| 7,735,311 B2 | 6/2010 | Eidelman et al. |
| 7,739,867 B2 | 6/2010 | Kenyon et al. |
| 7,758,334 B2 | 7/2010 | Shimo et al. |
| 7,775,460 B2 | 8/2010 | Berg et al. |
| 7,784,265 B2 | 8/2010 | Rasheed et al. |
| 7,828,546 B2 | 11/2010 | Wiedenhoefer et al. |
| 7,836,682 B2 | 11/2010 | Rasheed et al. |
| 7,841,167 B2 | 11/2010 | Rasheed et al. |
| 7,842,110 B2 | 11/2010 | Mansour et al. |
| 7,857,995 B2 | 12/2010 | Johnson et al. |
| 7,879,919 B2 | 2/2011 | Ernst et al. |
| 7,882,926 B2 | 2/2011 | Fullerton |
| 7,886,866 B2 | 2/2011 | Fullerton |
| 7,905,990 B2 | 3/2011 | Freel |
| 7,914,280 B2 | 3/2011 | Schlote et al. |
| 7,950,219 B2 | 5/2011 | Tangirala et al. |
| 7,964,004 B2 | 6/2011 | Koch et al. |
| 7,980,056 B2 | 7/2011 | Rasheed et al. |
| 8,007,688 B2 | 8/2011 | Dahlin et al. |
| 8,082,724 B2 | 12/2011 | Hirata et al. |
| 8,083,494 B2 | 12/2011 | Laforest et al. |
| 8,084,656 B2 | 12/2011 | Feldmann |
| 8,136,624 B2 | 3/2012 | Fullerton |
| 8,137,655 B2 | 3/2012 | Chornet et al. |
| 8,168,144 B2 | 5/2012 | Alyaser |
| 8,168,686 B2 | 5/2012 | Blevins et al. |
| 8,205,433 B2 | 6/2012 | Boespflug et al. |
| 8,302,377 B2 | 11/2012 | Rasheed et al. |
| 8,312,706 B2 | 11/2012 | Laforest et al. |
| 8,356,467 B2 | 1/2013 | Sprouse et al. |
| 8,381,527 B2 | 2/2013 | LaForest et al. |
| 8,539,752 B2 | 9/2013 | Brumgerg et al. |
| 8,580,152 B2 | 11/2013 | Sutradhar et al. |
| 8,585,789 B2 | 11/2013 | Sutradhar et al. |
| 8,707,674 B2 | 4/2014 | Moscinski et al. |
| 8,721,299 B2 | 5/2014 | Koch et al. |
| 8,726,800 B2 | 5/2014 | Murray et al. |
| 8,813,474 B2 | 8/2014 | Daniau et al. |
| 8,841,495 B2 | 9/2014 | Marker et al. |
| 8,889,746 B2 | 11/2014 | Kresnyak |
| 8,894,885 B2 | 11/2014 | Bell et al. |
| 8,899,010 B2 | 12/2014 | Kenyon et al. |
| 8,955,303 B2 | 2/2015 | Brzek et al. |
| 8,968,433 B2 | 3/2015 | Chandran |
| 9,011,561 B2 | 4/2015 | Chandran et al. |
| 9,080,513 B2 | 7/2015 | Ziminsky et al. |
| 9,084,978 B2 | 7/2015 | Peters |
| 9,140,456 B2 | 9/2015 | Kenyon et al. |
| 9,163,179 B2 | 10/2015 | McComish et al. |
| 9,168,501 B2 | 10/2015 | Ibsen et al. |
| 9,217,569 B2 | 12/2015 | Prade |
| 9,227,790 B2 | 1/2016 | Perez |
| 9,268,048 B2 | 2/2016 | Fullerton |
| 9,279,503 B2 | 3/2016 | DiSalvo et al. |
| 9,359,973 B2 | 6/2016 | Farshchian et al. |
| 9,388,355 B2 | 7/2016 | Mennell et al. |
| 9,499,404 B2 | 11/2016 | Chandran et al. |
| 9,512,997 B2 | 12/2016 | Zettner |
| 9,550,950 B2 | 1/2017 | Chandran et al. |
| 9,738,579 B2 | 8/2017 | Lucas et al. |
| 9,920,926 B1 | 3/2018 | Chandran et al. |
| 10,344,232 B2 | 7/2019 | Lucas et al. |
| 10,344,233 B2 | 7/2019 | Lucas et al. |
| 10,364,398 B2 | 7/2019 | Chandran et al. |
| 10,704,002 B2 | 7/2020 | Lucas et al. |
| 10,760,018 B2 | 9/2020 | Tiverios et al. |
| 10,975,320 B2 | 4/2021 | Tiverios et al. |

(56) References Cited

U.S. PATENT DOCUMENTS

| | | |
|---|---|---|
| 11,098,258 B2 | 8/2021 | Tiverios et al. |
| 11,370,982 B2 | 6/2022 | Chandran et al. |
| 11,525,097 B2 | 12/2022 | Tiverios et al. |
| 11,555,157 B2 | 1/2023 | Chandran et al. |
| 11,634,650 B2 | 4/2023 | Chandran et al. |
| 11,655,426 B2 | 5/2023 | Tiverios et al. |
| 11,680,215 B2 | 6/2023 | Tiverios et al. |
| 2001/0045375 A1 | 11/2001 | Thijssen et al. |
| 2002/0066396 A1 | 6/2002 | Torii et al. |
| 2002/0142172 A1 | 10/2002 | Brinker et al. |
| 2003/0143126 A1 | 7/2003 | Samson |
| 2003/0173291 A1 | 9/2003 | Schimel |
| 2004/0045272 A1 | 3/2004 | Miyoshi et al. |
| 2004/0058207 A1 | 3/2004 | Galloway |
| 2004/0182000 A1 | 9/2004 | Mansour et al. |
| 2004/0184900 A1 | 9/2004 | Christensen et al. |
| 2005/0050759 A1 | 3/2005 | Chandran et al. |
| 2005/0072152 A1 | 4/2005 | Suzuki et al. |
| 2006/0004237 A1 | 1/2006 | Appel et al. |
| 2006/0042955 A1 | 3/2006 | Villalobos |
| 2006/0045827 A1 | 3/2006 | Sprouse |
| 2006/0117952 A1 | 6/2006 | Bancon et al. |
| 2006/0130444 A1 | 6/2006 | Smith et al. |
| 2006/0131235 A1 | 6/2006 | Offeman et al. |
| 2006/0137246 A1 | 6/2006 | Kumar et al. |
| 2006/0162500 A1 | 7/2006 | Nuber et al. |
| 2006/0165582 A1 | 7/2006 | Brooker et al. |
| 2006/0236863 A1 | 10/2006 | Weist, Jr. et al. |
| 2006/0246388 A1 | 11/2006 | Feese et al. |
| 2006/0251821 A1 | 11/2006 | Eidelman |
| 2007/0049781 A1 | 3/2007 | Brown et al. |
| 2007/0137435 A1 | 6/2007 | Orth et al. |
| 2007/0186476 A1 | 8/2007 | Briesch et al. |
| 2007/0245627 A1 | 10/2007 | Chandran |
| 2007/0245629 A1 | 10/2007 | Chandran |
| 2008/0023338 A1 | 1/2008 | Stoots et al. |
| 2008/0115415 A1 | 5/2008 | Agrawal et al. |
| 2008/0155899 A1 | 7/2008 | Ramamurthy |
| 2008/0169449 A1 | 7/2008 | Mundschau |
| 2008/0178784 A1 | 7/2008 | Farone |
| 2008/0196308 A1 | 8/2008 | Hutton et al. |
| 2008/0222956 A1 | 9/2008 | Tsangaris et al. |
| 2008/0244976 A1 | 10/2008 | Paisley |
| 2008/0260629 A1 | 10/2008 | Morin et al. |
| 2008/0264254 A1 | 10/2008 | Song et al. |
| 2008/0282892 A1 | 11/2008 | Deckman et al. |
| 2008/0308769 A1 | 12/2008 | Marty et al. |
| 2009/0000194 A1 | 1/2009 | Fan et al. |
| 2009/0056225 A1 | 3/2009 | Schinski |
| 2009/0056537 A1 | 3/2009 | Neumann |
| 2009/0084035 A1 | 4/2009 | Wei |
| 2009/0084036 A1 | 4/2009 | Neumann |
| 2009/0084666 A1 | 4/2009 | Agrawal et al. |
| 2009/0139203 A1 | 6/2009 | Rasheed et al. |
| 2009/0151250 A1 | 6/2009 | Agrawal |
| 2009/0178338 A1 | 7/2009 | Leininger et al. |
| 2009/0183431 A1 | 7/2009 | Smit et al. |
| 2009/0186952 A1 | 7/2009 | Steynberg et al. |
| 2009/0191104 A1 | 7/2009 | Murakami et al. |
| 2009/0206007 A1 | 8/2009 | Allam |
| 2009/0217584 A1 | 9/2009 | Raman et al. |
| 2009/0220395 A1 | 9/2009 | Zanichelli et al. |
| 2009/0229464 A1 | 9/2009 | Robertson |
| 2009/0232729 A1 | 9/2009 | Genkin et al. |
| 2009/0246120 A1 | 10/2009 | Raman et al. |
| 2009/0247796 A1 | 10/2009 | Waycuilis et al. |
| 2009/0259082 A1 | 10/2009 | Deluga et al. |
| 2009/0300976 A1* | 12/2009 | Mansour ............ C10K 1/20 44/451 |
| 2009/0320446 A1 | 12/2009 | Gutmark et al. |
| 2009/0324458 A1 | 12/2009 | Robinson et al. |
| 2010/0011955 A1 | 1/2010 | Hufton et al. |
| 2010/0011956 A1 | 1/2010 | Neumann et al. |
| 2010/0018115 A1 | 1/2010 | Wallace et al. |
| 2010/0024300 A1 | 2/2010 | Chornet et al. |
| 2010/0040510 A1 | 2/2010 | Randhava et al. |
| 2010/0050516 A1 | 3/2010 | Murakami et al. |
| 2010/0050812 A1 | 3/2010 | Van Heeringen et al. |
| 2010/0051875 A1 | 3/2010 | Chornet et al. |
| 2010/0096594 A1 | 4/2010 | Dahlin et al. |
| 2010/0129691 A1 | 5/2010 | Dooher et al. |
| 2010/0158792 A1 | 6/2010 | Drnevich et al. |
| 2010/0162625 A1 | 7/2010 | Mills |
| 2010/0181539 A1 | 7/2010 | Apanel et al. |
| 2010/0196227 A1 | 8/2010 | Venderbosch et al. |
| 2010/0224835 A1 | 9/2010 | Chornet et al. |
| 2010/0243961 A1 | 9/2010 | Hilton et al. |
| 2010/0270505 A1 | 10/2010 | Gallaspy et al. |
| 2010/0273899 A1 | 10/2010 | Winter |
| 2010/0275514 A1 | 11/2010 | Paganessi et al. |
| 2010/0287981 A1 | 11/2010 | Chen et al. |
| 2010/0307335 A1 | 12/2010 | Hayward |
| 2011/0031103 A1 | 2/2011 | Deckman et al. |
| 2011/0034569 A1 | 2/2011 | Basu et al. |
| 2011/0036014 A1 | 2/2011 | Tsangaris et al. |
| 2011/0047961 A1 | 3/2011 | Kenyon et al. |
| 2011/0047962 A1 | 3/2011 | Keynon et al. |
| 2011/0048296 A1 | 3/2011 | Maghdissian et al. |
| 2011/0095233 A1 | 4/2011 | Hildebrandt et al. |
| 2011/0107945 A1 | 5/2011 | Suda |
| 2011/0116986 A1 | 5/2011 | Balint et al. |
| 2011/0127469 A1 | 6/2011 | Chaubey et al. |
| 2011/0139603 A1 | 6/2011 | Booth |
| 2011/0146152 A1 | 6/2011 | Vimalchand et al. |
| 2011/0146285 A1 | 6/2011 | Glaser et al. |
| 2011/0152593 A1 | 6/2011 | Kelly et al. |
| 2011/0168605 A1 | 7/2011 | Blevins et al. |
| 2011/0218254 A1 | 9/2011 | Chakravarti |
| 2011/0229382 A1 | 9/2011 | Frydman et al. |
| 2011/0248218 A1 | 10/2011 | Sutradhar et al. |
| 2011/0250661 A1 | 10/2011 | Sutradhar et al. |
| 2011/0297885 A1 | 12/2011 | Boerrigter et al. |
| 2012/0000175 A1 | 1/2012 | Wormser |
| 2012/0036778 A1 | 2/2012 | Stryzhak |
| 2012/0061618 A1 | 3/2012 | Santoianni et al. |
| 2012/0094198 A1 | 4/2012 | Chandran |
| 2012/0111109 A1 | 5/2012 | Chandran et al. |
| 2012/0131901 A1 | 5/2012 | Westervelt et al. |
| 2012/0134888 A1 | 5/2012 | Blevins et al. |
| 2012/0204814 A1 | 8/2012 | Zhang et al. |
| 2012/0213647 A1 | 8/2012 | Koch et al. |
| 2012/0238645 A1 | 9/2012 | Rüdlinger |
| 2012/0291351 A1 | 11/2012 | Bool et al. |
| 2013/0012605 A1 | 1/2013 | Zhou |
| 2013/0019785 A1 | 1/2013 | Saxena |
| 2013/0042595 A1 | 2/2013 | Rasheed et al. |
| 2013/0056685 A1 | 3/2013 | Badhe et al. |
| 2013/0065974 A1 | 3/2013 | Kresnyak |
| 2013/0109765 A1 | 5/2013 | Jiang et al. |
| 2013/0133305 A1 | 5/2013 | Depuy |
| 2013/0153826 A1 | 6/2013 | Paquet et al. |
| 2013/0161563 A1 | 6/2013 | Jiang et al. |
| 2013/0203142 A1 | 8/2013 | Young |
| 2013/0232873 A1 | 9/2013 | DePuy et al. |
| 2013/0306913 A1 | 11/2013 | Li et al. |
| 2013/0345325 A1 | 12/2013 | Lecomte et al. |
| 2014/0158940 A1 | 6/2014 | Navaee-Ardeh et al. |
| 2014/0224706 A1 | 8/2014 | Do et al. |
| 2014/0252276 A1 | 9/2014 | Chandran et al. |
| 2014/0296586 A1 | 10/2014 | Chandran et al. |
| 2014/0364676 A1 | 12/2014 | Chen et al. |
| 2015/0005398 A1 | 1/2015 | Chakravarti et al. |
| 2015/0080626 A1 | 3/2015 | Boon et al. |
| 2015/0093664 A1 | 4/2015 | Berlowitz et al. |
| 2015/0141535 A1 | 5/2015 | Kresnyak |
| 2015/0184091 A1 | 7/2015 | Chandran et al. |
| 2015/0203392 A1 | 7/2015 | Seiki et al. |
| 2015/0275110 A1 | 10/2015 | Karmakar |
| 2015/0299587 A1 | 10/2015 | Rensing |
| 2015/0315499 A1 | 11/2015 | Chandran et al. |
| 2015/0376510 A1 | 12/2015 | Lucas et al. |
| 2016/0001304 A1 | 1/2016 | Pavel et al. |
| 2016/0003480 A1 | 1/2016 | McCormish et al. |
| 2016/0031177 A1 | 2/2016 | Markovich et al. |

(56) References Cited

U.S. PATENT DOCUMENTS

| | | |
|---|---|---|
| 2016/0102259 A1 | 4/2016 | Bool et al. |
| 2016/0200993 A1 | 7/2016 | Lucas et al. |
| 2016/0326438 A1 | 11/2016 | Sorensen et al. |
| 2016/0376516 A1 | 12/2016 | Toberman |
| 2017/0058222 A1 | 3/2017 | Lucas et al. |
| 2017/0082067 A1 | 3/2017 | Maqbool |
| 2017/0320731 A1 | 11/2017 | Sozinho et al. |
| 2017/0369805 A1 | 12/2017 | Lucas et al. |
| 2018/0057760 A1 | 3/2018 | Chandran et al. |
| 2018/0057762 A1 | 3/2018 | Lucas et al. |
| 2019/0010050 A1* | 1/2019 | Chandran ............ H05K 999/99 |
| 2019/0359902 A1 | 11/2019 | Chandran et al. |
| 2020/0392420 A1 | 12/2020 | Tiverios et al. |
| 2021/0009412 A1 | 1/2021 | Knight et al. |
| 2021/0284924 A1 | 9/2021 | Chandran et al. |
| 2022/0081630 A1 | 3/2022 | Tiverios et al. |
| 2022/0325194 A1 | 10/2022 | Chandran et al. |
| 2023/0110311 A1 | 4/2023 | Tiverios et al. |
| 2023/0287286 A1 | 9/2023 | Tiverios et al. |
| 2023/0407197 A1 | 12/2023 | Chandran et al. |

FOREIGN PATENT DOCUMENTS

| | | |
|---|---|---|
| CA | 2705066 | 5/2009 |
| CA | 2820091 | 2/2010 |
| CA | 2879856 | 12/2012 |
| CN | 2319410 | 5/1999 |
| CN | 1710022 | 12/2005 |
| CN | 201077830 | 6/2008 |
| CN | 101848979 | 9/2010 |
| CN | 102076832 | 5/2011 |
| CN | 102083521 | 6/2011 |
| CN | 104822644 | 8/2015 |
| CN | 106635168 | 5/2017 |
| EP | 2275513 | 1/2011 |
| FR | 2743517 | 7/1997 |
| FR | 2758748 | 7/1998 |
| GB | 1395953 | 5/1975 |
| GB | 2580576 | 7/2020 |
| GB | 2581941 | 9/2020 |
| GB | 2591650 | 8/2021 |
| JP | 2003502812 | 1/2003 |
| JP | 3625817 | 3/2005 |
| KR | 101621206 | 5/2016 |
| KR | 1020160053146 | 5/2016 |
| VN | 10012021 | 12/2013 |
| WO | WO 1993/023709 | 11/1993 |
| WO | WO 2000/069994 | 11/2000 |
| WO | WO 2003/013714 | 2/2003 |
| WO | WO 2006/071109 | 7/2006 |
| WO | WO 2006/100572 | 9/2006 |
| WO | WO 2007/117590 | 10/2007 |
| WO | WO 2008/130260 | 10/2008 |
| WO | WO 2009/002191 | 12/2008 |
| WO | WO 2010/049592 | 5/2010 |
| WO | WO 2010/096626 | 8/2010 |
| WO | WO 2010/124077 | 10/2010 |
| WO | WO 2011/008446 | 1/2011 |
| WO | WO 2011/022591 | 2/2011 |
| WO | WO 2011/026307 | 3/2011 |
| WO | WO 2011/084730 | 7/2011 |
| WO | WO 2011/155962 | 12/2011 |
| WO | WO 2012/138751 | 10/2012 |
| WO | WO 2012/158536 | 11/2012 |
| WO | WO 2013/043603 | 3/2013 |
| WO | WO 2013/067532 | 5/2013 |
| WO | WO 2013/078423 | 5/2013 |
| WO | WO 2019/084152 | 5/2019 |

OTHER PUBLICATIONS

[No Author], "Methodology for Allocating Municipal Solid Waste to Biogenic and Non-Biogenic Energy," Energy Information Administration of the U.S. Department of Energy: Office of Coal, Nuclear, Electric and Alternate Fuels, May 2007, 18 pages.

[No Author], "The Role of Waste Incineration in Germany," Umweltbundesamt, Oct. 2008, 30 pages.

Björklund, "Environmental Systems Analysis of Waste Management—Experiences from Applications of the ORWARE Model," Doctoral Thesis, Royal Institute of Technology, Department of Chemical Engineering and Technology, Division of Industrial Ecology, Stockholm, Sweden, Dec. 2000, 66 pages.

Consonni et al., "Alternative strategies for energy recovery from municipal solid waste—Part B: Emission and cost estimates," Waste Management, 2005, 25(2):137-148.

Dave et al., "Plasma pyrolysis and gasification of plastic waste—a review," Journal of Scientific and Industrial Research, Mar. 2010, 69(3):177-179.

Fellner et al., "A New Method to Determine the Ratio of Electricity Production from Fossil and Biogenic Sources in Waste-to-Energy Plants," Environmental Science & Technology, Apr. 2007, 41(7):2579-2586.

Hall et al., "Installation and Operation of Sorbathene Solvent Vapor Recovery Units to Recover and Recycle Volatile Organic Compounds at Operating Sites Within the Dow Chemical Company," Proceedings from the Sixteenth National Industrial Energy Technology Conference, Houston, TX (Apr. 13-14, 1994).

Larsen et al., "CO2 emission factors for waste incineration: Influence from source separation of recyclable materials," Waste Management, Jul. 2011, 31(7):1597-1605.

Mponzi, "Production of Biofuels by Fischer Tropsch Synthesis," Master's Thesis, Lappeenranta University of Technology, Faculty of Chemical Technology, 2011, 94 pages.

Porteous, "Energy from waste incineration—a state of the art emissions review with an emphasis on public acceptability," Applied Energy, Oct. 2001, 70(2):157-167.

Séverin et al., "The biogenic content of process streams from mechanical-biological treatment plants producing solid recovered fuel. Do the manual sorting and selective dissolution determination methods correlate?," Waste Management, Jul. 2010, 30(7):1171-1182.

Thomas et al., "International expert group on life cycle assessment for integrated waste management," Journal of Cleaner Production, Feb. 2005, 13(3):321-326.

Zhang et al., "Gasification of municipal solid waste in the Plasma Gasification Melting process," Applied Energy, Feb. 2012, 90(1):106-112.

* cited by examiner

BIOREFINERY SUPERSTRUCTURE SYSTEM (BSS)

FEEDSTOCK DELIVERY SYSTEM

FEED ZONE DELIVERY SYSTEM (2050)

FEED ZONE DELIVERY SYSTEM (2050)

FEED ZONE DELIVERY SYSTEM (2050)

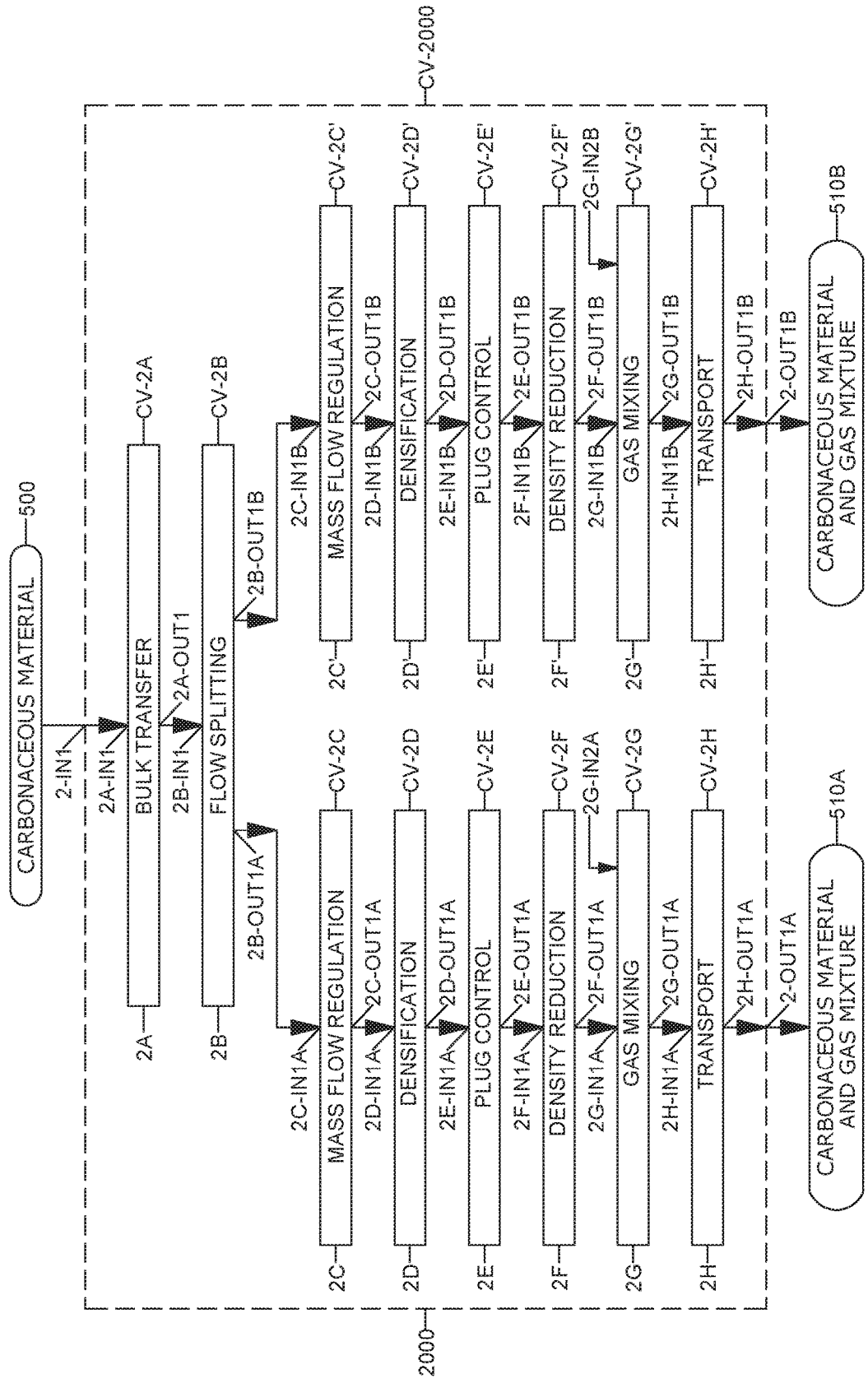

FEEDSTOCK DELIVERY SUBSYSTEMS

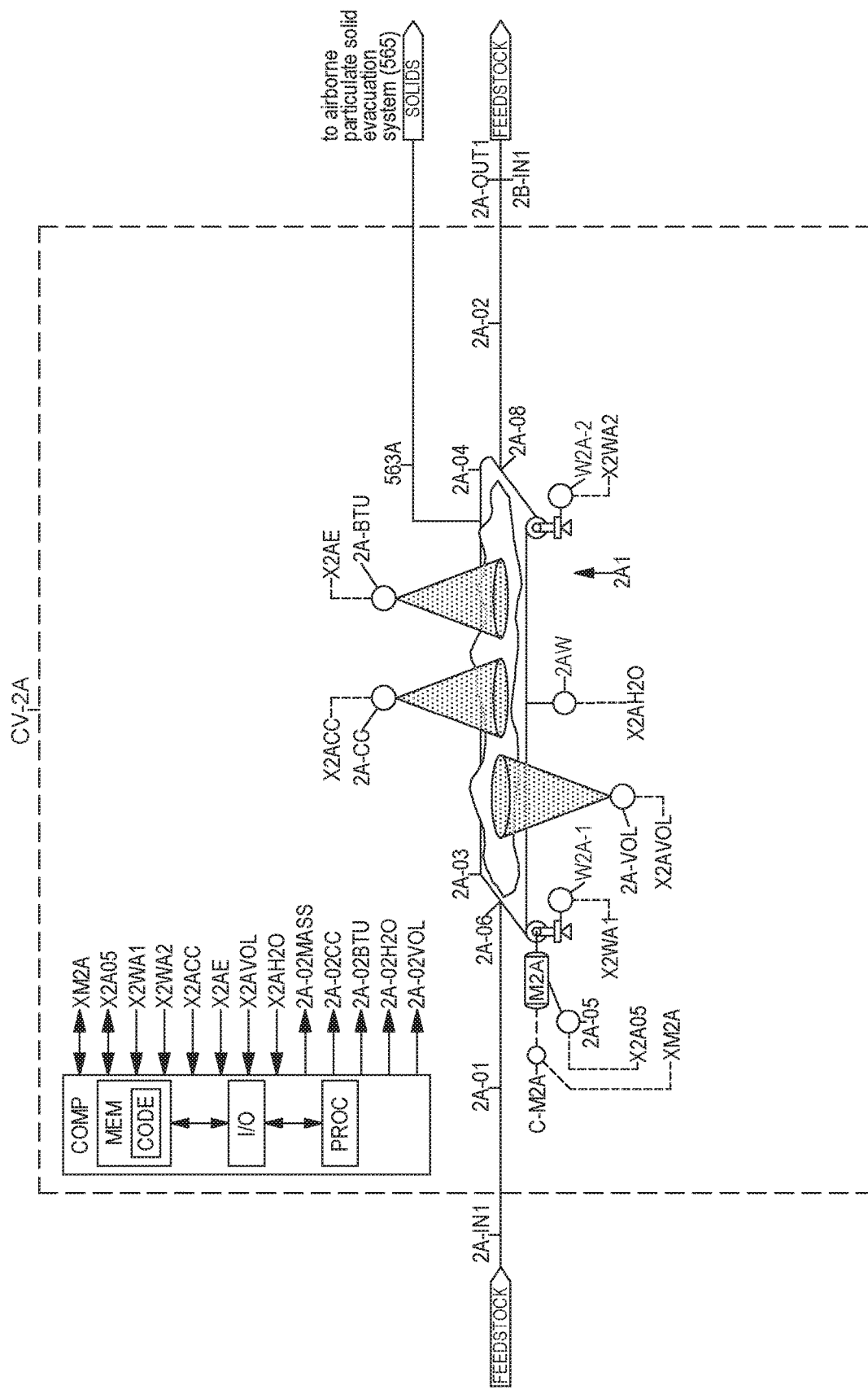

STEP 2B, FLOW SPLITTING

STEP 2C, MASS FLOW REGULATION

STEP 2C, MASS FLOW REGULATION

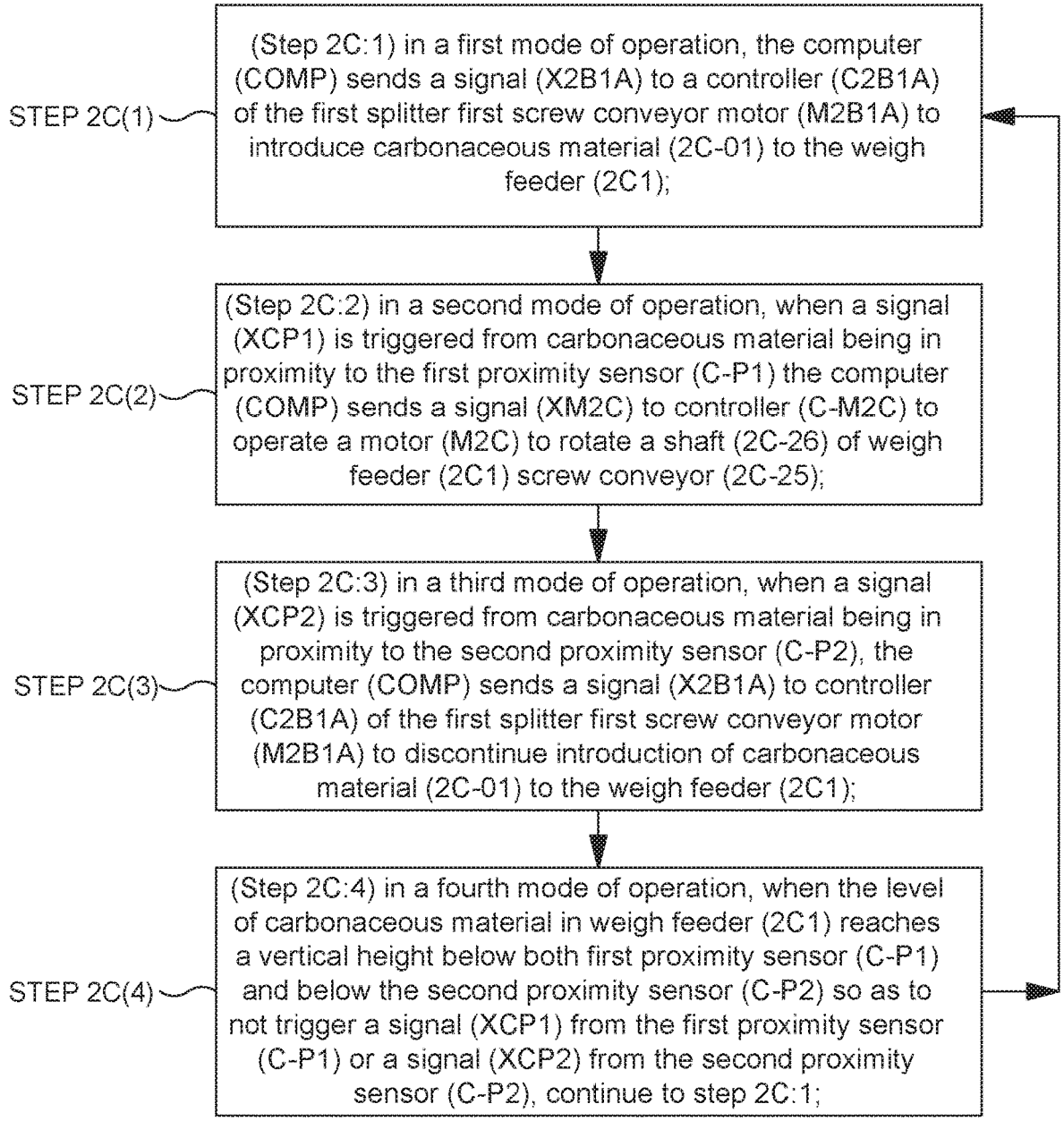

STEP 2D, DENSIFICATION

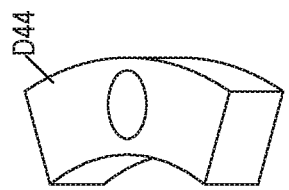
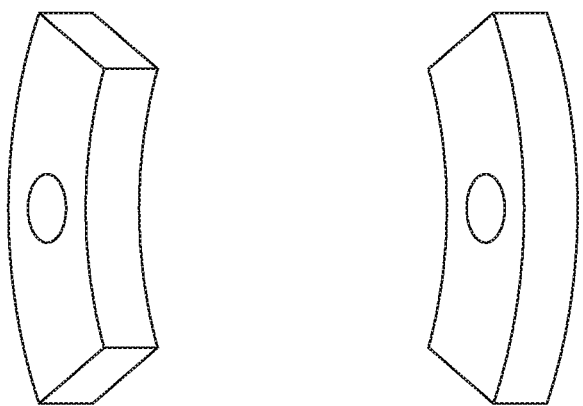
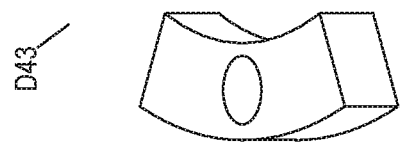
FIGURE 7B

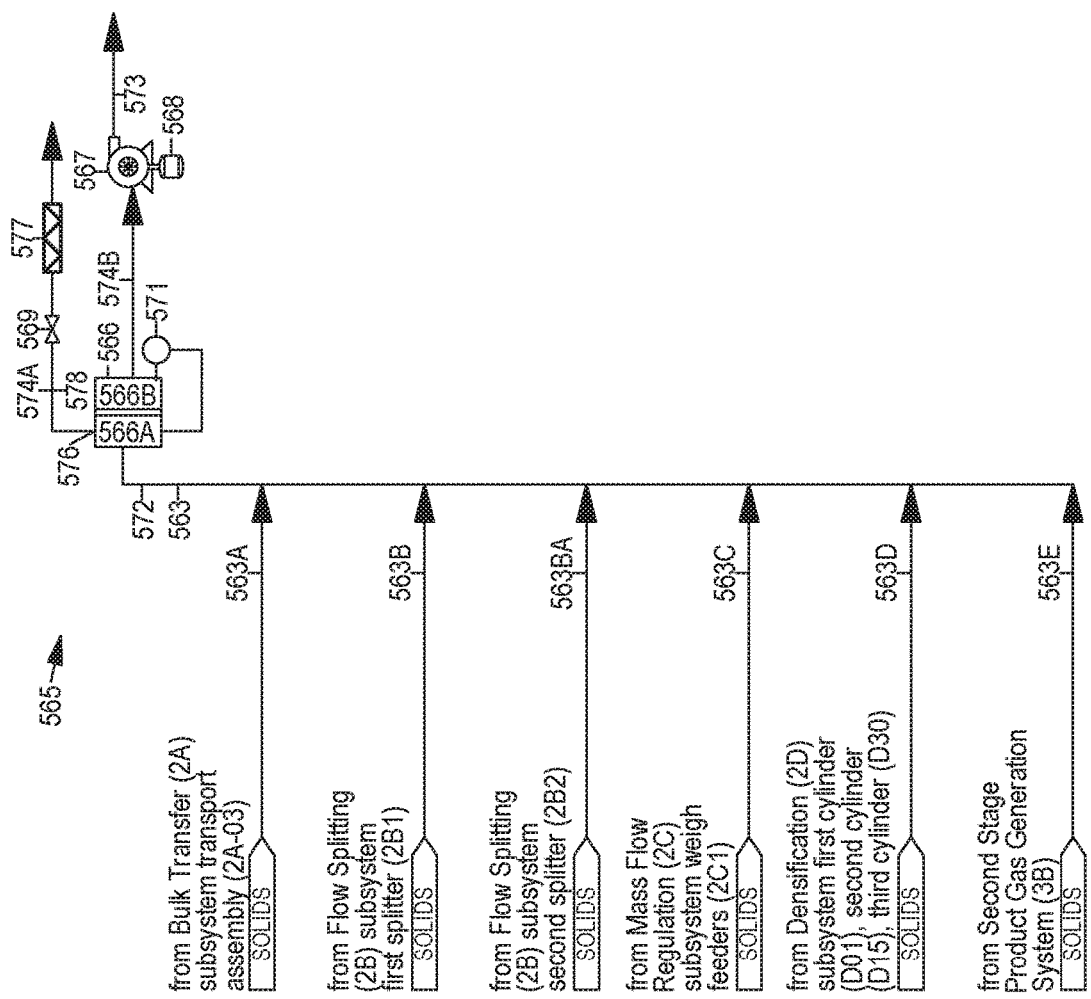

STEP 2E, PLUG CONTROL
CV-2E

STEP 2E, PLUG CONTROL CROSS-SECTIONAL VIEW (X2E)

STEP 2F, DENSITY REDUCTION

STEP 2G, GAS MIXING

FIGURE 10A

Gas Mixing Valve States for Automated Controller Operation

| DESCRIPTION | STATE 2G(1): START-UP | STATE 2G(2): NORMAL OPERATION | STATE 2G(3): SHUT DOWN |
|---|---|---|---|
| first isolation valve (VG1) | CLOSED | OPEN | CLOSED |
| second isolation valve (VG2) | CLOSED | OPEN | CLOSED |
| entry gas valve (VG3) | OPEN | CLOSED | OPEN |
| middle gas valve (VG4) | OPEN | CLOSED | OPEN |
| exit gas valve (VG5) | OPEN | OPEN | OPEN |
| gas evacuation valve (VG6) | CLOSED | CLOSED | OPEN |
| gas evacuation pressure sensor (P-G) | SET GAS EVACUATION VALVE (VG6) CONTROLLER (CG6) TO OPERATE AT PRESSURE GREATER THAN FIRST REACTOR PRESSURE (P-A); EVACUATE AIR FROM CHAMBER (G02) WITH A GAS (2G-03); PURGE AIR FROM CHAMBER (G02) BY USE OF A FIRST GAS SUPPLY (G10) TRANSFERRED TO CHAMBER VIA AN ENTRY GAS CONNECTION (G09) TO THE CHAMBER (G02) ENTRY SECTION (G21) AND THROUGH THE EVACUATION GAS CONNECTION (G22) AND EVACUATION GAS LINE (G24); | ISOLATED FROM PROCESS | SET GAS EVACUATION VALVE (VG6) CONTROLLER (CG6) TO OPERATE AT PRESSURE GREATER THAN FIRST REACTOR PRESSURE (P-A); EVACUATE PRODUCT GAS FROM CHAMBER (G02) WITH A GAS (2G-03); PURGE PRODUCT GAS FROM CHAMBER (G02) BY USE OF A FIRST GAS SUPPLY (G10) TRANSFERRED TO THE CHAMBER (G02) ENTRY SECTION (G21) AND THROUGH THE EVACUATION GAS CONNECTION (G22) AND EVACUATION GAS LINE (G24); |
| differential pressure sensor (DPG) | COMMENCE STATE 2G(2) WHEN DIFFERENTIAL PRESSURE SENSOR (DPG) AND FIRST REACTOR PRESSURE (P-A) ARE < 5 PSID; PRESSURIZE MIDDLE SECTION (G20) AND CHAMBER (G02) TO < 5 PSID BETWEEN FIRST REACTOR PRESSURE (P-A) AND CHAMBER (02) ENTRY SECTION (G19) PRESSURE VIA DIFFERENTIAL PRESSURE SENSOR (DPG); | ISOLATED FROM PROCESS | N/A |

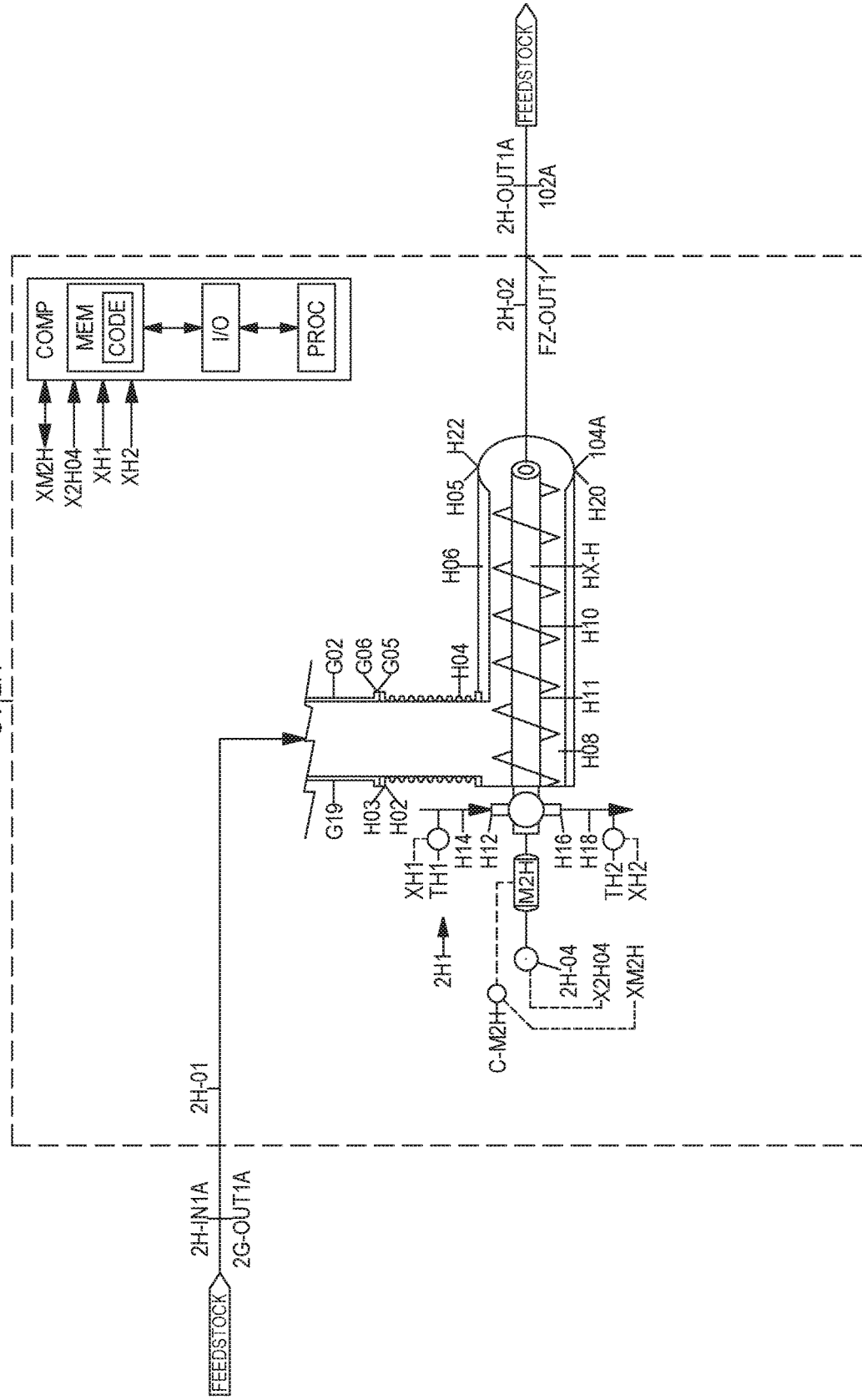

STATE 2D(1)

STATE 2D(2)

STATE 2D(3)

STATE 2D(4)

STATE 2D(5)

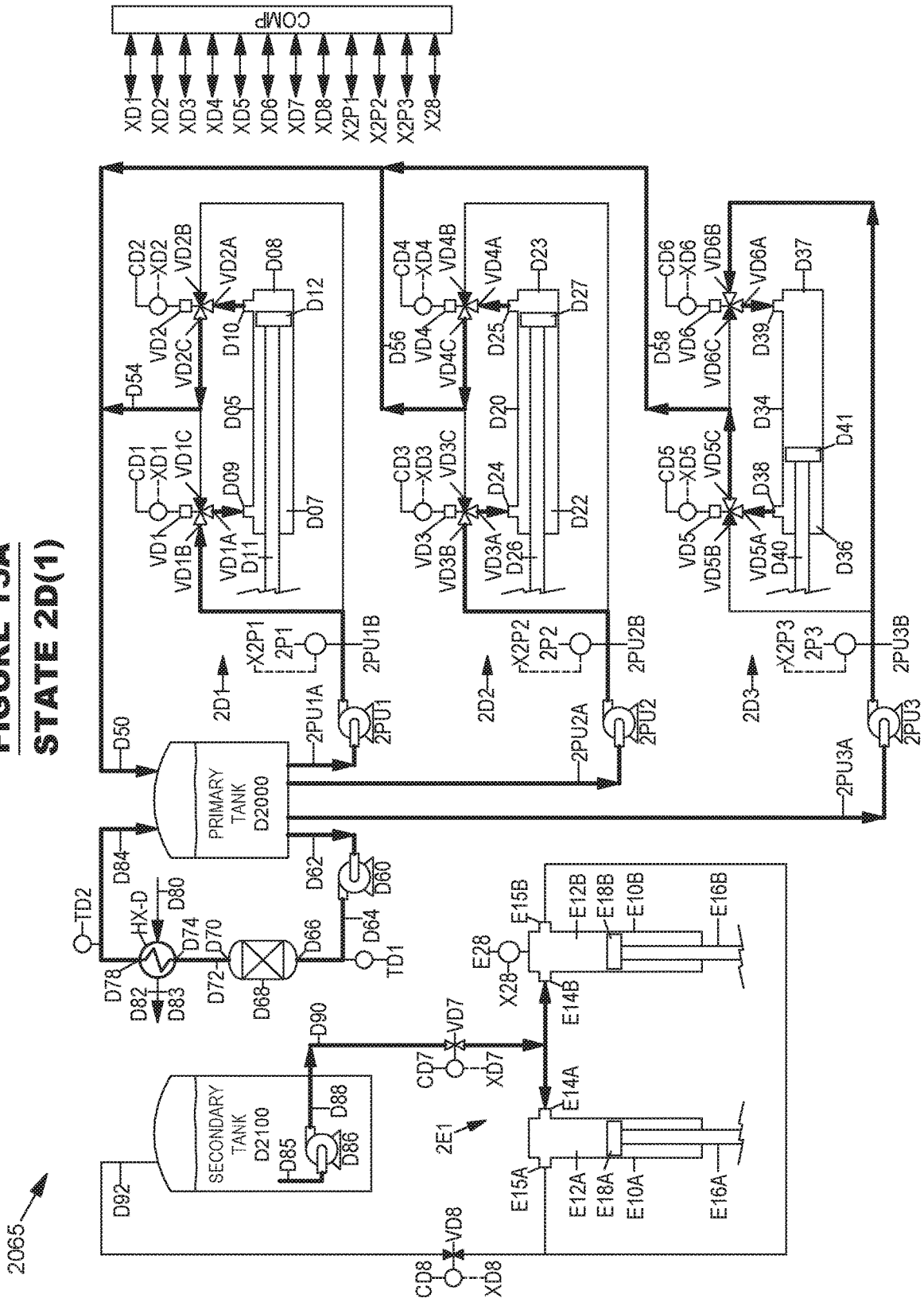

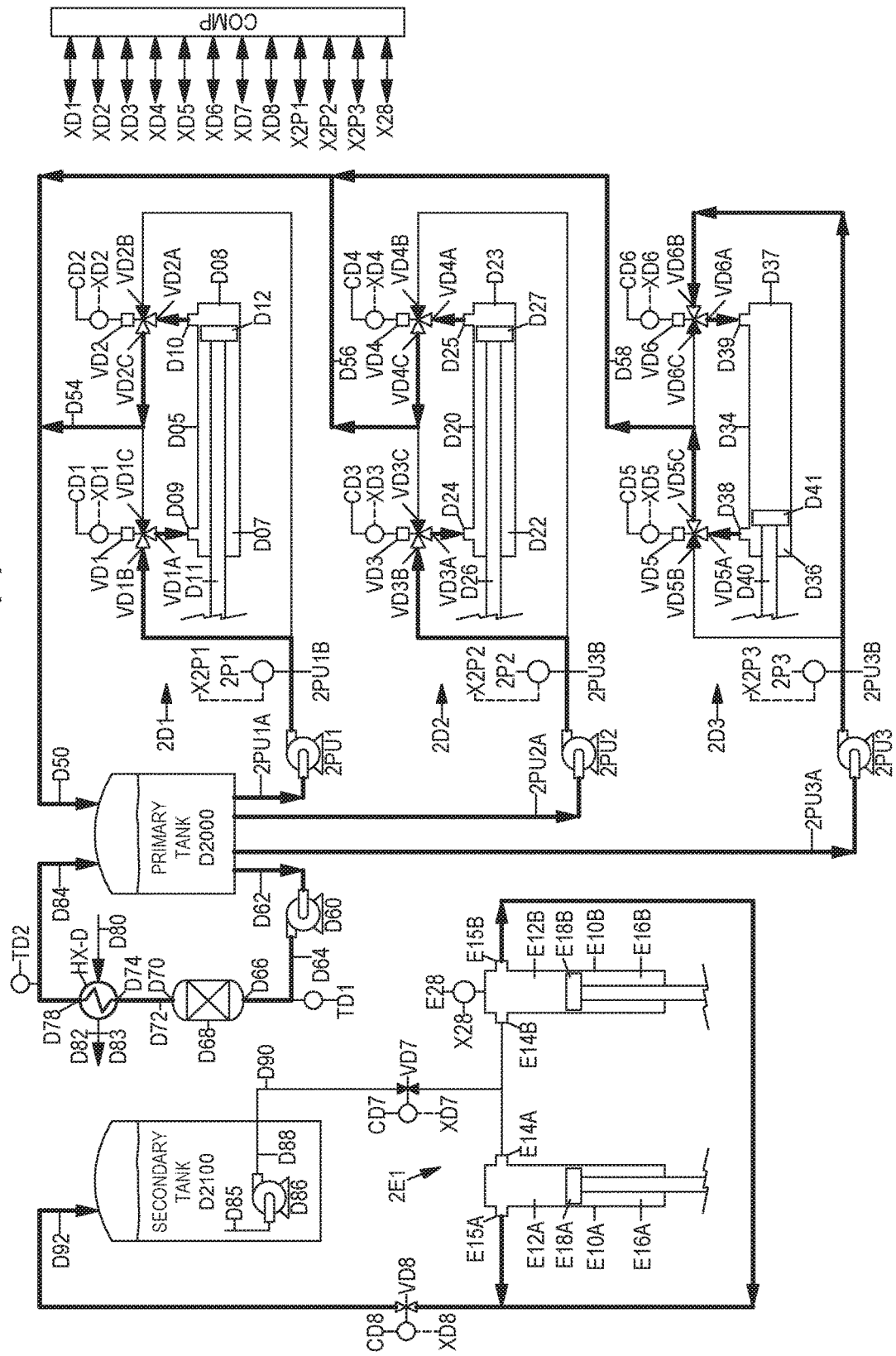

STATE 2D(3)

STATE 2D(4)

STATE 2D(5)

FIGURE 13F

| DESCRIPTION | STATE 2D(1): PLUG FORMATION | STATE 2D(2): PLUG SHREDDING, PREPARE TO ADVANCE TO PISTON 2 | STATE 2D(3): ADVANCE TO PISTON 2 | STATE 2D(4): PREPARE TO ADVANCE TO PISTON 3 | STATE 2D(5): ADVANCE TO PISTON 3 |
|---|---|---|---|---|---|
| first hydraulic cylinder front connection port valve (VD1) | | | | | |
| common port (VD1A) | OPEN | OPEN | OPEN | OPEN | OPEN |
| supply port (VD1B) | OPEN | OPEN | CLOSED | CLOSED | CLOSED |
| drain port (VD1C) | CLOSED | CLOSED | OPEN | OPEN | OPEN |
| first hydraulic cylinder rear connection port valve (VD2) | | | | | |
| common port (VD2A) | OPEN | OPEN | OPEN | OPEN | OPEN |
| supply port (VD2B) | CLOSED | CLOSED | OPEN | OPEN | OPEN |
| drain port (VD2C) | OPEN | OPEN | CLOSED | CLOSED | CLOSED |
| second hydraulic cylinder front connection port valve (VD3) | | | | | |
| common port (VD3A) | OPEN | OPEN | OPEN | OPEN | OPEN |
| supply port (VD3B) | OPEN | OPEN | OPEN | OPEN | CLOSED |
| drain port (VD3C) | CLOSED | CLOSED | CLOSED | CLOSED | OPEN |
| second hydraulic cylinder rear connection port valve (VD4) | | | | | |
| common port (VD4A) | OPEN | OPEN | OPEN | OPEN | OPEN |
| supply port (VD4B) | CLOSED | CLOSED | CLOSED | CLOSED | OPEN |
| drain port (VD4C) | OPEN | OPEN | OPEN | OPEN | CLOSED |
| third hydraulic cylinder front connection port valve (VD5) | | | | | |
| common port (VD5A) | OPEN | OPEN | OPEN | OPEN | OPEN |
| supply port (VD5B) | CLOSED | CLOSED | CLOSED | CLOSED | CLOSED |
| drain port (VD5C) | OPEN | OPEN | OPEN | OPEN | OPEN |
| third hydraulic cylinder rear connection port valve (VD6) | | | | | |
| common port (VD6A) | OPEN | OPEN | OPEN | OPEN | OPEN |
| supply port (VD6B) | OPEN | OPEN | OPEN | OPEN | OPEN |
| drain port (VD6C) | CLOSED | CLOSED | CLOSED | CLOSED | CLOSED |
| plug control rear connection port valve (VD7) | OPEN | CLOSED | OPEN | OPEN | OPEN |
| plug control drain valve (VD8) | CLOSED | OPEN | CLOSED | CLOSED | CLOSED |
| 2D1 POSITION | RETRACTED | RETRACTED | ADVANCED | ADVANCED | ADVANCED |
| 2D2 POSITION | RETRACTED | RETRACTED | RETRACTED | RETRACTED | ADVANCED |
| 2D3 POSITION | ADVANCED | ADVANCED | ADVANCED | RETRACTED | RETRACTED |
| 2E1 POSITION | ADVANCED | RETRACTED | ADVANCED | ADVANCED | ADVANCED |

FEEDSTOCK DELIVERY & PRODUCT GAS GENERATION SYSTEM (2075)

FEEDSTOCK DELIVERY & PRODUCT GAS GENERATION SYSTEM (2075)

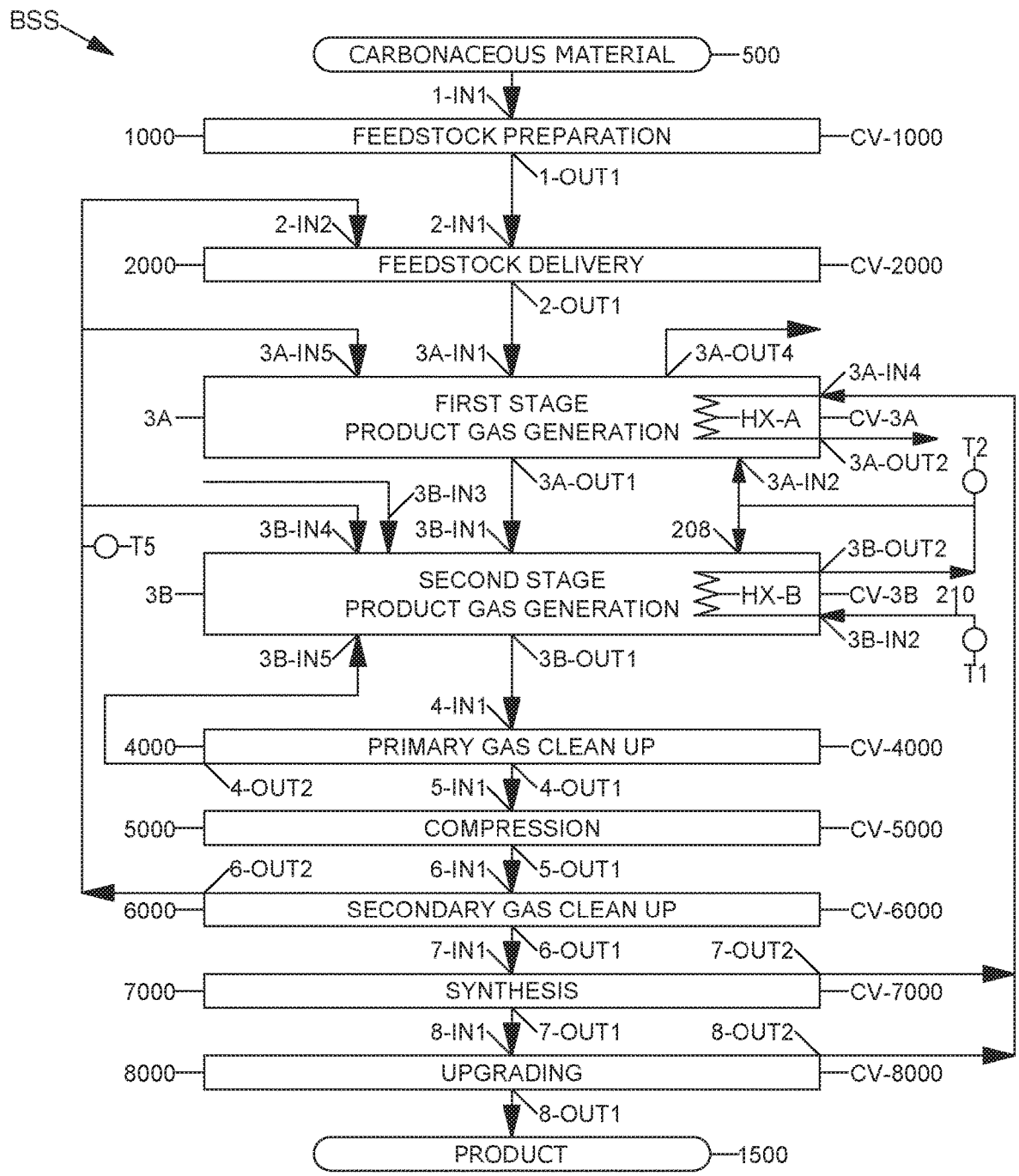

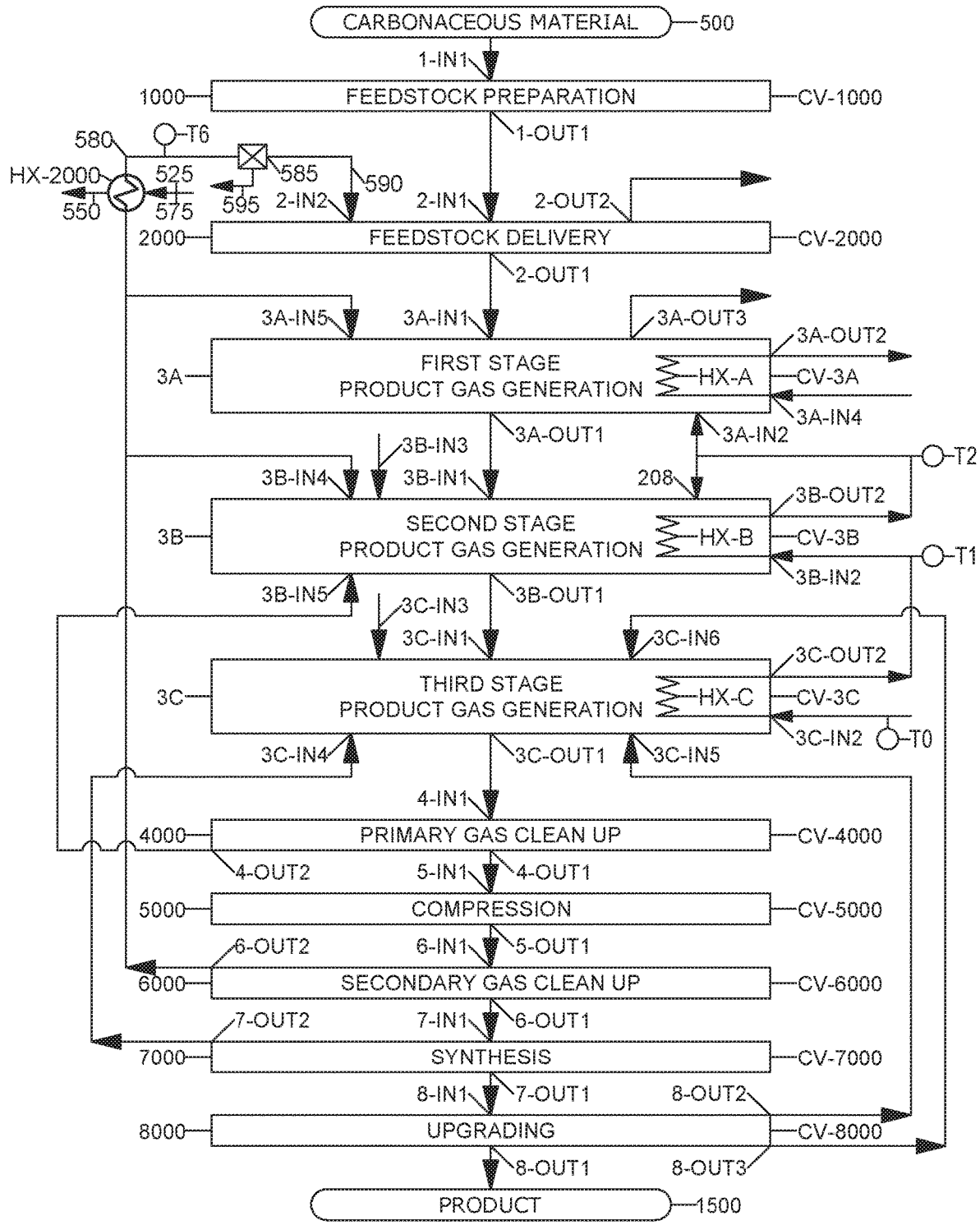

BIOREFINERY SUPERSTRUCTURE SYSTEM (BSS)

BIOREFINERY SUPERSTRUCTURE SYSTEM (BSS)

FIGURE 25

Classification Valve States for Automated Controller Operation

| STATE # | STATE 1 | STATE 2 | STATE 3 | STATE 4 | STATE 5 |
|---|---|---|---|---|---|
| DESCRIPTION | PREPARATION | TRANSFER | CLASSIFICATION | VENT | DRAIN |
| mixture transfer valve (V9,V9A,V9AA,V9B) | CLOSED | OPEN | CLOSED | CLOSED | CLOSED |
| classification gas transfer valve (V10,V10A,V10AA,V10B) | CLOSED | CLOSED | OPEN | CLOSED | CLOSED |
| bed material riser recycle transfer valve (V11,V11A,V11AA,V11B) | CLOSED | CLOSED | OPEN | CLOSED | CLOSED |
| depressurization vent valve (V12,V12A,V12AA,V12B) | CLOSED | CLOSED | CLOSED | OPEN | CLOSED |
| inert feedstock contaminant drain valve (V13,V13A,V13AA,V13B) | CLOSED | CLOSED | CLOSED | CLOSED | OPEN |

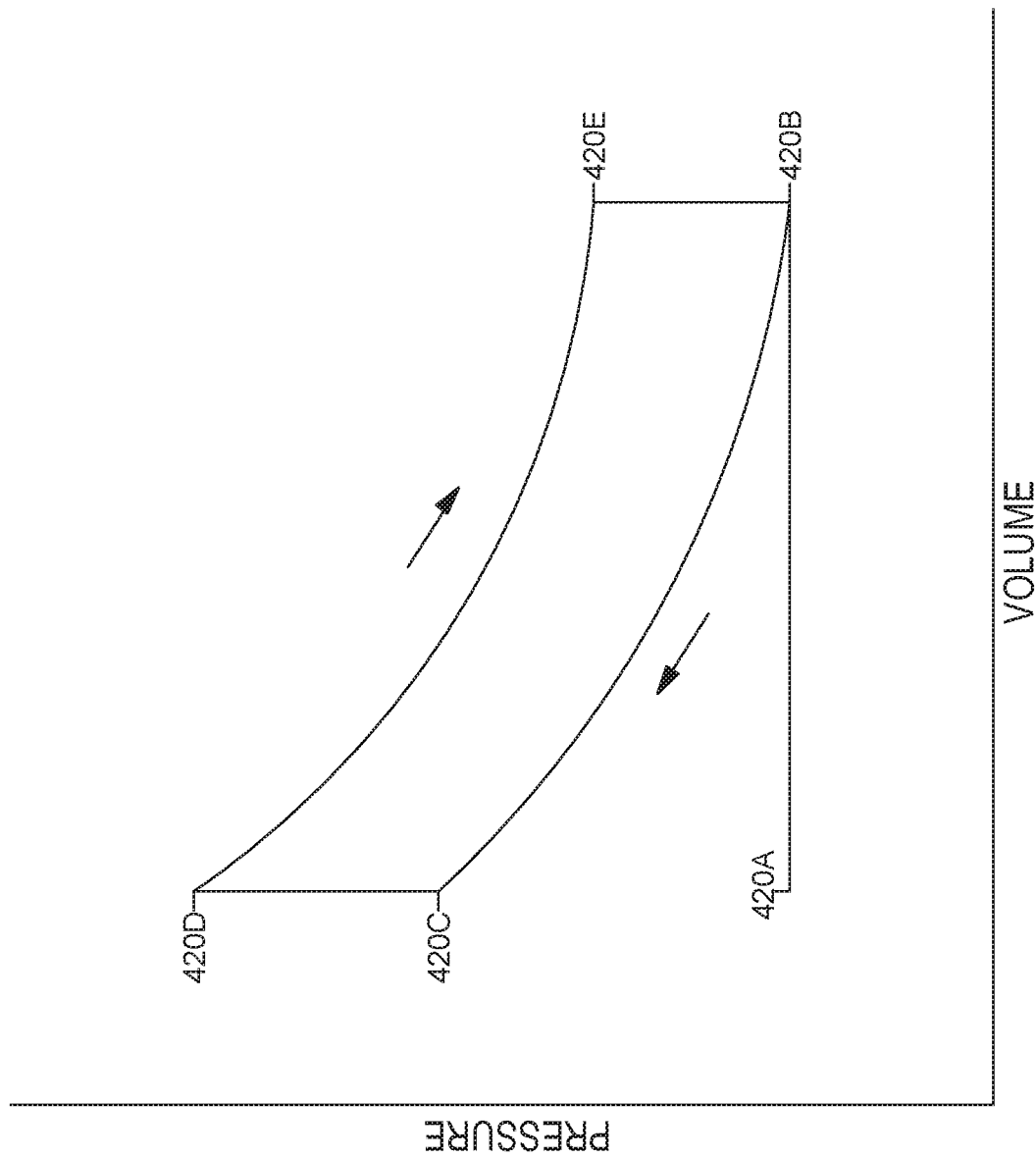

FIGURE 36

TABLE 1

| | COLUMN 1 (C1) | COLUMN 2 (C2) | COLUMN 3 (C3) |
|---|---|---|---|
| ROW 1 (R1) | NOMINAL DESIGN PARAMETERS CASE 1: NORMAL THROUGHPUT | | |
| ROW 2 (R2) | Feedstock Delivery (500 Dry MSW Carbonaceous Material Ton Per Day System) | | |
| ROW 3 (R3) | First Reactor Feedstock Injection Locations | | 6 |
| ROW 4 (R4) | Feeder System Cycles | cycles/minute | 4 |
| ROW 5 (R5) | Cycle Duration | seconds | 15 |
| ROW 6 (R6) | Plug Information | plugs/cycle | 1 |
| ROW 7 (R7) | | plugs/minute | 4 |
| ROW 8 (R8) | Total Carbonaceous Material to First Reactor | lb/hr wet | 45,782 |
| ROW 9 (R9) | | ton/hr wet | 23 |
| ROW 10 (R10) | | tons/day wet | 549 |
| ROW 11 (R11) | | lb/hr dry | 41,667 |
| ROW 12 (R12) | | ton/hr dry | 41,845 |
| ROW 13 (R13) | | tons/day dry | 500 |
| ROW 14 (R14) | Carbonaceous Material to Each Of 6 First Reactor Feedstock Injection Locations | lb/hr wet | 7,630 |
| ROW 15 (R15) | | lb/minute | 127 |
| ROW 16 (R16) | | plug lb/cycle | 32 |
| ROW 17 (R17) | | ton/hr wet | 3.8 |
| ROW 18 (R18) | | tons/day wet | 92 |
| ROW 19 (R19) | | lb/hr dry | 6,944 |
| ROW 20 (R20) | | ton/hr dry | 3.47 |
| ROW 21 (R21) | | tons/day dry | 83 |
| ROW 22 (R22) | $CO_2$ Purge To Feedstock Delivery | lb/hr | 3,190 |
| ROW 23 (R23) | $CO_2$ Purge To Carbonaceous Material to Each First Reactor Feedstock Injection Location | lb/hr | 532 |
| ROW 24 (R24) | Ratio of Carbonaceous Material to $CO_2$ To Each First Reactor Feedstock Injection Location | lb MSW/lb $CO_2$ | 14 |

FIGURE 37

TABLE 2

| | COLUMN 1 (C1) | COLUMN 2 (C2) | COLUMN 3 (C3) |
|---|---|---|---|
| ROW 1 (R1) | NOMINAL DESIGN PARAMETERS CASE 2: MAXIMUM THROUGHPUT | | |
| ROW 2 (R2) | Maximum Throughput Design Parameters | | 125% |
| ROW 3 (R3) | Feeder System Cycles | cycles/minute | 4 |
| ROW 4 (R4) | Cycle Duration | seconds | 15 |
| ROW 5 (R5) | Plug Information | plugs/cycle | 1 |
| ROW 6 (R6) | | plugs/minute | 4 |
| ROW 7 (R7) | Carbonaceous Material to Each First Reactor | lb/hr wet | 9,538 |
| ROW 8 (R8) | Feedstock Injection Location | lb/minute | 159 |
| ROW 9 (R9) | | plug lb/cycle | 39.74 |
| ROW 10 (R10) | | ton/hr wet | 4.77 |
| ROW 11 (R11) | | tons/day wet | 114.46 |
| ROW 12 (R12) | | lb/hr dry | 8,681 |
| ROW 13 (R13) | | ton/hr dry | 4.34 |
| ROW 14 (R14) | | tons/day dry | 104 |
| ROW 15 (R15) | Total Carbonaceous Material to First Reactor | tons/day dry | 625 |

DENSIFICATION SYSTEM

DENSIFICATION SYSTEM
STATE 0: RETRACTED STATE

DENSIFICATION SYSTEM
STATE 1: LOADING STATE

DENSIFICATION SYSTEM
STATE 1: LOADING STATE

DENSIFICATION SYSTEM
STATE 2: COMPRESSION STATE

DENSIFICATION SYSTEM
STATE 1: LOADING STATE

DENSIFICATION SYSTEM
STATE 2: COMPRESSION STATE

DENSIFICATION SYSTEM
STATE 1: LOADING STATE

DENSIFICATION SYSTEM
STATE 2: COMPRESSION STATE

DENSIFICATION SYSTEM
STATE 1: LOADING STATE

DENSIFICATION SYSTEM
STATE 3: UNLOCKED BACKSTOP STATE

DENSIFICATION SYSTEM
STATE 4: EJECTION STATE

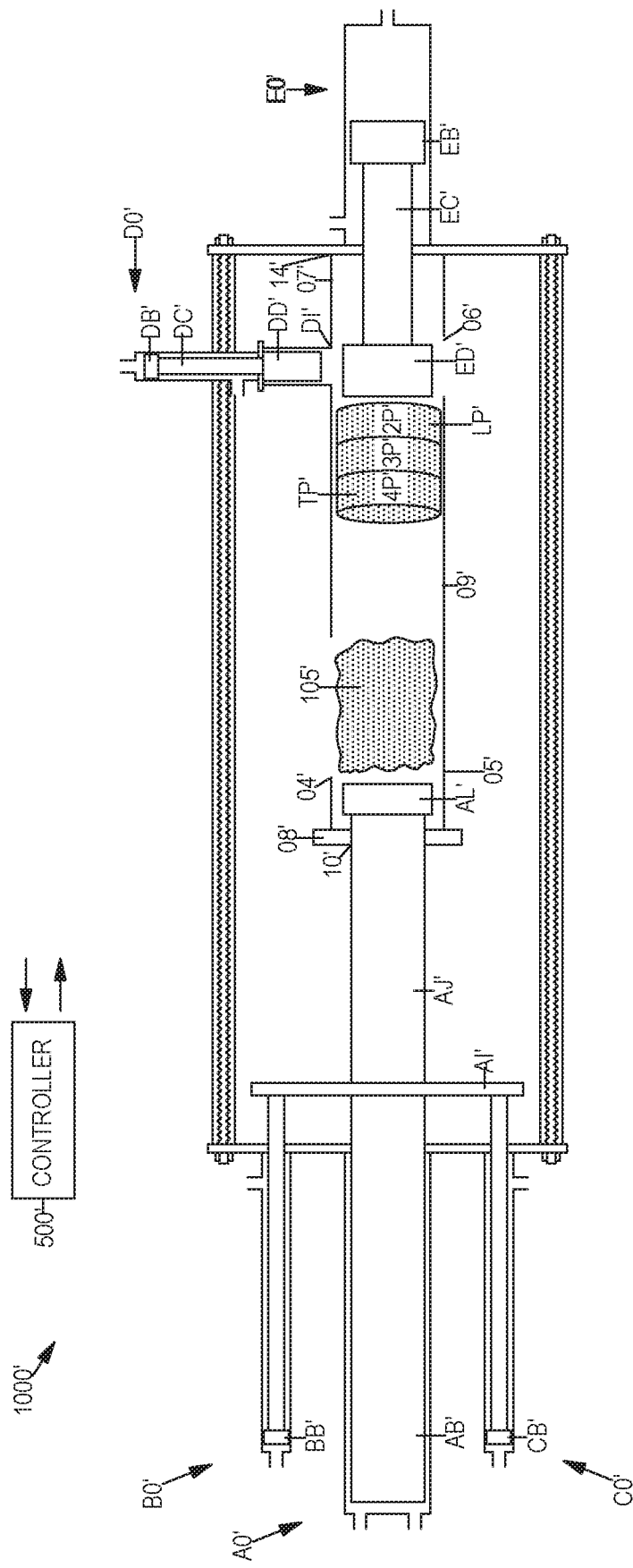

SYSTEM AND METHOD FOR LIQUID FUEL PRODUCTION FROM CARBONACEOUS MATERIALS USING RECYCLED CONDITIONED SYNGAS

CROSS REFERENCE TO RELATED APPLICATION

This application is a continuation application of, and claims priority to, U.S. patent application Ser. No. 16/814,892, for "System and Method for Liquid Fuel Production from Carbonaceous Materials Using Recycled Conditioned Syngas", filed on Mar. 10, 2020, now allowed. The disclosure of the foregoing applications are incorporated here by reference.

TECHNICAL FIELD

The present disclosure is directed to systems and methods for the production of liquid fuels and chemicals from carbonaceous materials. More particularly, it concerns such systems and methods in which a portion of conditioned syngas produced during the process is recycled to help produce additional syngas.

BACKGROUND

In recent years, there has been a shift towards innovative energy and environmental technologies to moderate climate change, reduce greenhouse gas emissions, reduce air and water pollution, promote economic development, expand energy supply options, increase energy security, decrease dependence on imported oil, and strengthen rural economies.

One of these technologies entails conversion of a carbonaceous feedstock into a product gas which can then be converted into liquid fuels, hydrocarbons and other useful compounds. Carbonaceous feedstock along with one or more gaseous or liquid reactants are introduced into a pressurized reactor where they undergo one or more thermochemical reactions to produce the product gas. Ideally, the carbonaceous feedstock is introduced into the reactor such that: feedstock throughput is high, the feedstock has high surface area to promote thermochemical reactions, the feedstock is distributed within the reactor, and the pressure of the reactor is maintained, even as the carbonaceous feedstock is continuously being introduced into the reactor.

A liquid fuels production system should be able to produce liquid fuels from large quantities of carbonaceous materials. However, processing large quantities of carbonaceous materials requires having sufficient throughput in each of a number of serially connected systems. These include feeder systems, gas production systems, gas clean-up systems, synthesis systems and gas upgrading systems. The capacities of the various systems should be selected so that they collectively cooperate to meet up-time and fuel production requirements while also maximizing the return on investment (ROI).

SUMMARY

In one aspect, the subject matter of the present application is directed to a method of producing liquid fuel and/or chemicals from a carbonaceous material. The method includes providing a steam reformer having a plurality of pulse combustion heat exchangers in thermal contact with a particulate heat transfer material. Carbonaceous material is introduced into the steam reformer along with superheated steam. A first portion of conditioned syngas is combusted in the pulse combustion heat exchangers to thereby indirectly heat the particulate heat transfer material and cause the carbonaceous material to react with the superheated steam and produce a first reactor product gas which includes at least carbon monoxide, carbon dioxide, hydrogen, and hydrocarbons. In a hydrocarbon reformer, a second portion of conditioned syngas, an oxygen-containing gas and at least a portion of the first reactor product gas are reacted to produce an improved syngas having a higher concentration of carbon monoxide and a lower concentration of hydrocarbons than in the first reactor product gas. The improved syngas is subjected to one or more gas clean-up steps to produce new conditioned syngas. A first portion of the new conditioned syngas in transferred to a synthesis system to produce tail gas and at least one from the group consisting of liquid fuel and chemicals. A second portion of the new conditioned syngas is transferred to the steam reformer for use as the first portion of conditioned syngas, and to the hydrocarbon reformer for use as the second portion of conditioned syngas.

In another aspect, the subject matter of the present application is directed to a system for producing liquid fuel and/or chemicals from a carbonaceous material. The system includes a steam reformer, a hydrocarbon reformer, at least one gas clean-up system and a synthesis system.

The steam reformer has a plurality of pulse combustion heat exchangers in thermal contact with a particulate heat transfer material, the steam reformer connected to a source of carbonaceous material and a source of superheated steam, the pulse combustion heat exchangers connected to a first source of conditioned syngas for combusting therein to indirectly heat the particulate heat transfer material and cause the carbonaceous material to react with the superheated steam and produce a first reactor product gas which includes at least carbon monoxide, carbon dioxide, hydrogen and hydrocarbons.

The hydrocarbon reformer is connected to a second source of conditioned syngas, a source of oxygen-containing gas and further configured to receive a portion of the first reactor product gas, the hydrocarbon reformer configured to produce an improved syngas having a higher concentration of carbon monoxide and a lower concentration of hydrocarbons than in the first reactor product gas.

The at least one gas clean-up system is configured to receive the improved syngas and remove at least one contaminant in the improved syngas to produce a new conditioned syngas, the at least one gas clean-up system having a gas clean-up system output through which the new conditioned syngas exits.

The synthesis system is connected to the gas clean-up system output and configured to receive a first portion of the new conditioned syngas and output: (i) tail gas, and (ii) at least one from the group consisting of liquid fuel and chemicals. The gas clean-up system output serves as the first source of conditioned syngas connected to the pulse combustion heat exchangers, and also serves as the second source of conditioned syngas connected to the hydrocarbon reformer.

BRIEF DESCRIPTION OF THE DRAWINGS

The accompanying figures show schematic process flowcharts of preferred embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

FIG. 2D shows a simplistic block flow control volume diagram of one embodiment of a Feedstock Delivery System (2000) including the non-limiting subsystems or sequence steps of Bulk Transfer (2A), Flow Splitting (2B), Mass Flow Regulation (2C), Densification (2D), Plug Control (2E), Density Reduction (2F), Gas Mixing (2G), and Transport (2H).

FIG. 3 elaborates upon the non-limiting embodiment of FIG. 2 further including a description of the Bulk Transfer (2A) subsystem or sequence step of the Feedstock Delivery System (2000).

FIG. 6A shows a non-limiting embodiment of a Mass Flow Regulation (2C) method.

FIG. 7B elaborates upon a non-limiting embodiment of FIG. 7A further including a detailed three dimensional view of a first flange support (D44) that may be placed in between the first cylinder first flange (D02) and the first hydraulic cylinder flange (D06).

FIG. 7C shows the entry conduit (563) of the airborne particulate solid evacuation system (565) connected to a network of conduits including the bulk transfer entry conduit (563A), flow splitting entry conduit (563B), flow splitting entry conduit (563BA), mass flow regulation entry conduit (563C), densification entry conduit (563D), and the solids transfer entry conduit (563E).

FIG. 10A depicts the Gas Mixing Valve States for Automated Controller Operation of typical start-up, normal operation, and shut-down procedures. FIG. 10A is to be used in conjunction with FIG. 10 and depicts a listing of valve states that may be used in a variety of methods to operate valves associated with the gas and carbonaceous material mixing system (2G1).

FIG. 11 elaborates upon the non-limiting embodiment of FIG. 2A further including a description of the Transport (2H) subsystem or sequence step of the Feedstock Delivery System (2000).

FIG. 13A shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a first mode of operation under conditions of state 2D(1).

FIG. 13B shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a second mode of operation under conditions of state 2D(2).

FIG. 13F depicts the Densification Valve States for Automated Controller Operation of typical normal operation procedure.

FIG. 14A further includes a first solids separation device (150), second reactor (200), and second solids separation device (250) which are in fluid communicating with a third reactor (300).

FIG. 16 shows a framework of an entire Biorefinery Superstructure System (BSS) configured to employ the use of the two-stage energy integrated product gas generation scheme.

FIG. 17 shows a framework of an entire Biorefinery Superstructure System (BSS) configured to employ the use of the three-stage energy integrated product gas generation scheme.

equipped with a dense bed zone (AZ-A), feed zone (AZ-B), and splash zone (AZ-C), along with the first reactor carbonaceous material and gas input (104), valves, sensors, and controllers.

Figure 18:
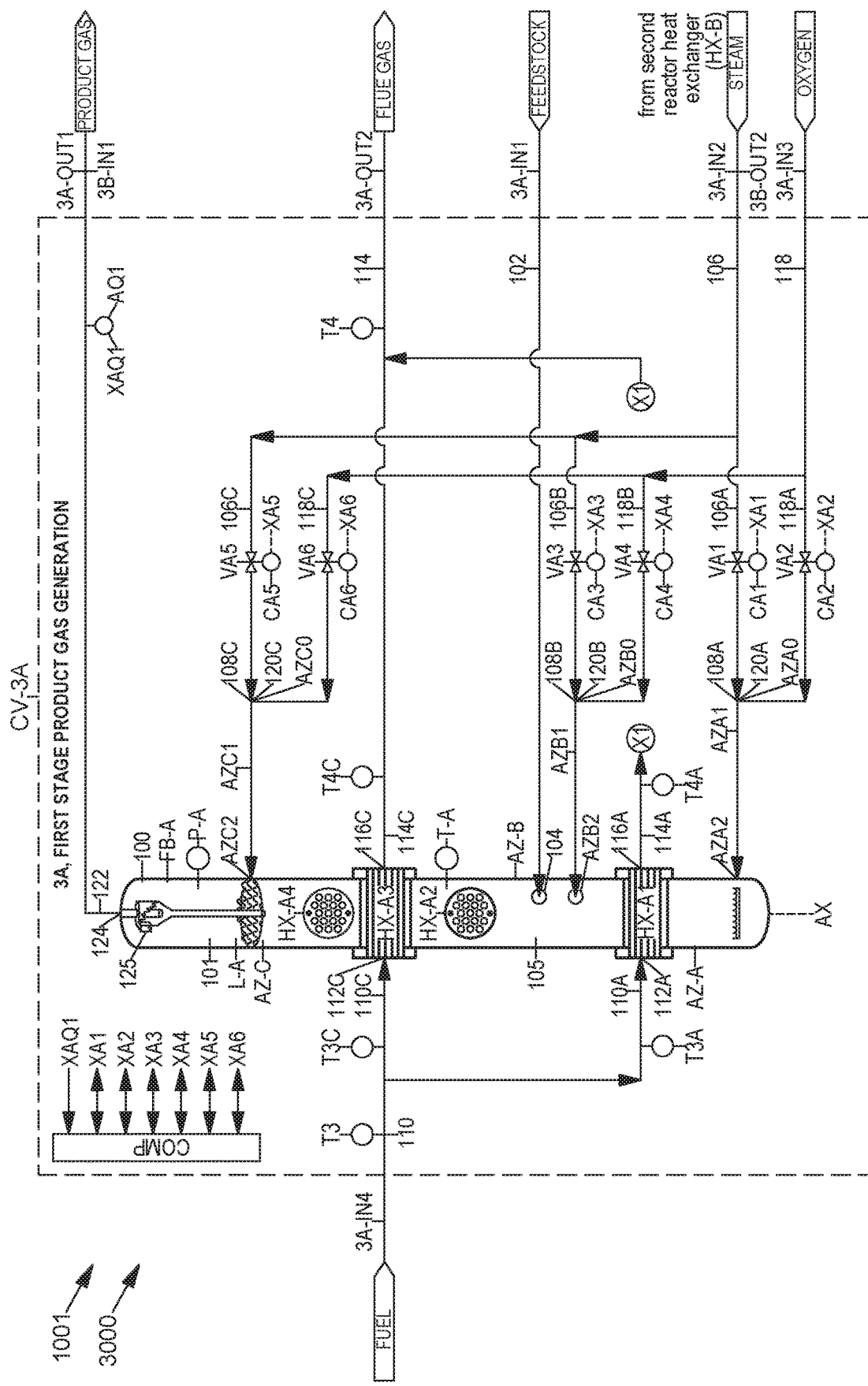
FIG. 18 is a detailed view showing a non-limiting embodiment of a First Stage Product Gas Generation Control Volume (CV-3A) and First Stage Product Gas Generation System (3A) of a three-stage energy-integrated product gas generation system (1001) including a first reactor (100)
Figure 19:
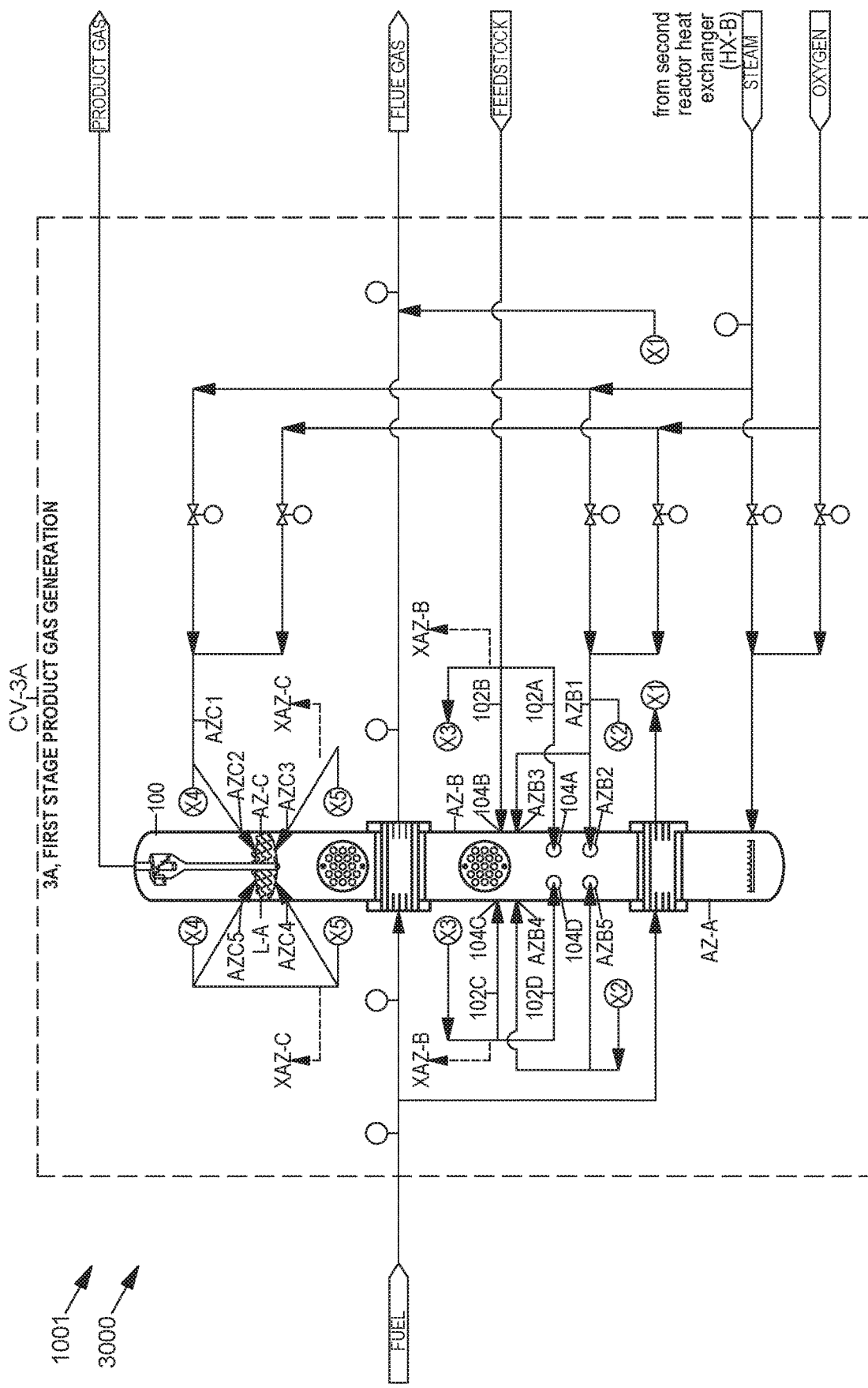

FIG. 19 elaborates upon the non-limiting embodiment of FIG. 18 further including multiple carbonaceous material and gas inputs (104A, 104B, 104C, 104D) and multiple feed zone steam/oxygen inputs (AZB2, AZB3, AZB4, AZB5) positioned in the feed zone (AZ-B) along with multiple splash zone steam/oxygen inputs (AZC2, AZC3, AZC4, AZC5) positioned in the splash zone (AZ-C).

Figure 20:
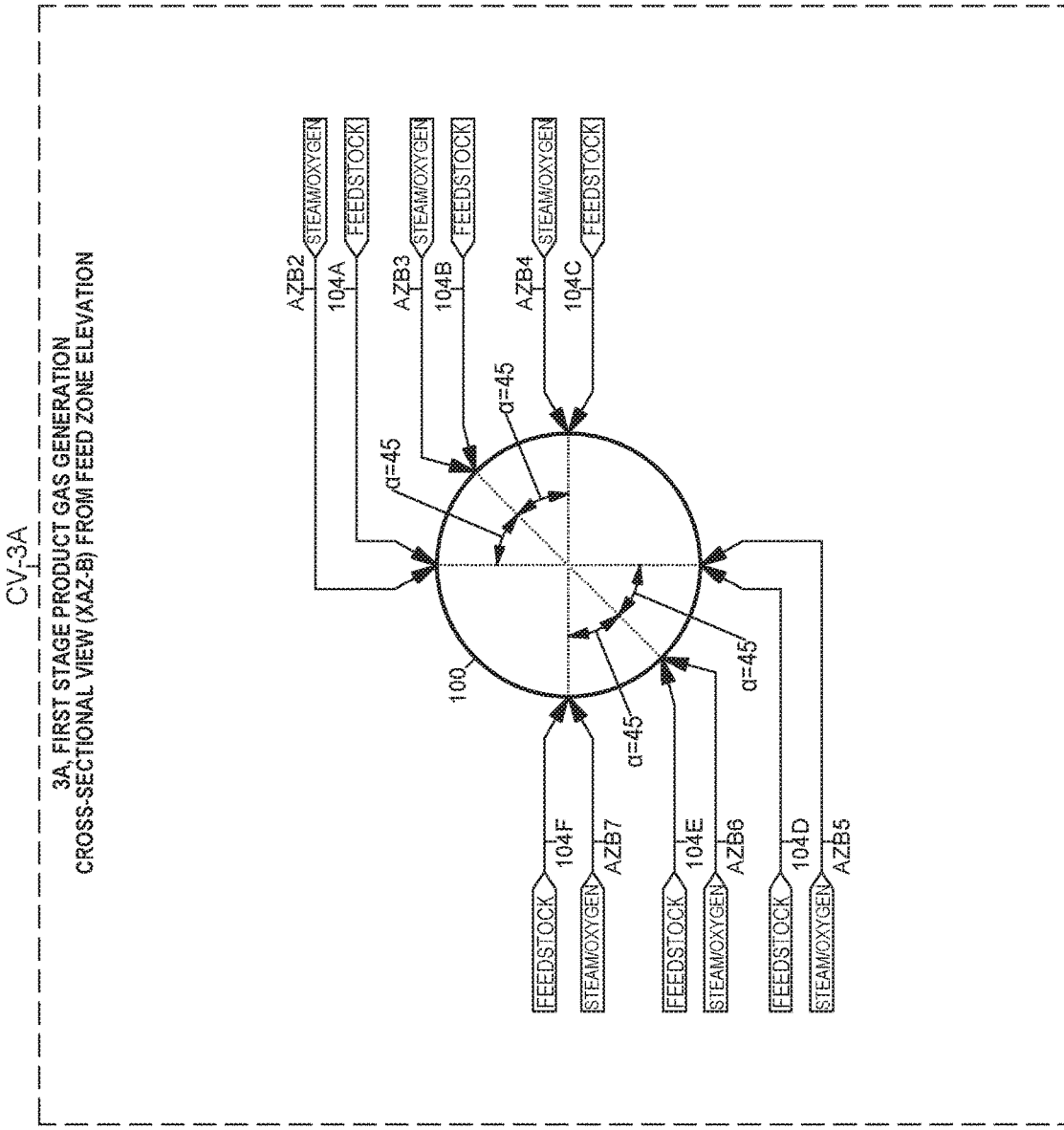

FIG. 20 shows a non-limiting embodiment of a first reactor feed zone circular cross-sectional view (XAZ-B) from the embodiment of FIG. 19.

Figure 21:
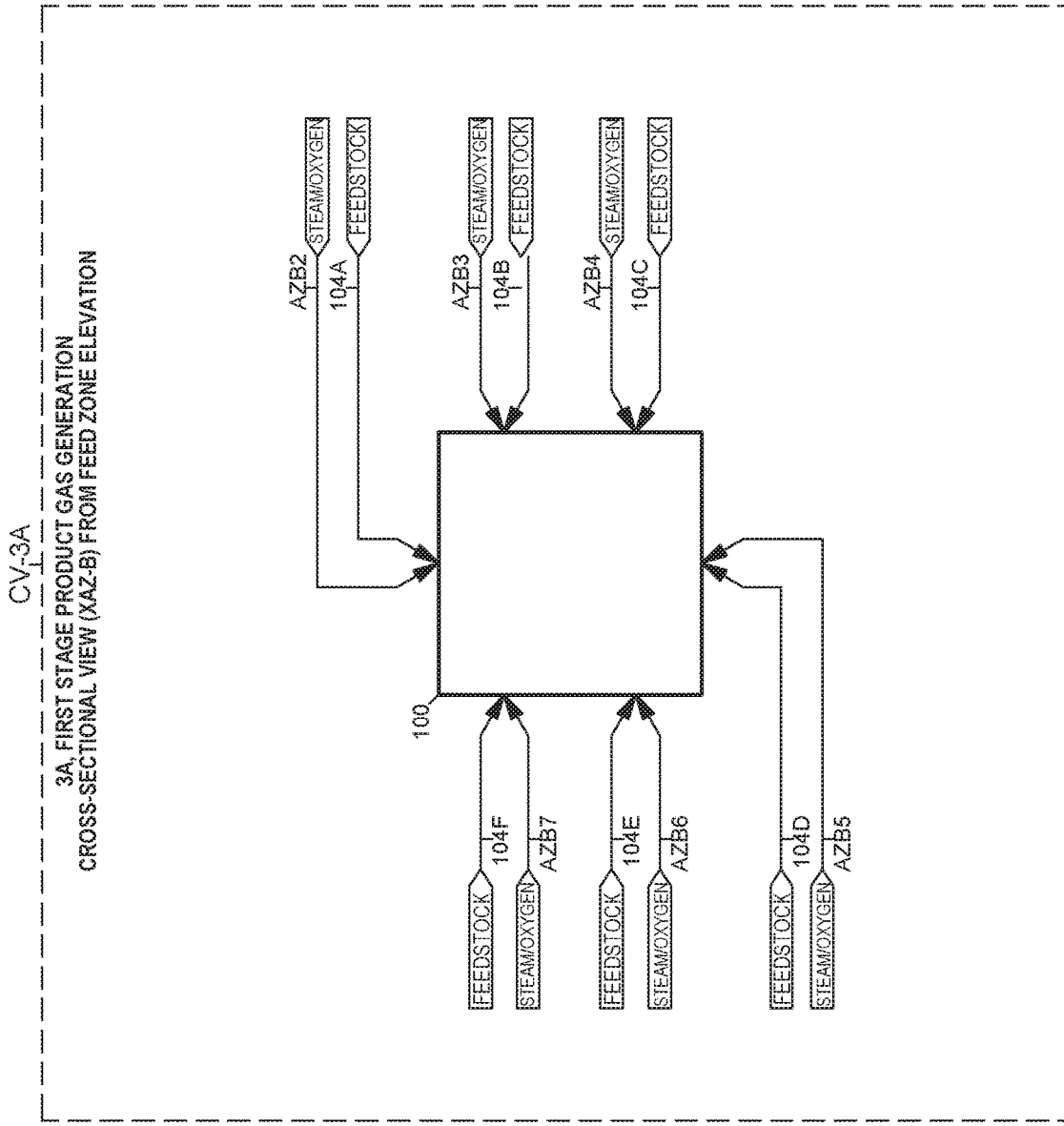

FIG. 21 shows a non-limiting embodiment of a first reactor feed zone cross-sectional view (XAZ-B) from the embodiment of FIG. 20, however, FIG. 21 shows a rectangular first reactor (100) cross-sectional view.

Figure 22:
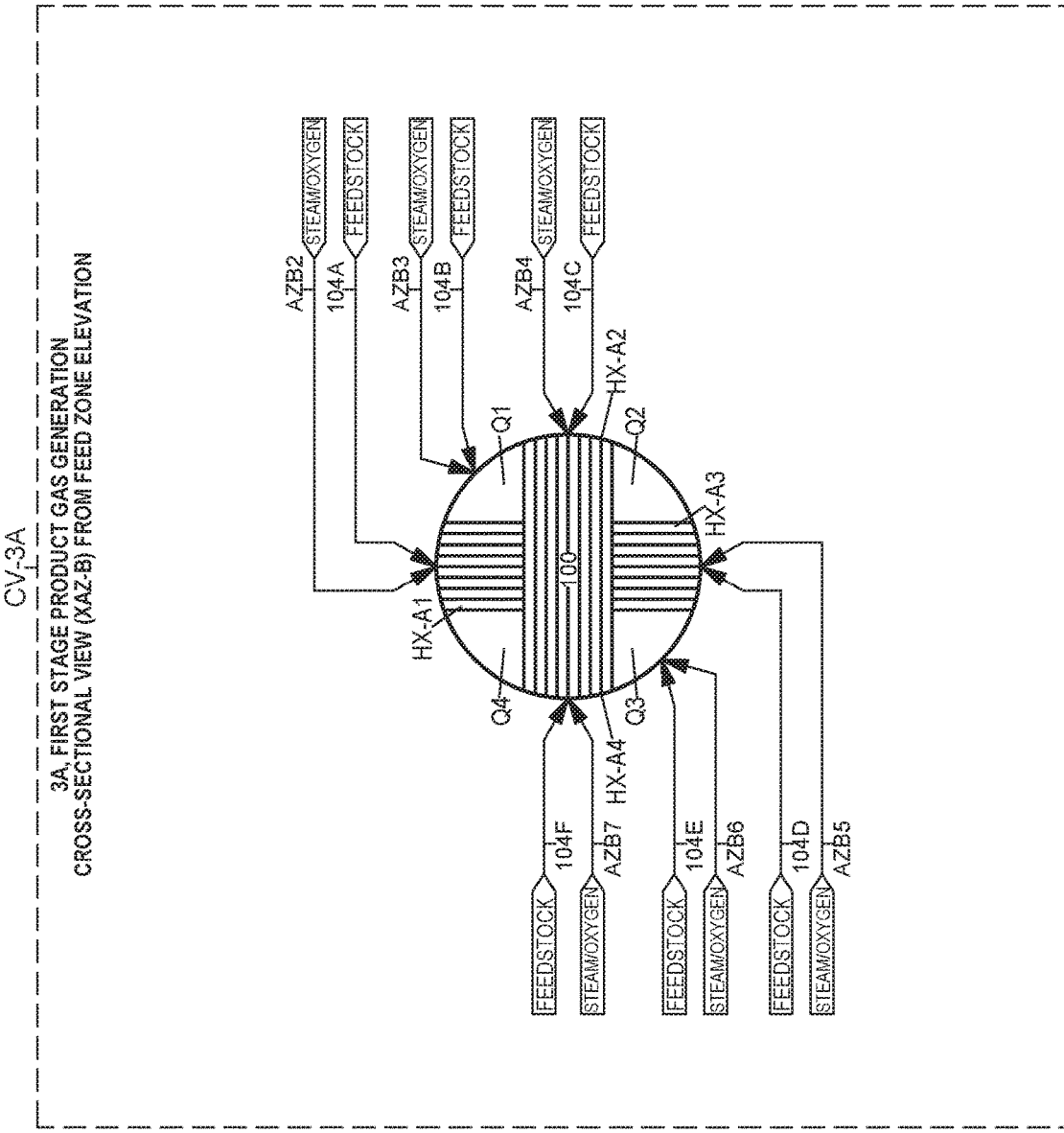

FIG. 22 shows a non-limiting embodiment of a first reactor feed zone cross-sectional view (XAZ-B) from the embodiment of FIG. 19 where only two of the six first reactor (100) carbonaceous material and gas inputs (104B, 104E) are configured to inject carbonaceous material into vertically extending quadrants (Q1, Q2, Q3, Q4).

Figure 23:
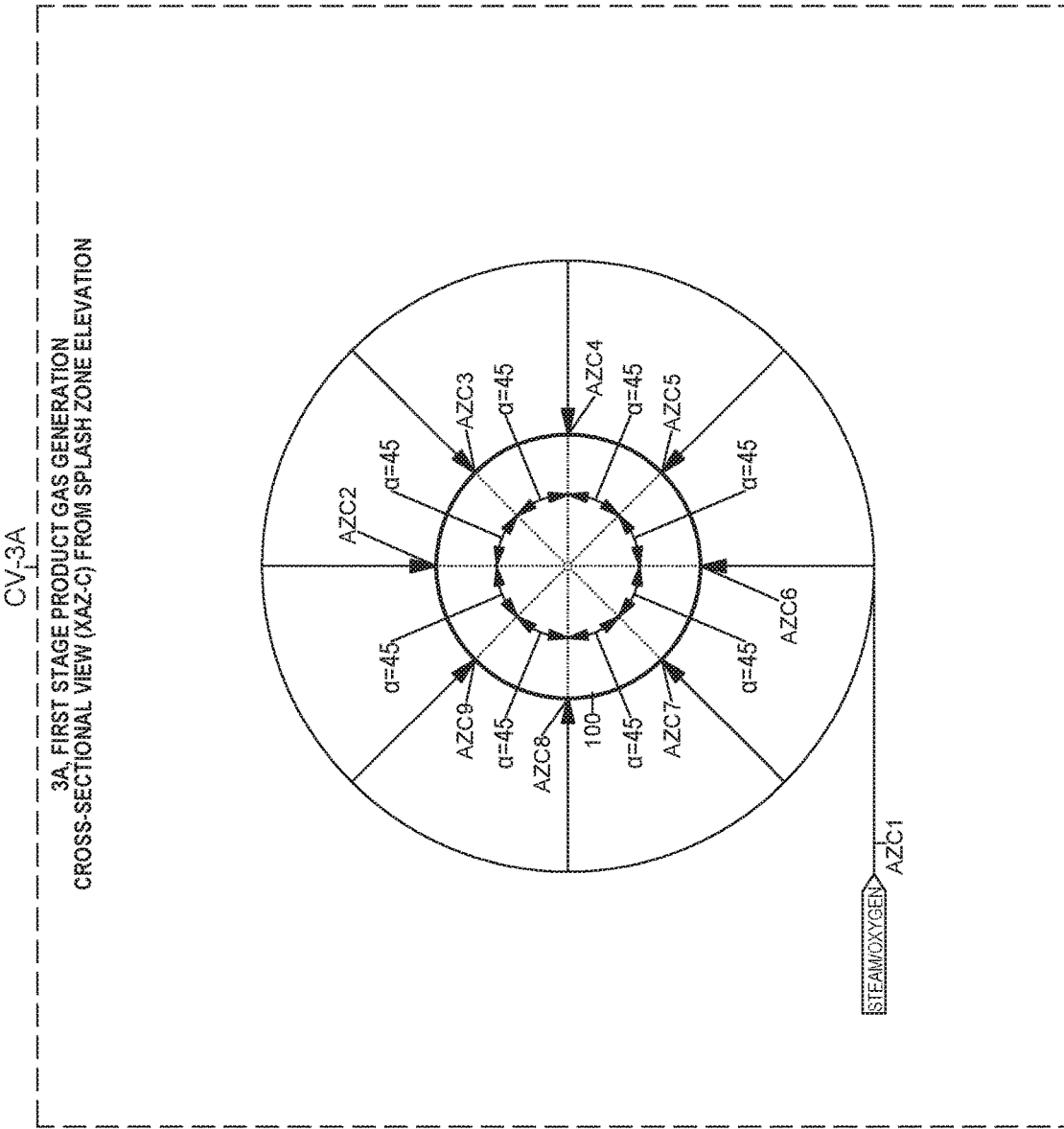

FIG. 23 shows a non-limiting embodiment of a first reactor splash zone cross-sectional view (XAZ-C) from the embodiment of FIG. 19.

Figure 24:
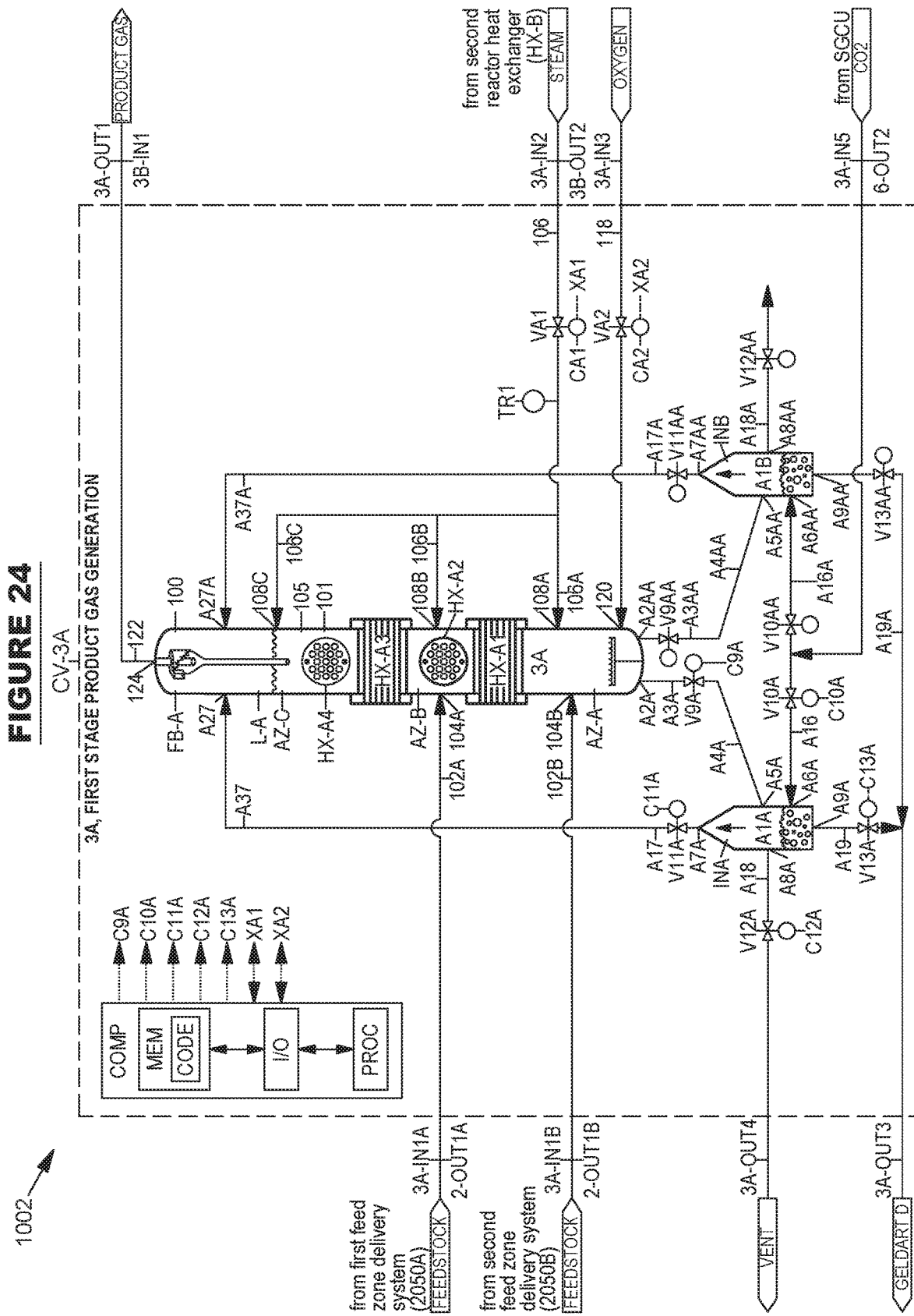

FIG. 24 elaborates upon the non-limiting embodiment of FIG. 18 further including two particulate classification chambers (A1A, A1B) that are configured to accept a bed material, inert feedstock contaminant mixture (A4A, A4AA), and a classifier gas (A16, A16A) to clean and recycle the bed material portion back to the first interior (101) of the first reactor (100) while removing the inert feedstock contaminant portion from the system as a solids output (3A-OUT3).

FIG. 25 depicts the Classification Valve States for Automated Controller Operation of a typical particulate classification procedure. FIG. 25 is to be used in conjunction with FIG. 18 and depicts a listing of valve states that may be used in a variety of methods to operate valves associated with the particulate classification chambers (A1A, A1B).

Figure 26:
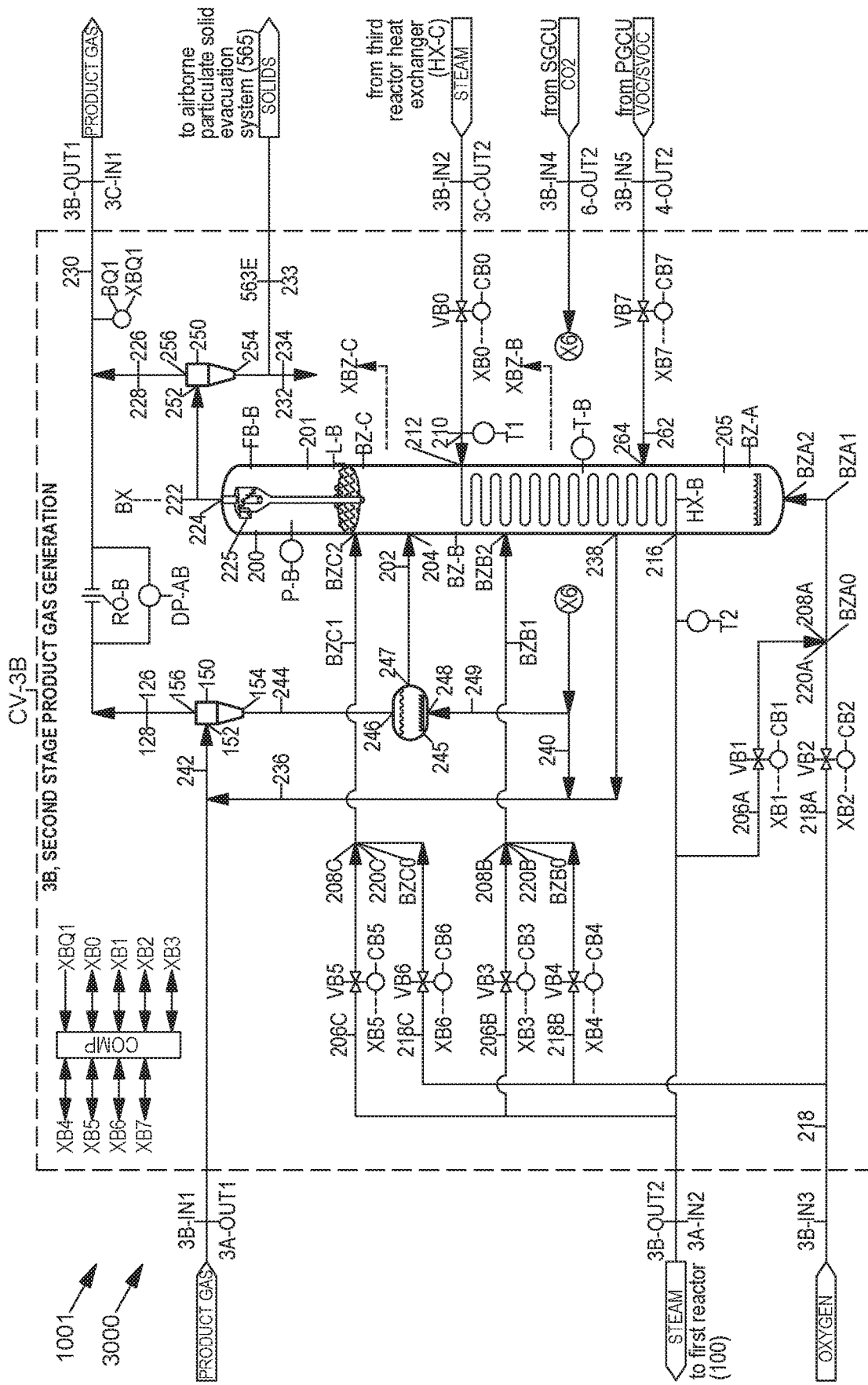

FIG. 26 is a detailed view showing a non-limiting embodiment of a Second Stage Product Gas Generation Control Volume (CV-3B) and Second Stage Product Gas Generation System (3B) of a three-stage energy-integrated product gas generation system (1001) including a second reactor (200) equipped with a dense bed zone (BZ-A), feed zone (BZ-B), and splash zone (BZ-C), along with a second reactor heat exchanger (HX-B), first solids separation device (150), second solids separation device (250), solids flow regulator (245), riser (236), dipleg (244), and valves, sensors, and controllers.

Figure 27:
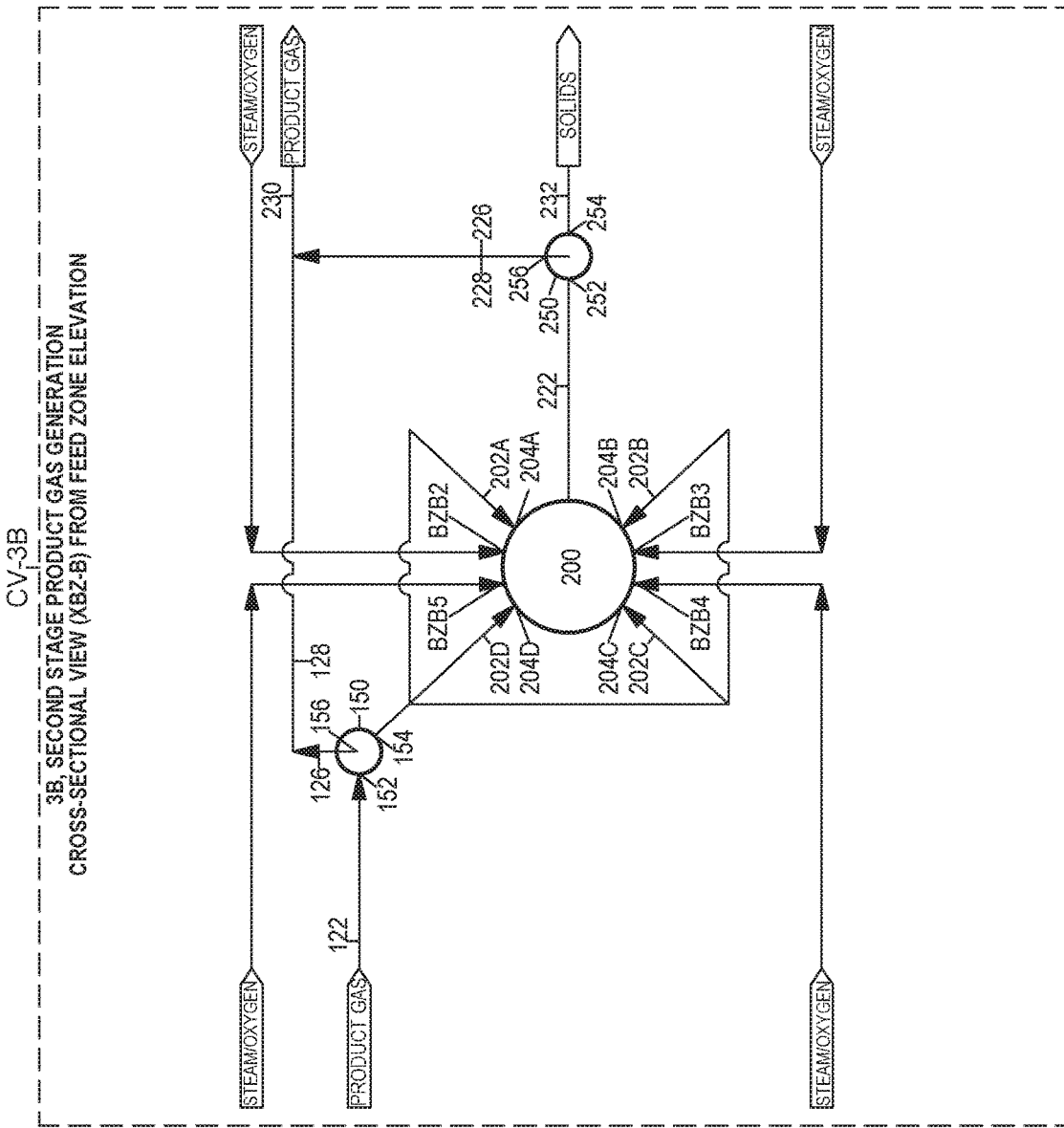

FIG. 27 shows a non-limiting embodiment of a second reactor feed zone cross-sectional view (XBZ-B) of the embodiment in FIG. 26, including: one first solids separation device (150); four second reactor first char inputs (204A, 204B, 204C, 204D); four feed zone steam/oxygen inputs (BZB2, BZB3, BZB4, BZB5); and, where the combined reactor product gas conduit (230) is configured to blend the char depleted first reactor product gas (126) with the solids depleted second reactor product gas (226).

Figure 28:
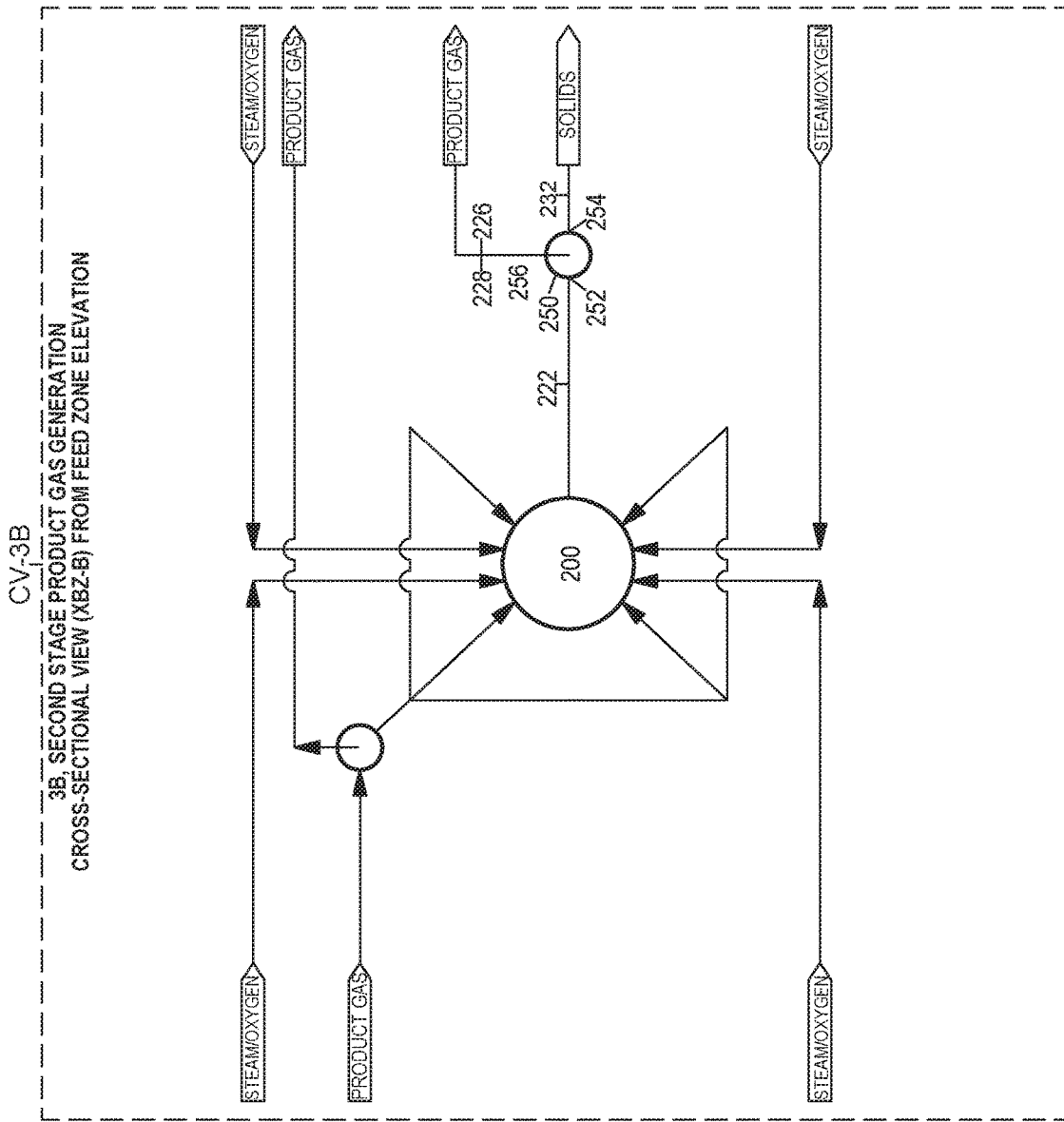

FIG. 28 shows a non-limiting embodiment of a second reactor feed zone cross-sectional view (XBZ-B) of the embodiment in FIG. 26 where the char depleted first reactor product gas (126) is not combined with the solids depleted second reactor product gas (226).

Figure 29:
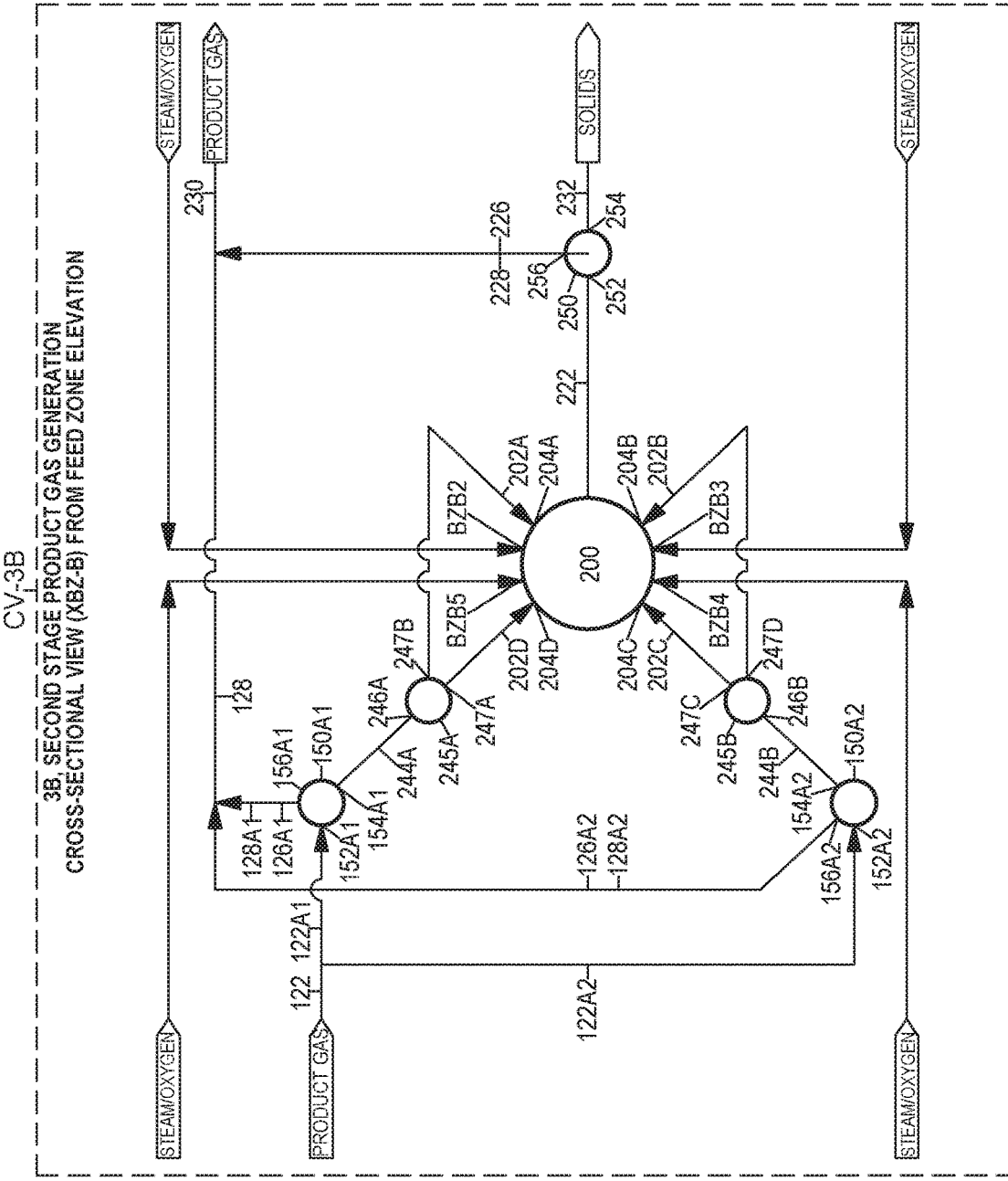

FIG. 29 shows a non-limiting embodiment of a second reactor feed zone cross-sectional view (XBZ-B) of the embodiment in FIG. 26, including: two first solids separation devices (150A1, 150A2); two solids flow regulators (245A, 245B); four second reactor first char inputs (204A, 204B, 204C, 204D); four feed zone steam/oxygen inputs (BZB2, BZB3, BZB4, BZB5); and, where the combined reactor product gas conduit (230) is configured to blend the char depleted first reactor product gas (126A1, 126A2) with the solids depleted second reactor product gas (226).

Figure 30:
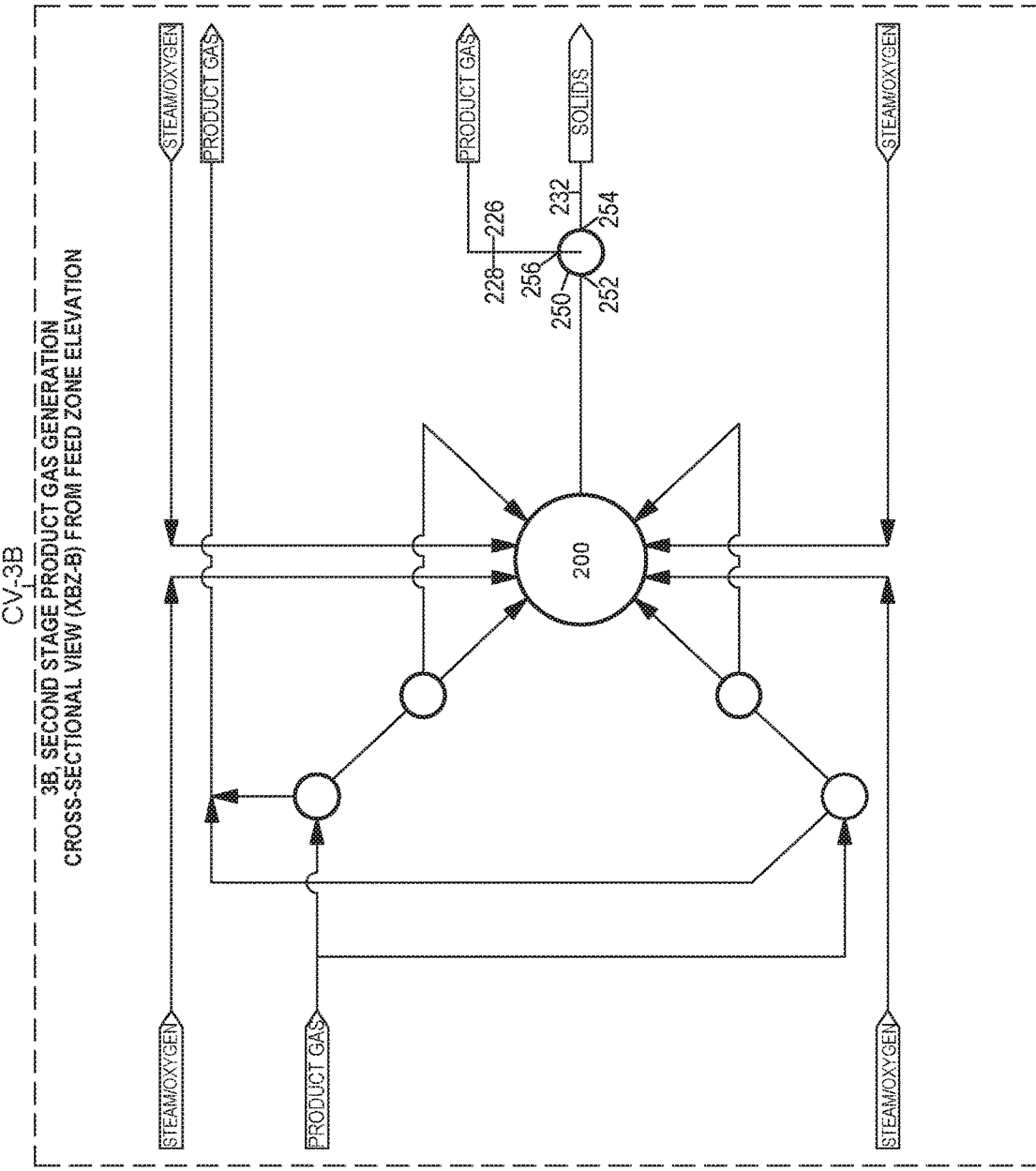

FIG. 30 shows a non-limiting embodiment of a second reactor feed zone cross-sectional view (XBZ-B) of the embodiment in FIG. 26 where the char depleted first reactor product gas (126A1, 126A2) is not combined with the solids depleted second reactor product gas (226).

Figure 31:
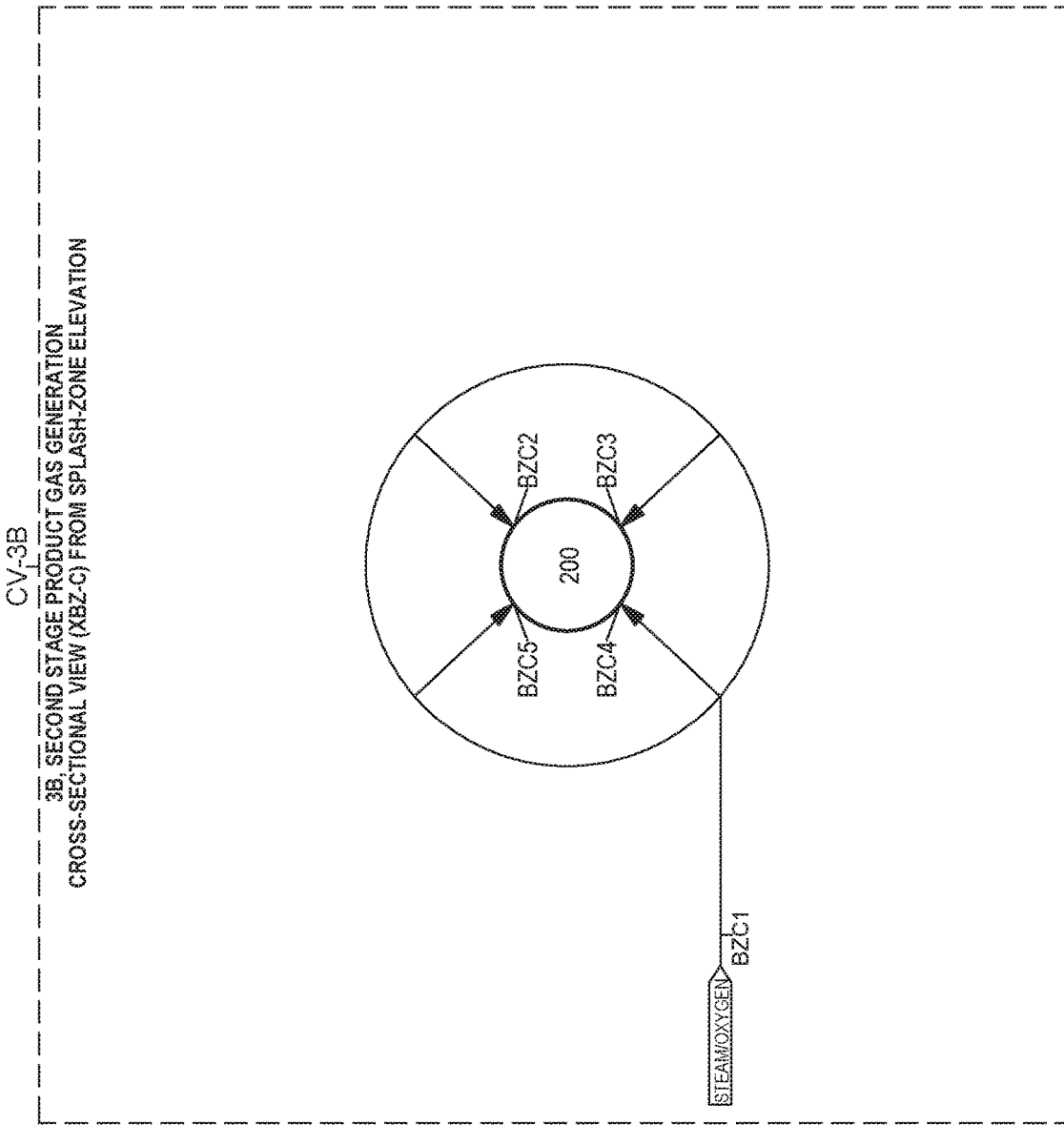

FIG. 31 shows a non-limiting embodiment of a second reactor splash zone cross-sectional view (XBZ-C) of the embodiment in FIG. 26, including four splash zone steam/oxygen inputs (BZC2, BZC3, BZC4, BZC5) configured to accept a source of splash zone steam/oxygen (BZC1).

Figure 32:
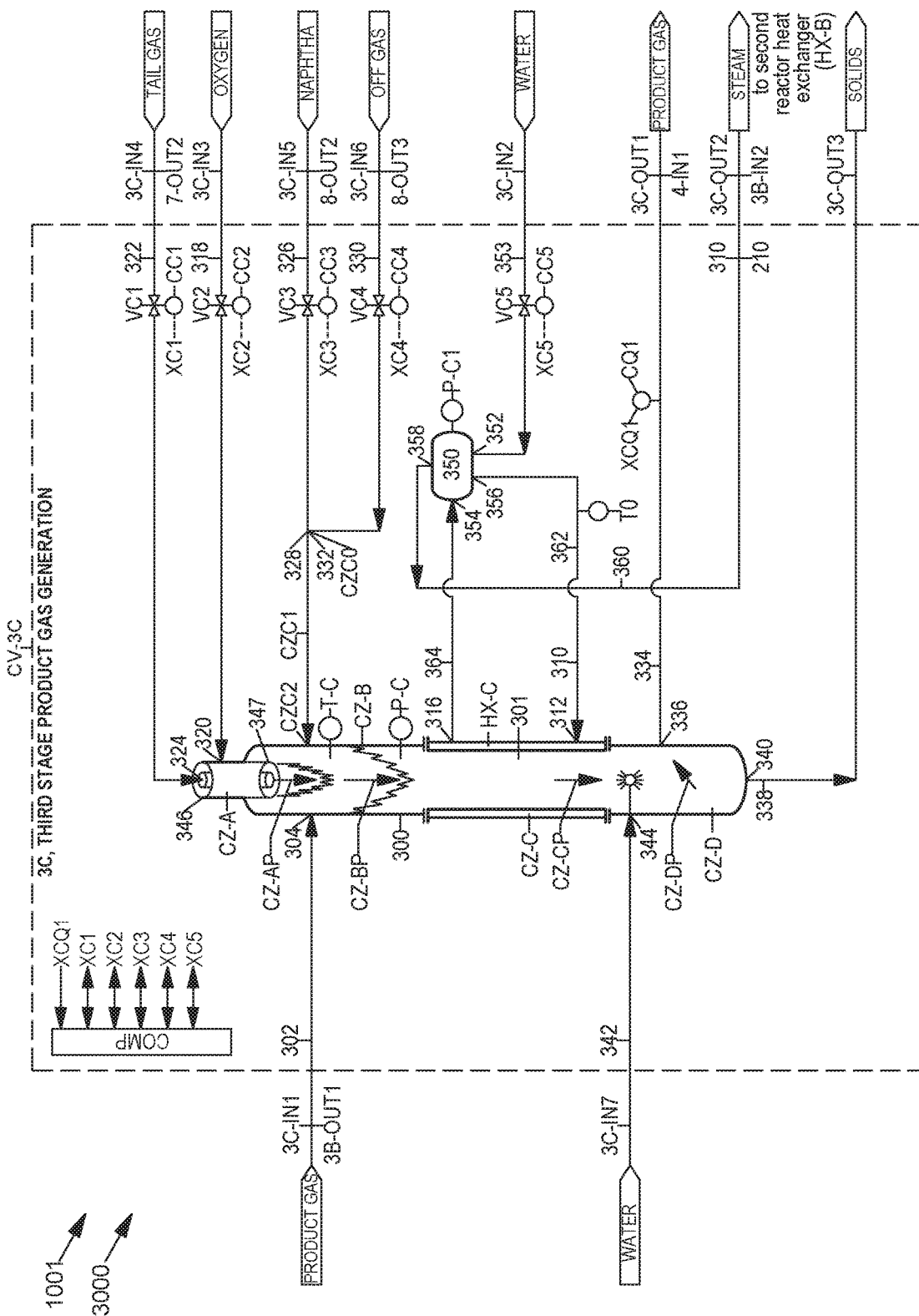

FIG. 32 shows a detailed view of one non-limiting embodiment of a Third Stage Product Gas Generation Control Volume (CV-3C) and Third Stage Product Gas Generation System (3C) of a three-stage energy-integrated product gas generation system (1001) showing a third reactor (300) equipped with a third interior (301), and also showing a combustion zone (CZ-A), reaction zone (CZ-B), cooling zone (CZ-C), quench zone (CZ-D), steam drum (350), and valves, sensors, and controllers.

Figure 14:
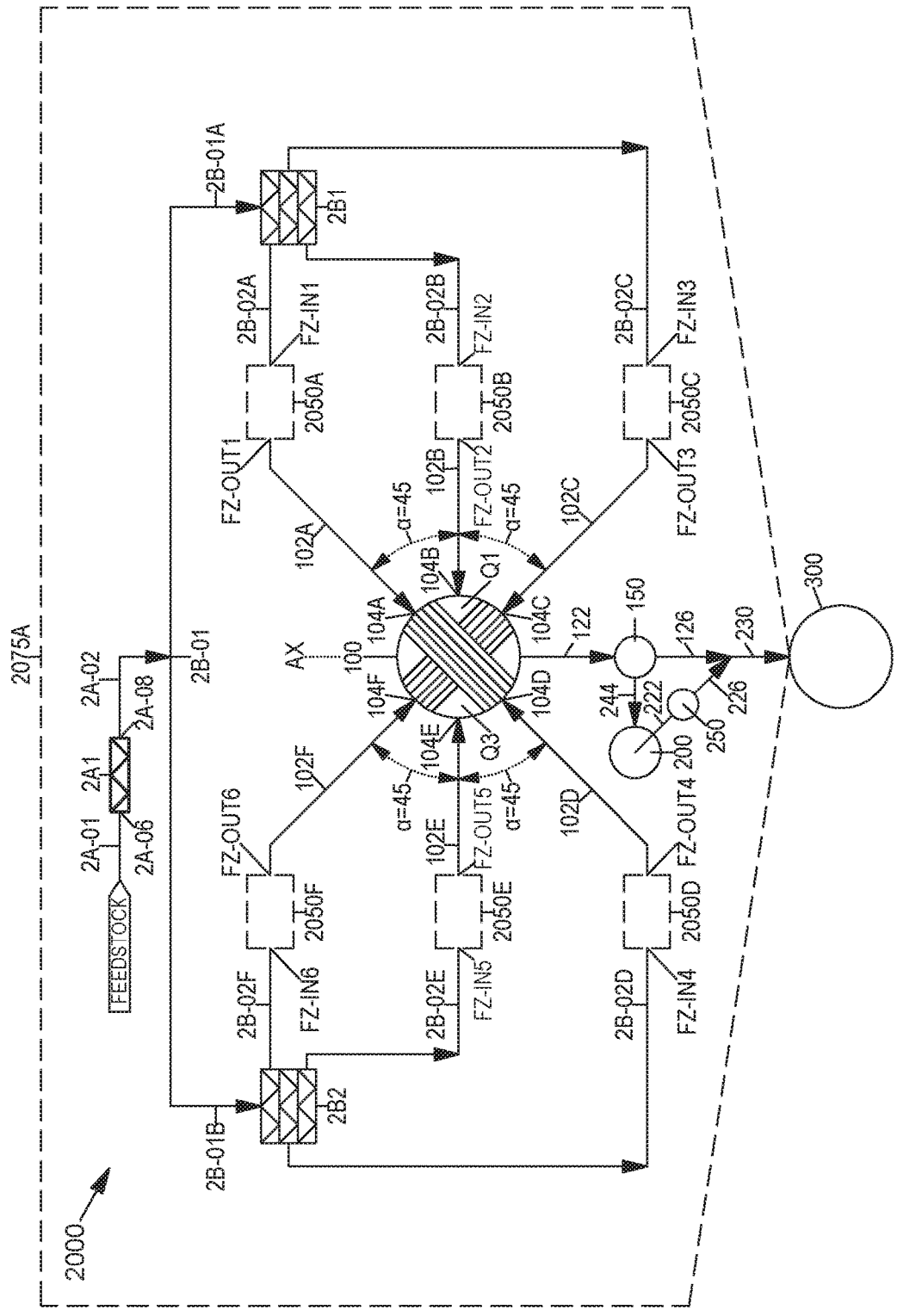
FIG. 14 shows a non-limiting embodiment of a feedstock delivery and product gas generation system (2075) including a bulk transfer system (2A1) connected to a first splitter (2B1) and a second splitter (2B2), where the first splitter (2B1) is in fluid communication with a first reactor (100) through a plurality of feed zone delivery system (2050A, 2050B, 2050C), and the second splitter (2B2) is in fluid communication with a first reactor (100) through a plurality of feed zone delivery systems (2050D, 2050E, 2050F), and further including a first solids separation device (150), second reactor (200), and second solids separation device (250) which are in fluid communicating with a third reactor (300).
Figure 33:
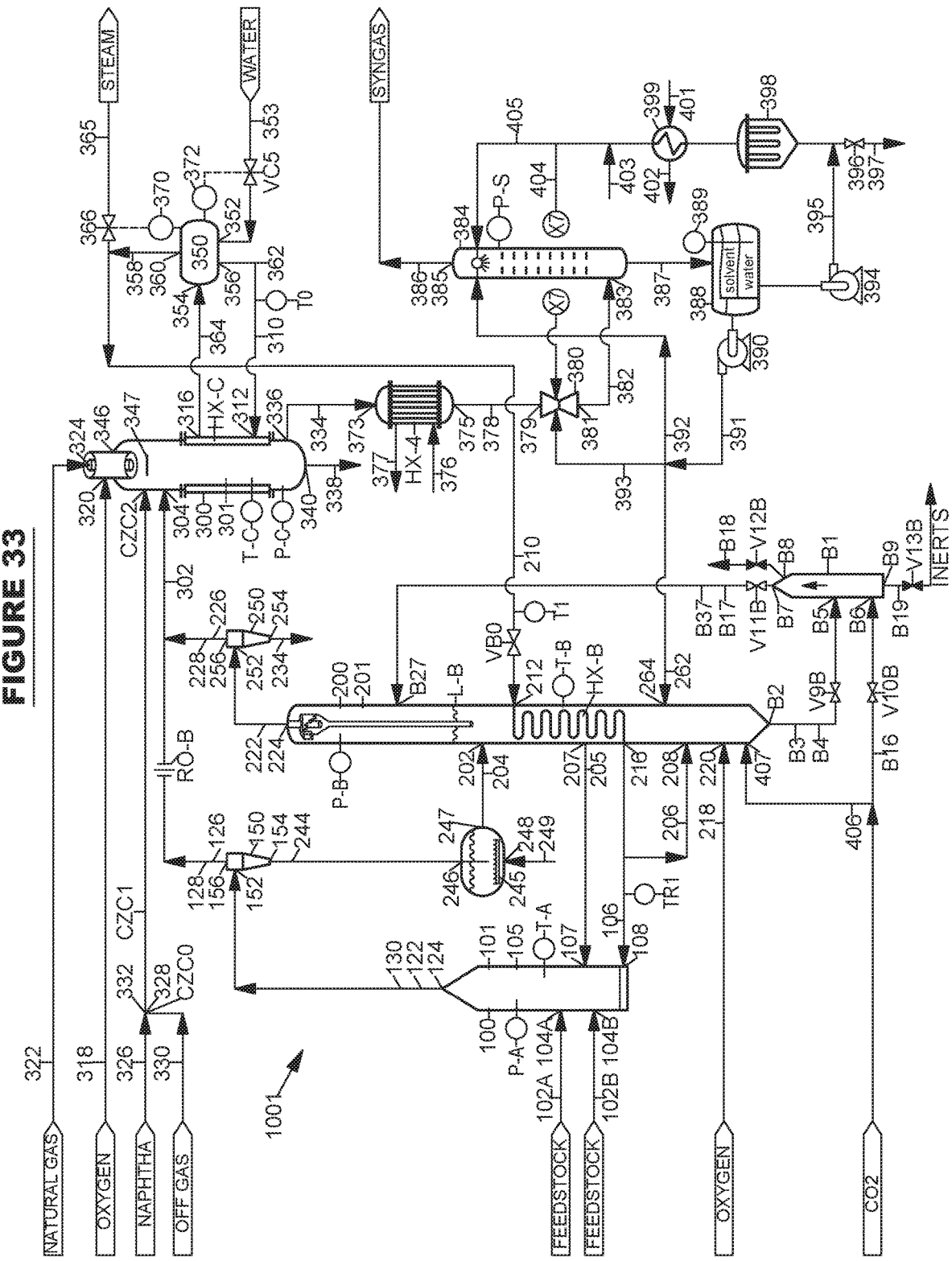

FIG. 33 is to be used in conjunction with FIG. 14 and depicts carbonaceous material processing system including a first splitter (2B1), a first feed zone delivery system (2050A), a second feed zone delivery system (2050B), first reactor (100), first solids separation device (150), dipleg (244), solids flow regulator (245), second reactor (200), particulate classification chamber (B1), second solids separation device (250), second reactor heat exchanger (HX-B), third reactor (300), third reactor heat exchanger (HX-C), steam drum (350), Primary Gas Clean Up Heat Exchanger (HX-4), venturi scrubber (380), scrubber (384), separator (388), separator (398), and a heat exchanger (399).

Figure 34:
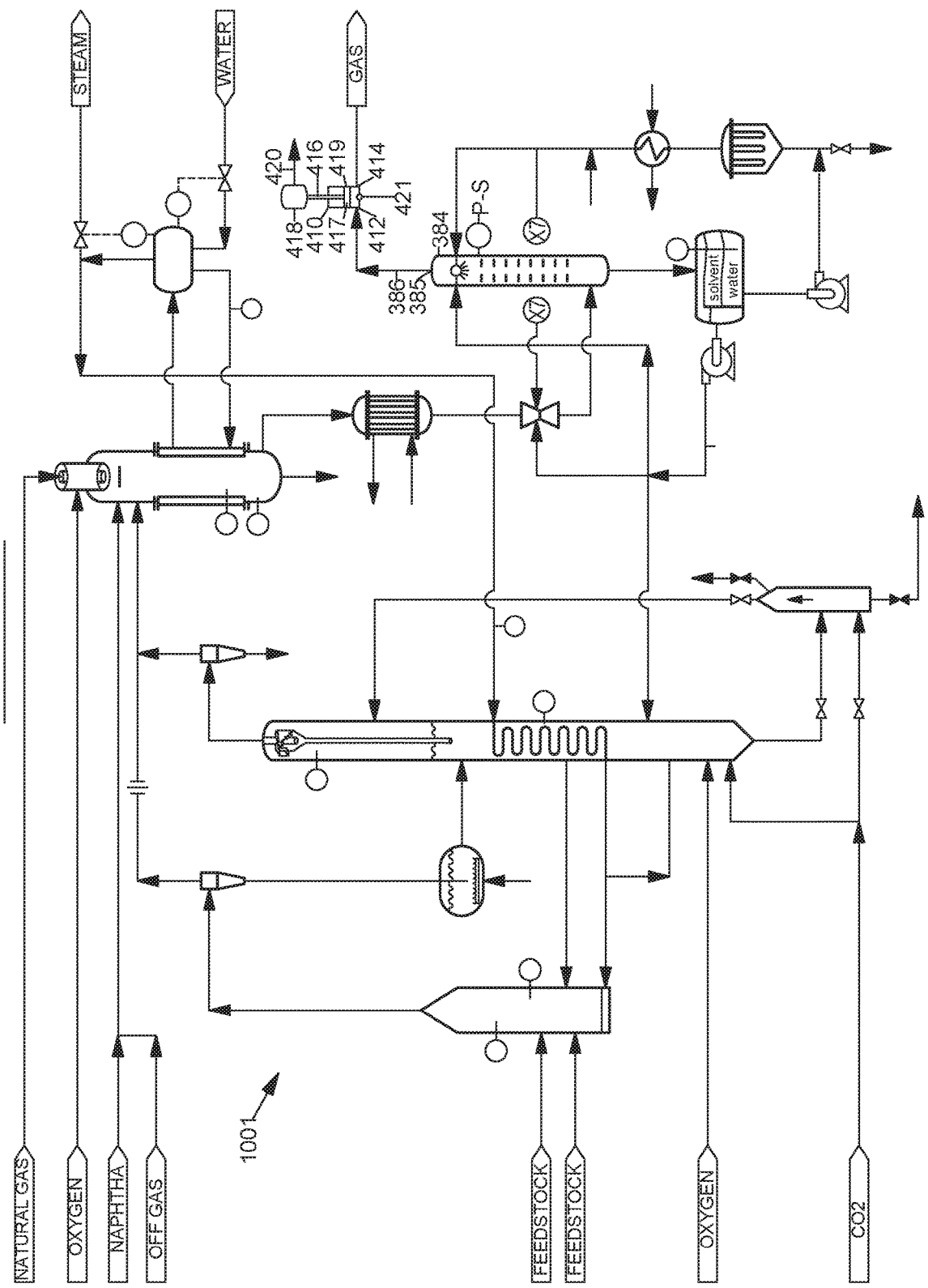

FIG. 34 refers to a variation of the system of FIG. 33 however further including an engine (410) connected to the scrubber product gas outlet conduit (386) connected to a shaft (416), and a generator (418) and configured for power output (420).

FIG. 35 discloses a pressure-volume diagram describing the idealized thermodynamic cycle of FIG. 34.

FIG. 36 presents Table 1: Nominal Design Parameters Case 1: Normal Throughput for a 500 Dry MSW Carbonaceous Material Ton Per Day Feedstock Delivery System.

FIG. 37 presents Table 2: Maximum Throughput for a 500 Dry MSW Carbonaceous Material Ton Per Day Feedstock Delivery System.

Figure 38:
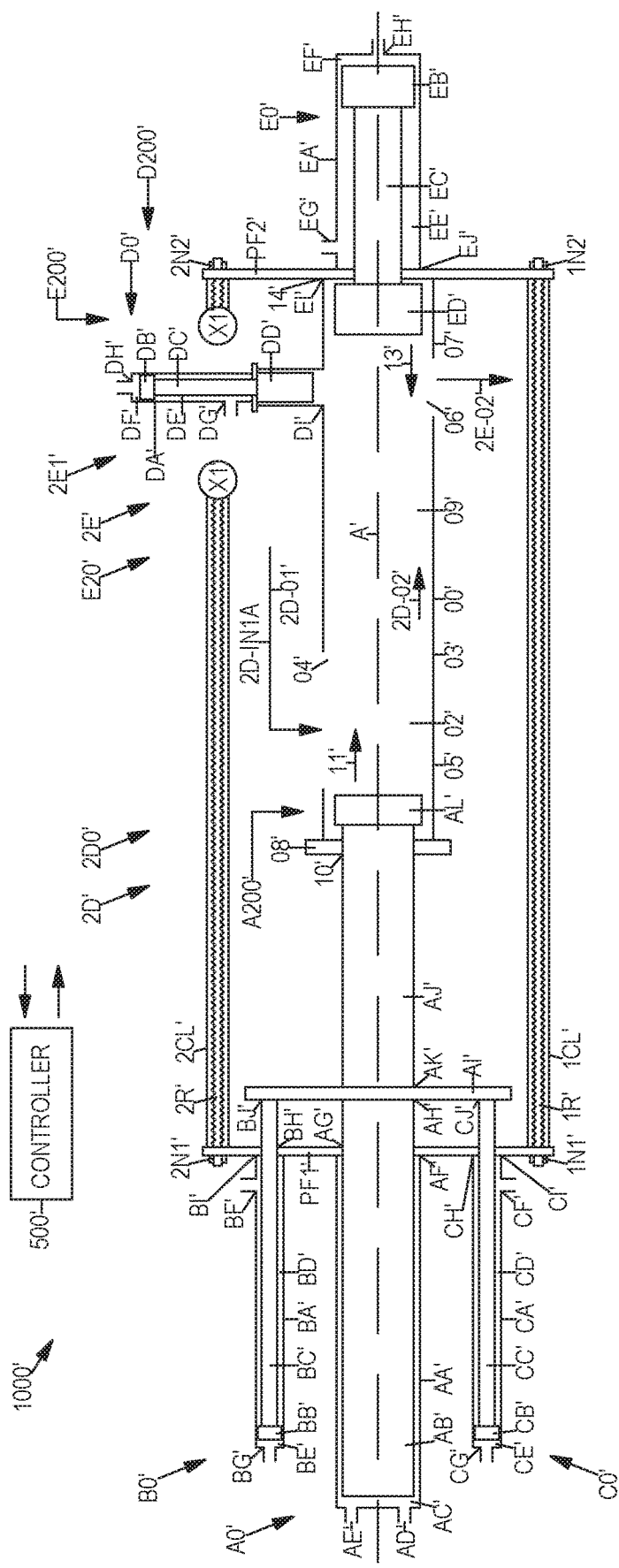

FIG. 38 displays one non-limiting embodiment of a densification system (1000') for compressing and ejecting compressed material.

Figure 39:
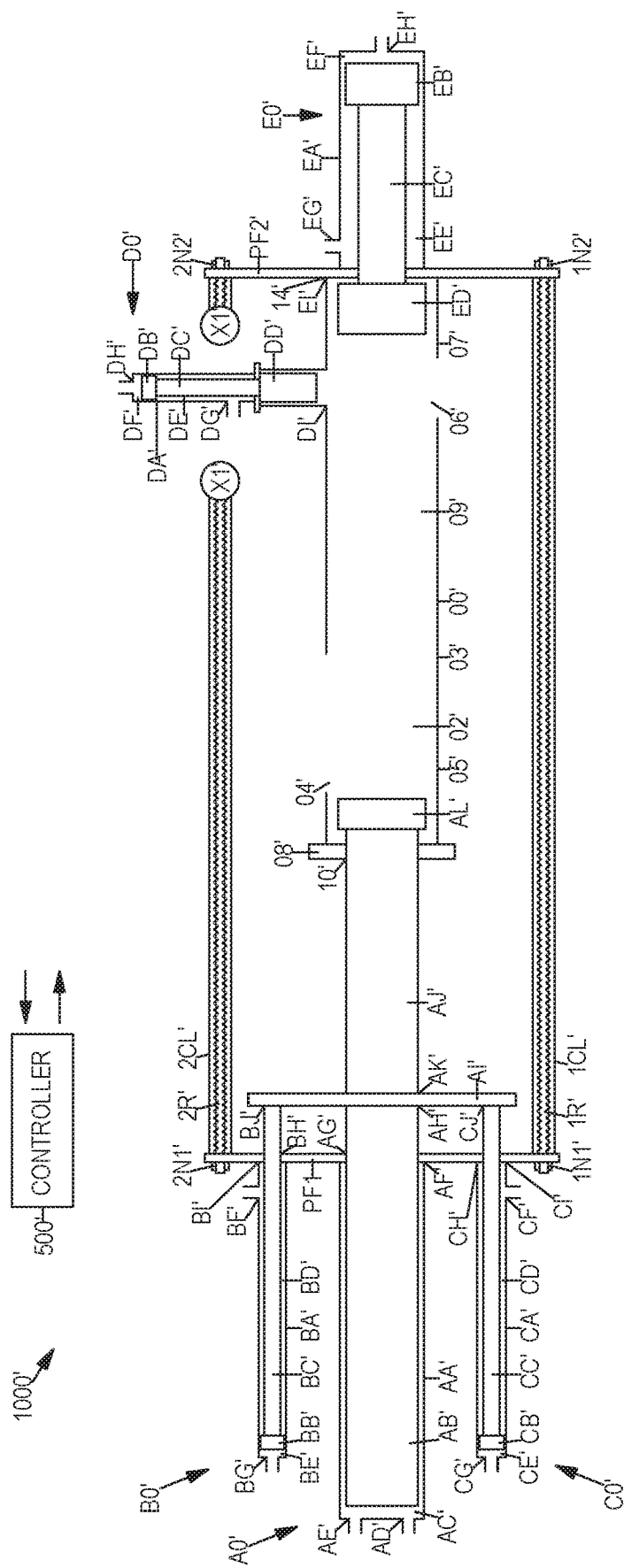

FIG. 39 displays one non-limiting embodiment of a densification system (1000') in an initial retracted state (state 0).

Figure 40:
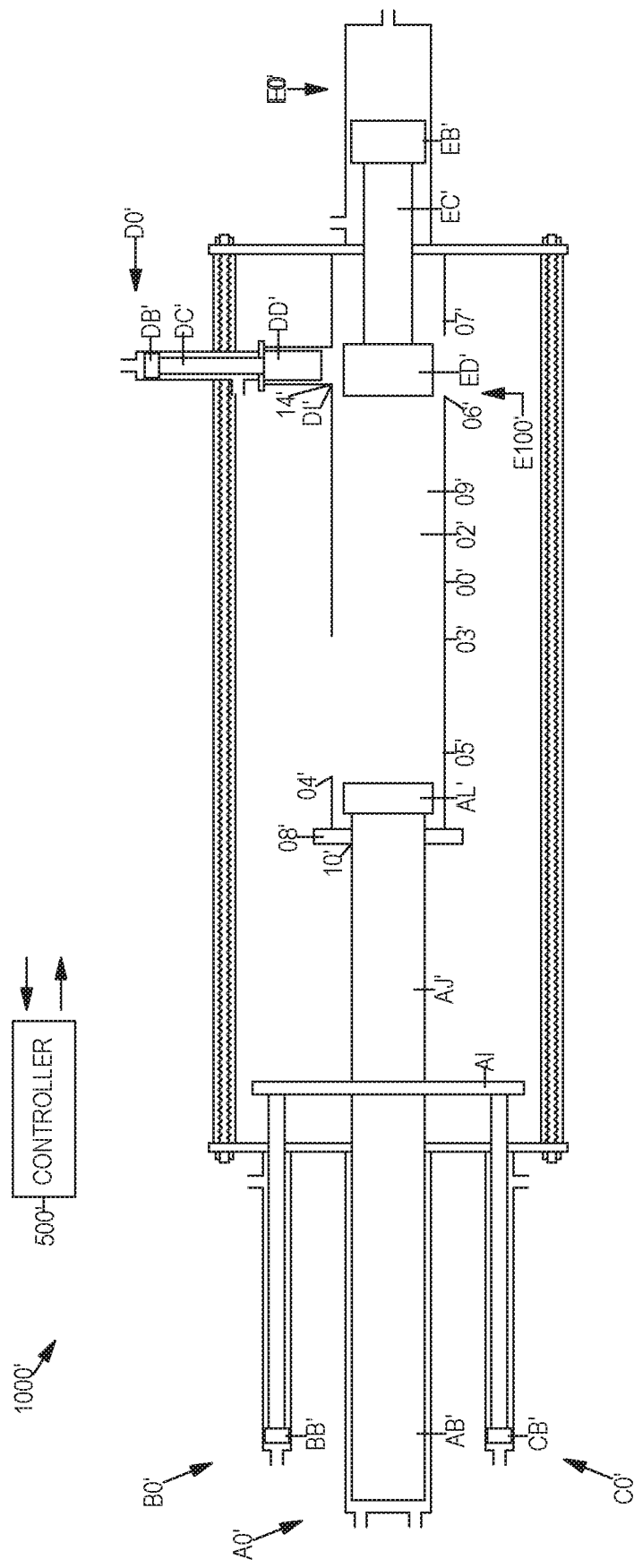

FIG. 40 displays one non-limiting embodiment of a densification system (1000') in a first mode of operation (state 1: loading state).

Figure 41:
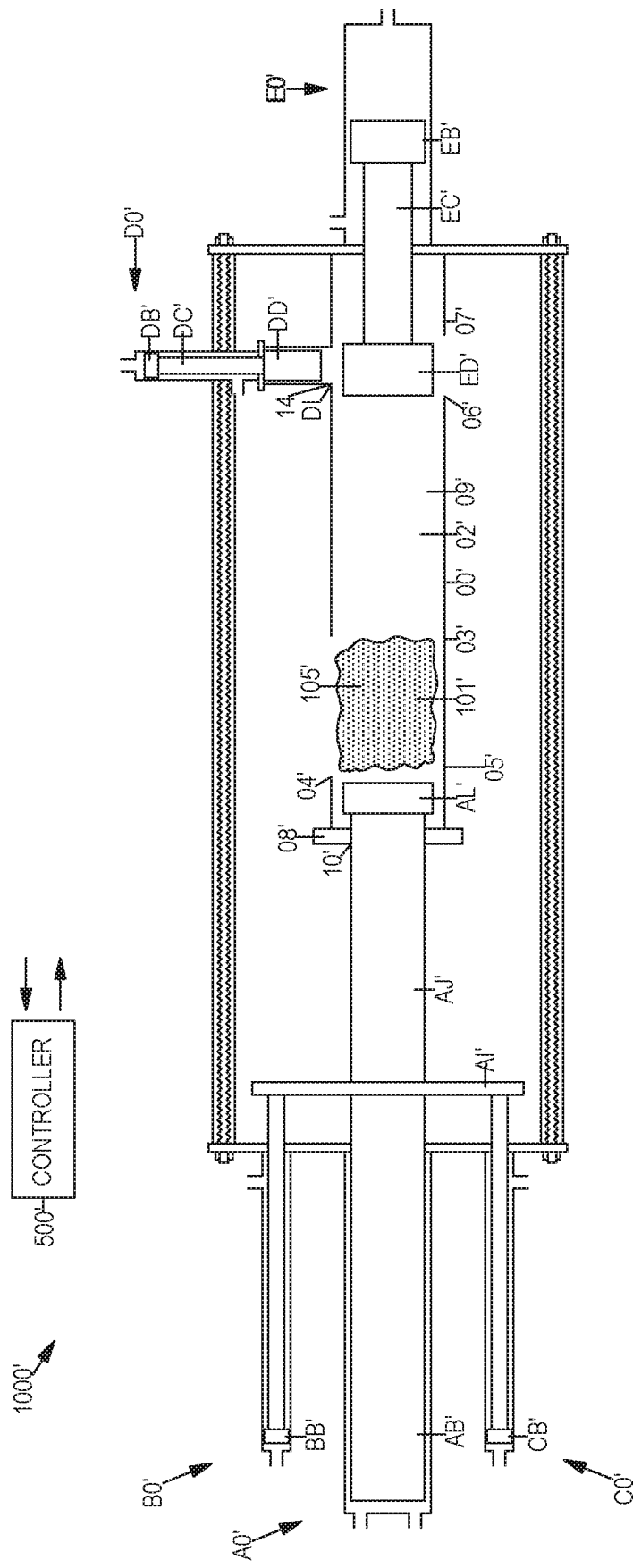

FIG. 41 elaborates upon the non-limiting embodiment of FIG. 40 wherein the densification system (1000') is displayed in a first mode of operation (state 1: loading state)

showing a first discrete charge of compressible material (105') entering the compression chamber (00') via the inlet (04').

Figure 42:
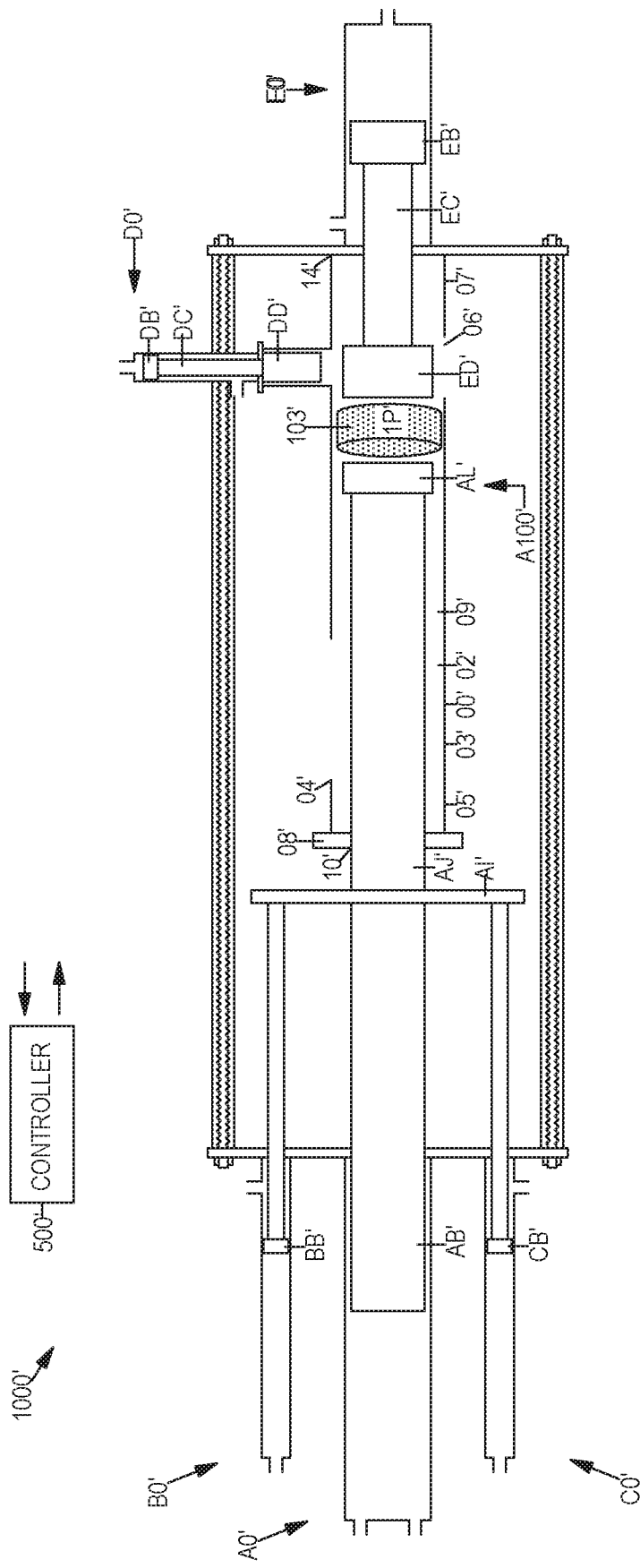

FIG. 42 elaborates upon the non-limiting embodiment of FIG. 41 and displays one non-limiting embodiment of a densification system (1000') in a second mode of operation (state 2: compression state).

Figure 43:
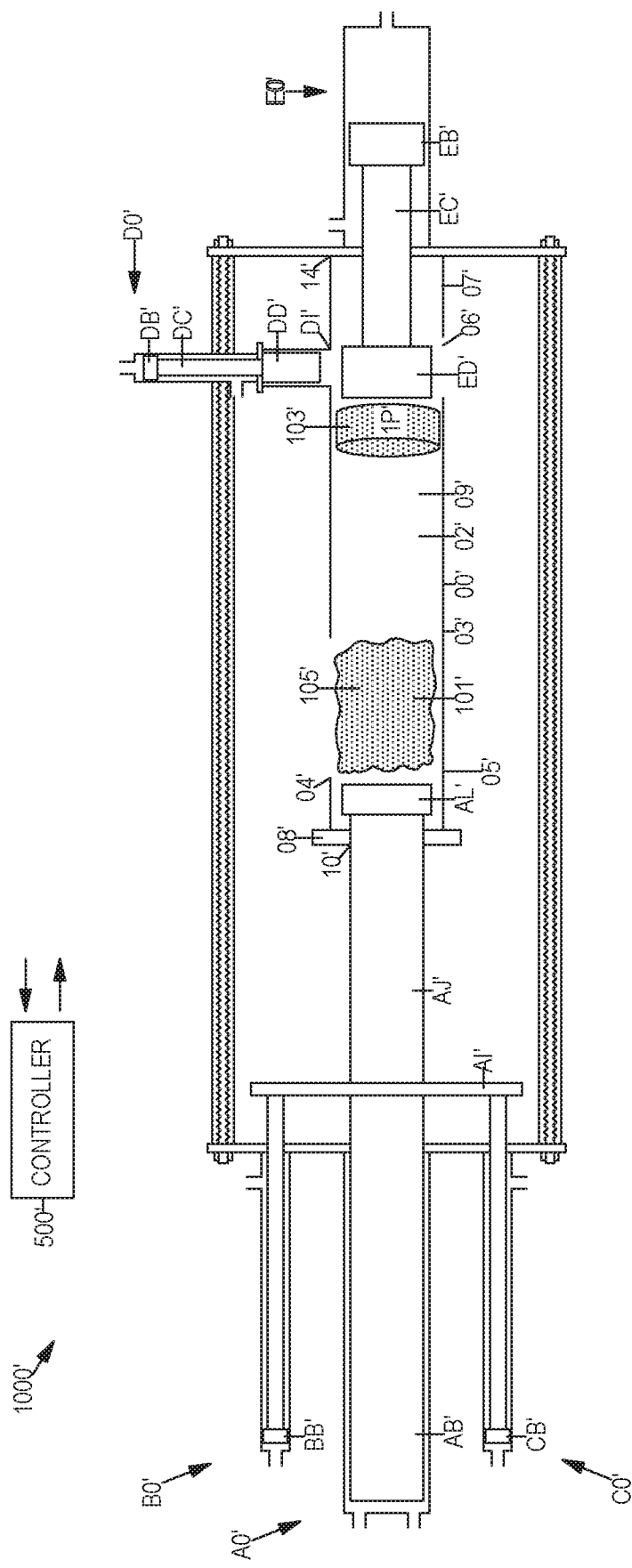

FIG. 43 elaborates upon the non-limiting embodiment of FIG. 42 showing the densification system (1000') again in a first mode of operation (state 1: loading state) and accepting a second discrete charge of compressible material (105') entering the compression chamber (00') via the inlet (04') while a first plug (1P') of compressed material remains in the compression region (09') of the compression chamber (00').

Figure 44:
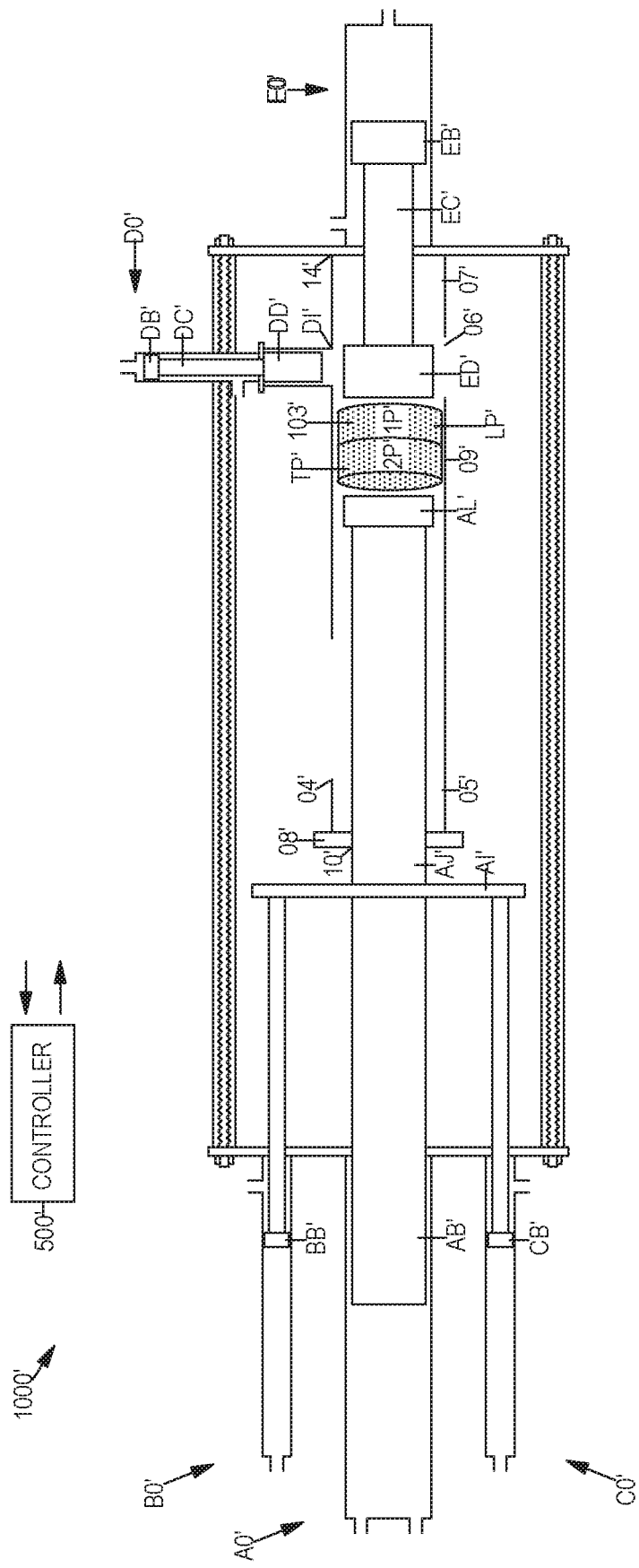

FIG. 44 elaborates upon the non-limiting embodiment of FIG. 43 showing the densification system (1000') again in a second mode of operation (state 2: compression state) but now compressing the second discrete charge of compressible material (105') into a second plug (2P') of compressed material.

Figure 45:
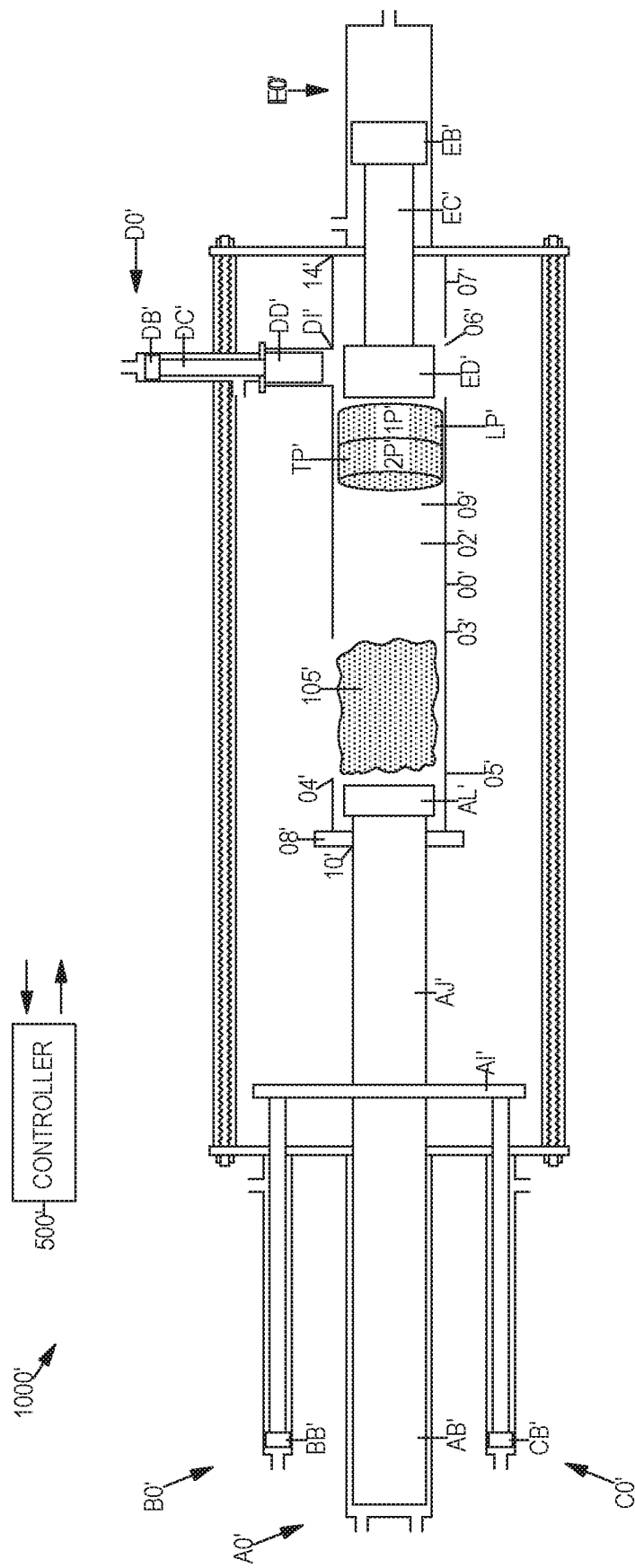

FIG. 45 elaborates upon the non-limiting embodiment of FIG. 44 showing the densification system (1000') again in a first mode of operation (state 1: loading state) and accepting a third discrete charge of compressible material (105') entering the compression chamber (00') via the inlet (04') while a first plug (1P') and second plug (2P') of compressed material remains in the compression region (09') of the compression chamber (00').

Figure 46:
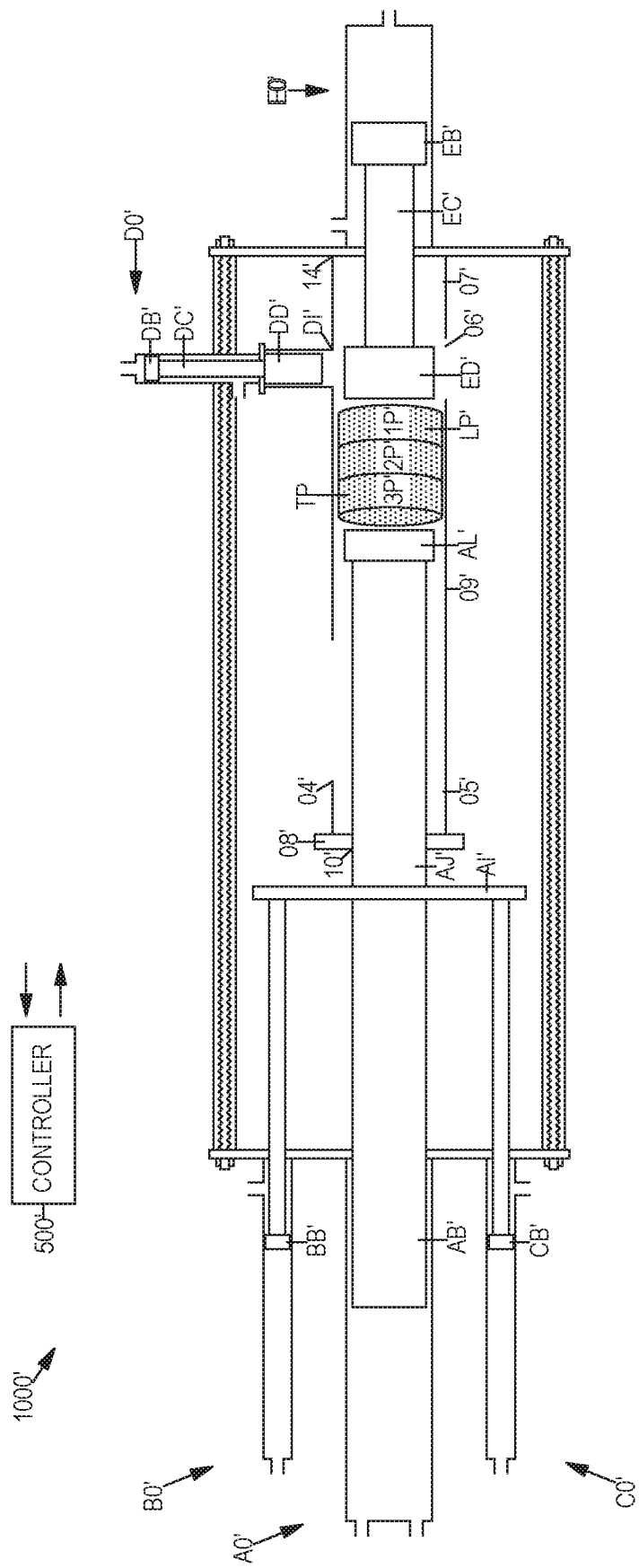

FIG. 46 elaborates upon the non-limiting embodiment of FIG. 45 showing the densification system (1000') again in a second mode of operation (state 2: compression state) but now compressing the third discrete charge of compressible material (105') into a third plug (3P') of compressed material.

Figure 47:
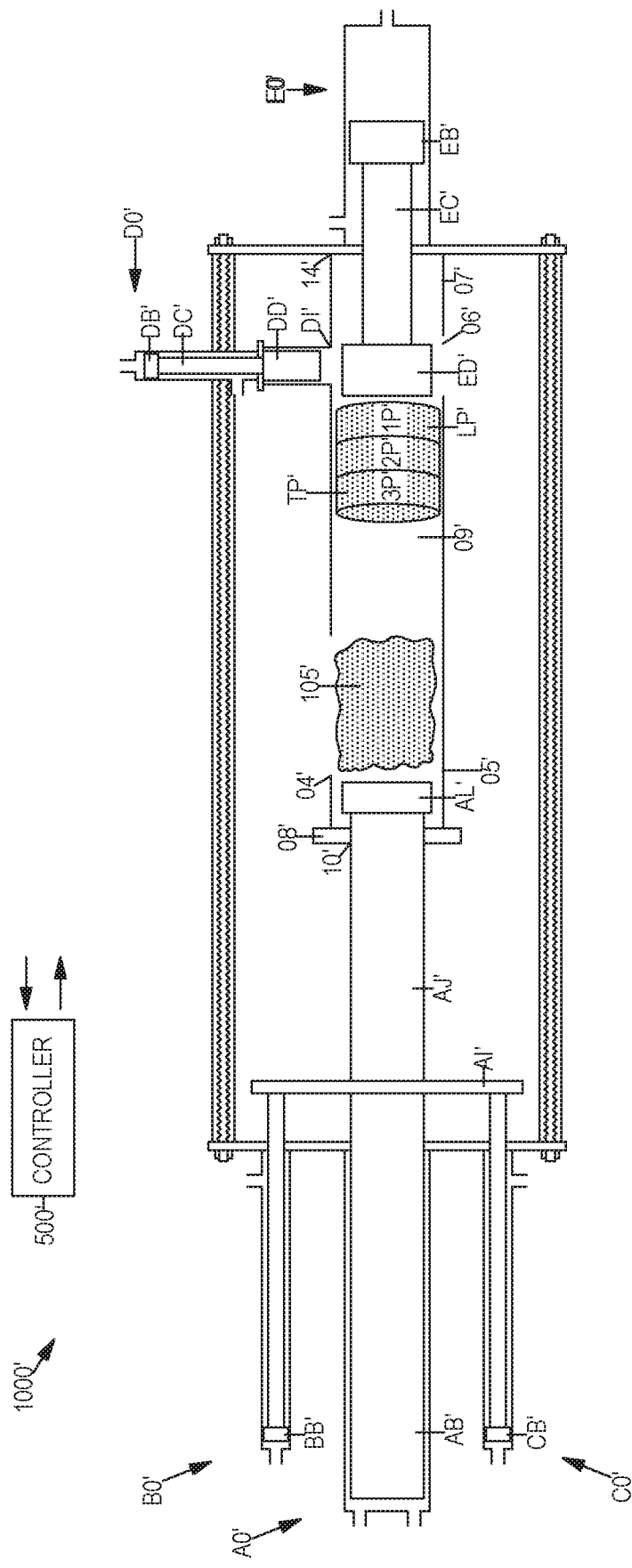

FIG. 47 elaborates upon the non-limiting embodiment of FIG. 46 showing the densification system (1000') again in a first mode of operation (state 1: loading state) and accepting a fourth discrete charge of compressible material (105') entering the compression chamber (00') via the inlet (04') while a first plug (1P'), second plug (2P'), and third plug (3P') of compressed material remains in the compression region (09') of the compression chamber (00').

Figure 48:
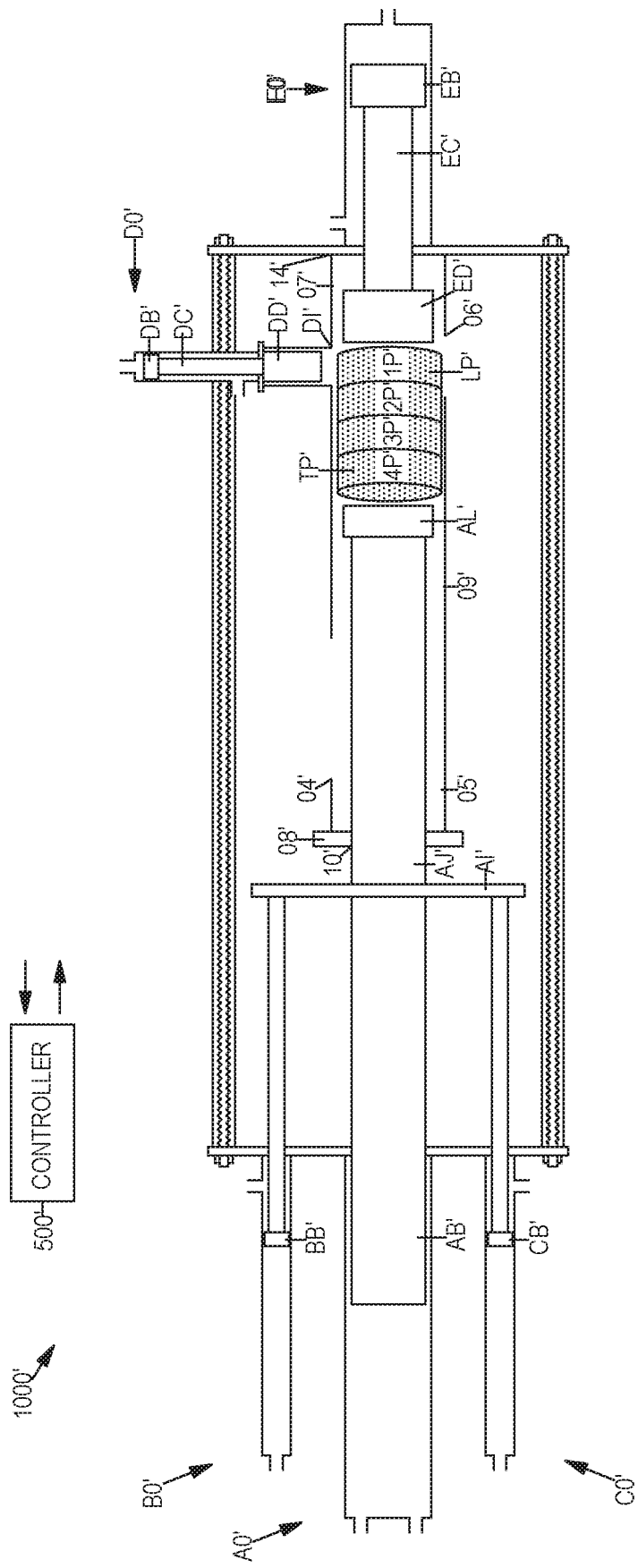

FIG. 48 elaborates upon the non-limiting embodiment of FIG. 47 and displays one non-limiting embodiment of a densification system (1000') in a third mode of operation (state 3: unlocked backstop state).

Figure 49:
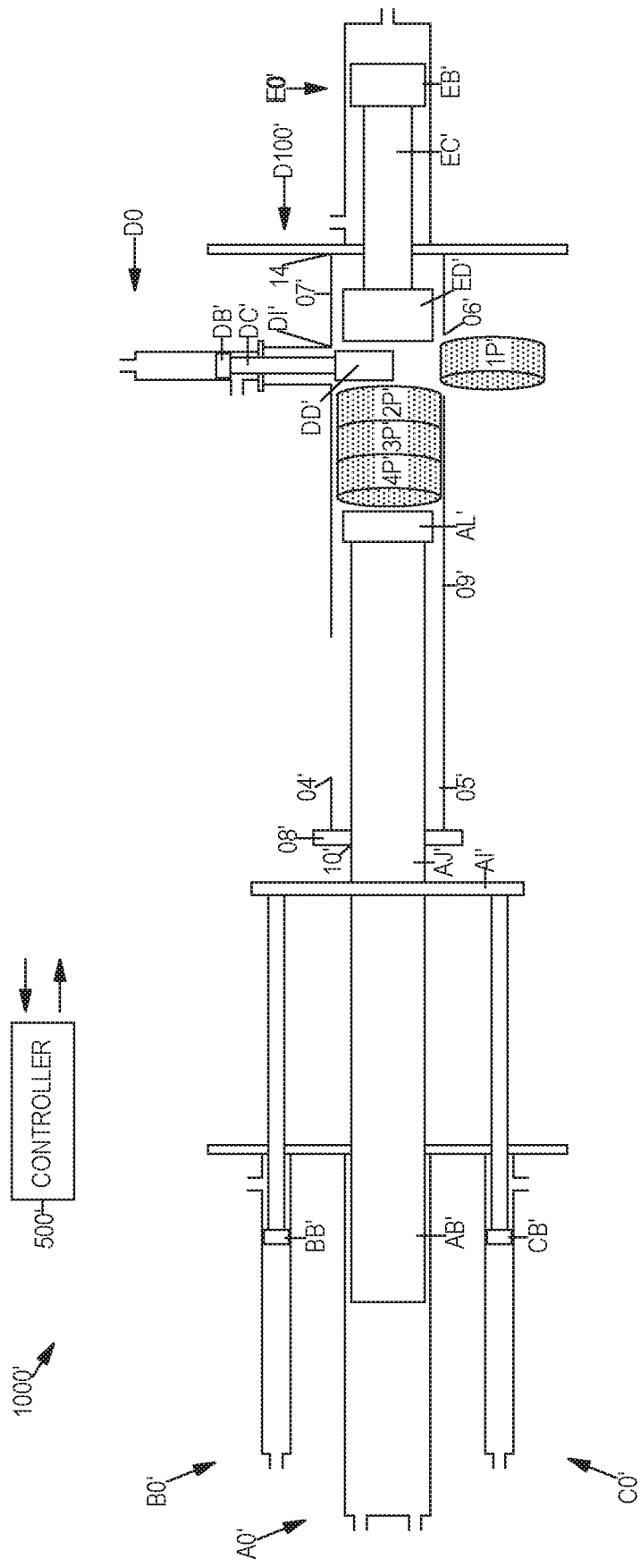

FIG. 49 elaborates upon the non-limiting embodiment of FIG. 48 and displays one non-limiting embodiment of a densification system (1000') in a fourth mode of operation (state 4: ejection state).

FIG. 50 elaborates upon the non-limiting embodiment of FIG. 49 and displays one non-limiting embodiment of a densification system (1000') again in a first mode of operation (state 1: loading state) and accepting a fifth discrete charge of compressible material (105') entering the compression chamber (00') via the inlet (04') while a second plug (2P'), and third plug (3P'), and fourth plug (4P') of compressed material remain in the compression region (09') of the compression chamber (00').

DETAILED DESCRIPTION

Notation and Nomenclature

Before the disclosed systems and processes are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

The idea of a control volume is an extremely general concept used widely in the study and practice of chemical engineering. Control volumes may be used in applications that analyze physical systems by utilization of the laws of conservation of mass and energy. They may be employed during the analysis of input and output data of an arbitrary space, or region, usually being a chemical process, or a portion of a chemical process. They may be used to define process streams entering a single piece of chemical equipment that performs a certain task, or they may be used to define process streams entering a collection of equipment, and assets which work together to perform a certain task.

With respect to the surrounding text, a control volume is meaningful in terms of defining the boundaries of a feedstock delivery or a particular product gas generation sequence step or a sequence step related to the overarching topography of an entire biorefinery superstructure system. The arrangements of equipment contained within each control volume are the preferred ways of accomplishing each sequence step. Furthermore, all preferred embodiments are non-limiting in that any number of combinations of unit operations, equipment and assets, including pumping, piping, and instrumentation, may be used as an alternate. However, it has been our realization that the preferred embodiments that make up each sequence step are those which work best to generate a product gas from a carbonaceous material using a feedstock delivery system integrated with at least one thermochemical reactor that cooperates to efficiently and substantially completely convert a carbonaceous material into product gas. In embodiments, successive upstream and downstream thermochemical reactors are implemented and integrated together with a feedstock delivery system and configured to share heat from successive endothermic and exothermic reactions. Nonetheless, any types of unit operations or processes may be used within any control volume shown as long as it accomplishes the goal of that particular sequence step.

As used herein the term "carbonaceous material" refers to a solid or liquid substance that contains carbon such as for instance, agricultural residues, agro-industrial residues, animal waste, biomass, cardboard, coal, coke, energy crops, farm slurries, fishery waste, food waste, fruit processing waste, lignite, municipal solid waste (MSW), paper, paper mill residues, paper mill sludge, paper mill spent liquors, plastics, refuse derived fuel (RDF), sewage sludge, tires, urban waste, wood products, wood wastes and a variety of others. All carbonaceous materials contain both "fixed carbon feedstock components" and "volatile feedstock components", such as for example woody biomass, MSW, or RDF.

As used herein the term "char" refers to a carbon-containing solid residue derived from a carbonaceous material and is comprised of the "fixed carbon feedstock components" of a carbonaceous material. Char also includes ash.

As used herein the term "char-carbon" refers to the mass fraction of carbon that is contained within the char transferred from the first reactor to the second reactor.

As used herein the term "char-ash" refers to the mass fraction of ash that is contained within the char transferred from the first reactor to the second reactor.

As used herein the term "fixed carbon feedstock components" refers to feedstock components present in a carbonaceous material other than volatile feedstock components, contaminants, ash or moisture. Fixed carbon feedstock components are usually solid combustible residue remaining after the removal of moisture and volatile feedstock components from a carbonaceous material.

As used herein the term "volatile feedstock components" refers to components within a carbonaceous material other than fixed carbon feedstock components, contaminants, ash or moisture.

As used herein the term "inert feedstock contaminants" or "inert contaminants" refers to Geldart Group D particles contained within a MSW and/or RDF carbonaceous material. Geldart Group D solids comprise whole units and/or fragments of one or more of the group consisting of allen wrenches, ball bearings, batteries, bolts, bottle caps, broaches, bushings, buttons, cable, cement, chains, clips, coins, computer hard drive shreds, door hinges, door knobs, drill bits, drill bushings, drywall anchors, electrical components, electrical plugs, eye bolts, fabric snaps, fasteners, fish hooks, flash drives, fuses, gears, glass, gravel, grommets, hose clamps, hose fittings, jewelry, key chains, key stock, lathe blades, light bulb bases, magnets, metal audio-visual components, metal brackets, metal shards, metal surgical supplies, mirror shreds, nails, needles, nuts, pins, pipe fittings, pushpins, razor blades, reamers, retaining rings, rivets, rocks, rods, router bits, saw blades, screws, sockets, springs, sprockets, staples, studs, syringes, USB connectors, washers, wire, wire connectors, and zippers.

Generally speaking, Geldart grouping is a function of bed material particle size and density and the pressure at which the fluidized bed operates. In the present context which is related to systems and/or methods for converting municipal solid waste (MSW) into a product gas using a fluidized bed, Geldart C Group solids range in size from between about 0 and 29.99 microns, Geldart A Group solids range in size from between about 30 microns to 99.99 microns, Geldart B Group solids range in size from between about 100 and 999.99 microns, and, Geldart D Group solids range in size greater than about 1,000 microns.

As used herein the term "product gas" refers to volatile reaction products, syngas, or flue gas discharged from a thermochemical reactor undergoing thermochemical processes including hydrous devolatilization, pyrolysis, steam reforming, partial oxidation, dry reforming, or combustion.

As used herein the term "syngas" refers to a mixture of carbon monoxide (CO), hydrogen (H2), and other vapors/gases, also including char, if any and usually produced when a carbonaceous material reacts with steam (H2O), carbon dioxide (CO2) and/or oxygen (O2). While steam is the reactant in steam reforming, CO2 is the reactant in dry reforming. Generally, for operation at a specified temperature, the kinetics of steam reforming is faster than that of dry reforming and so steam reforming tends to be favored and more prevalent. Syngas might also include aromatic hydrocarbons such as volatile organic compounds (VOC) and/or semi-volatile organic compounds (VOC).

As used herein the term "volatile organic compounds" or acronym "(VOC)" or "VOC" refer to aromatics including benzene, toluene, phenol, styrene, xylene, and cresol. It also refers to low molecular weight hydrocarbons like methane, ethane, ethylene, propane, propylene, etc.

As used herein the term "semi-volatile organic compounds" or acronym "(SVOC)" or "SVOC" refer to polyaromatics, such as indene, indane, naphthalene, methylnaphthalene, acenaphthylene, acenaphthalene, anthracene, phenanthrene, (methyl-) anthracenes/phenanthrenes, pyrene/fluoranthene, methylpyrenes/benzofluorenes, chrysene, benz[a]anthracene, methylchrysenes, methylbenz [a]anthracenes, perylene, benzo[a]pyrene, dibenz[a,kl]anthracene, and dibenz[a,h]anthracene.

As used herein the term "volatile reaction products" refers to vapor or gaseous organic species that were once present in a solid or liquid state as volatile feedstock components of a carbonaceous material wherein their conversion or vaporization to the vapor or gaseous state was promoted by the processes of either hydrous devolatilization and/or pyrolysis. Volatile reaction products may contain both, non-condensable species, and condensable species which are desirable for collection and refinement.

As used herein the term "oxygen-containing gas" refers to air, oxygen-enriched-air i.e. greater than 21 mole % O2, and substantially pure oxygen, i.e. greater than about 95 mole % oxygen (the remainder usually comprising N2 and rare gases). As used herein the term "oxygen-containing gas" refers to air, oxygen-enriched-air i.e. greater than 21 mole % O2, and substantially pure oxygen, i.e. greater than about 95 mole % oxygen (the remainder usually comprising N2 and rare gases). In embodiments, an air separation unit (ASU) is used to produce a source of "oxygen-containing gas" from air. In embodiments, a plurality of air separation unit (ASU) are used to produce a source of "oxygen-containing gas" from air.

In embodiments, the air separation unit (ASU) includes a fractional distillation unit. In embodiments, the air separation unit (ASU) includes a plurality of fractional distillation unit. In embodiments, the air separation unit (ASU) includes a cryogenic air separation unit. In embodiments, the air separation unit (ASU) includes a plurality of cryogenic air separation units. In embodiments, the air separation unit (ASU) includes a membrane or a plurality of membranes. In embodiments, the air separation unit (ASU) includes a pressure swing adsorption (PSA) unit. In embodiments, the air separation unit (ASU) includes a plurality of pressure swing adsorption (PSA) units. In embodiments, the air separation unit (ASU) includes a vacuum pressure swing adsorption (VPSA) unit. In embodiments, the air separation unit (ASU) includes a plurality of vacuum pressure swing adsorption (VPSA) units. In embodiments, the air separation unit (ASU) includes one or more selected from the group consisting of a fractional distillation unit, cryogenic air separation unit, a membrane, a pressure swing adsorption (PSA) unit, a vacuum pressure swing adsorption (VPSA) unit. In embodiments, the air separation unit (ASU) includes two or more selected from the group consisting of a fractional distillation unit, cryogenic air separation unit, a membrane, a pressure swing adsorption (PSA) unit, a vacuum pressure swing adsorption (VPSA) unit.

As used herein the term "flue gas" refers to a vapor or gaseous mixture containing varying amounts of nitrogen (N2), carbon dioxide (CO2), water (H2O), and oxygen (O2). Flue gas is generated from the thermochemical process of combustion.

As used herein the term "thermochemical process" refers to a broad classification including various processes that can convert a carbonaceous material into product gas. Among the numerous thermochemical processes or systems that can be considered for the conversion of a carbonaceous material, the present disclosure contemplates: hydrous devolatilization, pyrolysis, steam reforming, partial oxidation, dry reforming, and/or combustion. Thermochemical processes may be either endothermic or exothermic in nature depending upon the specific set of processing conditions employed. Stoichiometry and composition of the reactants, type of reactants, reactor temperature and pressure, heating rate of the carbonaceous material, residence time, carbonaceous material properties, and catalyst or bed additives all dictate what sub classification of thermochemical processing the system exhibits.

As used herein the term "thermochemical reactor" refers to a reactor that accepts a carbonaceous material, char, VOC, SVOC, or product gas and converts it into one or more product gases.

Hydrous Devolatilization Reaction:

As used herein the term "hydrous devolatilization" refers to an endothermic thermochemical process wherein volatile feedstock components of a carbonaceous material are converted primarily into volatile reaction products in a steam environment. Typically, this sub classification of a thermochemical process involves the use of steam as a reactant and involves temperatures ranging from 320° C. and 569.99° C. (608° F. and 1,057.98° F.), depending upon the carbonaceous material chemistry. Hydrous devolatilization permits release and thermochemical reaction of volatile feedstock components leaving the fixed carbon feedstock components mostly unreacted as dictated by kinetics.

Carbonaceous material+steam+heat→Volatile Reaction Products+Fixed Carbon Feedstock Components+steam Pyrolysis Reaction:

As used herein the term "pyrolysis" or "devolatilization" is the endothermic thermal degradation reaction that organic material goes through in its conversion into a more reactive liquid/vapor/gas state.

Carbonaceous material+heat→VOC+SVOC+H2O+ CO+CO2+H2+CH4+Other Organic Gases (CxHyOz)+Fixed Carbon Feedstock Components Steam Reforming Reactions:

As used herein the term "steam reforming" refers to a thermochemical process where steam reacts with a carbonaceous material to yield syngas. The main reaction is endothermic (consumes heat) wherein the operating temperature range is between 570° C. and 900° C. (1,058° F. and 1,652° F.), depending upon the feedstock chemistry.

H2O+C+Heat→H2+CO

Water Gas Shift Reaction:

As used herein the term "water-gas shift" refers to a thermochemical process comprising a specific chemical reaction that occurs simultaneously with the steam reforming reaction to yield hydrogen and carbon dioxide. The main reaction is exothermic (releases heat) wherein the operating temperature range is between 570° C. and 900° C. (1,058° F. and 1,652° F.), depending upon the feedstock chemistry.

H2O+CO→H2+CO2+Heat

Dry Reforming Reaction:

As used herein the term "dry reforming" refers to a thermochemical process comprising a specific chemical reaction where carbon dioxide is used to convert a carbonaceous material into carbon monoxide. The reaction is endothermic (consumes heat) wherein the operating temperature range is between 600° C. and 1,000° C. (1,112° F. and 1,832° F.), depending upon the feedstock chemistry.

CO2+C+Heat→2CO

Partial Oxidation Reaction:

As used herein the term "partial oxidation" refers to a thermochemical process wherein substoichiometric oxidation of a carbonaceous material takes place to exothermically produce carbon monoxide, carbon dioxide and/or water vapor. The reactions are exothermic (release heat) wherein the operating temperature range is between 500° C. and 1,400° C. (932° F. and 2,552° F.), depending upon the feedstock chemistry. Oxygen reacts exothermically (releases heat): 1) with the carbonaceous material to produce carbon monoxide and carbon dioxide; 2) with hydrogen to produce water vapor; and 3) with carbon monoxide to produce carbon dioxide.

4C+3O2→CO+CO2+Heat

C+½O2→CO+Heat

H2+½O2→H2O+Heat

CO+½O2→CO2+Heat

Combustion Reaction:

As used herein the term "combustion" refers to an exothermic (releases heat) thermochemical process wherein at least the stoichiometric oxidation of a carbonaceous material takes place to generate flue gas.

C+O2→CO2+Heat

CH4+O2→CO2+2H2O+Heat

Some of these reactions are fast and tend to approach chemical equilibrium while others are slow and remain far from reaching equilibrium. The composition of the product gas will depend upon both quantitative and qualitative factors. Some are unit specific i.e. fluidized bed size/scale specific and others are feedstock specific. The quantitative parameters are: carbonaceous material properties, carbonaceous material injection flux, reactor operating temperature, pressure, gas and solids residence times, carbonaceous material heating rate, fluidization medium and fluidization flux; the qualitative factors are: degree of bed mixing and gas/solid contact, and uniformity of fluidization and carbonaceous material injection.

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

Figure 1:
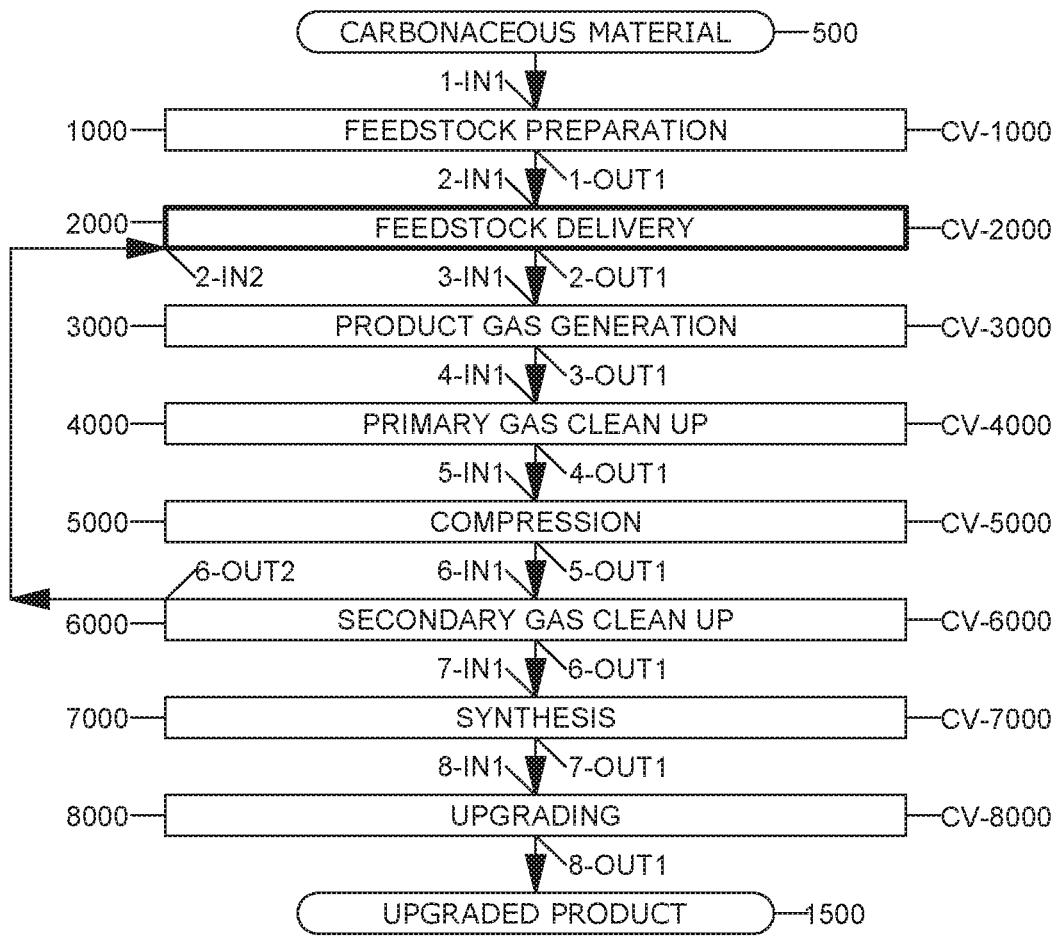
FIG. 1 shows a simplistic block flow control volume diagram of one embodiment of a Biorefinery Superstructure System (BSS).

FIG. 1:

FIG. 1 shows a simplistic block flow control volume diagram of one embodiment of a Biorefinery Superstructure System (BSS). In embodiments, the Biorefinery Superstructure System (BSS) is a liquid fuel production system.

The Biorefinery Superstructure System (BSS) of FIG. 1 is comprised of a: Feedstock Preparation System (1000) contained within a Feedstock Preparation Control Volume (CV-1000); a Feedstock Delivery System (2000) contained within a Feedstock Delivery Control Volume (CV-2000); a Product Gas Generation System (3000) contained within a Product Gas Generation Control Volume (CV-3000); a Primary Gas Clean-Up System (4000) contained within a Primary Gas Clean-Up Control Volume (CV-4000); a Compression System (5000) contained within a Compression Control Volume (CV-5000); a Secondary Gas Clean-Up System (6000) contained within a Secondary Gas Clean-Up Control Volume (CV-6000); a Synthesis System (7000) contained within a Synthesis Control Volume (CV-7000); and, an Upgrading System (8000) contained within a Upgrading Control Volume (CV-8000).

The Feedstock Preparation System (1000) is configured to accept a carbonaceous material (500) via a carbonaceous material input (1-IN1) and discharge a carbonaceous material output (1-OUT1). Some typical sequence steps or systems that might be utilized in the Feedstock Preparation System (1000) include, Large Objects Removal, Recyclables Removal, Ferrous Metal Removal, Size Reduction, Water Removal, Non-Ferrous Metal Removal, Polyvinyl Chloride Removal, Glass Removal, Size Reduction, and Pathogen Removal.

The Feedstock Delivery System (2000) is configured to accept carbonaceous material via a feedstock input (2-IN1) from the output (1-OUT1) of the Feedstock Preparation System (1000) to realize a mixture of carbonaceous and gas that is transferred via a mixture output (2-OUT1). The Feedstock Delivery System (2000) is also configured to accept feedstock via a feedstock gas input (2-IN2) from the carbon dioxide output (6-OUT2) of the Secondary Gas Clean-Up System (6000) to realize mixture of carbonaceous and gas that is transferred via a mixture output (2-OUT1).

The Product Gas Generation System (3000) is configured to accept a carbonaceous material and gas input (3-IN1) from the mixture output (2-OUT1) of the Feedstock Delivery System (2000) and react the carbonaceous material through at least one thermochemical process to realize a product gas output (3-OUT1).

The Primary Gas Clean-Up System (4000) is configured to accept a product gas via the primary gas clean-up input (4-IN1) from the output (3-OUT1) of the Product Gas Generation System (3000). The Primary Gas Clean-Up System (4000) may also be configured to generate electricity from a portion of the product gas through any conventional well-known system such as a gas turbine, combined cycle, and/or steam turbine. The Primary Gas Clean-Up System (4000) is configured to reduce the temperature, remove solids, SVOC, VOC, and water from the product gas transported through the primary gas clean-up input (4-IN1) to in turn discharge a product gas via a primary gas clean-up output (4-OUT1).

The Compression System (5000) accepts the product gas from the primary gas clean-up output (4-OUT1) of the Primary Gas Clean-Up System (4000) as a compression system input (5-IN1). The Compression System (5000) is configured to accept a product gas via the compression system input (5-IN1) and increase its pressure to form a product gas discharged via the compression system output (5-OUT1) at a greater pressure than the product gas transferred from the compression system input (5-IN1).

The Secondary Gas Clean-Up System (6000) accepts the product gas from the compression system output (5-OUT1) from the Compression System (5000) as a carbon dioxide laden product gas input (6-IN1). The Secondary Gas Clean-Up System (6000) is configured to accept a carbon dioxide laden product gas via a secondary gas clean-up input (6-IN1) and remove carbon dioxide therefrom to generate both a carbon dioxide transferred from the carbon dioxide output (6-OUT2) and a carbon dioxide depleted product gas transferred via the secondary gas clean-up system output (6-OUT1). The Secondary Gas Clean-Up System (6000) has a carbon dioxide laden product gas transferred via the secondary gas clean-up input (6-IN1) and a secondary gas clean-up system output (6-OUT1). The carbon dioxide depleted product gas transferred through the secondary gas clean-up system output (6-OUT1) has a lesser amount of carbon dioxide relative to the carbon dioxide laden product gas transferred through the secondary gas clean-up input (6-IN1). Membrane based carbon dioxide removal systems and processes are preferred to remove carbon dioxide from product gas, however other alternate systems and methods may be utilized to remove carbon dioxide, not limited to adsorption or absorption based carbon dioxide removal systems and processes.

The carbon dioxide depleted product gas transferred through the secondary gas clean-up system output (6-OUT1) is routed to the downstream Synthesis System (7000) via the synthesis system input (7-IN1). The Synthesis System (7000) is configured to accept the product gas transferred through the secondary gas clean-up system output (6-OUT1) from the Secondary Gas Clean-Up System (6000) via the synthesis system input (7-IN1) and catalytically synthesize a synthesis product that is discharged via a synthesis system output (7-OUT1). In embodiments, the synthesis system contains a catalyst and can produce liquid fuels such as mixed alcohols (e.g., a mixture of both ethanol and methanol), dimethyl ether, Fischer-Tropsch products, or the like.

In embodiments, the synthesis system includes a bioreactor containing microorganisms. The microorganisms produce a liquid fuel (e.g., ethanol, 1-butanol, 2-butanol) and/or chemicals within the bioreactor.

In embodiments, the liquid fuel and/or a chemical produced in the bioreactor is then distilled. In embodiments, the liquid fuel and/or a chemical produced in the bioreactor is then removed using a membrane. In embodiments, the liquid fuel and/or a chemical produced in the bioreactor is then dehydrated using pressure swing adsorption. In embodiments, the liquid fuel and/or a chemical produced in the bioreactor is then dehydrated using an adsorbent. In embodiments, the liquid fuel and/or a chemical produced in the bioreactor is then dehydrated using 3 angstrom molecular sieves.

In embodiments, the chemical produced in the bioreactor includes one or more selected from the group consisting of: 3-hydroxypropionate; mevalonate; mevalonic acid; isoprene; aromatics; benzoate (p-hydroxyl, 2-amino, dihydroxy); salicylate; 1-propanol; 1,2-propanediol; (R)-1,2-propanediol; (S)-1,2-propanediol; mixed isomers of 1,2-propanediol; acetoin; methyl ethyl ketone; branched-chain amino acids; valine, leucine, isoleucine; succinate; lactate; 2,3-butanediol; (R,R)-2,3-butanediol; meso-2,3-butanediol; mixed isomers of 2,3-butanediol; citramalate; 1,3-butanediol; (R)-1,3-butanediol; (S)-1,3-butanediol; mixed isomers of 1,3-butanediol; 3-hydroxybutyrate; (R)-3-hydroxybutyrate; (S)-3-hydroxybutyrate; mixed isomers of 3-hydroxybutyrate; butyrate; acetone; isopropanol; acetate; 1,3-butadiene; biopolymers; isobutene; long chain alcohols.

In embodiments, when ethanol is produced in the bioreactor, it is then distilled. In embodiments, the ethanol produced in the bioreactor is then removed using a membrane. In embodiments, the ethanol produced in the bioreactor is then dehydrated using pressure swing adsorption. In embodiments, the ethanol produced in the bioreactor is then dehydrated using an adsorbent. In embodiments, the ethanol produced in the bioreactor is then dehydrated using 3 angstrom molecular sieves.

In embodiments, the bioreactor includes one or more type of bioreactors selected from the group consisting of a continuous stirred tank bioreactor, a bubble column bioreactor, a microbubble reactor, an airlift bioreactor, a fluidized bed bioreactor, a packed bed bioreactor, a photo-bioreactor, and combinations thereof. In embodiments, the microorganisms used within the bioreactor include genetically modified organisms. In embodiments, the microorganisms used within the bioreactor do not include genetically modified organisms. In embodiments, the microorganisms used within the bioreactor include gas fermenting organisms. In embodiments, the microorganisms used within the bioreactor undergo anaerobic respiration. In embodiments, the microorganisms used within the bioreactor undergo fermentation. In embodiments, the microorganisms used within the bioreactor include anaerobic bacteria. In embodiments, the bioreactor includes a liquid nutrient medium used for culturing the microorganisms and the ethanol is produced within the bioreactor by the microorganisms which secrete ethanol which accumulates within the liquid nutrient medium.

A synthesis product transferred via the synthesis system output (7-OUT1) is discharged from the Synthesis System (7000) and is routed to the Upgrading System (8000) where it is accepted as a synthesis product input (8-IN1). The Upgrading System (8000) is configured to generate an upgraded product (1500) including upgraded liquid fuels such as jet fuel, gasoline, diesel, alcohols such as ethanol, and the like, and other useful chemical compounds, discharged via an upgraded product output (8-OUT1).

Figure 2:
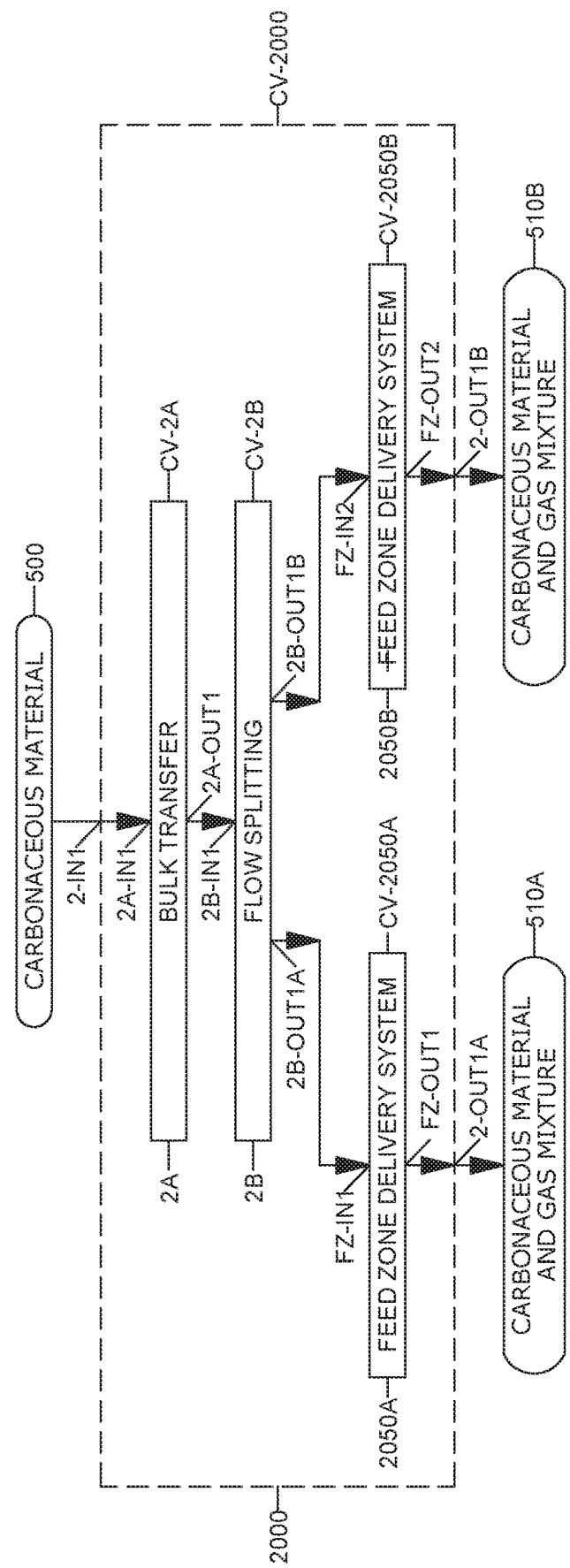
FIG. 2 shows a simplistic block flow control volume diagram of one embodiment of a Feedstock Delivery System (2000) including the non-limiting subsystems or sequence steps of Bulk Transfer (2A), Flow Splitting (2B), and a plurality of feed zone delivery systems (2050A, 2050B).

FIG. 2:

FIG. 2 shows a simplistic block flow control volume diagram of one embodiment of a Feedstock Delivery System (2000) including the non-limiting subsystems or sequence steps of Bulk Transfer (2A), Flow Splitting (2B), and a plurality of feed zone delivery systems (2050A, 2050B).

The Feedstock Delivery System (2000) is configured to accept carbonaceous material via a feedstock input (2-IN1) and output a plurality of streams of carbonaceous material and gas mixture (510A, 510B) for delivery to a downstream Product Gas Generation System (3000) (not shown).

For the Feedstock Delivery System (2000) to be able to realize a plurality of carbonaceous material and gas mixtures (510A, 510B) suitable to transfer to a downstream Product Gas Generation System (3000) (not shown), a variety of combinations and permutations of feed zone delivery system (2050) subsystems or sequence steps may be undertaken.

The Feedstock Delivery System (2000) of FIG. 2 is contained within a Feedstock Delivery Control Volume (CV-2000) and is comprised of several subsystems, including: a Bulk Transfer (2A) subsystem contained within a Bulk Transfer Control Volume (CV-2A); a Flow Splitting (2B) subsystem contained within a Flow Splitting Control Volume (CV-2B); and a plurality of feed zone delivery systems (2050A, 2050B) contained within a plurality of feed zone delivery system control volumes (CV-2050A, CV-2050B).

The Feedstock Delivery System (2000) is configured to accept carbonaceous material via a feedstock input (2-IN1) from the output (1-OUT1) (not shown) of the Feedstock Preparation System (1000) (not shown) to realize a plurality of mixtures of carbonaceous and gas that are transferred via mixture outputs (2-OUT1A, 2OUT1B).

The Bulk Transfer (2A) subsystem is configured to accept carbonaceous material via an input (2A-IN1) as a feedstock input (2-IN1) to the Feedstock Delivery System (2000) and discharge a carbonaceous material output (2A-OUT1).

The Flow Splitting (2B) subsystem is configured to accept a carbonaceous material input (2B-IN1) and discharge carbonaceous material via a plurality of outputs (2B-OUT1A, 2B-OUT1B).

A plurality of feed zone delivery systems (2050A, 2050B) are configured to accept carbonaceous material as feed zone delivery system inputs (FZ-IN1, FZ-IN2) from said plurality of Flow Splitting (2B) outputs (2B-OUT1A, 2B-OUT1B) and in turn each discharge a first feed zone delivery system output (FZ-OUT1) and a second feed zone delivery system output (FZ-OUT2).

FIG. 2 shows a first feed zone delivery system (2050A) having a first feed zone delivery system input (FZ-IN1) connected to the first output (2B-OUT1A) of the Flow Splitting (2B) subsystem. A second feed zone delivery system (2050B) is shown to have a second feed zone delivery system input (FZ-IN2) connected to the second output (2B-OUT1B) of the Flow Splitting (2B) subsystem. The first feed zone delivery system (2050A) has a first feed zone delivery system output (FZ-OUT1) that is the first mixture output (2-OUT1A) of the overall Feedstock Delivery System (2000) and is configured to discharge a first carbonaceous material and gas mixture (510A). The second feed zone delivery system (2050B) has a second feed zone delivery system output (FZ-OUT2) that is the second mixture output (2-OUT1B) of the overall Feedstock Delivery System (2000) and is configured to discharge a second carbonaceous material and gas mixture (510B).

Figure 2A:
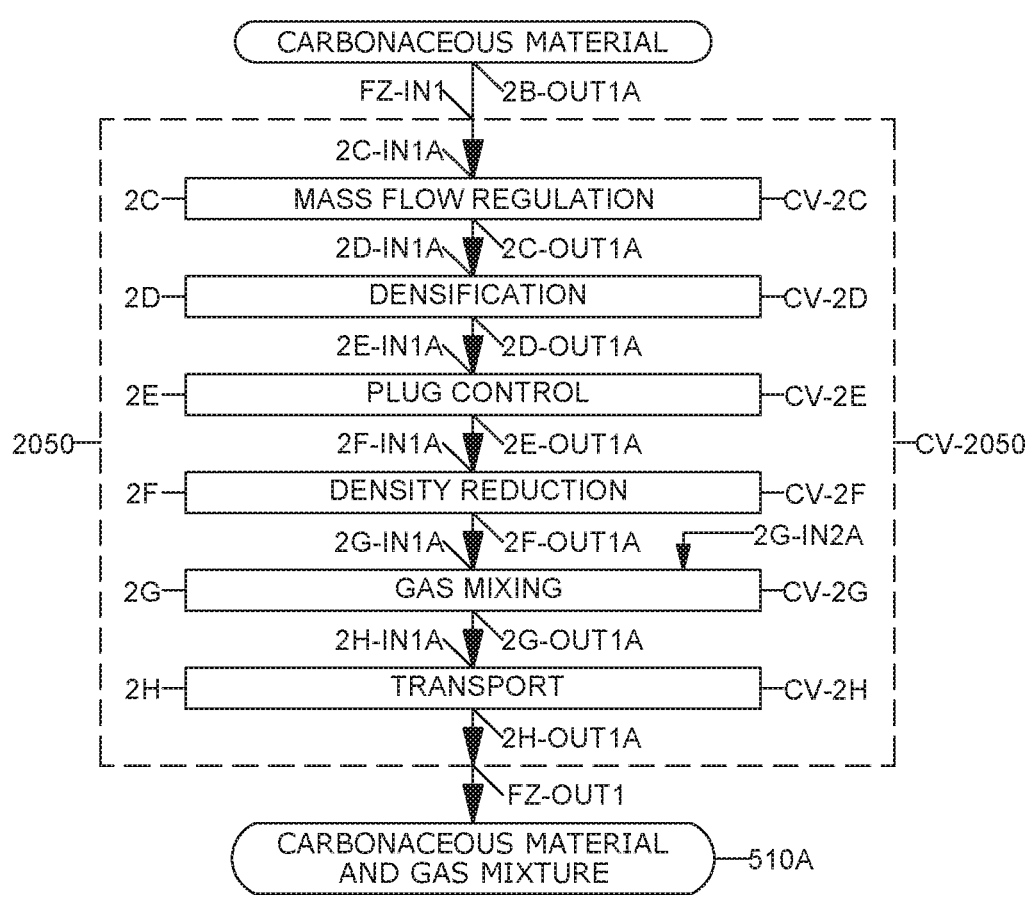
FIG. 2A elaborates upon FIG. 2 and shows one non-limiting embodiment of a feed zone delivery system (2050) including the subsystems or sequence steps of Mass Flow Regulation (2C), Densification (2D), Plug Control (2E), Density Reduction (2F), Gas Mixing (2G), and Transport (2H).

FIG. 2A:

FIG. 2A elaborates upon FIG. 2 and shows one non-limiting embodiment of a feed zone delivery system (2050) including the subsystems or sequence steps of Mass Flow Regulation (2C), Densification (2D), Plug Control (2E), Density Reduction (2F), Gas Mixing (2G), and Transport (2H).

The feed zone delivery system (2050) of FIG. 2A is contained within a feed zone delivery system control volume (CV-2050). The feed zone delivery system (2050) includes a Mass Flow Regulation (2C) subsystem contained within a Mass Flow Regulation Control Volume (CV-2C; a Densification (2D) subsystem contained within a Densification Control Volume (CV-2D); a Plug Control (2E) subsystem contained within a Plug Control Control Volume (CV-2E); a Density Reduction (2F) subsystem contained within a Density Reduction Control Volume (CV-2F); a Gas Mixing (2G) subsystem contained within a Gas Mixing Control Volume (CV-2G); and, a Transport (2H) subsystem contained within a Transport Control Volume (CV-2H).

Figure 2B:
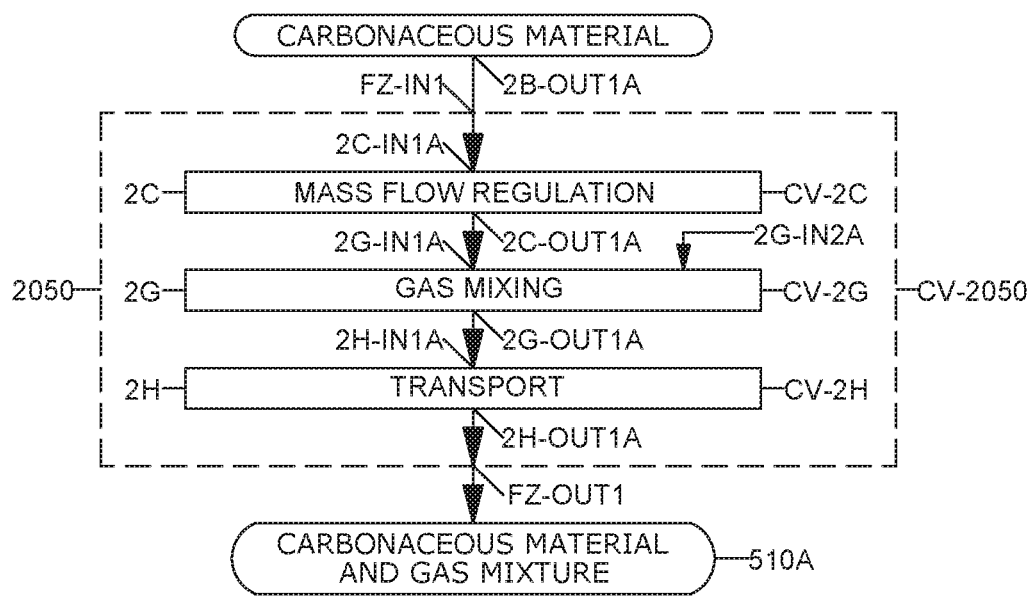
FIG. 2B elaborates upon FIG. 2 and shows one non-limiting embodiment of a feed zone delivery system (2050) including the subsystems or sequence steps of Mass Flow Regulation (2C), Gas Mixing (2G), and Transport (2H).

FIG. 2B:

FIG. 2B elaborates upon FIG. 2 and shows one non-limiting embodiment of a feed zone delivery system (2050) including the subsystems or sequence steps of Mass Flow Regulation (2C), Gas Mixing (2G), and Transport (2H).

Figure 2C:
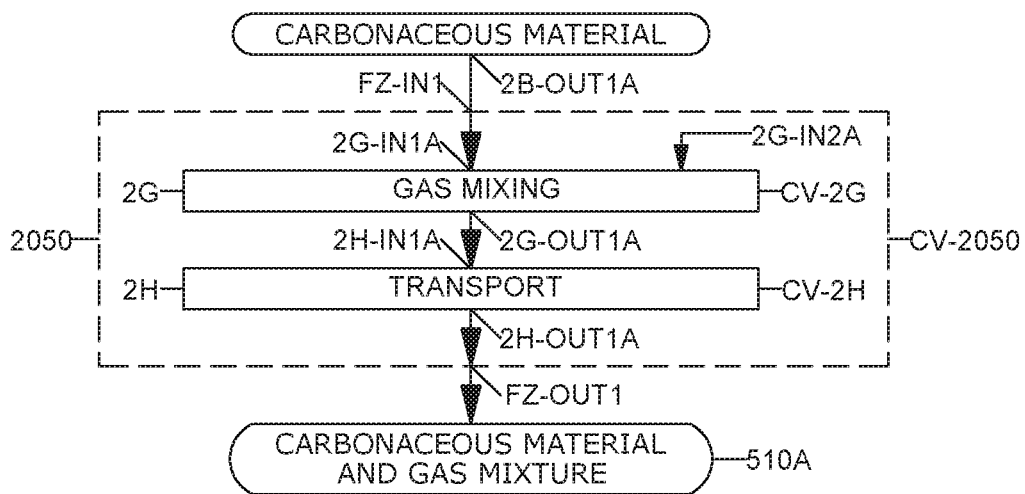
FIG. 2C elaborates upon FIG. 2 and shows one non-limiting embodiment of a feed zone delivery system (2050) including the subsystems or sequence steps of Gas Mixing (2G) and Transport (2H).

FIG. 2C:

FIG. 2C elaborates upon FIG. 2 and shows one non-limiting embodiment of a feed zone delivery system (2050) including the subsystems or sequence steps of Gas Mixing (2G) and Transport (2H).

FIG. 2D:

FIG. 2D shows a simplistic block flow control volume diagram of one embodiment of a Feedstock Delivery System (2000) including the non-limiting subsystems or sequence steps of Bulk Transfer (2A), Flow Splitting (2B), Mass Flow Regulation (2C), Densification (2D), Plug Control (2E), Density Reduction (2F), Gas Mixing (2G), and Transport (2H).

The Feedstock Delivery System (2000) is configured to accept carbonaceous material via a feedstock input (2-IN1) and output a plurality of streams of carbonaceous material and gas mixture (510A, 510B) for delivery to a downstream Product Gas Generation System (3000) (not shown). For the Feedstock Delivery System (2000) to be able to realize a plurality of carbonaceous material and gas mixtures (510A, 510B) suitable to transfer to a downstream Product Gas Generation System (3000) (not shown), a variety of sequence steps may be undertaken which may be accomplished in a variety of feedstock delivery subsystems.

The Feedstock Delivery System (2000) of FIG. 2 is contained within a Feedstock Delivery Control Volume (CV-2000) and is comprised of several subsystems, including: a Bulk Transfer (2A) subsystem contained within a Bulk Transfer Control Volume (CV-2A); a Flow Splitting (2B) subsystem contained within a Flow Splitting Control Volume (CV-2B); a plurality of Mass Flow Regulation (2C, 2C') subsystems contained within a plurality of Mass Flow Regulation Control Volumes (CV-2C, CV-2C'); a plurality of Densification (2D, 2D') subsystems contained within a plurality of Densification Control Volumes (CV-2D, CV-2D'); a plurality of Plug Control (2E, 2E') subsystems contained within a plurality of Plug Control Control Volumes (CV-2E, CV-2E'); a plurality of Density Reduction (2F, 2F') subsystems contained within a plurality of Density Reduction Control Volumes (CV-2F, CV-2F'); a plurality of Gas Mixing (2G, 2G') subsystems contained within a plurality of Gas Mixing Control Volumes (CV-2G, CV-2G'); and, a plurality of Transport (2H, 2H') subsystems contained within a plurality of Transport Control Volumes (CV-2H, CV-2H').

The Feedstock Delivery System (2000) is configured to accept carbonaceous material via a feedstock input (2-IN1) from the output (1-OUT1) (not shown) of the Feedstock Preparation System (1000) (not shown) to realize a plurality of mixture of carbonaceous and gas that are transferred via mixture outputs (2-OUT1A, 2OUT1B).

The Bulk Transfer (2A) subsystem is configured to accept a carbonaceous material via an input (2A-IN1) as a feedstock input (2-IN1) to the Feedstock Delivery System (2000) and discharge a mixture of carbonaceous material and gas via a mixture output (2A-OUT1).

The Flow Splitting (2B) subsystem is configured to accept a carbonaceous material input (2B-IN1) and discharge carbonaceous material via a plurality of mixture outputs (2B-OUT1A, 2B-OUT1B).

A plurality of Mass Flow Regulation (2C, 2C') subsystems are configured to accept carbonaceous material as an input (2C-IN1A, 2C-IN1B) from said plurality of Flow Splitting (2B) outputs (2B-OUT1A, 2B-OUT1B) and in turn each discharge a mixture output (2C-OUT1A, 2C-OUT1B).

A plurality of Densification (2D, 2D') subsystems are each configured to accept carbonaceous material as an input (2D-IN1A, 2D-IN1B) from each Mass Flow Regulation (2C, 2C') output (2C-OUT1A, 2C-OUT1B) and in turn each discharge a mixture output (2D-OUT1A, 2D-OUT1B).

A plurality of Plug Control (2E, 2E') subsystems are each configured to accept carbonaceous material as an input (2E-IN1A, 2E-IN1B) from each Densification (2D, 2D') output (2D-OUT1A, 2D-OUT1B) and in turn each discharge a mixture output (2E-OUT1A, 2E-OUT1B).

A plurality of Density Reduction (2F, 2F') subsystems are each configured to accept carbonaceous material as an input (2F-IN1A, 2F-IN1B) from each Plug Control (2E, 2E') output (2E-OUT1A, 2E-OUT1B) and in turn each discharge a mixture output (2F-OUT1A, 2F-OUT1B).

A plurality of Gas Mixing (2G, 2G') subsystems are each configured to accept carbonaceous material as an input (2G-IN1A, 2G-IN1B) from each Density Reduction (2F, 2F') mixture output (2F-OUT1A, 2F-OUT1B) and are configured to accept a gas input (2G-IN2A, 2G-IN2B) and mix the gas with the carbonaceous material to discharge a mixture output (2G-OUT1A, 2G-OUT1B) comprised of a mixture of gas and carbonaceous material.

A plurality of Transport (2H, 2H') subsystems are each configured to accept mixture of gas and carbonaceous material as an input (2H-IN1A, 2H-IN1B) from each Gas Mixing (2G, 2G') output (2G-OUT1A, 2G-OUT1B) and in turn each discharge an output (2H-OUT1A, 2H-OUT1B) including a first carbonaceous material and gas mixture (510A) and a second carbonaceous material and gas mixture (510B).

Figure 2E:
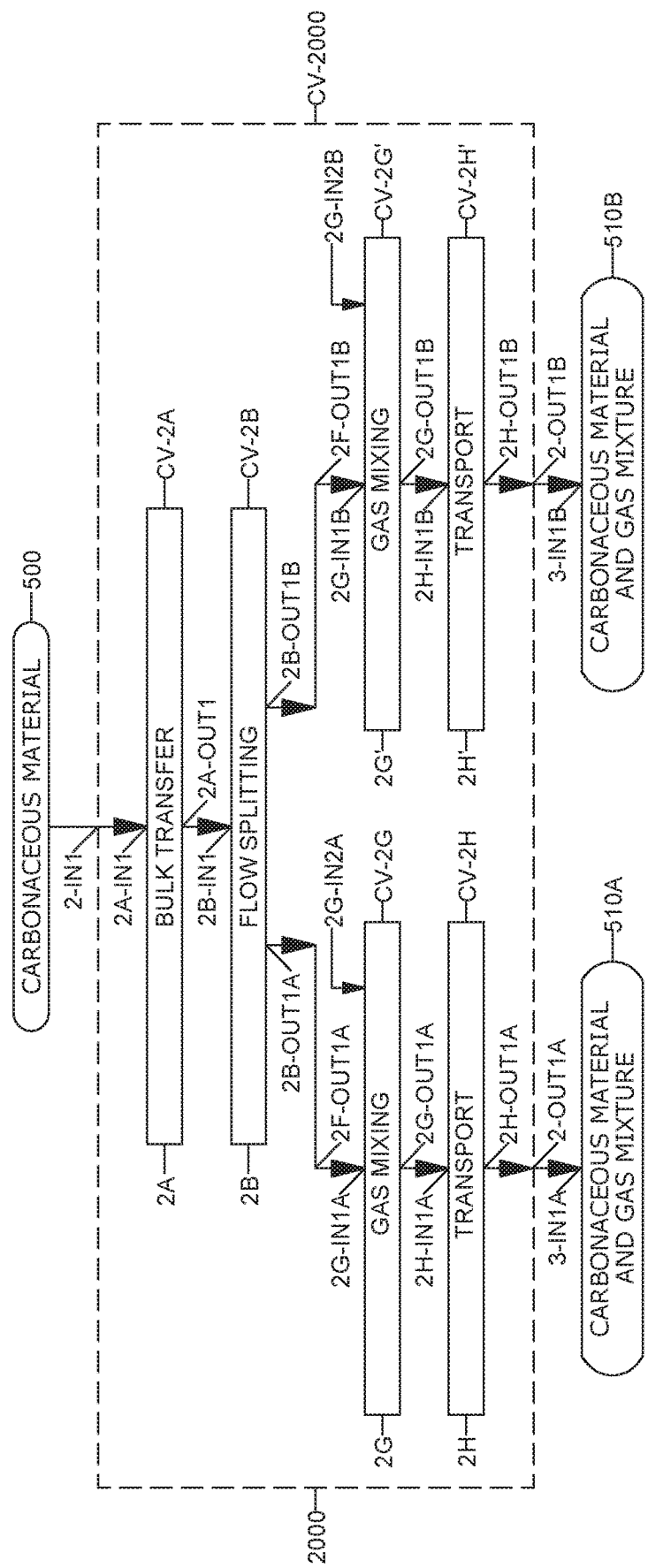
FIG. 2E shows a simplistic block flow control volume diagram of one embodiment of a Feedstock Delivery System (2000) including the non-limiting subsystems or sequence steps of Bulk Transfer (2A), Flow Splitting (2B), Gas Mixing (2G), and Transport (2H).

FIG. 2E:

FIG. 2E shows a simplistic block flow control volume diagram of one embodiment of a Feedstock Delivery System (2000) including the non-limiting subsystems or sequence steps of Bulk Transfer (2A), Flow Splitting (2B), Gas Mixing (2G), and Transport (2H).

The Feedstock Delivery System (2000) is configured to accept carbonaceous material via a feedstock input (2-IN1) and output a plurality of streams of carbonaceous material and gas mixture (510A, 510B) for delivery to a downstream Product Gas Generation System (3000) (not shown). For the Feedstock Delivery System (2000) to be able to realize a plurality of carbonaceous material and gas mixtures (510A, 510B) suitable to transfer to a downstream Product Gas Generation System (3000) (not shown), a variety of sequence steps may be undertaken which may be accomplished in a variety of feedstock delivery subsystems.

The Feedstock Delivery System (2000) of FIG. 2A is contained within a Feedstock Delivery Control Volume (CV-2000) and is comprised of several subsystems, including: a Bulk Transfer (2A) subsystem contained within a Bulk Transfer Control Volume (CV-2A); a Flow Splitting (2B) subsystem contained within a Flow Splitting Control Volume (CV-2B); a plurality of Gas Mixing (2G, 2G') subsystems contained within a plurality of Gas Mixing Control Volumes (CV-2G, CV-2G'); and a plurality of Transport (2H, 2H') subsystems contained within a plurality of Transport Control Volumes (CV-2H, CV-2H').

The Feedstock Delivery System (2000) is configured to accept a carbonaceous material via a feedstock input (2-IN1) from the output (1-OUT1) (not shown) of the Feedstock Preparation System (1000) (not shown) to realize a plurality of mixtures of carbonaceous and gas via mixture outputs (2-OUT1A, 2OUT1B).

The Bulk Transfer (2A) subsystem is configured to accept a carbonaceous material via an input (2A-IN1) as a feedstock input (2-IN1) to the Feedstock Delivery System (2000) and discharge a carbonaceous material output (2A-OUT1).

The Flow Splitting (2B) subsystem is configured to accept a carbonaceous material input (2B-IN1) and discharge carbonaceous material via a plurality of outputs (2B-OUT1A, 2B-OUT1B).

A plurality of Gas Mixing (2G, 2G') subsystems are each configured to accept carbonaceous material as an input (2G-IN1A, 2G-IN1B) from said plurality of Flow Splitting (2B) outputs (2B-OUT1A, 2B-OUT1B) and configured to accept a gas input (2G-IN2A, 2G-IN2B) and mix the gas with the carbonaceous material to discharge an output (2G-OUT1A, 2G-OUT1B) comprised of a mixture of gas and carbonaceous material.

A plurality of Transport (2H, 2H') subsystems are each configured to accept mixtures of gas and carbonaceous material as an input (2H-IN1A, 2H-IN1B) from each Gas Mixing (2G, 2G') output (2G-OUT1A, 2G-OUT1B) and in turn each discharge an output (2H-OUT1A, 2H-OUT1B) including a first carbonaceous material and gas mixture (510A) and a second carbonaceous material and gas mixture (510B).

FIG. 3:

FIG. 3 elaborates upon the non-limiting embodiment of FIG. 2 further including a description of the Bulk Transfer (2A) subsystem or sequence step of the Feedstock Delivery System (2000).

Figure 4:
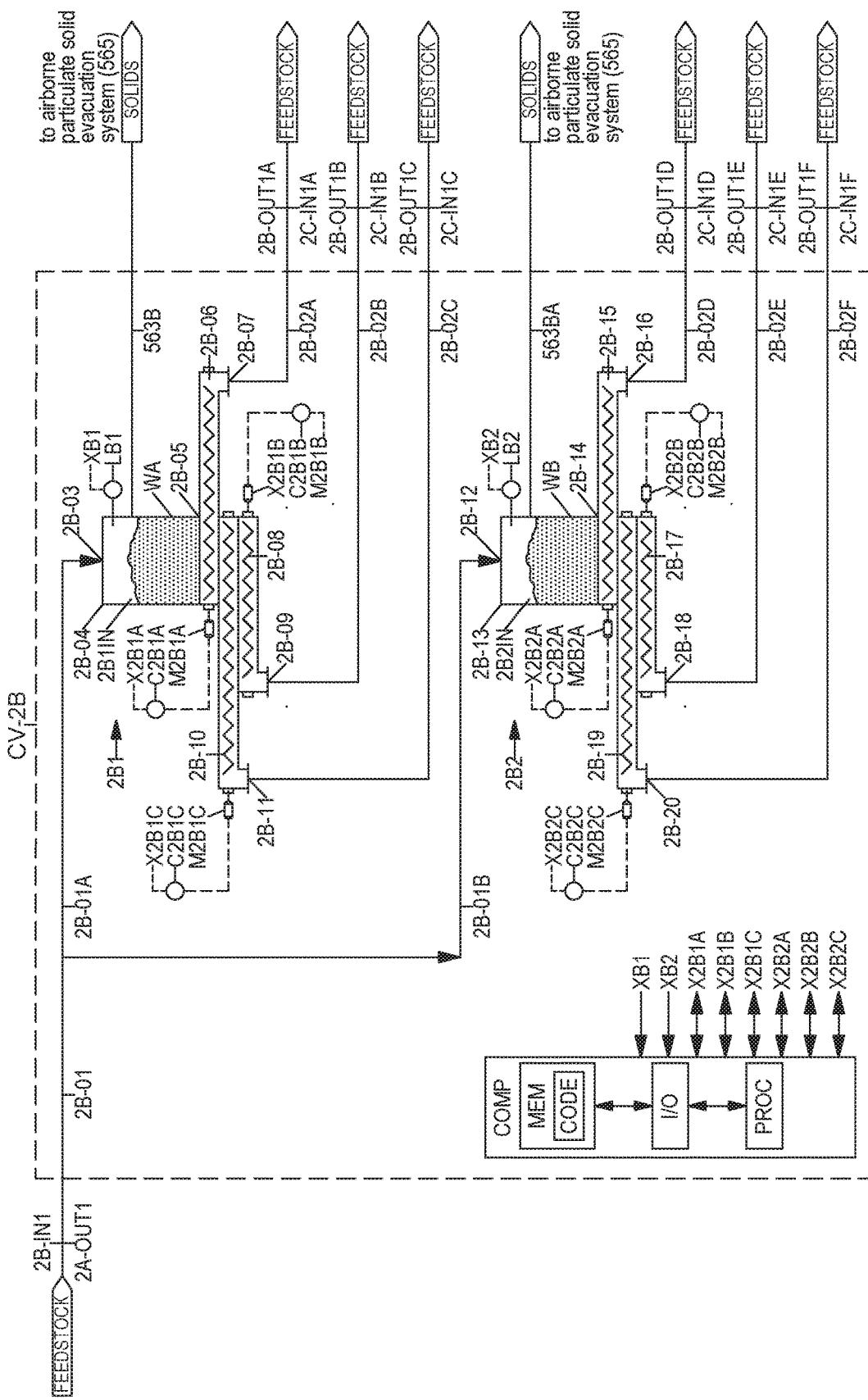
FIG. 4 elaborates upon the non-limiting embodiment of FIG. 2 further including a description of the Flow Splitting (2B) subsystem or sequence step of the Feedstock Delivery System (2000).

The Bulk Transfer (2A) subsystem is shown contained within a Bulk Transfer Control Volume (CV-2A). The Bulk Transfer (2A) subsystem is configured to accept a bulk carbonaceous material (2A-01) input (2A-IN1) (not shown) as a feedstock input (2-IN1) and discharge a bulk carbonaceous material (2A-02) as an output (2A-OUT1). The Bulk Transfer (2A) subsystem includes a bulk transfer system (2A1) that has an input (2A-06) and an output (2A-08). The output (2A-OUT1) of the Bulk Transfer (2A) subsystem is the input (2B-IN1) to the Flow Splitting (2B) subsystem as depicted in FIG. 4.

The Bulk Transfer (2A) subsystem and sequence steps integrates fast, simple, mobile, or inexpensive sensors to analyze carbonaceous material quality with advanced process logic process control strategies for improved system analytics. This is done by using a transport assembly (2A-03) to measure the mass flow rate (2A-02MASS), carbon content (2A-02CC), energy content (2A-02BTU), water content (2A-02H2O), and volatiles content (2A-02VOL), of the bulk carbonaceous material (2A-01) transferred through the bulk transfer system (2A1) from the input (2A-IN1) to the output (2A-OUT1). Several advanced logistics systems and methods are disclosed herein that help to address the cost, availability, reliability, and consistency of carbonaceous material preparation and delivery systems by using sophisticated approaches to promote the deployment of affordable, scalable, and sustainable production of hydrocarbon fuels. In some embodiments, the disclosure places emphasis on the integration of improved system analytics using fast, simple, mobile, or inexpensive sensors to analyze carbonaceous material quality with advanced process logic process control strategies.

The transport assembly (2A-03) includes a conveyor belt (2A-04) equipped with a motor (M2A), and controller (C-M2A) that is configured to input or output a signal (XM2A) to the computer (COMP). The motor (M2A) of the conveyor belt (2A-04) is equipped with a speed sensor (2A-05) that is configured to input or output a signal (X2A05) to the computer (COMP). The conveyor belt (2A-04) is also equipped with a first mass sensor (W2A-1) configured to output a signal (X2WA1) and a second mass sensor (W2A-2) configured to output a signal (X2WA2). Each mass sensor (W2A-1, W2A-2) is preferably of the compression load cell, tension cell, or shear cell type, however other types may be utilized as well.

The conveyor belt (2A-04), motor (M2A), speed sensor (2A-05), and plurality of mass sensors (W2A-1, W2A-2), cooperate to form an integrated weighting device and mass flow control system that is integrated with the computer (COMP) to provide the total mass flow rate (2A-02MASS) transferred through the bulk transfer system (2A1) from the input (2A-06) to the output (2A-08) and subsequently to the plurality of downstream splitters (2B1, 2B2) (not shown). In other embodiments, the speed sensor (2A-05) can be directly integrated with the conveyor belt (2A-04) as opposed to its motor (M2A). In embodiments, an optical source, slotted rotating disc, and optical sensor may be used to determine the speed at which the conveyor belt (2A-04) operates. An optical sensor senses transitions of a rotating slotted disc for providing signal pulses to the micro controller at a rate corresponding to the rotational rate of the motor shaft.

The bulk transfer system (2A1) may be equipped with a carbon content measurement unit (2A-CC) configured to output a signal (X2ACC) to the computer (COMP) to provide the carbon content (2A-02CC) of the carbonaceous material (2A-04) transferred through the bulk transfer system (2A1) from the input (2A-06) to the output (2A-08) and subsequently to the plurality of downstream splitters (2B1, 2B2). The bulk transfer system (2A1) may be equipped with an energy content measurement unit (2A-BTU) configured to output a signal (X2AE) to the computer (COMP) to provide the energy content (2A-02BTU) of the carbonaceous material (2A-04) transferred through the bulk transfer system (2A1) from the input (2A-06) to the output (2A-08) and subsequently to the plurality of downstream splitters (2B1, 2B2). The bulk transfer system (2A1) may be equipped with a volatiles content measurement unit (2A-VOL) configured to output a signal (X2AVOL) to the computer (COMP) to provide the volatiles content (2A-02VOL) of the carbonaceous material (2A-04) transferred through the bulk transfer system (2A1) from the input (2A-06) to the output (2A-08) and subsequently to the plurality of downstream splitters (2B1, 2B2). The bulk transfer system (2A1) may be equipped with a water content measurement unit (2AW) configured to output a signal (X2AH2O) to the computer (COMP) to provide the water content (2A-02H2O) of the carbonaceous material (2A-04) transferred through the bulk transfer system (2A1) from the input (2A-06) to the output (2A-08) and subsequently to the plurality of downstream splitters (2B1, 2B2).

A sensor is typically referred to as a type of control loop hardware that is equipped to measure a specific process variable or sensed value and transmit that measurement to a controller, or to a control computer, or to both. Examples of process variables include, but are not limited to, flow rates, pressures, temperatures, product gas compositions, ratio of constituents within the product gas composition (e.g.—hydrogen to carbon monoxide ratio, or carbon monoxide to carbon dioxide ratio), and carbonaceous material composition such as (i) ultimate analysis (C, H, O), (ii) proximate analysis, and/or (iii) energy content of a carbonaceous material. Carbon is typically a constituent of a carbonaceous material and typically carbon is a process variable obtained through the methods which involve obtaining the ultimate analysis of a carbonaceous material. The carbon content of a carbonaceous material may be a process variable measured or obtained by a sensor. The hydrogen content of a carbonaceous material may be a process variable measured or obtained by a sensor. The oxygen content of a carbonaceous material may be a process variable measured or obtained by a sensor. And, in turn, the ultimate analysis of a carbonaceous material, which includes the carbon, hydrogen and/or oxygen may also be a process variable measured or obtained by one sensor or multiple sensors.

In some embodiments, the present disclosure places emphasis on carbonaceous material quality verification and process integration via utilization of various fast, reliable, mobile, wireless, low in cost, widely available, and easy to use sensors that may be adapted to measure process variables and capable of integration with advanced process control schemes including feedback, feedforward, backpressure, ratio, cascade, or differential.

In some embodiments, the present disclosure describes a robust feedstock delivery system that is configured to accommodate widely variable feedstocks irrespective to variation in geographic diversity or seasonal changes and consistently produce a carbonaceous material having predictable and reliable characteristics while at the same time being integrated with an advanced feedstock delivery system capable of employing advanced logic control, logistics, and sophisticated inventory management methods to improve facility availability, reliability, and consistently meet performance targets.

In some embodiments, the present disclosure emphasizes innovation related to a versatile feedstock preparation and delivery system adapted to utilize sophisticated logistics systems for carbonaceous materials that result in superior operational flexibility to accommodate feedstock variability, and resultantly improve feedstock availability for delivery, reliability of feedstock supply, and consistent feedstock quality, while using control logic to integrate signals from measurements and sensors of carbonaceous material composition with downstream process controllers, actuators, and valves.

In some embodiments, the present disclosure emphasizes the use of simple, timely, accurate instruments to verify or measure feedstock quality specifications at points of collection, consolidation, delivery, or storage, and integrate signals from measurements and sensors with downstream process controllers, actuators, and valves. In some embodiments, the present disclosure emphasizes the use of fast, simple, and inexpensive devices to accurately determine carbonaceous material quality and integrate signals from measurements and sensors with downstream process controllers, actuators, and valves.

Various process control methodologies may be used throughout the various non-limiting embodiments of the disclosure. For example, (a) feedback, (b) feed-forward, and (c) ratio control are some of the high priority control schemes that may be incorporated to realize efficient process optimization for economical operation of the described feedstock delivery and product gas generation system. Some control systems will have one or more of the aforesaid type of control schemes which may or may not cooperate together to realize efficient energy integration and maximize carbon conversion between the two successive thermochemical reaction environments.

Selection of the most suitable control loop hardware and control plant control logic and methodologies plays an important position in development and commercialization of economically attractive technologies to convert carbonaceous materials into valuable products and energy. Control loop hardware generally includes sensors, controllers, and actuators. Sensors, controllers, and actuators are typically mechanical, electrical, digital devices, or combinations of each. Sensors are usually configured to measure process variables either continuously or discretely by taking individual periodic measurements at discrete times. Flow rate, pressure, and temperature are typically process variables or sensed values that are available or measured continuously, however, these variables may also be obtained through discrete measurements updated at discrete times. Product gas composition and carbonaceous material composition such as (i) ultimate analysis (C, H, O), (ii) proximate analysis, (iii) energy content, or (iv) water content of a carbonaceous material are typically process variables that are available or measured through discrete measurements updated at discrete times, however these variables may also be obtained continuously.

Product gas composition and carbonaceous material composition such as (i) ultimate analysis (C, H, O), (ii) proximate analysis, and/or (iii) energy content of a carbonaceous material are process variables that are typically obtained through discrete measurements updated at discrete times, however, these variables may be read continuously as well, due to advancements in analytical data acquisition technologies with advanced capabilities. Nonetheless, although modern advancements have made mechanical, electrical, and digital sensor devices commercially available which continuously measure process variables, such as product gas composition and carbonaceous material composition, the focus of this disclosure is to expand upon the art through specific improved advancements related to selection and/or implementation of the control logic behind various process control schemes and high priority control loops. The exact type of preferred sensors contemplated in the disclosure are of varying priority when compared to the preferred selection of important control loops and logic schemes that utilize or incorporate process variables or sensed values obtained from such sensors. Thus in turn, the exact types of preferred sensors contemplated in the disclosure may in some instances be, in fact, improvements over the level of art known at the time of filing and as a result are of paramount importance with respect to the selection of logic behind utilizing the sensed values obtained from such sensors.

A control computer (COMP) is configured to accept a variety of signals from process variables using a variety of sensors and/or controllers, and then apply advanced process logic control methodologies, strategies and/or sequences to realize modulation of actuators and/or valves to effectuate optimal operation of the feedstock delivery and product gas generation system. A process controller or control computer applies the control approach and methodology for the entire control loop on a continuous basis, a discrete basis, or a hybrid combination of a continuous basis and a discrete basis. Further, a control computer may be applied to implement the control methodology by utilizing process variables obtained by either a continuous sensor, a discrete sensor, or a combination of a continuous sensor and a discrete sensor and hold the control action at a constant set-point at that specific control output until a later time when that control algorithm is executed. The time between successive interrogations or application of the control algorithm is applied by the control computer is defined as the control interval. The control interval for a continuous sensor is typically shorter than that of a discrete sensor and based upon commercially available mechanical, electrical, or digital continuous or discrete sensors, the control interval or control time can vary from 0.2 milliseconds, to 0.5 seconds, to 1.0 second, to 10 seconds, to 30 seconds, to 1 minute, to 5 minutes, to 10 minutes, to 30 minutes, to 1 hour, to 10 hours, or longer. The output from the control computer is transmitted to a controller device. From application of the control logic, the control computer can send a variety of signals to a variety of controllers. A wide variety of sensor technologies exist for measuring the composition of carbonaceous materials. Some of the categories of commercially available sensor technologies that may be used in the analysis of carbonaceous materials are electric, digital, acoustic, microwave, terahertz, NIR, FTIR, Raman spectroscopy, and X-ray.

Advancements in the art of sensors can provide continuous or discrete measurement of (i) ultimate analysis (C, H, O), (ii) proximate analysis, or (iii) energy content of a carbonaceous material that may often be characterized as an unpredictable and often wet substance, such as MSW. Typically, such sensors also require that the carbonaceous material is conveyed past the sensor by a mechanical or pneumatic device such as a conveyor belt or bucket elevator or carbonaceous feeder system such as a lock hopper system, rotary feeder, plug-forming feeder, non-plug-forming feeder, extrusion and/or injection system, and/or pneumatic feed system. However, the preferred method of utilizing such sensors incorporates a conveyor belt installed upstream of a multi-stage piston feeder.

Any conceivable type of material conveyance system or feeder system may be utilized as long as the carbonaceous material is made available to the sensor to measure either at least one of the (i) ultimate analysis (C, H, and/or O), (ii) proximate analysis, and/or (iii) energy content of a carbonaceous material. It is preferred that the carbonaceous material is made accessible to the sensor or group of sensors to measure the (i) ultimate analysis (C, H, and/or O), (ii) proximate analysis, and/or (iii) energy content of a carbonaceous material in a spread-out fashion over a conveyor belt, in a screw conveyor, as a plug, de-densified carbonaceous material, or in any other conceivable fashion insofar as the sensor is positioned in an accessible manner to allow the sensor to analyze the carbonaceous material.

Of particular interest in the present disclosure is the preferred sensor used to measure the (i) ultimate analysis, or at least one of the carbon, hydrogen, and/or oxygen content of a carbonaceous material transported to the reactor is of the X-ray type sensor which beams through, at, or upon the carbonaceous material to measure at least one of the carbon, hydrogen, or oxygen content of the carbonaceous material in either a continuous or discrete manner.

Of particular interest in the present disclosure is the preferred sensor used to measure (ii) proximate analysis, or at least the volatiles content or fixed carbon content of a carbonaceous material is that of a thermogravimetric analyzer (TGA) type which allows for a continuous or discrete measurement of either or both of the volatile content or fixed carbon content components of a carbonaceous material.

Of particular interest in the present disclosure is the preferred sensor used to measure (iii) energy content of a carbonaceous material which is a combination of two sensors including a Raman technique sensor and an X-ray analysis technique sensor to obtain chemical composition and density data of the carbonaceous material, respectively, and then fuse each sensed value data together into approximate energy concentrations to obtain the energy content of the carbonaceous material in either a continuous or discrete manner. Alternatively, in some non-limiting embodiments, it may be preferred to use a single sensor that utilizes a Raman technique together with an X-ray analysis technique to obtain carbonaceous material chemical composition and carbonaceous material density data, respectively, and then fuse this data together into approximate energy concentrations to obtain an energy content of the carbonaceous material in either a continuous or discrete manner. Such a sensor that is a combination of Raman and X-ray analysis techniques in some embodiments is the preferred sensor to measure the energy content of a carbonaceous material, however any type of energy content sensor and/or system and/or method may be employed to accomplish the goal of measuring the energy content of a carbonaceous material. Furthermore, as methods to probe more intricate physical characteristics become more commonplace, some manner of correlational relationships could potentially be developed and improved upon. Nonetheless, the preferred method for obtaining a continuous or discrete measurement of the energy value of the carbonaceous material includes an assessment of the approximate chemical composition towards an energy value and is achieved preferably with a sensor or sensors that take a combination of several different source/detector pairs to obtain a continuous or discrete measurement of the energy content of the carbonaceous material.

Such aforementioned analytical techniques work for a wide range of carbonaceous materials and preferably analyze the carbonaceous material as it is spread-out on a conveyor or within a screw conveyor before it gets to the first reactor. Nonetheless, the methods disclosed herein are not limited to any specific sensor or technique to measure the (i) ultimate analysis (C, H, and/or O), (ii) proximate analysis, and/or (iii) energy content of a carbonaceous material, but instead, the non-limiting embodiments contemplated in this disclosure are directed towards the application of the process variables or sensed values obtained from such sensors. Further, any sort of commercially available sensor or combination of sensors may be used so long as the sensor or sensors measure the process variables or sensed values of (i) ultimate analysis (C, H, and/or O), (ii) proximate analysis, and/or (iii) energy content of a carbonaceous material transferred to the first reactor. Any type of sensor may be used to measure either the carbon content, hydrogen content, oxygen content, volatiles content, fixed carbon content, and/or energy content of a carbonaceous material in a continuous or discrete manner so long as the sensor or sensors provide a process controller with the process variables or sensed values of the sensors analyzing the carbonaceous material.

In embodiments, the signals from controllers or sensors are inputted or outputted to and from a computer (COMP) by a user or operator via an input/output interface (I/O) as disclosed in FIG. 3. Program and sequencing instructions may be executed to perform particular computational functions such as automated operation of the valves, actuators, controllers, motors, or the like.

In one exemplary embodiment, a computer (COMP) includes a processor (PROC) coupled to a system memory (MEM) via an input/output interface (I/O). The processor (PROC) may be any suitable processor capable of executing instructions. System memory (MEM) may be configured to store instructions and data accessible by processor (PROC). In various embodiments, system memory (MEM) may be implemented using any suitable memory technology. In the illustrated embodiment, program instructions and data implementing desired functions are shown stored within system memory (MEM) as code (CODE). In embodiments, the I/O interface (I/O) may be configured to coordinate I/O traffic between processor (PROC) and system memory (MEM).

In some embodiments, the I/O interface (I/O) is configured for a user or operator to input necessary sequencing protocol into the computer (COMP) for process execution, including sequence timing and repetition of a given number of states to realize a desired sequence of steps and/or states. In embodiments, the signals operatively coupled to a controller, valve, actuator, motor, or the like, may be an input value to be entered into the computer (COMP) by the I/O interface (I/O).

The system is fully flexible to be tuned, configured, and optimized to provide an environment for scheduling the appropriate process parameters by programmatically controlling the opening and closing of valves at specific time intervals, or strategically and systematically opening, closing, turning on, turning off, modulating, controlling, or operating motors, valves, or actuators at specific time intervals at specific times.

In embodiments, a user or operator may define control loops, cycle times, step numbers, and states which may be programmed into the computer (COMP) by an operator accessible input/output interface (I/O).

In some embodiments, the functional controls of the BSS system, as disclosed herein, solve numerous technical challenges associated with consistently realizing a predictable and reliable supply of carbonaceous material having a consistent composition, density, or moisture.

FIG. 4:

FIG. 4 elaborates upon the non-limiting embodiment of FIG. 2 further including a description of the Flow Splitting (2B) subsystem or sequence step of the Feedstock Delivery System (2000).

The Flow Splitting (2B) subsystem is shown contained within a Flow Splitting Control Volume (CV-2B). The input (2B-IN1) to the Flow Splitting (2B) subsystem is the output (2A-OUT1) of the Bulk Transfer (2A) (not shown). The Flow Splitting (2B) subsystem is configured to accept a bulk carbonaceous material (2B-01) input (2B-IN1) and discharge a plurality of split carbonaceous material streams (2B-02A, 2B-02B, 2B-02C, 2B-02D, 2B-02E, 2B-02F) via a outputs (2B-OUT1A, 2B-OUT1B, 2B-OUT1C, 2B-OUT1D, 2B-OUT1E, 2B-OUT1F).

Specifically, FIG. 4 shows the Flow Splitting (2B) subsystem accepting a stream of bulk carbonaceous material (2B-01) and apportioning it into a first split stream (2B-01A) that is introduced to a first splitter (2B1) and a second split stream (2B-01B) that is introduced to a second splitter (2B2). The first splitter (2B1) has an interior (2B1IN) and accepts a first split stream (2B-01A) to the interior (2B1IN) via a splitter input (2B-03). The second splitter (2B2) has an interior (2B2IN) and accepts a second split stream (2B-01B) to the interior (2B2IN) via a splitter input (2B-12). A splitter input (2B-03, 2B-12) is located at the top section (2B-04, 2B-13) of each splitter (2B1, 2B2).

The first splitter (2B1) has an interior (2B1IN) and a splitter input (2B-03) located at a top section (2B-04) and a bottom section (2B-05) in fluid communication with a first splitter first screw conveyor (2B-06), first splitter second screw conveyor (2B-08), and a first splitter third screw conveyor (2B-10). The first splitter first screw conveyor (2B-06) has a motor (M2B1A) with a controller (C2B1A) that is configured to input and output a signal (X2B1A) to the computer (COMP) and is configured to transport a first split carbonaceous material stream (2B-02A) from the interior (2B1IN) of the first splitter (2B1) via a first output (2B-07). The first splitter second screw conveyor (2B-08) has a motor (M2B1B) with a controller (C2B1B) that is configured to input and output a signal (X2B1B) to the computer (COMP) and is configured to transport a second split carbonaceous material stream (2B-02B) from the interior (2B1IN) of the first splitter (2B1) via a second output (2B-09). The first splitter third screw conveyor (2B-10) has a motor (M2B1C) with a controller (C2B1C) that is configured to input and output a signal (X2B1C) to the computer (COMP) and is configured to transport a third split carbonaceous material stream (2B-02C) from the interior (2B1IN) of the first splitter (2B1) via a third output (2B-11). The first splitter (2B1) has an interior (2B1IN) defined by at least one side wall (WA) with a first splitter level sensor (LB1) connected thereto that is configured to input and output a signal (XB1) to the computer (COMP).

The second splitter (2B2) has an interior (2B2IN) and a splitter input (2B-12) located at a top section (2B-13) and a bottom section (2B-14) in fluid communication with a second splitter first screw conveyor (2B-15), second splitter second screw conveyor (2B-17), and a second splitter third screw conveyor (2B-19). The second splitter first screw conveyor (2B-15) has a motor (M2B2A) with a controller (C2B2A) that is configured to input and output a signal (X2B2A) to the computer (COMP) and is configured to transport a fourth split carbonaceous material stream (2B-02D) from the interior (2B2IN) of the second splitter (2B2) via a first output (2B-16). The second splitter second screw conveyor (2B-17) has a motor (M2B2B) with a controller (C2B2B) that is configured to input and output a signal (X2B2B) to the computer (COMP) and is configured to transport a fifth split carbonaceous material stream (2B-02E) from the interior (2B2IN) of the second splitter (2B2) via a second output (2B-18). The second splitter third screw conveyor (2B-19) has a motor (M2B2C) with a controller (C2B2C) that is configured to input and output a signal (X2B2C) to the computer (COMP) and is configured to transport a sixth split carbonaceous material stream (2B-02F) from the interior (2B2IN) of the second splitter (2B2) via a third output (2B-20). The second splitter (2B2) has an interior (2B2IN) defined by at least one side wall (WB) with a second splitter level sensor (LB2) connected thereto that is configured to input and output a signal (XB2) to the computer (COMP).

Figure 5:
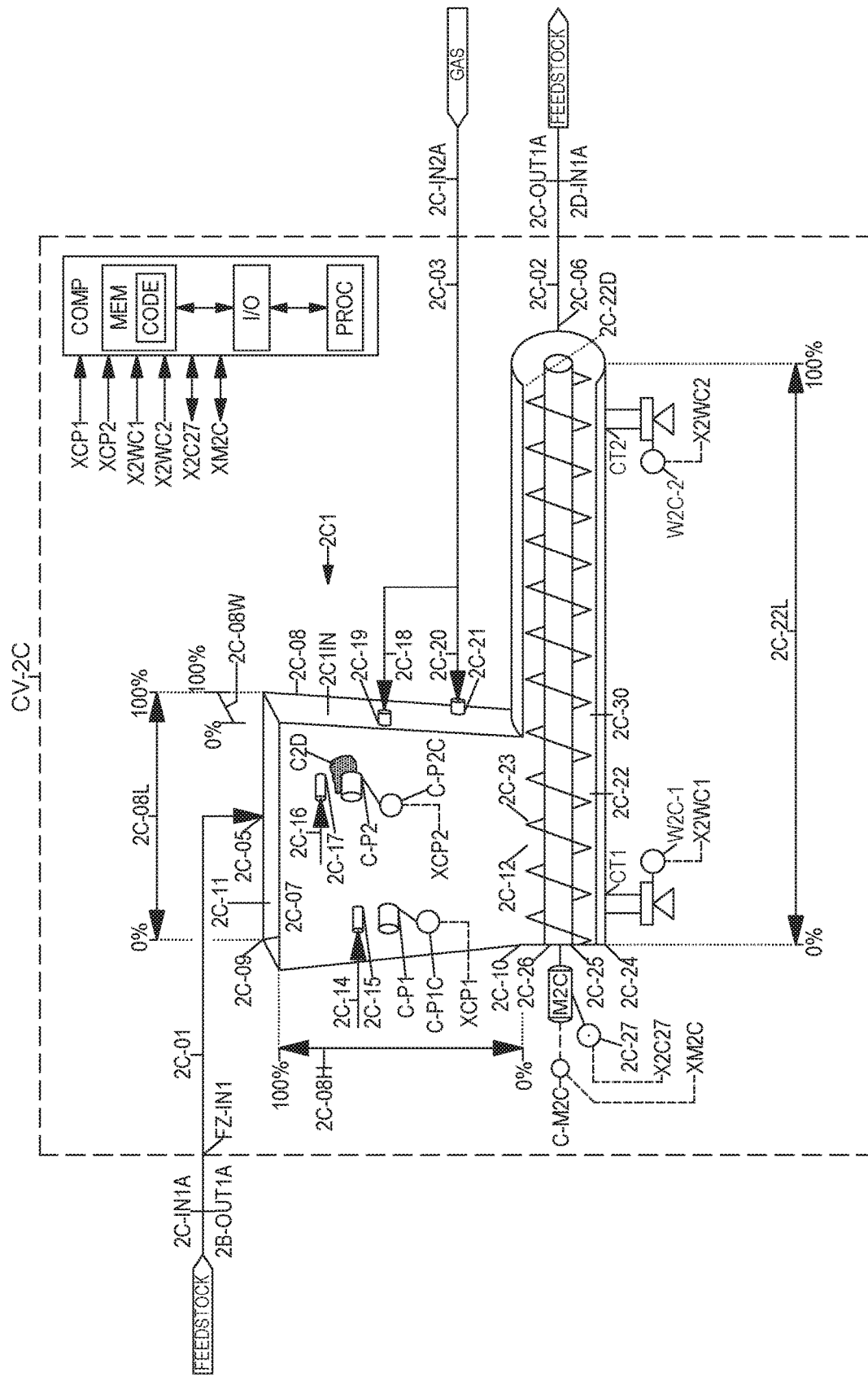
FIG. 5 elaborates upon the non-limiting embodiment of FIG. 2A further including a description of the Mass Flow Regulation (2C) subsystem or sequence step of the Feedstock Delivery System (2000).

A plurality of outputs (2B-OUT1A, 2B-OUT1B, 2B-OUT1C, 2B-OUT1D, 2B-OUT1E, 2B-OUT1F) from the Flow Splitting (2B) subsystem are the plurality of inputs (2C-IN1A, 2C-IN1B, 2C-IN1C, 2C-IN1D, 2C-IN1E, 2C-IN1F) to the downstream feed zone delivery system (2050A, 2050B, 2050C, 2050D, 2050E, 2050F) as depicted in FIG. 14. A plurality of outputs (2B-OUT1A, 2B-OUT1B, 2B-OUT1C, 2B-OUT1D, 2B-OUT1E, 2B-OUT1F) from the Flow Splitting (2B) subsystem are the plurality of inputs (2C-IN1A, 2C-IN1B, 2C-IN1C, 2C-IN1D, 2C-IN1E, 2C-IN1F) to the downstream Mass Flow Regulation (2C) subsystems as depicted in FIG. 5. The output (2A-OUT1) of the Bulk Transfer (2A) subsystem is the input (2B-IN1) to the Flow Splitting (2B) subsystem as depicted in FIG. 4.

FIG. 5:

FIG. 5 elaborates upon the non-limiting embodiment of FIG. 2A further including a description of the Mass Flow Regulation (2C) subsystem or sequence step of the Feedstock Delivery System (2000).

Each of the plurality of outputs (2B-OUT1, 2B-OUT1A, 2B-OUT1B, 2B-OUT1C, 2B-OUT1D, 2B-OUT1E, 2B-OUT1F) from the Flow Splitting (2B) subsystem of FIG. 4 may be provided to a plurality of inputs (2C-IN1A, 2C-IN1B, 2C-IN1C, 2C-IN1D, 2C-IN1E, 2C-IN1F) to the downstream Mass Flow Regulation (2C) subsystems as depicted in FIG. 5.

FIG. 5 shows one example of a Mass Flow Regulation (2C) subsystem accepting a carbonaceous material (2C-01) as an input (2C-IN1A) from a first output (2B-OUT1A) of a Flow Splitting (2B) subsystem.

The Mass Flow Regulation (2C) subsystem is shown contained within a Mass Flow Regulation Control Volume (CV-2C). The Mass Flow Regulation (2C) subsystem is configured to accept a carbonaceous material (2C-01) input (2C-IN1A) from at least one of the outputs (2B-OUT1A) from the Flow Splitting (2B) subsystem of FIG. 4, and discharge a stream of carbonaceous material (2C-02) via an output (2C-OUT1A). The Mass Flow Regulation (2C) subsystem is also configured to accept a gas (2C-03) via a gas input (2C-IN2A). The gas (2C-03) is preferably air, however it can be nitrogen, carbon dioxide, or product gas. The carbonaceous material (2C-02) output (2C-OUT1A) from the Mass Flow Regulation Control Volume (CV-2C) is the input (2D-IN1) to a downstream Densification Control Volume (CV-2D) shown in FIG. 6.

A weigh feeder (2C1) is used to regulate the mass flow rate of the carbonaceous material (2C-01) passing from the feeder input (2C-05) to the feeder output (2C-06). The weigh feeder (2C1) has a feeder input (2C-05) and a feeder output (2C-06). The feeder input (2C-05) is synonymous with the feed zone delivery system input (2C-04A) as disclosed in FIG. 14.

The weigh feeder (2C1) is comprised of a receiving unit (2C-07) and a transport unit (2C-22). The receiving unit (2C-07) has an interior (2C1IN) defined by at least one side wall (2C-08) having a height (2C-08H), width (2C-08W), and length (2C-08L), that constitute a volume (2C-V1) (not shown). The receiving unit (2C-07) may be cylindrical, rectangular, trapezoidal or any other conceivable shape. The receiving unit (2C-07) has a top opening (2C-11) at a top section (2C-09) and a bottom opening (2C-12) at a bottom section (2C-10). The feeder input (2C-05) is located at a top section (2C-09) and the bottom section (2C-10) is in fluid communication with a transport unit (2C-22). The feeder input (2C-05) is preferably positioned in a top opening (2C-11) at the top section (2C-09) of the receiving unit (2C-07). The receiving unit (2C-07) is configured to receive carbonaceous material (2C-01) to the interior (2C1IN) via a feeder input (2C-05).

The side wall (2C-08) of the receiving unit (2C-07) is equipped with a connection (C-P1C) for a first proximity sensor (C-P1) which is configured to output a signal (XCP1) to the computer (COMP) when carbonaceous material is within close proximity to the first proximity sensor (C-P1). A first gas nozzle (2C-15) with a first gas supply (2C-14) is located immediately within the vicinity above the first proximity sensor (C-P1) and configured to blow off carbonaceous material dust which may build up on top of the first proximity sensor (C-P1). The side wall (2C-08) of the receiving unit (2C-07) is equipped with a connection (C-P2C) for a second proximity sensor (C-P2) which is configured to output a signal (XCP2) to the computer (COMP) when carbonaceous material is within close proximity to the second proximity sensor (C-P2). A second gas nozzle (2C-17) with a second gas supply (2C-16) is located immediately within the vicinity above the second proximity sensor (C-P2) and configured to blow off carbonaceous material dust which may build up on top of the second proximity sensor (C-P2). FIG. 5 shows the first proximity sensor (C-P1) connection (C-P1C) located at a vertical height lesser than and below the second proximity sensor (C-P2) connection (C-P2C).

In embodiments, a proximity sensor may be a capacitive-type sensor such as model #CJ10-30GM-E2 marketed by Pepperl+Fuchs™. Capacitive sensing is a technology, based on capacitive coupling, that can detect and measure the presence or absence of carbonaceous material which has a dielectric different from air. Many types of sensors use capacitive sensing, including sensors to detect and measure proximity or level. Proximity sensors are equivalent to level sensors. Capacitive proximity switches are dependent on the material characteristics of the carbonaceous material. When a dielectric material, such as carbonaceous material, is placed in the electric field emitted by a proximity sensor, electric charges do not flow through the material, but only slightly shift from their average equilibrium positions causing dielectric polarization. In embodiments, dust or carbonaceous material can build up on the proximity sensor and therefore a supply of gas is needed to continuously purge the sensor to clear accumulation of dust or carbonaceous material on the sensor. Accumulation or build-up of dust or carbonaceous material on the proximity sensor may result in a false reading where the sensor indicates that a carbonaceous material is present at the height of the sensor when in fact it is not.

For illustrative purposes, FIG. 5 shows dust accumulation (C2D) on the second proximity sensor (C-P2). The purpose of the second gas nozzle (2C-17) is to provide a first gas supply (2C-16) to the second proximity sensor (C-P2) to avoid and prevent dust accumulation (C2D). The presence of dust accumulation (C2D) on any portion of the first proximity sensor (C-P2) may result in a false signal (XCP2) from the second proximity sensor (C-P2) to the computer (COMP). Dust accumulation (C2D) on the second proximity sensor (C-P2) results in the signal (XCP2) to the computer (COMP) indicating that the second proximity sensor (C-P2) reads a level of carbonaceous material within the interior (2C1IN) of the receiving unit (2C-07) at a first sensor height (2C-08H), when in fact, it is not.

The side wall (2C-08) of the receiving unit (2C-07) is equipped with a third gas connection (2C-19) configured to introduce a third gas supply (2C-18) along the width (2C-08W) of the receiving unit (2C-07) of the weigh feeder (2C1) to prevent bridging of the carbonaceous material (2C-01) between the feeder input (2C-05) to the feeder output (2C-06). The side wall (2C-08) of the receiving unit (2C-07) is equipped with a fourth gas connection (2C-21) configured to introduce a fourth gas supply (2C-20) along the width (2C-08W) of the receiving unit (2C-07) of the weigh feeder (2C1) to prevent bridging of the carbonaceous material (2C-01) between the feeder input (2C-05) to the feeder output (2C-06). FIG. 5 shows the fourth gas connection (2C-21) located at a vertical height lesser than and below the third gas connection (2C-19).

The bottom section (2C-10) of the receiving unit (2C-07) is in fluid communication with the transport unit (2C-22). The transport unit (2C-22) has an interior (2C-23) defined by at least one side wall (2C-24). The transport unit (2C-22) has a height (2C-22H) (not shown), width (2C-22W) (not shown), and length (2C-22L) that constitute a volume (2C-V2) (not shown). FIG. 5 does not show the height (2C-22H) (not shown), nor width (2C-22W) (not shown), because they equal each other if the transport unit (2C-22) takes the form of a circular cross-section and as a result only a diameter (2C-22D) is shown. It is to be noted that the geometry of the transport unit (2C-22) may be circular, rectangular, trapezoidal, or any other shape.

Carbonaceous material (2C-01) is transferred from the interior (2C1IN) of the receiving unit (2C-07) to the interior (2C-23) of the transport unit (2C-22). A screw conveyor (2C-25) has a shaft (2C-26) equipped with a shaft rotation measurement unit (2C-27) and a motor (M2C) with a controller (C-M2C) is disposed within the interior (2C-23) of the transport unit (2C-22). The shaft rotation measurement unit (2C-27) is configured to input and output a signal (X2C27) to or from the computer (COMP) indicative of the rotations per minute (RPM) of the shaft (2C-26) of the screw conveyor (2C-25). The controller (C-M2C) of the motor (M2C) is configured to input and output a signal (XM2C) to or from the computer (COMP) to rotate the shaft (2C-26) of the screw conveyor (2C-25).

A weight measurement unit (2C-30) is operatively coupled to the weigh feeder (2C1). The embodiment shown in FIG. 5 shows the weight measurement unit (2C-30) including a first mass sensor (W2C-1) and a second mass sensor (W2C-2) located at opposing ends along the length (2C-22L) of the transport unit (2C-22). The first mass sensor (W2C-1) is located at a first transport unit connection (CT1) along the length (2C-22L) of the transport unit (2C-22). The second mass sensor (W2C-2) is located at a second transport unit connection (CT2) along the length (2C-22L) of the transport unit (2C-22). The first mass sensor (W2C-1) is configured to output a first signal (X2WC1) to the computer (COMP). The second mass sensor (W2C-2) is configured to output a second signal (X2WC2) to the computer (COMP).

In embodiments, each mass sensor (W2C-1, W2C-2) is preferably of the compression load cell, tension cell, or shear cell type, however other types may be utilized as well. Each mass sensor (W2C-1, W2C-2) shown in FIG. 5 is displayed beneath the weigh feeder (2C1) so that the weigh feeder (2C1) is pressing onto each mass sensor (W2C-1, W2C-2) and each mass sensor (W2C-1, W2C-2) is connected to the transport unit (2C-22) via a first transport unit connection (CT1) and a second transport unit connection (CT2).

Figure 6:
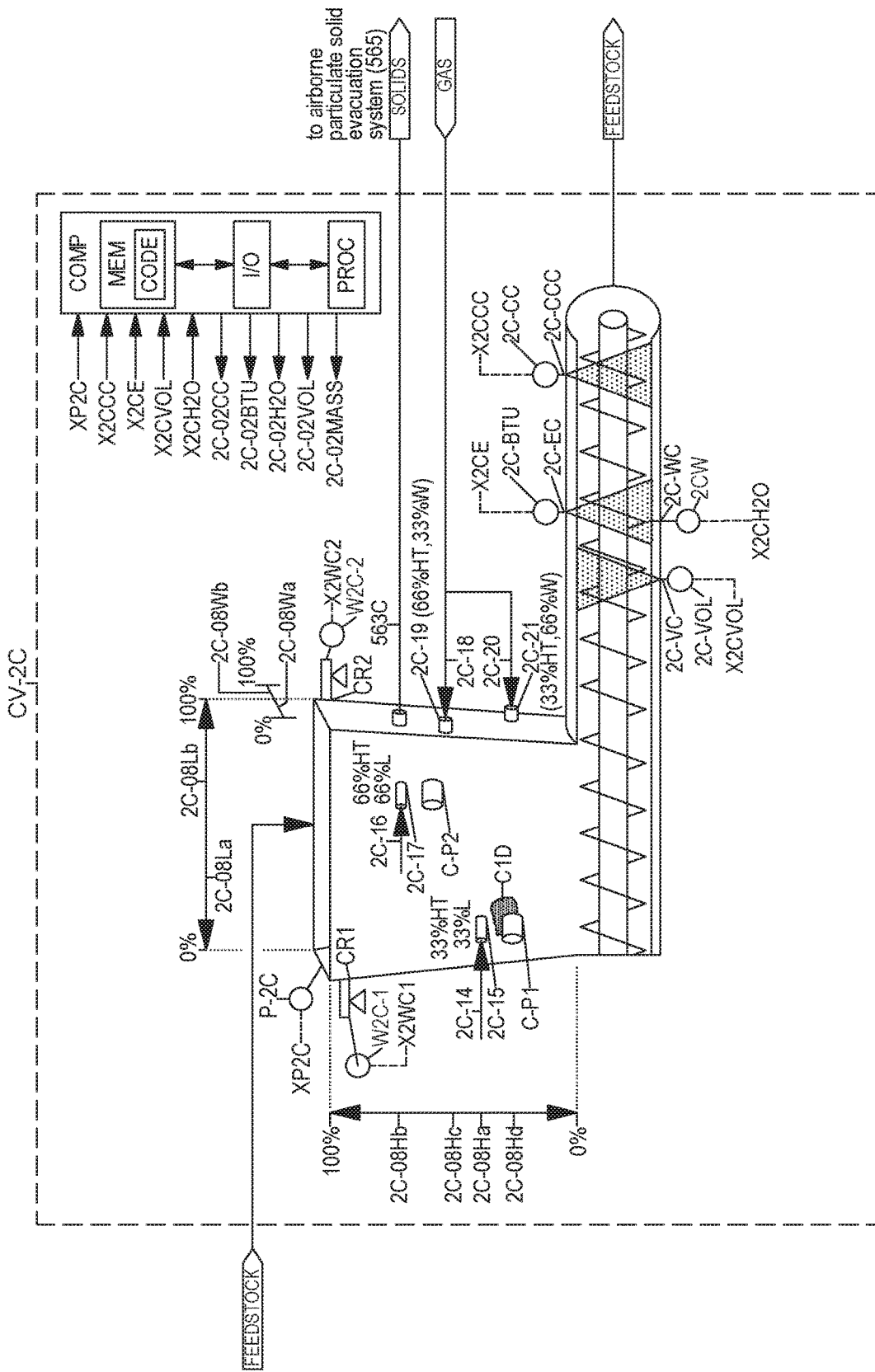
FIG. 6 elaborates upon another non-limiting embodiment of FIG. 5 further including a description of the Mass Flow Regulation (2C) subsystem or sequence step of the Feedstock Delivery System (2000).

FIG. 6:

FIG. 6 elaborates upon another non-limiting embodiment of FIG. 5 further including a description of the Mass Flow Regulation (2C) subsystem or sequence step of the Feedstock Delivery System (2000).

The embodiment of FIG. 6 displays the weigh feeder (2C1) suspended from each mass sensor (W2C-1, W2C-2). Each mass sensor (W2C-1, W2C-2) is located above the transport unit (2C-22) and is connected to the receiving unit (2C-07) via a first receiving unit connection (CR1) and a second receiving unit connection (CR2).

FIG. 6 also displays the location of the connection (C-P1C) for a first proximity sensor (C-P1) is at a first sensor height (2C-08Ha) preferably at about 33% of the height (2C-08H) of the side wall (2C-08) of the receiving unit (2C-07) and at a first sensor length (2C-08La) preferably at about 33% of the length (2C-08L) of the side wall (2C-08) of the receiving unit (2C-07).

The location of the connection (C-P2C) for a second proximity sensor (C-P2) is at a second sensor height (2C-08Hb) preferably at about 66% of the height (2C-08H) of the side wall (2C-08) of the receiving unit (2C-07) and at a second sensor length (2C-08Lb) preferably at about 66% of the length (2C-08L) of the side wall (2C-08) of the receiving unit (2C-07).

FIG. 6 displays the location of the third gas connection (2C-19) in a side wall (2C-08) of a rectangular receiving unit (2C-07) at a third gas connection height (2C-08Hc) and a third gas connection width (2C-08Wa). The third gas supply height (2C-08Hc) is preferably at about 66% of the height (2C-08H) of the side wall (2C-08) of the receiving unit (2C-07). The third gas supply width (2C-08Ha) is preferably at about 33% of the height (2C-08H) of the side wall (2C-08) of the receiving unit (2C-07).

FIG. 6 displays the location of the fourth gas connection (2C-21) in a side wall (2C-08) of a rectangular receiving unit (2C-07) at a fourth gas connection height (2C-08Hd) and a fourth gas connection width (2C-08Wb). The fourth gas supply height (2C-08Hd) is preferably at about 33% of the height (2C-08H) of the side wall (2C-08) of the receiving unit (2C-07). The fourth gas supply width (2C-08Wa) is preferably at about 66% of the height (2C-08H) of the side wall (2C-08) of the receiving unit (2C-07).

FIG. 6 displays the weigh feeder (2C1) equipped with a carbon content measurement unit (2C-CC), energy content measurement unit (2C-BTU), volatiles content measurement unit (2C-VOL), water content measurement unit (2CW), and pressure sensor (P-2C).

Specifically, the transport unit (2C-22) is equipped with a connection (2C-CCC) for a carbon content measurement unit (2C-CC) that is configured to analyze carbonaceous material transported from the through the weigh feeder (2C1) and send a signal (X2CCC) to the computer (COMP) to output the carbon content (2C-02CC) of the carbonaceous material (2C-02) discharged from the transport unit (2C-22).

The transport unit (2C-22) is equipped with a connection (2C-EC) for an energy content measurement unit (2C-BTU) that is configured to analyze carbonaceous material transported through the weigh feeder (2C1) and send a signal (X2CE) to the computer (COMP) to output the energy content (2C-02BTU) of the carbonaceous material (2C-02) discharged from the transport unit (2C-22).

The transport unit (2C-22) is equipped with a connection (2C-VC) for a volatiles content measurement unit (2C-VOL) that is configured to analyze carbonaceous material transported through the weigh feeder (2C1) and send a signal (X2CVOL) to the computer (COMP) to output the volatiles content (2C-02VOL) of the carbonaceous material (2C-02) discharged from the transport unit (2C-22).

The transport unit (2C-22) is equipped with a connection (2C-WC) for a water content measurement unit (2CW) that is configured to analyze carbonaceous material transported through the weigh feeder (2C1) and send a signal (X2CH2O) to the computer (COMP) to output the water content (2C-02H2O) of the carbonaceous material (2C-02) discharged from the transport unit (2C-22).

The receiving unit (2C-07) is equipped with a pressure sensor (P-2C) that is configured to measure the pressure within the interior (2C1IN) and output a signal (XP2C) to the computer (COMP).

For illustrative purposes, FIG. 6 shows dust accumulation (C1D) on the first proximity sensor (C-P1). The purpose of the first gas nozzle (2C-15) is to provide a first gas supply (2C-14) to the first proximity sensor (C-P1) to avoid and prevent dust accumulation (C1D). The presence of dust accumulation (C1D) on any portion of the first proximity sensor (C-P1) may result in a false signal (XCP1) from the first proximity sensor (C-P1) to the computer (COMP). Dust accumulation (C1D) on the first proximity sensor (C-P1) results in the signal (XCP1) to the computer (COMP) indicating that the first proximity sensor (C-P1) reads a level of carbonaceous material within the interior (2C1IN) of the receiving unit (2C-07) at a first sensor height (2C-08Hd), when in fact, it is not.

FIG. 6A:

FIG. 6A shows a non-limiting embodiment of a Mass Flow Regulation (2C) method. The following method elaborates upon the disclosure in FIG. 5 and FIG. 6.

(Step 2C:1) in a first mode of operation, the computer (COMP) sends a signal (X2B1A) to a controller (C2B1A) of the first splitter first screw conveyor motor (M2B1A) to introduce carbonaceous material (2C-01) to the weigh feeder (2C1);

(Step 2C:2) in a second mode of operation, when a signal (XCP1) is triggered from carbonaceous material being in proximity to the first proximity sensor (C-P1) the computer (COMP) sends a signal (XM2C) to controller (C-M2C) to operate a motor (M2C) to rotate a shaft (2C-26) of weigh feeder (2C1) screw conveyor (2C-25);

(Step 2C:3) in a third mode of operation, when a signal (XCP2) is triggered from carbonaceous material being in proximity to the second proximity sensor (C-P2), the computer (COMP) sends a signal (X2B1A) to controller (C2B1A) of the first splitter first screw conveyor motor (M2B1A) to discontinue introduction of carbonaceous material (2C-01) to the weigh feeder (2C1); and, (Step 2C:4) in a fourth mode of operation, when the level of carbonaceous material in weigh feeder (2C1) reaches a vertical height below both first proximity sensor (C-P1) and below the second proximity sensor (C-P2) so as to not trigger a signal (XCP1) from the first proximity sensor (C-P1) or a signal (XCP2) from the second proximity sensor (C-P2), continue to step 2C:1.

Figure 7:
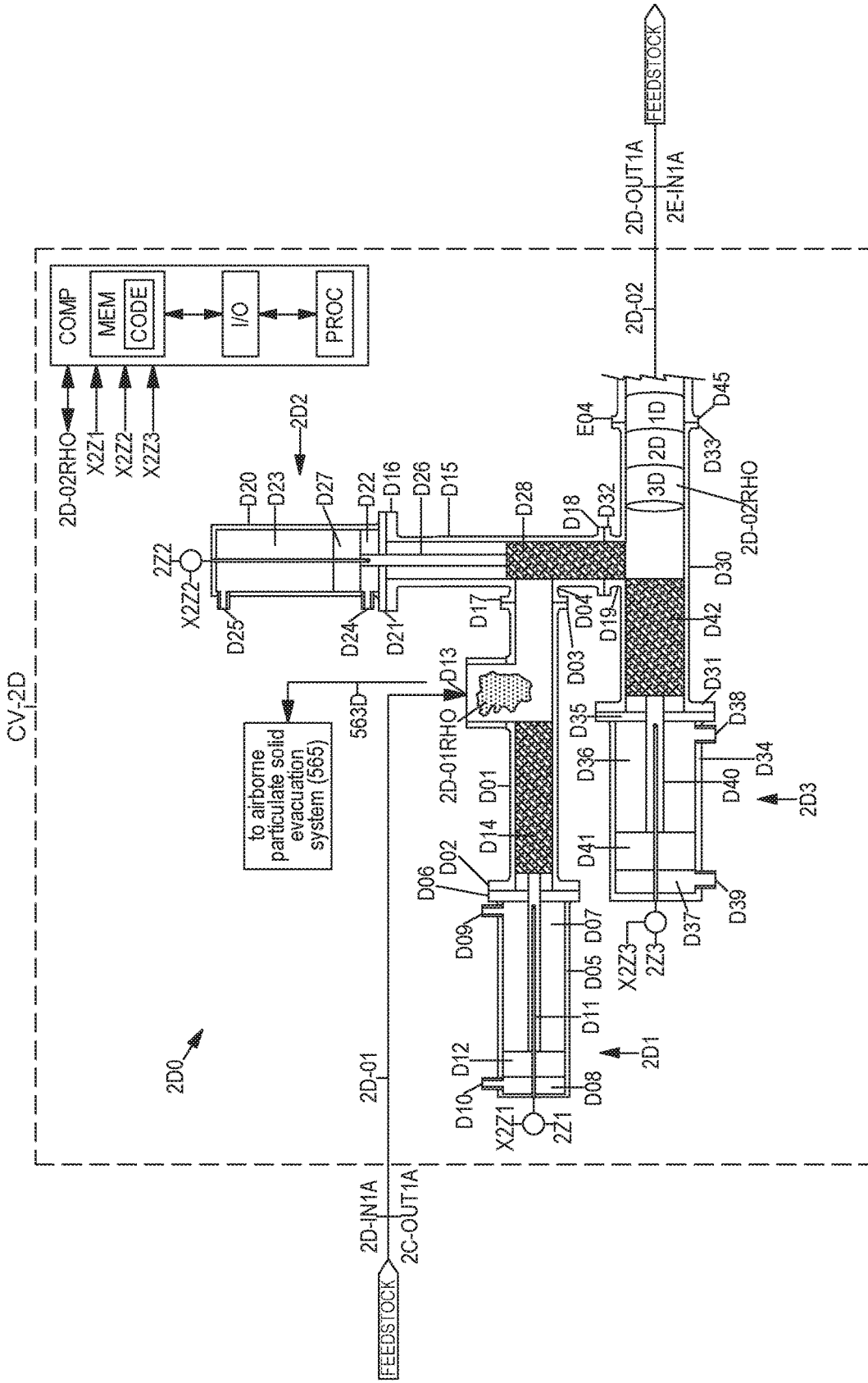
FIG. 7 elaborates upon a non-limiting embodiment of FIG. 2A further including a description of the Densification (2D) subsystem or sequence step of the Feedstock Delivery System (2000).

FIG. 7:

FIG. 7 elaborates upon a non-limiting embodiment of FIG. 2A further including a description of the Densification (2D) subsystem or sequence step of the Feedstock Delivery System (2000). FIG. 7 shows one example of a Densification (2D) subsystem accepting a carbonaceous material (2D-01) as an input (2D-IN1A) from an output (2C-OUT1A) of a Mass Flow Regulation (2C) subsystem. The Densification (2D) subsystem is shown contained within a Densification Control Volume (CV-2D). The Densification (2D) subsystem is configured to accept a carbonaceous material (2D-01) at a first lower density (2D-01RHO) via an input (2D-IN1A) and compress the carbonaceous material to discharge a densified carbonaceous material (2D-02) at a second higher density (2D-02RHO) via an output (2D-OUT1A). The densified carbonaceous material (2D-02) is then transferred via the output (2D-OUT1A) and may be routed downstream, for example, to a Plug Control (2E) subsystem via an input (2E-IN1A). The Densification (2D) subsystem of FIG. 7 includes a densification system (2D0) comprised of a first piston cylinder assembly (2D1), second piston cylinder assembly (2D2), and a third piston cylinder assembly (2D3).

In embodiments, the first lower density (2D-01rho) may range from about 4 lb/ft3 to about 14 lb/ft3 for MSW carbonaceous material (2D-01). In embodiments, the first lower density (2D-01rho) may range from about 5 lb/ft3 to about 20 lb/ft3 for other types of carbonaceous materials (2D-01), such as wood, biomass, or the like. In embodiments, the first lower density (2D-01rho) may range from about 20 lb/ft3 to about 50 lb/ft3 for cubed or briquette carbonaceous material (2D-01).

In embodiments, the carbonaceous material (2D-01) introduced to the densification system (2D0) is comprised of cubes ready for transport to be used as an energy source. In embodiments, the cubed carbonaceous material (2D-01) introduced to the densification system (2D0) may range from about 0.50 inches to about 3 inches length and formed by use of an upstream cube forming machine.

In embodiments, the cubed carbonaceous material (2D-01) introduced to the densification system (2D0) may be formed using a cubing system create a body having a substantially constant cross sectional shape along its length. Densification is an important unit operation involved in utilization of initially lower density material, because it reduces handling, storage and transportation costs. Pelleting and cubing are two prominent existing technologies used for the densification of carbonaceous material feedstocks. The cubing process allows for greater particle size in the finished product as compared to pellets produce in a conventional pellet mill. In embodiments, carbonaceous material is introduced into an upstream cubing system prior to being introduced to the densification system (2D0). Cubing systems are well known in the art and exhibit high compression pressures on the carbonaceous material from about 1,000 PSIG to about 6,000 PSIG as the material to be cubed enters the series of dies to create an effective product which is extruded through the dies. Preferably the carbonaceous material introduced to the densification system (2D0) is first cubed using a substantially square die to form an extruded body of square cross-section and square flakes. However, advancement in the cubing dies may reveal that it is our preference to form an extruded body of circular cross-section using a substantially circular die to form an extruded body of circular cross-section and circular flakes. However, the die could be also any other shape.

In embodiments, each plug (1D, 2D, 3D, 4D, 5D, 6D) of densified carbonaceous material (2D-02) at a second higher density (2D-02rho) has a length of about 10 inches to 15 inches. In embodiments, each plug (1D, 2D, 3D, 4D, 5D, 6D) of densified carbonaceous material (2D-02) at a second higher density (2D-02rho) has a diameter of about 10 inches to 15 inches. In embodiments, each plug (1D, 2D, 3D, 4D, 5D, 6D) of densified carbonaceous material (2D-02) at a second higher density (2D-02rho) has a length to diameter ratio of less than 1.5.

The first piston cylinder assembly (2D1) includes a first cylinder (D01), having a first cylinder first flange (D02), first cylinder second flange (D03) connected to a first cylindrical pipe branch opening (D04). The first piston cylinder assembly (2D1) also includes a first hydraulic cylinder (D05), having a first hydraulic cylinder flange (D06), first hydraulic cylinder front cylinder space (D07), first hydraulic cylinder rear cylinder space (D08), first hydraulic cylinder front connection port (D09), and a first hydraulic cylinder rear connection port (D10). A first rod (D11) is connected to the first piston (D12) that reciprocates inside of the first hydraulic cylinder (D05). A first ram (D14) is connected to the first rod (D11) and is configured to reciprocate inside of the first cylinder (D01). A first piston rod linear transducer (2Z1) is connected to the first hydraulic cylinder rear cylinder space (D08) of the first hydraulic cylinder (D05) to ascertain the position of the reciprocating first piston (D12) within the first hydraulic cylinder (D05).

The first piston rod linear transducer (2Z1) is configured to output a signal (X2Z1) to the computer (COMP) to permit carbonaceous material (2D-01) to be transferred to the first piston cylinder assembly (2D1) in front of the first ram (D14) only when the first ram (D14) is in the retracted position. A densifier input (D13) is configured to introduce carbonaceous material (2D-01) to the first piston cylinder assembly (2D1) in front of the first ram (D14). The first cylinder first flange (D02) of the first cylinder (D01) is connected to the first hydraulic cylinder flange (D06) of the first hydraulic cylinder (D05).

The second piston cylinder assembly (2D2) includes a second cylinder (D15), having a second cylinder first flange (D16), second cylinder second flange (D17), second cylinder third flange (D18) connected to a second cylindrical pipe branch opening (D19). The second piston cylinder assembly (2D2) also includes a second hydraulic cylinder (D20), having a second hydraulic cylinder flange (D21), second hydraulic cylinder front cylinder space (D22), second hydraulic cylinder rear cylinder space (D23), second hydraulic cylinder front connection port (D24), and a second hydraulic cylinder rear connection port (D25). A second rod (D26) is connected to a second piston (D27) that reciprocates inside of the second hydraulic cylinder (D20). A second ram (D28) is connected to the second rod (D26) and is configured to reciprocate inside of the second cylinder (D15).

A second piston rod linear transducer (2Z2) is connected to the second hydraulic cylinder rear cylinder space (D23) of the second hydraulic cylinder (D20) to ascertain the position of the reciprocating second piston (D27) within the second hydraulic cylinder (D20). The second piston rod linear transducer (2Z2) is configured to output a signal (X2Z2) to the computer (COMP) to permit carbonaceous material to be transferred to the second piston cylinder assembly (2D2) in front of the second ram (D26) only when the second ram (D26) is in the retracted position.

A first cylindrical pipe branch opening (D04) is configured to introduce carbonaceous material from the first piston cylinder assembly (2D1) to the second piston cylinder assembly (2D2) in front of the second ram (D28). The first cylinder second flange (D03) of the first cylinder (D01) is connected to the second cylinder second flange (D17) of the second cylinder (D15). The second cylinder first flange (D16) of the second cylinder (D15) is connected to the second hydraulic cylinder flange (D21) of the second hydraulic cylinder (D20). The second cylinder third flange (D18) of the second cylinder (D15) is connected to the third cylinder second flange (D32) of the third cylinder (D30). A second cylindrical pipe branch opening (D19) is configured to introduce carbonaceous material from the second piston cylinder assembly (2D2) to the third piston cylinder assembly (2D3) in front of the third ram (D42).

The third piston cylinder assembly (2D3) includes a third cylinder (D30), having a third cylinder first flange (D31), third cylinder second flange (D32), and a third cylinder third flange (D33). The third piston cylinder assembly (2D3) also includes a third hydraulic cylinder (D34), having a third hydraulic cylinder flange (D35), third hydraulic cylinder front cylinder space (D36), third hydraulic cylinder rear cylinder space (D37), third hydraulic cylinder front connection port (D38), and a third hydraulic cylinder rear connection port (D39). A third rod (D40) is connected to a third piston (D41) that reciprocates inside of the third hydraulic cylinder (D34). A third ram (D42) is connected to the third rod (D40) and is configured to reciprocate inside of the third cylinder (D30).

A third piston rod linear transducer (2Z3) is connected to the third hydraulic cylinder rear cylinder space (D37) of the third hydraulic cylinder (D34) to ascertain the position of the reciprocating third piston (D41) within the third hydraulic cylinder (D34). The third piston rod linear transducer (2Z3) is configured to output a signal (X2Z3) to the computer (COMP) to permit carbonaceous material to be transferred to the third piston cylinder assembly (2D3) in front of the third ram (D42) only when the third ram (D42) is in the retracted position.

A second cylindrical pipe branch opening (D19) is configured to introduce carbonaceous material from the second piston cylinder assembly (2D2) to the third piston cylinder assembly (2D3) in front of the third ram (D42). The third cylinder first flange (D31) of the third cylinder (D30) is connected to the third hydraulic cylinder flange (D35) of the third hydraulic cylinder (D34). The third cylinder third flange (D33) or the densifier output (D45) of the third cylinder (D30) is connected to the plug control assembly first flange (E04) of a downstream Plug Control (2E) subsystem (not shown). The reciprocating action of the third ram (D42) within the third cylinder (D30) is configured to form a series of plugs (1D, 2D, 2D) that are contained within the third cylinder (D30) and form a pressure seal between the densifier input (D13) and the densifier output (D45). The Densification (2D) subsystem is configured to develop multiple high density plugs that are gas tight. Therefore, the plugs (1D, 2D, 3D) create a pressure seal or boundary between downstream densifier output (D45) and the densifier input (D13).

In embodiments, the first cylinder first flange (D02) may be connected to the first hydraulic cylinder flange (D06) via slender structural units used as a tie and capable of carrying tensile loads, such as a tie-rod. In embodiments, the second cylinder first flange (D16) may be connected to the second hydraulic cylinder flange (D21) via slender structural units used as a tie and capable of carrying tensile loads, such as a tie-rod. In embodiments, the third cylinder first flange (D31) may be connected to the third hydraulic cylinder flange (D35) via slender structural units used as a tie and capable of carrying tensile loads, such as a tie-rod. Tie rods may be connected at the ends in various ways known to persons having an ordinary skill in the art to which it pertains, but it is desirable that the strength of the connection should be at least equal to the strength of the rod. The ends may be threaded and passed through drilled holes or shackles and retained by nuts screwed on the ends.

FIG. 36 presents Table 1: Nominal Design Parameters Case 1: Normal Throughput for a 500 Dry MSW Carbonaceous Material Ton Per Day Feedstock Delivery System. FIG. 37 presents Table 2: Maximum Throughput for a 500 Dry MSW Carbonaceous Material Ton Per Day Feedstock Delivery System.

Figure 7A:
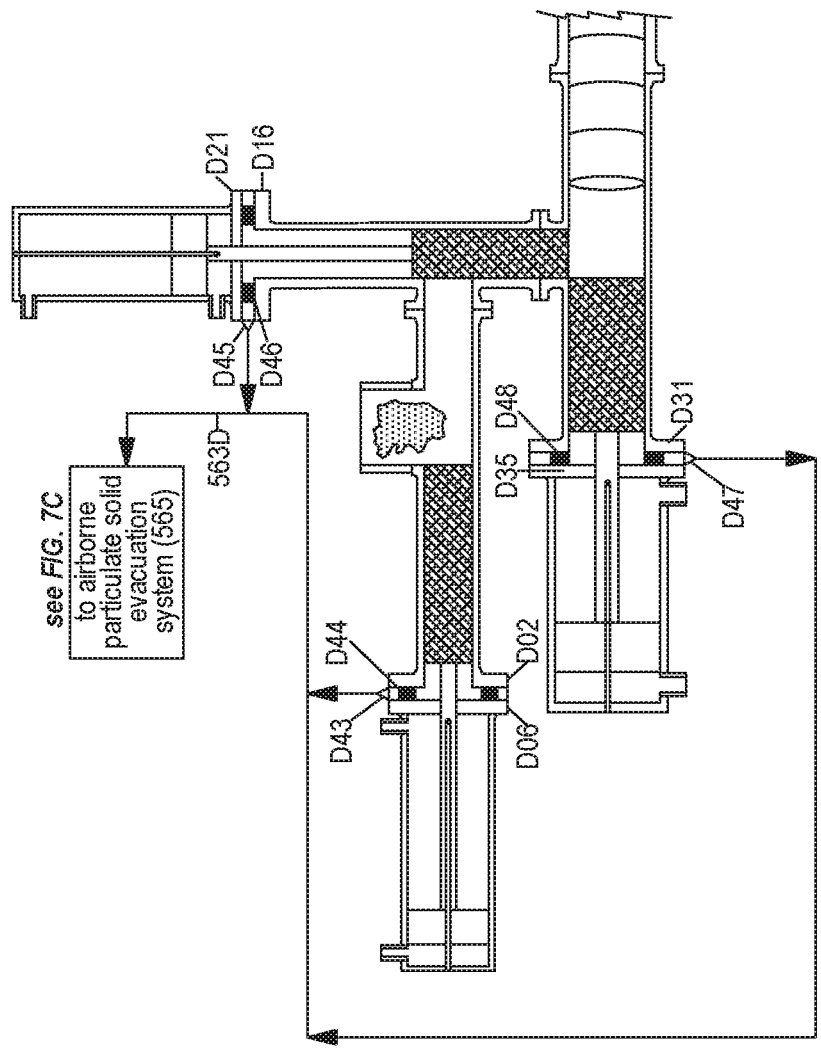
FIG. 7A elaborates upon a non-limiting embodiment of FIG. 7 wherein the Densification (2D) subsystem or sequence step is in fluid communication with an airborne particulate solid evacuation system (565) via a densification entry conduit (563D).

FIG. 7A:

FIG. 7A elaborates upon a non-limiting embodiment of FIG. 7 wherein the Densification (2D) subsystem or sequence step is in fluid communication with an airborne particulate solid evacuation system (565) via a densification entry conduit (563D). The airborne particulate solid evacuation system (565) is described in the detail in the text below and accompanied FIG. 17.

FIG. 7A shows a densification entry conduit (563D) equipped to capture airborne particulate solids from the vicinity around each densification system (2D0). Specifically, airborne particulate solids may be removed via the densification entry conduit (563D) from the air surrounding each densifier input (D13) or at the transitions between the (i) first cylinder first flange (D02) and first hydraulic cylinder flange (D06); (ii) second cylinder first flange (D16) and second hydraulic cylinder flange (D21); (iii) third cylinder first flange (D31) and third hydraulic cylinder flange (D35).

To mitigate against the risks of fire or deflagration hazards associated with particulate solids suspended in air, active dust or particulate solid evacuation methods are implemented and described. The airborne particulate solid evacuation system (565) captures airborne particulate solids that would ordinarily escape from the perimeter of the operating equipment of the Densification (2D) subsystem.

The high velocity densification entry conduit (563D) operates at a capture velocity sufficient to allow airborne particulate solids to be captured and drawn into the airborne particulate solid evacuation system (565). In embodiments, the densification entry conduit (563D) operates within a velocity pressure range from about 0.10 inches of water to about 1.50 inches of water. In embodiments, the densification entry conduit (563D) operates with velocity ranging from about 100 feet per minute to about 5000 feet per minute.

The densification entry conduit (563D) operates within a velocity pressure range sufficient to pull away fine dust or particulate solids from behind either of the first ram (D14), second ram (D28), of third ram (D42). Shut down will be required if fine dust or particulate solids migrate to and build up behind either the first ram (D14), second ram (D28), of third ram (D42). Eventually as the pistons (2D1, 2D2, 2 D3) cycle through advancement and retraction modes of operations, fine dust or particulate solids migrate to and build up behind either the first ram (D14), second ram (D28), of third ram (D42) requiring the system to be taken apart and cleaned out wasting precious time. Thus, eventually, fine dust or particulate solids migrate to and build up behind either the first ram (D14), second ram (D28), of third ram (D42) prevents each pistons (2D1, 2D2, 2 D3) to fully retract. Fine dust or particulate solids accumulate in the following areas about the vicinity around each densification system (2D0): (i) the first ram (D14) and upon the surface of the first hydraulic cylinder flange (D06); (ii) the second ram (D28) and upon the surface of the second hydraulic cylinder flange (D21); (iii) the third ram (D42) and upon the surface of the third hydraulic cylinder flange (D35).

FIG. 7A shows a densification entry conduit (563D) in fluid communication with a first ram particulate solids evacuation port (D43), a second ram particulate solids evacuation port (D45), and, a third ram particulate solids evacuation port (D47). A first flange support (D44) is provided in between the first cylinder first flange (D02) and first hydraulic cylinder flange (D06) so as to provide secure connection while permitting fine dust or particulate solids to be drawn through the first ram particulate solids evacuation port (D43) and to prevent their accumulation behind the first ram (D14) and upon the surface of the first hydraulic cylinder flange (D06). A second flange support (D46) is provided in between the second cylinder first flange (D16) and second hydraulic cylinder flange (D21) so as to provide secure connection while permitting fine dust or particulate solids to be drawn through the second ram particulate solids evacuation port (D45) and to prevent their accumulation behind the second ram (D28) and upon the surface of the second hydraulic cylinder flange (D21). A third flange support (D48) is provided in between the third cylinder first flange (D31) and third hydraulic cylinder flange (D35) so as to provide secure connection while permitting fine dust or particulate solids to be drawn through the third ram particulate solids evacuation port (D47) and to prevent their accumulation behind the third ram (D42) and upon the surface of the third hydraulic cylinder flange (D35).

FIG. 7B:

FIG. 7B elaborates upon a non-limiting embodiment of FIG. 7A further including a detailed three dimensional view of a first flange support (D44) that may be placed in between the first cylinder first flange (D02) and the first hydraulic cylinder flange (D06). The first ram particulate solids evacuation port (D43) is in fluid communication with the densification entry conduit (563D) which evacuates solids from behind the first ram (D14). The flange support (D44) allows the first cylinder first flange (D02) and the first hydraulic cylinder flange (D06) to be connected to one another. The first ram particulate solids evacuation port (D43) allows for solids to be transferred from the first cylinder (D01) and into the airborne particulate solid evacuation system (565). Each of the second ram particulate solids evacuation port (D45), second flange support (D46), third ram particulate solids evacuation port (D47), and third flange support (D48) are similar to the first ram particulate solids evacuation port (D43) and first flange support (D44) shown in FIG. 7B.

FIG. 7C:

FIG. 7C shows the entry conduit (563) of the airborne particulate solid evacuation system (565) connected to a network of conduits including the bulk transfer entry conduit (563A), flow splitting entry conduit (563B), flow splitting entry conduit (563BA), mass flow regulation entry conduit (563C), densification entry conduit (563D), and the solids transfer entry conduit (563E).

FIG. 7C depicts an airborne particulate solid evacuation system (565) configured to remove particulate solids from a variety of areas of the Feedstock Delivery System (2000) and Product Gas Generation System (3000). In embodiments, the airborne particulate solid evacuation system (565) is configured to remove particulate solids suspended in the air from various areas of the Feedstock Delivery System (2000) and Product Gas Generation System (3000).

To mitigate against the risks of fire or deflagration hazards associated with particulate solids suspended in air, active dust or particulate solid evacuation methods are implemented and described. The airborne particulate solid evacuation system (565) captures airborne particulate solids that would ordinarily escape from the operating equipment of the Feedstock Delivery System (2000) and Product Gas Generation System (3000).

The airborne particulate solid evacuation system (565) employs a high velocity entry conduit (563), a filter (566), and a fan (567) driven by a motor (568). A valve (569) is provided to remove solid particulates (574) that were filtered out from the gas phase. A transport unit (577) such as a conveyor, screw auger, belt, bucket elevator, or the like may be employed to transport the filtered solids away from the airborne particulate solid evacuation system (565).

Active dust or particulate solid evacuation methods are employed about the Bulk Transfer (2A), Flow Splitting (2B), Mass Flow Regulation (2C), Densification (2D) subsystems of the Feedstock Delivery System (2000). Further, particulate solid evacuation methods are employed in the Product Gas Generation System (3000), specifically the solids transfer conduit (234) discharged from the second solids separation device (250). Active airborne particulate solid evacuation methods include the use of ducting provided to a high velocity entry conduit (563) collecting the airborne particulate solids.

The high velocity entry conduit (563) operates at a capture velocity sufficient to allow airborne particulate solids to be captured and drawn into the airborne particulate solid evacuation system (565). In embodiments, the entry conduit (563) operates within a velocity pressure range from about 0.10 inches of water to about 1.50 inches of water. In embodiments, the entry conduit (563) operates with velocity ranging from about 100 feet per minute to about 5000 feet per minute.

The airborne particulate solid evacuation system (565) captures airborne particulate solids from a variety of locations throughout the Feedstock Delivery System (2000) and Product Gas Generation System (3000), including: (i) the Bulk Transfer (2A) subsystem via a bulk transfer entry conduit (563A) as depicted in FIG. 3; (ii) the Flow Splitting (2B) subsystem via a flow splitting entry conduit (563B) as depicted in FIG. 4; (iii) the Mass Flow Regulation (2C) subsystem via a mass flow regulation entry conduit (563C) as depicted in FIG. 6; (iv) the Densification (2D) subsystem via a densification entry conduit (563D) as depicted in FIG. 7 and FIG. 7A; and, (v) the Second Stage Product Gas Generation System (3B) via a solids transfer entry conduit (563E) as depicted in FIG. 26 through which a portion (233) of the second reactor separated solids (232) flows through.

The bulk transfer entry conduit (563A) captures airborne particulate solids from the transport assembly (2A-03). The flow splitting entry conduit (563B) captures airborne particulate solids from the first splitter (2B1) and second splitter (2B2). Specifically, airborne particulate solids are shown in FIG. 4 to be removed via the flow splitting entry conduit (563B) from the first splitter (2B1) and the flow splitting entry conduit (563BA) from the second splitter (2B2).

Airborne particulate solids may also be removed via the flow splitting entry conduits (563B, 563BA) from the first output (2B-07), second output (2B-09), and third output (2B-11) of the first splitter (2B1) and the first output (2B-16), second output (2B-18), and third output (2B-20) of the second splitter (2A2).

The mass flow regulation entry conduit (563C) captures airborne particulate solids from each weigh feeder (2C1). Specifically, airborne particulate solids may be removed via the mass flow regulation entry conduit (563C) from receiving unit (2C-07) of each weigh feeder (2C1).

The densification entry conduit (563D) captures airborne particulate solids from the vicinity around each densification system (2D0). Specifically, airborne particulate solids may be removed via the densification entry conduit (563D) from the transitions between the (i) first cylinder first flange (D02) and first hydraulic cylinder flange (D06); (ii) second cylinder first flange (D16) and second hydraulic cylinder flange (D21); (iii) third cylinder first flange (D31) and third hydraulic cylinder flange (D35).

The solids transfer entry conduit (563E) captures airborne particulate solids from the second solids separation device (250) and solids transfer conduit (234). Specifically, airborne particulate solids may be removed via the solids transfer entry conduit (563E) from the solids transfer conduit (234) with a specific focus on removal of airborne particulate solids from valves which may be positioned in the solids transfer conduit (234) that regulate the flow of second reactor separated solids (232).

In embodiments, particulate solids may be in the form of dust from the carbonaceous material within the Feedstock Delivery System (2000). Particulate solids may be in the form of dust from the carbonaceous material within the Bulk Transfer (2A), Flow Splitting (2B), Mass Flow Regulation (2C), Densification (2D) subsystems of the Feedstock Delivery System (2000). In embodiments, particulate solids may be ash or char contained within the portion (233) of the second reactor separated solids (232) discharged from the second solids separation device (250) and solids transfer conduit (234) as shown on FIG. 26. A portion (233) of the second reactor separated solids (232) from the second solids separation device (250) and solids transfer conduit (234) may be routed to the airborne particulate solid evacuation system (565) as shown on FIG. 7C and FIG. 26.

The airborne particulate solid evacuation system (565) is comprised of an entry conduit (563), a filter (566), a fan (567) driven by a motor (568), and a valve (569) in fluid communication with a transport unit (577). The filter (566) includes an entry section (566A) and an exit section (566B). The particulate solids that enter the filter (566) are retained within the entry section (566A). Based on size exclusion, the openings of the filter do not permit the particulate solids to pass into from the entry section (566A) to the exit section (566B). A differential pressure sensor (571) is equipped to measure the pressure difference between the entry section (566A) and an exit section (566B) across the filter (566).

A particulate solid laden gas (572) enters the entry section (566A) of the filter (566). The particulate solid laden gas (572) is comprised of a particulate solid portion (574A) and a gas portion (574B). The particulate solid portion (574A) can be dust or particulate solids from the carbonaceous material within the Feedstock Delivery System (2000). The particulate solid portion (574A) may be combustible. The particulate solids portion (574A) may be ash or char contained within the portion (233) of the second reactor separated solids (232) provided from the second solids separation device (250) and solids transfer conduit (234) as shown on FIG. 26. The embodiment of FIG. 7C shows the gas portion (574B) to be air.

The gas portion (574B) of the of the particulate solid laden gas (572) is transferred through the filter (566) from the entry section (566A) to the exit section (566B). The gas portion (574B) is a particulate solid depleted gas (573) since it has a lesser amount of particulate solids in relation to the particulate solid laden gas (572) that enters the entry section (566A) of the filter (566).

The particulate solids portion (574A) of the particulate solid laden gas (572) is retained within the entry section (566A) of the filter (566). A particulate solid depleted gas (573) is discharged from the exit section (566B) of the filter (566) and vented to a safe location. The filtered particulate solids portion (574A) of the particulate solid laden gas (572) that is retained within the entry section (566A) may be removed via an entry section output (576) via a valve (567) and transport unit (577).

In embodiments, each of the bulk transfer entry conduit (563A), flow splitting entry conduit (563B), flow splitting entry conduit (563BA), mass flow regulation entry conduit (563C), densification entry conduit (563D), and the solids transfer entry conduit (563E) operate within a velocity pressure range from about 0.10 inches of water to about 1.50 inches of water. In embodiments, each of the bulk transfer entry conduit (563A), flow splitting entry conduit (563B), flow splitting entry conduit (563BA), mass flow regulation entry conduit (563C), densification entry conduit (563D), and the solids transfer entry conduit (563E) operate with velocity ranging from about 100 feet per minute to about 5000 feet per minute.

Figure 8:
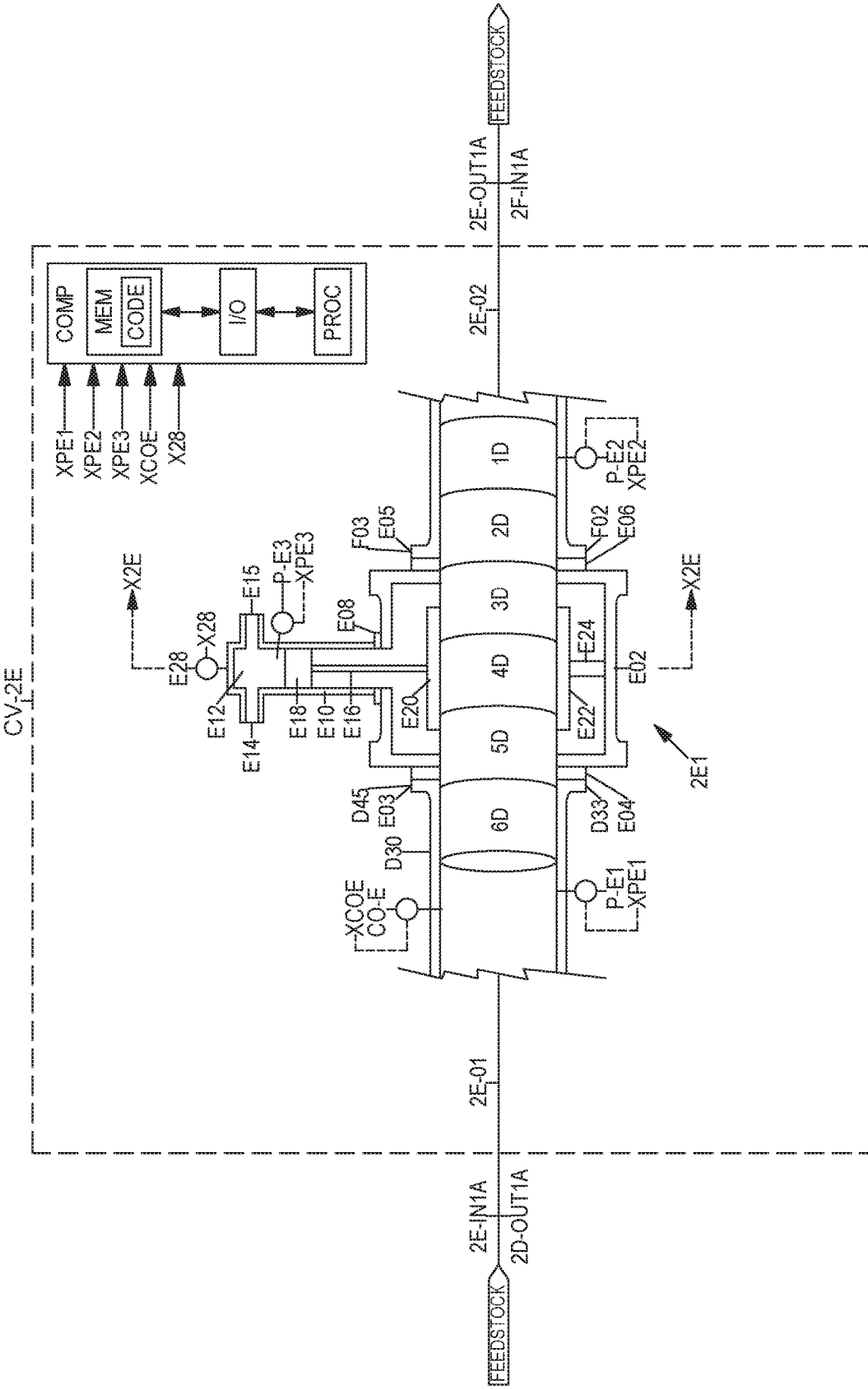
FIG. 8 elaborates upon the non-limiting embodiment of FIG. 2A further including a description of the Plug Control (2E) subsystem or sequence step of the Feedstock Delivery System (2000).

FIG. 8:

FIG. 8 elaborates upon the non-limiting embodiment of FIG. 2A further including a description of the Plug Control (2E) subsystem or sequence step of the Feedstock Delivery System (2000). FIG. 8 shows one example of a Plug Control (2E) subsystem accepting a carbonaceous material (2E-01) as an input (2E-IN1A) from an output (2D-OUT1A) of a Densification (2D) subsystem. The Plug Control (2E) subsystem is shown contained within a Plug Control Control Volume (CV-2E).

The Plug Control (2E) subsystem is configured to accept a plug (1D, 2D, 3D, 4D, 5D, 6D) of carbonaceous material and exert a force upon the plug (1D, 2D, 3D, 4D, 5D, 6D) to hold it in place while subsequent plugs are formed as they are compressed up against the plug (1D, 2D, 3D, 4D, 5D, 6D) that has said force exerted upon. The Plug Control (2E) subsystem is configured to accept a plug (1D, 2D, 3D, 4D, 5D, 6D) of carbonaceous material and exert a force upon the plug (1D, 2D, 3D, 4D, 5D, 6D) to hold it in place while a first subsequent material (D+1) is compressed up against the plug (1D, 2D, 3D, 4D, 5D, 6D) that has said force exerted upon. As a plug is made from the first subsequent material (D+1), the Plug Control (2E) subsystem is configured to exert a force upon the plug formed from the first subsequent material (D+1) to hold it in place while a second subsequent material (D+2) is compressed up against the plug formed from the first subsequent material (D+1) that has a force exerted upon.

The Plug Control (2E) is configured to accept a plug (1D, 2D, 3D, 4D, 5D, 6D) of carbonaceous material (2E-01) via an input (2E-IN1A), exert a force upon the plug (1D, 2D, 3D, 4D, 5D, 6D) by use of a plug control system (2E1), and discharge the carbonaceous material (2E-02) via an output (2E-OUT1A) for transfer downstream to an input (2F-IN1A) of a Density Reduction (2F) subsystem (not shown).

The Plug Control (2E) subsystem of FIG. 8 includes a plug control system (2E1) having a plug control cylinder (E02) with a plug control assembly first flange (E04), plug control assembly second flange (E06), and a plug control assembly third flange (E08). The plug control assembly first flange (E04) is the plug control input (E03). The plug control assembly third flange (E08) is the plug control output (E05).

The Plug Control (2E) subsystem of FIG. 8 also includes a plug control hydraulic cylinder (E10) with a plug control hydraulic cylinder rear cylinder space (E12), plug control hydraulic cylinder rear connection port (E14), and a plug control hydraulic cylinder drain port (E15). A plug control rod (E16) is connected to the plug control piston (E18) that reciprocates inside of the plug control hydraulic cylinder (E10). A ram (E20) is connected to the plug control rod (E16) and is configured to reciprocate inside of the plug control cylinder (E02) and exert a force upon at least one plug (1D, 2D, 3D, 4D, 5D, 6D) contained within the plug control cylinder (E02).

A plug control rod linear transducer (E28) is connected to the plug control hydraulic cylinder rear cylinder space (E12) of the plug control hydraulic cylinder (E10) to ascertain the position of the reciprocating plug control piston (E18) within the plug control hydraulic cylinder (E10). Each of the plugs (1D, 2D, 3D, 4D, 5D, 6D) passing from the plug control input (E03) to the plug control output (E05) comes into contact with a plug guide (E22). The plug guide (E22) is connected to a plug guide support (E24) which is in turn connected to the plug control cylinder (E02). The plug control assembly first flange (E04) is connected to the upstream third cylinder third flange (D33). The plug control assembly second flange (E06) is connected to a downstream density reduction system first flange (F02). The plug control assembly third flange (E08) is connected to the plug control hydraulic cylinder (E10).

Figure 8A:
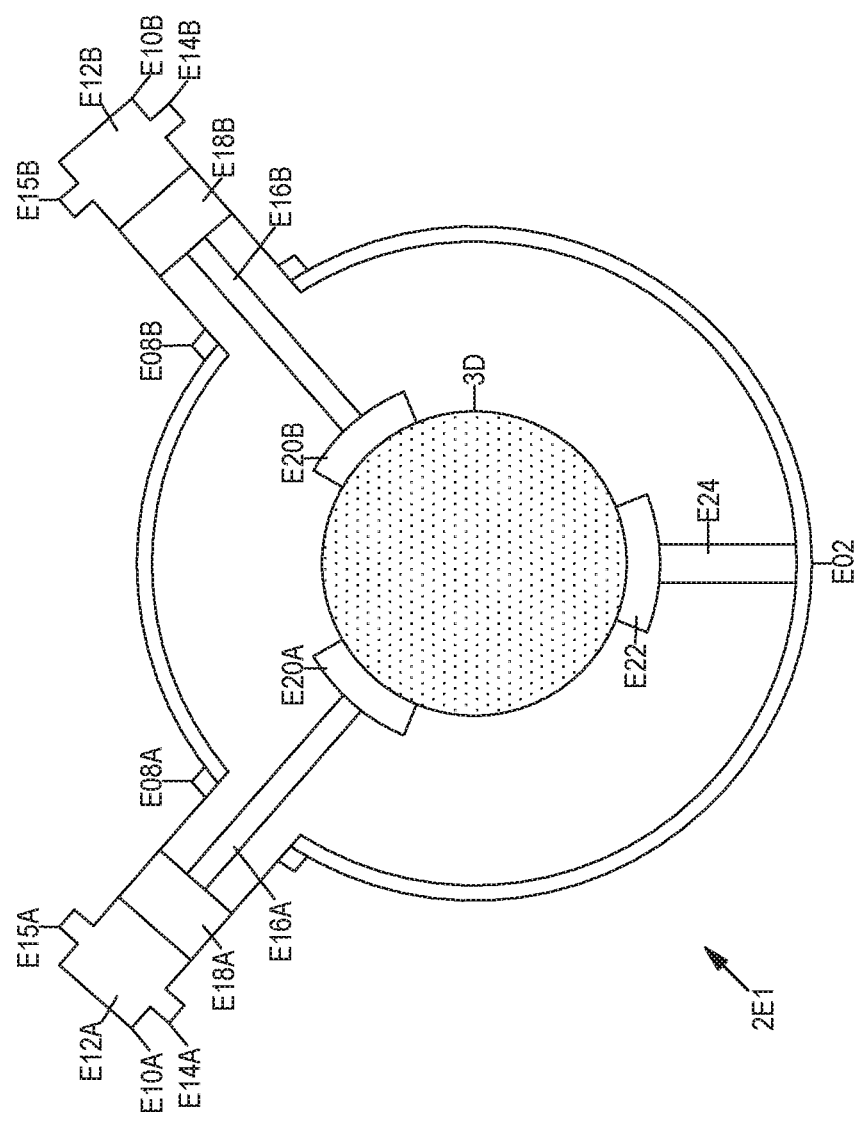
FIG. 8A elaborates upon a non-limiting embodiment of FIG. 8 further including plug control cross-sectional view (X2E) of one embodiment of a Plug Control (2E) subsystem or sequence step of the Feedstock Delivery System (2000).

A first pressure sensor (P-E1) is proximate the plug control assembly first flange (E04) and is configured to output a signal (XPE1) to the computer (COMP). A second pressure sensor (P-E2) is proximate the plug control assembly second flange (E06) and is configured to output a signal (XPE2) to the computer (COMP). A third pressure sensor (P-E3) is connected to the plug control hydraulic cylinder rear cylinder space (E12) of the plug control hydraulic cylinder (E10) and is configured to output a signal (XPE3) to the computer (COMP). In embodiments, the difference in the signal (XPE1) from the first pressure sensor (P-E1) and the signal (XPE2) from the second pressure sensor (P-E2) is the difference between atmospheric pressure and the first reactor pressure (P-A). In embodiments, the difference in the signal (XPE1) from the first pressure sensor (P-E1) and the signal (XPE2) ranges from about 9 PSID to about 75 PSID. In embodiments, the pressure drop across the plurality of plugs (1D, 2D, 3D) ranges from about 9 PSID to about 75 PSID. A carbon monoxide sensor (CO-E) is proximate the plug control assembly first flange (E04) and is configured to output a signal (XCOE) to the computer (COMP). FIG. 8A refers to plug control cross-sectional view (X2E).

The force exerted by the ram (E20, E20A, E20B) must hold plugs in position and create a stop against which the last plug is formed. The force exerted by the ram (E20, E20A, E20B) on the plugs must also be greater than the force exerted by the advancement of the third ram (D42) to resist the forces of the plug forming third piston (D41). The advancement of the ram (E20, E20A, E20B) is configured to momentarily open, allowing the third pressing piston (D41) to advance the line of plugs (1D, 2D, 3D, 4D, 5D, 6D), expelling last plug (1D) from the plug control system (2E1).

FIG. 8A:

FIG. 8A elaborates upon a non-limiting embodiment of FIG. 8 further including plug control cross-sectional view (X2E) of one embodiment of a Plug Control (2E) subsystem or sequence step of the Feedstock Delivery System (2000).

FIG. 8A depicts one embodiment of a plug control cross-sectional view (X2E) including a plug control cylinder (E02), having a plug guide (E22), plug guide support (E24), and a plurality of plug control hydraulic cylinders (E10A, E10B) having a plurality of plug control rods (E16A, E16B) that are operatively in communication with at least one plug (3D) passing through the plug control system (2E1).

A first plug control assembly third flange (E08A) connects the first plug control hydraulic cylinder (E10A) to the plug control cylinder (E02). The first plug control hydraulic cylinder (E10A) is comprised of a first plug control hydraulic cylinder rear cylinder space (E12A), first plug control hydraulic cylinder rear connection port (E14A), and a first plug control hydraulic cylinder drain port (E15A). A first plug control rod (E16A) is connected to a first plug control piston (E18A) that reciprocates inside of the first plug control hydraulic cylinder (E10A). A first ram (E20A) is connected to the first plug control rod (E16A) and is configured to reciprocate inside of the plug control cylinder (E02) and exert a force upon at least one plug (1D, 2D, 3D, 4D, 5D, 6D) contained within the plug control cylinder (E02).

A second plug control assembly third flange (E08B) connects the second plug control hydraulic cylinder (E10B) to the plug control cylinder (E02). The second plug control hydraulic cylinder (E10B) is comprised of a second plug control hydraulic cylinder rear cylinder space (E12B), second plug control hydraulic cylinder rear connection port (E14B), and a second plug control hydraulic cylinder drain port (E15B). A second plug control rod (E16B) is connected to a second plug control piston (E18B) that reciprocates inside of the second plug control hydraulic cylinder (E10B). A second ram (E20B) is connected to the second plug control rod (E16B) and is configured to reciprocate inside of the plug control cylinder (E02) and exert a force upon at least one plug (1D, 2D, 3D, 4D, 5D, 6D) contained within the plug control cylinder (E02).

Figure 9:
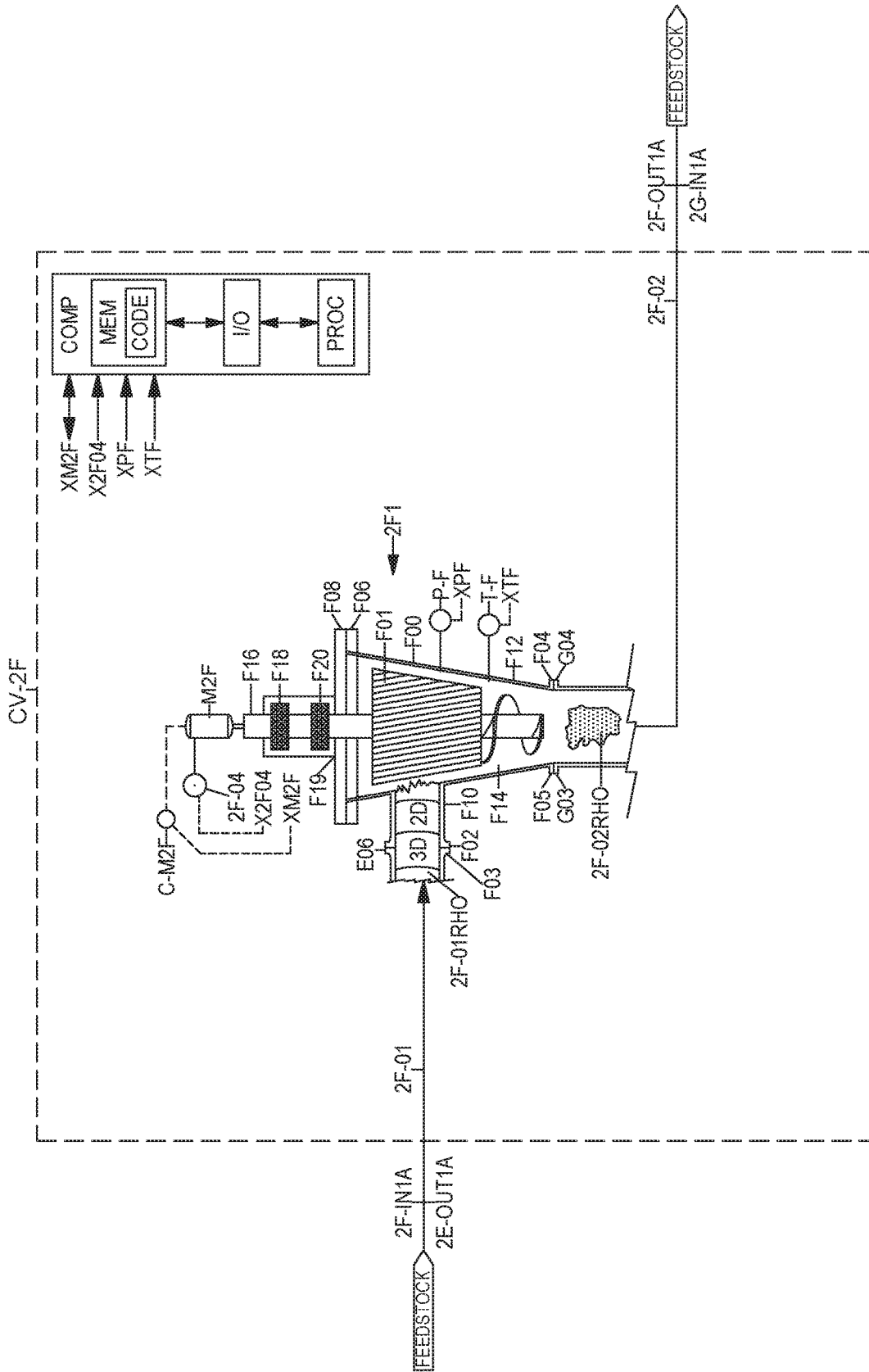
FIG. 9 elaborates upon the non-limiting embodiment of FIG. 2A further including a description of the Density Reduction (2F) subsystem or sequence step of the Feedstock Delivery System (2000).

FIG. 9:

FIG. 9 elaborates upon the non-limiting embodiment of FIG. 2A further including a description of the Density Reduction (2F) subsystem or sequence step of the Feedstock Delivery System (2000).

FIG. 9 depicts one embodiment of a Density Reduction (2F) subsystem accepting densified carbonaceous material (2F-01) as an input (2F-IN1A) from an upstream output (2E-OUT1A) of a Plug Control (2E) subsystem (not shown). The Density Reduction (2F) subsystem is configured to reduce the density of the densified carbonaceous material (2F-01) received at a first higher density (2F-01RHO) to form a reduced density carbonaceous material (2F-02) that is discharged at a second lower density (2F-02RHO) via an output (2F-OUT1A) that is an input (2G-IN1A) to a downstream Gas Mixing (2G) subsystem (not shown). The Density Reduction (2F) subsystem is shown contained within a Density Reduction Control Volume (CV-2F).

The Density Reduction (2F) subsystem of FIG. 9 includes a density reduction system (2F1) having a chamber (F00) with a density reduction system first flange (F02), density reduction chamber second flange (F04), and a density reduction chamber third flange (F06).

The density reduction system first flange (F02) is the density reduction input (F03). The density reduction chamber second flange (F04) is the density reduction output (F05). The density reduction system first flange (F02) is connected to an upstream plug control assembly second flange (E06) in a Plug Control (2E) subsystem (not shown). The density reduction chamber second flange (F04) is connected to a downstream chamber first flange (G04) in a Gas Mixing (2G) subsystem (not shown).

The density reduction chamber third flange (F06) is connected to the density reduction chamber seal (F08). The density reduction chamber seal (F08) is configured to enclose the chamber (F00) and contains an aperture (F19) through which the shaft (F16) of the shredder (F01) fits through. The chamber (F00) has an interior (F14) defined by at least one side wall (F12) with a shredder (F01) disposed therein. The shredder (F01) may be of the vertical long shaft single drum shredder as depicted in FIG. 9, or it may be of the horizontal dual roll shredder type.

The chamber (F00) is equipped with a density reduction chamber pressure sensor (P-F) that is configured to output a signal (XPF) to the computer (COMP). The chamber (F00) also is equipped with a density reduction chamber temperature sensor (T-F) that is configured to output a signal (XTF) to the computer (COMP). The density reduction chamber pressure sensor (P-F) outputs a signal (XPF) ranging from 9 PSIA to about 75 PSIG. The shredder (F01) has a shaft (F16) with an integrated motor (M2F) and controller (C-M2F) that is configured to input and output a signal (XM2F) to and from the computer (COMP). The shaft (F16) of the shredder (F01) is equipped with a shaft rotation measurement unit (2F-04) that is configured to input and output a signal (X2F04) to and from the computer (COMP). The shaft (F16) of the shredder (F01) is equipped with a plurality of seals (F18, F20) configured to seal against the pressure within the chamber (F00). More specifically, a first seal (F18) and second seal (F20) are operatively coupled to the shaft (F16) of the shredder (F01) to seal against the rotation of the shaft (F16) as it is operated by the motor (M2F) and controller (C-M2F). In embodiments, the first seal (F18) and second seal (F20) must seal against the first reactor pressure (P-A) as depicted in FIG. 14. In embodiments, the first seal (F18) and second seal (F20) seal against a pressure ranging from about 9 PSID to about 75 PSID.

Figure 10:
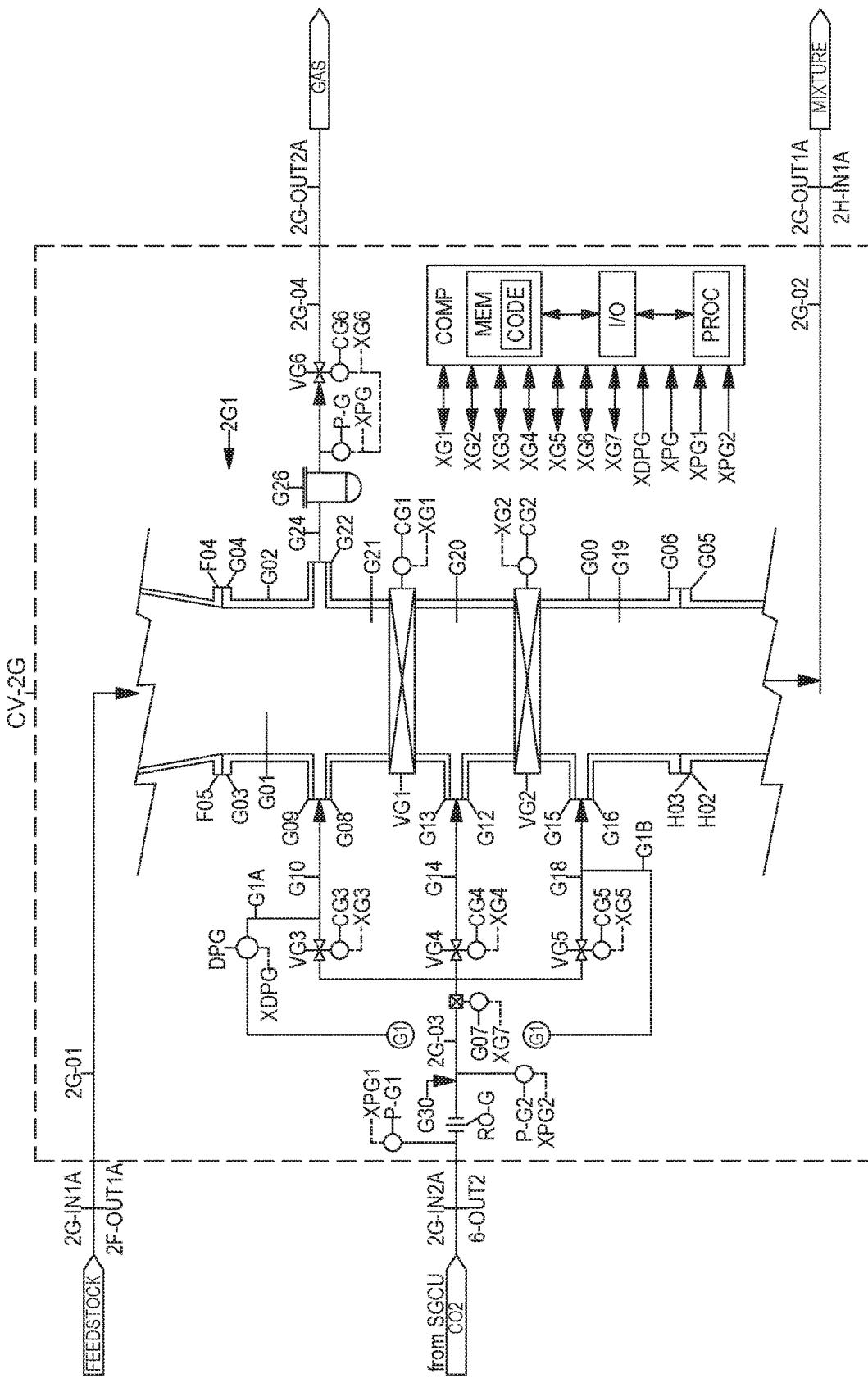
FIG. 10 elaborates upon the non-limiting embodiment of FIG. 2A further including a description of the Gas Mixing (2G) subsystem or sequence step of the Feedstock Delivery System (2000).

FIG. 10:

FIG. 10 elaborates upon the non-limiting embodiment of FIG. 2A further including a description of the Gas Mixing (2G) subsystem or sequence step of the Feedstock Delivery System (2000).

FIG. 10 depicts one embodiment of a Gas Mixing (2G) subsystem having a carbonaceous material (2G-01) as an input (2G-IN1A) from an upstream output (2F-OUT1A) of a Density Reduction (2F) subsystem (not shown). The Gas Mixing (2G) subsystem has a carbonaceous material (2G-01) as an input (2G-IN1A) from an upstream output (2F-OUT1A) of a Density Reduction (2F) subsystem (not shown). The Gas Mixing (2G) subsystem is configured to accept a mixing gas (2G-03) via a gas input (2G-IN2A) from the carbon dioxide output (6-OUT2) of a downstream Secondary Gas Clean Up System (6000) (not shown). The Gas Mixing (2G) subsystem is configured to mix the carbonaceous material (2G-01) with the mixing gas (2G-03) to form a carbonaceous material and gas mixture (2G-02) that is discharged from the Gas Mixing (2G) subsystem via an output (2G-OUT1A) for transfer as an input (2H-IN1A) to a downstream Transport (2H) subsystem (not shown). The Gas Mixing (2G) subsystem is also configured to discharge a gas (2G-04) via a gas output (2G-OUT2A) during start-up, shut-down, and troubleshooting modes of operation. The Gas Mixing (2G) subsystem is shown contained within a Gas Mixing Control Volume (CV-2G).

The Gas Mixing (2G) subsystem of FIG. 10 includes a gas and carbonaceous material mixing system (2G1) having a mixing chamber carbonaceous material stream input (G03) as a chamber first flange (G04) and a mixing output (G05) as a chamber second flange (G06). The chamber first flange (G04) is connected to the density reduction chamber second flange (F04) or density reduction output (F05) of an upstream Density Reduction (2F) subsystem (not shown). The chamber second flange (G06) is connected to the transport assembly first flange (H02) or transport input (H03) of a downstream Transport (2H) subsystem (not shown).

The carbonaceous material mixing system (2G1) further includes a mixing chamber (G00) between the mixing chamber carbonaceous material stream input (G03) and the first mixing output (G05). The mixing chamber (G00) has an interior (G01) defined by at least one side wall (G02). At least one isolation valves (VG1, VG2) is positioned in the mixing chamber (G00) between the mixing chamber carbonaceous material stream input (G03) and the first mixing output (G05), thereby separating the mixing chamber (G00) into an entry section (G21), middle section (G20), and exit section (G19). The first isolation valve (VG1) is equipped with a controller (CG1) that is configured to input or output a signal (XG1) to or from the computer (COMP). The second isolation valve (VG2) is equipped with a controller (CG2) that is configured to input or output a signal (XG2) to or from the computer (COMP).

The entry section (G21) above the first isolation valve (VG1) and above the second isolation valve (VG2) is equipped with a mixing chamber gas input (G08) via an entry gas connection (G09) that is configured to receive a source of mixing gas (2G-03) as a first gas supply (G10). An entry section gas input valve (VG3) is operatively connected to the entry gas connection (G09) and configured to introduce a first gas supply (G10) to the entry section (G21) of the chamber (G00) by use of a controller (CG3) that is equipped to input or output a signal (XG3) to or from the computer (COMP).

The middle section (G20) in between the first isolation valve (VG1) and second isolation valve (VG2) is equipped with a mixing chamber gas input (G12) via a middle gas connection (G13) that is configured to receive a source of mixing gas (2G-03) as a second gas supply (G14). A middle section gas input valve (VG4) is operatively connected to the middle gas connection (G13) and configured to introduce a second gas supply (G14) to the middle section (G20) of the chamber (G00) by use of a controller (CG4) that is equipped to input or output a signal (XG4) to or from the computer (COMP).

The exit section (G19) below the first isolation valve (VG1) and below the second isolation valve (VG2) is equipped with a mixing chamber gas input (G16) via an exit gas connection (G15) that is configured to receive a source of mixing gas (2G-03) as a third gas supply (G18). An exit section gas input valve (VG5) is operatively connected to the exit gas connection (G15) and configured to introduce a third gas supply (G18) to the exit section (G19) of the chamber (G00) by use of a controller (CG5) that is equipped to input or output a signal (XG5) to or from the computer (COMP).

A mixing gas flow sensor (G07) is in fluid communication with the entry gas connection (G09), middle gas connection (G13), and exit gas connection (G15) and configured to send a signal (XG7) to the to the computer (COMP) indicative of the flow of mixing gas (2G-03) transferred to either the entry section (G21), middle section (G20), and/or exit section (G19) of the chamber (G00). A source of compressed air (D30) may be made available to transfer gas (2G-03) to the mixing chamber (G00).

A first gas supply pressure sensor (P-G1) is equipped to measure the pressure of the gas (2G-03) transferred to the gas and carbonaceous material mixing system (2G1) via the gas input (2G-IN2A). The first gas supply pressure sensor (P-G1) is configured to output a signal (XPG1) to the computer (COMP). A restriction (RO-G) such as an orifice, pressure reduction device including a valve or any other such pressure reducing apparatus may be positioned to reduce the pressure of the gas (2G-03) transferred to the gas and carbonaceous material mixing system (2G1) via the gas input (2G-IN2A). A second first gas supply pressure sensor (P-G2) is equipped to measure the pressure of the gas (2G-03) that has passed through the restriction (RO-G). The second gas supply pressure sensor (P-G2) is configured to output a signal (XPG2) to the computer (COMP). The pressure drop across the restriction (RO-G) is configured to range from about 5 PSIG to about 2,000 PSIG.

An evacuation gas line (G22) is connected to the entry section (G21) of the chamber (G00) and is connected to an evacuation gas line (G24) with a particulate filter (G26) interposed thereon. The particulate filter (G26) is positioned in the evacuation gas line (G24). A gas evacuation pressure sensor (P-G) and gas evacuation valve (VG6) are also positioned downstream of the particulate filter (G26) in the evacuation gas line (G24). The particulate filter (G26) prevents particulates from coming into contact with the gas evacuation pressure sensor (P-G) and gas evacuation valve (VG6). The gas evacuation valve (VG6) is configured to output a gas (2G-04) during start-up, shut-down, and troubleshooting modes of operation.

The gas evacuation valve (VG6) is equipped with a controller (CG6) that is configured to input or output a signal (XG6) to or from the computer (COMP). A gas evacuation pressure sensor (P-G) is configured to output a gas evacuation pressure sensor signal (XPG) to the computer (COMP) indicative of the pressure within the entry section (G21) of the chamber (G00).

The gas evacuation valve (VG6) may be operatively controlled by a control loop involving the gas evacuation pressure sensor (P-G) so as to set a user-defined chamber (G00) entry section (G21) operating pressure and to evacuate a gas (2G-04) from the entry section (G21) during start-up, shut-down, and troubleshooting modes of operation. This way, a mixing gas (2G-03) can be used to purge out undesirable gases (2G-04) from the entry section (G21) of the chamber (G00) when the first and second isolation valves (VG1, VG2) are in the closed position. Evacuation of gas (2G-04) may take place under a variety of operational circumstances. For example, product gas may be evacuated from the entry section (G21) of the chamber (G00) when the first and second isolation valves (VG1, VG2) are in the closed position so as to realize a safe environment upstream subsystems for maintenance purposes.

An entry impulse line (G1A) is connected to the entry gas connection (G09) and an exit impulse line (G1B) is connected to the exit gas connection (G15). A differential pressure sensor (DPG) is connected to the entry impulse line (G1A) and the exit impulse line (G1B) and is configured to send a signal (XDPG) to the computer (COMP) indicative of the differential pressure between the entry section (G21) and exit section (G19) of the chamber (G00). For clarity and illustrative purposes, connector impulse line (G1) is shown connecting the exit impulse line (G1B) to the differential pressure sensor (DPG).

FIG. 10A:

FIG. 10A depicts the Gas Mixing Valve States for Automated Controller Operation of typical start-up, normal operation, and shut-down procedures. FIG. 10A is to be used in conjunction with FIG. 10 and depicts a listing of valve states that may be used in a variety of methods to operate valves associated with the gas and carbonaceous material mixing system (2G1).

It is contemplated that in some embodiments, sequence steps of a gas mixing method may be chosen from any number of states listed in FIG. 10A. In embodiments, sequence steps of a gas mixing method may be chosen from a combination of state 1, state 2, and/or state 3, and may incorporate methods or techniques described herein and to be implemented as program instructions and data capable of being stored or conveyed via a computer (COMP). In embodiments, the gas mixing sequence may have only three steps which entail each of those listed in FIG. 10A, wherein: step 1 is state 1; step 2 is state 2; and, step 3 is state 3. State 2G(1) is typically performed at start-up. State 2G(2) is realized during normal operation. State 2G(3) is typically performed during shut-down.

In state 2G(1) the first isolation valve (VG1), second isolation valve (VG2), and gas evacuation valve (VG6) are closed. The entry section gas input valve (VG3), middle section gas input valve (VG4), and exit section gas input valve (VG5) are open. The gas evacuation pressure sensor (P-G) is operatively in communication with the gas evacuation valve (VG6) and controller (CG6). The gas evacuation valve (VG6) is set by an operator to a user-defined pressure greater than first reactor pressure (P-A). Undesirable gas (2G-04), such as air, is evacuated from the chamber (G00) by use of a gas (2G-03). Undesirable gas (2G-04), such as air, is purged from the chamber (G00) by use of a first gas supply (G10) transferred through the entry gas connection (G09), into the entry section (G21) of the chamber (G00), and through the evacuation gas connection (G22) and evacuation gas line (G24).

In state 2G(2) the first isolation valve (VG1), second isolation valve (VG2), and exit section gas input valve (VG5) are open. Carbonaceous material (2G-01) is fed to the mixing chamber (G00). A gas (2G-03) is fed to the mixing chamber (G00). The carbonaceous material (2G-01) and gas (2G-03) mix within the mixing chamber (G00) and a carbonaceous material and gas mixture (2G-02) is transferred downstream. It is to be noted that the exit section gas input valve (VG5) is indicated as open in state 2G(2), however, alternately, the entry section gas input valve (VG3) or middle section gas input valve (VG4) may also be open in addition to the exit section gas input valve (VG5) being open during state 2G(2). It may in some instances make sense for all three of the entry section gas input valve (VG3), middle section gas input valve (VG4), and exit section gas input valve (VG5), to be open during state 2G(2) so as to always maintain a positive flow through each one of the entry gas connection (G09), middle gas connection (G13), and exit gas connection (G15) to prevent clogging with carbonaceous material, particulate heat transfer material, volatile reaction products, or SVOC or VOC.

Figure 10B:
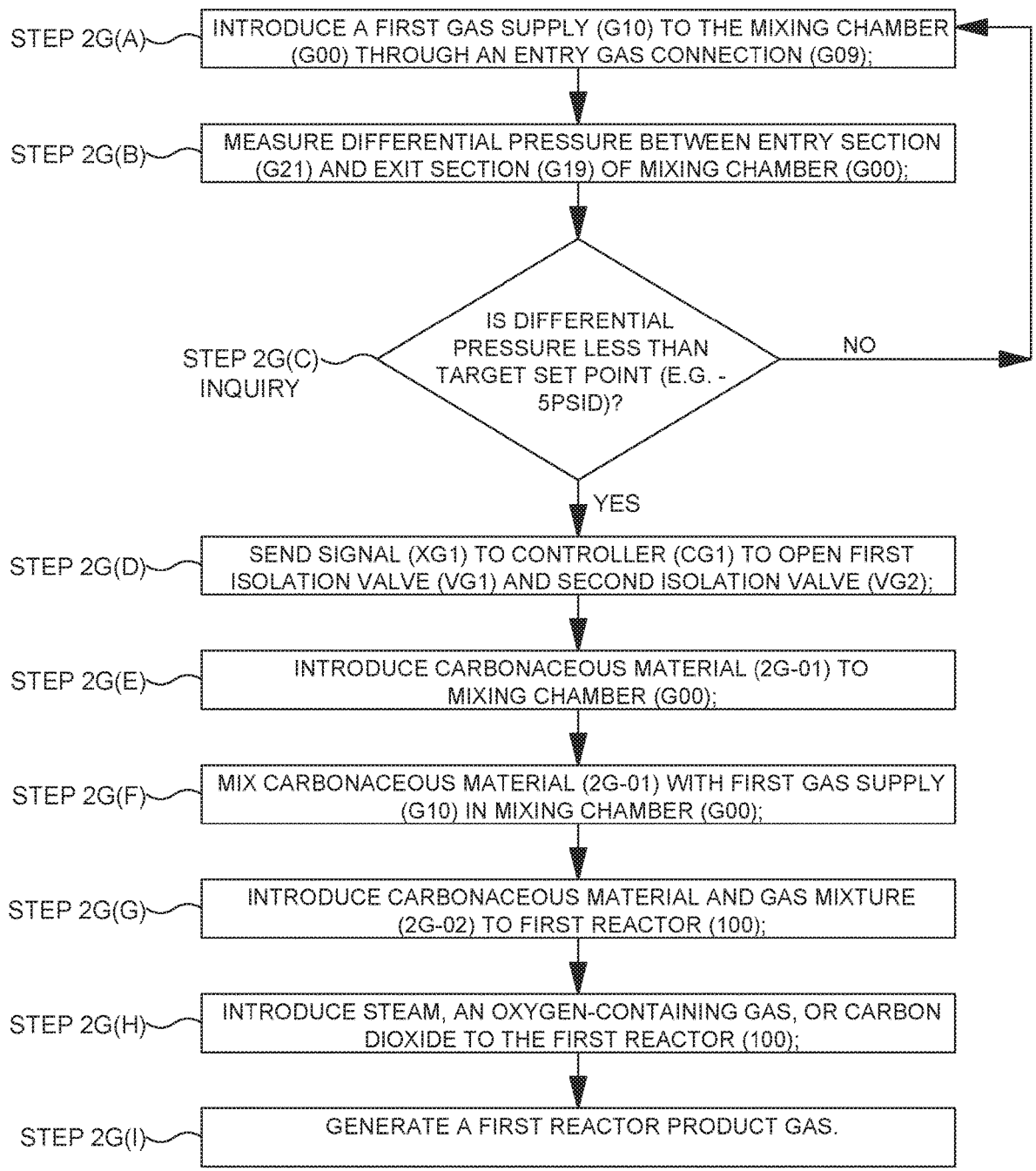
FIG. 10B shows a non-limiting embodiment of a Gas Mixing (2G) method.

In state 2G(3), the first isolation valve (VG1) and second isolation valve (VG2) are closed. The entry section gas input valve (VG3), middle section gas input valve (VG4), exit section gas input valve (VG5), and gas evacuation valve (VG6) are open. The gas evacuation pressure sensor (P-G)

is operatively in communication with the gas evacuation valve (VG6) and controller (CG6). The gas evacuation valve (VG6) is set by an operator to a user-defined pressure greater than first reactor pressure (P-A). Undesirable gas (2G-04), such as product gas, is evacuated from the chamber (G00) by use of a gas (2G-03) such as carbon dioxide or air. Undesirable gas (2G-04), such as product gas, is purged from the chamber (G00) by use of a first gas supply (G10) transferred through the entry gas connection (G09), into the entry section (G21) of the chamber (G00), and through the evacuation gas connection (G22) and evacuation gas line (G24). FIG. 10B:

FIG. 10B shows a non-limiting embodiment of a Gas Mixing (2G) method. The following method may be used in conjunction with the content disclosed in FIG. 10 and FIG. 10A.

STEP 2G(A)—Introduce a first gas supply (G10) to the mixing chamber (G00) through an entry gas connection (G09);

STEP 2G(B)—Measure differential pressure between entry section (G21) and exit section (G19) of mixing chamber (G00);

STEP 2G(C)—Compare signal (XDPG) from the differential pressure sensor (DPG) to target set point. If the signal (XDPG) from the differential pressure sensor (DPG) is greater than target set point, go back to step 2G(A). If the signal (XDPG) from the differential pressure sensor (DPG) is less than or equal to the target set point, then continue to step 2G:D. In embodiments, the target set point is 5 PSIG which can be inputted to an operator to the computer (COMP).

STEP 2G(D)—Send signal (XG1) to controller (CG1) to open the first isolation valve (VG1) and second isolation valve (VG2); STEP 2G(E)—Introduce carbonaceous material (2G-01) to mixing chamber (G00);

STEP 2G(F)—Mix carbonaceous material (2G-01) with gas (2C-03) in mixing chamber (G00);

STEP 2G(G)—Introduce carbonaceous material and gas mixture (2G-02) to first reactor (100); STEP 2G(H)—Introduce steam, and/or oxygen-containing gas, and/or carbon dioxide to the first reactor (100); and, STEP 2G(I)—Generate a first reactor product gas.

For example, STEP 2G(A)—Carbon dioxide is transferred from the carbon dioxide output (6-OUT2) Secondary Gas Clean Up System (6000) to the gas input (2G-IN2A) of the Gas Mixing (2G) subsystem and into the entry section (G21) of the mixing chamber (G00). The first isolation valve (VG1) and second isolation valve (VG2) are both closed. The gas evacuation valve (VG6) is closed. The exit section gas input valve (VG5) is open to purge a third gas supply (G18) through the exit gas connection (G15) and into the exit section (G19) of the chamber (G00) and into the transport assembly (2H1). The middle section gas input valve (VG4) is open to maintain a positive pressure in the middle section (G20) by providing a second gas supply (G14) to the middle gas connection (G13). The entry section gas input valve (VG3) is open to pressurize the entry section (G21) of the chamber (G00). A source of compressed air (D30) may alternately be added to the mixing chamber (G00) through an entry gas connection (G09).

The first reactor pressure (P-A) may operate at a pressure within the pressure range of about 9 PSIA to about 75 PSIG. The Secondary Gas Clean Up System (6000) may operate at a pressure within the pressure range of about 5 PSIG to about 750 PSIG.

Any conceivable gas may be used to mix with the carbonaceous material. The claims are not to be construed to expressly limit the mixing gas with any of the gases mentioned in the specification. In embodiments, the mixing gas may be carbon dioxide, air, an oxygen-containing gas, product gas, hydrogen, carbon monoxide, nitrogen, methane, ethane, ethylene, acetylene, propylene, propane, hydrocarbons, VOC, flue gas, biorefinery off-gases, argon, helium, noble gases, natural gas, or the like.

The pressure drop across the restriction is within the range of about 5 to 750 PSID (pounds per square inch difference). In embodiments, the pressure drop across the restriction is at least 5 PSID. In embodiments, the pressure drop across the restriction is at least 5 PSID. In embodiments, the pressure drop across the restriction is at least 10 PSID. In embodiments, the pressure drop across the restriction is at least 15 PSID. In embodiments, the pressure drop across the restriction is at least 20 PSID. In embodiments, the pressure drop across the restriction is at least 25 PSID. In embodiments, the pressure drop across the restriction is at least 30 PSID. In embodiments, the pressure drop across the restriction is at least 35 PSID. In embodiments, the pressure drop across the restriction is at least 40 PSID. In embodiments, the pressure drop across the restriction is at least 45 PSID. In embodiments, the pressure drop across the restriction is at least 50 PSID. In embodiments, the pressure drop across the restriction is at least 55 PSID. In embodiments, the pressure drop across the restriction is at least 60 PSID. In embodiments, the pressure drop across the restriction is at least 65 PSID. In embodiments, the pressure drop across the restriction is at least 70 PSID. In embodiments, the pressure drop across the restriction is at least 75 PSID. In embodiments, the pressure drop across the restriction is at least 80 PSID. In embodiments, the pressure drop across the restriction is at least 85 PSID. In embodiments, the pressure drop across the restriction is at least 90 PSID. In embodiments, the pressure drop across the restriction is at least 95 PSID. In embodiments, the pressure drop across the restriction is at least 100 PSID. In embodiments, the pressure drop across the restriction is at least 110 PSID. In embodiments, the pressure drop across the restriction is at least 120 PSID. In embodiments, the pressure drop across the restriction is at least 130 PSID. In embodiments, the pressure drop across the restriction is at least 140 PSID. In embodiments, the pressure drop across the restriction is at least 150 PSID. In embodiments, the pressure drop across the restriction is at least 160 PSID. In embodiments, the pressure drop across the restriction is at least 170 PSID. In embodiments, the pressure drop across the restriction is at least 180 PSID. In embodiments, the pressure drop across the restriction is at least 190 PSID. In embodiments, the pressure drop across the restriction is at least 200 PSID. In embodiments, the pressure drop across the restriction is at least 225 PSID. In embodiments, the pressure drop across the restriction is at least 250 PSID. In embodiments, the pressure drop across the restriction is at least 275 PSID. In embodiments, the pressure drop across the restriction is at least 300 PSID. In embodiments, the pressure drop across the restriction is at least 350 PSID. In embodiments, the pressure drop across the restriction is at least 400 PSID. In embodiments, the pressure drop across the restriction is at least 450 PSID. In embodiments, the pressure drop across the restriction is at least 500 PSID. In embodiments, the pressure drop across the restriction is at least 550 PSID. In embodiments, the pressure drop across the restriction is at least 600 PSID. In embodiments, the pressure drop across the restriction is at least 650 PSID. In embodiments, the pressure drop across the restriction is at least 700 PSID. In embodiments, the pressure drop across the restriction is at least 750 PSID.

Alternately, the pressure drop across the first mixing gas input valve (VG3, VG3A, VG3B, VG3C, VG3D, VG3E, VG3F) or the middle section gas input valve (VG4) is within the range of about 5 to 750 PSID. In embodiments, the pressure drop across either mixing gas input valve (VG3, VG3A, VG3B, VG3C, VG3D, VG3E, VG3F, VG4) is at least 5 PSID. In embodiments, the pressure drop across either mixing gas input valve (VG3, VG3A, VG3B, VG3C, VG3D, VG3E, VG3F, VG4) is at least 10 PSID. In embodiments, the pressure drop across either mixing gas input valve (VG3, VG3A, VG3B, VG3C, VG3D, VG3E, VG3F, VG4) is at least 15 PSID. In embodiments, the pressure drop across either mixing gas input valve (VG3, VG3A, VG3B, VG3C, VG3D, VG3E, VG3F, VG4) is at least 20 PSID. In embodiments, the pressure drop across either mixing gas input valve (VG3, VG3A, VG3B, VG3C, VG3D, VG3E, VG3F, VG4) is at least 25 PSID. In embodiments, the pressure drop across either mixing gas input valve (VG3, VG3A, VG3B, VG3C, VG3D, VG3E, VG3F, VG4) is at least 30 PSID. In embodiments, the pressure drop across either mixing gas input valve (VG3, VG3A, VG3B, VG3C, VG3D, VG3E, VG3F, VG4) is at least 35 PSID. In embodiments, the pressure drop across either mixing gas input valve (VG3, VG3A, VG3B, VG3C, VG3D, VG3E, VG3F, VG4) is at least 40 PSID. In embodiments, the pressure drop across either mixing gas input valve (VG3, VG3A, VG3B, VG3C, VG3D, VG3E, VG3F, VG4) is at least 45 PSID. In embodiments, the pressure drop across either mixing gas input valve (VG3, VG3A, VG3B, VG3C, VG3D, VG3E, VG3F, VG4) is at least 50 PSID. In embodiments, the pressure drop across either mixing gas input valve (VG3, VG3A, VG3B, VG3C, VG3D, VG3E, VG3F, VG4) is at least 55 PSID. In embodiments, the pressure drop across either mixing gas input valve (VG3, VG3A, VG3B, VG3C, VG3D, VG3E, VG3F, VG4) is at least 60 PSID. In embodiments, the pressure drop across either mixing gas input valve (VG3, VG3A, VG3B, VG3C, VG3D, VG3E, VG3F, VG4) is at least 65 PSID. In embodiments, the pressure drop across either mixing gas input valve (VG3, VG3A, VG3B, VG3C, VG3D, VG3E, VG3F, VG4) is at least 70 PSID. In embodiments, the pressure drop across either mixing gas input valve (VG3, VG3A, VG3B, VG3C, VG3D, VG3E, VG3F, VG4) is at least 75 PSID. In embodiments, the pressure drop across either mixing gas input valve (VG3, VG3A, VG3B, VG3C, VG3D, VG3E, VG3F, VG4) is at least 80 PSID. In embodiments, the pressure drop across either mixing gas input valve (VG3, VG3A, VG3B, VG3C, VG3D, VG3E, VG3F, VG4) is at least 85 PSID. In embodiments, the pressure drop across either mixing gas input valve (VG3, VG3A, VG3B, VG3C, VG3D, VG3E, VG3F, VG4) is at least 90 PSID. In embodiments, the pressure drop across either mixing gas input valve (VG3, VG3A, VG3B, VG3C, VG3D, VG3E, VG3F, VG4) is at least 95 PSID. In embodiments, the pressure drop across either mixing gas input valve (VG3, VG3A, VG3B, VG3C, VG3D, VG3E, VG3F, VG4) is at least 100 PSID. In embodiments, the pressure drop across either mixing gas input valve (VG3, VG3A, VG3B, VG3C, VG3D, VG3E, VG3F, VG4) is at least 110 PSID. In embodiments, the pressure drop across either mixing gas input valve (VG3, VG3A, VG3B, VG3C, VG3D, VG3E, VG3F, VG4) is at least 120 PSID. In embodiments, the pressure drop across either mixing gas input valve (VG3, VG3A, VG3B, VG3C, VG3D, VG3E, VG3F, VG4) is at least 130 PSID. In embodiments, the pressure drop across either mixing gas input valve (VG3, VG3A, VG3B, VG3C, VG3D, VG3E, VG3F, VG4) is at least 140 PSID. In embodiments, the pressure drop across either mixing gas input valve (VG3, VG3A, VG3B, VG3C, VG3D, VG3E, VG3F, VG4) is at least 150 PSID. In embodiments, the pressure drop across either mixing gas input valve (VG3, VG3A, VG3B, VG3C, VG3D, VG3E, VG3F, VG4) is at least 160 PSID. In embodiments, the pressure drop across either mixing gas input valve (VG3, VG3A, VG3B, VG3C, VG3D, VG3E, VG3F, VG4) is at least 170 PSID. In embodiments, the pressure drop across either mixing gas input valve (VG3, VG3A, VG3B, VG3C, VG3D, VG3E, VG3F, VG4) is at least 180 PSID. In embodiments, the pressure drop across either mixing gas input valve (VG3, VG3A, VG3B, VG3C, VG3D, VG3E, VG3F, VG4) is at least 190 PSID. In embodiments, the pressure drop across either mixing gas input valve (VG3, VG3A, VG3B, VG3C, VG3D, VG3E, VG3F, VG4) is at least 200 PSID. In embodiments, the pressure drop across either mixing gas input valve (VG3, VG3A, VG3B, VG3C, VG3D, VG3E, VG3F, VG4) is at least 225 PSID. In embodiments, the pressure drop across either mixing gas input valve (VG3, VG3A, VG3B, VG3C, VG3D, VG3E, VG3F, VG4) is at least 250 PSID. In embodiments, the pressure drop across either mixing gas input valve (VG3, VG3A, VG3B, VG3C, VG3D, VG3E, VG3F, VG4) is at least 275 PSID. In embodiments, the pressure drop across either mixing gas input valve (VG3, VG3A, VG3B, VG3C, VG3D, VG3E, VG3F, VG4) is at least 300 PSID. In embodiments, the pressure drop across either mixing gas input valve (VG3, VG3A, VG3B, VG3C, VG3D, VG3E, VG3F, VG4) is at least 350 PSID. In embodiments, the pressure drop across either mixing gas input valve (VG3, VG3A, VG3B, VG3C, VG3D, VG3E, VG3F, VG4) is at least 400 PSID. In embodiments, the pressure drop across either mixing gas input valve (VG3, VG3A, VG3B, VG3C, VG3D, VG3E, VG3F, VG4) is at least 450 PSID. In embodiments, the pressure drop across either mixing gas input valve (VG3, VG3A, VG3B, VG3C, VG3D, VG3E, VG3F, VG4) is at least 500 PSID. In embodiments, the pressure drop across either mixing gas input valve (VG3, VG3A, VG3B, VG3C, VG3D, VG3E, VG3F, VG4) is at least 550 PSID. In embodiments, the pressure drop across either mixing gas input valve (VG3, VG3A, VG3B, VG3C, VG3D, VG3E, VG3F, VG4) is at least 600 PSID. In embodiments, the pressure drop across either mixing gas input valve (VG3, VG3A, VG3B, VG3C, VG3D, VG3E, VG3F, VG4) is at least 650 PSID. In embodiments, the pressure drop across either mixing gas input valve (VG3, VG3A, VG3B, VG3C, VG3D, VG3E, VG3F, VG4) is at least 700 PSID. In embodiments, the pressure drop across either mixing gas input valve (VG3, VG3A, VG3B, VG3C, VG3D, VG3E, VG3F, VG4) is at least 750 PSID.

The entry section (G21) of the mixing chamber (G00) is exposed to a source of pressurized gas (2C-03). The exit section (G19) of the mixing chamber (G00) is exposed to the first reactor (100) which may operate at a temperature between 570° C. and 1,000° C. (1,058° F. and 1,832° F.).

The third gas supply (G18) provided to the exit section (G19) via an exit gas connection (G15) serves to prevent back flow of steam, oxygen-containing gas, carbon dioxide, product gas, or first reactor particulate heat transfer material (105) to the interior (G01) of the mixing chamber (G00).

STEP 2G(B)—A differential pressure sensor (DPG) measures the difference in pressure of the entry section (G21) and exit section (G19) of the mixing chamber (G00). Pressure from the entry section (G21) of the mixing chamber (G00) is read by the differential pressure sensor (DPG) via an entry impulse line (G1A). Pressure from the exit section (G19) of the mixing chamber (G00) is read by the differential pressure sensor (DPG) via an exit impulse line (G1B).

The differential pressure sensor (DPG) transmits a signal of the pressure difference between the entry section (G21) and the exit section (G19).

STEP 2G(C)—The signal (XDPG) from the differential pressure sensor (DPG) is compared to a target set point. A target set point of 5 PSID. The entry section (G21) of the mixing chamber G00) is being pressurized by a first gas supply (G10). As gas is (2C-03) is transferred to the entry section (G21), the pressure within the interior (G01) of the mixing chamber (G00) increases. A pressure boundary is formed at one end in an upstream densification system (2D0) and at the other end by the surface of the closed first isolation valve (VG1). In case the first isolation valve (VG1) has a leak in it, a pressure boundary is formed at one end in an upstream densification system (2D0) and at the other end by the surface of the closed second isolation valve (VG2).

When the signal (XDPG) from the differential pressure sensor (DPG) is greater than target set point continue to introduce a first gas supply (G10) to the mixing chamber (G00) through an entry gas connection (G09). For example, if the signal (XDPG) from the differential pressure sensor (DPG) was 20 PSID then this would be greater than the target set point of 5 PSID and the system would resume introducing a first gas supply (G10) to the mixing chamber (G00). For example, if the signal (XDPG) from the differential pressure sensor (DPG) was 5 PSID then this would be equal to the target set point of 5 PSID and the system may continue on to step 2G(D). For example, if the signal (XDPG) from the differential pressure sensor (DPG) was 4 PSID then this would be less than the target set point of 5 PSID and the system may continue on to step 2G(D).

STEP 2G(D)—The computer (COMP) sends a signal (XG1, XG2) to controllers (CG1, CG2) to open the first isolation valve (VG1) and the second isolation valve (VG2).

STEP 2G(E)—carbonaceous material (2G-01) is introduced to the mixing chamber (G00). There is minimal, if any, but likely no pressure drop signal (XDPG) across the first isolation valve (VG1) and the second isolation valve (VG1). The pressure of the mixing chamber (G00) and the first reactor (100) are equilibrated. The third gas supply (G18) provided to the exit section (G19) via an exit gas connection (G15) to prevent back flow of carbonaceous material, steam, oxygen-containing gas, carbon dioxide, product gas, or first reactor particulate heat transfer material (105) to the interior (G01) of the mixing chamber (G00).

STEP 2G(F)—Carbonaceous material (2G-01) is mixed with the gas (2C-03) in mixing chamber (G00).

STEP 2G(G)—The carbonaceous material and gas mixture (2G-02) is transferred to the first reactor (100) which may operate at a temperature between 570° C. and 1,000° C. (1,058° F. and 1,832° F.).

STEP 2G(H)— Steam, an oxygen-containing gas, and carbon dioxide are introduced into the first reactor (100); and, STEP 2G(I)—A first reactor product gas is generated.

FIG. 11:

FIG. 11 elaborates upon the non-limiting embodiment of FIG. 2A further including a description of the Transport (2H) subsystem or sequence step of the Feedstock Delivery System (2000).

FIG. 11 elaborates upon the non-limiting embodiment of FIG. 2A further including a description of the Transport (2H) subsystem or sequence step of the Feedstock Delivery System (2000). FIG. 11 shows one example of a Transport (2H) subsystem accepting a carbonaceous material and gas mixture (2H-01) as an input (2H-IN1A) from an output (2G-OUT1A) of a Gas Mixing (2G) subsystem. The Transport (2H) subsystem is shown contained within a Transport Control Volume (CV-2H).

The Transport (2H) subsystem is configured to accept a carbonaceous material and gas mixture (2H-01) and transfer it from the transport input (H03) to the transport output (H05) for delivery to a first reactor (100) as a carbonaceous material and gas mixture (102A) via an output (2H-OUT1A) or a first feed zone delivery system output (FZ-OUT1). The Transport (2H) subsystem includes a transport assembly (2H1) and has a transport assembly first flange (H02) and a transport assembly second flange (H2O). The transport assembly first flange (H02) is the transport input (H03). The transport assembly second flange (H2O) is the transport output (H05). The transport output (H05) is also the feedstock delivery system output (H22). The transport assembly first flange (H02) is shown connected to the chamber second flange (G06) of the exit section (G19) of the mixing chamber (G00) within the Gas Mixing (2G) subsystem. The transport assembly second flange (H2O) is shown connected to a first reactor first carbonaceous material and gas input (104A).

An expansion joint (H04) is interposed in the transport assembly (2H1) between the transport assembly first flange (H02) and the transport assembly second flange (H2O). The transport assembly (2H1) has at least one side wall (H06) defining an interior (H08). A screw conveyor (H10) is disposed within the interior (H08) of the transport assembly (2H1). The screw conveyor (H10) has a shaft (H11), motor (M2H), and integrated controller (C-M2H) that is configured to input or output a signal (XM2H) to the computer (COMP). The shaft (H11) of the screw conveyor (H10) is also equipped with a shaft rotation measurement unit (2H-04) that is configured to input or output a signal (X2H04) to the computer (COMP). The screw conveyor (H10) may in some instances be a heat exchange auger (HX-H) having a heat transfer medium input (H12) configured to accept a heat transfer medium supply (H14) and a heat transfer medium output (H16) configured to discharge a heat transfer medium return (H18).

A heat transfer medium supply inlet temperature sensor (TH1) is in fluid communication with the heat transfer medium input (H12) and is configured to measure the temperature of the heat transfer medium supply (H14) and output a signal (XH1) to the computer (COMP). A heat transfer medium discharge output temperature sensor (TH2) is in fluid communication with the heat transfer medium output (H16) and is configured to measure the temperature of the heat transfer medium return (H18) and output a signal (XH2) to the computer (COMP). The heat transfer medium supply (H14) has a lesser temperature than that of the heat transfer medium return (H18). In embodiments, the heat transfer medium supply inlet temperature sensor (TH1) to the heat exchange auger (HX-H) reads in a range from about 60 degrees F. to about 90 degrees F. In embodiments, the heat transfer medium discharge output temperature sensor (TH2) from the heat exchange auger (HX-H) reads in a range from about 100 degrees F. to about 150 degrees F. A carbonaceous material and gas mixture (2H-02) is conveyed from the interior (H08), through the flights of the screw conveyor (H10) and transferred into the first reactor (100).

Figure 12A:
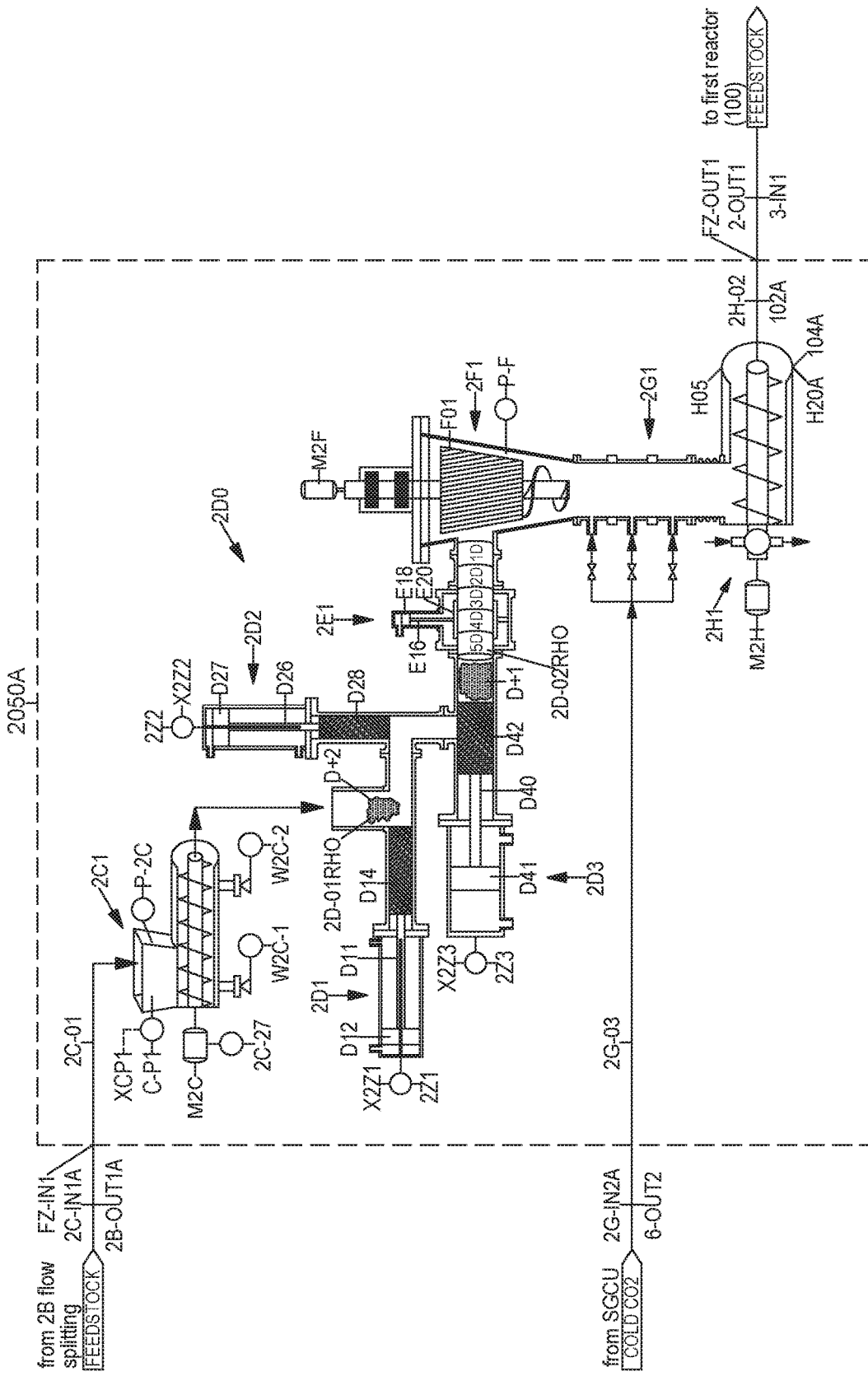
FIG. 12A shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a first mode of operation under conditions of state 2D(1).

FIG. 12A:

FIG. 12A shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a first mode of operation under conditions of state 2D(1).

FIG. 12A is to be used in conjunction with FIG. 13A and FIG. 13F. FIG. 12A and FIG. 13A depict aspects of the feed zone delivery system (2050). FIGS. 12A and 13A depicts the feed zone delivery system (2050) in a first mode of operation under conditions of state 2D(1).

It is contemplated that in some embodiments, sequence steps of a feed zone delivery method may be chosen from any number of states listed in FIG. 13F. In embodiments, sequence steps of a feed zone delivery method may be chosen from a combination of state 2D(1), state 2D(2), state 2D(3), state 2D(4), and/or state 2D(5) and may incorporate methods or techniques described herein to be implemented as program instructions and data capable of being stored or conveyed via a computer (COMP). In embodiments, the feed zone delivery method may have five steps which entail each of those listed in FIG. 13F, wherein: step 1 is state 2D(1); step 2 is state 2D(2); step 3 is state 2D(3); step 4 is state 2D(4), and step 5 is state 2D(5).

Figure 12B:
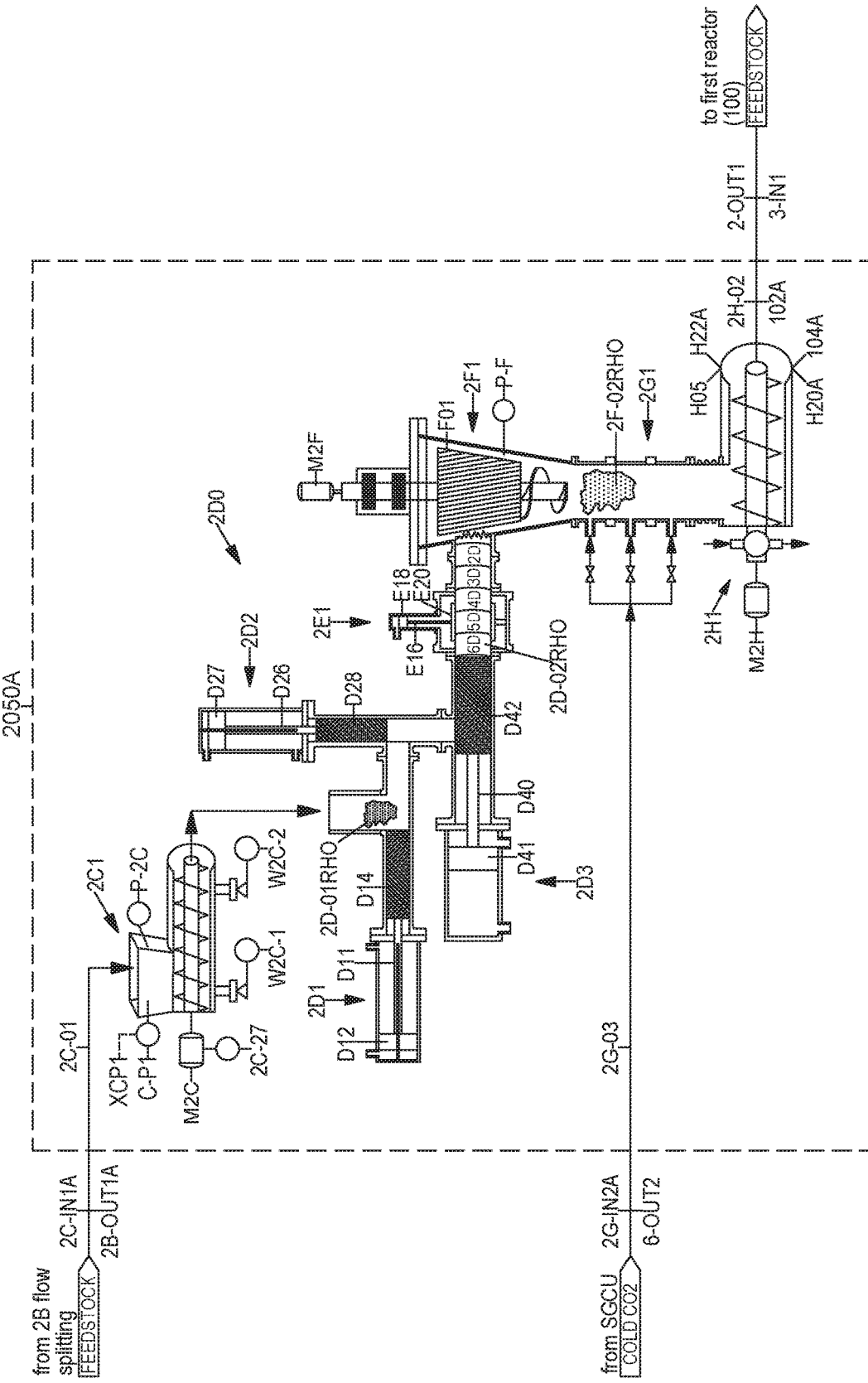
FIG. 12B shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a second mode of operation under conditions of state 2D(2).
Figure 12C:
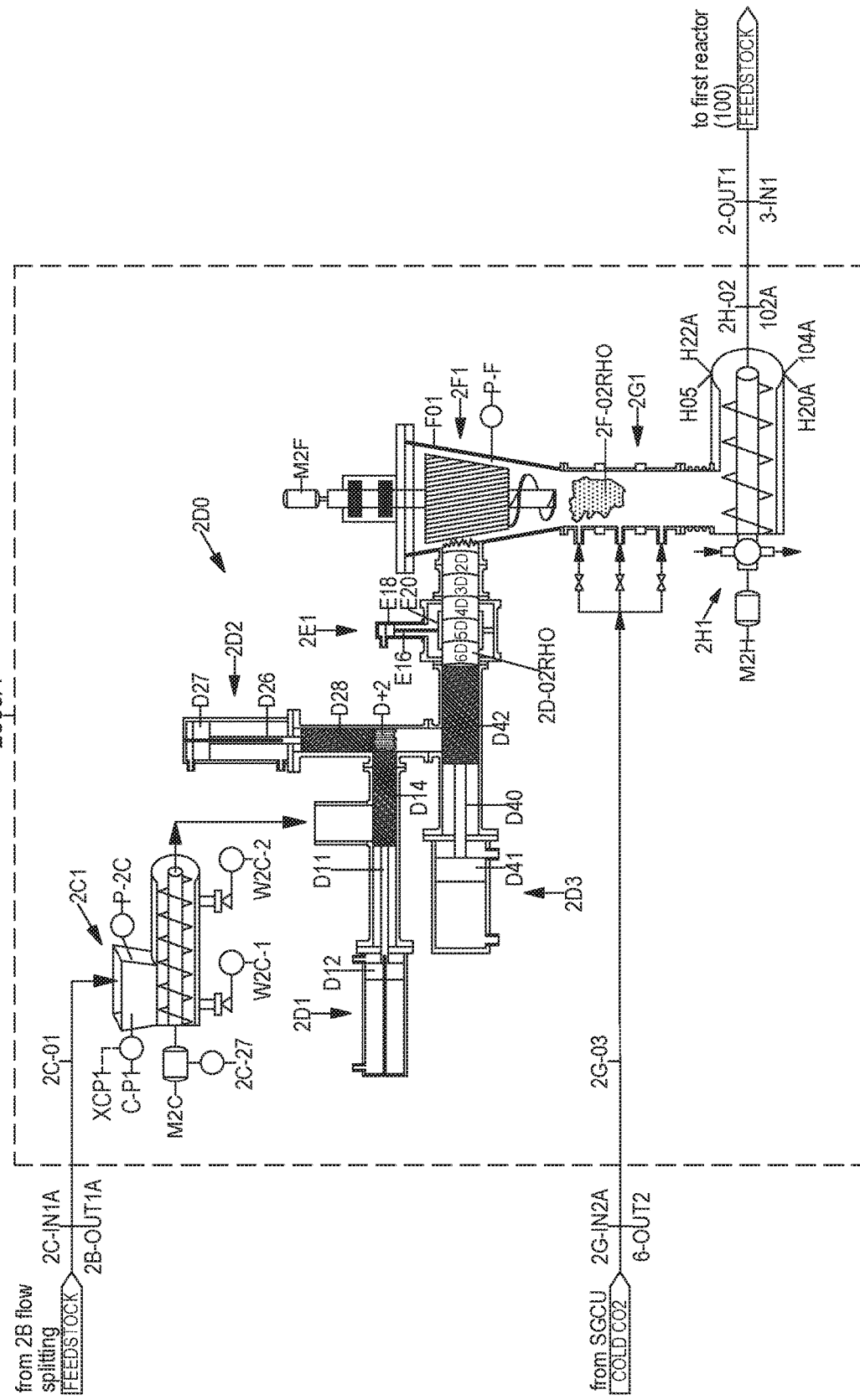
FIG. 12C shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a third mode of operation under conditions of state 2D(3).
Figure 12D:
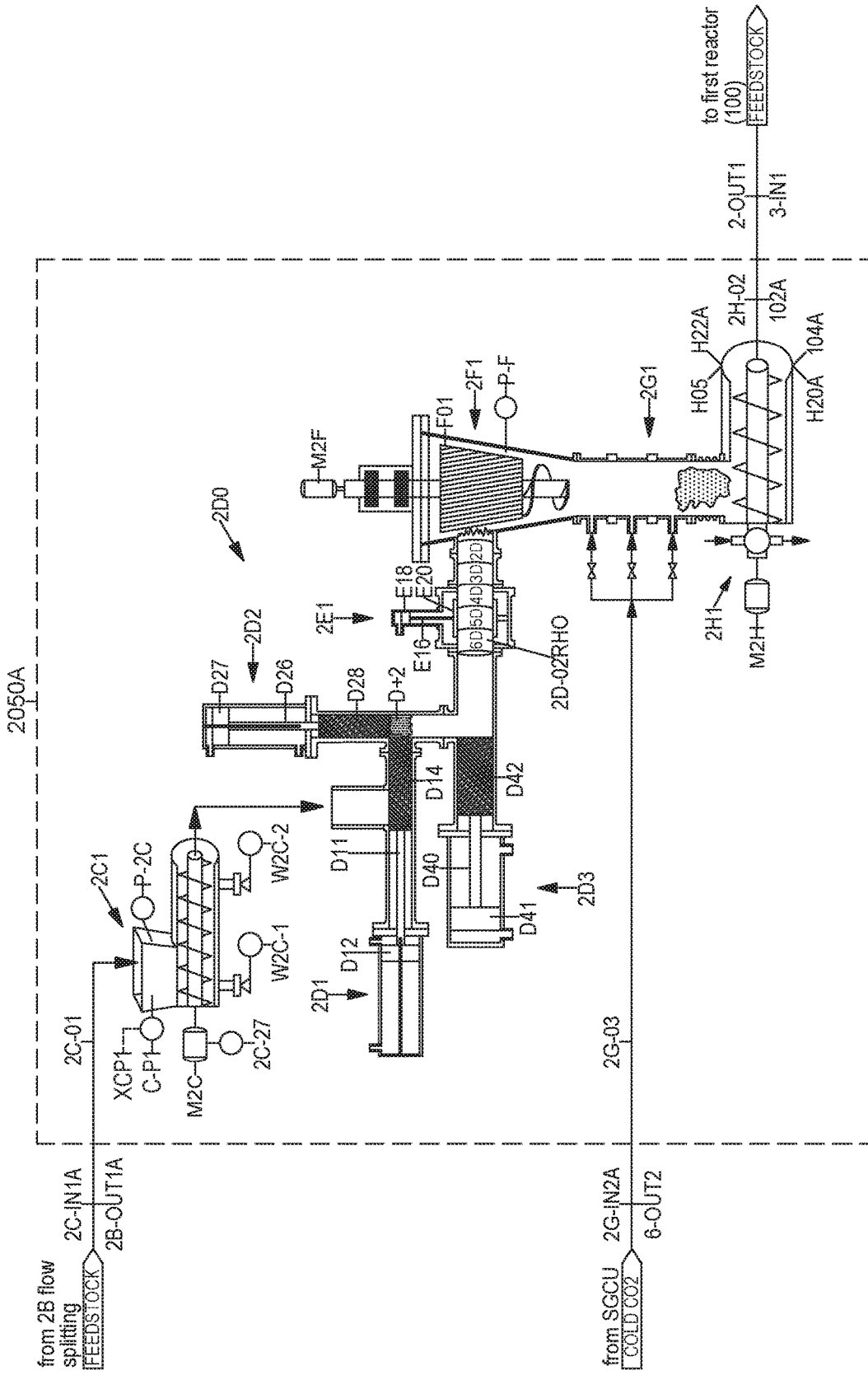
FIG. 12D shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a fourth mode of operation under conditions of state 2D(4).
Figure 12E:
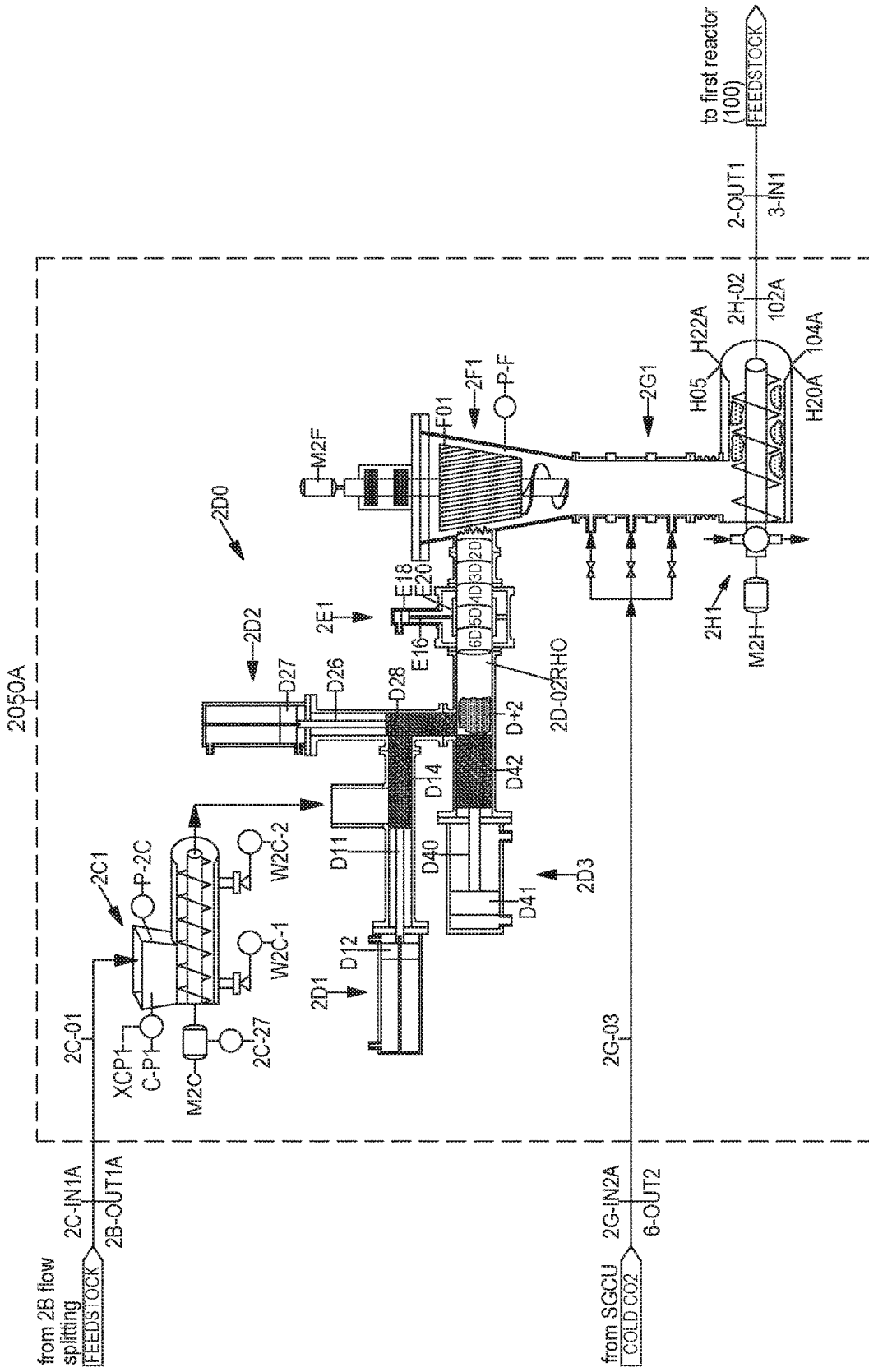
FIG. 12E shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a fifth mode of operation under conditions of state 2D(5).
Figure 13C:
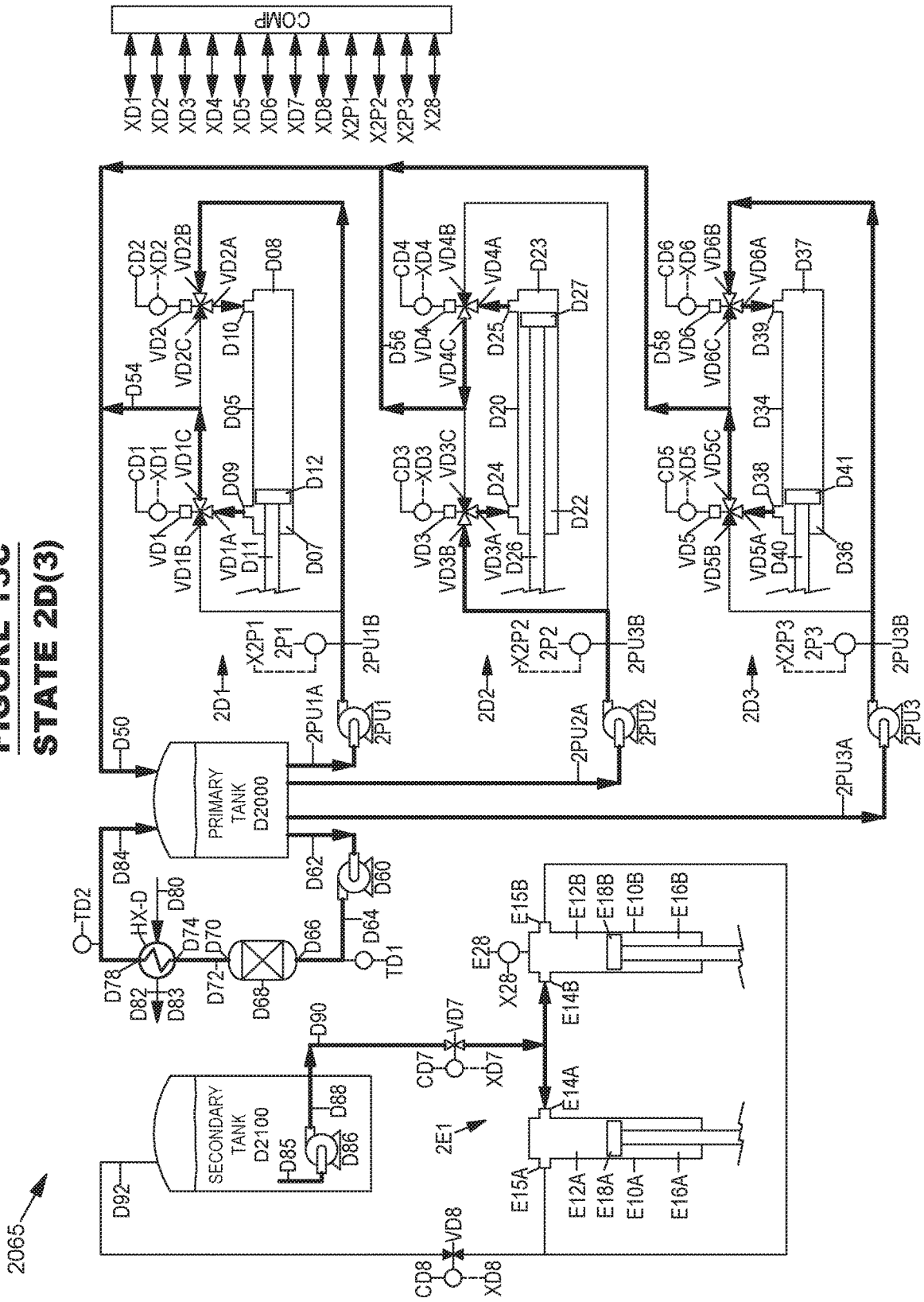
FIG. 13C shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a third mode of operation under conditions of state 2D(3).
Figure 13D:
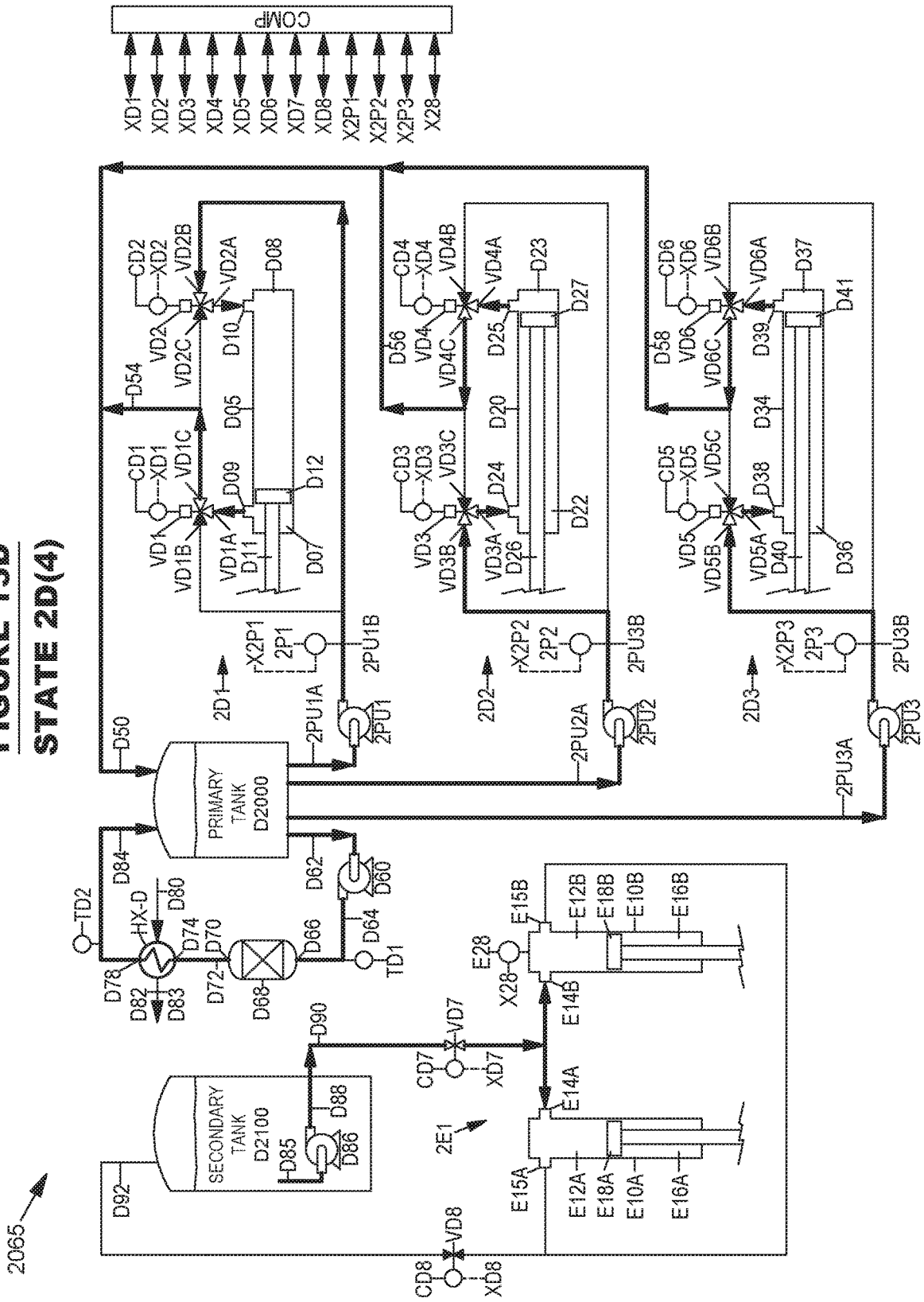
FIG. 13D shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a fourth mode of operation under conditions of state 2D(4).
Figure 13E:
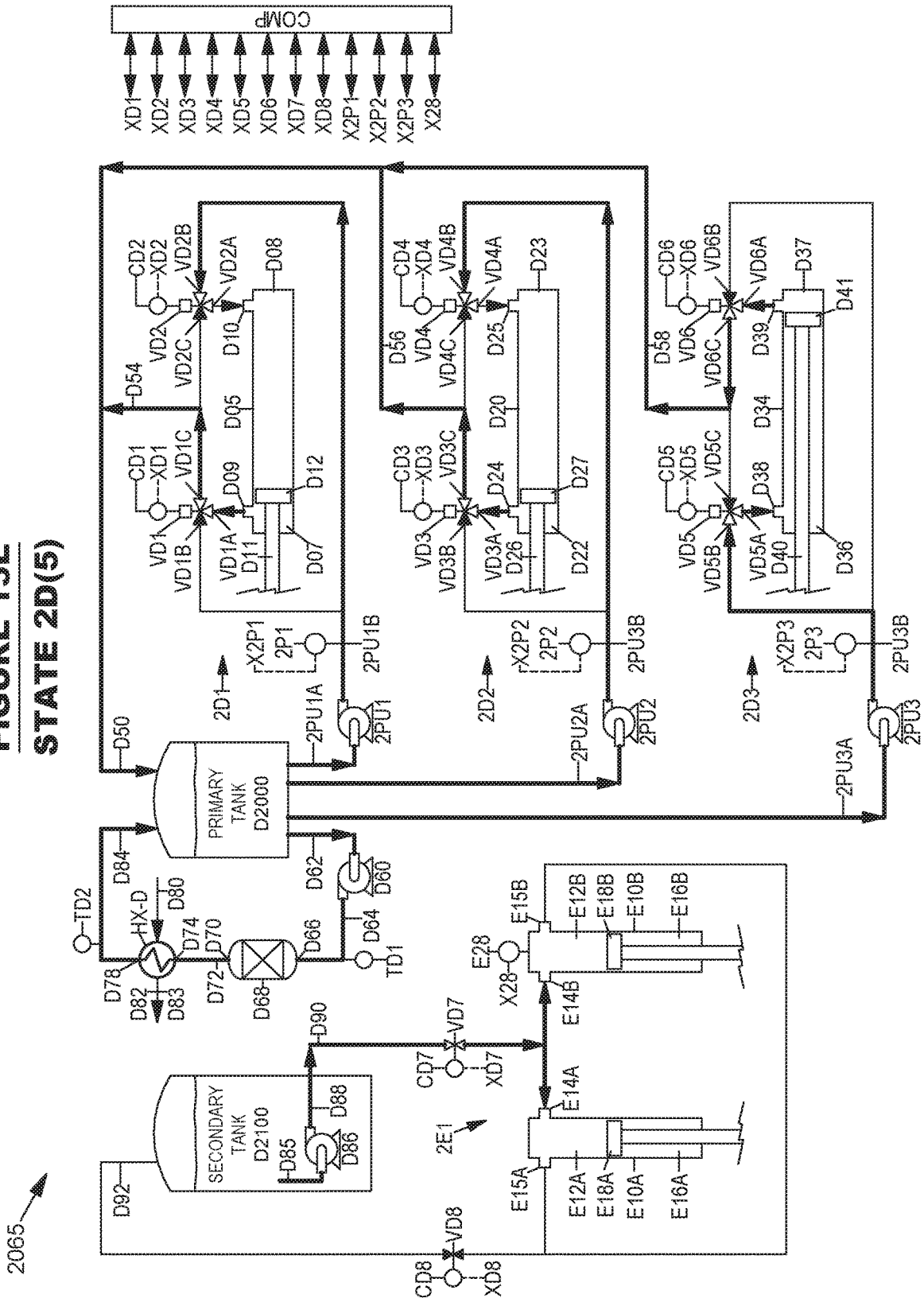
FIG. 13E shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a fifth mode of operation under conditions of state 2D(5).

FIGS. 12A and 13A depict the feed zone delivery system (2050) in a first mode of operation under conditions of state 2D(1). FIGS. 12B and 13B depicts the feed zone delivery system (2050) in a second mode of operation under conditions of state 2D(2). FIGS. 12C and 13C depict the feed zone delivery system (2050) in a third mode of operation under conditions of state 2D(3). FIGS. 12D and 13D depict the feed zone delivery system (2050) in a fourth mode of operation under conditions of state 2D(4). FIGS. 12E and 13E depict the feed zone delivery system (2050) in a fifth mode of operation under conditions of state 2D(5). FIG. 13F is to be used in conjunction with FIG. 12A, 12B, 12C, 12D, 12E, 13A, 13B, 13C, 13D, 13E and depicts a listing of valve states that may be used in a variety of methods to operate valves associated with the densification system (2D0).

FIG. 12A depicts a first feed zone delivery system (2050A) having a first feed zone delivery system input (FZ-IN1) and a first feed zone delivery system output (FZ-OUT1). The first feed zone delivery system input (FZ-IN1) is shown to accept carbonaceous material (2C-01) through an input (2C-IN1A) via the first output (2B-OUT1A) of an upstream Flow Splitting (2B) subsystem. The first feed zone delivery system output (FZ-OUT1) is shown to discharge a carbonaceous material and gas mixture (2H-02) through a mixture output (2-OUT1) to the carbonaceous material and gas mixture input (3-IN1) of a downstream Product Gas Generation System (3000).

The first feed zone delivery system (2050A) is also shown to accept a mixing gas (2G-03) from a gas input (2G-IN2A) via a carbon dioxide output (6-OUT2) of a downstream Secondary Gas Clean Up System (6000). The first feed zone delivery system (2050A) is configured to mix the carbonaceous material (2C-01) with the mixing gas (2G-03) within the gas and carbonaceous material mixing system (2G1) and output a carbonaceous material and gas mixture (2H-02) for transfer to downstream first reactor (100) as a carbonaceous material and gas mixture (102A).

The first feed zone delivery system (2050A) described in FIG. 12A includes a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and transport assembly (2H1). The first piston cylinder assembly (2D1), second piston cylinder assembly (2D2), third piston cylinder assembly (2D3), make up a densification system (2D0).

The weigh feeder (2C1) connected to a first piston cylinder assembly (2D1). The weigh feeder (2C1) is operatively connected to an upstream first splitter (2B1) and is configured to receive carbonaceous material (2C-01) therefrom. The first piston cylinder assembly (2D1) is connected to a second piston cylinder assembly (2D2) and configured to transfer carbonaceous material thereto. The second piston cylinder assembly (2D2) is connected to a third piston cylinder assembly (2D3) and configured to transfer carbonaceous material thereto. The third piston cylinder assembly (2D3) is connected to a plug control system (2E1) and is configured to compress carbonaceous material to create a pressure seal or boundary between the downstream first reactor (100) and atmospheric pressure of the upstream weigh feeder (2C1).

The plug control system (2E1) is connected to a density reduction system (2F1) and is configured to exert a force upon the compressed carbonaceous material to hold the compressed carbonaceous material in position and to create a stop against which the last plug is formed. The plug control system (2E1) is configured to resist the compression forces caused by the advancing motion forming third piston cylinder assembly (2D3).

The density reduction system (2F1) is connected to a gas and carbonaceous material mixing system (2G1) and is configured to reduce the density of the densified carbonaceous material received at a first higher density to form a reduced density carbonaceous material that is discharged at a second lower density.

The gas and carbonaceous material mixing system (2G1) is connected to a transport assembly (2H1) and is configured to mix the carbonaceous material with a mixing gas (2G-03) to form a carbonaceous material and gas mixture.

The transport assembly (2H1) is operatively connected to a downstream first reactor (100) and is configured to accept and transfer the carbonaceous material and gas mixture from the downstream gas and carbonaceous material mixing system (2G1) to the downstream first reactor (100)

The weigh feeder (2C1) is shown to have a first proximity sensor (C-P1), motor (M2C), shaft rotation measurement unit (2C-27), first mass sensor (W2C-1), second mass sensor (W2C-2), and pressure sensor (P-2C). The motor (M2C) of the weigh feeder (2C1) is operated so that the shaft rotation measurement unit (2C-27) is operatively coupled with at least one mass sensor (W2C-1, W2C-2) to output a carbonaceous material (2C-01) with a known mass flow rate (2C-02MASS).

The densification system (2D0) is shown to include a first piston cylinder assembly (2D1), second piston cylinder assembly (2D2), and third piston cylinder assembly (2D3) and is configured to accept a carbonaceous material at a first lower density (2D-01RHO) compress it, and output a densified carbonaceous material at a second higher density (2D-02RHO).

The first piston cylinder assembly (2D1) is shown to include a first piston (D12) operatively connected to a first ram (D14) by a first rod (D11). The second piston cylinder assembly (2D2) is shown to include a second piston (D27) operatively connected to a second ram (D28) by a second rod (D26). The third piston cylinder assembly (2D3) is shown to include a third piston (D41) operatively connected to a third ram (D42) by a third rod (D40). The third piston cylinder assembly (2D3) is shown to have created a series of five plugs (1D, 2D, 3D, 4D, 5D). The five plugs (1D, 2D, 3D, 4D, 5D) depicted in FIG. 12A are comprised of a first plug (1D), a second plug (2D), a third plug (3D), a fourth plug (4D), and a fifth plug (5D).

FIG. 12A shows state 2D(1) the: 2D1 position retracted; 2D2 position retracted; 2D3 position advancing; and the 2E1 position advanced. A first subsequent material (D+1) is shown positioned in front of the advancing motion of the third ram (D42). The first subsequent material (D+1) is advanced from the third piston cylinder assembly (2D3) to the plug control system (2E1) to become a sixth plug (6D). As the sixth plug (6D) is being formed by the advancing motion of the third ram (D42), the first plug (1D) is displaced from the plug control system (2E1) into the density reduction system (2F1) where the plug is shredded. A second subsequent material (D+2) is shown being transferred from the weigh feeder (2C1) to the first piston cylinder assembly (2D1) in front of the first ram (D14). The second subsequent material (D+2) is advanced from the first piston cylinder assembly (2D1), to the second piston cylinder assembly (2D2), to the third piston cylinder assembly (2D3), and then to the plug control system (2E1) to become a seventh plug (7D).

The plug control system (2E1) is shown to include a plug control piston (E18) operatively connected to a ram (E20) by a plug control rod (E16). The density reduction system (2F1) is shown to have a shredder (F01), a motor (M2F), and a density reduction chamber pressure sensor (P-F). The gas and carbonaceous material mixing system (2G1) is connected to the transport assembly (2H1). The transport assembly (2H1) is shown to have a motor (M2H).

FIG. 12B:

FIG. 12B shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a second mode of operation under conditions of state 2D(2). FIGS. 12B and 13B depicts the feed zone delivery system (2050) in a second mode of operation under conditions of state 2D(2).

FIG. 12B shows state 2D(2) involving the: 2D1 position retracted; 2D2 position retracted; 2D3 position advanced; and the 2E1 position retracted. State 2D(2) involves the plug control piston (E18), plug control rod (E16), and ram (E20) of the plug control system (2E1) momentarily retracting, allowing the third rod (D40) to compress the first subsequent material (D+1) into a sixth plug (6D), while advancing the line of plugs (1D, 2D, 3D, 4D, 5D), and expelling last plug (1D) into the density reduction system (2F1) for density reduction via the shredder (F01).

A first subsequent material (D+1) is shown positioned in front of the advancing motion of the third ram (D42). The first subsequent material (D+1) is advanced from the third piston cylinder assembly (2D3) to the plug control system (2E1) to become a sixth plug (6D). As the sixth plug (6D) is being formed by the advancing motion of the third ram (D42), the first plug (D1) is displaced from the plug control system (2E1) into the density reduction system (2F1) where the plug is shredded.

FIG. 12C:

FIG. 12C shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a third mode of operation under conditions of state 2D(3). FIGS. 12C and 13C depicts the feed zone delivery system (2050) in a third mode of operation under conditions of state 2D(3).

FIG. 12C shows state 2D(3) involving the: 2D1 position advanced; 2D2 position retracted; 2D3 position advanced; and the 2E1 position advanced. A second subsequent material (D+2) is shown being transferred from the first piston cylinder assembly (2D1) to the second piston cylinder assembly (2D2) in front of the second ram (D28). The second subsequent material (D+2) is advanced from the first piston cylinder assembly (2D1), to the second piston cylinder assembly (2D2), to the third piston cylinder assembly (2D3), and then to the plug control system (2E1) to become a seventh plug (7D). The plug control piston (E18), plug control rod (E16), and ram (E20) of the plug control system (2E1) are shown in the advanced position to hold the plugs (2D, 3D, 4D, 5D, 6D) in place.

FIG. 12D:

FIG. 12D shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a fourth mode of operation under conditions of state 2D(4). FIGS. 12D and 13D depicts the feed zone delivery system (2050) in a fourth mode of operation under conditions of state 2D(4).

FIG. 12D shows state 2D(4) involving the: 2D1 position advanced; 2D2 position retracted; 2D3 position retracted; and the 2E1 position advanced. The third piston (D41), third rod (D40), and third ram (D42), are shown in the retracted positon so as to allow the second subsequent material (D+2) to be transferred from the second piston cylinder assembly (2D2) to in front of the third ram (D42) of the third piston cylinder assembly (2D3). The first piston (D12), first rod (D11), and first ram (D14), of the first piston cylinder assembly (2D1) are shown in the advanced position to act as a safety mechanism wherein at least one ram (D14, D28, D42) is always in the advanced position. The plug control piston (E18), plug control rod (E16), and ram (E20) of the plug control system (2E1) are shown in the advanced position to hold the plugs (2D, 3D, 4D, 5D, 6D) in place.

FIG. 12E:

FIG. 12E shows a non-limiting embodiment of a feed zone delivery system (2050) including a weigh feeder (2C1), first piston cylinder assembly (2D1), second piston cylinder assembly (2D2), third piston cylinder assembly (2D3), plug control system (2E1), density reduction system (2F1), gas and carbonaceous material mixing system (2G1), and a transport assembly (2H1) in a fifth mode of operation under conditions of state 2D(5). FIGS. 12E and 13E depicts the feed zone delivery system (2050) in a fifth mode of operation under conditions of state 2D(5).

FIG. 12E shows state 2D(5) involving the: 2D1 position advanced; 2D2 position advanced; 2D3 position retracted; and the 2E1 position advanced. The second piston (D27), second rod (D26), and second ram (D28) of the second piston cylinder assembly (2D2) are shown in the advanced positon to transfer the second subsequent material (D+2) in front of the retracted third ram (D42) of the third piston cylinder assembly (2D3). The first piston (D12), first rod (D11), and first ram (D14), of the first piston cylinder assembly (2D1) are shown in the advanced position. The plug control piston (E18), plug control rod (E16), and ram (E20) of the plug control system (2E1) are shown in the advanced position to hold the plugs (2D, 3D, 4D, 5D, 6D) in place.

FIG. 13A:

FIG. 13A shows a non-limiting embodiment of a hydraulic compression circuit (2065) including a primary tank (D2000) in fluid communication with first piston cylinder assembly (2D1), second piston cylinder assembly (2D2), and third piston cylinder assembly (2D3), and a secondary tank (D2100) in fluid communication with a plug control system (2E1) in a first mode of operation under conditions of state 2D(1). FIG. 13A depicts the system of FIG. 12A in a first mode of operation under conditions of state 2D(1).

FIGS. 13A-13E depict a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1).

The hydraulic compression circuit (2065) includes: (i) a primary tank (D2000) in fluid communication with first piston cylinder assembly (2D1), second piston cylinder assembly (2D2), and third piston cylinder assembly (2D3); (ii) a secondary tank (D2100) in fluid communication with a plug control system (2E1); and, (iii) a secondary tank (D2100) also in fluid communication with an oil filter (D68) and an oil heat exchanger (HX-D).

A primary tank (D2000) provides the hydraulic fluid that is used in the densification system (2D0). The primary tank (D2000) is in fluid communication with a first piston cylinder assembly (2D1), second piston cylinder assembly (2D2), and third piston cylinder assembly (2D3) to advance or retract the first piston (D12), second piston (D27), or third piston (D41).

The first piston cylinder assembly (2D1) has a first hydraulic cylinder (D05) with a first piston (D12) connected to a first rod (D11). FIG. 12A shows the first rod (D11) connected to the first ram (D14). The first piston (D12) reciprocates within the first hydraulic cylinder (D05) in between the first hydraulic cylinder front cylinder space (D07) and the first hydraulic cylinder rear cylinder space (D08). The first piston (D12) divides the first hydraulic cylinder (D05) into a first hydraulic cylinder front cylinder space (D07) and a first hydraulic cylinder rear cylinder space (D08).

Hydraulic fluid that is contained within the first hydraulic cylinder front cylinder space (D07) must enter and leave from the first hydraulic cylinder front connection port (D09). Hydraulic fluid that is contained within the first hydraulic cylinder rear cylinder space (D08) must enter and leave from the first hydraulic cylinder rear connection port (D10). Hydraulic fluid that is contained within the first hydraulic cylinder front cylinder space (D07) cannot exit the first hydraulic cylinder (D05) through the first hydraulic cylinder rear connection port (D10). Hydraulic fluid that is contained within the first hydraulic cylinder rear cylinder space (D08) cannot exit the first hydraulic cylinder (D05) through the first hydraulic cylinder front connection port (D09).

The second piston cylinder assembly (2D2) has a second hydraulic cylinder (D20) with a second piston (D27) connected to a second rod (D26). FIG. 12A shows the second rod (D26) connected to the second ram (D28). The second piston (D27) reciprocates within the second hydraulic cylinder (D20) in between the second hydraulic cylinder front cylinder space (D22) and the second hydraulic cylinder rear cylinder space (D23). The second piston (D27) divides the second hydraulic cylinder (D20) into a second hydraulic cylinder front cylinder space (D22) and a second hydraulic cylinder rear cylinder space (D23).

Hydraulic fluid that is contained within the second hydraulic cylinder front cylinder space (D22) must enter and leave from the second hydraulic cylinder front connection port (D24). Hydraulic fluid that is contained within the second hydraulic cylinder rear cylinder space (D23) must enter and leave from the second hydraulic cylinder rear connection port (D25). Hydraulic fluid that is contained within the second hydraulic cylinder front cylinder space (D22) cannot exit the second hydraulic cylinder (D20) through the second hydraulic cylinder rear connection port (D25). Hydraulic fluid that is contained within the second hydraulic cylinder rear cylinder space (D23) cannot exit the second hydraulic cylinder (D20) through the second hydraulic cylinder front connection port (D24).

The third piston cylinder assembly (2D3) has a third hydraulic cylinder (D34) with a third piston (D41) connected to a third rod (D40). FIG. 12A shows the third rod (D40) connected to the third ram (D42). The third piston (D41) reciprocates within the third hydraulic cylinder (D34) in between the third hydraulic cylinder front cylinder space (D36) and the third hydraulic cylinder rear cylinder space (D37). The third piston (D41) divides the third hydraulic cylinder (D34) into a third hydraulic cylinder front cylinder space (D36) and a third hydraulic cylinder rear cylinder space (D37).

Hydraulic fluid that is contained within the third hydraulic cylinder front cylinder space (D36) must enter and leave from the third hydraulic cylinder front connection port (D38). Hydraulic fluid that is contained within the third hydraulic cylinder rear cylinder space (D37) must enter and leave from the third hydraulic cylinder rear connection port (D39). Hydraulic fluid that is contained within the third hydraulic cylinder front cylinder space (D36) cannot exit the third hydraulic cylinder (D34) through the third hydraulic cylinder rear connection port (D39). Hydraulic fluid that is contained within the third hydraulic cylinder rear cylinder space (D37) cannot exit the third hydraulic cylinder (D34) through the third hydraulic cylinder front connection port (D38).

The primary tank (D2000) is in fluid communication with first hydraulic cylinder front connection port (D09) and the first hydraulic cylinder rear connection port (D10) of the first piston cylinder assembly (2D1) via a first piston cylinder assembly pump (2PU1). The first piston cylinder assembly pump (2PU1) is connected at one end to a primary tank (D2000) via a suction line (2PU1A) and connected at another end to a first hydraulic cylinder front connection port (D09) and the first hydraulic cylinder rear connection port (D10) of the first hydraulic cylinder (D05) via a discharge line (2PU1B). A first hydraulic cylinder pressure sensor (2P1) is positioned on the first piston cylinder assembly pump (2PU1) discharge line (2PU1B) and is configured to input and output a signal (X2P1) to the computer (COMP). A first hydraulic cylinder front connection port valve (VD1) is positioned on the first hydraulic cylinder front connection port (D09) to direct flow of hydraulic oil to and from the first hydraulic cylinder front cylinder space (D07). The first hydraulic cylinder front connection port valve (VD1) has a common port (VD1A), supply port (VD1B), and drain port (VD1C), with a controller (CD1) that is configured to input or output a signal (XD1) to or from the computer (COMP). The common port (VD1A) is connected to the first hydraulic cylinder front connection port (D09). The supply port (VD1B) is connected to the first piston cylinder assembly pump (2PU1) discharge line (2PU1B). The drain port (VD1C) is connected to the first hydraulic cylinder drain line (D54). A first hydraulic cylinder rear connection port valve (VD2) is positioned on the first hydraulic cylinder rear connection port (D10) to direct flow of hydraulic oil to and from the first hydraulic cylinder rear cylinder space (D08). The first hydraulic cylinder rear connection port valve (VD2) has a common port (VD2A), supply port (VD2B), and drain port (VD2C), with a controller (CD2) that is configured to input or output a signal (XD2) to or from the computer (COMP). The common port (VD2A) is connected to the first hydraulic cylinder rear connection port (D10). The supply port (VD2B) is connected to the first piston cylinder assembly pump (2PU1) discharge line (2PU1B). The drain port (VD2C) is connected to the first hydraulic cylinder drain line (D54).

The primary tank (D2000) is in fluid communication with second hydraulic cylinder front connection port (D24) and the second hydraulic cylinder rear connection port (D25) of the second piston cylinder assembly (2D2) via a second piston cylinder assembly pump (2PU2). The second piston cylinder assembly pump (2PU2) is connected at one end to a primary tank (D2000) via a suction line (2PU2A) and connected at another end to a second hydraulic cylinder front connection port (D24) and the second hydraulic cylinder rear connection port (D25) of the second hydraulic cylinder (D20) via a discharge line (2PU2B). A second hydraulic cylinder pressure sensor (2P2) is positioned on the second piston cylinder assembly pump (2PU2) discharge line (2PU2B) and is configured to input and output a signal (X2P2) to the computer (COMP). A second hydraulic cylinder front connection port valve (VD3) is positioned on the second hydraulic cylinder front connection port (D24) to direct flow of hydraulic oil to and from the second hydraulic cylinder front cylinder space (D22). The second hydraulic cylinder front connection port valve (VD3) has a common port (VD3A), supply port (VD3B), and drain port (VD3C), with a controller (CD3) that is configured to input or output a signal (XD3) to or from the computer (COMP). The common port (VD3A) is connected to the second hydraulic cylinder front connection port (D24). The supply port (VD3B) is connected to the second piston cylinder assembly pump (2PU2) discharge line (2PU2B). The drain port (VD3C) is connected to the second hydraulic cylinder drain line (D56). A second hydraulic cylinder rear connection port valve (VD4) is positioned on the second hydraulic cylinder rear connection port (D25) to direct flow of hydraulic oil to and from the second hydraulic cylinder rear cylinder space (D23). The second hydraulic cylinder rear connection port valve (VD4) has a common port (VD4A), supply port (VD4B), and drain port (VD4C), with a controller (CD4) that is configured to input or output a signal (XD4) to or from the computer (COMP). The common port (VD4A) is connected to the second hydraulic cylinder rear connection port (D25). The supply port (VD4B) is connected to the second piston cylinder assembly pump (2PU2) discharge line (2PU2B). The drain port (VD4C) is connected to the second hydraulic cylinder drain line (D56).

The primary tank (D2000) is in fluid communication with third hydraulic cylinder front connection port (D38) and the third hydraulic cylinder rear connection port (D39) of the third piston cylinder assembly (2D3) via a third piston cylinder assembly pump (2PU3). The third piston cylinder assembly pump (2PU3) is connected at one end to a primary tank (D2000) via a suction line (2PU3A) and connected at another end to a third hydraulic cylinder front connection port (D38) and the third hydraulic cylinder rear connection port (D39) of the third hydraulic cylinder (D34) via a discharge line (2PU3B). A third hydraulic cylinder pressure sensor (2P3) is positioned on the third piston cylinder assembly pump (2PU3) discharge line (2PU3B) and is configured to input and output a signal (X2P3) to the computer (COMP). A third hydraulic cylinder front connection port valve (VD5) is positioned on the third hydraulic cylinder front connection port (D38) to direct flow of hydraulic oil to and from the third hydraulic cylinder front cylinder space (D36). The third hydraulic cylinder front connection port valve (VD5) has a common port (VD5A), supply port (VD5B), and drain port (VD5C), with a controller (CD5) that is configured to input or output a signal (XD5) to or from the computer (COMP). The common port (VD5A) is connected to the third hydraulic cylinder front connection port (D38). The supply port (VD5B) is connected to the third piston cylinder assembly pump (2PU3) discharge line (2PU3B). The drain port (VD5C) is connected to the third hydraulic cylinder drain line (D58). A third hydraulic cylinder rear connection port valve (VD6) is positioned on the third hydraulic cylinder rear connection port (D39) to direct flow of hydraulic oil to and from the third hydraulic cylinder rear cylinder space (D37). The third hydraulic cylinder rear connection port valve (VD6) has a common port (VD6A), supply port (VD6B), and drain port (VD6C), with a controller (CD6) that is configured to input or output a signal (XD6) to or from the computer (COMP). The common port (VD6A) is connected to the third hydraulic cylinder rear connection port (D39). The supply port (VD6B) is connected to the third piston cylinder assembly pump (2PU3) discharge line (2PU3B). The drain port (VD6C) is connected to the third hydraulic cylinder drain line (D58).

It is to be noted that the aforementioned valves (VD1, VD2, VD3, VD4, VD5, VD6) are three-way valves and hydraulic fluid may pass from the supply port to the common port or from the common port to the drain port through these valves. Hydraulic fluid may never pass from the supply port to the drain port.

A first hydraulic cylinder drain line (D54) is in fluid communication with first hydraulic cylinder front connection port (D09) and the first hydraulic cylinder rear connection port (D10) of the first hydraulic cylinder (D05). The first hydraulic cylinder drain line (D54) is also in fluid communication with a primary tank (D2000) via a common drain line (D50).

The first hydraulic cylinder drain line (D54) is configured to transfer hydraulic fluid displaced from either the first hydraulic cylinder front cylinder space (D07) or first hydraulic cylinder rear cylinder space (D08) by the advancing or retracting motion of the first piston (D12) to the primary tank (D2000).

A second hydraulic cylinder drain line (D56) is in fluid communication with second hydraulic cylinder front connection port (D24) and the second hydraulic cylinder rear connection port (D25) of the second hydraulic cylinder (D20). The second hydraulic cylinder drain line (D56) is also in fluid communication with a primary tank (D2000) via a common drain line (D50). The second hydraulic cylinder drain line (D56) is configured to transfer hydraulic fluid displaced from either the second hydraulic cylinder front cylinder space (D22) or second hydraulic cylinder rear cylinder space (D23) by the advancing or retracting motion of the second piston (D27) to the primary tank (D2000).

A third hydraulic cylinder drain line (D58) is in fluid communication with third hydraulic cylinder front connection port (D38) and the third hydraulic cylinder rear connection port (D39) of the third hydraulic cylinder (D34). The third hydraulic cylinder drain line (D58) is also in fluid communication with a primary tank (D2000) via a common drain line (D50). The third hydraulic cylinder drain line (D58) is configured to transfer hydraulic fluid displaced from either the third hydraulic cylinder front cylinder space (D36) or third hydraulic cylinder rear cylinder space (D37) by the advancing or retracting motion of the third piston (D41) to the primary tank (D2000).

An oil filter (D68) and an oil heat exchanger (HX-D) are in fluid communication with the primary tank (D2000). An oil heat exchanger supply pump (D60) is connected at one end to the primary tank (D2000) via a suction line (D62) and connected at another end to an oil filter (D68) via a discharge line (D64). The oil filter (D68) has an oil filter input (D66) and an oil filter output (D70). The oil filter input (D66) is connected to the discharge line (D64) of the oil heat exchanger supply pump (D60). The oil filter output (D70) is connected to an oil heat exchanger (HX-D) via an oil heat exchanger transfer conduit (D72).

The oil heat exchanger (HX-D) has an oil heat exchanger input (D74) and an oil heat exchanger output (D78). The oil heat exchanger output (D74) is connected to the oil filter output (D70) via an oil heat exchanger transfer conduit (D72). The oil heat exchanger output (D78) is connected to the primary tank (D2000) via a filtered and cooled oil transfer conduit (D84). The oil heat exchanger supply pump (D60) is configured to transfer particulate-laden hydraulic fluid at a first higher hydraulic oil inlet temperature (TD1) to an oil filter (D68) and then to an oil heat exchanger (HX-D) to realize a second lower hydraulic oil inlet temperature (TD2) that is depleted of particulates. The oil heat exchanger (HX-D) has a heat transfer medium input (D80) and a heat transfer medium output (D82) that is configured to convey a heat transfer medium (air, water, gas, liquid) therethrough to reduce the temperature of the hydraulic oil transferred from the oil heat exchanger input (D74) to the oil heat exchanger output (D78).

The secondary tank (D2100) is in fluid communication with a plug control system (2E1). The suction line (D85) of a secondary tank transfer pump (D86) is submerged beneath the level of hydraulic fluid within the secondary tank (D2100). The secondary tank transfer pump (D86) has a suction line (D85) in fluid communication with the secondary tank (D2100) and a discharge line (D88) in fluid communication with the first plug control hydraulic cylinder rear connection port (E14A) and the second plug control hydraulic cylinder rear connection port (E14B).

The first plug control hydraulic cylinder rear connection port (E14A) and the second plug control hydraulic cylinder rear connection port (E14B) are shown to be in fluid communication with one another and configured to receive a source of hydraulic fluid via a plug control transfer line (D90). The plug control system (2E1) shown in FIG. 13A depicts the embodiment shown in FIG. 8A and includes both a first plug control hydraulic cylinder (E10A) and a second plug control hydraulic cylinder (E10B).

The first plug control hydraulic cylinder (E10A) has a first plug control hydraulic cylinder rear cylinder space (E12A), first plug control hydraulic cylinder rear connection port (E14A), first plug control hydraulic cylinder drain port (E15A), and a first plug control piston (E18A), connected to a first plug control rod (E16A). FIG. 8A shows the first plug control rod (E16A) connected to the first ram (E20A).

The second plug control hydraulic cylinder (E10B) has a second plug control hydraulic cylinder rear cylinder space (E12B), second plug control hydraulic cylinder rear connection port (E14B), second plug control hydraulic cylinder drain port (E15B), and a second plug control piston (E18B) connected to a second plug control rod (E16B). FIG. 8A shows the second plug control rod (E16B) connected to the second ram (E20B).

The first plug control hydraulic cylinder drain port (E15A) is in fluid communication with the second plug control hydraulic cylinder drain port (E15B). The first plug control hydraulic cylinder drain port (E15A) and second plug control hydraulic cylinder drain port (E15B) are both connected to the secondary tank (D2100) via a plug control drain line (D92).

The plug control drain line (D92) is configured to evacuate hydraulic fluid displaced from the first plug control hydraulic cylinder rear cylinder space (E12A) via the first plug control hydraulic cylinder drain port (E15A) and the second plug control hydraulic cylinder rear cylinder space (E12B) via the second plug control hydraulic cylinder drain port (E15B).

A plug control rear connection port valve (VD7) is positioned in the plug control transfer line (D90) to regulate flow transferred from the secondary tank transfer pump (D86) to the first plug control hydraulic cylinder rear connection port (E14A) and the second plug control hydraulic cylinder rear connection port (E14B). The plug control rear connection port valve (VD7) is equipped with a controller (CD7) that is configured to input and output a signal (XD7) to and from the computer (COMP).

A plug control drain valve (VD8) is positioned in the plug control drain line (D92) to regulate flow transferred from the first plug control hydraulic cylinder drain port (E15A) and the second plug control hydraulic cylinder drain port (E15B) to the secondary tank (D2100). The plug control drain valve (VD8) is equipped with a controller (CD8) that is configured to input and output a signal (XD8) to and from the computer (COMP).

State 2D(1) involves the following states of operation. In the first hydraulic cylinder front connection port valve (VD1), the common port (VD1A) is open, supply port (VD1B) is open, and the drain port (VD1C) is closed. In the first hydraulic cylinder rear connection port valve (VD2), the common port (VD2A) is open, supply port (VD2B) is closed, and the drain port (VD2C) is open. In the second hydraulic cylinder front connection port valve (VD3) common port (VD3A) open, supply port (VD3B) open, and the drain port (VD3C) closed. The second hydraulic cylinder rear connection port valve (VD4), the common port (VD4A) is open, supply port (VD4B) is closed, and the drain port is (VD4C) open. In the third hydraulic cylinder front connection port valve (VD5), the common port (VD5A) open, supply port (VD5B) closed, and the drain port (VD5C) open. The third hydraulic cylinder rear connection port valve (VD6) common port (VD6A) open, supply port (VD6B) open, and the drain port is (VD6C) closed. The plug control rear connection port valve (VD7) is open. The plug control drain valve (VD8) is closed. 2D1 is in the retracted position. 2D2 is in the retracted position. 2D3 is in the advancing position. 2E1 is in the advanced position.

FIG. 13B:

FIG. 13B shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a second mode of operation under conditions of state 2D(2). FIG. 13B depicts the system of FIG. 12B in a second mode of operation under conditions of state 2D(2).

State 2D(2) involves the following states of operation. The first hydraulic cylinder front connection port valve (VD1) common port (VD1A) open, supply port (VD1B) open, and the drain port (VD1C) closed. The first hydraulic cylinder rear connection port valve (VD2) common port (VD2A) open, supply port (VD2B) closed, and the drain port (VD2C) open. The second hydraulic cylinder front connection port valve (VD3) common port (VD3A) open, supply port (VD3B) open, and the drain port (VD3C) closed. The second hydraulic cylinder rear connection port valve (VD4) common port (VD4A) open, supply port (VD4B) closed, and the drain port (VD4C) open. The third hydraulic cylinder front connection port valve (VD5) common port (VD5A) open, supply port (VD5B) closed, and the drain port (VD5C) open. The third hydraulic cylinder rear connection port valve (VD6) common port (VD6A) open, supply port (VD6B) open, and the drain port (VD6C) closed. The plug control rear connection port valve (VD7) is closed. The plug control drain valve (VD8) is open. 2D1 is in the retracted position. 2D2 is in the retracted position. 2D3 is in the advanced position. 2E1 is in the retracted position.

FIG. 13C:

FIG. 13C shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a third mode of operation under conditions of state 2D(3). FIG. 13C depicts the system of FIG. 12C in a third mode of operation under conditions of state 2D(3).

State 2D(3) involves the following states of operation. The first hydraulic cylinder front connection port valve (VD1) common port (VD1A) open, supply port (VD1B) closed, and the drain port (VD1C) open. The first hydraulic cylinder rear connection port valve (VD2) common port (VD2A) open, supply port (VD2B) open, and the drain port (VD2C) closed. The second hydraulic cylinder front connection port valve (VD3) common port (VD3A) open, supply port (VD3B) open, and the drain port (VD3C) closed. The second hydraulic cylinder rear connection port valve (VD4) common port (VD4A) open, supply port (VD4B) closed, and the drain port (VD4C) open. The third hydraulic cylinder front connection port valve (VD5) common port (VD5A) open, supply port (VD5B) closed, and the drain port (VD5C) open. The third hydraulic cylinder rear connection port valve (VD6) common port (VD6A) open, supply port (VD6B) open, and the drain port (VD6C) closed. The plug control rear connection port valve (VD7) is open. The plug control drain valve (VD8) is closed. 2D1 is in the advanced position. 2D2 is in the retracted position. 2D3 is in the advanced position. 2E1 is in the advanced position.

FIG. 13D:

FIG. 13D shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a fourth mode of operation under conditions of state 2D(4). FIG. 13D depicts the system of FIG. 12D in a fourth mode of operation under conditions of state 2D(4).

State 2D(4) involves the following states of operation. The first hydraulic cylinder front connection port valve (VD1) common port (VD1A) open, supply port (VD1B) closed, and the drain port (VD1C) open. The first hydraulic cylinder rear connection port valve (VD2) common port (VD2A) open, supply port (VD2B) open, and the drain port (VD2C) closed. The second hydraulic cylinder front connection port valve (VD3) common port (VD3A) open, supply port (VD3B) open, and the drain port (VD3C) closed. The second hydraulic cylinder rear connection port valve (VD4) common port (VD4A) open, supply port (VD4B) closed, and the drain port (VD4C) open. The third hydraulic cylinder front connection port valve (VD5) common port (VD5A) open, supply port (VD5B) open, and the drain port (VD5C) closed. The third hydraulic cylinder rear connection port valve (VD6) common port (VD6A) open, supply port (VD6B) closed, and the drain port (VD6C) open. The plug control rear connection port valve (VD7) is open. The plug control drain valve (VD8) is closed. 2D1 is in the advanced position. 2D2 is in the retracted position. 2D3 is in the retracted position. 2E1 is in the advanced position.

FIG. 13E:

FIG. 13E shows a non-limiting embodiment of a hydraulic compression circuit (2065) including a primary tank (D2000) in fluid communication with first piston cylinder assembly (2D1), second piston cylinder assembly (2D2), third piston cylinder assembly (2D3) and a secondary tank (D2100) in fluid communication with a plug control system (2E1) in a fifth mode of operation under conditions of state 2D(5). FIG. 13E depicts the system of FIG. 12E in a fifth mode of operation under conditions of state 2D(5).

State 2D(5) involves the following states of operation. The first hydraulic cylinder front connection port valve (VD1) common port (VD1A) open, supply port (VD1B) closed, and the drain port (VD1C) open. The first hydraulic cylinder rear connection port valve (VD2) common port (VD2A) open, supply port (VD2B) open, and the drain port (VD2C) closed. The second hydraulic cylinder front connection port valve (VD3) common port (VD3A) open, supply port (VD3B) closed, and the drain port (VD3C) open. The second hydraulic cylinder rear connection port valve (VD4) common port (VD4A) open, supply port (VD4B) open, and the drain port (VD4C) closed. The third hydraulic cylinder front connection port valve (VD5) common port (VD5A) open, supply port (VD5B) open, and the drain port (VD5C) closed. The third hydraulic cylinder rear connection port valve (VD6) common port (VD6A) open, supply port (VD6B) closed, and the drain port (VD6C) open. The plug control rear connection port valve (VD7) is open. The plug control drain valve (VD8) is closed. 2D1 is in the advanced position. 2D2 is in the advanced position. 2D3 is in the retracted position. 2E1 is in the advanced position.

FIG. 13F:

FIG. 13F depicts the Densification Valve States for Automated Controller Operation of typical normal operation procedure. FIG. 13F is to be used in conjunction with FIG. 12A, 12B, 12C, 12D, 12E, 13A, 13B, 13C, 13D, 13E and depicts a listing of valve states that may be used in a variety of methods to operate valves associated with the densification system (2D0).

FIG. 14:

FIG. 14 shows a non-limiting embodiment of a feedstock delivery and product gas generation system (2075) including a bulk transfer system (2A1) connected to a first splitter (2B1) and a second splitter (2B2), where the first splitter (2B1) is in fluid communication with a first reactor (100) through a plurality of feed zone delivery systems (2050A, 2050B, 2050C), and the second splitter (2B2) is in fluid communication with a first reactor (100) through a plurality of feed zone delivery systems (2050D, 2050E, 2050F), and further including a first solids separation device (150), second reactor (200), and second solids separation device (250) which are in fluid communicating with a third reactor (300).

FIG. 14 displays one non-limiting embodiment of a feedstock delivery and product gas generation system (2075A) including a bulk transfer system (2A1) equipped to transfer a bulk carbonaceous material (2B-01) to a first splitter (2B1) via a first split stream (2B-01A) and to a second splitter (2B2) via a second split stream (2B-01B).

The first splitter (2B1) is equipped to output a first split carbonaceous material stream (2B-02A), a second split carbonaceous material stream (2B-02B), and a third split carbonaceous material stream (2B-02C). The second splitter (2B2) is equipped to output a fourth split carbonaceous material stream (2B-02D), a fifth split carbonaceous material stream (2B-02E), and a sixth split carbonaceous material stream (2B-02F).

The first split carbonaceous material stream (2B-02A) is transferred from the first splitter (2B1) to a first feed zone delivery system (2050A) having a first feed zone delivery system input (FZ-IN1) and a first feed zone delivery system output (FZ-OUT1). A first carbonaceous material and gas mixture (102A) is discharged from the first feed zone delivery system (2050A) via the first feed zone delivery system output (FZ-OUT1) and provided to a first carbonaceous material and gas input (104A) of the first reactor (100).

The second split carbonaceous material stream (2B-02B) is transferred from the first splitter (2B1) to a second feed zone delivery system (2050B) having a second feed zone delivery system input (FZ-IN2) and a second feed zone delivery system output (FZ-OUT2). A second carbonaceous material and gas mixture (102B) is discharged from the second feed zone delivery system (2050B) via the second feed zone delivery system output (FZ-OUT2) and provided to the second carbonaceous material and gas input (104B) of the first reactor (100).

The third split carbonaceous material stream (2B-02C) is transferred from the first splitter (2B1) to a third feed zone delivery system (2050C) having a third feed zone delivery system input (FZ-IN3) and a third feed zone delivery system output (FZ-OUT3). A third carbonaceous material and gas mixture (102C) is discharged from the third feed zone delivery system (2050C) via the third feed zone delivery system output (FZ-OUT3) and provided to the third carbonaceous material and gas input (104C) of the first reactor (100).

The fourth split carbonaceous material stream (2B-02D) is transferred from the second splitter (2B2) to a fourth feed zone delivery system (2050D) having a fourth feed zone delivery system input (FZ-IN4) and a fourth feed zone delivery system output (FZ-OUT4). A fourth carbonaceous material and gas mixture (102D) is discharged from the fourth feed zone delivery system (2050D) via the fourth feed zone delivery system output (FZ-OUT4) and provided to the fourth carbonaceous material and gas input (104D) of the first reactor (100).

The fifth split carbonaceous material stream (2B-02E) is transferred from the second splitter (2B2) to a fifth feed zone delivery system (2050E) having a fifth feed zone delivery system input (FZ-IN5) and a fifth feed zone delivery system output (FZ-OUT5). A fifth carbonaceous material and gas mixture (102E) is discharged from the fifth feed zone delivery system (2050E) via the fifth feed zone delivery system output (FZ-OUT5) and provided to the fifth carbonaceous material and gas input (104E) of the first reactor (100).

The sixth split carbonaceous material stream (2B-02F) is transferred from the second splitter (2B2) to a sixth feed zone delivery system (2050F) having a sixth feed zone delivery system input (FZ-IN6) and a sixth feed zone delivery system output (FZ-OUT6). A sixth carbonaceous material and gas mixture (102F) is discharged from the sixth feed zone delivery system (2050F) via the sixth feed zone delivery system output (FZ-OUT6) and provided to the sixth carbonaceous material and gas input (104F) of the first reactor (100).

The first reactor (100) has four carbonaceous material and gas inputs (104A, 104C, 104D, 104F) which, in a view of the reactor along the longitudinal reactor axis (AX), are equally circumferentially spaced apart from one another; and each of four feed zone delivery systems (2050A, 2050C, 2050D, 2050F) has its feed zone delivery system output (FZ-OUT1, FZ-OUT3, FZ-OUT4, FZ-OUT6) connected to one of the four carbonaceous material and gas inputs (104A, 104C, 104D, 104F) of the first reactor (100). The first reactor has two additional carbonaceous material and gas inputs (104B, 104E) which, in a view of the reactor along the longitudinal reactor axis (AX), are (i) equally circumferentially spaced apart from one another and (ii) are circumferentially spaced apart from said four first carbonaceous material and gas inputs (104A, 104C, 104D, 104F); and each of two additional feed zone delivery systems (2050B, 2050E) has its feed zone delivery system output (FZ-OUT2, FZ-OUT5) connected to one of the two additional carbonaceous material and gas inputs (104B, 104E) of the first reactor (100).

The feedstock delivery and product gas generation system (2075B) further includes a first reactor (100) connected to a first solids separation device (150) and configured transport a first reactor product gas (122) from the first reactor (100) to the first solids separation device (150). The first solids separation device (150) is connected at one end to a second reactor (200) and at the other end to a third reactor (300). The first solids separation device (150) is configured to remove char from the first reactor product gas (122) and route the char to the second reactor (200) via a dipleg (244). A char depleted first reactor product gas (126) is evacuated from the first solids separation device (150) and transferred to the third reactor (300) via a combined reactor product gas conduit (230). The second reactor (200) is configured to react the char separated out from the first solids separation device (150) and output a second reactor product gas (222) to be transferred to a second solids separation device (250). The second solids separation device (250) is configured to remove solids from the second reactor product gas (222) and route the solids depleted second reactor product gas (226) to the third reactor (300) via a combined reactor product gas conduit (230).

Figure 14A:
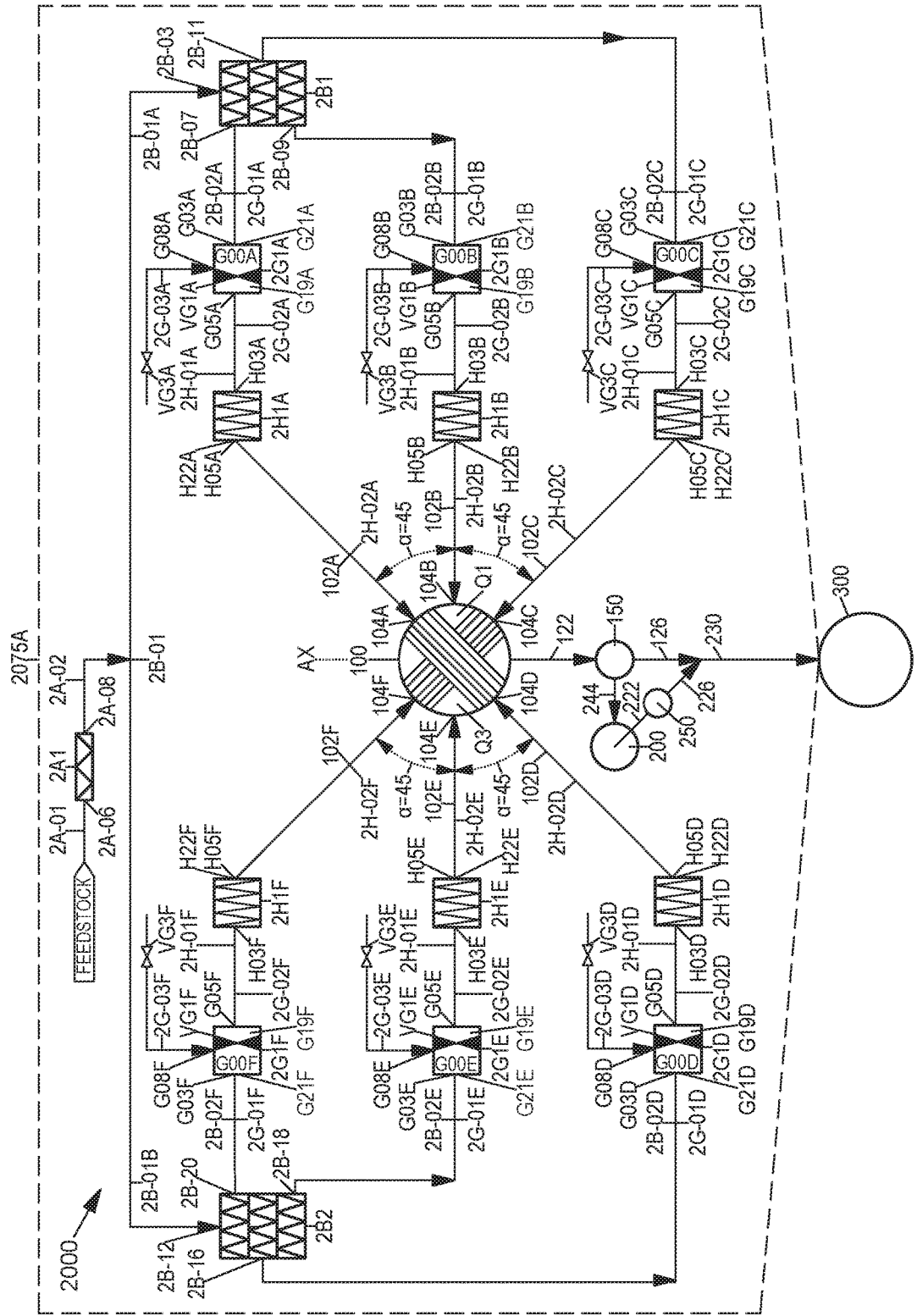
FIG. 14A shows a non-limiting embodiment of a feedstock delivery and product gas generation system (2075) including a Feedstock Delivery System (2000) comprised of a bulk transfer system (2A1) connected to a first splitter (2B1) and a second splitter (2B2), where the splitters (2B1, 2B2) are in fluid communication with a first reactor (100) through a plurality of gas and carbonaceous material mixing systems (2G1A, 2G1B, 2G1C 2G1D, 2G1E, 2G1F) and a plurality of transport assemblies (2H1A, 2H1B, 2H1C, 2H1D, 2H1E, 2H1F).

FIG. 14A:

FIG. 14A shows a non-limiting embodiment of a feedstock delivery and product gas generation system (2075) including a Feedstock Delivery System (2000) comprised of a bulk transfer system (2A1) connected to a first splitter (2B1) and a second splitter (2B2), where the splitters (2B1, 2B2) are in fluid communication with a first reactor (100) through a plurality of gas and carbonaceous material mixing systems (2G1A, 2G1B, 2G1C 2G1D, 2G1E, 2G1F) and a plurality of transport assemblies (2H1A, 2H1B, 2H1C, 2H1D, 2H1E, 2H1F). FIG. 14A further includes a first solids separation device (150), second reactor (200), and second solids separation device (250) which are in fluid communicating with a third reactor (300).

A bulk transfer system (2A1) accepts a bulk carbonaceous material (2A-01) through an input (2A-06) and discharges a bulk carbonaceous material (2A-02) via an output (2A-08). A bulk carbonaceous material (2B-01) is transferred from the bulk transfer system (2A1) to a first splitter (2B1) and a second splitter (2B2). The splitters (2B1, 2B2) are in fluid communication with a first reactor (100) through a plurality of gas and carbonaceous material mixing systems (2G1A, 2G1B, 2G1C 2G1D, 2G1E, 2G1F) and a plurality of transport assemblies (2H1A, 2H1B, 2H1C, 2H1D, 2H1E, 2H1F).

The first splitter (2B1) is connected to the bulk transfer system (2A1). The first splitter (2B1) has a splitter input (2B-03) that is configured to accept a portion of the bulk carbonaceous material (2A-01) discharged via the output (2A-08) as a first split stream (2B-01A). The second splitter (2B2) is connected to the bulk transfer system (2A1). The second splitter (2B2) has a splitter input (2B-12) that is configured to accept a portion of the bulk carbonaceous material (2A-01) discharged via the output (2A-08) as a second split stream (2B-01B).

The first splitter (2B1) has a first output (2B-07), second output (2B-09), and a third output (2B-11). The second splitter (2A2) has a first output (2B-16), second output (2B-18), and a third output (2B-20). The first output (2B-07) of the first splitter (2B1) is connected to the first mixing chamber carbonaceous material stream input (G03A) of the first mixing chamber (G00A) and is configured to transport a first split carbonaceous material stream (2B-02A) from the first splitter (2B1) to the first mixing chamber (G00A). The second output (2B-09) of the first splitter (2B1) is connected to the second mixing chamber carbonaceous material stream input (G03B) of the second mixing chamber (G00B) and is configured to transport a second split carbonaceous material stream (2B-02B) from the first splitter (2B1) to the second mixing chamber (G00B). The third output (2B-11) of the first splitter (2B1) is connected to the third mixing chamber carbonaceous material stream input (G03C) of the third mixing chamber (G00C) and is configured to transport a third split carbonaceous material stream (2B-02C) from the first splitter (2B1) to the third mixing chamber (G00C).

The first output (2B-16) of the second splitter (2B2) is connected to the fourth mixing chamber carbonaceous material stream input (G03D) of the fourth mixing chamber (G00D) and is configured to transport a fourth split carbonaceous material stream (2B-02D) from the second splitter (2B2) to the fourth mixing chamber (G00D). The second output (2B-18) of the second splitter (2A2) is connected to the fifth mixing chamber carbonaceous material stream input (G03E) of the fifth mixing chamber (G00E) and is configured to transport a fifth split carbonaceous material stream (2B-02E) from the second splitter (2B2) to the fifth mixing chamber (G00E). The third output (2B-20) of the second splitter (2A2) is connected to the sixth mixing chamber carbonaceous material stream input (G03F) of the sixth mixing chamber (G00F) and is configured to transport a sixth split carbonaceous material stream (2B-02F) from the second splitter (2B2) to the sixth mixing chamber (G00F).

The first mixing chamber (G00A) has a first mixing chamber gas input (G08A) configured to accept a first mixing gas (2G-03A) for mixing with the first carbonaceous material (2G-01A) transferred to the first mixing chamber (G00A) from the first output (2B-07) of the first splitter (2B1). The second mixing chamber (G00B) has a second mixing chamber gas input (G08B) configured to accept a second mixing gas (2G-03B) for mixing with the second carbonaceous material (2G-01B) transferred to the second mixing chamber (G00B) from the second output (2B-09) of the first splitter (2B1). The third mixing chamber (G00C) has a third mixing chamber gas input (G08C) configured to accept a third mixing gas (2G-03C) for mixing with the third carbonaceous material (2G-01C) transferred to the third mixing chamber (G00C) from the third output (2B-11) of the first splitter (2B1).

The fourth mixing chamber (G00D) has a fourth mixing chamber gas input (G08D) configured to accept a fourth mixing gas (2G-03D) for mixing with the fourth carbonaceous material (2G-01D) transferred to the fourth mixing chamber (G00D) from the first output (2B-16) of the second splitter (2B2). The fifth mixing chamber (G00E) has a fifth mixing chamber gas input (G08E) configured to accept a fifth mixing gas (2G-03E) for mixing with the fifth carbonaceous material (2G-01E) transferred to the fifth mixing chamber (G00E) from the second output (2B-18) of the second splitter (2B2). The sixth mixing chamber (G00F) has a sixth mixing chamber gas input (G08F) configured to accept a sixth mixing gas (2G-03F) for mixing with the sixth carbonaceous material (2G-01F) transferred to the sixth mixing chamber (G00F) from the third output (2B-20) of the second splitter (2B2).

A first mixing gas input valve (VG3, VG3A, VG3B, VG3C, VG3D, VG3E, VG3F) is configured to regulate the flow of the mixing gas (2G-03A, 2G-03B, 2G-03C, 2G-03D, 2G-03E, 2G-03F) to each mixing chamber (G00A, G00B, G00C, G00D, G00E, G00F). Each mixing chamber (G00A, G00B, G00C, G00D, G00E, G00F) has a first isolation valve (VG1A, VG1B, VG1C, VG1D, VG1E, VG1F) that separates the mixing chamber (G00A, G00B, G00C, G00D, G00E, G00F) into an entry section (G21, G21A, G21B, G21C, G21D, G21E, G21F) and an exit section (G19, G19A, G19B, G19C, G19D, G19E, G19F).

The first mixing chamber (G00A) has a first mixing output (G05A) configured to discharge a first carbonaceous material and gas mixture (2G-02A) to a first transport input (H03A) of a first transport assembly (2H1A). The second mixing chamber (G00B) has a second mixing output (G05B) configured to discharge a second carbonaceous material and gas mixture (2G-02B) to a second transport input (H03B) of a second transport assembly (2H1B). The third mixing chamber (G00C) has a third mixing output (G05C) configured to discharge a third carbonaceous material and gas mixture (2G-02C) to a third transport input (H03C) of a third transport assembly (2H1C).

The fourth mixing chamber (G00D) has a fourth mixing output (G05D) configured to discharge a fourth carbonaceous material and gas mixture (2G-02D) to a fourth transport input (H03D) of a fourth transport assembly (2H1D). The fifth mixing chamber (G00E) has a fifth mixing output (G05E) configured to discharge a fifth carbonaceous material and gas mixture (2G-02E) to a fifth transport input (H03E) of a fifth transport assembly (2H1E). The sixth mixing chamber (G00F) has a sixth mixing output (G05F) configured to discharge a sixth carbonaceous material and gas mixture (2G-02F) to a sixth transport input (H03F) of a sixth transport assembly (2H1F).

A first transport assembly (2H1A) accepts a first carbonaceous material and gas mixture (2H-01A) from the first mixing output (G05A) of the first mixing chamber (G00A) for transport to a first carbonaceous material and gas input (104A) of a first reactor (100) via a first transport output (H05A). A second transport assembly (2H1B) accepts a second carbonaceous material and gas mixture (2H-01B) from the second mixing output (G05B) of the second mixing chamber (G00B) for transport to a second carbonaceous material and gas input (104B) of a first reactor (100) via a second transport output (H05B). A third transport assembly (2H1C) accepts a third carbonaceous material and gas mixture (2H-01C) from the third mixing output (G05C) of the third mixing chamber (G00C) for transport to a third carbonaceous material and gas input (104C) of a first reactor (100) via a third transport output (H05C).

A fourth transport assembly (2H1D) accepts a fourth carbonaceous material and gas mixture (2H-01D) from the fourth mixing output (G05D) of the fourth mixing chamber (G00D) for transport to a fourth carbonaceous material and gas input (104D) of a first reactor (100) via a fourth transport output (H05D). A fifth transport assembly (2H1E) accepts a fifth carbonaceous material and gas mixture (2H-01E) from the fifth mixing output (G05E) of the fifth mixing chamber (G00E) for transport to a fifth carbonaceous material and gas input (104E) of a first reactor (100) via a fifth transport output (H05E). A sixth transport assembly (2H1F) accepts a sixth carbonaceous material and gas mixture (2H-01F) from the sixth mixing output (G05F) of the sixth mixing chamber (G00F) for transport to a sixth carbonaceous material and gas input (104F) of a first reactor (100) via a sixth transport output (H05A).

Each transport assembly (2H1A, 2H1B, 2H1C, 2H1D, 2H1E, 2H1F) has a transport input (H03A, H03B, H03C, H03D, H03E, H03F) and a transport output (H05A, H05B, H05C, H05D, H05E, H05F). Each transport output (H05A, H05B, H05C, H05D, H05E, H05F) is connected to a carbonaceous material and gas input (104A, 104B, 104C, 104D, 104E, 104F) circumferentially positioned about the perimeter of a first reactor (100) and configured to transfer a carbonaceous material and gas mixture (102A, 102B, 102C, 102D, 102E, 102F) to the first reactor (100).

FIG. 14A depicts each transport assembly (2H1A, 2H1B, 2H1C, 2H1D, 2H1E, 2H1F) configured to discharge a carbonaceous material and gas mixture (2H-02A, 2H-02B, 2H-02C, 2H-02D, 2H-02E, 2H-02F) via a transport output (H05A, H05B, H05C, H05D, H05E, H05F) for transfer to the first reactor (100).

The first transport output (H05A) is the first feedstock delivery system output (H22A). The second transport output (H05B) is the second feedstock delivery system output (H22B). The third transport output (H05C) is the third feedstock delivery system output (H22C). The fourth transport output (H05D) is the fourth feedstock delivery system output (H22D). The fifth transport output (H05E) is the fifth feedstock delivery system output (H22E). The sixth transport output (H05F) is the sixth feedstock delivery system output (H22F).

FIG. 14A illustrates the second carbonaceous material and gas input (104B) introduced to the first quadrant (Q1) of the first reactor (100) and the fifth carbonaceous material and gas input (104E) introduced to the third quadrant (Q3) of the first reactor (100). The first reactor (100) reacts the carbonaceous material and gas mixtures (102A, 102B, 102C, 102D, 102E, 102F) with steam, an oxygen-containing gas, and/or carbon dioxide and outputs a first reactor product gas (122) for transfer to a first solids separation device (150). The first solids separation device (150) separates char from the first reactor product gas (122) for transfer to a second reactor (200) via a dipleg (244). A char depleted first reactor product gas (126) having a depleted amount of char relative to the first reactor product gas (122) is evacuated from the first solids separation device (150).

The second reactor (200) reacts the separated char with steam, an oxygen-containing gas, and/or carbon dioxide and outputs a second reactor product gas (222) for transfer to a second solids separation device (250). A solids depleted second reactor product gas (226) having a depleted amount of solids relative to the second reactor product gas (222) is evacuated from the second solids separation device (250). The char depleted first reactor product gas (126) is combined with the solids depleted second reactor product gas (226) in a combined reactor product gas conduit (230) and transferred to a third reactor (300). FIG. 14A depicts a feedstock delivery and product gas generation system (2075) that includes a Feedstock Delivery System (2000), first reactor (100), first solids separation device (150), second reactor (200), second solids separation device (250), and third reactor (300).

Figure 15:
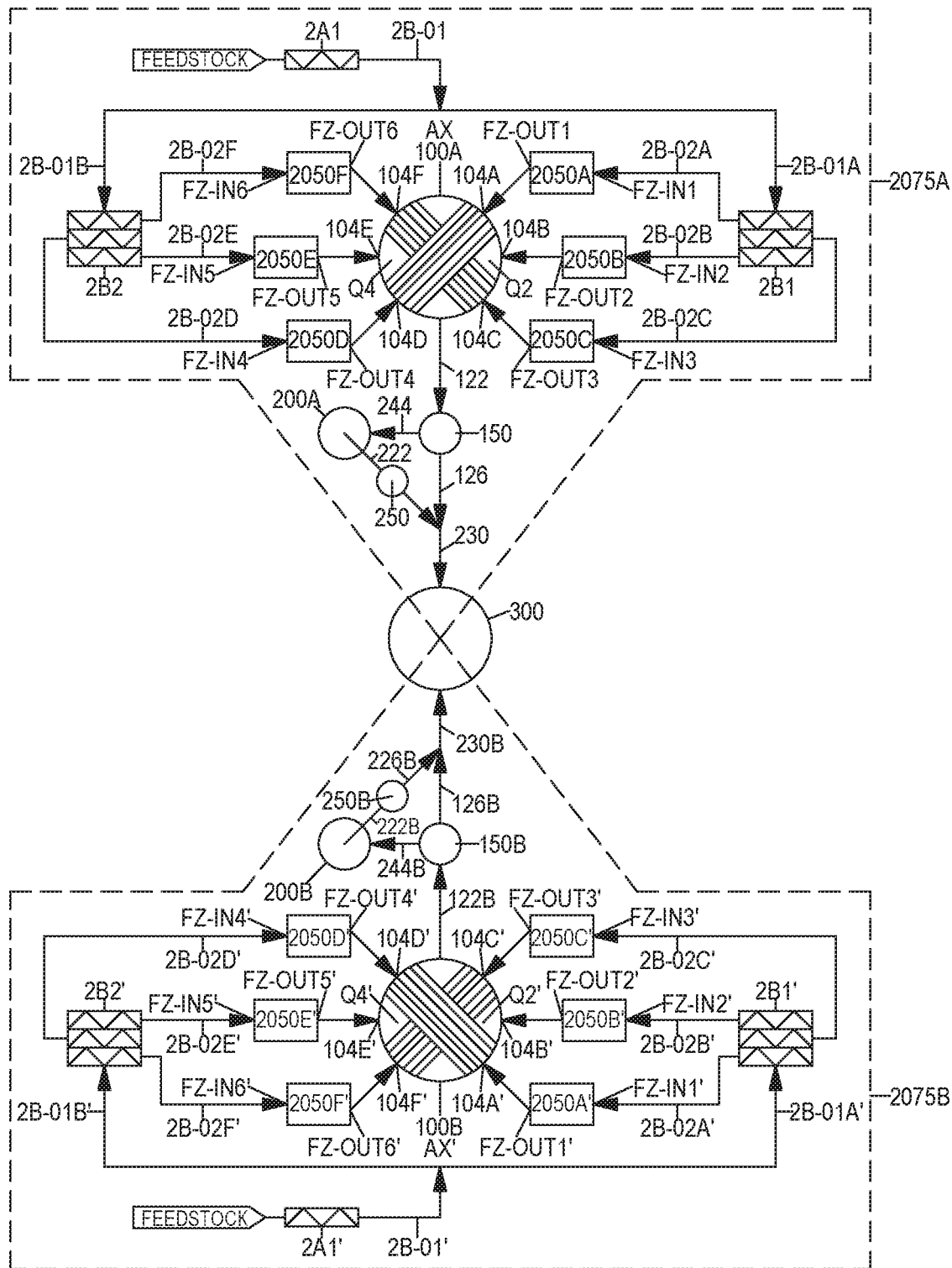
FIG. 15 shows a non-limiting embodiment disclosing two feedstock delivery and product gas generation systems (2075A, 2075B) of FIG. 14 operatively connected and in fluid communication with one common third reactor (300).

FIG. 15:

FIG. 15 shows a non-limiting embodiment disclosing two feedstock delivery and product gas generation systems (2075A, 2075B) of FIG. 14 operatively connected and in fluid communication with one common third reactor (300). FIG. 15 elaborates upon the system of FIG. 14 but shows a plurality of product gas generation systems (2075A, 2075B) operatively connected and in fluid communication with one common third reactor (300). FIG. 15 displays one non-limiting embodiment of a plurality of feedstock delivery and product gas generation systems (2075A, 2075B).

The feedstock delivery and product gas generation systems (2075B) includes a bulk transfer system (2A1') equipped to transfer a bulk carbonaceous material (2B-01') to a first splitter (2B1') via a first split stream (2B-01A') and to a second splitter (2B2') via a second split stream (2B-01B'). The first splitter (2B1') is equipped to output a first split carbonaceous material stream (2B-02A'), a second split carbonaceous material stream (2B-02B'), and a third split carbonaceous material stream (2B-02C'). The second splitter (2B2') is equipped to output a fourth split carbonaceous material stream (2B-02D'), a fifth split carbonaceous material stream (2B-02E'), and a sixth split carbonaceous material stream (2B-02F').

The first split carbonaceous material stream (2B-02A') is transferred from the first splitter (2B1') to a first feed zone delivery system (2050A') having a first feed zone delivery system input (FZ-IN1') and a first feed zone delivery system output (FZ-OUT1'). A first carbonaceous material and gas mixture (102A') is discharged from the first feed zone delivery system (2050A') via the first feed zone delivery system output (FZ-OUT1') and provided to a first carbonaceous material and gas input (104A') of the first reactor (100B).

The second split carbonaceous material stream (2B-02B') is transferred from the first splitter (2B1') to a second feed zone delivery system (2050B) having a second feed zone delivery system input (FZ-IN2') and a second feed zone delivery system output (FZ-OUT2'). A second carbonaceous material and gas mixture (102B) is discharged from the second feed zone delivery system (2050B) via the second feed zone delivery system output (FZ-OUT2') and provided to the second carbonaceous material and gas input (104B) of the first reactor (100B).

The third split carbonaceous material stream (2B-02C') is transferred from the first splitter (2B1') to a third feed zone delivery system (2050C') having a third feed zone delivery system input (FZ-IN3') and a third feed zone delivery system output (FZ-OUT3'). A third carbonaceous material and gas mixture (102C') is discharged from the third feed zone delivery system (2050C') via the third feed zone delivery system output (FZ-OUT3') and provided to the third carbonaceous material and gas input (104C') of the first reactor (100B).

The fourth split carbonaceous material stream (2B-02D') is transferred from the second splitter (2B2') to a fourth feed zone delivery system (2050D') having a fourth feed zone delivery system input (FZ-IN4') and a fourth feed zone delivery system output (FZ-OUT4'). A fourth carbonaceous material and gas mixture (102D') is discharged from the fourth feed zone delivery system (2050D') via the fourth feed zone delivery system output (FZ-OUT4') and provided to the fourth carbonaceous material and gas input (104D') of the first reactor (100B).

The fifth split carbonaceous material stream (2B-02E') is transferred from the second splitter (2B2') to a fifth feed zone delivery system (2050E') having a fifth feed zone delivery system input (FZ-IN5') and a fifth feed zone delivery system output (FZ-OUT5'). A fifth carbonaceous material and gas mixture (102E') is discharged from the fifth feed zone delivery system (2050E') via the fifth feed zone delivery system output (FZ-OUT5') and provided to the fifth carbonaceous material and gas input (104E') of the first reactor (100B).

The sixth split carbonaceous material stream (2B-02F') is transferred from the second splitter (2B2') to a sixth feed zone delivery system (2050F') having a sixth feed zone delivery system input (FZ-IN6') and a sixth feed zone delivery system output (FZ-OUT6'). A sixth carbonaceous material and gas mixture (102F') is discharged from the sixth feed zone delivery system (2050F') via the sixth feed zone delivery system output (FZ-OUT6') and provided to the sixth carbonaceous material and gas input (104F') of the first reactor (100B).

The first reactor (100') has four carbonaceous material and gas inputs (104A', 104C', 104D', 104F') which, in a view of the reactor along the longitudinal reactor axis (AX'), are equally circumferentially spaced apart from one another; and each of four feed zone delivery systems (2050A', 2050B', 2050C', 2050D') has its feed zone delivery system output (FZ-OUT1', FZ-OUT3', FZ-OUT4', FZ-OUT6') connected to one of the four carbonaceous material and gas inputs (104A', 104C', 104D', 104F') of the first reactor (100B). The first reactor has two additional carbonaceous material and gas inputs (104B', 104E') which, in a view of the reactor along the longitudinal reactor axis (AX'), are (i) equally circumferentially spaced apart from one another and (ii) are circumferentially spaced apart from said four first carbonaceous material and gas inputs (104A', 104C', 104D', 104F'); and each of two additional feed zone delivery systems (2050B', 2050E') has its feed zone delivery system output (FZ-OUT2', FZ-OUT5') connected to one of the two additional carbonaceous material and gas inputs (104B', 104E') of the first reactor (100B).

The feedstock delivery and product gas generation system (2075A') further includes a first reactor (100B) connected to a first solids separation device (150B) and configured transport a first reactor product gas (122B) from the first reactor (100B) to the first solids separation device (150B). The first solids separation device (150B) is connected at one end to a second reactor (200B) and at the other end to a third reactor (300). The first solids separation device (150B) is configured to remove char from the first reactor product gas (122B) and route the char to the second reactor (200B) via a dipleg (244B). A char depleted first reactor product gas (126B) is evacuated from the first solids separation device (15B) and transferred to the third reactor (300) via a combined reactor product gas conduit (230B). The second reactor (200B) is configured to react the char separated out from the first solids separation device (150B) and output a second reactor product gas (222B) to be transferred to a second solids separation device (250B). The second solids separation device (250B) is configured to remove solids from the second reactor product gas (222B) and route the solids depleted second reactor product gas (226B) to the third reactor (300) via a combined reactor product gas conduit (230B).

FIG. 16:

FIG. 16 shows a framework of an entire Biorefinery Superstructure System (BSS) configured to employ the use of the two-stage energy integrated product gas generation scheme.

The Biorefinery Superstructure System (BSS) of FIG. 16 is comprised of a: Feedstock Preparation System (1000) contained within a Feedstock Preparation Control Volume (CV-1000); a Feedstock Delivery System (2000) contained within a Feedstock Delivery Control Volume (CV-2000); a First Stage Product Gas Generation System (3A) contained within a First Stage Product Gas Generation Control Volume (CV-3A); a Second Stage Product Gas Generation System (3B) contained within a Second Stage Product Gas Generation Control Volume (CV-3B); a Primary Gas Clean-Up System (4000) contained within a Primary Gas Clean-Up Control Volume (CV-4000); a Compression System (5000) contained within a Compression Control Volume (CV-5000); a Secondary Gas Clean-Up System (6000) contained within a Secondary Gas Clean-Up Control Volume (CV-6000); a Synthesis System (7000) contained within a Synthesis Control Volume (CV-7000); and, an Upgrading System (8000) contained within a Upgrading Control Volume (CV-8000).

The Feedstock Preparation System (1000) is configured to accept a carbonaceous material input (1-IN1) and discharge a carbonaceous material output (1-OUT1). Some typical sequence systems that might be utilized in the Feedstock Preparation System (1000) include, Large Objects Removal, Recyclables Removal, Ferrous Metal Removal, Size Reduction, Water Removal, Non-Ferrous Metal Removal, Polyvinyl Chloride Removal, Glass Removal, Size Reduction, and Pathogen Removal.

The Feedstock Delivery System (2000) is configured to accept a carbonaceous material via a feedstock input (2-IN1) from the output (1-OUT1) of the Feedstock Preparation System (1000) and blend the carbonaceous material from the feedstock input (2-IN1) with the feedstock gas input (2-IN2) to realize a mixture of carbonaceous material and gas via a mixture output (2-OUT1).

The gas transferred to the feedstock gas input (2-IN2) to the Feedstock Delivery System (2000) is the carbon dioxide output (6-OUT2) from the downstream Secondary Gas Clean-Up System (6000).

The First Stage Product Gas Generation System (3A) is configured to accept the mixture of carbonaceous material and gas via the mixture output (2-OUT1) from the Feedstock Delivery System (2000) as a reactor mixture input (3A-IN1) and react the carbonaceous material transported through the reactor mixture input (3A-IN1) with a reactant provided by the first reactor reactant input (3A-IN2) to generate a first reactor product gas transferred via a first reactor gas output (3A-OUT1).

The First Stage Product Gas Generation System (3A) is also equipped with a first stage gas input (3A-IN5) coming from the carbon dioxide output (6-OUT2) of the downstream Secondary Gas Clean-Up System (6000). In embodiments, the first stage gas input (3A-IN5) coming from the carbon dioxide output (6-OUT2) of the downstream Secondary Gas Clean-Up System (6000) exits at a gas output temperature (T5) from about 300 degrees F. to about 550 degrees F.

The First Stage Product Gas Generation System (3A) is configured to output solids (3A-OUT4) in the form of Geldart Group D solids in the form of inert feedstock contaminants.

The Second Stage Product Gas Generation System (3B) accepts the first reactor product gas transferred via a first reactor gas output (3A-OUT1) as a second reactor gas input (3B-IN1) and exothermically reacts a portion of the contents of the first reactor product transferred via the second reactor gas input (3B-IN1) with oxygen-containing gas input (3B-IN3) to generate heat and product gas to be evacuated from the Second Stage Product Gas Generation System (3B) via a second reactor gas output (3B-OUT1). The Second Stage Product Gas Generation System (3B) is also equipped with a second stage gas input (3B-IN4) coming from the carbon dioxide output (6-OUT2) of the downstream Secondary Gas Clean-Up System (6000).

A second reactor heat exchanger (HX-B) is in thermal contact with the exothermic reaction taking place between at least a portion of the char contained within the product gas transferred through the second reactor gas input (3B-IN1) with oxygen-containing gas input (3B-IN3) within the Second Stage Product Gas Generation System (3B). The second reactor heat exchanger (HX-B) is configured to accept a heat transfer medium, such as water, from a second reactor heat transfer medium input (3B-IN2) and transfer heat from the exothermic reaction taking place between the Second Stage Product Gas Generation System (3B) to the contents of the heat transfer medium input (3B-IN2) to result in a second reactor heat transfer medium output (3B-OUT2).

The first reactor reactant input (3A-IN2) is in fluid communication with the second reactor heat transfer medium output (3B-OUT2) and is configured to introduce at least a portion of the contents therein into the First Stage Product Gas Generation System (3A) to react with the carbonaceous material (500) to realize a first reactor product gas transferred via a first reactor gas output (3A-OUT1).

The second reactor reactant input (208) is in fluid communication with the second reactor heat transfer medium output (3B-OUT2) and is configured to introduce at least a portion of the contents therein into the Second Stage Product Gas Generation System (3B) to exothermically react with a portion of the contents of the first reactor product gas transferred through the second reactor gas input (3B-IN1) to realize a second reactor product gas transferred via a second reactor gas output (3B-OUT1).

A first reactor heat exchanger (HX-A) is in thermal contact with the First Stage Product Gas Generation System (3A) to provide the energy to endothermically react the carbonaceous material (500) with the first reactor reactant input (3A-IN2) to realize a first reactor product gas transferred via a first reactor gas output (3A-OUT1).

The first reactor heat exchanger (HX-A) is comprised of a fuel input (3A-IN4) and a combustion products output (3A-OUT2) and is configured to combust the contents of the fuel input (3A-IN4) to indirectly heat the contents within the First Stage Product Gas Generation System (3A) which in turn then promotes the endothermic reaction between a portion of the contents of the second reactor heat transfer medium output (3B-OUT2) to react with the carbonaceous material (500) to realize a first reactor product gas transferred via a first reactor gas output (3A-OUT1).

The fuel input (3A-IN4) to the first reactor heat exchanger (HX-A) may be provided by the downstream Synthesis System (7000) as a first synthesis hydrocarbon output (7-OUT2) and may be comprised of Fischer-Tropsch products such as tail gas.

The fuel input (3A-IN4) to the first reactor heat exchanger (HX-A) may be provided by the downstream Upgrading System (8000) as a first hydrocarbon output (8-OUT2) such as naphtha.

The Second Stage Product Gas Generation System (3B) is also configured to accept a fuel output (4-OUT2) such as char, SVOC, VOC, or solvent from a downstream Primary Gas Clean-Up System (4000) as a fuel input (3B-IN5).

The Primary Gas Clean-Up System (4000) is equipped to accept a product gas transferred through the primary gas clean-up input (4-IN1) from the second reactor gas output (3B-OUT1) of the Second Stage Product Gas Generation System (3B). The Primary Gas Clean-Up System (4000) may also be configured to generate electricity from a portion of the product gas through any conventional well-known system such as a gas turbine, combined cycle, and/or steam turbine.

The Primary Gas Clean-Up System (4000) is configured to reduce the temperature, remove solids, SVOC, VOC, and water from the product gas transported through the primary gas clean-up input (4-IN1) to in turn discharge a product gas via the primary gas clean-up output (4-OUT1).

A fuel output (4-OUT2) Including VOC, SVOC, char, or solvent, may also be discharged from the Primary Gas Clean-Up System (4000) and introduced to the Second Stage Product Gas Generation System (3B) as a fuel input (3B-IN5).

The Compression System (5000) is configured to accept and increase the pressure of the product gas transferred from the primary gas clean-up output (4-OUT1) from the Primary Gas Clean-Up System (4000) to in turn discharge a product gas via the compression system output (5-OUT1).

The Secondary Gas Clean-Up System (6000) is configured to accept and remove at least carbon dioxide from the product gas transferred from the compression system output (5-OUT1) of the Compression System (5000) to output both a carbon dioxide depleted product gas via a secondary gas clean-up system output (6-OUT1) and carbon dioxide via a carbon dioxide output (6-OUT2). FIG. 16 displays a Biorefinery Superstructure System (BSS) equipped with a Secondary Gas Clean-Up System (6000) configured to remove carbon dioxide from product gas. The Secondary Gas Clean-Up System (6000) has a secondary gas clean-up input (6-IN1) and a secondary gas clean-up system output (6-OUT1). Membrane based carbon dioxide removal systems and processes are preferred to remove carbon dioxide from product gas, however other alternate systems and methods may be utilized to remove carbon dioxide, not limited to adsorption or absorption based carbon dioxide removal systems and processes. FIG. 16 displays the Secondary Gas Clean-Up System (6000) discharging carbon dioxide via a carbon dioxide output (6-OUT2) to both the (1) First Stage Product Gas Generation System (3A), and to the (2) the Feedstock Delivery System (2000) to be combined with a carbonaceous material (500). The carbon dioxide transferred through the carbon dioxide output (6-OUT2) may be routed upstream to either to the: Second Stage Product Gas Generation System (3B) as second stage gas input (3B-IN4); First Stage Product Gas Generation System (3A) as a first stage gas input (3A-IN5); or, the Feedstock Delivery System (2000) as a feedstock gas input (2-IN2).

The carbon dioxide depleted product gas transferred via the secondary gas clean-up system output (6-OUT1) is routed to the downstream Synthesis System (7000) via the synthesis system input (7-IN1).

The Synthesis System (7000) is configured to accept the product gas transferred via the secondary gas clean-up system output (6-OUT1) from the Secondary Gas Clean-Up System (6000) via the synthesis system input (7-IN1) and catalytically synthesize hydrocarbons from the product gas transferred through the synthesis system input (7-IN1). In embodiments, the synthesis system contains a catalyst and can produce liquid fuels such as mixed alcohols (e.g., a mixture of both ethanol and methanol), dimethyl ether, Fischer-Tropsch products, or the like.

A synthesis product transferred via the synthesis system output (7-OUT1) is discharged from the Synthesis System (7000) and is routed to the Upgrading System (8000) where it is accepted as a synthesis product input (8-IN1).

A first synthesis hydrocarbon output (7-OUT2), including Fischer-Tropsch products, such as tail gas, may also be discharged from the Synthesis System (7000) for use as a fuel input (3A-IN4) in the first reactor first heat exchanger (HX-A) of the upstream First Stage Product Gas Generation System (3A).

The Upgrading System (8000) is configured to generate an upgraded product (1500) including upgraded liquid fuels such as jet fuel, gasoline, diesel, alcohols such as ethanol, and the like, and other useful chemical compounds, discharged via an upgraded product output (8-OUT1).

A first hydrocarbon output (8-OUT2), such as naphtha, may also be discharged from the Upgrading System (8000) for use as a fuel input (3A-IN4) in the first reactor first heat exchanger (HX-A) of the upstream First Stage Product Gas Generation System (3A).

FIG. 16 discloses a method of converting a carbonaceous material into at least one liquid fuel, the method comprising:
 (a) combining a carbonaceous material and carbon dioxide in a feedstock delivery system;
 (b) introducing the combined carbonaceous material and carbon dioxide into a first reactor containing a first particulate heat transfer material;
 (c) introducing steam into the first reactor;
 (d) reacting the carbonaceous material with steam and carbon dioxide in an endothermic thermochemical reaction to generate a first reactor product gas containing char;
 (e) introducing a portion of the char into a second reactor containing a second particulate heat transfer material;
 (f) introducing an oxygen-containing gas into the second reactor;
 (g) reacting the char with the oxygen-containing gas in the second reactor, in an exothermic thermochemical reaction to generate a second reactor product gas;
 (h) transferring heat, via a second reactor heat exchanger, from the exothermic thermochemical reaction to a first heat transfer medium in thermal contact with the second reactor, the heat transfer medium comprising steam;
 (i) introducing at least a portion of the heated first heat transfer medium into the first reactor for use as the source of steam in (c);
 (j) compressing the first and/or second reactor product gas to thereby form a compressed product gas;
 (k) removing carbon dioxide from the compressed product gas, and supplying at least a first portion of the removed carbon dioxide to the feedstock delivery system for combining with carbonaceous material in step (a);
 (l) reacting the compressed product gas with a catalyst after removing carbon dioxide; and,
 (m) synthesizing at least one liquid fuel from the compressed product gas, after reacting the compressed product gas with a catalyst.

FIG. 16 also discloses cleaning the first particulate heat transfer material with a second portion of the removed carbon dioxide, to remove inert feedstock contaminant from the first reactor. Cleaning the bed material with carbon dioxide to remove unreacted Geldart Group D inert feedstock contaminants can be accomplished through any disclosed system such as in referring to techniques, methods and systems disclosed in FIG. 24 and/or FIG. 25. The systems and methods disclosed in FIG. 24 and FIG. 25 describe several meritorious aspects and advantages for cleaning bed material contained within the first reactor with carbon dioxide to remove unreacted Geldart Group D inert feedstock contaminants.

FIG. 16, used in conjunction with FIG. 24 and FIG. 25, further discloses a method for converting municipal solid waste (MSW) into at least one liquid fuel, the MSW containing Geldart Group D inert feedstock contaminants, the method comprising:
 (i) combining the MSW and carbon dioxide in a feedstock delivery system;
 (ii) producing a first reactor product gas;
 (iii) compressing at least a portion of the first reactor product gas to thereby form a compressed product gas;
 (iv) removing carbon dioxide from the compressed product gas, and supplying a first portion of the removed carbon dioxide to the feedstock delivery system for combining with the MSW in step (i) and supplying a second portion of the removed carbon dioxide as said portion of the first reactor product gas for entraining the bed material in step (ii);
 (v) reacting the compressed product gas with a catalyst after removing carbon dioxide; and,
 (vi) synthesizing at least one liquid fuel from the compressed product gas, after reacting the compressed product gas with a catalyst.

FIG. 16, used in conjunction with FIG. 24 and FIG. 25, further discloses a method for converting municipal solid waste (MSW) into at least one liquid fuel, the MSW containing Geldart Group D inert feedstock contaminants, the method comprising:
 (a) combining the MSW and carbon dioxide in a feedstock delivery system;
 (b) introducing the combined MSW and carbon dioxide into a first interior (101) of a first reactor (100) containing bed material;
 (c) introducing steam into the first reactor;
 (d) reacting the MSW, with steam and carbon dioxide, in an endothermic thermochemical reaction to generate a first reactor product gas containing char and leaving unreacted Geldart Group D inert feedstock contaminants in the bed material;
 (e) cleaning the bed material with carbon dioxide to remove said unreacted Geldart Group D inert feedstock contaminants;
 (f) introducing a portion of the char into a second reactor containing a second particulate heat transfer material;
 (g) introducing an oxygen-containing gas into the second reactor;
 (h) reacting the char with the oxygen-containing gas in the second reactor, in an exothermic thermochemical reaction to generate a second reactor product gas;
 (i) compressing the first and/or second reactor product gas to thereby form a compressed product gas;
 (j) removing carbon dioxide from the compressed product gas, and supplying a first portion of the removed carbon dioxide to the feedstock delivery system for combining with the MSW in step (a); and supplying a second portion of the removed carbon dioxide to clean the bed material in step (e);
 (k) reacting the compressed product gas with a catalyst after removing carbon dioxide; and (l) synthesizing at least one liquid fuel from the compressed product gas, after reacting the compressed product gas with a catalyst; wherein: the Geldart Group D inert feedstock contaminants comprise whole units and/or fragments of one or more from the group consisting of allen wrenches, ball bearings, batteries, bolts, bottle caps, broaches, bushings, buttons, cable, cement, chains, clips, coins, computer hard drive shreds, door hinges, door knobs, drill bits, drill bushings, drywall anchors, electrical components, electrical plugs, eye bolts, fabric snaps, fasteners, fish hooks, flash drives, fuses, gears, glass, gravel, grommets, hose clamps, hose fittings, jewelry, key chains, key stock, lathe blades, light bulb bases, magnets, metal audio-visual components, metal brackets, metal shards, metal surgical supplies, mirror shreds, nails, needles, nuts, pins, pipe fittings, pushpins, razor blades, reamers, retaining rings, rivets, rocks, rods, router bits, saw blades, screws, sockets, springs, sprockets, staples, studs, syringes, USB connectors, washers, wire, wire connectors, and zippers.

FIG. 17:

FIG. 17 shows a framework of an entire Biorefinery Superstructure System (BSS) configured to employ the use of the three-stage energy integrated product gas generation scheme.

The Biorefinery Superstructure System (BSS) of FIG. 17 is comprised of a: Feedstock Preparation System (1000) contained within a Feedstock Preparation Control Volume (CV-1000); a Feedstock Delivery System (2000) contained within a Feedstock Delivery Control Volume (CV-2000); a First Stage Product Gas Generation System (3A) contained within a First Stage Product Gas Generation Control Volume (CV-3A); a Second Stage Product Gas Generation System (3B) contained within a Second Stage Product Gas Generation Control Volume (CV-3B); a Third Stage Product Gas Generation System (3C) contained within a Third Stage Product Gas Generation Control Volume (CV-3C); a Primary Gas Clean-Up System (4000) contained within a Primary Gas Clean-Up Control Volume (CV-4000); a Compression System (5000) contained within a Compression Control Volume (CV-5000); a Secondary Gas Clean-Up System (6000) contained within a Secondary Gas Clean-Up Control Volume (CV-6000); a Synthesis System (7000) contained within a Synthesis Control Volume (CV-7000); and, an Upgrading System (8000) contained within a Upgrading Control Volume (CV-8000).

The Feedstock Preparation System (1000) is configured to accept a carbonaceous material (500), such as municipal solid waste (MSW), via a carbonaceous material input (1-IN1) and discharge a carbonaceous material output (1-OUT1). Some typical sequence steps or systems that might be utilized in the Feedstock Preparation System (1000) include, Large Objects Removal, Recyclables Removal, Ferrous Metal Removal, Size Reduction, Water Removal, Non-Ferrous Metal Removal, Polyvinyl Chloride Removal, Glass Removal, Size Reduction, and Pathogen Removal. The Feedstock Preparation System (1000) is configured to accept a source of municipal solid waste (MSW) and produce a prepared municipal solid waste (MSW) therefrom, wherein the prepared municipal solid waste (MSW) has undergone one or more processing steps selected from the group consisting of Large Objects Removal, Recyclables Removal, Ferrous Metal Removal, Size Reduction, Water Removal, Non-Ferrous Metal Removal, Polyvinyl Chloride Removal, Glass Removal, Size Reduction, and Pathogen Removal.

The Feedstock Delivery System (2000) is configured to accept a carbonaceous material via a feedstock input (2-IN1) from the output (1-OUT1) of the Feedstock Preparation System (1000) and blend the carbonaceous material from the feedstock input (2-IN1) with the gas from the feedstock gas input (2-IN2) to realize mixture of carbonaceous material and gas via a mixture output (2-OUT1). The gas transferred to the feedstock gas input (2-IN2) to the Feedstock Delivery System (2000) is the carbon dioxide transferred through the carbon dioxide output (6-OUT2) from the downstream Secondary Gas Clean-Up System (6000).

A Feedstock Delivery System CO2 Heat Exchanger (HX-2000) may be positioned upstream of the feedstock gas input (2-IN2) to the Feedstock Delivery System (2000) to reduce the temperature of the carbon dioxide transferred from the downstream Secondary Gas Clean-Up System (6000) and realize a reduced temperature gas (580). The Feedstock Delivery System CO2 Heat Exchanger (HX-2000) has a heat transfer medium (575), such as water, air, or any suitable liquid, vapor, or gas. The HX-2000 heat transfer medium (575) enters the HX-2000 via a heat transfer medium inlet (525) at a first temperature, and exits HX-2000 via a HX-2000 heat transfer medium outlet (550) at a second, higher temperature. Heat is removed from carbon dioxide transferred through the carbon dioxide output (6-OUT2) transferred from the Secondary Gas Clean Up System (6000) to the Feedstock Delivery System (2000) as a feedstock gas input (2-IN2) to result in a reduced temperature gas (580). In embodiments, the reduced temperature gas (580) enters the Feedstock Delivery System (2000) at a gas input temperature (T6) ranging from about 60 degrees F. to about 185 degrees F.

A water removal system (585) may be positioned upstream of the feedstock gas input (2-IN2) to the Feedstock Delivery System (2000) to remove water or moisture within the carbon dioxide transferred from the downstream Secondary Gas Clean-Up System (6000) and realize a water-depleted gas (590). Water (595) may be removed from carbon dioxide transferred from the carbon dioxide output (6-OUT2) transferred from the Secondary Gas Clean Up System (6000) to the Feedstock Delivery System (2000) as a feedstock gas input (2-IN2) to result in a water-depleted gas (590). Any suitable unit operation may suffice so long as it accomplished the goal of removing water from a carbon dioxide gas transferred from the Secondary Gas Clean-Up System (6000) to the Feedstock Delivery System (2000). Gas-liquid separators, flash drums, breakpots, knock-out drums, coalescers, deentrainment mesh, diffusers, desiccants, adsorbents, gas dryers, or any sort of separation unit operation known to those skilled in the art to which it pertains may be used so long as the selected water separation technology separates removes water from the carbon dioxide.

The First Stage Product Gas Generation System (3A) contained within the First Stage Product Gas Generation Control Volume (CV-3A) is configured to accept the carbonaceous material and gas mixture via the mixture output (2-OUT1) from the Feedstock Delivery System (2000) as a reactor mixture input (3A-IN1) and react the carbonaceous material transported through the reactor mixture input (3A-IN1) with a reactant provided by the first reactor reactant input (3A-IN2) to generate a first reactor product gas transferred via a first reactor gas output (3A-OUT1). The First Stage Product Gas Generation System (3A) is also equipped with a first stage gas input (3A-IN5) including carbon dioxide coming from the carbon dioxide output (6-OUT2) of the downstream Secondary Gas Clean-Up System (6000). The First Stage Product Gas Generation System (3A) is configured to output solids (3A-OUT3) in the form of Geldart Group D solids in the form of inert feedstock contaminants.

The Second Stage Product Gas Generation System (3B) contained within the Second Stage Product Gas Generation Control Volume (CV-3B) accepts the first reactor product gas transferred via a first reactor gas output (3A-OUT1) as a second reactor gas input (3B-IN1) and exothermically reacts a portion of the contents of the first reactor product gas that is transferred through the second reactor gas input (3B-IN1) with oxygen-containing gas input (3B-IN3) to generate heat and product gas to be evacuated from the Second Stage Product Gas Generation System (3B) via a second reactor gas output (3B-OUT1). The Second Stage Product Gas Generation System (3B) is also equipped with a second stage gas input (3B-IN4) including carbon dioxide coming from the carbon dioxide output (6-OUT2) of the downstream Secondary Gas Clean-Up System (6000).

A second reactor heat exchanger (HX-B) is in thermal contact with the exothermic reaction taking place between at least a portion of the char contained within the product gas transferred through the second reactor gas input (3B-IN1) with oxygen-containing gas input (3B-IN3) within the Second Stage Product Gas Generation System (3B). The second reactor heat exchanger (HX-B) is configured to accept a heat transfer medium, such as water, from a second reactor heat transfer medium input (3B-IN2) and transfer heat from the exothermic reaction taking place between the Second Stage Product Gas Generation System (3B) to the contents of the heat transfer medium input (3B-IN2) to result in a second reactor heat transfer medium output (3B-OUT2). The temperature (T2) of the second reactor heat transfer medium output (3B-OUT2) is greater than the temperature (T1) of the second reactor heat transfer medium input (3B-IN2). In embodiments, the first reactor reactant temperature (TR1) is about equal to the second reactor outlet temperature (T2). In embodiments, the first reactor reactant temperature (TR1) is less than the second reactor outlet temperature (T2) due to heat losses in piping while transferring the heat transfer medium from the outlet of the second reactor heat exchanger (HX-B) to the First Stage Product Gas Generation System (3A).

The first reactor reactant input (3A-IN2) is in fluid communication with the second reactor heat transfer medium output (3B-OUT2) and is configured to introduce at least a portion of the contents therein into the First Stage Product Gas Generation System (3A) to react with the carbonaceous material (500) to realize a first reactor product gas transferred via a first reactor gas output (3A-OUT1).

The second reactor reactant input (208) is in fluid communication with the second reactor heat transfer medium output (3B-OUT2) and is configured to introduce at least a portion of the contents therein into the Second Stage Product Gas Generation System (3B) to exothermically react with a portion of the contents of the first reactor product gas transferred through the second reactor gas input (3B-IN1) to realize a second reactor product gas transferred via a second reactor gas output (3B-OUT1).

A first reactor heat exchanger (HX-A) is in thermal contact with the First Stage Product Gas Generation System (3A) to provide the energy to endothermically react the carbonaceous material (500) with the first reactor reactant input (3A-IN2) to realize a first reactor product gas transferred via a first reactor gas output (3A-OUT1).

The first reactor heat exchanger (HX-A) is comprised of a fuel input (3A-IN4) and a combustion products output (3A-OUT2) and is configured to combust the contents of the fuel input (3A-IN4) to indirectly heat the contents within the First Stage Product Gas Generation System (3A) which in turn then promotes the endothermic reaction between a portion of the contents of the first reactor reactant input (3A-IN2) to react with the carbonaceous material and gas mixture (510) to realize a first reactor product gas transferred via a first reactor gas output (3A-OUT1).

In embodiments, the fuel input (3A-IN4) to the first reactor heat exchanger (HX-A) may be a methane containing gas such as natural gas, as seen in FIG. 17. In embodiments, the fuel input (3A-IN4) to the first reactor heat exchanger (HX-A) may be provided by the downstream Synthesis System (7000) as a first synthesis hydrocarbon output (7-OUT2) and may be comprised of Fischer-Tropsch products such as tail gas. In embodiments, the fuel input (3A-IN4) to the first reactor heat exchanger (HX-A) may be provided by the downstream upgrading System (8000) as a first hydrocarbon output (8-OUT2) such as naphtha.

The Second Stage Product Gas Generation System (3B) is also configured to accept a fuel output (4-OUT2) such as char, SVOC, VOC, or solvent from a downstream Primary Gas Clean-Up System (4000) as a fuel input (3B-IN5).

The Third Stage Product Gas Generation System (3C) contained within the Third Stage Product Gas Generation Control Volume (CV-3C) accepts the product gas from the second reactor gas output (3B-OUT1) from the Second Stage Product Gas Generation System (3B) as a combined product gas via the third reactor gas input (3C-IN1) and exothermically reacts a portion thereof with an oxygen-containing gas input (3C-IN3) to generate heat and a third reactor product gas transferred via the third reactor output (3C-OUT1).

A third reactor heat exchanger (HX-C) is in thermal contact with the Third Stage Product Gas Generation System (3C). The third reactor heat exchanger (HX-C) is in thermal contact with the exothermic reaction between the combined product gas transferred via the third reactor gas input (3C-IN1) and the oxygen-containing gas input (3C-IN3). The third reactor heat exchanger (HX-C) is configured to accept a heat transfer medium, such as water or steam, at a third reactor heat transfer medium inlet temperature (T0), from a third reactor heat transfer medium input (3C-IN2) and transfer heat from the exothermic reaction taking place between the Third Stage Product Gas Generation System (3C) to the contents of the heat transfer medium input (3C-IN2) to result in a third reactor heat transfer medium output (3C-OUT2). The third reactor heat transfer medium output (3C-OUT2) is in fluid communication with the second reactor heat transfer medium input (3B-IN2) of the second reactor heat exchanger (HX-B).

The Third Stage Product Gas Generation System (3C) is also configured to accept a first hydrocarbon input (3C-IN4) from the first synthesis hydrocarbon output (7-OUT2) of a downstream Synthesis System (7000) contained within a Synthesis Control Volume (CV-7000). The Third Stage Product Gas Generation System (3C) is also configured to accept a second hydrocarbon input (3C-IN5) from the first hydrocarbon output (8-OUT2) of a downstream Upgrading System (8000) contained within an Upgrading Control Volume (CV-8000). The Third Stage Product Gas Generation System (3C) is also configured to accept a third hydrocarbon input (3C-IN6) from the second hydrocarbon output (8-OUT3) of a downstream Upgrading System (8000) contained within an Upgrading Control Volume (CV-8000). The first hydrocarbon input (3C-IN4), second hydrocarbon input (3C-IN5), or third hydrocarbon input (3C-IN6) may be reacted in a thermochemical process within the third reactor (300) to generate product gas. The Third Stage Product Gas Generation System (3C) may also be configured to generate power from a portion of the third reactor heat transfer medium output (3C-OUT2).

The Primary Gas Clean-Up System (4000) is equipped to accept a product gas via the primary gas clean-up input (4-IN1) from the third reactor output (3C-OUT1) of the Third Stage Product Gas Generation System (3C). The Primary Gas Clean-Up System (4000) may also be configured to generate electricity from a portion of the product gas through any conventional well-known system such as a gas turbine, combined cycle, and/or steam turbine. The Primary Gas Clean-Up System (4000) is configured to reduce the temperature, remove solids, SVOC, VOC, and water from the product gas transported through the primary gas clean-up input (4-IN1) to in turn discharge a product gas via the primary gas clean-up output (4-OUT1). A fuel output (4-OUT2) not only including VOC, SVOC, char, or solvent, may also be discharged from the Primary Gas Clean-Up System (4000) and introduced to the Second Stage Product Gas Generation System (3B) as a fuel input (3B-IN5).

The Compression System (5000) accepts the product gas from the primary gas clean-up output (4-OUT1) of the Primary Gas Clean-Up System (4000) as a compression system input (5-IN1). The Compression System (5000) is configured to accept a product gas via the compression system input (5-IN1) and increase its pressure to form a product gas transferred via the compression system output (5-OUT1) at a greater pressure than the product gas transferred from the compression system input (5-IN1).

The Secondary Gas Clean-Up System (6000) accepts the product gas transferred through the product gas output (5-OUT1) from the Compression System (5000) as a carbon dioxide laden product gas transferred through the secondary gas clean-up input (6-IN1). The Secondary Gas Clean-Up System (6000) is configured to accept a carbon dioxide laden product gas via the secondary gas clean-up input (6-IN1) and remove carbon dioxide therefrom to generate both carbon dioxide transferred via a carbon dioxide output (6-OUT2) and a carbon dioxide depleted product gas transferred via the secondary gas clean-up system output (6-OUT1). The Secondary Gas Clean-Up System (6000) has a secondary gas clean-up input (6-IN1) and a secondary gas clean-up system output (6-OUT1). The carbon dioxide depleted product gas transferred via the secondary gas clean-up system output (6-OUT1) has a lesser amount of carbon dioxide relative to the carbon dioxide laden product gas transferred through the secondary gas clean-up input (6-IN1). Membrane based carbon dioxide removal systems and processes are preferred to remove carbon dioxide from product gas, however other alternate systems and methods may be utilized to remove carbon dioxide, not limited to adsorption or absorption based carbon dioxide removal systems and processes.

The carbon dioxide depleted product gas transferred via the secondary gas clean-up system output (6-OUT1) is routed to the downstream Synthesis System (7000) via the synthesis system input (7-IN1). The carbon dioxide transferred through the carbon dioxide output (6-OUT2) may be routed upstream to either to the: Second Stage Product Gas Generation System (3B) as a second stage gas input (3B-IN4); First Stage Product Gas Generation System (3A) as a first stage gas input (3A-IN5); or, the Feedstock Delivery System (2000) as a feedstock gas input (2-IN2). A heat exchanger (HX-2000) may be positioned in between the feedstock gas input (2-IN2) of the Feedstock Delivery System (2000) and the Secondary Gas Clean-Up System (6000) of the carbon dioxide output (6-OUT2).

The Synthesis System (7000) is configured to accept the product gas from the secondary gas clean-up system output (6-OUT1) from the Secondary Gas Clean-Up System (6000) via the synthesis system input (7-IN1) and catalytically synthesize a synthesis product that is discharged via the synthesis system output (7-OUT1). In embodiments, the synthesis system contains a catalyst and can produce liquid fuels such as mixed alcohols, (e.g., a mixture of both ethanol and methanol), dimethyl ether, Fischer-Tropsch products, or the like.

A synthesis product transferred through the synthesis system output (7-OUT1) is discharged from the Synthesis System (7000) and is routed to the Upgrading System (8000) where it is accepted as a synthesis product input (8-IN1).

A first synthesis hydrocarbon output (7-OUT2), including Fischer-Tropsch products, may be discharged from the Synthesis System (7000) for use as a first hydrocarbon input (3C-IN4) to the third reactor (300) of the upstream Third Stage Product Gas Generation System (3C). In embodiments, a first synthesis hydrocarbon output (7-OUT2), including Fischer-Tropsch products, may be discharged from the Synthesis System (7000) for use as a fuel input (3A-IN4) in the first reactor first heat exchanger (HX-A) of the upstream First Stage Product Gas Generation System (3A).

The Upgrading System (8000) is configured to generate an upgraded product (1500) including upgraded liquid fuels such as jet fuel, gasoline, diesel, alcohols such as ethanol, and the like, and other useful chemical compounds, discharged via an upgraded product output (8-OUT1).

A first hydrocarbon output (8-OUT2), such as naphtha, may be discharged from the Upgrading System (8000) for use as a second hydrocarbon input (3C-IN5) in the third reactor (300) of the upstream Third Stage Product Gas Generation System (3C). A second hydrocarbon output (8-OUT3), such as off gases, may be discharged from the Upgrading System (8000) for use as a third hydrocarbon input (3C-IN6) in the third reactor (300) of the upstream Third Stage Product Gas Generation System (3C). In embodiments, a first hydrocarbon output (8-OUT2), such as naphtha, may also be discharged from the Upgrading System (8000) for use as a fuel input (3A-IN4) in the first reactor first heat exchanger (HX-A) of the upstream First Stage Product Gas Generation System (3A). In embodiments, a second hydrocarbon output (8-OUT3), such as off gases, may be discharged from the Upgrading System (8000) for use as a fuel input (3A-IN4) in the first reactor first heat exchanger (HX-A) of the upstream First Stage Product Gas Generation System (3A).

FIG. 25 discloses a method for converting carbonaceous material into at least one liquid fuel, the method comprising:
(i) combining the carbonaceous material and carbon dioxide in a feedstock delivery system;
(ii) producing a third reactor product gas in accordance with the method of FIG. 2;
(iii) compressing at least a portion of the third reactor product gas to thereby form a compressed product gas;
(iv) removing carbon dioxide from the compressed product gas, and supplying a first portion of the removed carbon dioxide to the feedstock delivery system for combining with the carbonaceous material in step (i);
(v) reacting the compressed product gas with a catalyst after removing carbon dioxide; and (vi) synthesizing at least one liquid fuel from the compressed product gas, after reacting the compressed product gas with a catalyst.

FIG. 17 further discloses method for converting municipal solid waste (MSW) into at least one liquid fuel, the MSW containing Geldart Group D inert feedstock contaminants, the method comprising:
(a) combining the MSW and carbon dioxide in a feedstock delivery system;
(b) introducing, into a first interior of a first reactor containing bed material, steam and the combined MSW and carbon dioxide from the feedstock delivery system;
(c) reacting, in the first reactor, the MSW with steam and carbon dioxide, in an endothermic thermochemical reaction to generate a first reactor product gas containing char and leaving unreacted Geldart Group D inert feedstock contaminants in the bed material;
(d) cleaning the bed material with carbon dioxide to remove said unreacted Geldart Group D inert feedstock contaminants;
(e) introducing, into a second reactor containing a second particulate heat transfer material, an oxygen-containing gas and a portion of the char;
(f) reacting, in the second reactor, the char with the oxygen-containing gas, in an exothermic thermochemical reaction to generate a second reactor product gas;
(g) introducing, into a third reactor, an oxygen-containing gas and the first reactor product gas generated in step (c) and the second reactor product gas generated in step (f);
(h) reacting, in the third reactor, the product gas with the oxygen-containing gas, in an exothermic thermochemical reaction to generate a third reactor product gas;
(i) compressing the first and/or second reactor product gas to thereby form a compressed product gas;
(j) removing carbon dioxide from the compressed product gas, and supplying a first portion of the removed carbon dioxide to the feedstock delivery system for combining with the MSW in step (a); and supplying a second portion of the removed carbon dioxide to clean the bed material in step (d);
(k) reacting the compressed product gas with a catalyst after removing carbon dioxide; and
(l) synthesizing at least one liquid fuel from the compressed product gas, after reacting the compressed product gas with a catalyst;
wherein:
the Geldart Group D inert feedstock contaminants comprise whole units and/or fragments of one or more from the group consisting of allen wrenches, ball bearings, batteries, bolts, bottle caps, broaches, bushings, buttons, cable, cement, chains, clips, coins, computer hard drive shreds, door hinges, door knobs, drill bits, drill bushings, drywall anchors, electrical components, electrical plugs, eye bolts, fabric snaps, fasteners, fish hooks, flash drives, fuses, gears, glass, gravel, grommets, hose clamps, hose fittings, jewelry, key chains, key stock, lathe blades, light bulb bases, magnets, metal audio-visual components, metal brackets, metal shards, metal surgical supplies, mirror shreds, nails, needles, nuts, pins, pipe fittings, pushpins, razor blades, reamers, retaining rings, rivets, rocks, rods, router bits, saw blades, screws, sockets, springs, sprockets, staples, studs, syringes, USB connectors, washers, wire, wire connectors, and zippers.

Figure 17A:
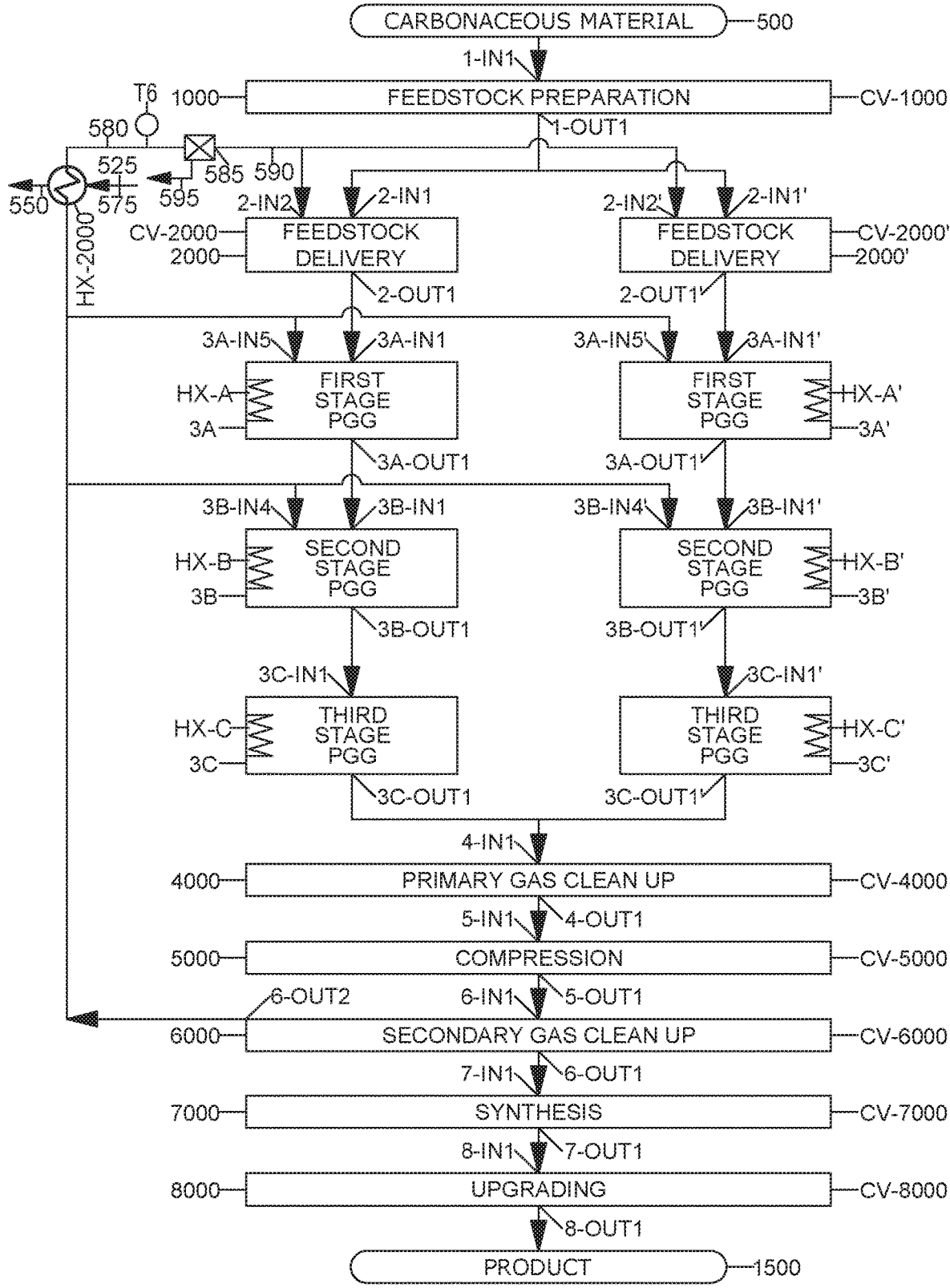
FIG. 17A shows a framework of an entire Biorefinery Superstructure System (BSS) configured to employ the use of a Feedstock Preparation System (1000), a plurality of Feedstock Delivery Systems (2000, 2000'), a plurality of First Stage Product Gas Generation Systems (3A, 3A'), a plurality of Second Stage Product Gas Generation Systems (3B, 3B'), and a plurality of Third Stage Product Gas Generation Systems (3C, 3C'), with a Primary Gas Clean-Up System (4000), a Compression System (5000), a Secondary Gas Clean-Up System (6000), a Synthesis System (7000), and an Upgrading System (8000).

FIG. 17A:

FIG. 17A shows a framework of an entire Biorefinery Superstructure System (BSS) configured to employ the use of a Feedstock Preparation System (1000), a plurality of Feedstock Delivery Systems (2000, 2000'), a plurality of First Stage Product Gas Generation Systems (3A, 3A'), a plurality of Second Stage Product Gas Generation Systems (3B, 3B'), and a plurality of Third Stage Product Gas Generation Systems (3C, 3C'), with a Primary Gas Clean-Up System (4000), a Compression System (5000), a Secondary Gas Clean-Up System (6000), a Synthesis System (7000), and an Upgrading System (8000).

The Biorefinery Superstructure System (BSS) of FIG. 17A is comprised of a:

Feedstock Preparation System (1000) contained within a Feedstock Preparation Control Volume (CV-1000);

two Feedstock Delivery Systems (2000, 2000') contained within a two Feedstock Delivery Control Volumes (CV-2000, CV-2000');

two First Stage Product Gas Generation Systems (3A, 3A') contained within two First Stage Product Gas Generation Control Volumes (CV-3A, CV-3A');

two Second Stage Product Gas Generation Systems (3B, 3B') contained within two Second Stage Product Gas Generation Control Volumes (CV-3B, CV-3B');

two Third Stage Product Gas Generation Systems (3C, 3C') contained within two Third Stage Product Gas Generation Control Volumes (CV-3C, CV-3C');

a Primary Gas Clean-Up System (4000) contained within a Primary Gas Clean-Up Control Volume (CV-4000);

a Compression System (5000) contained within a Compression Control Volume (CV-5000);

a Secondary Gas Clean-Up System (6000) contained within a Secondary Gas Clean-Up Control Volume (CV-6000);

a Synthesis System (7000) contained within a Synthesis Control Volume (CV-7000); and, an Upgrading System (8000) contained within an Upgrading Control Volume (CV-8000).

The Feedstock Preparation System (1000) provides carbonaceous material to a plurality of Feedstock Delivery Systems (2000, 2000'). Each Feedstock Delivery Systems (2000, 2000') feeds a separate First Stage Product Gas Generation System (3A, 3A'). FIG. 17A shows two trains each having a Feedstock Delivery System (2000, 2000'), First Stage Product Gas Generation System (3A, 3A'), Second Stage Product Gas Generation System (3B, 3B'), and a Third Stage Product Gas Generation System (3C, 3C'). The term (PGG) refers to a Product Gas Generation System as shown in FIG. 17A.

The Feedstock Preparation System (1000) is configured to accept a carbonaceous material (500) via a carbonaceous material input (1-IN1) and discharge a carbonaceous material output (1-OUT1). Some typical sequence steps or systems that might be utilized in the Feedstock Preparation System (1000) include, Large Objects Removal, Recyclables Removal, Ferrous Metal Removal, Size Reduction, Water Removal, Non-Ferrous Metal Removal, Polyvinyl Chloride Removal, Glass Removal, Size Reduction, and Pathogen Removal.

Each Feedstock Delivery System (2000, 2000') is configured to accept a carbonaceous material via a feedstock input (2-IN1, 2-IN1') from the output (1-OUT1) of the Feedstock Preparation System (1000) and blend the carbonaceous material from the feedstock input (2-IN1, 2-IN1') with carbon dioxide to realize a mixture output (2-OUT1, 2-OUT1'). The carbon dioxide input to the Feedstock Delivery System (2000) is the carbon dioxide output from the downstream Secondary Gas Clean-Up System (6000).

Each First Stage Product Gas Generation System (3A, 3A') contained within a First Stage Product Gas Generation Control Volume (CV-3A, CV-3A') is configured to accept carbonaceous material and gas via the mixture output (2-OUT1, 2-OUT1') from the Feedstock Delivery System (2000, 2000') as a reactor mixture input (3A-IN1, 3A-IN1') and react the carbonaceous material transported through the reactor mixture input (3A-IN1, 3A-IN1') with a reactant provided by the first reactor reactant input to generate a first reactor product gas transferred via a first reactor gas output (3A-OUT1, 3A-OUT1'). Each First Stage Product Gas Generation System (3A, 3A') is also equipped with a gas input coming from the carbon dioxide output of the downstream Secondary Gas Clean-Up System (6000, 6000'). Each First Stage Product Gas Generation System (3A, 3A') is configured to output solids in the form of Geldart Group D solids in the form of inert feedstock contaminants.

Each Second Stage Product Gas Generation System (3B, 3B') contained within the Second Stage Product Gas Generation Control Volume (CV-3B, CV-3B') accepts the first reactor product gas transferred via a first reactor gas output (3A-OUT1, 3A-OUT1') as a second reactor gas input (3B-IN1, 3B-IN1') and exothermically reacts a portion of the contents of the first reactor product gas transferred through the second reactor gas input (3B-IN1, 3B-IN1') with oxygen-containing gas input to generate heat and product gas to be evacuated from the Second Stage Product Gas Generation System (3B, 3B') via a second reactor gas output (3B-OUT1, 3B-OUT1'). Each Second Stage Product Gas Generation System (3B, 3B') is also equipped with a gas input coming from the carbon dioxide output of the downstream Secondary Gas Clean-Up System (6000, 6000').

A second reactor heat exchanger (HX-B, HX-B') is in thermal contact with the exothermic reaction taking place between at least a portion of the char contained within the product gas transferred through the second reactor gas input (3B-IN1, 3B-IN1') with oxygen-containing gas within the Second Stage Product Gas Generation System (3B, 3B'). Each second reactor heat exchanger (HX-B, HX-B') is configured to accept a heat transfer medium, such as water, or steam, and transfer heat from the exothermic reaction taking place between the Second Stage Product Gas Generation System (3B, 3B') to the heat transfer medium.

As shown in FIG. 17, the first reactor reactant input (3A-IN2) is in fluid communication with the second reactor heat transfer medium output (3B-OUT2) and is configured to introduce at least a portion of the contents therein into the First Stage Product Gas Generation System (3A) to react with the carbonaceous material (500) to realize a first reactor product gas transferred via a first reactor gas output (3A-OUT1).

The second reactor reactant input (208) is in fluid communication with the second reactor heat transfer medium output (3B-OUT2) and is configured to introduce at least a portion of the contents therein into the Second Stage Product Gas Generation System (3B) to exothermically react with a portion of the contents of the first reactor product gas transferred through the second reactor gas input (3B-IN1) to realize a second reactor product gas transferred via a second reactor gas output (3B-OUT1).

A first reactor heat exchanger (HX-A, HX-A') is in thermal contact with each First Stage Product Gas Generation System (3A, 3A') to provide the energy to endothermically react the carbonaceous material (500) with the first reactor reactant input (3A-IN2, 3A-IN2') to realize a first reactor product gas transferred via a first reactor gas output (3A-OUT1, 3A-OUT1').

As shown in FIGS. 17 and 17A, each first reactor heat exchanger (HX-A, HX-A') is comprised of a fuel input (3A-IN4) and a combustion products output (3A-OUT2) and is configured to combust the contents of the fuel input (3A-IN4) to indirectly heat the contents within the First Stage Product Gas Generation System (3A) which in turn then promotes the endothermic reaction between a portion of the contents of the first reactor reactant input (3A-IN2) to react with the carbonaceous material and gas mixture (510) to realize a first reactor product gas transferred via a first reactor gas output (3A-OUT1).

In embodiments, the fuel input (3A-IN4) to the first reactor heat exchanger (HX-A) may be a methane containing gas such as natural gas, as seen in FIG. 17. In embodiments, the fuel input (3A-IN4) to the first reactor heat exchanger (HX-A) may be provided by the downstream Synthesis System (7000) as a first synthesis hydrocarbon output (7-OUT2) and may be comprised of Fischer-Tropsch products such as tail gas. In embodiments, the fuel input (3A-IN4) to the first reactor heat exchanger (HX-A) may be provided by the downstream upgrading System (8000) as a first hydrocarbon output (8-OUT2) such as naphtha.

Each Second Stage Product Gas Generation System (3B, 3B') is also configured to accept a fuel such as char, SVOC, VOC, or solvent from a downstream Primary Gas Clean-Up System (4000) as a fuel input (3B-IN5).

Each Third Stage Product Gas Generation System (3C, 3C') contained within the Third Stage Product Gas Generation Control Volume (CV-3C, CV-3C') accepts the second reactor product gas from the second reactor gas output (3B-OUT1, 3B-OUT1') from each Second Stage Product Gas Generation System (3B, 3B') as a combined product gas transferred via the third reactor gas input (3C-IN1, 3C-IN1') and exothermically reacts a portion thereof with an oxygen-containing gas to generate heat and a third reactor product transferred via the third reactor output (3C-OUT1, 3C-OUT1').

A third reactor heat exchanger (HX-C, HX-C') is in thermal contact with each Third Stage Product Gas Generation System (3C, 3C'). Each third reactor heat exchanger (HX-C, HX-C') is in thermal contact with the exothermic reaction between the combined product gas transferred via the third reactor gas input (3C-IN1, 3C-IN1') and an oxygen-containing gas. The third reactor heat exchanger (HX-C, HX-C') is configured to accept a heat transfer medium, such as water or steam, at a third reactor heat transfer medium inlet temperature (T0), from a third reactor heat transfer medium input (3C-IN2) and transfer heat from the exothermic reaction taking place between the Third Stage Product Gas Generation System (3C, 3C') to the contents of the heat transfer medium input (3C-IN2) to result in a third reactor heat transfer medium output (3C-OUT2). The third reactor heat transfer medium output (3C-OUT2) is in fluid communication with the second reactor heat transfer medium input (3B-IN2) of the second reactor heat exchanger (HX-B, HX-B').

Each Third Stage Product Gas Generation System (3C, 3C') is also configured to accept a first hydrocarbon input (3C-IN4) from the first synthesis hydrocarbon output (7-OUT2) of a downstream Synthesis System (7000) contained within a Synthesis Control Volume (CV-7000). Each Third Stage Product Gas Generation System (3C, 3C') is also configured to accept a second hydrocarbon input (3C-IN5) from the first hydrocarbon output (8-OUT2) of a downstream Upgrading System (8000) contained within an Upgrading Control Volume (CV-8000). Each Third Stage Product Gas Generation System (3C, 3C') is also configured to accept a third hydrocarbon input (3C-IN6) from the second hydrocarbon output (8-OUT3) of a downstream Upgrading System (8000) contained within an Upgrading Control Volume (CV-8000). The first hydrocarbon input (3C-IN4), second hydrocarbon input (3C-IN5), or third hydrocarbon input (3C-IN6) may be reacted in a thermochemical process within the third reactor (300) to generate product gas. Each Third Stage Product Gas Generation System (3C, 3C') may also be configured to generate power from a portion of the third reactor heat transfer medium output (3C-OUT2).

The Primary Gas Clean-Up System (4000) is equipped to accept product gas via the primary gas clean-up input (4-IN1) from each third reactor output (3C-OUT1, 3C-OUT1') from each Third Stage Product Gas Generation System (3C, 3C'). The Primary Gas Clean-Up System (4000) may also be configured to generate electricity from a portion of the product gas through any conventional well-known system such as a gas turbine, combined cycle, and/or steam turbine. The Primary Gas Clean-Up System (4000) is configured to reduce the temperature, remove solids, SVOC, VOC, and water from the product gas transported through the primary gas clean-up input (4-IN1) to in turn discharge a product gas (referred to as a "primary conditioned syngas") via the primary gas clean-up output (4-OUT1). A fuel output (4-OUT2) not only including VOC, SVOC, char, or solvent, may also be discharged from the Primary Gas Clean-Up System (4000) and introduced to each Second Stage Product Gas Generation System (3B, 3B') as a fuel input (3B-IN5).

The Compression System (5000) accepts the product gas (i.e., the primary conditioned syngas) via the primary gas clean-up output (4-OUT1) of the Primary Gas Clean-Up System (4000) as a compression system input (5-IN1). The Compression System (5000) is configured to accept a product gas from the compression system input (5-IN1) and increase its pressure to form a product gas transferred via the compression system output (5-OUT1) at a greater pressure than the product gas transferred from the compression system input (5-IN1).

The Secondary Gas Clean-Up System (6000) accepts the compressed product gas (i.e., the compressed primary conditioned syngas) from the compression system output (5-OUT1) from the Compression System (5000) as a carbon dioxide laden product gas transferred via the secondary gas clean-up input (6-IN1). The Secondary Gas Clean-Up System (6000) is configured to accept a carbon dioxide laden product gas via the secondary gas clean-up input (6-IN1) and remove carbon dioxide therefrom to generate both a carbon dioxide via the carbon dioxide output (6-OUT2) and a carbon dioxide depleted product gas (which may be considered a "secondary conditioned syngas") transferred via the secondary gas clean-up system output (6-OUT1). The Secondary Gas Clean-Up System (6000) has a secondary gas clean-up input (6-IN1) and a secondary gas clean-up system output (6-OUT1). The carbon dioxide depleted product gas transferred via the secondary gas clean-up system output (6-OUT1) has a lesser amount of carbon dioxide relative to the carbon dioxide laden product gas transferred through the secondary gas clean-up input (6-IN1). Membrane based carbon dioxide removal systems and processes are preferred to remove carbon dioxide from product gas, however other alternate systems and methods may be utilized to remove carbon dioxide, not limited to adsorption or absorption based carbon dioxide removal systems and processes.

The carbon dioxide depleted product gas (secondary conditioned syngas) transferred via the secondary gas clean-up system output (6-OUT1) is routed to the downstream Synthesis System (7000) via the synthesis system input (7-IN1). The carbon dioxide transferred through the carbon dioxide output (6-OUT2) may be routed upstream to either to the: each Second Stage Product Gas Generation System (3B, 3B') as a second stage gas input (3B-IN4); First Stage Product Gas Generation System (3A, 3A') as a first stage gas input (3A-IN5); or, the Feedstock Delivery System (2000, 2000') as a feedstock gas input (2-IN2). A heat exchanger (HX-2000) may be positioned in between the feedstock gas input (2-IN2) of each Feedstock Delivery System (2000, 2000') and the Secondary Gas Clean-Up System (6000) of the carbon dioxide output (6-OUT2).

The Synthesis System (7000) is configured to accept the product gas (secondary conditioned syngas) from the secondary gas clean-up system output (6-OUT1) from the Secondary Gas Clean-Up System (6000) via the synthesis system input (7-IN1) and catalytically synthesize a synthesis product that is discharged via the synthesis system output (7-OUT1). In embodiments, the synthesis system contains a catalyst and can produce liquid fuels such as mixed alcohols (e.g., a mixture of both ethanol and methanol), dimethyl ether, Fischer-Tropsch products, or the like.

A synthesis product transferred through the synthesis system output (7-OUT1) is discharged from the Synthesis System (7000) and is routed to the Upgrading System (8000) where it is accepted as a synthesis product input (8-IN1).

A first synthesis hydrocarbon output (7-OUT2), including Fischer-Tropsch products, may be discharged from the Synthesis System (7000) for use as a first hydrocarbon input (3C-IN4) to the third reactor (300) of the upstream Third Stage Product Gas Generation System (3C). In embodiments, a first synthesis hydrocarbon output (7-OUT2), including Fischer-Tropsch products, may be discharged from the Synthesis System (7000) for use as a fuel input (3A-IN4) in each first reactor first heat exchanger (HX-A, HX-A') of either upstream First Stage Product Gas Generation System (3A, 3A').

The Upgrading System (8000) is configured to generate an upgraded product (1500) including upgraded liquid fuels such as jet fuel, gasoline, diesel, alcohols such as ethanol, and the like, and other useful chemical compounds, discharged via an upgraded product output (8-OUT1).

A first hydrocarbon output (8-OUT2), such as naphtha, may be discharged from the Upgrading System (8000) for use as a second hydrocarbon input (3C-IN5) in a third reactor (300, 300') of either upstream Third Stage Product Gas Generation System (3C, 3C'). A second hydrocarbon output (8-OUT3), such as off gases, may be discharged from the Upgrading System (8000) for use as a third hydrocarbon input (3C-IN6) in a third reactor (300) of either the upstream Third Stage Product Gas Generation System (3C, 3C'). In embodiments, a first hydrocarbon output (8-OUT2), such as naphtha, may also be discharged from the Upgrading System (8000) for use as a fuel input (3A-IN4) in a first reactor first heat exchanger (HX-A, HX-A') of either upstream First Stage Product Gas Generation System (3A, 3A'). In embodiments, a second hydrocarbon output (8-OUT3), such as off gases, may be discharged from the Upgrading System (8000) for use as a fuel input (3A-IN4) in a first reactor first heat exchanger (HX-A, HX-A') of either upstream First Stage Product Gas Generation System (3A, 3A').

Each Feedstock Delivery System (2000, 2000') is configured to accept a carbonaceous material via a feedstock input (2-IN1, 2-IN1') from the output (1-OUT1) of the Feedstock Preparation System (1000) and blend the carbonaceous material from the feedstock input (2-IN1) with gas from the feedstock gas input (2-IN2) to realize a carbonaceous material and gas via the mixture output (2-OUT1). A plurality of Feedstock Preparation Systems (1000, 1000') may be used but are not shown in FIG. 17A. The gas transferred to each feedstock gas input (2-IN2, 2-IN2') to each Feedstock Delivery System (2000, 2000') may be carbon dioxide transferred through the carbon dioxide output (6-OUT2) of the downstream Secondary Gas Clean-Up System (6000).

A Feedstock Delivery System CO2 Heat Exchanger (HX-2000) may be positioned upstream of the feedstock gas inputs (2-IN2, 2-IN2') to each Feedstock Delivery System (2000, 2000') to reduce the temperature of the carbon dioxide transferred from the downstream Secondary Gas Clean-Up System (6000) and realize a reduced temperature gas (580). The Feedstock Delivery System CO2 Heat Exchanger (HX-2000) has a heat transfer medium (575), such as water, air, or any suitable liquid, vapor, or gas. The HX-2000 heat transfer medium (575) enters the HX-2000 via a heat transfer medium inlet (525) at a first temperature, and exits HX-2000 via a HX-2000 heat transfer medium outlet (550) at a second, higher temperature. Heat is removed from carbon dioxide routed from the carbon dioxide output (6-OUT2) transferred from the Secondary Gas Clean Up System (6000) to each Feedstock Delivery System (2000, 2000') as feedstock gas inputs (2-IN2, 2-IN2') to result in a reduced temperature gas (580). In embodiments, the reduced temperature gas (580) enters the Feedstock Delivery System (2000) at a gas input temperature (T6) ranging from about 60 degrees F. to about 185 degrees F.

A water removal system (585) may be positioned upstream of the feedstock gas inputs (2-IN2, 2-IN2') to each Feedstock Delivery System (2000, 2000') to remove water or moisture within the carbon dioxide transferred from the downstream Secondary Gas Clean-Up System (6000) and realize a water-depleted gas (590). Water (595) may be removed from carbon dioxide transferred via the carbon dioxide output (6-OUT2) transferred from the Secondary Gas Clean Up System (6000) to each Feedstock Delivery System (2000, 2000') as feedstock gas inputs (2-IN2, 2-IN2') to result in a water-depleted gas (590). Any suitable unit operation may suffice so long as it accomplished the goal of removing water from a carbon dioxide gas transferred from the Secondary Gas Clean-Up System (6000) to each Feedstock Delivery System (2000, 2000'). Gas-liquid separators, flash drums, breakpots, knock-out drums, coalescers, deentrainment mesh, diffusers, desiccants, adsorbents, gas dryers, or any sort of separation unit operation known to those skilled in the art to which it pertains may be used so long as the selected water separation technology separates removes water from the carbon dioxide.

Each First Stage Product Gas Generation System (3A, 3A') is also equipped with a first stage gas input (3A-IN5, 3A-IN5') that is configured to accept carbon dioxide from the carbon dioxide output (6-OUT2) of the downstream Secondary Gas Clean-Up System (6000). In embodiments, the first stage gas input (3A-IN5, 3A-IN5') coming from the carbon dioxide output (6-OUT2) of the downstream Secondary Gas Clean-Up System (6000) exits at a gas output temperature (T5) from about 300 degrees F. to about 550 degrees F.

Each Second Stage Product Gas Generation System (3B, 3B') is also equipped with a second stage gas input (3B-IN4, 3B-IN4') that is configured to accept carbon dioxide from the carbon dioxide output (6-OUT2) of the downstream Secondary Gas Clean-Up System (6000).

The carbon dioxide from the carbon dioxide output (6-OUT2) may be routed upstream to either to: either Second Stage Product Gas Generation System (3B, 3B') as a second stage gas input (3B-IN4, 3B-IN4'); either First Stage Product Gas Generation System (3A, 3A') as a first stage gas input (3A-IN5, 3A-IN5'); or, to either Feedstock Delivery System (2000, 2000') as a feedstock gas input (2-IN2, 2-IN2').

FIG. 17A discloses a liquid fuel product system, including:

(a) a plurality of feedstock delivery systems (2000, 2000'), each comprising a feedstock input (2-IN1, 2-IN1') configured to accept carbonaceous material, a feedstock gas input (2-IN2, 2-IN2') configured to accept carbon dioxide, and a mixture output (2-OUT1, 2-OUT1'); wherein each feedstock delivery system (2000, 2000') is configured to blend the carbonaceous material with carbon dioxide to generate a carbonaceous material and gas mixture which is discharged via the mixture output (2-OUT1, 2-OUT1');

(b) a plurality of first stage product gas generation systems (3A, 3A'), each comprising a first reactor mixture input (3A-IN1, 3A-IN1') configured to accept at least a portion of said carbonaceous material and gas mixture, and a first reactor gas output (3A-OUT1, 3A-OUT1'), wherein each first stage product gas generation system is configured to react the carbonaceous material with steam and optionally also with an oxygen-containing gas and/or carbon dioxide to generate first reactor product gas which is discharged via said first reactor gas output (3A-OUT1, 3A-OUT1');

(c) a plurality of second stage product gas generation systems (3B, 3B'), each comprising a second reactor gas input (3B-IN1, 3B-IN1') configured to accept at least a portion of said first reactor product gas, and a second reactor gas output (3B-OUT1, 3B-OUT1'), wherein each second stage product gas generation system (3B, 3B') is configured to react the first reactor product gas with an oxygen-containing gas and optionally also with steam and/or carbon dioxide to generate heat and a second reactor product gas which is discharged via said second reactor gas output (3B-OUT1, 3B-OUT1');

(d) a plurality of third stage product gas generation systems (3C, 3C'), each comprising a third reactor gas input (3C-IN1, 3C-IN1') configured to accept at least a portion of said second reactor product gas, and a third reactor output (3C-OUT1, 3C-OUT1'), wherein each third stage product gas generation system (3C, 3C') is configured to exothermically react a portion of the second reactor product gas with an oxygen-containing gas and optionally also with a hydrocarbon to generate heat and a third reactor product gas which is discharged via the third reactor output (3C-OUT1, 3C-OUT1');

(e) a primary gas clean-up system (4000) comprising a primary gas clean-up input (4-IN1) configured to accept third reactor product gas from the plurality of the third reactor outputs (3C-OUT1, 3C-OUT1'), and a primary gas clean-up output (4-OUT1); wherein the primary gas clean-up system (4000) is configured to reduce the temperature, and remove solids and water from the third reactor product gas and discharge primary product gas (primary conditioned syngas) via the primary gas clean-up output (4-OUT1);

(f) a compression system (5000) comprising a compression system input (5-IN1) configured to accept the primary product gas at a first pressure from the primary gas clean-up output (4-OUT1), and a compression system output (5-OUT1), wherein the compression system (5000) is configured to increase a pressure of the primary product gas and discharge compressed product gas (compressed primary conditioned syngas) via the compression system output (5-OUT1) at a second pressure greater than the first pressure at which the primary product gas (primary conditioned syngas) entered via the compression system input (5-IN1), and wherein the compressed product gas comprising carbon dioxide;

(g) a secondary gas clean-up system (6000) comprising a secondary gas clean-up input (6-IN1) configured to accept the compressed product gas (compressed primary conditioned syngas), a secondary gas clean-up system output (6-OUT1), and a carbon dioxide output (6-OUT2), wherein the secondary gas clean-up system (6000) is configured to remove carbon dioxide from the compressed product gas to thereby generate a carbon dioxide depleted secondary product gas (secondary conditioned syngas) that is discharged via the secondary gas clean-up system output (6-OUT1), and discharge carbon dioxide via the carbon dioxide output (6-OUT2); and (h) a synthesis system (7000) comprising a synthesis system input (7-IN1) configured to accept the carbon dioxide depleted secondary product gas (secondary conditioned syngas), and a synthesis system output (7-OUT1), wherein the synthesis system is configured to catalytically synthesize a synthesis product that is discharged via the synthesis system output (7-OUT1), and wherein the synthesis product includes one or more from the group consisting of mixed alcohols, ethanol methanol, dimethyl ether, and Fischer-Tropsch products.

It is to be noted that all reference numerals in FIG. 17 can be applied to the content disclosed in FIG. 17A. Each Feedstock Delivery System (2000, 2000'), each First Stage Product Gas Generation System (3A, 3A'), each Second Stage Product Gas Generation System (3B, 3B'), and each Third Stage Product Gas Generation System (3C, 3C') disclosed in FIG. 17A may include all of the embodiments disclosed in FIG. 17.

Figure 17B:
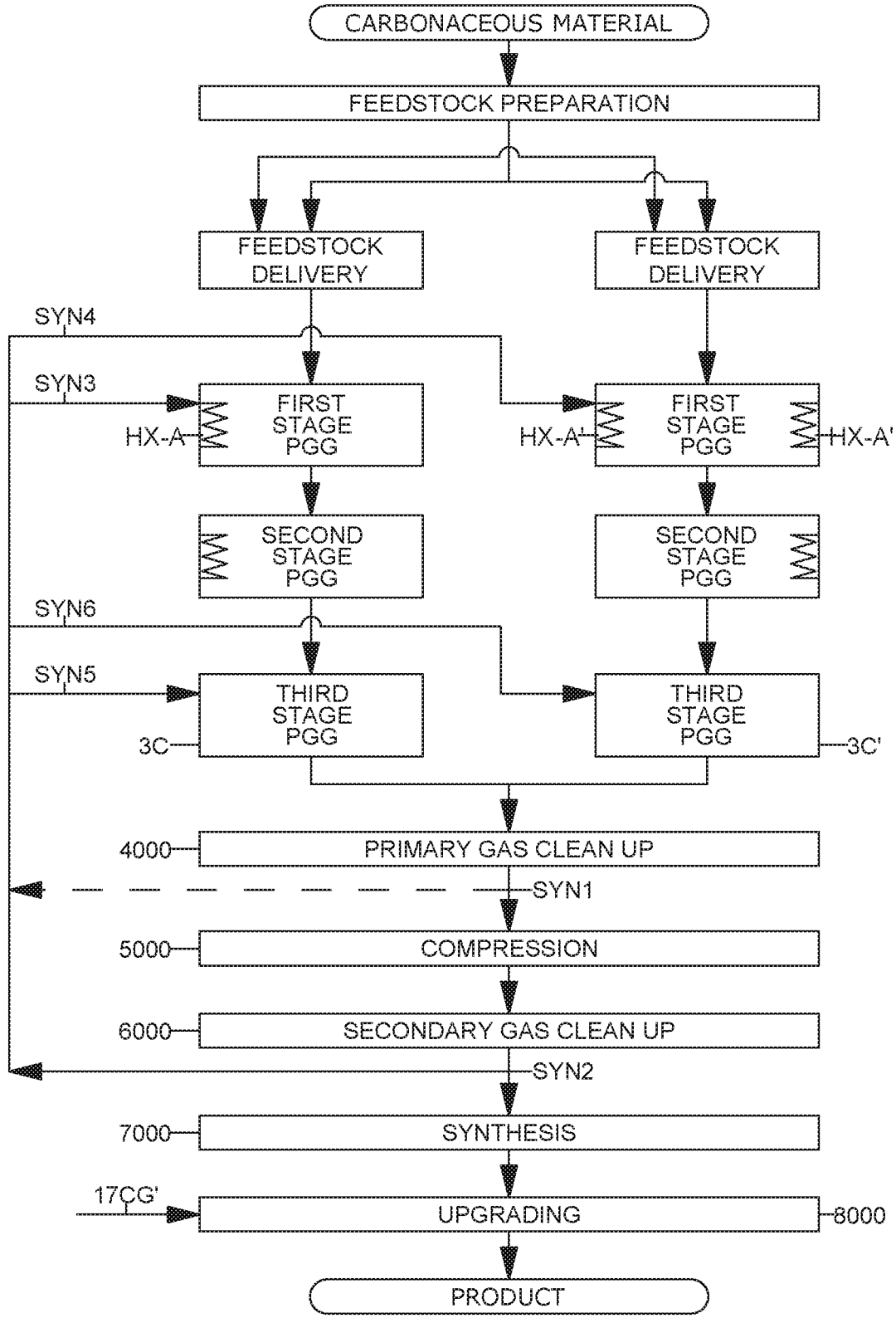
FIG. 17B elaborates upon the framework of the entire Biorefinery Superstructure System (BSS) disclosed in FIG. 17A and shows the Secondary Gas Clean-Up System (6000) having a syngas recycle stream output (6-OUT3) which outputs a secondary conditioned syngas (SYN2). The secondary conditioned syngas (SYN2) may be used as a fuel (110, 110A, 110B) source in the: plurality of First Stage Product Gas Generation Systems (3A, 3A') contained within plurality of the First Stage Product Gas Generation Control Volumes (CV-3A, CV-3A'); and the plurality of Third Stage Product Gas Generation Systems (3C, 3C') contained within plurality of the Third Stage Product Gas Generation Control Volumes (CV-3C, CV-3C').

FIG. 17B:

FIG. 17B elaborates upon the framework of the entire Biorefinery Superstructure System (BSS) disclosed in FIG. 17A and shows the Primary Gas Clean-Up System (4000) outputting a primary conditioned syngas (SYN1) and the Secondary Gas Clean-Up System (6000) outputting a secondary conditioned syngas (SYN2). The secondary conditioned syngas (SYN2) may be used as a fuel (110, 110A, 110B) source in the: plurality of First Stage Product Gas Generation Systems (3A, 3A') contained within plurality of the First Stage Product Gas Generation Control Volumes (CV-3A, CV-3A'); and the plurality of Third Stage Product Gas Generation Systems (3C, 3C') contained within plurality of the Third Stage Product Gas Generation Control Volumes (CV-3C, CV-3C'). Alternatively, or additionally, the primary conditioned syngas (SYN1) may be used as the fuel (110, 110A, 110B), as depicted by the laterally extending broken arrow in FIG. 17B.

Thus, in some embodiments, a conditioned syngas (i.e., a syngas that has been subject to processing to remove one or more undesirable substances therefrom) is recycled and introduced into (1) the first reactor heat exchangers (HX-A, HX-A') which are in thermal contact with the First Stage Product Gas Generation Systems (3A, 3A') to provide the energy to endothermically react the carbonaceous material (500); and (2) the Third Stage Product Gas Generation Systems (3C, 3C') for use in the combustion zone (CZ-A) and/or the reaction zone (CZ-B) for use as the first hydrocarbon stream (322) and/or the second hydrocarbon stream input (328) (as depicted in FIG. 32). Thus, at least a portion of conditioned syngas, produced during the clean-up process, is recycled to help make additional syngas. This is especially advantageous in those instances where other combustible gases, such as natural gas, are not available as an input gas to the pulse combustion units and the combustion zones (CZ-A), and/or the reaction zone (CZ-B).

As discussed further below with respect to FIG. 17C, additional products, such as tail gas, naphtha, and first and second off-gases may also be transferred, for use as a fuel, to the first reactor heat exchangers (HX-A, HX-A') of the First Stage Product Gas Generation Systems and/or to the Third Stage Product Gas Generation Systems (i.e. the hydrocarbon reformers).

As seen in FIG. 17B, the recycled secondary and/or primary conditioned syngas (SYN2, SYN1) is split into a plurality of recycled syngas streams (SYN3, SYN4, SYN5, SYN6). Of these, a first set of recycled syngas streams (SYN3, SYN4) may be transferred to the first reactor heat exchangers (HX-A, HX-A') to drive the pulse combustion devices, while a second set of recycled syngas streams (SYN5, STN6) may be transferred to the Third Stage Product Gas Generation Systems (3C, 3C') for use in the combustion zone (CZ-A) and/or the reaction zone (CZ-B).

FIG. 17C

Figure 17C:
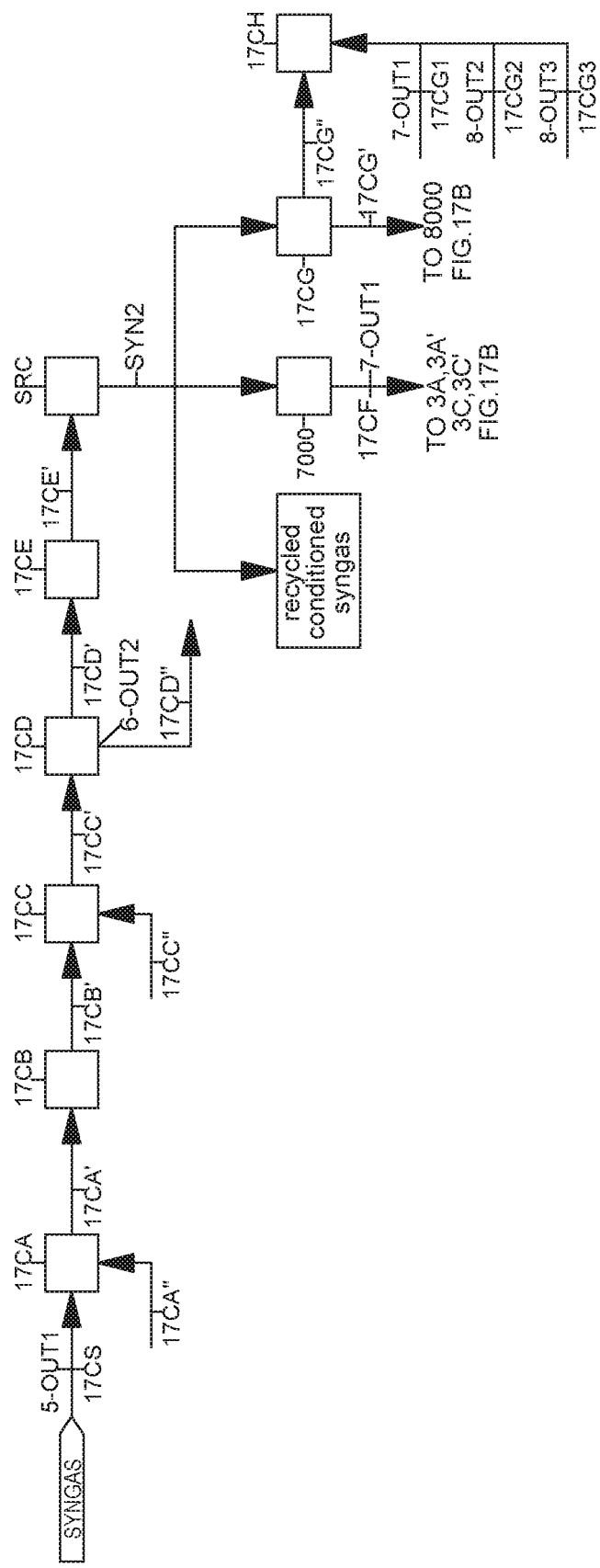
FIG. 17C shows a non-limiting embodiment of a Secondary Gas Clean-Up System (6000) having a syngas recycle stream output (6-OUT3) as depicted in FIG. 17B which outputs the secondary conditioned syngas (SYN2). Again, the secondary conditioned syngas may be used as a fuel (110, 110A, 110B) source in the plurality of First Stage Product Gas Generation Systems (3A, 3A'); and also for use as the first hydrocarbon stream (322) and/or the second hydrocarbon stream (328) within the plurality of Third Stage Product Gas Generation Systems (3C, 3C').

FIG. 17C shows a non-limiting embodiment of a Secondary Gas Clean-Up System (6000) of the sort seen in FIG. 17B. The Secondary Gas Clean-Up System (6000) is configured to accept a compressed primary conditioned syngas (17CS) from the output (5-OUT1) of the Compression System (5000). In embodiments, the Secondary Gas Clean-Up System (6000) as shown in FIG. 17C includes: a COS/HCN Hydrolysis System (17CA); a Metal Removal System (17CB); a Water Gas Shift Reactor System (17CC); a Carbon Dioxide Removal System (17CD); a Sulfur Guard Bed (17CE); and a Syngas Compressor (17CF, SRC).

The Secondary Gas Clean-Up System (6000) may also include a Hydrogen Separation System (17CG); and a Gas Turbine System (17CH).

In embodiments, the Secondary Gas Clean-Up System (6000) as shown in FIG. 17C includes: a COS/HCN Hydrolysis System (17CA) configured to accept a compressed primary conditioned syngas (17CS) from the output (5-OUT1) of the compression system (5000) (as shown in FIGS. 16, 17, 17A, 17B). The COS/HCN Hydrolysis System (17CA) is configured to hydrolyze carbonyl sulfide into carbon dioxide and hydrogen sulfide. Water (17CA") in the form of steam may be injected into the COS/HCN Hydrolysis System (17CA) to aid the carbonyl sulfide to react with water to hydrolyze into hydrogen sulfide and carbon dioxide. The first intermediate syngas (17CA') is discharged from the COS/HCN Hydrolysis System (17CA) and is introduced to a Metal Removal System (17CB).

The Metal Removal System (17CB) is configured to removal metals from the first intermediate syngas (17CA') discharged from the COS/HCN Hydrolysis System (17CA). In embodiments, the metals include mercury, arsenic, lead, or cadmium. Second intermediate syngas (17CB') is discharged from the Metal Removal System (17CB) and is introduced to a Water Gas Shift Reactor System (17CC).

The Water Gas Shift Reactor System (17CC) is configured to react carbon monoxide and water vapor within the second intermediate syngas (17CB') to form carbon dioxide and hydrogen. Water (17CC") in the form of steam may be injected into the Water Gas Shift Reactor System (17CC) to react with the carbon monoxide within the second intermediate syngas (17CB') to produce carbon dioxide and hydrogen. Third intermediate syngas (17CC') is discharged from the Water Gas Shift Reactor System (17CC) and is introduced to a Carbon Dioxide Removal System (17CD).

The Carbon Dioxide Removal System (17CD) is configured to remove carbon dioxide (17CD") from the third intermediate syngas (17CC') discharged from the Water Gas Shift Reactor System (17CC). In embodiments, the carbon dioxide (17CD") removed with the Carbon Dioxide Removal System (17CD) is showed as the carbon dioxide output (6-OUT2) as seen in FIGS. 16, 17, 17A, 17B) and provided to a variety of places mentioned elsewhere in the specification. Fourth intermediate syngas (17CD') discharged from the Carbon Dioxide Removal System (17CD) is introduced to a Sulfur Guard Bed (17CE) to further remove sulfur therefrom and produce a fifth intermediate syngas (17CE'). It is understood that not all of these removal units (17CA, 17CB, 17CC, 17CD and 17CE) need be present and, in other embodiments, different removal units may be provided.

In some embodiments, such as seen in FIG. 17C, the fifth intermediate syngas (17CE') discharged from the Sulfur Guard Bed (17CE) is introduced to a Syngas Compressor (SRC) to produce the secondary conditioned syngas (SYN2). However, in other embodiments, the fifth intermediate syngas (17CE') may, without compression, serve as the secondary conditioned syngas (SYN2).

In the embodiment seen in FIG. 17C, the Syngas Compressor (SRC) is configured to compress the fifth intermediate syngas (17CE') (discharged from the Sulfur Guard Bed (17CE) after which a first portion of the resulting secondary conditioned syngas (SYN2) may be supplied to a number of other units.

A first portion of the secondary conditioned syngas (SYN2) may be supplied to the synthesis system (7000), which then produces liquid fuel and tail gas (17CG1).

In embodiments, at least a portion of the tail gas (17CG1) discharged from the synthesis system output (7-OUT1) may also be provided to the Gas Turbine System (17CH) for the production of electricity.

In embodiments, both a first portion of conditioned syngas (e.g., the secondary conditioned syngas SYN2) and at least a portion of the tail gas (17CG1) may be transferred to the pulse combustion hear exchanger and combusted to provide indirect heat for the particulate heat transfer material in the first reactor.

A second portion of the secondary conditioned syngas (SYN2) may be recycled back to the first reactor heat exchangers (HX-A, HX-A') and/or to the both Third Stage Product Gas Generation Systems (3C, 3C'), to help in the creation of more first reactor product gas and improved syngas, respectively.

A third portion of the secondary conditioned syngas (SYN2) may be supplied to a Hydrogen Separation System (17CG). The Hydrogen Separation System (17CG) is configured to remove hydrogen (17CG') from the secondary conditioned syngas (SYN2) and produce a first off-gas stream (17CG").

In embodiments, at least a portion of the first off-gas stream can be provided to a Gas Turbine System (17CH) for the production of electricity which may be used anywhere within the Biorefinery Superstructure System (BSS).

In embodiments, at least a portion of first off-gas stream may be transferred to the pulse combustion heat exchangers, and combusted to provide indirect heat for the particulate heat transfer material in the first reactor.

In embodiments, both a first portion of conditioned syngas (e.g., the secondary conditioned syngas SYN2) and at least a portion of the first off-gas stream may be transferred to the pulse combustion hear exchangers and combusted to provide indirect heat for the particulate heat transfer material in the first reactor.

In embodiments, both a second portion of the conditioned syngas (e.g., the secondary conditioned syngas SYN2) and a portion of the first off-gas stream may be transferred to the hydrocarbon reformer (i.e., the third reactor) to help form the improved syngas.

Hydrogen (17CG') discharged from the Hydrogen Separation System (17CG) may then be provided to the Upgrading System (8000) as shown in FIGS. 16, 17, 17A, 17B. At least a portion of the liquid fuel produced by synthesis system is also provided to the Upgrading System (8000).

The Upgrading System (8000) is configured to produce one or more upgraded fuels, naphtha (17CG2) which is discharged from the first hydrocarbon output (8-OUT2) of the Upgrading System (8000), and a second off-gas stream (17CG3) which is discharged from the second hydrocarbon output (8-OUT3) of the Upgrading System (8000).

In embodiments, at least a portion of the naphtha (17CG2) may also be provided to the Gas Turbine System (17CH) for the production of electricity. In embodiments, both a second portion of the conditioned syngas (e.g., the secondary conditioned syngas SYN2) and a portion of the naphtha may be transferred to the hydrocarbon reformer (i.e., the third reactor) to help form the improved syngas.

In embodiments, at least a portion of the off gases stream (17CG3) may also be provided to the Gas Turbine System (17CH) for the production of electricity.

In embodiments, at least a portion of second off-gas stream may be transferred to the pulse combustion heat exchangers, and combusted to provide indirect heat for the particulate heat transfer material in the first reactor.

In embodiments, both a first portion of conditioned syngas (e.g., the secondary conditioned syngas SYN2) and at least a portion of the second off-gas stream may be transferred to the pulse combustion hear exchangers and combusted to provide indirect heat for the particulate heat transfer material in the first reactor.

FIG. 18:

FIG. 18 is a detailed view showing a non-limiting embodiment of a First Stage Product Gas Generation Control Volume (CV-3A) and First Stage Product Gas Generation System (3A) of a three-stage energy-integrated product gas generation system (1001) including a first reactor (100) equipped with a dense bed zone (AZ-A), feed zone (AZ-B), and splash zone (AZ-C), along with the first reactor carbonaceous material and gas input (104), valves, sensors, and controllers.

FIG. 18 shows a first reactor (100) having a first interior (101) provided with a first dense bed zone (AZ-A), a first feed zone (AZ-B) above the first dense bed zone (AZ-A), and a first splash zone (AZ-C) above the first feed zone (AZ-B). The first splash zone (AZ-C) is proximate to the first fluid bed level (L-A) and below the first freeboard zone (FB-A). In embodiments, the dense bed zone (AZ-A) corresponds to the lower portion of the dense bed within the first interior (101). In embodiments, the feed zone (AZ-B) is located above the dense bed zone (AZ-A). In embodiments, the splash zone (AZ-C) may be located above the feed zone (AZ-B) and below the first fluid bed level (L-A).

The system (1001) according to FIG. 18, comprises four first reactor heat exchangers (HX-A1, HX-A2, HX-A3, HX-A4) in thermal contact with the first interior (101) of the first reactor (100). The four first reactor heat exchangers (HX-A1, HX-A2, HX-A3, HX-A4) are positioned in the first interior (101) and vertically spaced apart from one another along the height dimension of the first interior (101).

The first reactor first heat exchanger (HX-A1) is comprised of: a first reactor first heat exchanger fuel inlet (112A) configured to introduce a first reactor first heat exchanger fuel (110A) at a first inlet temperature (T3A); and a first reactor first heat exchanger combustion stream outlet (116A) configured to discharge a first reactor first heat exchanger combustion stream (114A) at a higher, second outlet temperature (T4A).

The first reactor third heat exchanger (HX-A3) is comprised of: a first reactor third heat exchanger fuel inlet (112C) configured to introduce a first reactor third heat exchanger fuel (110C) at a first inlet temperature (T3C); and a first reactor third heat exchanger combustion stream outlet (116C) configured to discharge a first reactor third heat exchanger combustion stream (114C) at a higher, second outlet temperature (T4C).

Connection X1 shows the first reactor first heat exchanger combustion stream (114A) being routed to be combined with the discharge of the first reactor third heat exchanger combustion stream (114C) from the first reactor third heat exchanger combustion stream outlet (116C) of the first reactor first heat exchanger (HX-A1) to form a combined combustion stream (114).

FIG. 18 further depicts the First Stage Product Gas Generation Control Volume (CV-3A) having a First Stage Product Gas Generation System (3A) configured to accept a fuel input (3A-IN4) as a heat exchanger fuel (110, 110A, 110B, 110C, 110D) for the four first reactor heat exchangers (HX-A1, HX-A2, HX-A3, HX-A4). Each first reactor heat exchangers (HX-A1, HX-A2, HX-A3, HX-A4) is shown in be in physical contact with the first reactor particulate heat transfer material (105) and configured to discharge a combustion products output (3A-OUT2) as a combustion stream (114). The term particulate heat transfer material (105) and bed material are synonymous.

The embodiment of FIG. 18 shows the heat of reaction is supplied to the particulate heat transfer material (105) of the first reactor (100) indirectly by heat exchangers (HX-A1, HX-A3) such as pulse combustion device. Any type of heat exchanger may be used, such as pulse heater tailpipes, electrical heater rods in thermowells, fuel cells, heat pipes, fire-tubes, annulus-type heat exchangers, or radiant tubes. The embodiment of FIG. 18 also shows the heat of reaction also being supplied to the particulate heat transfer material (105) of the first reactor (100) directly by utilization of a fuel (3A-IN4) such as a mixture of hydrocarbons and an oxygen-containing gas. A portion of the product gas may be supplied as fuel (110) to the pulse combustion devices and combustion of these gases provides the heat necessary for the indirect endothermic thermochemical processes taking place within the first interior (101) of the first reactor (100). In one embodiment, the heat exchangers (HX-A1, HX-A3) may be a pulse combustion device that combusts a source of fuel (110) to form a pulse combustion stream (114) comprising flue gas. The pulse combustion stream (114) indirectly heats the particulate heat transfer material (105) of the first reactor (100). As used therein, indirectly heating the bed means that the pulse combustion stream (114) does not contact the contents of the bed material (105) of the first reactor (100).

In some embodiments, the combustion of the fuel and oxygen-containing gas contained in the first reactor heat exchanger fuel (110) takes place within the first reactor heat exchangers (HX-A1, HX-A3). As a result, the first reactor heat exchanger fuel inlet temperature (T3) will be less than the first reactor heat exchanger combined combustion stream outlet temperature (T4). In some embodiments, the combustion of the fuel and oxygen-containing gas contained in the first reactor heat exchanger fuel (110) takes place outside of and prior to entering the first reactor heat exchangers (HX-A1, HX-A3). As a result, the first reactor heat exchanger combined combustion stream outlet temperature (T4) will be less than the first reactor heat exchanger fuel inlet temperature (T3). Heat exchangers for transferring thermal energy to a particulate heat transfer material (105) contained within the interior (101) of a first reactor are well known in the art and as such the details and design are not particularly relevant here.

In embodiments, the first reactor particulate heat transfer material (105) is comprised of Geldart Group A or Group B solids in the form of inert material or catalyst or sorbent or engineered particles. The engineered particles may be made of alumina, zirconia, sand, olivine sand, limestone, dolomite, or catalytic materials, any of which may be hollow in form, such as microballoons or microspheres. The preferred first reactor particulate heat transfer material (105) is Geldart Group B alumina microballons. The first reactor particulate heat transfer material (105) enhances mixing, heat and mass transfer, and reaction between the carbonaceous material and gas mixture (102) and the reactant or oxygen-containing gas introduced to the first reactor (100).

A reactor mixture input (3A-IN1) is introduced to the First Stage Product Gas Generation Control Volume (CV-3A) as a first reactor carbonaceous material and gas input (104) and is configured to provide a carbonaceous material and gas mixture (102) to the feed zone (AZ-B) of the first reactor (100).

A carbonaceous material and gas mixture (102) are introduced to the interior (101) of the first reactor (100) for intimate contact with the heated particulate heat transfer material (105), reactant (106, 106A, 106B, 106C) and oxygen-containing gas (218, 218A, 218B, 218C) to produce a first reactor product gas (122) that is discharged from the interior (101) of the first reactor (100) via a first reactor product gas output (124).

The first reactor product gas output (124) exits the First Stage Product Gas Generation Control Volume (CV-3A) through a first reactor product gas transferred via a first reactor gas output (3A-OUT1) and enters the Second Stage Product Gas Generation Control Volume (CV-3B) as a second reactor gas input (3B-IN1).

FIG. 18 depicts steam being introduced to the First Stage Product Gas Generation Control Volume (CV-3A) as a reactant (106) via a first reactor reactant input (3A-IN2) or a second reactor heat transfer medium output (3B-OUT2) to be made available to any combination of (i) the corresponding first reactor dense bed zone (AZ-A), (ii) the first reactor feed zone (AZ-B), and (iii) the first reactor splash zone (AZ-C).

Further, FIG. 18 depicts an oxygen-containing gas (118) being introduced to the First Stage Product Gas Generation Control Volume (CV-3A) through an oxygen-containing gas input (3A-IN3) to be made available to any combination of (i) the corresponding first reactor dense bed zone (AZ-A), (ii) the first reactor feed zone (AZ-B), and (iii) the first reactor splash zone (AZ-C).

FIG. 18 depicts the system (1001) further including: a first reactor dense bed zone reactant input (108A) and first reactor dense bed zone oxygen-containing gas input (120A) in fluid communication with a dense bed zone steam/oxygen connection (AZA0). The dense bed zone steam/oxygen connection (AZA0) is in fluid communication with the dense bed zone steam/oxygen input (AZA2) and is configured to transport the dense bed zone steam/oxygen (AZA1) to the first reactor (100) dense bed zone (AZ-A). The first reactor (100) dense bed zone steam/oxygen (AZA1) is a mixture of the first reactor dense bed zone reactant (106A) and first reactor dense bed zone oxygen-containing gas (118A).

A first reactor dense bed zone reactant valve (VA1), configured to accept a signal (XA1) from a controller (CA1), is installed upstream of the input (108A) to control the amount of reactant (106A) supplied to the first reactor (100) dense bed zone (AZ-A). A first reactor dense bed zone oxygen-containing gas valve (VA2), configured to accept a signal (XA2) from a controller (CA2), is installed upstream of the input (120A) to control the amount of oxygen-containing gas (118A) supplied to the first reactor (100) dense bed zone (AZ-A).

FIG. 18 depicts the system (1001) further including: a first reactor feed zone reactant input (108B) and first reactor feed zone oxygen-containing gas input (120B) in fluid communication with a feed zone steam/oxygen connection (AZB0). The feed zone steam/oxygen connection (AZB0) is in fluid communication with the feed zone steam/oxygen input (AZB2) and configured to transport the feed zone steam/oxygen (AZB1) to the first reactor (100) feed zone (AZ-B). The first reactor (100) feed zone steam/oxygen (AZB1) is a mixture of the first reactor feed zone reactant (106B) and first reactor feed zone oxygen-containing gas (118B).

A first reactor feed zone reactant valve (VA3), configured to accept a signal (XA3) from a controller (CA3), is installed upstream of the input (108B) to control the amount of reactant (106B) supplied to the first reactor (100) feed zone (AZ-B). A first reactor feed zone oxygen-containing gas valve (VA4), configured to accept a signal (XA4) from a controller (CA4), is installed upstream of the input (120B) to control the amount of oxygen-containing gas (118B) supplied to the first reactor (100) feed zone (AZ-B).

FIG. 18 depicts the system (1001) further including: a first reactor splash zone reactant input (108C) and first reactor splash zone oxygen-containing gas input (120C) in fluid communication with a splash zone steam/oxygen connection (AZC0). The splash zone steam/oxygen connection (AZC0) is in fluid communication with the splash zone steam/oxygen input (AZC2) and configured to transport the splash zone steam/oxygen (AZC1) to the first reactor (100) splash zone (AZ-C). The first reactor (100) splash zone steam/oxygen (AZC1) is a mixture of the first reactor splash zone reactant (106C) and first reactor splash zone oxygen-containing gas (118C).

A first reactor splash zone reactant valve (VA5), configured to accept a signal (XA5) from a controller (CA5) is installed upstream of the input (108C) to control the amount of reactant (106C) supplied to the first reactor (100) splash zone (AZ-C). A first reactor splash zone oxygen-containing gas valve (VA6), configured to accept a signal (XA6) from a controller (CA6) is installed upstream of the input (120C) to control the amount of oxygen-containing gas (118C) supplied to the first reactor (100) splash zone (AZ-C). An internal cyclone (125) is shown in the freeboard zone (FB-A) of the first reactor (100).

A first reactor product gas first quality sensor (AQ1) is installed on the discharge of the first reactor product gas output (124) to measure the composition of the first reactor product gas (122). Specifically, the first reactor product gas first quality sensor (AQ1) is configured to measure content of CO, H2, and CO2 within the first reactor product gas (122). VOC, SVOC, H2S, COS may also me measured by the first reactor product gas first quality sensor (AQ1). The signal (XAQ1) from the first reactor product gas first quality sensor (AQ1) is outputted to the to the computer (COMP). The first reactor product gas first quality sensor (AQ1) may also provide an analysis of wide range of organic and inorganic species, wherein its analysis is unaffected by concentration fluctuations, and where the analysis is unaffected by interferences. The ideal instrument is a combined GC and FTIR Gas Analyzer that is fast, very sensitive and is a mobile apparatus that can deal with process environment. The unique spectral analysis methodology of a combined GC and FTIR Gas Analyzer solves interference challenges in real time using unique approach to background spectra. It is also extremely sensitive, stable, and fast analysis of thousands of organic and inorganic species.

The following signals are configured to be inputs or outputs from the computer (COMP): first reactor dense bed zone reactant valve signal (XA1); first reactor dense bed zone oxygen-containing gas valve signal (XA2); first reactor feed zone reactant valve signal (XA3); first reactor feed zone oxygen-containing gas valve signal (XA4); first reactor splash zone reactant valve signal (XA5); and first reactor splash zone oxygen-containing gas valve signal (XA6).

FIG. 19:

FIG. 19 elaborates upon the non-limiting embodiment of FIG. 18 further including multiple carbonaceous material and gas inputs (104A, 104B, 104C, 104D) and multiple feed zone steam/oxygen inputs (AZB2, AZB3, AZB4, AZB5) positioned in the feed zone (AZ-B) along with multiple splash zone steam/oxygen inputs (AZC2, AZC3, AZC4, AZC5) positioned in the splash zone (AZ-C). FIG. 19 depicts four carbonaceous material and gas inputs (104A, 104B, 104C, 104D) to the feed zone (AZ-B) of the first interior (101) of the first reactor (100). Each carbonaceous material and gas input (104A, 104B, 104C, 104D) has a corresponding steam/oxygen input (AZB2, AZB3, AZB4, AZB5).

Specifically, the first reactor first carbonaceous material and gas input (104A) has its own source of feed zone steam/oxygen (AZB1) introduced from the first feed zone steam/oxygen input (AZB2). The second carbonaceous material and gas input (104B) has its own source of feed zone steam/oxygen (AZB1) introduced from the second feed zone steam/oxygen input (AZB3). The third carbonaceous material and gas input (104C) has its own source of feed zone steam/oxygen (AZB1) introduced from the third feed zone steam/oxygen input (AZB4). The fourth carbonaceous material and gad input (104D) has its own source of feed zone steam/oxygen (AZB1) introduced from the fourth feed zone steam/oxygen input (AZB5). Connection X2 indicates the feed zone steam/oxygen (AZB1) being introduced to the third feed zone steam/oxygen input (AZB4) and the fourth feed zone steam/oxygen input (AZB5). Connection X3 indicates the carbonaceous material and gas mixture (102C and 102D) being introduced to a third carbonaceous material and gas input (104C) and a fourth carbonaceous material and gas input (104D), respectively.

FIG. 19 depicts four splash zone steam/oxygen inputs (AZC2, AZC3, AZC4, AZC5) to the splash zone (AZ-C) of the first interior (101) of the first reactor (100). Each of the four splash zone steam/oxygen inputs (AZC2, AZC3, AZC4, AZC5) is fed from a common source of splash zone steam/oxygen (AZC1) for delivery to the splash zone (AZ-C) of the first interior (101) of the first reactor (100). Connection X4 indicates the splash zone steam/oxygen (AZC1) being introduced to the second splash zone steam/oxygen input (AZC3), third splash zone steam/oxygen input (AZC4), and the fourth splash zone steam/oxygen input (AZC5). Connection X5 indicates the splash zone steam/oxygen (AZC1) being introduced to the second splash zone steam/oxygen input (AZC3). Note that although only four carbonaceous material and gas inputs (104A, 104B, 104C, 104D) it is preferred to have six inputs as later indicated in FIG. 20 and FIG. 21.

FIG. 19 also shows the perspective of a first reactor feed zone cross-sectional view (XAZ-B) that will be elaborated upon in FIGS. 20, 21, and 22. FIG. 19 also shows the perspective of a first reactor splash zone cross-sectional view (XAZ-C) that will be elaborated upon in FIG. 23.

FIG. 19 also shows the first reactor first carbonaceous material and gas input (104A) and the first reactor second carbonaceous material and gas input (104B) introduced to the interior (101) of the first reactor at different planes at different vertical heights about the first reactor (100). FIG. 19 also shows the first reactor third carbonaceous material and gas input (104C) and the first reactor fourth carbonaceous material and gas input (104D) introduced to the interior (101) of the first reactor (100) at different planes at different vertical heights about the first reactor (100).

FIG. 20:

FIG. 20 shows a non-limiting embodiment of a first reactor feed zone circular cross-sectional view (XAZ-B) from the embodiment of FIG. 19. In embodiments, six carbonaceous material inputs (104A, 104B, 104C, 104D, 104E, 104F) are positioned about the circumference of the first reactor (100). FIG. 20 also depicts each of the six carbonaceous material inputs (104A, 104B, 104C, 104D, 104E, 104F) having its own dedicated source of feed zone steam/oxygen introduced through a respective feed zone steam/oxygen input (AZB2, AZB3, AZB4, AZB5, AZB6). The first feed zone steam/oxygen input (AZB2) has a first reactor first carbonaceous material input (104A). The first reactor second carbonaceous material input (104B) has a second feed zone steam/oxygen input (AZB3). The first reactor third carbonaceous material input (104C) has a third feed zone steam/oxygen input (AZB4). The first reactor fourth carbonaceous material input (104D) has a fourth feed zone steam/oxygen input (AZB5). The first reactor fifth carbonaceous material input (104E) has a fifth feed zone steam/oxygen input (AZB6). The first reactor sixth carbonaceous material input (104F) has a sixth feed zone steam/oxygen input (AZB7).

Four of the six carbonaceous material inputs (104A, 104C, 104D, 104F) are positioned 90 degrees from one another. Two of the six carbonaceous material inputs (104B, 104E) are positioned 180 degrees from one another at angles of 45 degrees and 225 degrees leaving the angled positions of 135 degrees and 315 degrees vacant where the angle 0 degrees and 360 degrees are at the twelve-o-clock position on the circular diagram depicting the first reactor (100).

FIG. 21:

FIG. 21 shows a non-limiting embodiment of a first reactor feed zone cross-sectional view (XAZ-B) from the embodiment of FIG. 20, however, FIG. 21 shows a rectangular first reactor (100) cross-sectional view. In embodiments, six carbonaceous material inputs (104A, 104B, 104C, 104D, 104E, 104F) are positioned about the perimeter of the first reactor (100).

Similar to FIG. 20, FIG. 21 shown each of the six carbonaceous material and gas inputs (104A, 104B, 104C, 104D, 104E, 104F) having its own dedicated source of feed zone steam/oxygen introduced through a respective feed zone steam/oxygen input (AZB2, AZB3, AZB4, AZB5, AZB6). The first feed zone steam/oxygen input (AZB2) has a first reactor first carbonaceous material input (104A). The first reactor second carbonaceous material and gas input (104B) has a second feed zone steam/oxygen input (AZB3). The first reactor third carbonaceous material input (104C) has a third feed zone steam/oxygen input (AZB4). The first reactor fourth carbonaceous material input (104D) has a fourth feed zone steam/oxygen input (AZB5). The first reactor fifth carbonaceous material input (104E) has a fifth feed zone steam/oxygen input (AZB6). The first reactor sixth carbonaceous material input (104F) has a sixth feed zone steam/oxygen input (AZB7).

FIG. 22:

FIG. 22 shows a non-limiting embodiment of a first reactor feed zone cross-sectional view (XAZ-B) from the embodiment of FIG. 19 where only two of the six first reactor (100) carbonaceous material and gas inputs (104B, 104E) are configured to inject carbonaceous material into vertically extending quadrants (Q1, Q2, Q3, Q4). FIG. 22 elaborates upon the preference to have only two of the six first reactor carbonaceous material inputs (104B, 104E) configured to inject a mixture of carbonaceous material and gas into the vertically extending quadrants (Q1, Q3). Further, each of the six carbonaceous material and gas inputs (104A, 104B, 104C, 104D, 104E, 104F) has its own dedicated steam/oxygen input (AZB2, AZB3, AZB4, AZB5, AZB6, AZB7), respectfully. FIG. 22 depicts four first reactor heat exchangers (HX-A1, HX-A2, HX-A3, HX-A4) positioned in the first interior (101) and vertically spaced apart from one another along the height dimension of the first interior (101); wherein: alternate first reactor heat exchangers along said first height dimension are arranged orthogonal to one another such that, in a top view of the first interior (101), the four first reactor heat exchangers (HX-A1, HX-A2, HX-A3, HX-A4) define four open vertically extending quadrants (Q1, Q2, Q3, Q4).

FIG. 23:

FIG. 23 shows a non-limiting embodiment of a first reactor splash zone cross-sectional view (XAZ-C) from the embodiment of FIG. 19. In embodiments, eight separate splash zone steam/oxygen inputs (AZC2, AZC3, AZC4, AZC5, AZC6, AZC7, AZC8, AZC9) are shown equidistantly spaced apart at 45 degree angles to one another about the circumference of the first reactor (100). Each of the eight separate splash zone steam/oxygen inputs (AZC2, AZC3, AZC4, AZC5, AZC6, AZC7, AZC8, AZC9) accepts a source of splash zone steam/oxygen (AZC1).

FIG. 24:

FIG. 24 elaborates upon the non-limiting embodiment of FIG. 18 further including two particulate classification chambers (A1A, A1B) that are configured to accept a bed material, inert feedstock contaminant mixture (A4A, A4AA), and a classifier gas (A16, A16A) and to clean and recycle the bed material portion back to the first interior (101) of the first reactor (100) while removing the inert feedstock contaminant portion from the system as a solids output (3A-OUT3).

The product gas generation and particulate classification system (1002) shown in FIG. 24 depicts a Product Gas Generation System (3A) configured to produce both a product gas (122) and classified inert feedstock contaminants (A19, A19A) from a carbonaceous material and gas mixture (102). The system (1002) comprises a first splitter (2B1) as seen in FIG. 14 in fluid communication with a first feed zone delivery system (2050A) and a second feed zone delivery system (2050B); a first feed zone delivery system (2050A) as seen in FIG. 14 wherein the first feed zone delivery system (2050A) includes at least a Gas Mixing (2G) subsystem and a Transport (2H) subsystem of FIG. 2E; a second feed zone delivery system (2050B) as seen in FIG. 14 wherein the second feed zone delivery system (2050B) includes at least Gas Mixing (2G) subsystem and a Transport (2H) subsystem of FIG. 2E; a first reactor (100) having a first interior (101) and comprising:

a first carbonaceous material and gas input (104A) provided by a first feed zone delivery system (2050A) and configured to input a first carbonaceous material and gas mixture (102A) to the first interior (101) of the first reactor (100);

a second carbonaceous material and gas input (104B) provided by a second feed zone delivery system (2050B) and configured to input a second carbonaceous material and gas mixture (102B) to the first interior (101) of the first reactor (100); and, a first reactor reactant input (108A, 108B, 108C) to the first interior (101); a first reactor product gas output (124) from the first interior (101); a classified recycled bed material input (A27, A27A) to the first interior (101); and, a bed material and inert feedstock contaminant mixture output (A2A, A2AA) from the first interior (101).

In embodiments, the first feed zone delivery system (2050A) and second feed zone delivery system (2050B) include a Mass Flow Regulation (2C) subsystem, Densification (2D) subsystem, Plug Control (2E) subsystem, Density Reduction (2F) subsystem, Gas Mixing (2G) subsystem, and a Transport (2H) subsystem.

In embodiments, the first feed zone delivery system (2050A) and second feed zone delivery system (2050B) include a Mass Flow Regulation (2C) subsystem, Densification (2D) subsystem, Plug Control (2E) subsystem, Density Reduction (2F) subsystem, Gas Mixing (2G) subsystem, and a Transport (2H) subsystem as seen in FIG. 2A. In embodiments, the first feed zone delivery system (2050A) and second feed zone delivery system (2050B) include a Mass Flow Regulation (2C) subsystem, Gas Mixing (2G) subsystem, and a Transport (2H) subsystem as seen in FIG. 2B. In other non-limiting embodiments, the first feed zone delivery system (2050A) and second feed zone delivery system (2050B) include any combination or permutation of the subsystems including Transport (2H), Gas Mixing (2G), Density Reduction (2F), Plug Control (2E), Densification (2D), Mass Flow Regulation (2C) as seen in FIG. 2A noting that any order of any possibility of any combination or permutation of subsystems 2C, 2D, 2E, 2F, 2G, 2H being in a sequence falls within the bounds of this disclosure.

A first carbonaceous material and gas input (104A) provides a first carbonaceous material and gas mixture (102A) to the interior (101) of the first reactor (100) via a first reactor mixture input (3A-IN1A) from an upstream first feed zone delivery system (2050A). A second carbonaceous material and gas input (104B) provides a second carbonaceous material and gas mixture (102B) to the interior (101) of the first reactor (100) via a second reactor mixture input (3A-IN1B) from an upstream second feed zone delivery system (2050B).

The First Stage Product Gas Generation System (3A) is shown accepting a first reactor mixture input (3A-IN1A) from the first feed zone delivery system (2050A) as a first carbonaceous material and gas via the mixture output (2-OUT1A). The First Stage Product Gas Generation System (3A) is shown accepting a second reactor mixture input (3A-IN1B) from the second feed zone delivery system (2050B) as a second carbonaceous material and gas via the mixture output (2-OUT1B).

The system (1002) further comprises two particulate classification chambers (A1A, A1B) each having a classifier interior (INA, INB) and comprising: a bed material and inert feedstock contaminant mixture input (A5A, A5AA), a classifier gas input (A6A, A6AA), a classified recycled bed material output (A7A, A7AA), a classifier depressurization gas output (A8A, A8AA), and a classifier inert feedstock contaminant output (A9A, A9AA).

The system (1002) shown in FIG. 24 depicts one first reactor (100) equipped with two particulate classification chambers (A1A, A1B). Each particulate classification chamber (A1A, A1B) is equipped with a bed material and inert feedstock contaminant mixture input (A5A, A5AA) in fluid communication with the first interior (101) of the first reactor (100) through a bed material and inert feedstock contaminant mixture output (A2A, A2AA) and a bed material and inert feedstock contaminant mixture transfer conduit (A3A, A3AA). Each bed material and inert feedstock contaminant mixture input (A5A, A5AA) is configured to introduce a bed material and inert feedstock contaminant mixture (A4A, A4AA) to the interior (INA, INB) via a bed material and inert feedstock contaminant mixture transfer conduit (A3A, A3AA).

The bed material and inert feedstock contaminant mixture (A4A, A4AA) is comprised of a bed material portion and an inert feedstock contaminant portion. The bed material portion is synonymous with the first reactor particulate heat transfer material (105).

MSW and/or RDF are carbonaceous materials that contain inert feedstock contaminants in the form of Geldart Group D particles comprising whole units and/or fragments of one or more from the group consisting of allen wrenches, ball bearings, batteries, bolts, bottle caps, broaches, bushings, buttons, cable, cement, chains, clips, coins, computer hard drive shreds, door hinges, door knobs, drill bits, drill bushings, drywall anchors, electrical components, electrical plugs, eye bolts, fabric snaps, fasteners, fish hooks, flash drives, fuses, gears, glass, gravel, grommets, hose clamps, hose fittings, jewelry, key chains, key stock, lathe blades, light bulb bases, magnets, metal audio-visual components, metal brackets, metal shards, metal surgical supplies, mirror shreds, nails, needles, nuts, pins, pipe fittings, pushpins, razor blades, reamers, retaining rings, rivets, rocks, rods, router bits, saw blades, screws, sockets, springs, sprockets, staples, studs, syringes, USB connectors, washers, wire, wire connectors, and zippers. Thus when MSW and/or RDF are transferred to the first reactor (100), inert feedstock contaminants contained therein, are also unavoidably transferred to the first reactor (100) as well.

The inert feedstock contaminant portion of the MSW within the carbonaceous material and gas mixture (102) of FIG. 24 is that which cannot be converted into a product gas (122) and as a result, accumulates within the interior (101) of the first reactor (100). It is therefore desirable to be able to remove Geldart Group D inert feedstock contaminant solids which may accumulate within the first reactor (100). Thus it is therefore desirable to be able to clean bed material by classification or via the removal of Geldart Group D inert feedstock contaminant solids therefrom to permit continuous and uninterrupted operation within the first reactor (100).

The accumulation of Geldart Group D inert feedstock contaminant solids within the first reactor (100) inhibits continuous operation of the first reactor (100) and may cause defluidization within the first reactor (100). Defluidization of the first reactor (100) may be caused by unpredictable and unavoidable buildup of larger Geldart particles, in comparison to the mean bed particle characteristic, introduced to the interior (101). For example, FIG. 24 depicts an interior (101) comprised of a fluidized bed of a mean bed particle characteristic of Geldart Group B solids which may become defluidized by buildup or accumulation of comparatively larger, coarser and/or heavier Geldart Group D solids that are introduced to the fluidized bed with the carbonaceous material (102).

A mixture transfer valve (V9, V9A, V9AA) is interposed in each mixture transfer conduit (A3A, A3AA) in between the first reactor (100) and each particulate classification chamber (A1A, A1B) to start and stop flow of the contents transferred therein, and to isolate the particulate classification chamber (A1A, A1B) from the first reactor (100).

Each particulate classification chamber (A1A, A1B) is equipped with a classifier gas input (A6A, A6AA) configured to introduce a classifier gas (A16, A16A) to each interior (IN1, INB). The classifier gas input (A6A, A6AA) may carbon dioxide provided from the carbon dioxide output (6-OUT2) of a downstream Secondary Gas Clean-Up System (6000) as seen in FIGS. 16 and 17. The classifier gas (A16, A16A) is preferably carbon dioxide. However, the classifier gas (A16, A16A) may be any gas as deemed appropriate, such as nitrogen, product gas, air, hydrocarbons, biorefinery off-gases, or the like.

A classification gas transfer valve (V10, V10A, V10AA) is configured to regulate classifier gas (A16, A16A) flow through the classifier gas input (A6A, A6AA) to the interior (INA, INB) of the particulate classification chamber (A1A, A1B). Each particulate classification chamber (A1A, A1B) is equipped with a classified recycled bed material output (A7A, A7AA) in fluid communication with the interior (101) of the first reactor (100) via a classified recycled bed material input (A27, A27A) and a classifier riser (A17, A17A).

The classified recycled bed material input (A27, A27A) is preferably positioned at or above the fluid bed level (L-A) of the first reactor (100) so as to let the recycled bed material or particulate heat transfer material (105) to be recycled back to the interior (101) of the first reactor (100) in an unimpeded manner.

A bed material riser recycle transfer valve (V11, V11A, V11AA) is interposed in each classifier riser (A17, A17A) in between the first reactor (100) and each particulate classification chamber (A1A, A1B) to start and stop flow of the contents transferred therein, and to isolate the particulate classification chamber (A1A, A1B) from the first reactor (100).

Each particulate classification chamber (A1A, A1B) is equipped with a classifier inert feedstock contaminant output (A9A, A9AA) configured to remove classified inert feedstock contaminants (A19, A19A) from the interior (INA, INB).

An inert feedstock contaminant drain valve (V13, V13A, V13AA) is configured to start and stop flow of classified inert feedstock contaminants (A19, A19A) transferring through the classifier inert feedstock contaminant output (A9A, A9AA).

Each particulate classification chamber (A1A, A1B) may also be equipped with a classifier depressurization gas output (A8A, A8AA) configured to evacuate classifier depressurization gas (A18, A18A) from the interior (INA, INB) thus reducing the pressure contained therein.

A depressurization vent valve (V12, V12A, V12AA) is configured to start and stop flow of classifier depressurization gas (A18, A18A) transferred through the classifier depressurization gas output (A8A, A8AA).

The classified recycled bed material output (A7A, A7AA) is configured to output a classified recycled bed material (A37, A37A) to the interior (101) of the first reactor (100). In embodiments, the classifier riser (A17, A17A) conveys the classified recycled bed material (A37, A37A) to the interior (101) of the first reactor (100) in a suspension of gas (A16, A16A) and conveyed in a dilute-phase flow regime.

A first reactor mixture input (3A-IN1A) and a second reactor mixture input (3A-IN1B) are introduced to the feed zone (AZ-B) of the first reactor (100) as a first carbonaceous material and gas mixture (102A) and a second carbonaceous material and gas mixture (102B). The first carbonaceous material and gas mixture (102A) and a second carbonaceous material and gas mixture (102B) are introduced to the interior (101) of the first reactor (100) for intimate contact with the heated particulate heat transfer material (105), reactants (106, 106A, 106B, 106C) and oxygen-containing gas (118, 118a, 118B, 118C) contained within the interior (101) to produce a first reactor product gas (122) that is discharged from the interior (101) of the first reactor (100) via a first reactor product gas output (124). The first reactor product gas (122) includes first syngas comprising carbon monoxide and hydrogen. It also includes char, volatiles and other gases.

FIG. 24 is to be used in conjunction with FIG. 25 which depicts a valve sequencing diagram that describes the method of operating the sequence of the product gas generation and particulate classification system (1002) embodiment shown in FIG. 24.

FIG. 24 shows one embodiment of the product gas generation and particulate classification system (1002) equipped with a variety of sensors, valves, assets and controllers which are all configured to methodically and systematically manipulate the operation of the particulate classification chamber (A1A, A1B) to accept a variety of inputs and discharge a variety of outputs to and from the first reactor (100).

The particulate classification chamber (A1A, A1B) is configured to accept the bed material and inert feedstock contaminant mixture (A4A, A4AA) transferred from the interior (101) of the first reactor (100). In embodiments, the bed material and inert feedstock contaminant mixture (A4A, A4AA) are conveyed in a dense phase flow regime through the mixture transfer conduit (A3A, A3AA) into the classifier interior (INA, INB). The bed material and inert feedstock contaminant mixture (A4A, A4AA) is comprised of a bed material portion and an inert feedstock contaminant portion. The bed material and inert feedstock contaminant mixture (A4A, A4AA) is transferred to the classifier interior (INA, INB) via a mixture transfer conduit (A3A, A3AA) and flow is regulated through modulation or actuation of an associated mixture transfer valve (V9A, V9AA).

In embodiments, FIG. 24 shows the first reactor (100) having particulate heat transfer material (105) with a mean bed particle characteristic including Geldart Group B solids. Therefore, the bed material portion of the mixture (A4A, A4AA) is comprised of Geldart Group B solids and the inert feedstock contaminant portion is comprised of Geldart Group D solids. The embodiment of FIG. 24 shows the classification chamber (A1A, A1B) configured to accept a classifier gas (A16, A16A), such as carbon dioxide, the supply of which is regulated through modulation or actuation of a classification gas transfer valve (V10A, V10AA).

In response to accepting the gas (A16, A16A), the classification chamber (A1A, A1B) is configured to output: (1) a bed material portion to be returned to the first reactor (100); and, (2) an inert feedstock contaminant portion to be discharged from the classifier chamber (A1A, A1B). As a result, the bed material and inert feedstock contaminant mixture (A4A, A4AA) is cleaned to separate the bed material portion (Geldart Group B solids) from the inert feedstock contaminant portion (Geldart Group D solids). The cleaned and separated bed material portion (Geldart Group B solids) is then available to be used again in the first reactor (100) in a thermochemical process to generate a product gas.

The system in FIG. 24 displays a first reactor (100) configured to accept a carbonaceous material and gas mixture (102A, 102B), such as MSW containing inert feedstock contaminants. The system in FIG. 24 also displays a first reactor (100) configured to accept a first reactor reactant input (3A-IN2A) or the second reactor heat transfer medium output (3B-OUT2), such as steam, from the third reactor heat exchanger (HX-C) (not shown). The system in FIG. 24 also displays a first reactor (100) configured to accept an oxygen-containing gas (118) through an input (3A-IN3).

FIG. 16 and FIG. 17 display a Biorefinery Superstructure System (BSS) equipped with a Secondary Gas Clean-Up System (6000) configured to remove carbon dioxide from product gas. The Secondary Gas Clean-Up System (6000) has a secondary gas clean-up input (6-IN1) and a secondary gas clean-up system output (6-OUT1). Membrane based carbon dioxide removal systems and processes are preferred to remove carbon dioxide from product gas, however other alternate systems and methods may be utilized to remove carbon dioxide, not limited to adsorption or absorption based carbon dioxide removal systems and processes.

FIG. 16 and FIG. 17 display the Secondary Gas Clean-Up System (6000) discharging carbon dioxide via a carbon dioxide output (6-OUT2) to both the (1) First Stage Product Gas Generation System (3A), for use as a classifier gas (A16, A16A), and to the (2) the Feedstock Delivery System (2000) to be combined with a carbonaceous material (500). Thus FIG. 24 displays the product gas generation and particulate classification system (1002) in the context of a Biorefinery Superstructure System (BSS) as depicted in FIG. 16 and FIG. 17 and displays the introduction of the combined carbonaceous material and carbon dioxide into a first reactor via a reactor mixture input (3A-IN1).

Thus FIG. 24 depicts the system (1002) configured to react the MSW carbonaceous material with steam, carbon dioxide, and an oxygen-containing gas in a thermochemical process to generate a first reactor product gas containing char. For example, in embodiments, the first reactor (100) in FIG. 24 operates under a combination of steam reforming, water-gas shift, dry reforming, and partial oxidation thermochemical processes. FIG. 24 also shows combustion taking place within the first reactor first heat exchangers (HX-A1, HX-A2, HX-A3, HX-A4) to indirectly heat the first reactor particulate heat transfer material (105) contained within the first reactor (100). The first reactor particulate heat transfer material (105) essentially is a bed material and inert feedstock contaminant mixture due to the introduction of MSW introduced to the reactor that contains inert feedstock contaminants that build up within the interior (101) of the first reactor (100).

The product gas shown generated in FIG. 24 contains carbon dioxide, which is then later separated out in the Secondary Gas Clean-Up System (6000) to allow the carbon dioxide to be recycled back to the (1) Feedstock Delivery System (2000) to be combined with a carbonaceous material for transfer to the first reactor (100), and the (2) First Stage Product Gas Generation System (3A) for use as a classifier gas (A16, A16A) to clean the bed material. Thus the first particulate heat transfer material may be cleaned with a gas, or a portion of the product gas generated in the first reactor (100), such as for example, the carbon dioxide portion of the product gas generated in the first reactor that is recycled from a downstream Secondary Gas Clean-Up System (6000).

The embodiment of FIG. 24 shows the bed material portion comprised of Geldart Group A or B solids free of inert contaminants, transferred and regulated through actuation or modulation of a bed material riser recycle transfer valve (V11A, V11AA) that is positioned on a classifier riser (A17, A17A).

The embodiment of FIG. 24 also shows the classification chamber (A1A, A1B) configured to transfer Geldart Group D solids free of Geldart Group A or B solids as an inert feedstock contaminant portion from the classifier chamber (A1A, A1B) for removal from the via an inert feedstock contaminant drain valve (V13A, V13AA) positioned on the classifier inert feedstock contaminant output (A9A, A9AA).

A depressurization vent valve (V12A, V12AA) may optionally be utilized to evacuate residual pressured gas from the contents of the classification chamber (A1A, A1B) to prevent erosion and solids abrasion of solids passing through the inert feedstock contaminant drain valve (V13A, V13AA).

In embodiments, FIG. 24 depicts a municipal solid waste (MSW) energy recovery system for converting MSW containing inert feedstock contaminants, into a product gas (122), the system comprising:
  (a) a first splitter (2B1) in fluid communication with a first feed zone delivery system (2050A) and a second feed zone delivery system (2050B);
  (b) a first feed zone delivery system (2050A) as seen in FIG. 14 wherein the first feed zone delivery system (2050A) includes at least a Gas Mixing (2G) subsystem and a Transport (2H) subsystem of FIG. 2E;
  (c) a second feed zone delivery system (2050B) as seen in FIG. 14 wherein the second feed zone delivery system (2050B) includes at least Gas Mixing (2G) subsystem and a Transport (2H) subsystem of FIG. 2E;
  (d) a first reactor (100) comprising: a first reactor interior (101) suitable for accommodating a bed material and endothermically reacting MSW in the presence of steam to produce product gas; a first carbonaceous material and gas input (104A) provided by a first feed zone delivery system (2050A) and configured to input a first carbonaceous material and gas mixture (102A) to the first interior (101) of the first reactor (100); a second carbonaceous material and gas input (104B) provided by a second feed zone delivery system (2050B) and configured to input a second carbonaceous material and gas mixture (102B) to the first interior (101) of the first reactor (100);
  (e) a first reactor reactant input (108A, 108B, 108C) for introducing steam into the first interior (101); a first reactor product gas output (124) through which product gas is removed; a classified recycled bed material input (A27, A27A) in fluid communication with an upper portion of the first reactor interior (101); a particulate output (A2A, A2AA) connected to a lower portion of the first reactor interior, and through which a mixture (A4A, A4AA) of bed material and unreacted inert feedstock contaminants selectively exits the first reactor interior; and
  (f) a plurality of particulate classification chambers (A1A, A1B) in fluid communication with the first reactor interior (101), each chamber comprising:

(i) a mixture input (A5A, A5AA) connected to the particulate output (A2A, A2AA), for receiving said mixture from the first reactor interior (101);
(ii) a classifier gas input (A6A, A6AA) connected to a source of classifier gas (A16, A16A), for receiving classifier gas to promote separation of said bed material from said unreacted inert feedstock contaminants within said chamber;
(iii) a bed material output (A7A, A7AA) connected to the classified recycled bed material input (A27, A27A) of the first reactor interior (101) via a classifier riser conduit (A17, A17A), for returning bed material separated from said mixture to the first reactor interior; and
(iv) a contaminant output (A9A, A9AA) for removing unreacted inert feedstock contaminants (A19, A19A) which have been separated from said mixture, within the chamber.

In embodiments, FIG. 24 discloses a mixture transfer valve (V9A, V9AA) positioned between the particulate output (A2A, A2AA) and the mixture input (A5A, A5AA), to selectively control transfer of said mixture from the first reactor to the chamber; a classification gas transfer valve (V10A, V10AA) positioned between the source of classifier gas (A16, A16A) and the classifier gas input (A6A, A6AA), to selectively provide said classifier gas to the chamber; a bed material riser recycle transfer valve (V11A, V11AA) positioned between the bed material output (A7A, A7AA) and the classified recycled bed material input (A27, A27A), to selectively return bed material separated from said mixture, to the first reactor interior; and an inert feedstock contaminant drain valve (V13A, V13AA) configured to selectively remove unreacted inert feedstock contaminants (A19, A19A) which have been separated from said mixture. In embodiments, each chamber further comprises a classifier depressurization gas output (A8A, A8AA) and a depressurization vent valve (V12A, V12AA) connected to the classifier depressurization gas output (A8A, A8AA) to selectively vent the chamber.

In embodiments, FIG. 24 depicts a computer (COMP) configured to operate the system in any one of a plurality of states disclosed in FIG. 25, including: a first state in which all of said valves are closed; a second state in which the mixture transfer valve (V9A, V9AA) is open and the remainder of said valves are closed, to allow said mixture to enter the chamber; a third state in which the classification gas transfer valve (V10A, V10AA) and the bed material riser recycle transfer valve (V11A, V11AA) are open and the remainder of said valves are closed, to promote separation of said bed material from said mixture and recycling of separated bed material back into the first reactor; a fourth state in which the depressurization vent valve (V12A, V12AA) is open and the remainder of said valves are closed, to allow the chamber to vent; and a fifth state in which the inert feedstock contaminant drain valve (V13A, V13AA) is open and the remainder of said valves are closed, to remove unreacted inert feedstock contaminants from the chamber. In embodiments, the classifier gas may be carbon dioxide. In embodiments, the product gas (122) generated comprises carbon dioxide and a first portion of the carbon dioxide in the product gas (122) may be introduced into the chamber as the classifier gas.

In embodiments, FIG. 24 further discloses that the inert feedstock contaminants comprise a plurality of different Geldart Group D solids having a size greater than 1000 microns; and the Geldart Group D solids may comprise whole units and/or fragments of one or more of the group consisting of allen wrenches, ball bearings, batteries, bolts, bottle caps, broaches, bushings, buttons, cable, cement, chains, clips, coins, computer hard drive shreds, door hinges, door knobs, drill bits, drill bushings, drywall anchors, electrical components, electrical plugs, eye bolts, fabric snaps, fasteners, fish hooks, flash drives, fuses, gears, glass, gravel, grommets, hose clamps, hose fittings, jewelry, key chains, key stock, lathe blades, light bulb bases, magnets, metal audio-visual components, metal brackets, metal shards, metal surgical supplies, mirror shreds, nails, needles, nuts, pins, pipe fittings, pushpins, razor blades, reamers, retaining rings, rivets, rocks, rods, router bits, saw blades, screws, sockets, springs, sprockets, staples, studs, syringes, USB connectors, washers, wire, wire connectors, and zippers.

In embodiments, the bed material separated from the mixture and returned to the first reactor interior may comprise Geldart Group A solids ranging in size from about 30 microns to about 99.99 microns. These Geldart Group A solids may comprise one or more of the group consisting of inert material, catalyst, sorbent, engineered particles and combinations thereof. The engineered particles comprise one or more of the group consisting of alumina, zirconia, sand, olivine sand, limestone, dolomite, catalytic materials, microballoons, microspheres, and combinations thereof.

In embodiments, the bed material separated from said mixture and returned to the first reactor interior may comprise Geldart Group B solids ranging in size from about 100 to about 999.99 microns. There Geldart Group B solids may be from one or more of group consisting of inert material, catalyst, sorbent, and engineered particles. These engineered particles may comprise one or more of the group consisting of alumina, zirconia, sand, olivine sand, limestone, dolomite, catalytic materials, microballoons, microspheres, and combinations thereof.

In embodiments, the first reactor is operated at a temperature between 320° C. and about 900° C. to endothermically react the MSW in the presence of steam to produce product gas. In embodiments, the first reactor operates at any combination or permutation of thermochemical processes or reactions identified above. In embodiments, the first reactor is operated at a temperature between 500° C. and about 1400° C. to exothermically react the MSW in the presence of an oxygen-containing gas to produce product gas. In embodiments, the first reactor operates at any combination or permutation of thermochemical processes or reactions identified above.

FIG. 25:

FIG. 25 depicts the Classification Valve States for Automated Controller Operation of a typical particulate classification procedure. FIG. 25 is to be used in conjunction with FIG. 24 and depicts a listing of valve states that may be used in a variety of methods to operate valves associated with the particulate classification chambers (A1A, A1B). FIG. 25 identifies five separate discrete valve states of which any number of states can be selected to result in a sequence of steps for the classification of bed material and recovery of inert feedstock contaminants to prevent defluidization within the first reactor (100).

In embodiments, methods may be implemented for operating the product gas generation and classification system depicted in FIG. 24 by using the discrete states listed in FIG. 25 to realize a sequence of steps. FIG. 24 depicts a computer (COMP) that is configured to communicate and cooperate with controllers and valves associated with the particulate classification chambers (A1A, A1B). The computer (COMP) may be configured to operate the system using any combinations and permutations of states listed in FIG. 25.

It is contemplated that in some embodiments, sequence steps of a classification method may be chosen from any number of states listed in FIG. 25. In embodiments, sequence steps of a classification method may be chosen from a combination of state 1, state 2, state 3, state 4, and/or state 5, and may incorporate methods or techniques described herein and to be implemented as program instructions and data capable of being stored or conveyed via a master controller. In embodiments, the classification sequence may have only five steps which entail each of those listed in FIG. 25, wherein: step 1 is state 1; step 2 is state 2; step 3 is state 3; step 4 is state 4; and, step 5 is state 5. This may be typical if a carbonaceous material comprising MSW is fed into the first reactor that has a relatively greater than average amount of inert feedstock contaminants, where states 1 through 3 are not repeated because a sufficient quantity of inert feedstock contaminants is sufficiently present within the classifier prior to proceeding with state 4 and state 5 to vent and drain the classifier, respectively.

In embodiments, state 1, state 2, and state 3 may be repeated at least once prior to implementing state 4 and state 5. For example, the classification sequence may have eight steps, wherein states 1 through 3 are repeated once prior to proceeding with state 4 and state 5, wherein: step 1 is state 1; step 2 is state 2; step 3 is state 3; step 4 is state 1; and step 5 is state 2; step 6 is state 3; step 7 is state 4; and, step 8 is state 5. Thus, a classification sequence may entail a multitude of different combinations and permutations of sequence steps given the operator or user defined states to be repeated. For example, from a practical perspective, if a carbonaceous material comprising MSW is fed into the first reactor that has a relatively minimal amount of inert feedstock contaminants, states 1 through 3 may be repeated at least once, or several times, to ensure that a sufficient quantity of inert feedstock contaminants is present within the classifier vessel prior to proceeding with states 4 and state 5 to vent and drain the classifier, respectively.

Nonetheless, any combination or permutation of classifier method states and steps may be selected by a user or operator to realize the goal of cleaning the first particulate heat transfer material with a gas, such as carbon dioxide recycled from a downstream Secondary Gas Clean-Up System (6000), in a systematic, logical, and directed manner. The objective of the classifier (A1A) is to achieve 99% separation of the bed material portion from the inert feedstock contaminant portion in the classification state 3.

Disclosed methods or techniques may include the execution and implementation of states associated with the Automated Controller Operated Classification Valve Sequence Matrix as depicted in FIG. 25. Embodiments of the sequencing methods including steps and states may be implemented by program instructions entered into the computer (COMP) by a user or operator via an input/output interface (I/O) as disclosed in FIG. 24. Program and sequencing instructions may be executed to perform a particular computational functions such as automated operation of the valves associated with the product gas generation and classification system as depicted in FIG. 24.

The following describes various further embodiments of the systems and methods discussed above, and presents exemplary techniques and uses illustrating variations. Thus, the computer (COMP) may implement automation of the following controllers and their respective valves: mixture transfer valve controller (C9A, C9AA); classification gas transfer valve controller (C10A, C10AA); bed material riser recycle transfer valve controller (C11A, C11AA); depressurization vent valve controller (C12A, C12AA); and, inert feedstock contaminant drain valve controller (C13A, C13AA).

Controllers are shown only on the first of two shown particulate classification vessels (A1A) for simplicity in FIG. 24. However, it is to be noted that each valve depicted in FIG. 24 has an associated controller that acts in communication with the computer (COMP).

FIG. 26:

FIG. 26 is a detailed view showing a non-limiting embodiment of a Second Stage Product Gas Generation Control Volume (CV-3B) and Second Stage Product Gas Generation System (3B) of a three-stage energy-integrated product gas generation system (1001) including a second reactor (200) equipped with a dense bed zone (BZ-A), feed zone (BZ-B), and splash zone (BZ-C), along with a second reactor heat exchanger (HX-B), first solids separation device (150), second solids separation device (250), solids flow regulator (245), riser (236), dipleg (244), and valves, sensors, and controllers.

FIG. 26 shows a second reactor (200) having a second interior (201) provided with a dense bed zone (BZ-A), a feed zone (BZ-B) above the dense bed zone (BZ-A), and a splash zone (BZ-C) above the feed zone (BZ-B). The splash zone (BZ-C) is proximate to the fluid bed level (L-B) and below the freeboard zone (FB-B). In embodiments, the dense bed zone (BZ-A) corresponds to the lower portion of the dense bed within the second interior (201). In embodiments, the feed zone (BZ-B) is located above the dense bed zone (BZ-A). In embodiments, the splash zone (BZ-C) may be located above the feed zone (BZ-B) and below the second fluid bed level (L-B). The embodiment shown in FIG. 26 depicts the second reactor heat exchanger (HX-B) immersed below the fluid bed level (L-B) of the second reactor (200).

The second reactor heat exchanger (HX-B) comprises: a second reactor heat transfer medium inlet (212) configured to receive a heat transfer medium (210) at a second reactor inlet temperature (T1); and a second reactor heat transfer medium outlet (216) configured to output the heat transfer medium (210), at a higher, second reactor outlet temperature (T2).

A second reactor heat transfer medium supply valve (VB0), configured to accept a signal (XB0) from a controller (CB0) is installed upstream of the second reactor heat transfer medium inlet (212) to control the amount of heat transfer medium (210) supplied to the second reactor heat exchanger (HX-B). The heat transfer medium (210) is supplied via the second reactor heat transfer medium input (3B-IN2) or third reactor heat transfer medium output (3C-OUT2). As depicted in FIG. 17, a portion of the third reactor heat transfer medium (310) is used as the second reactor heat transfer medium (210). Thus, the inlet (212) of the second reactor heat exchanger (HX-B) is fluidly in communication with the outlet (316) of the third reactor heat exchanger (HX-C).

The upstream first reactor (100) is in fluid communication with the second reactor heat transfer medium outlet (216) of the second reactor heat exchanger (HX-B) and is configured to introduce at least a portion of second reactor heat transfer medium (210) into the first reactor (100) via a first reactor reactant input (3A-IN2) or a second reactor heat transfer medium output (3B-OUT2). Therefore, the upstream first reactor (100) is also in fluid communication with the third reactor heat transfer medium outlet (316) of the third reactor heat exchanger (HX-C) and is configured to introduce at least a portion of the third reactor heat transfer medium (310) into the first reactor (100).

The second interior (201) of the second reactor (200) is in fluid communication with the second reactor heat transfer medium outlet (216) of the second reactor heat exchanger (HX-B) and is configured to introduce at least a portion of second reactor heat transfer medium (210) into the second reactor (200). Therefore, the second interior (201) of the second reactor (200) is in fluid communication with the third reactor heat transfer medium outlet (316) of the third reactor heat exchanger (HX-C) and is configured to introduce at least a portion of the third reactor heat transfer medium (310) into the second reactor (200).

FIG. 26 further illustrates a Second Stage Product Gas Generation Control Volume (CV-3B) and Second Stage Product Gas Generation System (3B) showing a first reactor product gas transferred via a second reactor gas input (3B-IN1) entering as a first solids separation device (150) as a first reactor product gas transferred via a first reactor gas output (3A-OUT1). FIG. 26 further illustrates a Second Stage Product Gas Generation Control Volume (CV-3B) and Second Stage Product Gas Generation System (3B) discharging a second reactor product gas via a second reactor gas output (3B-OUT1) as a combined product gas transferred via the third reactor gas input (3C-IN1) to the Third Stage Product Gas Generation System (3C) within the Third Stage Product Gas Generation Control Volume (CV-3C).

The first solids separation device (150) is comprised of: a first separation input (152) in fluid communication with the first reactor product gas output (124); a first separation char output (154) in fluid communication with the second reactor char input (204); and a first separation gas output (156). The second reactor (200) is configured to accept a char (202) through a second reactor char input (204) routed to the second interior (201) via a dipleg (244).

A riser (236) connects the interior (201) of the second reactor (200) with the terminal portion (242) of the conduit that connects the first reactor product gas output (124) with the first separation input (152). The riser (236) is configured to transport particulate heat transfer material (205) from the interior (201) of the second reactor (200) via riser connection (238) to the first separation input (152).

In embodiments, the second reactor particulate heat transfer material (205) is comprised of Geldart Group A or Group B solids in the form of inert material or catalyst or sorbent or engineered particles. The engineered particles may be made of alumina, zirconia, sand, olivine sand, limestone, dolomite, or catalytic materials, any of which may be hollow in form, such as microballoons or microspheres. The preferred second reactor particulate heat transfer material (205) is Geldart Group B alumina microballons. The second reactor particulate heat transfer material (205) enhances mixing, heat and mass transfer, and reaction between the char (202) and the reactant (206A, 206B, 206C) or oxygen-containing gas (218A, 218B, 218C) introduced to the second reactor (200).

A riser conveying fluid (240) is preferably introduced to the riser (236) to assist in uniform flow of particulate heat transfer material (205) from the interior (201) of the second reactor (200) to the first separation input (152).

A solids flow regulator (245) is interposed in between the first separation char output (154) and the second reactor char input (204) and configured as a sealing apparatus to prevent backflow of particulate heat transfer material (205) from the interior (201) of the second reactor (200). The solids flow regulator (245) is comprised of: a solids flow regulator solids input (246) configured to receive char (202) and solids (205) separated from the first separation char output (154) of the first solids separation device (150); a solids flow regulator solids output (247) configured to output char (202) and solids (205) to the second reactor char input (204) via a dipleg (244); a solids flow regulator gas input (248) to accept a solids flow regulator gas (249).

Connection X6 in FIG. 26 shows a second stage gas input (3B-IN4) being used as the riser conveying fluid (240) including carbon dioxide originating from a downstream Secondary Gas Clean-Up System (6000) as a carbon dioxide output (6-OUT2) also as depicted in FIG. 16 and FIG. 17. In embodiments, the solids flow regulator gas (249) is carbon dioxide that originates from a downstream Secondary Gas Clean-Up System (6000) from the carbon dioxide output (6-OUT2) and is transferred from connection X6 to the solids flow regulator gas input (248).

The first separation char output (154) of the first solids separation device (150) is configured to output char (202) and is in fluid communication with the second reactor (200) via a second reactor char input (204). The first separation gas output (156) of the first solids separation device (150) is configured to output a char depleted first reactor product gas (126) via a char depleted first reactor product gas conduit (128).

The second reactor (200) comprises: a second reactor char input (204) to the second feed zone (BZ-B), said second reactor char input (204) being in fluid communication with the first reactor product gas output (124); a second reactor dense bed zone reactant input (208A) configured to introduce a second reactor dense bed zone reactant (206A) to the second dense bed zone (BZ-A); a second reactor feed zone reactant input (208B) configured to introduce a second reactor feed zone reactant (206B) to the second feed zone (BZ-B); a second reactor splash zone reactant input (208C) configured to introduce a second reactor splash zone reactant (206C) to the second splash zone (BZ-C); a second reactor dense bed zone oxygen-containing gas input (220A) configured to introduce a second reactor dense bed zone oxygen-containing gas (218A) to the second dense bed zone (BZ-A); a second reactor feed zone oxygen-containing gas input (220B) configured to introduce a second reactor feed zone oxygen-containing gas (218B) to the second feed zone (BZ-B); a second reactor splash zone oxygen-containing gas input (220C) configured to introduce a second reactor splash zone oxygen-containing gas (218C) to the second splash zone (BZ-C); a second reactor product gas output (224); and, a second reactor heat exchanger (HX-B) in thermal contact with the second interior (201); wherein:

the second reactor heat exchanger (HX-B) is configured to receive a heat transfer medium (210) at a second reactor inlet temperature (T1) and output the heat transfer medium (210), at a higher, second reactor outlet temperature (T2), via a second reactor heat transfer medium outlet (216); and, the second reactor heat transfer medium outlet (216) is configured to be selectively in fluid communication with any combination of the first reactor dense bed zone reactant input (108A), the first reactor feed zone reactant input (108B) and the first reactor splash zone reactant input (108C); and, the second reactor heat transfer medium outlet (216) is configured to be selectively in fluid communication with any combination of the second reactor dense bed zone reactant input (208A), second reactor feed zone reactant input (208B) and the second reactor splash zone reactant input (208C); whereby: at least a portion of the heat transfer medium (210) is capable of being introduced into any combination of: (i) the corresponding second reactor (200) dense bed zone (BZ-A), (ii)

the second reactor (200) feed zone (BZ-B), and (iii) the second reactor (200) splash zone (BZ-C).

Further, FIG. 26 depicts an oxygen-containing gas (218) being introduced to the Second Stage Product Gas Generation Control Volume (CV-3B) as an oxygen-containing gas input (3B-IN3) to be made available to any combination of: (i) the corresponding second reactor (200) dense bed zone (BZ-A), (ii) the second reactor (200) feed zone (BZ-B), (iii) the second reactor (200) splash zone (BZ-C).

FIG. 26 depicts the system (1001) further including: a second reactor dense bed zone reactant input (208A) and second reactor dense bed zone oxygen-containing gas input (220A) in fluid communication with a dense bed zone steam/oxygen connection (BZA0). The dense bed zone steam/oxygen connection (BZA0) is in fluid communication with the dense bed zone steam/oxygen (BZA2) and configured to transport the dense bed zone steam/oxygen (BZA1) to the second reactor (200) dense bed zone (BZ-A). The second reactor (200) dense bed zone steam/oxygen (BZA1) is a mixture of the second reactor dense bed zone reactant (206A) and second reactor dense bed zone oxygen-containing gas (218A).

A second reactor dense bed zone reactant valve (VB1), configured to accept a signal (XB1) from a controller (CB1) is installed upstream of the input (208A) to control the amount of reactant (206A) supplied to the second reactor (200) dense bed zone (BZ-A). A second reactor dense bed zone oxygen-containing gas valve (VB2), configured to accept a signal (XB2) from a controller (CB2) is installed upstream of the input (220A) to control the amount of oxygen-containing gas (218A) supplied to the second reactor (200) dense bed zone (BZ-A).

FIG. 26 depicts the system (1001) further including: a second reactor feed zone reactant input (208B) and second reactor feed zone oxygen-containing gas input (220B) in fluid communication with a feed zone steam/oxygen connection (BZB0). The feed zone steam/oxygen connection (BZB0) is in fluid communication with the feed zone steam/oxygen input (BZB2) and configured to transport the feed zone steam/oxygen (BZB1) to the second reactor (200) feed zone (BZ-B). The second reactor (200) feed zone steam/oxygen (BZB1) is a mixture of the second reactor feed zone reactant (206B) and second reactor feed zone oxygen-containing gas (218B).

A second reactor feed zone reactant valve (VB3), configured to accept a signal (XB3) from a controller (CB3) is installed upstream of the input (208B) to control the amount of reactant (206B) supplied to the second reactor (200) feed zone (BZ-B). A second reactor feed zone oxygen-containing gas valve (VB4), configured to accept a signal (XB4) from a controller (CB4) is installed upstream of the input (220B) to control the amount of oxygen-containing gas (218B) supplied to the second reactor (200) feed zone (BZ-B).

FIG. 26 depicts the system (1001) further including: a second reactor splash zone reactant input (208C) and second reactor splash zone oxygen-containing gas input (220C) in fluid communication with a splash zone steam/oxygen connection (BZC0). The splash zone steam/oxygen connection (BZC0) is in fluid communication with the splash zone steam/oxygen input (BZC2) and configured to transport the splash zone steam/oxygen (BZC1) to the second reactor (200) splash zone (BZ-C). The second reactor (200) splash zone steam/oxygen (BZC1) is a mixture of the second reactor splash zone reactant (206C) and second reactor splash zone oxygen-containing gas (218C).

A second reactor splash zone reactant valve (VB5), configured to accept a signal (XB5) from a controller (CB5) is installed upstream of the input (208C) to control the amount of reactant (206C) supplied to the second reactor (200) splash zone (BZ-C). A second reactor splash zone oxygen-containing gas valve (VB6), configured to accept a signal (XB6) from a controller (CB6) is installed upstream of the input (220C) to control the amount of oxygen-containing gas (218C) supplied to the second reactor (100) splash zone (BZ-C).

An internal cyclone (225) is shown in the freeboard zone (FB-B) of the second reactor (200). A restriction orifice differential pressure sensor (DP-AB) is shown to measure the pressure drop across the restriction orifice (RO-B). A fuel input (264) is shown on the second reactor (200) and is configured to introduce a source of fuel (262) to the interior (201) of the second reactor (200). In embodiments, the fuel (262) may be provided to the second reactor (200) via a fuel input (3B-IN5) transferred from a fuel output (4-OUT2) from a downstream Primary Gas Clean Up System (4000) as depicted in FIG. 25 and FIG. 26. The fuel output (4-OUT2) may include VOC, SVOC, hydrocarbons such as solvents, Fischer Tropsch Products such as naphtha, or carbonaceous materials in the liquid, solid, or slurry form including coal or char.

A second reactor hydrocarbon valve (VB7) is positioned upstream of the fuel input (264) on the second reactor (200), and is configured to accept a signal (XB7) from a controller (CB7) to control the amount of fuel (262) supplied to the second reactor (200).

Char (202) is introduced to the interior (201) of the second reactor (200) for intimate contact with the particulate heat transfer material (205), reactants (206A, 206B, 206C), and oxygen-containing gas (218, 218A, 218B, 218C) to produce a second reactor product gas (222) that is discharged via a second reactor product gas output (224). The second reactor product gas (222) includes second syngas comprising carbon monoxide and hydrogen. It also includes volatiles and other gases.

The second solids separation device (250) is configured to accept a second reactor product gas (222) and output a solids depleted second reactor product gas (226) via a solids depleted second reactor product gas conduit (228). The second solids separation device (250) has a second separation input (252) in fluid communication with the second reactor product gas output (224). The second solids separation device (250) has a second separation solids output (254) in fluid communication with a solids transfer conduit (234) and is configured to output second reactor separated solids (232) such as char or ash. The second separation gas output (256) of the solids separation device (250) is in fluid communication with the char depleted first reactor product gas conduit (128) or the combined reactor product gas conduit (230). A portion (233) of the second reactor separated solids (232) may be transferred to an airborne particulate solid evacuation system (565) as shown in FIG. 17.

FIG. 26 refers to a second reactor feed zone cross-sectional view (XBZ-B) that will be elaborated upon in FIGS. 27, 28, 29, and 30. FIG. 26 also refers to a second reactor splash zone cross-sectional view (XBZ-C) that will be elaborated upon in FIG. 31.

A combined product gas first quality sensor (BQ1) is installed on the combined reactor product gas conduit (230) to measure the composition of the combined char depleted first reactor product gas (126) and solids depleted second reactor product gas (226) transferred to the third reactor (300). Specifically, the combined product gas first quality sensor (BQ1) is configured to measure the content of CO, H2, and CO2 within the combined reactor product gas conduit (230). VOC, SVOC, H2S, COS may also me measured by the combined product gas first quality sensor (BQ1). The signal (XBQ1) from the combined product gas first quality sensor (BQ1) is outputted to the to the computer (COMP). The combined product gas first quality sensor (BQ1) may also provide an analysis of wide range of organic and inorganic species, wherein its analysis is unaffected by concentration fluctuations, and where the analysis is unaffected by interferences. The ideal instrument is a combined GC and FTIR Gas Analyzer that is fast, very sensitive and is a mobile apparatus that can deal with process environment. The unique spectral analysis methodology of a combined GC and FTIR Gas Analyzer solves interference challenges in real time using unique approach to background spectra. It is also extremely sensitive, stable, and fast analysis of thousands of organic and inorganic species.

The following signals are configured to be inputs or outputs from the computer (COMP): combined product gas first quality sensor signal (XBQ1); second reactor heat transfer medium supply valve signal (XB0); second reactor dense bed zone reactant valve signal (XB1); second reactor dense bed zone oxygen-containing gas valve signal (XB2); second reactor feed zone reactant valve signal (XB3); second reactor feed zone oxygen-containing gas valve signal (XB4); second reactor splash zone reactant valve signal (XB5); second reactor splash zone oxygen-containing gas valve signal (XB6); and second reactor hydrocarbon valve signal (XB7).

FIG. 27:

FIG. 27 shows a non-limiting embodiment of a second reactor feed zone cross-sectional view (XBZ-B) of the embodiment in FIG. 26, including: one first solids separation device (150); four second reactor first char inputs (204A, 204B, 204C, 204D); four feed zone steam/oxygen inputs (BZB2, BZB3, BZB4, BZB5); and, where the combined reactor product gas conduit (230) is configured to blend the first reactor product gas (126) with the second reactor product gas (226). FIG. 27 depicts four separate second reactor char inputs (204A, 204B, 204C, 204D) for transferring four separate streams of char (202A, 202B, 202C, 202D) to the feed zone (BZ-B) of the second reactor (200). The four separate streams of char (202A, 202B, 202C, 202D) may be reacted with the four feed zone steam/oxygen inputs (BZB2, BZB3, BZB4, BZB5) to generate a second reactor product gas (222). The second reactor product gas (222) may in turn be routed to the inlet (252) of a second solids separation device (250). The second solids separation device (250) is configured to separate solids (232) from the product gas (222) to result in a solids depleted second reactor product gas (226). The solids depleted second reactor product gas (226) is shown to be routed to the combined reactor product gas conduit (230) via a conduit (228). The first reactor product gas (126) may be combined with the second reactor product gas (226) in a combined reactor product gas conduit (230).

FIG. 28:

FIG. 28 shows a non-limiting embodiment of a second reactor feed zone cross-sectional view (XBZ-B) of the embodiment in FIG. 26 where the first reactor product gas (126) is not combined with the second reactor product gas (226).

FIG. 29:

FIG. 29 shows a non-limiting embodiment of a second reactor feed zone cross-sectional view (XBZ-B) of the embodiment in FIG. 26, including: two first solids separation devices (150A1, 150A2); two solids flow regulators (245A, 245B); four second reactor first char inputs (204A, 204B, 204C, 204D); four feed zone steam/oxygen inputs (BZB2, BZB3, BZB4, BZB5); and, where the combined reactor product gas conduit (230) is configured to blend the first reactor product gas (126A1, 126A2) with the second reactor product gas (226).

FIG. 29 elaborates upon the embodiment where each of two first solids separation devices (150A1, 150A2) accept a portion of the first reactor product gas (122). One first solids separation device (150A) accepts a portion of the first reactor product gas (122A1) via a first separation input (152A1). Another first solids separation device (150B) accepts another portion of the first reactor product gas (122A2) via a first separation input (152A2). Each first solids separation device has a dipleg (244A, 244B) that is connected to a respective solids flow regulator (245A, 245B).

One first solids separation device (150A1) accepts a portion of the first reactor product gas (122A1) removes char (202A, 202D) therefrom for transfer to the second reactor (200) and outputs a char depleted first reactor product gas (126A1) via a char depleted first reactor product gas conduit (128A1). Another first solids separation device (150A2) accepts a portion of the first reactor product gas (122A2) removes char (202B, 202C) therefrom for transfer to the second reactor (200) and outputs a char depleted first reactor product gas (126A2) via a char depleted first reactor product gas conduit (128A2). Each char depleted first reactor product gas conduit (128A1, 128A2) may be combined into one common conduit (128).

The first separation char output (154A1) on one first solids separation device (150A1) is in fluid communication with the first solids flow regulator solids input (246A) of the first solids flow regulator (245A) via a dipleg (244A). The first separation char output (154A2) on the other first solids separation device (150A2) is in fluid communication with the second solids flow regulator solids input (246B) of the second solids flow regulator (245B) via a dipleg (244B).

One solids slow regulator (245A) has a first solids flow regulator solids output (247A) and a second solids flow regulator solids output (247B). The first solids flow regulator solids output (247A) is in fluid communication with the second reactor fourth char input (204D) and is configured to transfer char (202D) to the second reactor (200). The second solids flow regulator solids output (247B) is in fluid communication with the second reactor first char input (204A) and is configured to transfer char (202A) to the second reactor (200).

Another solids slow regulator (245B) has a third solids flow regulator solids output (247C) and a fourth solids flow regulator solids output (247D). The third solids flow regulator solids output (247C) is in fluid communication with the second reactor third char input (204C) and is configured to transfer char (202C) to the second reactor (200). The fourth solids flow regulator solids output (247D) is in fluid communication with the second reactor second char input (204B) and is configured to transfer char (202B) to the second reactor (200).

FIG. 30:

FIG. 30 shows a non-limiting embodiment of a second reactor feed zone cross-sectional view (XBZ-B) of the embodiment in FIG. 26 where the first reactor product gas (126A1, 126A2) is not combined with the second reactor product gas (226).

FIG. 31:

FIG. 31 shows a non-limiting embodiment of a second reactor splash zone cross-sectional view (XBZ-C) of the embodiment in FIG. 26, including four splash zone steam/ oxygen inputs (BZC2, BZC3, BZC4, BZC5) configured to accept a source of splash zone steam/oxygen (BZC1).
FIG. 32:

FIG. 32 shows a detailed view of one non-limiting embodiment of a Third Stage Product Gas Generation Control Volume (CV-3C) and Third Stage Product Gas Generation System (3C) of a three-stage energy-integrated product gas generation system (1001) showing a third reactor (300) equipped with a third interior (301), and also showing a combustion zone (CZ-A), reaction zone (CZ-B), cooling zone (CZ-C), quench zone (CZ-E), steam drum (350), and valves, sensors, and controllers.

FIG. 23 displays a Third Stage Product Gas Generation System (3C) contained within a Third Stage Product Gas Generation Control Volume (CV-3C) and configured to accept second reactor product from the second reactor gas output (3B-OUT1) from a Second Stage Product Gas Generation System (3B). The third reactor (300) within the Third Stage Product Gas Generation System (3C) is shown to accept the second reactor product gas from the second reactor gas output (3B-OUT1) as a combined product gas transferred via the third reactor gas input (3C-IN1).

In some embodiments, as shown in FIG. 32, the third reactor (300) may be a cylindrical, down-flow, non-catalytic, refractory-lined, steel pressure vessel. In embodiments, the third reactor (300) may be rectangular. Within the interior (301) of the third reactor (300) are several distinct zones that are disposed one after the other in the axial direction of the interior (301). Four zones exist within the interior (301) of the third reactor (300): (1) combustion zone (CZ-A), (2) reaction zone (CZ-B), (3) cooling zone (CZ-C), (4) quench zone (CZ-D).

Combustion Zone

The combustion zone (CZ-A) combusts a first hydrocarbon stream (322) with a third reactor oxygen-containing gas (318) to generate a combustion zone output (CZ-AP) or combustion stream. In embodiments, the oxygen-containing gas (318) is introduced to the combustion zone (CZ-A) in superstoichiometric amounts in proportion and relative to the first hydrocarbon stream (322) so as to substantially, completely combust the first hydrocarbon stream (322) to generate CO2 and heat along with an unreacted amount of oxygen-containing gas (318). In embodiments, a superstoichiometric amount of oxygen is provided to the combustion zone (CZ-A) so that when all of the hydrocarbon stream (322) is burned, there is still excess oxygen-containing gas (318) left over.

The combustion zone (CZ-A) accepts a third reactor oxygen-containing gas (318) through a third reactor oxygen-containing gas input (320) or an oxygen-containing gas input (3C-IN3). The combustion zone (CZ-A) also accepts a first hydrocarbon stream (322) through a first hydrocarbon stream input (324) or a first hydrocarbon input (3C-IN4). In embodiments, the first hydrocarbon input (3C-IN4) to the Third Stage Product Gas Generation System (3C) may be a first synthesis hydrocarbon output (7-OUT2) such as Fischer Tropsch tail gas transferred from a downstream Synthesis System (7000). In other embodiments, the first hydrocarbon stream (322) may be natural gas, or naphtha, or off-gas from a downstream Upgrading System (8000). The first hydrocarbon stream (322), in some instances, may be product gas, or even landfill gas including a complex mix of different gases created by the action of microorganisms within a landfill.

A first hydrocarbon valve (VC1) may be configured to regulate the flow of the first hydrocarbon stream (322) to the first hydrocarbon stream input (324). The first hydrocarbon valve (VC1) has a controller (CC1) configured to input or output a signal (XC1). A third reactor oxygen-containing gas valve (VC2) may be configured to regulate the flow of the third reactor oxygen-containing gas (318) through the third reactor oxygen-containing gas input (320). The third reactor oxygen-containing gas valve (VC2) has a controller (CC2) configured to input or output a signal (XC2).

A second hydrocarbon valve (VC3) may be configured to regulate the flow of the second hydrocarbon stream (326) to the second hydrocarbon stream input (328). The second hydrocarbon valve (VC3) has a controller (CC3) configured to input or output a signal (XC3). A third hydrocarbon valve (VC4) may be configured to regulate the flow of the third hydrocarbon stream (330) to the third hydrocarbon stream input (332). The third hydrocarbon valve (VC4) has a controller (CC4) configured to input or output a signal (XC4). A third reactor heat transfer medium valve (VC5) may be configured to regulate the flow of the third reactor heat transfer medium (310) to the steam drum (350). The third reactor heat transfer medium valve (VC5) has a controller (CC5) configured to input or output a signal (XC5).

An oxygen-containing gas (318) is provided to the third reactor (300) so that the hydrocarbon (322) is reacted at an elevated reaction temperature sufficient to convert the hydrocarbon (322) substantially completely into carbon dioxide. Therefore, a combustion zone output (CZ-AP) includes carbon dioxide, heat, and left over oxygen-containing gas (318), and is discharged from the combustion zone (CZ-A) to the reaction zone (CZ-B) of the third reactor (300). A sufficient oxygen-containing gas (318) is provided to the third reactor (300) so that excess oxygen-containing gas (318) remains unreacted and exits the burner (346) and thus is also present in the combustion stream discharged from the combustion zone (CZ-A).

In embodiments, an annulus type burner may be employed to react the first hydrocarbon stream (322) with the third reactor oxygen-containing gas (318) through the thermochemical process of combustion. In embodiments, the burner (346) is a multi-orifice, co-annular, burner provided with an arrangement of several passages coaxial with the longitudinal axis of the burner. Multi-orifice burners comprising arrangements of annular concentric channels for reacting an oxygen-containing gas (318) with a stream of hydrocarbons (322) may, in some instances, have a reduced area to permit a high velocity stream to take place and result in very rapid and complete reaction of the combustion stream (CZ-A) with the combined product gas (302) introduced to the third reactor (300) to form a reaction stream. The design of the burner (346) is not particularly relevant. Various types of burners may be used. Preferably, a burner is selected that is configured to react a combustible hydrocarbon stream (322) with a stream of oxygen-containing gas (318). The burner may be equipped with an ignitor.

In embodiments, the burner (346) is that of an annulus type. In embodiments, the burner (346) may be of the type configured to accept a hydrocarbon stream (322) and oxygen-containing gas stream (318) through concentric ports, wherein the oxygen-containing gas (318) is injected into an annular port, and the hydrocarbon stream (322) is injected to the central port. The burner (346) ensures rapid and intimate mixing and combustion of the hydrocarbon (322) with the oxygen-containing gas (318). The hydrocarbon stream (322) and oxygen-containing gas (318) are introduced under pressure and combustion of the hydrocarbon (322) is completed in the burner (346) and terminates at the burner nozzle (347). In embodiments, the burner is constructed such that the reaction between the hydrocarbon (322) and the oxygen-containing gas (318) takes place entirely outside the burner (346) and only at the burner nozzle (347) so as to provide protection of the burner (346) from overheating and from direct oxidation. In embodiments, the burner (346) or the burner nozzle (347) is equipped with a cooling water circuit (not shown).

In embodiments, the burner nozzle (347) may be defined by a restriction constituting a reduction in area to provide an increase in velocity of the combustion stream (CZ-AP) exiting the burner nozzle (347). The restriction may even be in some instances a baffle or an impingement plate on which the flame of the combustion stream is stabilized. The burner nozzle (347) may have a restricting or constricting throat zone, or orifice to accelerate velocity of the combustion stream (CZ-AP) in the transition from the combustion zone (CZ-A) to the reaction zone (CZ-B). A restriction, orifice, baffle, or impingement surface is advantageous to shield the combustion zone (CZ-A) from pressure fluctuations of the reaction zone (CZ-B) to mediate operational difficulties such as burner oscillation, flash-back, detonation, and blow-out.

In some embodiments, combustion stream (CZ-AP) exiting the burner nozzle (347) may be transferred at velocities within the range of 200 feet per minute (ft/m) to the speed of sound under the existing conditions. But advantageously the combustion stream (CZ-AP) that is discharged from the combustion zone (CZ-A), via the burner nozzle (347), is at a velocity between 50 and 300 feet per second (ft/s) and typically less than 200 ft/s.

The combined product gas (302) must not be allowed to remain at high temperatures for more than a fraction of a second, or more than a few seconds, the critical reaction period limits being about 0.0001 second to about 5 seconds. Normally it is advantageous to maintain reaction time between the combined product gas (302) and combustion stream (CZ-AP) of 0.1 to 5.0 seconds to sufficiently completely partially oxidize SVOC, VOC, and char into additional hydrogen and carbon monoxide. Preferably the residence time of the combined product gas (302) and combustion stream (CZ-AP) in the reaction zone is about 3 seconds.

The combustion zone output (CZ-AP) is discharged from the combustion zone (CZ-A) to the reaction zone (CZ-B). The combustion stream is comprised of an intensely hot mixture of carbon dioxide and excess oxygen-containing gas. The heat generated between the combustion of the hydrocarbon (322) with the oxygen-containing gas (318) in turn elevates the temperature of the excess unreacted oxygen-containing gas (318) contained within the combustion zone output (CZ-AP) to a temperature up to 1,500° C. (2,732° F.). It is preferred to operate the combustion zone (CZ-A) at about 1,300° C. (2,372° F.). In embodiments, the combustion stream (CZ-AP) exiting the combustion zone (CZ-A) and entering the reaction zone (CZ-B) operates at about temperature can range from about 1,100° C. (2,0172° F.) to 1,600° C. (2,912° F.). In embodiments, a baffle or impingement plate might be installed to shield the combustion zone (CZ-A) from the reaction zone (CZ-B).

Combustion occurs in the combustion zone (CZ-A) to generate CO2, H2O, and heat. Heat generated in the combustion zone (CZ-A) elevates the temperature of the super-stoichiometric oxygen-containing gas (318) which is then transferred to the reaction zone (CZ-B) as an intensely hot combustion stream (CZ-AP).

In some embodiments, the burner (346) is a Helmholtz pulse combustion resonator. An oxygen-containing gas (318) may be introduced into the outer annular region of the burner (346) and a hydrocarbon (322) may be introduced into the central section of the burner (346). Thus, the burner (346) may serve to act as an aerodynamic valve, or diode, such that self-aspiration of the oxygen-containing gas (318) is effected in response to an oscillating pressure in the combustion zone (CZ-A). A burner (346) may operate as a pulse combustor, and typically operates in the following manner. A hydrocarbon (322) enters the combustion zone (CZ-A). An oxygen-containing gas (318) enters the combustion zone (CZ-A). An ignition or spark source (not shown) detonates the explosive mixture during start-up. A sudden increase in volume, triggered by the rapid increase in temperature and evolution of combustion stream (CZ-AP), pressurizes combustion zone (CZ-A). As the hot combustion stream (CZ-AP) expands, the burner (346) and nozzle (347) form of a fluidic diode, permit preferential flow in the direction of the reaction zone (CZ-B). The gaseous combustion stream (CZ-AP), exiting combustion zone (CZ-A), possesses significant momentum. A vacuum is created in combustion zone (CZ-A) due to the inertia of the combustion stream (CZ-A) passing through the burner nozzle (347), and permits only a small fraction of the combustion stream (CZ-AP) to return to combustion zone (CZ-A), with the balance of the combustion stream (CZ-AP) exiting through the nozzle (347). Because the combustion zone (CZ-A) pressure is then lower than the supply pressure of both the oxygen-containing gas (318) and the hydrocarbon (322), the oxygen-containing gas (318) and the hydrocarbon (322) mixtures are drawn into combustion zone (CZ-A) where auto-ignition takes place. Again, the burner (346) and nozzle (347) constrains reverse flow, and the cycle begins anew. Once the first cycle is initiated, operation is thereafter self-sustaining or self-aspirating.

A preferred pulse combustor burner (346) used herein, and as noted above, is based on a Helmholtz configuration with an aerodynamic valve. The pressure fluctuations, which are combustion-induced in the Helmholtz resonator-shaped combustion burner (346), coupled with the fluidic diodicity of the aerodynamic valve burner (346) and nozzle (347), cause a biased flow of the combustion stream (CZ-AP) from the combustion zone (CZ-A), through the nozzle (347) and into the reaction zone (CZ-B). This results in the oxygen-containing gas (318) being self-aspirated by the combustion zone (CZ-A) and for an average pressure boost to develop in the combustion zone (CZ-A) to expel the products of combustion at a high average flow velocity (typically over 300 ft/s) into and through the nozzle (347).

The production of an intense acoustic wave is an inherent characteristic of pulse combustion. Sound intensity adjacent to the wall of combustion zone (CZ-A) is normally in the range of 110-190 dB. The range may be altered depending on the desired acoustic field frequency to accommodate the specific application undertaken by the pulse combustor.

Reaction Zone

The reaction zone (CZ-B) is configured to react a combined product gas (302) generated in upstream reactors (100, 200) with the hot excess oxygen-containing gas contained in the combustion stream (CZ-AP) to generate additional hydrogen and carbon monoxide. The reaction zone (CZ-B) of the third reactor (300) accepts a combined product gas (302) through a combined product gas input (304) transferred through the third reactor gas input (3C-IN1). The combined product gas (302) enters the reaction zone (CZ-B) and is introduced from the second reactor gas output (3B-OUT1) of the Second Stage Product Gas Generation System (3B). The hot combustion stream (CZ-AP) is transferred from the combustion zone (CZ-A) to the reaction zone (CZ-B) through the burner nozzle (347) at preferably a high velocity to realize a stable flame and enhance mixing and reaction between the combustion stream (CZ-AP) and the combined product gas (302).

Mixing and reaction of the combustion stream (CZ-AP) with the combined product gas (302) entering the third reactor (300) must be thorough and nearly instantaneous. Sudden and furious mixing of at least a portion of the first reactor product gas (122), or the combined product gas (302), with the combustion stream (CZ-AP) takes place in the reaction zone (CZ-B) of the third reactor (300). As a result, a reaction zone output (CZ-BP) or a reaction stream, is discharged from the reaction zone (CZ-B) to the cooling zone (CZ-C).

The reaction zone (CZ-B) may also accept a second hydrocarbon stream (326) through a second hydrocarbon stream input (328) or a second hydrocarbon input (3C-IN5). The second hydrocarbon input (3C-IN5) to the Third Stage Product Gas Generation System (3C) may in some instances be naphtha transferred via a first hydrocarbon output (8-OUT2) from a downstream Upgrading System (8000). The reaction zone (CZ-B) may also accept a third hydrocarbon stream (330) through a third hydrocarbon stream input (332) or a third hydrocarbon input (3C-IN6). The third hydrocarbon input (3C-IN6) to the Third Stage Product Gas Generation System (3C) may in some instances be an off-gas transferred via a second hydrocarbon output (8-OUT3) from a downstream Upgrading System (8000). The second hydrocarbon stream input (328) and the third hydrocarbon stream input (332) may be fluidly in communication with the reaction zone (CZ-B) within the interior (301) of the third reactor (300) via a combined hydrocarbon connection (CZC0), combined hydrocarbon transfer line (CZC1) and a combined hydrocarbon input (CZC2).

The hot unreacted oxygen-containing gas contained within the combustion stream (CZ-AP) reacts with the combined product gas (302) from the first reactor (100) and second reactor (200). The hot unreacted oxygen-containing gas contained within the combustion stream (CZ-AP) optionally reacts with a second hydrocarbon stream (326) and/or the third hydrocarbon stream (330). Intense mixing and exothermic reaction occurs in the reaction zone (CZ-B) between the combustion stream (CZ-AP) and the combined product gas (302) and hydrocarbons (326, 330). In some instances, near instantaneous blending of the combustion stream (CZ-AP) with the combined product gas (302) and/or hydrocarbons (326, 330) is effectuated. Thus, the reaction zone (CZ-B) also permits the mixing of the combined product gas (302) and hydrocarbons (326, 330) with the intensely hot combustion stream (CZ-AP) to take place.

The reaction zone (CZ-B) permits sufficient residence time for substantially complete reaction of the SVOC, VOC and char contained within at least a portion of the first reactor product gas (122) to take place with the unreacted hot oxygen-containing gas carried through from the combustion stream (CZ-AP). The reaction zone (CZ-B) permits sufficient residence time for substantially complete reaction of the SVOC, VOC and char contained within the combined product gas (302) to take place with the unreacted hot oxygen-containing gas carried through from the combustion stream (CZ-AP). The reaction zone (CZ-B) also permits sufficient residence time for substantially complete partial oxidation reaction of the carbon and hydrogen contained within the hydrocarbon stream (326, 330) for conversion into product gas.

In embodiments, additional hydrogen and carbon monoxide is generated from the exothermic partial oxidation reaction between the SVOC, VOC, and char contained within the combined product gas (302) and the hot excess oxygen-containing gas of the combustion stream (CZ-AP). In embodiments, additional hydrogen and carbon monoxide is also generated from exothermic partial oxidation reaction between hydrocarbon streams (326, 330) with the hot excess oxygen-containing gas of the combustion stream (CZ-AP). In embodiments, more hydrogen and carbon monoxide exits the reaction zone (CZ-B) than what enters the reaction zone (CZ-B). The reaction stream (CZ-BP) is transferred from the reaction zone (CZ-B) to the cooling zone (CZ-C). In embodiments, a baffle, or impingement plate, might be installed to shield the reaction zone (CZ-B) from the cooling zone (CZ-C).

Cooling Zone

The cooling zone (CZ-C) is configured to transfer heat from the reaction stream (CZ-BP) to a heat transfer medium (310) which can then in turn be used as a reactant (106, 206) in an upstream reactor (100, 200). The cooling zone (CZ-C) is configured to accept a reaction stream (CZ-BP) from the reaction zone (CZ-B) and remove heat therefrom to in turn generate a cooling zone output (CZ-CP) or cooled stream. The cooled stream (CZ-CP) leaving the cooling zone (CZ-C) has a lower, reduced temperature relative to that of the reaction stream (CZ-BP) that enters the cooling zone (CZ-C) from the reaction zone (CZ-B).

Removal of heat from the reaction stream (CZ-BP) may be accomplished by use of a third reactor heat exchanger (HX-C) in thermal contact with the interior (301) of the third reactor (300). More specifically, the third reactor heat exchanger (HX-C), in thermal contact with the cooling zone (CZ-C) of the interior (301) of the third reactor (300), indirectly transfers heat from the reaction stream (CZ-BP) to a third reactor heat transfer medium (310). The third reactor heat exchanger (HX-C) may be any type of heat transfer device known in the art, and is equipped with a heat transfer medium inlet (312) and a heat transfer medium outlet (316). FIG. 32 depicts a heat transfer medium (310) being made available and introduced to the heat transfer medium inlet (312) on the lower portion of the cooling zone (CZ-C). FIG. 32 also depicts a heat transfer medium (310) being discharged from the third reactor heat exchanger (HX-C) via an outlet (316) on the upper portion of the cooling zone (CZ-C).

A third reactor heat transfer medium (310) or a third reactor heat exchanger heat transfer medium input (3C-IN2) is made available to the Third Stage Product Gas Generation System (3C). Specifically, third reactor heat transfer medium (310) is made available to a steam drum (350) via a steam drum heat transfer medium supply inlet (352). A third reactor heat transfer medium valve (VC5), with a controller (CC5) and signal (XC5) is provided to regulate the flow of the heat transfer medium to the steam drum (350). The heat transfer medium depicted in FIG. 32 is water and liquid phase water is provided to the third reactor heat exchanger (HX-C) from the steam drum (350) at a third reactor heat transfer medium inlet temperature (T0). The steam drum (350) has third reactor steam drum pressure (P-C1). In embodiments, the steam drum (350) contains liquid and vapor phase water. A portion of the liquid phase water is transferred from the steam drum (350) via an outlet (356) and a heat transfer medium conduit (362) to the third reactor heat transfer medium inlet (312).

The steam drum heat transfer medium outlet (356) of the steam drum (350) are in fluid communication with the third reactor heat transfer medium inlet (312) via a heat transfer medium conduit (362). The steam drum heat transfer medium reactor inlet (354) of the steam drum (350) is in fluid communication with the third reactor heat transfer medium outlet (316) via a heat transfer medium conduit (364). The steam drum heat transfer medium outlet (358) of the steam drum (350) is in fluid communication with the second reactor heat exchanger (HX-B). More specifically, the steam drum heat transfer medium outlet (358) of the steam drum (350) is in fluid communication with the second reactor heat transfer medium inlet (212) via a heat transfer medium conduit (360). Thus, the third reactor heat transfer medium outlet (316) of the third reactor heat exchanger (HX-C) is in fluid communication with the second reactor heat transfer medium inlet (212) of the second reactor heat exchanger (HX-B) via a steam drum (350) and heat transfer conduits (360, 364).

FIG. 32 depicts a heat transfer medium (310) being introduced to the inlet (312) of the third reactor heat exchanger (HX-C) via a steam drum. A portion of the liquid phase heat transfer medium contained within the third reactor heat exchanger (HX-C) accepts heat from the reaction stream (CZ-BP) flowing down through cooling zone (CZ-C) within the interior (301) of the third reactor (300). At least a portion of the heat transferred from the reaction stream (CZ-BP) to the heat transfer medium (310) generates steam which is then transferred back to the steam drum (350). The vapor phase heat transfer medium (310) that exits the outlet (316) of the third reactor heat exchanger (HX-C), and transferred to the steam drum (350) is then routed to the inlet (212) of the second reactor heat exchanger via a heat transfer medium conduit (360) or a second reactor heat transfer medium input (3B-IN2) or a third reactor heat transfer medium output (3C-OUT2). Thus, a portion of the third reactor heat transfer medium (310) accepts heat from a portion of the heat generated in the third reactor (300) and is ultimately used as (i) heat transfer medium (210) in the second reactor heat exchanger, (ii) a reactant (106A, 106B, 106C) in the first reactor (100), and/or (iii) a reactant (206A, 206B, 206C) in the second reactor (200).

The Third Stage Product Gas Generation System (3C) outputs a third reactor heat transfer medium output (3C-OUT2) to the Second Stage Product Gas Generation System (3B) as a second reactor heat transfer medium input (3B-IN2). A cooling zone output (CZ-CP) or cooled stream is discharged from the cooling zone (CZ-C) and is introduced to the quench zone (CZ-D). The cooled stream (CZ-CP) leaving the cooling zone (CZ-C) is lesser in temperature than the reaction stream (CZ-BP) entering the cooling zone (CZ-C).

Quench Zone

The quench zone (CZ-D) is configured to accept a cooling zone output (CZ-CP) or cooled stream, along with a source of third reactor quench water (342), and output a quench zone output (CZ-DP) or quenched stream. A source of quench water (342) is introduced to the quench zone (CZ-D) within the interior (301) of the third reactor (300). The quench water (342) is made available to the Third Stage Product Gas Generation System (3C) via a quench water input (3C-IN7).

In embodiments, the quenched stream (CZ-DP) may be synonymous with the third reactor product gas (334) that is discharged from the third reactor (300) via a third reactor product gas output (336). The quenched third reactor product gas (334) is evacuated from the Third Stage Product Gas Generation System (3C) via third reactor output (3C-OUT1) and is made available to a downstream Primary Gas Clean Up System (4000) via a product gas transferred via the primary gas clean-up input (4-IN1). The quench zone (CZ-D) is also configured to output a third reactor slag (338) via a third reactor slag output (340). The slag (338) may be evacuated from the Third Stage Product Gas Generation System (3C) via a solids output (3C-OUT3).

The quench zone (CZ-D) is optional in the event of the need to maximize the heat recovery in a downstream Primary Gas Clean Up Heat Exchanger (HX-4) located in a downstream Primary Gas Clean Up Control Volume (CV-4000). In other embodiments, where the quench stream (CZ-DP) is optional and omitted, the cooled stream (CZ-CP) may be synonymous with the third reactor product gas (334) that is discharged from the third reactor (300) via a third reactor product gas output (336). In embodiments, the product gas, or syngas, that passes through the primary gas clean-up is referred to as a source of conditioned syngas. In embodiments, the product gas, or syngas, that passes through the secondary gas clean-up is referred to as a source of conditioned syngas.

Thus, in turn, FIG. 32 depicts a system and process for the partial oxidation of SVOC and VOC contained within a product gas stream, comprising:
(a) combusting a hydrocarbon stream with oxygen to form a combustion stream comprised of CO2, H2O, and oxygen;
(b) reacting VOC and SVOC within the combustion stream to form a reaction stream;
(c) cooling the reaction stream with a heat transfer medium;
(d) superheating the heat transfer medium in a second reactor heat exchanger;
(e) introducing the superheated heat transfer medium to a first reactor as a reactant; and,
(f) introducing the superheated heat transfer medium to a second reactor as a reactant.

Further, FIG. 32 depicts a:
(a) third reactor (300) having a third interior (301) and comprising: a combustion zone (CZ-A) configured to accept both a third reactor oxygen-containing gas (318) through a third reactor oxygen-containing gas input (320) and a first hydrocarbon stream (322) through a first hydrocarbon stream input (324) and output a combustion zone output (CZ-AP) through a burner (346);
(b) a reaction zone (CZ-C) configured to accept both the product gas created by the first reactor (100) and product gas created by the second reactor (200) through a product gas input (304); and react with the combustion zone output (CZ-AP) to output a reaction zone output (CZ-BP);
(c) a cooling zone (CZ-C) configured to accept a third reactor heat transfer medium (310) through third reactor heat transfer medium inlet (312); and transfer thermal energy from the reaction zone output (CZ-BP) to the third reactor heat transfer medium (310) for output via a third reactor heat transfer medium outlet (316) while also outputting a cooling zone output (CZ-CP); and,
(e) a quench zone (CZ-D) configured to accept a third reactor quench water (342) through a third reactor quench water input (344) and release third reactor product gas (334) through a third reactor product gas output (336).

wherein the combustion zone (CZ-A) is configured to combust at least a portion of the first hydrocarbon stream (322) to generate a combustion zone output (CZ-AP) comprised of a heated stream of oxygen-containing gas, CO2, and H2O; and, wherein the reaction zone (CZ-B) is configured to react the combustion zone output (CZ-AP) with CH4, unreacted carbon within elutriated char, or aromatic hydrocarbons contained within product gas created by both the first reactor (100) and the second reactor (200) to generate additional carbon monoxide (CO) and hydrogen (H2).

In embodiments, the first reactor (300) is synonymous with the term steam reformer (300) since the first reactor steam reforms carbonaceous material in the presence of steam and optionally one or more other gases, e.g., air, carbon dioxide, oxygen, to form a first reactor product gas (122) including syngas comprising carbon monoxide, hydrogen, char, volatiles and one or more other gases.

In embodiments, the second reactor (200) is synonymous with the expression carbon trim cell (200), since the second reactor accepts char from the first reactor, and reduces (i.e., "trims") carbon content by converting it into a second reactor product gas (222), also including syngas comprising carbon monoxide, hydrogen, volatiles and one or more other gases.

In embodiments, the third reactor (300) is synonymous with the term hydrocarbon reformer (300) since the third reactor reforms hydrocarbons contained within product gases created by both the first reactor (100) and the second reactor (200) into additional carbon monoxide (CO) and hydrogen (H2). This results in an improved syngas having a higher concentration of carbon monoxide and hydrogen, relative to that found in both the first reactor product gas (122) and the second reactor product gas (222).

While a preferred embodiment includes first, second and third reactors, it is nonetheless possible to have only the first and third reactors, with the char created by the first reactor not being converted into the second reactor product gas (222), and only the first reactor product gas (112) being input into the third reactor.

The first reactor product gas (122) has a first H2 to CO ratio and a first CO to CO2 ratio. The second reactor product gas (222) has a second H2 to CO ratio and a second CO to CO2 ratio. The third reactor product gas (334) has a third H2 to CO ratio and a third CO to CO2 ratio.

In embodiments, the first H2 to CO ratio is greater than the second H2 to CO ratio. In embodiments, the second CO to CO2 ratio is greater than the first CO to CO2 ratio. In embodiments, the third H2 to CO ratio is lower than both the first H2 to CO ratio and the second H2 to CO ratio. In embodiments, the third CO to CO2 ratio is greater than both the first CO to CO2 ratio and the second CO to CO2 ratio.

A third reactor product gas first quality sensor (CQ1) is installed on the discharge of the third reactor product gas output (336) to measure the composition of the third reactor product gas (334) transferred to the Primary Gas Clean Up System (4000). Specifically, the third reactor product gas first quality sensor (CQ1) is configured to measure the content of O2, CO, H2, CO2, and CH4 within the third reactor product gas (334). VOC, SVOC, H2S, COS may also me measured by the third reactor product gas first quality sensor (CQ1). The signal (XCQ1) from the third reactor product gas first quality sensor (CQ1) is outputted to the to the computer (COMP). The third reactor product gas first quality sensor (CQ1) may also provide an analysis of wide range of organic and inorganic species, wherein its analysis is unaffected by concentration fluctuations, and where the analysis is unaffected by interferences. The ideal instrument is a combined GC and FTIR Gas Analyzer that is fast, very sensitive and is a mobile apparatus that can deal with process environment. The unique spectral analysis methodology of a combined GC and FTIR Gas Analyzer solves interference challenges in real time using unique approach to background spectra. It is also extremely sensitive, stable, and fast analysis of thousands of organic and inorganic species.

The following signals are configured to be inputs or outputs from the computer (COMP): third reactor product gas first quality sensor signal (XCQ1); first hydrocarbon valve signal (XC1); third reactor oxygen-containing gas valve signal (XC2); second hydrocarbon valve signal (XC3); third hydrocarbon valve signal (XC4); and, third reactor heat transfer medium valve signal (XC5).

FIG. 33:

FIG. 33 is to be used in conjunction with FIG. 14 and depicts carbonaceous material processing system including a first splitter (2B1), a first feed zone delivery system (2050A), a second feed zone delivery system (2050B), first reactor (100), first solids separation device (150), dipleg (244), solids flow regulator (245), second reactor (200), particulate classification chamber (B1), second solids separation device (250), second reactor heat exchanger (HX-B), third reactor (300), third reactor heat exchanger (HX-C), steam drum (350), Primary Gas Clean Up Heat Exchanger (HX-4), venturi scrubber (380), scrubber (384), separator (388), separator (398), and a heat exchanger (399).

The a three-stage product gas generation system (1001) shown in FIG. 33 comprises a first splitter (2B1) as seen in FIG. 14 in fluid communication with a first feed zone delivery system (2050A) and a second feed zone delivery system (2050B).

In embodiments, the system (1000) of FIG. 33 includes: a first feed zone delivery system (2050A) as seen in FIG. 14 wherein the first feed zone delivery system (2050A) includes at least a Gas Mixing (2G) subsystem and a Transport (2H) subsystem of FIG. 2E; a second feed zone delivery system (2050B) as seen in FIG. 14 wherein the second feed zone delivery system (2050B) includes at least Gas Mixing (2G) subsystem and a Transport (2H) subsystem of FIG. 2E; a first reactor (100) having a first interior (101) and comprising: a first carbonaceous material and gas input (104A) provided by a first feed zone delivery system (2050A) and configured to input a first carbonaceous material and gas mixture (102A) to the first interior (101) of the first reactor (100); a second carbonaceous material and gas input (104B) provided by a second feed zone delivery system (2050B) and configured to input a second carbonaceous material and gas mixture (102B) to the first interior (101) of the first reactor (100).

In embodiments, the first feed zone delivery system (2050A) and second feed zone delivery system (2050B) used in FIG. 33 include a Mass Flow Regulation (2C) subsystem, Densification (2D) subsystem, Plug Control (2E) subsystem, Density Reduction (2F) subsystem, Gas Mixing (2G) subsystem, and a Transport (2H) subsystem.

In embodiments, the first feed zone delivery system (2050A) and second feed zone delivery system (2050B) include a Mass Flow Regulation (2C) subsystem, Densification (2D) subsystem, Plug Control (2E) subsystem, Density Reduction (2F) subsystem, Gas Mixing (2G) subsystem, and a Transport (2H) subsystem as seen in FIG. 2A. In embodiments, the first feed zone delivery system (2050A) and second feed zone delivery system (2050B) include a Mass Flow Regulation (2C) subsystem, Gas Mixing (2G) subsystem, and a Transport (2H) subsystem as seen in FIG. 2B. In other non-limiting embodiments, the first feed zone delivery system (2050A) and second feed zone delivery system (2050B) include any combination or permutation of the subsystems including Transport (2H), Gas Mixing (2G), Density Reduction (2F), Plug Control (2E), Densification (2D), Mass Flow Regulation (2C) as seen in FIG. 2A noting that any order of any possibility of any combination or permutation of subsystems 2C, 2D, 2E, 2F, 2G, 2H being in a sequence falls within the bounds of this disclosure.

In embodiments, the first reactor pressure (P-A) is greater in pressure than the pressure within each weigh feeder (2C1), second reactor (200), third reactor (100), venturi scrubber (380), and scrubber (384). In embodiments, the first reactor pressure (P-A) has a pressure that is lesser than the pressure within each weigh feeder (2C1), second reactor (200), third reactor (100), venturi scrubber (380), and scrubber (384).

In embodiments, the pressure signal from the first reactor pressure (P-A) may be greater than the signal from the pressure sensor (P-2C) of an upstream weigh feeder (2C1). In embodiments, the pressure signal from the first reactor pressure (P-A) may be lesser than the signal from the pressure sensor (P-2C) of an upstream weigh feeder (2C1).

In embodiments, the first reactor (100) has a pressure that is greater than the pressure within each weigh feeder (2C1) and the first reactor (100) has a greater pressure than the second reactor (200). In embodiments, the first reactor (100) has a pressure that is less than the pressure within each weigh feeder (2C1) and the first reactor (100) has a lower pressure than the second reactor (200).

The first reactor (100) accepts a plurality of carbonaceous material and gas mixtures (102A, 102B) through a first reactor carbonaceous material input (104). The first reactor reactant (106) is steam transferred from the outlet (216) of the second reactor heat exchanger (HX-B) at a first reactor reactant temperature (TR1). The first reactor (100) also accepts a first reactor solids input (107) from a second reactor solids output (207), wherein the first reactor solids input (107) is configured to receive, into the first interior (101), second reactor particulate heat transfer material (205) present in the second interior (201). Thus, the second reactor particulate heat transfer material (205) is used as the first reactor particulate heat transfer material (105) and the first reactor particulate heat transfer material (105) is used as the second reactor particulate heat transfer material (205). A first reactor product gas (122) is discharged from the interior (101) of the first reactor (100) via a first reactor product gas output (124).

FIG. 33 depicts a three-stage product gas generation system (1001), further comprising a second reactor solids output (207) and a first reactor solids input (107) in fluid communication with the second reactor solids output (207), wherein the first reactor solids input (107) is configured to receive, into the first interior (101), second reactor particulate heat transfer material (205) present in the second interior (201).

FIG. 18, FIG. 19, FIG. 24, and FIG. 33 show a first reactor (100) configured to accept steam as a reactant (106) at a rate of about 0.125:1 to about 3:1 lb/lb dry carbonaceous material. The system of FIG. 18, FIG. 19, FIG. 24, and FIG. 33 shows a first reactor (100) configured to accept a carbonaceous material and gas mixture (102) so that the carbon dioxide is fed to the first reactor (100) at a rate of about 0:1 to about 1:1 lb/lb dry carbonaceous material. The system of FIG. 18, FIG. 19, and FIG. 24 shows a first reactor (100) configured to accept an oxygen-containing gas (118) at a rate of about 0:1 to about 0.5:1 lb/lb dry carbonaceous material (102).

In embodiments, the MSW carbonaceous feedstock depicted in FIG. 14, FIG. 16, FIG. 17, FIG. 36, and FIG. 37 has a carbon content≥48%; BTU content ≥8,400 Btu/lb; maximum inert feedstock contaminants ≤2%, by weight; sulfur ≤0.15%; chlorine ≤0.125%; ash ≤7.5% (this amount includes the inert feedstock contaminants); alkali content i.e. sum($Na_2O+K_2O+Li_2O$) by weight/HHV≤1 lb/MMBtu; glass content ≤0.1%; MSW-derived carbonaceous material feedstock Particle size distribution Fines ≤15%, by weight, in the size range of 800 micron or less ≤1" minus.

Char-carbon refers to the mass fraction of carbon that is contained within the char (202) transferred from the first reactor (100) to the second reactor (200). In embodiments, the char-carbon contained within char (202) transferred from the first reactor (100) to the second reactor (200) ranges from about 90% carbon to about 10% carbon on a weight basis.

The maximum MSW carbonaceous material moisture content ≤10%; the moisture should be reasonably uniformly distributed across the different MSW components (wood, paper, fiber etc.) and the different particle size fractions and not be concentrated in a narrow size fraction or component class.

The first reactor in FIG. 14, FIG. 19, and FIG. 33 each have 6) First Reactor Feedstock Injection Locations (FIG. 36, Table 1, Column C-D, Row 4) where each carbonaceous material and gas input (104A, 104B, 104C, 104D, 104E, 104F) is configured to accept a carbonaceous material and gas mixture (102A, 102B, 102C, 102D, 102E, 102F) from a feed zone delivery system (2050A, 2050B, 2050C, 2050D, 2050E, 2050F) that operates at 4 Feeder System Cycles per minute (FIG. 36, Table 1, Column D, Row 5).

Each Feeder System Cycle Duration is 15 seconds (FIG. 36, Table 1, Column D, Row 6). Each Feeder System Cycle produces 1 plug per cycle (FIG. 36, Table 1, Column D, Row 7) and generates 4 plugs per minute (FIG. 36, Table 1, Column D, Row 8). The length of a commercial size plug is about 11 inches to about 13 inches. The diameter of a commercial size plug is about 11 inches to about 13 inches.

The Total Carbonaceous Material to First Reactor is 45,782 lb/hr wet (FIG. 36, Table 1, Column D, Row 9), that is also 23 tons/hr wet (FIG. 36, Table 1, Column D, Row 10), 549 tons/day wet (FIG. 36, Table 1, Column D, Row 11), 41,667 lb/hr dry (FIG. 36, Table 1, Column D, Row 12), 41,845 ton/hr dry (FIG. 36, Table 1, Column D, Row 13), and 500 tons/day dry (FIG. 36, Table 1, Column D, Row 14).

7,630 lb/hr wet carbonaceous material (FIG. 36, Table 1, Column D, Row 15) is transferred to each of six carbonaceous material and gas input (104A, 104B, 104C, 104D, 104E, 104F) also at 127 lb/minute (FIG. 36, Table 1, Column D, Row 16), 32 plug lb/cycle (FIG. 36, Table 1, Column D, Row 17), 3.8 ton/hr wet (FIG. 36, Table 1, Column D, Row 18), 92 tons/day wet (FIG. 36, Table 1, Column D, Row 19), 6,944 lb/hr dry (FIG. 36, Table 1, Column D, Row 20), 3.47 ton/hr dry (FIG. 36, Table 1, Column D, Row 21), and 83 tons/day dry (FIG. 36, Table 1, Column D, Row 22).

532 lb/hr of carbon dioxide (FIG. 36, Table 1, Column D, Row 24) is transferred to each Gas Mixing (2G) subsystem located within in each feed zone delivery system (2050A, 2050B, 2050C, 2050D, 2050E, 2050F) prior to injection to the first reactor (100) via a carbonaceous material and gas inputs (104A, 104B, 104C, 104D, 104E, 104F). The mass ratio of MSW carbonaceous material to carbon dioxide transferred to each carbonaceous material and gas input (104A, 104B, 104C, 104D, 104E, 104F) is 14 lb MSW/lb CO2 (FIG. 36, Table 1, Column D, Row 25). When dividing ROW 15 by ROW 24, the quotient is ROW 25, while ROW 15 is the dividend, and ROW 24 the divisor.

In embodiments, the mass ratio of MSW carbonaceous material to gas transferred to each carbonaceous material and gas input (104A, 104B, 104C, 104D, 104E, 104F) is 0.01 lb MSW/lb gas. In embodiments, the mass ratio of MSW carbonaceous material to gas transferred to each carbonaceous material and gas input (104A, 104B, 104C, 104D, 104E, 104F) is 0.05 lb MSW/lb gas. In embodiments, the mass ratio of MSW carbonaceous material to gas transferred to each carbonaceous material and gas input (104A, 104B, 104C, 104D, 104E, 104F) is 1 lb MSW/lb gas. In embodiments, the mass ratio of MSW carbonaceous material to gas transferred to each carbonaceous material and gas input (104A, 104B, 104C, 104D, 104E, 104F) is 2 lb MSW/lb gas. In embodiments, the mass ratio of MSW carbonaceous material to gas transferred to each carbonaceous material and gas input (104A, 104B, 104C, 104D, 104E, 104F) is 3 lb MSW/lb gas. In embodiments, the mass ratio of MSW carbonaceous material to gas transferred to each carbonaceous material and gas input (104A, 104B, 104C, 104D, 104E, 104F) is 4 lb MSW/lb gas. In embodiments, the mass ratio of MSW carbonaceous material to gas transferred to each carbonaceous material and gas input (104A, 104B, 104C, 104D, 104E, 104F) is 5 lb MSW/lb gas. In embodiments, the mass ratio of MSW carbonaceous material to gas transferred to each carbonaceous material and gas input (104A, 104B, 104C, 104D, 104E, 104F) is 6 lb MSW/lb gas. In embodiments, the mass ratio of MSW carbonaceous material to gas transferred to each carbonaceous material and gas input (104A, 104B, 104C, 104D, 104E, 104F) is 7 lb MSW/lb gas. In embodiments, the mass ratio of MSW carbonaceous material to gas transferred to each carbonaceous material and gas input (104A, 104B, 104C, 104D, 104E, 104F) is 8 lb MSW/lb gas. In embodiments, the mass ratio of MSW carbonaceous material to gas transferred to each carbonaceous material and gas input (104A, 104B, 104C, 104D, 104E, 104F) is 9 lb MSW/lb gas. In embodiments, the mass ratio of MSW carbonaceous material to gas transferred to each carbonaceous material and gas input (104A, 104B, 104C, 104D, 104E, 104F) is 10 lb MSW/lb gas. In embodiments, the mass ratio of MSW carbonaceous material to gas transferred to each carbonaceous material and gas input (104A, 104B, 104C, 104D, 104E, 104F) is 11 lb MSW/lb gas. In embodiments, the mass ratio of MSW carbonaceous material to gas transferred to each carbonaceous material and gas input (104A, 104B, 104C, 104D, 104E, 104F) is 12 lb MSW/lb gas. In embodiments, the mass ratio of MSW carbonaceous material to gas transferred to each carbonaceous material and gas input (104A, 104B, 104C, 104D, 104E, 104F) is 13 lb MSW/lb gas. In embodiments, the mass ratio of MSW carbonaceous material to gas transferred to each carbonaceous material and gas input (104A, 104B, 104C, 104D, 104E, 104F) is 14 lb MSW/lb gas. In embodiments, the mass ratio of MSW carbonaceous material to gas transferred to each carbonaceous material and gas input (104A, 104B, 104C, 104D, 104E, 104F) is 15 lb MSW/lb gas. In embodiments, the mass ratio of MSW carbonaceous material to gas transferred to each carbonaceous material and gas input (104A, 104B, 104C, 104D, 104E, 104F) is 16 lb MSW/lb gas. In embodiments, the mass ratio of MSW carbonaceous material to gas transferred to each carbonaceous material and gas input (104A, 104B, 104C, 104D, 104E, 104F) is 17 lb MSW/lb gas. In embodiments, the mass ratio of MSW carbonaceous material to gas transferred to each carbonaceous material and gas input (104A, 104B, 104C, 104D, 104E, 104F) is 18 lb MSW/lb gas. In embodiments, the mass ratio of MSW carbonaceous material to gas transferred to each carbonaceous material and gas input (104A, 104B, 104C, 104D, 104E, 104F) is 19 lb MSW/lb gas. In embodiments, the mass ratio of MSW carbonaceous material to gas transferred to each carbonaceous material and gas input (104A, 104B, 104C, 104D, 104E, 104F) is 20 lb MSW/lb gas. In embodiments, the mass ratio of MSW carbonaceous material to gas transferred to each carbonaceous material and gas input (104A, 104B, 104C, 104D, 104E, 104F) is 21 lb MSW/lb gas. In embodiments, the mass ratio of MSW carbonaceous material to gas transferred to each carbonaceous material and gas input (104A, 104B, 104C, 104D, 104E, 104F) is 22 lb MSW/lb gas. In embodiments, the mass ratio of MSW carbonaceous material to gas transferred to each carbonaceous material and gas input (104A, 104B, 104C, 104D, 104E, 104F) is 23 lb MSW/lb gas. In embodiments, the mass ratio of MSW carbonaceous material to gas transferred to each carbonaceous material and gas input (104A, 104B, 104C, 104D, 104E, 104F) is 24 lb MSW/lb gas. In embodiments, the mass ratio of MSW carbonaceous material to gas transferred to each carbonaceous material and gas input (104A, 104B, 104C, 104D, 104E, 104F) is 25 lb MSW/lb gas. In embodiments, the mass ratio of MSW carbonaceous material to gas transferred to each carbonaceous material and gas input (104A, 104B, 104C, 104D, 104E, 104F) is 26 lb MSW/lb gas. In embodiments, the mass ratio of MSW carbonaceous material to gas transferred to each carbonaceous material and gas input (104A, 104B, 104C, 104D, 104E, 104F) is 27 lb MSW/lb gas. In embodiments, the mass ratio of MSW carbonaceous material to gas transferred to each carbonaceous material and gas input (104A, 104B, 104C, 104D, 104E, 104F) is 28 lb MSW/lb gas. In embodiments, the mass ratio of MSW carbonaceous material to gas transferred to each carbonaceous material and gas input (104A, 104B, 104C, 104D, 104E, 104F) is 29 lb MSW/lb gas. In embodiments, the mass ratio of MSW carbonaceous material to gas transferred to each carbonaceous material and gas input (104A, 104B, 104C, 104D, 104E, 104F) is 30 lb MSW/lb gas. In embodiments, the mass ratio of MSW carbonaceous material to gas transferred to each carbonaceous material and gas input (104A, 104B, 104C, 104D, 104E, 104F) is 31 lb MSW/lb gas. In embodiments, the mass ratio of MSW carbonaceous material to gas transferred to each carbonaceous material and gas input (104A, 104B, 104C, 104D, 104E, 104F) is 32 lb MSW/lb gas. In embodiments, the mass ratio of MSW carbonaceous material to gas transferred to each carbonaceous material and gas input (104A, 104B, 104C, 104D, 104E, 104F) is 33 lb MSW/lb gas. In embodiments, the mass ratio of MSW carbonaceous material to gas transferred to each carbonaceous material and gas input (104A, 104B, 104C, 104D, 104E, 104F) is 34 lb MSW/lb gas. In embodiments, the mass ratio of MSW carbonaceous material to gas transferred to each carbonaceous material and gas input (104A, 104B, 104C, 104D, 104E, 104F) is 35 lb MSW/lb gas. In embodiments, the mass ratio of MSW carbonaceous material to gas transferred to each carbonaceous material and gas input (104A, 104B, 104C, 104D, 104E, 104F) is 36 lb MSW/lb gas. In embodiments, the mass ratio of MSW carbonaceous material to gas transferred to each carbonaceous material and gas input (104A, 104B, 104C, 104D, 104E, 104F) is 37 lb MSW/lb gas. In embodiments, the mass ratio of MSW carbonaceous material to gas transferred to each carbonaceous material and gas input (104A, 104B, 104C, 104D, 104E, 104F) is 38 lb MSW/lb gas. In embodiments, the mass ratio of MSW carbonaceous material to gas transferred to each carbonaceous material and gas input (104A, 104B, 104C, 104D, 104E, 104F) is 39 lb MSW/lb gas. In embodiments, the mass ratio of MSW carbonaceous material to gas transferred to each carbonaceous material and gas input (104A, 104B, 104C, 104D, 104E, 104F) is 40 lb MSW/lb gas. In embodiments, the mass ratio of MSW carbonaceous material to gas transferred to each carbonaceous material and gas input (104A, 104B, 104C, 104D, 104E, 104F) is 41 lb MSW/lb gas. In embodiments, the mass ratio of MSW carbonaceous material to gas transferred to each carbonaceous material and gas input (104A, 104B, 104C, 104D, 104E, 104F) is 42 lb MSW/lb gas. In embodiments, the mass ratio of MSW carbonaceous material to gas transferred to each carbonaceous material and gas input (104A, 104B, 104C, 104D, 104E, 104F) is 43 lb MSW/lb gas. In embodiments, the mass ratio of MSW carbonaceous material to gas transferred to each carbonaceous material and gas input (104A, 104B, 104C, 104D, 104E, 104F) is 44 lb MSW/lb gas. In embodiments, the mass ratio of MSW carbonaceous material to gas transferred to each carbonaceous material and gas input (104A, 104B, 104C, 104D, 104E, 104F) is 45 lb MSW/lb gas. In embodiments, the mass ratio of MSW carbonaceous material to gas transferred to each carbonaceous material and gas input (104A, 104B, 104C, 104D, 104E, 104F) is 46 lb MSW/lb gas. In embodiments, the mass ratio of MSW carbonaceous material to gas transferred to each carbonaceous material and gas input (104A, 104B, 104C, 104D, 104E, 104F) is 47 lb MSW/lb gas. In embodiments, the mass ratio of MSW carbonaceous material to gas transferred to each carbonaceous material and gas input (104A, 104B, 104C, 104D, 104E, 104F) is 48 lb MSW/lb gas. In embodiments, the mass ratio of MSW carbonaceous material to gas transferred to each carbonaceous material and gas input (104A, 104B, 104C, 104D, 104E, 104F) is 49 lb MSW/lb gas. In embodiments, the mass ratio of MSW carbonaceous material to gas transferred to each carbonaceous material and gas input (104A, 104B, 104C, 104D, 104E, 104F) is 50 lb MSW/lb gas.

In embodiments, the mass ratio of MSW carbonaceous material to gas transferred to each carbonaceous material and gas input (104A, 104B, 104C, 104D, 104E, 104F) is 51 lb MSW/lb gas. In embodiments, the mass ratio of MSW carbonaceous material to gas transferred to each carbonaceous material and gas input (104A, 104B, 104C, 104D, 104E, 104F) is 52 lb MSW/lb gas. In embodiments, the mass ratio of MSW carbonaceous material to gas transferred to each carbonaceous material and gas input (104A, 104B, 104C, 104D, 104E, 104F) is 53 lb MSW/lb gas. In embodiments, the mass ratio of MSW carbonaceous material to gas transferred to each carbonaceous material and gas input (104A, 104B, 104C, 104D, 104E, 104F) is 54 lb MSW/lb gas. In embodiments, the mass ratio of MSW carbonaceous material to gas transferred to each carbonaceous material and gas input (104A, 104B, 104C, 104D, 104E, 104F) is 55 lb MSW/lb gas. In embodiments, the mass ratio of MSW carbonaceous material to gas transferred to each carbonaceous material and gas input (104A, 104B, 104C, 104D, 104E, 104F) is 56 lb MSW/lb gas. In embodiments, the mass ratio of MSW carbonaceous material to gas transferred to each carbonaceous material and gas input (104A, 104B, 104C, 104D, 104E, 104F) is 57 lb MSW/lb gas. In embodiments, the mass ratio of MSW carbonaceous material to gas transferred to each carbonaceous material and gas input (104A, 104B, 104C, 104D, 104E, 104F) is 58 lb MSW/lb gas. In embodiments, the mass ratio of MSW carbonaceous material to gas transferred to each carbonaceous material and gas input (104A, 104B, 104C, 104D, 104E, 104F) is 59 lb MSW/lb gas. In embodiments, the mass ratio of MSW carbonaceous material to gas transferred to each carbonaceous material and gas input (104A, 104B, 104C, 104D, 104E, 104F) is 60 lb MSW/lb gas. In embodiments, the mass ratio of MSW carbonaceous material to gas transferred to each carbonaceous material and gas input (104A, 104B, 104C, 104D, 104E, 104F) is 61 lb MSW/lb gas. In embodiments, the mass ratio of MSW carbonaceous material to gas transferred to each carbonaceous material and gas input (104A, 104B, 104C, 104D, 104E, 104F) is 62 lb MSW/lb gas. In embodiments, the mass ratio of MSW carbonaceous material to gas transferred to each carbonaceous material and gas input (104A, 104B, 104C, 104D, 104E, 104F) is 63 lb MSW/lb gas. In embodiments, the mass ratio of MSW carbonaceous material to gas transferred to each carbonaceous material and gas input (104A, 104B, 104C, 104D, 104E, 104F) is 64 lb MSW/lb gas. In embodiments, the mass ratio of MSW carbonaceous material to gas transferred to each carbonaceous material and gas input (104A, 104B, 104C, 104D, 104E, 104F) is 65 lb MSW/lb gas. In embodiments, the mass ratio of MSW carbonaceous material to gas transferred to each carbonaceous material and gas input (104A, 104B, 104C, 104D, 104E, 104F) is 66 lb MSW/lb gas. In embodiments, the mass ratio of MSW carbonaceous material to gas transferred to each carbonaceous material and gas input (104A, 104B, 104C, 104D, 104E, 104F) is 67 lb MSW/lb gas. In embodiments, the mass ratio of MSW carbonaceous material to gas transferred to each carbonaceous material and gas input (104A, 104B, 104C, 104D, 104E, 104F) is 68 lb MSW/lb gas. In embodiments, the mass ratio of MSW carbonaceous material to gas transferred to each carbonaceous material and gas input (104A, 104B, 104C, 104D, 104E, 104F) is 69 lb MSW/lb gas. In embodiments, the mass ratio of MSW carbonaceous material to gas transferred to each carbonaceous material and gas input (104A, 104B, 104C, 104D, 104E, 104F) is 70 lb MSW/lb gas. In embodiments, the mass ratio of MSW carbonaceous material to gas transferred to each carbonaceous material and gas input (104A, 104B, 104C, 104D, 104E, 104F) is 71 lb MSW/lb gas. In embodiments, the mass ratio of MSW carbonaceous material to gas transferred to each carbonaceous material and gas input (104A, 104B, 104C, 104D, 104E, 104F) is 72 lb MSW/lb gas. In embodiments, the mass ratio of MSW carbonaceous material to gas transferred to each carbonaceous material and gas input (104A, 104B, 104C, 104D, 104E, 104F) is 73 lb MSW/lb gas. In embodiments, the mass ratio of MSW carbonaceous material to gas transferred to each carbonaceous material and gas input (104A, 104B, 104C, 104D, 104E, 104F) is 74 lb MSW/lb gas. In embodiments, the mass ratio of MSW carbonaceous material to gas transferred to each carbonaceous material and gas input (104A, 104B, 104C, 104D, 104E, 104F) is 75 lb MSW/lb gas.

DECREASE DIVISOR TO INCREASE QUOTIENT AND ATTAIN MAXIMUM GAS MIXING RATIO—In embodiments, (i) the Carbonaceous Material to Each Of 6 First Reactor Feedstock Injection Locations (ROW 15 (R15)-ROW 22 (R22)) is held constant, and (ii) the CO2 Purge To Feedstock Delivery, in lb/hr, (ROW 23 (R23)) is decreased so that (iii) the Ratio of Carbonaceous Material to CO2 To Each First Reactor Feedstock Injection Location (ROW 25 (R25)) attains a maximum gas mixing ratio of 20 lb MSW/lb CO2, or 20 lb carbonaceous material/lb gas. In embodiments, (i) the dividend (ROW 15-ROW 22) is held constant, (ii) the divisor (ROW 25) is decreased to 254 lb/hr so that (iii) the quotient of ROW 25 is no greater than a maximum gas mixing ratio of 30 lb MSW/lb CO2, or 30 lb carbonaceous material/lb gas.

INCREASE DIVISOR TO DECREASE QUOTIENT AND ATTAIN A MINIMUM GAS MIXING RATIO—In embodiments, (i) the Carbonaceous Material to Each Of 6 First Reactor Feedstock Injection Locations (ROW 15 (R15)-ROW 22 (R22)) is held constant, and (ii) the CO2 Purge To Feedstock Delivery, in lb/hr, (ROW 23 (R23)) is increased so that (iii) the Ratio of Carbonaceous Material to CO2 To Each First Reactor Feedstock Injection Location (ROW 25 (R25)) attains a minimum gas mixing ratio of 2 lb MSW/lb CO2, or 2 lb carbonaceous material/lb gas. In embodiments, (i) the dividend (ROW 15-ROW 22) is held constant, (ii) the divisor (ROW 25) is increased to 1,562 lb/hr so that (iii) the quotient of ROW 25 is no less than a minimum gas mixing ratio of 5 lb MSW/lb CO2, or 5 lb carbonaceous material/lb gas.

The throughput through each feed zone delivery system (2050A, 2050B, 2050C, 2050D, 2050E, 2050F) can be increased by a factor of 25% by increasing the pound of the plug per cycle to 39.74 plug lb/cycle (FIG. 37, Table 2, Column D, Row 10). This results in 9,538 lb/hr of wet carbonaceous material (FIG. 37, Table 2, Column D, Row 8) transferred to each of six carbonaceous material and gas input (104A, 104B, 104C, 104D, 104E, 104F) also at 159 lb/minute (FIG. 37, Table 2, Column D, Row 9), 4.77 ton/hr wet (FIG. 37, Table 2, Column D, Row 11), 114.46 tons/day wet (FIG. 37, Table 2, Column D, Row 12), 8,681 lb/hr dry (FIG. 37, Table 2, Column D, Row 13), 4.34 ton/hr dry (FIG. 37, Table 2, Column D, Row 14), 104 tons/day dry (FIG. 37, Table 2, Column D, Row 15), 625 tons/day dry (FIG. 37, Table 2, Column D, Row 16).

Char-ash refers to the mass fraction of ash that is contained within the char (202) transferred from the first reactor (100) to the second reactor (200). In embodiments, the char-ash contained within char (202) transferred from the first reactor (100) to the second reactor (200) ranges from 90% ash to about 10% ash on a weight basis.

The system of FIG. 26 and FIG. 33 shows a second reactor (200) configured to accept steam as a reactant (206) at a rate of about 0:1 to about 2.5:1 lb/lb char-carbon contained in char (202) fed to the second reactor (200). The system of FIG. 26 and FIG. 33 shows a second reactor (200) configured to accept an oxygen-containing gas (208) at a rate of about 0.5:1 to about 2:1 lb/lb char-carbon contained in char (202) fed to the second reactor (200). The system of FIG. 33 shows a second reactor (200) configured to accept carbon dioxide (406) at a rate of about 0:1 to about 2.5:1 lb/lb char-carbon contained in char (202) fed to the second reactor (200).

In the embodiment of FIG. 33, the first reactor product gas output (124) of the first reactor (100) is in fluid communication with the input (152) of the solids separation device (15) via a riser (130). The first reactor (100) reacts the carbonaceous material and gas mixture (102) with the reactant (106) in the presence of the first reactor particulate heat transfer material (105) to generate product gas (122). The riser (130) is configured to transport a mixture of char (202), bed material (105), and product gas (122) to the first solids separation device (150). The first solids separation device (150) separates out the bed material (105) and a portion of the char (202) contained in the first reactor product gas (122) for transfer to the second reactor (200).

Product gas, including char and bed material are evacuated from the interior (101) of the first reactor (100) en route to the input (152) of the first solids separation device (150). Solids including char and bed material are separated out in the first solids separation device (150) and are transferred via a dipleg (244) to the input (246) of a solids flow regulator (245). A char depleted first reactor product gas (126) is evacuated from the first separation gas output (156) of the first solids separation device (150) en route to a third reactor (300) via a char depleted first reactor product gas conduit (128).

In embodiments, the pressure drop across the restriction orifice (RO-B) is typically less than 2 PSIG. In embodiments, the first reactor pressure (P-A) is about 30 PSIG. In embodiments, the second reactor pressure (P-B) is about 28 PSIG. In embodiments, the third reactor pressure is about 26 PSIG. In other embodiments, the first reactor (100) operates at slightly below atmospheric pressure (0.65 to 1 bar or 9.5 to 14.5 psia). In other embodiments, the first reactor pressure (P-A) may operate at a pressure within the pressure range of about 9 PSIA to about 75 PSIG. FIG. 33 depicts the first reactor temperature (T-A) between about 320° C. and 569.99° C. (608° F. and 1,057.98° F.) and utilizes an endothermic hydrous devolatilization thermochemical process within the interior (101). In other embodiments, FIG. 33 may depict the first reactor temperature (T-A) operating between about 570° C. and 900° C. (1,058° F. and 1,652° F.) and utilizing an endothermic steam reforming thermochemical process within the interior (101). In other embodiments, FIG. 33 may depict the first reactor temperature (T-A) operating between about 570° C. and 900° C. (1,058° F. and 1,652° F.) and utilizing an endothermic water-gas shift thermochemical process within the interior (101).

The solids flow regulator (245) accepts a gas (249) through a gas input (248) which prevents backflow and also aides in the transfer of bed material and char from the solids flow regulator (245) to the interior (201) of the second reactor (200). Bed material and char (202) exit the solids flow regulator (245) through an output (247) and are transported to a char input (204) on the second reactor (200).

The second reactor (200) has a second interior (201). The second reactor reactant (206) is steam transferred from the outlet (216) of the second reactor heat exchanger (HX-B) to the reactant inlet (208) of the second reactor (200). The second reactor (200) accepts an oxygen-containing gas (218) through a second reactor oxygen-containing gas input (220). The second reactor (200) accepts a second reactor carbon dioxide (406) through a second reactor carbon dioxide input (407).

FIG. 33 also depicts the second reactor temperature (T-B) to be between 500° C. and 1,400° C. (932° F. and 2,552° F.). The second reactor (200) of FIG. 27 has partial oxidation, steam reforming, water gas shift, and dry reforming thermochemical processes taking place therein.

The second reactor also has a particulate classification chamber (B1) including a mixture transfer valve (V9B), classification gas transfer valve (V10B), bed material riser recycle transfer valve (V11B), depressurization vent valve (V12B), and an inert feedstock contaminant drain valve (V13B). The particulate classification chamber (B1), or classifier, has a bed material & inert feedstock contaminant mixture input (B5), classifier gas input (B6), classified recycled bed material output (B7), classifier depressurization gas output (B8), and a classifier inert feedstock contaminant output (B9). The terms classifier, classifier vessel, particulate classification chamber, and variations thereof are treated as synonymous throughout the specification. A table of reference numerals is provided below to avoid confusion.

The bed material & inert feedstock contaminant mixture input (B5) on the particulate classification chamber (B1) in fluid communication with the bed material & inert feedstock contaminant mixture output (B2) on the second reactor (200) via a mixture transfer conduit (B3). The bed material riser recycle transfer valve (V11B) is located on the classifier riser (B17) in between the classified recycled bed material output (B7) of the particulate classification chamber (B1) and the classified recycled bed material input (B27) on the second reactor (200). The depressurization vent valve (V12B) is located approximate to the classifier depressurization gas output (B8) to control or regulate classifier depressurization gas (B18) evacuated from the particulate classification chamber (B1). The inert feedstock contaminant drain valve (V13B) is located approximate to the classifier inert feedstock contaminant output (B9) to control or regulate classified inert feedstock contaminants (B19) evacuated from the classifier.

A bed material and inert feedstock contaminant mixture (B4) is transferred from the interior (201) of the second reactor (200) to the interior of the particulate classification chamber (B1) through the mixture transfer conduit (B3). A mixture transfer valve (V9B) is interposed in the conduit (B3) in between the bed material & inert feedstock contaminant mixture output (B2) of the second reactor (200) and the mixture input (B5) on the classifier. The bed material and inert feedstock contaminant mixture (B4) has a bed material portion and an inert feedstock contaminant portion.

The classifier gas input (B6) on the particulate classification chamber (B1) is configured to accept a classifier gas (B16), such as carbon dioxide recycled from a downstream Secondary Gas Clean Up System (6000). The classification gas transfer valve (V10B) is located upstream of the classifier gas input (B6) to start and stop the flow of classifier gas (B16) to the particulate classification chamber (B1). The drag of the classifier gas (B16) on the bed material portion supplies an upward force which counteracts the force of gravity and lifts the classified recycled bed material (B37) through the classified recycled bed material output (B7), classifier riser (B17), and into the second reactor (200) via a classified recycled bed material input (B27). Due to the dependence of gas drag on object size and shape, the bed material portion in the particulate classification chamber (B1) is sorted vertically and can be separated, recycled, and cleaned in this manner. The classified inert feedstock contaminants (B19) left within the particulate classification chamber (B1) may be drained via a classifier inert feedstock contaminant output (B9).

FIG. 33 is to be used in conjunction with FIG. 25 which depicts a listing of valve states that may be used in a variety of methods to operate valves associated with the particulate classification chamber (B1). FIG. 25 identifies five separate discrete valve states of which any number of states can be selected to result in a sequence of steps for the classification of bed material and recovery of inert feedstock contaminants to prevent defluidization within the second reactor (200). Although not shown in FIG. 33, the following signals are configured to be inputs or outputs from the computer (COMP) for use in the Classification Valve States for Automated Controller Operation of a typical particulate classification procedure of FIG. 25: second reactor dense bed zone reactant valve signal (XB1); second reactor dense bed zone oxygen-containing gas valve signal (XB2); second reactor feed zone reactant valve signal (XB3); second reactor feed zone oxygen-containing gas valve signal (XB4); second reactor splash zone reactant valve signal (XB5); and, second reactor splash zone oxygen-containing gas valve signal (XB6).

The char (202) separated out from the first reactor product gas (122) is reacted in the second reactor (200) with the reactant (206), carbon dioxide (406), and an oxygen-containing gas (218) to generate a second reactor product gas (222) evacuated from the second reactor (200) via a second reactor product gas output (224). Exothermic reactions take place within the second reactor (200) between the char (202) and the oxygen-containing gas (218) in the presence of the second reactor particulate heat transfer material (205).

A second reactor heat exchanger (HX-B) is immersed beneath the fluid bed level (L-B) of the second reactor (200) to remove heat from the particulate heat transfer material (205) and in turn transfer heat to the second reactor heat transfer medium (210) contained within the second reactor heat exchanger (HX-B). A portion of the heated second reactor heat transfer medium (210) is used as a reactant (106, 206) in the first reactor (100) and second reactor (200).

The second reactor product gas (222) evacuated from the second reactor (200) through a second reactor product gas output (224) is routed to an input (252) of the second solids separation device (250). The second solids separation device (250) removes solids from the second reactor product gas (222) to produce a solids depleted second reactor product gas (226) that is evacuated from the second solids separation device (250) through an output (256) and a solids depleted second reactor product gas conduit (228). A solids output (254) on the second solids separation device (250) is configured to transfer separated solids (232) from the separation device (250) via a solids transfer conduit (234).

The char depleted first reactor product gas (126) is combined with the solids depleted second reactor product gas (226) to create a combined product gas (302) that is conveyed to the third reactor (300) through a combined product gas input (304). Generally, it is desirable to operate the first reactor and second reactor in a superficial fluidization velocity range between 0.5 ft/s to about 25.0 ft/s. FIG. 33 depicts the first reactor (100) operating in a superficial fluidization velocity range between 15 ft/s to about 25 ft/s. In embodiments, as in FIG. 18, FIG. 19. FIG. 24, and FIG. 33, it is preferable to operate the first reactor (100) in a superficial fluidization velocity range between 0.6 ft/s to about 1.2 ft/s. Specifically, in the embodiments of FIG. 18, FIG. 19. FIG. 24, and FIG. 33 it is preferable to operate the first reactor in a superficial fluidization velocity range between 0.8 ft/s to about 1 ft/s.

In embodiments, as in FIG. 26 and FIG. 33, it is preferable to operate the second reactor (200) in a superficial fluidization velocity range between 0.2 ft/s to about 0.8 ft/s. Specifically, in the embodiments of FIG. 26 and FIG. 33, it is preferable to operate the second reactor (200) in a superficial fluidization velocity range between 0.3 ft/s to about 0.5 ft/s. The second reactor (200) operates at a superficial fluidization velocity sufficient to drive the fine solids from the interior (201) towards the second solids separation device (250) for removal.

In embodiments, the carbon conversion rate in the first reactor (100) is in the range from about 50% to about 100%. In embodiments, the carbon conversion rate in the first reactor (100) is from about 75% to about 95%. In embodiments, the when the carbon conversion rate in the first reactor (100) is from about 75% to about 95%, the second reactor (200) converts the 50% to 99% of the char-carbon transferred from the first reactor (200) and sent to the second reactor (200). In some embodiments, the second reactor separated solids (232) range from about 0% to about 90% carbon and from about 100% to about 10% ash on a weight basis. In some embodiments, the second reactor separated solids (232) range from about 5% to about 30% carbon and from about 95% to about 70% ash on a weight basis.

The embodiment of FIG. 33 depicts a second reactor (200) equipped with particulate classification chamber (B1). The particulate classification chamber (B1) may be configured to classify, clean, and recycle bed material back to the interior (201) of the second reactor (200) while removing larger objects, such as agglomerates from the system.

In embodiments, it is preferable to use Geldart A particles as second reactor particulate heat transfer material (205) in second reactor (200). In other embodiments, it is preferable to use a mixture of Geldart B and Geldart A particles as second reactor particulate heat transfer material (205) in second reactor (200). Thus, the embodiment in FIG. 33 shows the second reactor particulate heat transfer material (205) being transferred to the first reactor (100) for use as the first reactor particulate heat transfer material (105).

Agglomeration can take place in the second reactor (200) when the char-ash introduced with the char (202) to the second reactor (200) is heated above its softening point temperature, and particles stick together to form larger or agglomerated particles. Agglomeration of char-ash particles together in the second reactor (200) may be compounded by binding or interlocking of two or more fluidized bed particulates together thus eventually increasing the mean particle size of the bed leading to defluidization. As a result growth and accumulation of agglomerates within the fluidized bed of the second reactor (200) transitions from proper fluidization to possible economically detrimental defluidization leading to unscheduled process termination and shut down. To mediate agglomeration in the second reactor (200), the second reactor (200) can be equipped with at least one particulate classification chamber (B1) to reliably and consistently remove from the system agglomerates from the second interior (201).

Further, since the embodiment shown in FIG. 33 has a first reactor (100) that is not equipped with a particulate classification chamber (B1), all of the inert feedstock contaminants introduced to the first reactor (100) are conveyed to the second reactor (200) for removal. Thus, the embodiments shown in FIG. 24 may also be applicable to the second reactor (200) of FIG. 33.

The third reactor (300) has a third interior (301). The third reactor (300) is configured to accept a combined product gas (302), and partially oxidize SVOC, VOC, and char contained therein to generate a third reactor product gas (334) and heat. The third reactor has a burner (346) that is configured to accept a first hydrocarbon stream (322), such as a methane containing gas (e.g.—natural gas) via a first hydrocarbon stream input (324). The third reactor has a burner (346) that is also configured to accept a superstoichiometric third reactor oxygen-containing gas (318) to substantially completely combust the first hydrocarbon stream (322) to generate a combustion stream including CO2, H2O and heat. Left over, unreacted, oxygen-containing gas is present in the combustion stream. The combustion stream is passed from the burner (346) of the third reactor (300) and partially oxidizes the SVOC, VOC, and char contained within the combined product gas (302) to generate additional hydrocarbon, carbon monoxide and heat.

The third reactor (300) is also configured to accept second hydrocarbon stream (326) via a second hydrocarbon stream input (328) and a third hydrocarbon stream (330) via a third hydrocarbon stream input (332). The second hydrocarbon stream input (328) and third hydrocarbon stream input (332) are in fluid communication with a third reactor via a combined hydrocarbon connection (CZC0), combined hydrocarbon (CZC1), and a combined hydrocarbon input (CZC2). The second hydrocarbon stream (326), may be naphtha, and the third hydrocarbon stream (330), may be off-gas, both of which may be transferred to the third reactor (300) from a downstream Upgrading System (8000). The carbon and hydrogen contained within the second hydrocarbon stream (326) and the third hydrocarbon stream (330) may undergo a thermochemical reaction between the oxygen-containing gas present in the combustion stream transferred from the burner (346) to the interior (301) of the third reactor (300) to generate additional hydrogen, carbon monoxide and heat.

A third reactor heat exchanger (HX-C) is in thermal contact with the interior (301) of the third reactor (300). The third reactor (HX-C) is comprised of a third reactor heat transfer medium inlet (312) and a third reactor heat transfer medium outlet (316) through which a third reactor heat transfer medium (310) flows. The heat generated by the partial oxidation reaction between the SVOC, VOC, and char contained within the combined product gas (302) and the oxygen-containing gas present in the combustion stream leaving the burner (346) is transferred to the third reactor heat transfer medium (310).

A steam drum (350) is configured to accept the heat transfer medium (310) from the third reactor heat transfer medium outlet (316) via an inlet (354) and transfer conduit. FIG. 33 portrays the heat transfer medium (310) transferred to the steam drum (350) to be liquid phase water. The steam drum is also configured to provide a heat transfer medium (310) to the third reactor heat transfer medium inlet (312) via an outlet (356) and transfer conduit (362). In embodiments, a supply (353) of liquid phase water for use as the third reactor heat transfer medium (310) is made available to the steam drum (350) via a steam drum heat transfer medium supply inlet (352) and a third reactor heat transfer medium valve (VC5). The steam drum (350) is equipped with a pressure sensor (370) and a level sensor (372).

The pressure sensor (370) with an integrated steam pressure control valve (366) maintain the steam drum (350) at a user-defined pressure and steam is discharged through a steam outlet (358) and conduit (360) as necessary to maintain a desired steam drum (350) operating pressure. A portion of the steam evacuated form the steam drum (350) is used as the second reactor heat transfer medium (210) and is routed to the inlet (212) of the second reactor heat exchanger (HX-B). A portion of the steam evacuated from the steam drum (350) may be routed elsewhere than the inlet (212) of the second reactor heat exchanger (HX-B) via a conduit (365).

A portion of the third reactor heat transfer medium (310) is used as the second reactor heat transfer medium (210). The second reactor heat transfer medium enters the inlet (212) of the second reactor heat exchanger (HX-B) at a first temperature T1. Heat from the interior (201) of the second reactor (200) is transferred through the second reactor heat exchanger (HX-B) and into the second reactor heat transfer medium (210). The second reactor heat transfer medium (210) is discharged from the outlet (216) of the second reactor heat exchanger (HX-B) and enters the first reactor (100) for use as a reactant (106). The first reactor reactant (106) enters the interior (101) of the first reactor (100) at a first reactor reactant temperature (TR1), that is greater than the temperature of the heat transfer medium (210) entering the second reactor heat exchanger, at a first inlet temperature (T1). Thus, a portion of the third reactor heat transfer medium (310) is used as the reactant (206) in the second reactor (200). And a portion of the third reactor heat transfer medium (310) is used as the reactant (106) in the first reactor (200).

The third reactor (300) is configured to output a third reactor slag (338) via a third reactor slag output (340). The third reactor is configured to output a third reactor product gas (334) from a third reactor product gas output (336) to the inlet (373) of a Primary Gas Clean Up Heat Exchanger (HX-4). The Primary Gas Clean Up Heat Exchanger (HX-4) has a product gas inlet (373) for accepting a third reactor product gas (334) and a product gas outlet (375) for discharging the product gas at a reduced temperature. The Primary Gas Clean Up Heat Exchanger (HX-4) is configured to remove heat from the third reactor product gas (334) to a heat transfer medium flowing from the Heat Exchanger (HX-4) from the heat transfer medium inlet (376) to the heat transfer medium outlet (377). It is preferable to operate the Primary Gas Clean Up Heat Exchanger (HX-4) with product gas velocities in each of the tubes from about 25 to about 125 ft/s.

A product gas outlet conduit (378) is positioned on the product gas outlet (375) of the Primary Gas Clean Up Heat Exchanger (HX-4) and is configured to transfer the third reactor product gas to the inlet (379) of a venturi scrubber (380). The Venturi Scrubber operates at a temperature below the SVOC condensation temperature and below the dewpoint of the excess steam contained within the product gas therefore condensing any SVOC and excess steam out into a liquid phase.

Solid char particulates entrained within the product gas come into contact with water provided by a venturi scrubber transfer conduit (404), and solvent provided by a venturi scrubber transfer conduit (393), at the divergent section of the venturi scrubber and said solid char particulates act as a nuclei for excess steam condensation and are displaced from the vapor phase and into the liquid phase. Connection X7 indicates water being transferred from water pump (394) pump discharge (395) to the venturi scrubber (380).

A mixture comprising product gas, SVOC, solids, solvent and water, is routed to the lower section of the scrubber (384) via a venturi scrubber product gas outlet conduit (382). The venturi scrubber product gas outlet (381) of the venturi scrubber (380) and the product gas inlet (383) of the scrubber (384) are in fluid communication via a venturi scrubber product gas outlet conduit (382).

The scrubber (384) serves as an entrainment separator for the venturi scrubber and is configured to receive the product gas, SVOC, solids, solvent and water and separately output a water and solids depleted product gas stream and a second mixture comprising SVOC, solids, solvent and water. The scrubber (384) also serves to capture one or more of other contaminants present including but not limited to HCl, HCN, $NH_3$, $H_2S$, and COS. A water and solids depleted product gas stream is evacuated from the scrubber (384) via a product gas outlet (385) and outlet conduit (386). Thus, the product gas emanating from the scrubber (384) has a depleted amount of solids and water relative to the product gas that is discharged from the third rector (300).

The scrubber (384), is preferably a vertically oriented cylindrical, or rectangular, pressure vessel having a lower section, and an upper section, along with a central section that contains a quantity of packed media either comprising raschig rings, pall rings, berl saddles, intalox packing, metal structured grid packing, hollow spherical packing, high performance thermoplastic packing, structured packing, synthetic woven fabric, or ceramic packing, or the like, wherein media is supported upon a suitable support grid system commonplace to industrial chemical equipment systems. The upper section of the scrubber (384) preferably contains a demister to enhance the removal of liquid droplets entrained in a vapor stream and to minimize carry-over losses of the sorption liquid. This demister is also positioned above the scrubber spray nozzle system, comprised of a plurality of spray nozzles, or spray balls, that introduce and substantially equally distribute the scrubbing absorption liquid to the scrubber onto the scrubber's central packing section so it may gravity-flow down through the scrubber central section. It is preferably to operate the scrubber (384) from about 50% flooding to 80% flooding. It is also preferable to operate the scrubber (384) with a pressure drop (in water/ft packing) from about 0.15 to about 0.55.

As the product gas passes up through the internal packing of the scrubber (384), excess steam within the product gas comes into intimate contact with water provided by conduit (405) and solvent provided by conduit (392). The water provided by conduit (405) is cooled prior to being introduced to the upper section of the scrubber (384) through the scrubber spray nozzle system. Steam is condensed into a liquid phase before being discharged from the scrubber (384) via the underflow downcomer (387). A separator (388), such as a decanter, is positioned to accept the flow of SVOC, solids, solvent and water from the downcomer (387). In embodiments, a separator (388) is configured to receive the mixture from downcomer (387) and separate the water within the mixture based upon immiscibility so that the SVOC, solids and solvent collect together to form a mixture above the water within the separator (388). The decanter separator (388) is further configured to separately output the water and the SVOC, solids and solvent mixture. The separator (388) may be equipped with a level sensor (389). The scrubber (384) has a sensor to measure the scrubber pressure (P-S) which in the embodiment of FIG. 33 operates at a pressure within the pressure range of about 9 PSIA to about 75 PSIG.

In embodiments, a process fluid (403), such as water, sodium hydroxide, or a dispersant, such as Nalco 3D TRASAR® 3DT120, may be added to the scrubber. The Nalco Dispersant (3DT120) is used as a declogger to prevent calcium-rich particles from depositing on the pipe wall and plugging the venturi-gas cooler piping.

Through a pump discharge (391), the solvent pump (390) is configured to transfer SVOC, solids and solvent to the second reactor (200) as fuel (262) via a fuel input (264). The solvent pump is also configured to transfer the SVOC, solids and solvent to the venturi scrubber (380) via a venturi scrubber transfer conduit (393). The solvent pump is also configured to transfer the SVOC, solids and solvent to the scrubber (384) via a scrubber transfer conduit (392).

Intimate gas to liquid contact within the scrubber (384) allows for the solvent to both, absorb SVOC from the syngas (if any), and enable solid carbon (if any), and solid ash, to become oleophilic and hydrophobic permitting said solids to become suspended within the solvent or water before both the solvent and carbon are discharged from the scrubber (384).

A heat exchanger (399) is installed in the water pump discharge (395) line after the solids separator (398). The heat exchanger (399) is preferably of the shell and tube type heat exchanger, wherein syngas steam condensate transferred to scrubbing operations resides on the tube-side, and a cooling water supply (401), and a cooling water return (402), communicate with the shell-side of the heat exchanger to fulfill the heat transfer requirements necessary to indirectly remove heat from the tube-side steam condensate recirculation scrubbing liquid.

FIG. 34:

FIG. 34 refers to a variation of the system of FIG. 33 however further including an engine (410) connected to the scrubber product gas outlet conduit (386) connected to a shaft (416), and a generator (418) and configured for power output (420).

FIG. 34 shows an engine (410) positioned in scrubber product gas outlet conduit (386). The engine (410) has a product gas inlet (412) and a gas outlet (414). At least one piston (417) is contained in at least one cylinder (419) within the engine (410). At least one spark plug (421) is positioned in at least one cylinder (419) within the engine (410). The cylinder (419) is configured to accept product gas through the product gas inlet (412) of the engine (410). At least one piston (417) is configured to reciprocate within the cylinder (419) so as to subject the product gas to changes of pressure, temperature, volume, addition of heat, and removal of heat in at least one idealized thermodynamic cycle.

The high-efficiency, low-emission gas engine (410) is equipped with a shaft (416) that is configured to turn a generator (418) for power output (420). The utility of the engine (410) is dependent upon the cleanliness of the product gas evacuated from the scrubber product gas outlet conduit (386). It is of paramount importance that the product gas transferred from the scrubber (384) and into the product gas inlet (412) of the engine (410) have minimal amount of particulates, SVOC, VOC, and water.

The preferred type of engine combusts a product gas having a syngas caloric value ranging from 120 BTU/scf to 400 BTU/scf, with the combustible constituents of the product gas being primarily H2 and CO. The actual or useful horsepower of an engine (410), usually determined from the force exerted on a friction brake or dynamometer connected to the drive shaft, is preferably within the range of power from a range of about 225 to 750 kWb. Further the operating parameters of the engine are preferably an Otto Cycle, four-stroke, and turbocharged. The preferred compression ratio is from about 9:1 to about 12:1.

FIG. 35:

FIG. 35 discloses a pressure-volume diagram describing the idealized thermodynamic cycle of FIG. 34. A pressure-volume diagram is shown in FIG. 35 to describe corresponding changes in volume and pressure in an engine (410) used to combust product gas for power output (420). Operation of the engine (410) can be explained in the following method:

Step 410A to 410B involves a mass of product gas (H2 and CO) being drawn into the engine (410) at a constant scrubber pressure (P-S) between about 9 PSIA to about 75 PSIG;

Step 410B to 410C is an adiabatic (isentropic) compression of the product gas (H2 and CO) as the piston (417) within the engine (410) moves from bottom dead center (BDC) to top dead center (TDC) within the cylinder (419);

Step 410C to 410D is a constant-volume heat transfer to the working product gas (H2 and CO) from a spark plug (421) while the piston is at top dead center. This process is intended to represent the ignition of the H2 and CO within the product gas and the subsequent rapid combustion into CO2 and H2O.

Step 410D to 410E is an adiabatic (isentropic) expansion causing the shaft (416) of the engine (410) to turn to drive a generator (418) for power output (420);

Step 410E to 410B completes the cycle by a constant-volume process in which heat is rejected from the generated combustion stream of CO2 and H2O while the piston is at bottom dead center.

Step 410B to 410A the combustion stream including CO2 and H2O is released via the gas outlet (414) of the engine (410).

FIG. 38

FIG. 38 displays one non-limiting embodiment of a densification system (1000') for compressing and ejecting compressed material. FIGS. 38-50 show one embodiment of a densification system (1000') for compressing and ejecting compressed material. The densification system (1000') includes a compression chamber (00') comprising a first end (05'), a second end (07'), an interior (02'), and a longitudinal axis (A') extending between the first and second ends (05', 07').

The compression chamber (00') has a chamber inlet (04') transverse to the longitudinal axis (A'), for introducing a discrete charge of compressible material (105') into the compression chamber interior (02'). The compression chamber (00') has a chamber outlet (06') transverse to the longitudinal axis (A'), for discharging compressed material (103') from the compression chamber interior (02'). The outlet (06') is longitudinally spaced apart from the chamber inlet (04'). The compression chamber (00') has a compression region (09') defined within the interior (02') of the compression chamber (00') between the inlet (04') and outlet (06'). The compression region (09') configured to simultaneously accommodate a plurality of discrete plugs (PP') of compressed material along with a discrete charge of compressible material (105'). The plurality of discrete plugs (PP') include at least a leading plug (LP') and a terminal plug (TP'). The leading plug (LP') is positioned closer to the chamber outlet (06') than to the chamber inlet (04'). The terminal plug (TP') is positioned closer to the chamber inlet (04') than the chamber outlet (06').

The densification system (1000') also includes a pair of piston cylinder assemblies including: primary piston cylinder assembly (A0') and a backstop piston cylinder assembly (E0'). The primary piston cylinder assembly (A0') is located at the compression chamber's first end (05') and includes a primary compression rod (AJ') having a compression head (AL') facing in a first direction (11') along the longitudinal axis (A'). The primary compression rod (AJ') and compression head (AL') are configured to advance and retract together within the interior (02') of the compression chamber (00'). The backstop piston cylinder assembly (E0') is located at the compression chamber's second end (07') and includes a backstop rod (EC') having a backstop head (ED') facing in a second direction (13') along the longitudinal axis (A'). The second direction (13') is opposite to the first direction (11'). The backstop rod (EC') and backstop head (ED') are configured to advance and retract together within the interior (02') of the compression chamber (00').

The compression head (AL') is configured to selectively move between a retracted position (A200') in which the compression head (AL') is outside the compression region (09'), and an advanced position (A100') in which the compression head (AL') is within the compression region (09') and applies a compressive force to a charge of compressible material located between the compression head (AL') and the backstop head (ED').

The backstop head (ED') is configured to selectively move between a retracted position (E200') in which the backstop head (ED') is outside the compression region (09'), and an advanced locked position (E100') in which the backstop head (ED') is locked in place within the compression region (09').

The knock-down piston cylinder assembly (D0') is connected to the compression chamber (00') and includes a knock-down rod (DC') having a knock-down head (DD'). The knock-down rod (DC') and the knock-down head (DD') are configured to selectively move from a retracted position to an advanced position to eject the leading plug (LP') from the compression chamber (00') via the chamber outlet (06').

The densification system (1000') also includes a controller (500') that is configured to operate the system so as to convert a sequence of discrete charges of compressible material entering the compression chamber (00') via the chamber inlet (04'), into a sequence of discrete plugs (PP') of compressed material (103') discharged from the compression chamber (00') interior (02') via the chamber outlet (06'), while at least one plug of compressed material remains in the compression region (09').

In embodiments, the compression chamber (00') is positioned in between a first press frame (PF1') which is axially spaced apart from a second press frame (PF2'). The first end (05') of the compression chamber (00') is spaced apart from the first press frame (PF1'). The second end (07') of the compression chamber (00') is connected to, and supported by, the second press frame (PF2').

The first press frame (PF1') is connected to the second press frame (PF2') by a plurality of hollow compression columns (1CL', 2CL', 3CL', 4CL') with a plurality of tie rods (1R', 2R', 3R', 4R') positioned within the plurality of hollow compression columns (1CL', 2CL', 3CL', 4CL'), each tie rod comprising opposite first and second ends.

FIG. 38 shows the first press frame (PF1') connected to the second press frame (PF2') via a first compression column (1CL') and a second compression column (2CL'). The first compression column (1CL') is hollow and permits a first tie rod (1R') to be inserted into it. A first tie rod first nut (1N1') and a first tie rod second nut (1N2') are threaded on the ends of the first tie rod (1R') to secure the first press frame (PF1') to the second press frame (PF2'). The second compression column (2CL') is hollow and permits a second tie rod (2R') to be inserted into it. A second tie rod first nut (2N1') and a second tie rod second nut (2N2') are threaded on the ends of the second tie rod (2R') to secure the first press frame (PF1') to the second press frame (PF2'). FIG. 38 shows a connector (X1') connecting the second compression column (2CL') so that the drawing is visually clearer.

The first press frame (PF1') comprises a plurality of first openings and the second press frame (PF2') comprises a plurality of second openings, each first opening being aligned with a corresponding one of the second openings. Opposite ends of each tie rod (1R', 2R', 3R', 4R') pass through aligned first and second openings. A tie rod first nut (1N1', 2N1', 3N1', 4N1') secures the first end of each tie rod (1R', 2R', 3R', 4R') to the first press frame (PF1'). A tie rod second nut (1N2', 2N2', 3N2', 4N2') secures the second end of each tie rod (1R', 2R', 3R', 4R') to the second press frame (PF2').

The primary piston cylinder assembly (A0') includes a primary cylinder (AA') and a primary piston (AB') configured to advance and retract within the primary cylinder (AA'), along the longitudinal axis (A'). The primary piston (AB') extends through a primary piston opening (AG') in the first press frame (PF1') and is connected to a platen (AI'). The platen (AI') is connected to the primary compression rod (AJ') via a compression rod connection (AK') and is and configured to move therewith. The primary compression rod (AJ') extends through a first rod opening (10') nearby the first end (05') of the compression chamber (00').

The primary piston cylinder assembly (A0') has a primary cylinder (AA') with a primary piston (AB') that reciprocates there within. The primary cylinder (AA') has a primary rear cylinder space (AC') with a primary first rear connection port (AD') and a primary second rear connection port (AE'). The primary cylinder (AA') is connected to the first press frame (PF1') via a primary frame connection (AF'). The primary piston (AB') extends through the first press frame (PF1') via a primary piston opening (AG'). The primary piston (AB') is connected to the platen (AI') via a primary piston platen connection (AH').

As shown in FIGS. 51-64, a plurality of guide blocks (GB1', GB2', GB3', GB4') are mounted on the platen (AI') and a plurality of wear plates (WP1', WP2', WP3', WP4') are mounted on and extend along a length of, a corresponding one of said plurality of compression columns (1CL', 2CL', 3CL', 4CL'). Each guide block (GB1', GB2', GB3', GB4') is configured to abut, and slide along, a corresponding one of the plurality of wear plates (WP1', WP2', WP3', WP4').

The backstop piston cylinder assembly (E0') includes a backstop cylinder (EA') and a backstop piston (EB') configured to advance and retract within the backstop cylinder (EA'), along the longitudinal axis (A'). The backstop piston (EB') is connected to the backstop rod (EC') and configured to move therewith. The backstop rod (EC') extends through a backstop piston opening (EI') formed in the second press frame (PF2'), and into the interior (02') of the compression chamber (00').

The backstop piston cylinder assembly (E0') has a backstop cylinder (EA') with a backstop piston (EB'). The backstop piston (EB') reciprocates within the backstop cylinder (EA'). The backstop piston (EB') is connected to a backstop rod (EC'). The backstop rod (EC') is connected to a backstop head (ED').

The backstop cylinder (EA') has a backstop front cylinder space (EE') and a backstop rear cylinder space (EF'). The backstop front cylinder space (EE') is equipped with a backstop front connection port (EG'). The backstop rear cylinder space (EF') is equipped with a backstop rear connection port (EH'). When a hydraulic fluid is introduced to the backstop rear connection port (EH') the backstop piston (EB') is moved from a backstop retracted position (E200') to an advanced locked position (E100'). When a hydraulic fluid is introduced to the backstop front connection port (EG') the backstop piston (EB') is moved from an advanced locked position (E100') to a backstop retracted position (E200').

The backstop rod (EC') extends through the second press frame (PF2') and into the interior (02') of the compression chamber (00') via a backstop piston opening (EI'). The backstop cylinder (EA') is connected to the second press frame (PF2') via a backstop frame connection (EJ').

The knock-down piston cylinder assembly (D0') includes knock-down cylinder (DA') and a knock-down piston (DB') configured to advance and retract within the knock-down cylinder (DA'). A knock-down piston (DB') is connected to the knock-down rod (DC') and configured to more therewith. The knock-down rod (DC') extends through a knock-down piston opening (DI') formed in the compression chamber (00').

The knock-down piston cylinder assembly (D0') includes a knock-down cylinder (DA'). A knock-down piston (DB') reciprocates within the knock-down cylinder (DA'). A knock-down rod (DC') is connected to the knock-down piston (DB'). A knock-down head (DD') is connected to the knock-down rod (DC'). The knock-down head (DD') extends into the interior (02') of the compression chamber (00') via a knock-down piston opening (DI').

The knock-down cylinder (DA') is equipped with a knock-down front cylinder space (DE') and a knock-down rear cylinder space (DF'). The knock-down front cylinder space (DE') is equipped with a knock-down front connection port (DG'). The knock-down rear cylinder space (DF') is equipped with a knock-down rear connection port (DH'). When a hydraulic fluid is introduced to the knock-down rear connection port (DH') the knock-down piston (DB') is moved from a knock-down retracted position (D200') to an advanced ejection position (D100'). When a hydraulic fluid is introduced to the knock-down front connection port (DG') the knock-down piston (DB') is moved from an advanced ejection position (D100') to a knock-down retracted position (D200').

The densification system (1000') also includes a first ancillary piston cylinder assembly (B0'). The first ancillary piston cylinder assembly (B0') includes a first ancillary cylinder (BA') having a first ancillary piston (BB') configured to advance and retract within the first ancillary cylinder (BA'), parallel the longitudinal axis (A'). The first ancillary piston cylinder assembly (B0') has a first ancillary rod (BC') connected to the first ancillary piston (BB'); the first ancillary rod (BC') extends through a first ancillary piston opening (BI') formed in the first press frame (PF1') and is connected to the platen (A1').

The first ancillary piston cylinder assembly (B0') includes a first ancillary cylinder (BA'). A first ancillary piston (BB') is configured to reciprocate within the first ancillary cylinder (BA'). A first ancillary rod (BC') is connected to the first ancillary piston (BB'). The first ancillary rod (BC') extends through the first press frame (PF1') via a first ancillary piston opening (BI') and is connected to the platen (AI') via a first ancillary platen connection (BJ'). The first ancillary cylinder (BA') is equipped with a first ancillary front cylinder space (BD') and a first ancillary rear cylinder space (BE').

The first ancillary front cylinder space (BD') is equipped with a first ancillary front connection port (BF'). The first ancillary rear cylinder space (BE') is equipped with a first ancillary rear connection port (BG'). The first ancillary cylinder (BA') is connected to the first press frame (PF1') via a first ancillary frame connection (BH').

The densification system (1000') also includes a second ancillary piston cylinder assembly (C0'). The second ancillary piston cylinder assembly (C0') includes a second ancillary cylinder (CA') having a second ancillary piston (CB') configured to advance and retract within the second ancillary cylinder (CA'), parallel to the longitudinal axis (A'). The second ancillary piston cylinder assembly (C0') has a second ancillary rod (CC') that is connected to the second ancillary piston (CB'); the second ancillary rod (CC') extends through a second ancillary piston opening (CI') in the first press frame (PF1') and is connected to the platen (AI').

The second ancillary piston cylinder assembly (C0') includes a second ancillary cylinder (CA'). A second ancillary piston (CB') is configured to reciprocate within the second ancillary cylinder (CA'). A second ancillary rod (CC') is connected to the second ancillary piston (CB'). The second ancillary rod (CC') extends through the first press frame (PF1') via a second ancillary piston opening (CI') and is connected to the platen (AI') via a second ancillary platen connection (CJ'). The second ancillary cylinder (CA') is equipped with a second ancillary front cylinder space (CD') and a second ancillary rear cylinder space (CE').

The second ancillary front cylinder space (CD') is equipped with a second ancillary front connection port (CF'). The second ancillary rear cylinder space (CE') is equipped with a second ancillary rear connection port (CG'). The second ancillary cylinder (CA') is connected to the first press frame (PF1') via a second ancillary frame connection (CH').

As shown below in Table 38, The densification system (1000') in configured to selectively occupy a plurality of states, including:

a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04') a compression state in which: the compression head (AL') is in the advanced position; the backstop head (ED') is in the advanced locked position; and the knock-down head (DD') is in the retracted position;

an unlocked backstop state in which: the compression head (AL') is in the advanced position; the backstop head (ED') is in the retracted position; and the knock-down head (DD') is in the retracted position; and an ejection state in which: the compression head (AL') is in the retracted position; the backstop head (ED') is in the retracted position; and the knock-down head (DD') is in the advanced position.

TABLE 38

| | STATE 0 retracted state | STATE 1 loading state | STATE 2 compression state | STATE 3 unlocked backstop state | STATE 4 ejection state |
|---|---|---|---|---|---|
| compression head (AL) | retracted | retracted | advanced | advanced | advanced |
| backstop head (ED) | retracted | advanced | advanced | retracted | retracted |
| knock-down head (DD) | retracted | retracted | retracted | retracted | advanced |

As shown in FIGS. 38 and 39, the densification system (1000') is configured to selectively occupy a retracted state in which: the compression head (AL') is in the retracted position; the backstop head (ED') is in the retracted position; and the knock-down head (DD') is in the retracted position.

The prior art systems and methods for the generation of densified carbonaceous materials have many drawbacks. First, U.S. Pat. No. 8,726,800 describes a method and mechanical press system for the generation of densified cylindrical ingots. This patent describes a first pressing ram and a second pressing ram operating in opposite directions and disposed in a compression chamber. However, the method in which it operates makes it not suitable to seal against pressure across the compression chamber. The system described in U.S. Pat. No. 8,726,800 is incapable of sealing against a downstream pressure. It is also unable to develop more than one successive densified ingot at a time within the compression chamber. This is because the developed densified ingot can only be made by both simultaneously compressing the ingot from both sides by the advancing force of both the first pressing ram and a second pressing ram advancing towards each other. This makes it impossible for the compression chamber to simultaneously accommodate a plurality of discrete plugs of compressed material. Further, the disclosure of U.S. Pat. No. 8,726,800 only contemplates densified materials having at most a diameter of 3.9 inches and a length of 5.9 inches, making it impractical to use in large-scale thermochemical applications that require densified plugs of greater diameter and length to meet industrial large feedstock throughputs.

In some embodiments, the primary piston cylinder assembly (A0'), first ancillary piston cylinder assembly (B0'), and second ancillary piston cylinder assembly (C0') can be configured as disclosed in U.S. patent application Ser. No. 14/775,071, filed on Sep. 11, 2015, filed as application No.

PCT/US2013/035616 on Apr. 8, 2013 and published as US 2016/0031177. The contents of U.S. patent application Ser. No. 14/775,071, filed on Sep. 11, 2015 are incorporated by reference in its entirety to extent necessary to make, use, and understand to present disclosure.

In some embodiments, the densification system (1000') disclosure herein can be included as a densification system (2D0, 2D0') and a plug control system (2E1, 2E1') within a feedstock delivery system (2000) of a Biorefinery Superstructure System (BSS).

FIGS. 38-50 elaborate upon a non-limiting embodiment of FIGS. 7 and 8 and further including a description a combined Densification (2D') and Plug Control (2E') subsystem or sequence step of the Feedstock Delivery System (2000). All of FIGS. 39-50 elaborate upon the densification system (1000) described in FIG. 38.

FIGS. 38-50 show one example of a combined Densification (2D') and Plug Control (2E') subsystem accepting a carbonaceous material (2D-01'), for example, as shown in FIG. 7, as an input (2D-IN1A) from an output (2C-OUT1A) of a Mass Flow Regulation (2C) subsystem. In embodiments, the densification system (1000') shown in FIG. 38 serves the purpose of both the Densification (2D') and Plug Control (2E') subsystems or sequence steps of the Feedstock Delivery System (2000). This is because the design of the densification system (1000') accept a carbonaceous material (2D-01') via an input (2D-IN1A) and compresses the carbonaceous material to discharge a densified carbonaceous material (2D-02'), and then a force is exerted by the ram (E20') to hold plugs of densified carbonaceous material (2D-02') in position and create a stop against which the last plug is formed.

The combined Densification (2D') and Plug Control (2E') subsystem is shown as a densification system (1000'). The densification system (1000') is configured to accept a carbonaceous material (2D-01') and compress the carbonaceous material to discharge a densified carbonaceous material (2D-02'). The densification system (1000') includes a densification system (2D0') comprised of at least a third piston cylinder assembly (2D3'). In embodiments, the third piston cylinder assembly (2D3') can be a primary piston cylinder assembly (A0'). The Plug Control (2E') subsystem of the densification system (1000') is configured to accept a plug (1P', 2P', 3P', 4P') of carbonaceous material and exert a force upon the plug (1P', 2P', 3P', 4P') to hold it in place while subsequent plugs are formed as they are compressed up against the plug (1P', 2P', 3P', 4P') that has said force exerted upon.

The Plug Control (2E') subsystem is configured to accept a plug (1P', 2P', 3P', 4P') of carbonaceous material and exert a force upon the plug (1P', 2P', 3P', 4P') to hold it in place while a first subsequent material is compressed up against the plug (1P', 2P' 3P', 4P') that has said force exerted upon. As a plug is made from the first subsequent material, the Plug Control (2E') subsystem is configured to exert a force upon the plug formed from the first subsequent material to hold it in place while a second subsequent material is compressed up against the plug formed from the first subsequent material that has a force exerted upon.

The Plug Control (2E') subsystem of FIGS. 38-50 includes a plug control system (2E1') having a plug control cylinder (E02'). In embodiments, the plug control cylinder (E02') may be a knock-down piston cylinder assembly (D0') or a backstop piston cylinder assembly (E0') or both.

In embodiments, the present disclosure describes a densification system (1000') for compressing and ejecting compressed material, comprising:

a compression chamber (00') comprising:

a first end (05'), a second end (07'), an interior (02'), and a longitudinal axis (A') extending between the first and second ends (05', 07');

a chamber inlet (04') transverse to the longitudinal axis (A'), for introducing a discrete charge of compressible material (105') into the compression chamber interior (02');

a chamber outlet (06') transverse to the longitudinal axis (A'), for discharging compressed material (103') from the compression chamber interior (02'), the outlet (06') being longitudinally spaced apart from the chamber inlet (04'); and a compression region (09') defined within the interior (02') of the compression chamber (00') between the inlet (04') and outlet (06'), the compression region (09') configured to simultaneously accommodate a plurality of discrete plugs (PP') of compressed material along with a charge of compressible material, the plurality of discrete plugs (PP') including at least a leading plug (LP') and a terminal plug (TP'), the leading plug (LP') being closer to the chamber outlet (06') than to the chamber inlet (04');

a pair of piston cylinder assemblies including:

a primary piston cylinder assembly (A0') located at the compression chamber's first end (05') and including a primary compression rod (AJ') having a compression head (AL') facing in a first direction (11') along the longitudinal axis (A'), the primary compression rod (AJ') and compression head (AL') configured to advance and retract together within the interior (02') of the compression chamber (00'), and a backstop piston cylinder assembly (E0') located at the compression chamber's second end (07') and including a backstop rod (EC') having a backstop head (ED') facing in a second direction (13') along the longitudinal axis (A'), the second direction (13') being opposite to the first direction (11'), the backstop rod (EC') and backstop head (ED') configured to advance and retract together within the interior (02') of the compression chamber (00'), wherein:

the compression head (AL') is configured to selectively move between a retracted position (A200') in which the compression head (AL') is outside the compression region (09'), and an advanced position (A100') in which the compression head (AL') is within the compression region (09') and applies a compressive force to a charge of compressible material located between the compression head (AL') and the backstop head (ED'); and the backstop head (ED') is configured to selectively move between a retracted position (E200') in which the backstop head (ED') is outside the compression region (09'), and an advanced locked position (E100') in which the backstop head (ED') is locked in place within the compression region (09');

a knock-down piston cylinder assembly (D0') connected to the compression chamber (00') and including a knock-down rod (DC') having a knock-down head (DD'), the knock-down rod (DC') and the knock-down head (DD') configured to selectively move from a retracted position to an advanced position to eject the leading plug (LP') from the compression chamber (00') via the chamber outlet (06'); and a controller (500') configured to operate the system so as to convert a sequence of discrete charges of compressible material entering the compression chamber (00') via the chamber inlet (04'), into a sequence of discrete plugs (PP') of compressed material (103') discharged from the compression chamber (00') interior (02') via the chamber outlet (06'), while at least one plug of compressed material remains in the compression region (09').

In embodiments, the compression chamber (00') is positioned in between a first press frame (PF1') which is axially spaced apart from a second press frame (PF2'); the first end (05') of the compression chamber (00') is spaced apart from the first press frame (PF1'); the second end (07') of the compression chamber (00') is connected to, and supported by, the second press frame (FP2'); and the first press frame (PF1') is connected to the second press frame (PF2') by a plurality of hollow compression columns (1CL', 2CL', 3CL', 4CL') with a plurality of tie rods (1R', 2R', 3R', 4R') positioned within the plurality of hollow compression columns (1CL', 2CL', 3CL', 4CL'), each tie rod comprising opposite first and second ends.

In embodiments, the first press frame (PF1') comprises a plurality of first openings and the second press frame (PF2') comprises a plurality of second openings, each first opening being aligned with a corresponding one of the second openings; opposite ends of each tie rod (1R', 2R', 3R', 4R') pass through aligned first and second openings; a tie rod first nut (1N1', 2N1', 3N1', 4N1') secures the first end of each tie rod (1R', 2R', 3R', 4R') to the first press frame (PF1'); and a tie rod second nut (1N2', 2N2', 3N2', 4N2') secures the second end of each tie rod (1R', 2R', 3R', 4R') to the second press frame (PF2').

In embodiments, the primary piston cylinder assembly (A0') includes a primary cylinder (AA') and a primary piston (AB') configured to advance and retract within the primary cylinder (AA'), along the longitudinal axis (A'); the primary piston (AB') extends through a primary piston opening (AG') in the first press frame (PF1') and is connected to a platen (AI'); the platen (AI') is connected to the primary compression rod (AJ') and configured to move therewith; and the primary compression rod (AJ') extends through a first rod opening (10') formed proximate the first end (05') of the compression chamber (00').

In embodiments, the densification system (1000') includes: a plurality of guide blocks (GB1', GB2', GB3', GB4') mounted on the platen (AI'); a plurality of wear plates (WP1', WP2', WP3', WP4'), each wear plate mounted on and extending along a length of, a corresponding one of said plurality of compression columns (1CL', 2CL', 3CL', 4CL'), wherein: each guide block (GB1', GB2', GB3', GB4') is configured to abut, and slide along, a corresponding one of the plurality of wear plates (WP1', WP2', WP3', WP4').

In embodiments, the backstop piston cylinder assembly (E0') includes a backstop cylinder (EA') and a backstop piston (EB') configured to advance and retract within the backstop cylinder (EA'), along the longitudinal axis (A'); the backstop piston (EB') is connected to the backstop rod (EC') and configured to move therewith; and the backstop rod (EC') extends through a backstop piston opening (EI') formed in the second press frame (PF2'), and into the interior (02') of the compression chamber (00').

In embodiments, the knock-down piston cylinder assembly (D0') includes knock-down cylinder (DA') and a knock-down piston (DB') configured to advance and retract within the knock-down cylinder (DA'); a knock-down piston (DB') is connected to the knock-down rod (DC') and configured o more therewith; and the knock-down rod (DC') extends through a knock-down piston opening (DI') formed in the compression chamber (00').

In embodiments, the densification system (1000') includes a first ancillary piston cylinder assembly (B0'), including: a first ancillary cylinder (BA') having a first ancillary piston (BB') configured to advance and retract within the first ancillary cylinder (BA'), parallel the longitudinal axis (A'); and a first ancillary rod (BC') connected to the first ancillary piston (BB'); wherein: the first ancillary rod (BC') extends through a first ancillary piston opening (BI') formed in the first press frame (PF1') and is connected to the platen (AP).

In embodiments, the densification system (1000') includes a second ancillary piston cylinder assembly (C0'), including: a second ancillary cylinder (CA') having a second ancillary piston (CB') configured to advance and retract within the second ancillary cylinder (CA'), parallel to the longitudinal axis (A'); and a second ancillary rod (CC') is connected to the second ancillary piston (CB'); wherein: the second ancillary rod (CC') extends through a second ancillary piston opening (CI') in the first press frame (PF1') and is connected to the platen (AI').

In embodiments, the densification system (1000') is configured to selectively occupy a plurality of states, including: a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04') a compression state in which: the compression head (AL') is in the advanced position; the backstop head (ED') is in the advanced locked position; and the knock-down head (DD') is in the retracted position; an unlocked backstop state in which: the compression head (AL') is in the advanced position; the backstop head (ED') is in the retracted position; and the knock-down head (DD') is in the retracted position; and an ejection state in which: the compression head (AL') is in the retracted position; the backstop head (ED') is in the retracted position; and the knock-down head (DD') is in the advanced position.

In embodiments, the densification system (1000') is further configured to selectively occupy a retracted state in which: the compression head (AL') is in the retracted position; the backstop head (ED') is in the retracted position; and the knock-down head (DD') is in the retracted position.

In embodiments, in a steady state mode of operation, the controller is configured to cause the system to repeatedly cycle through the following states: (a) the loading state; (b) then the compression state; (c) then the unlocked backstop state; and (d) then the ejection state, thereby discharging a leading plug of compressed material from the compression chamber with each cycle.

In embodiments, the controller is configured to cause the system to operate such that at least three plugs of compressed material remain in the compression region (09'), as the leading plug is discharged.

In embodiments, in a startup mode of operation, the controller is configured to cause the system to occupy the following states to discharge an initial plug of compressed material from the compression chamber: (a) the loading state followed by the compression state, at least two times in a row; (b) then the unlocked backstop state; and (c) then the ejection state, thereby discharging the initial plug of compressed material from the compression chamber, while at least one plug of compressed material remains in the compression region.

In embodiments, in said startup mode of operation and prior to occupying the unlocked backstop state: the controller is configured to cause the system to occupy the loading state followed by the compression state, three times in a row, thereby discharging the initial plug of compressed material from the compression chamber, while two plugs of compressed material remain in the compression region.

In embodiments, in said startup mode of operation and prior to occupying the unlocked backstop state: the controller is configured to cause the system to occupy the loading state followed by the compression state, four times in a row, thereby discharging the initial plug of compressed material from the compression chamber, while three plugs of compressed material remain in the compression region.

FIG. 39

FIG. 39 displays one non-limiting embodiment of a densification system (1000') in an initial retracted state (state 0).

FIG. 40

FIG. 40 displays one non-limiting embodiment of a densification system (1000') in a first mode of operation (state 1: loading state).

As shown in FIG. 40, the densification system (1000') is configured to selectively occupy a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04').

FIG. 41

FIG. 41 elaborates upon the non-limiting embodiment of FIG. 40 wherein the densification system (1000') is displayed in a first mode of operation (state 1: loading state) showing a first discrete charge of compressible material (105') entering the compression chamber (00') via the inlet (04').

As shown in FIG. 41, the densification system (1000') is configured to selectively occupy a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04'). FIG. 41 shows a first discrete charge of compressible material (105') being introduced to the interior (02') of the compression chamber (00'). The compressible material (105') may be carbonaceous material (101').

FIG. 42

FIG. 42 elaborates upon the non-limiting embodiment of FIG. 41 and displays one non-limiting embodiment of a densification system (1000') in a second mode of operation (state 2: compression state).

As shown in FIG. 42, the densification system (1000') is configured to selectively occupy a compression state in which: the compression head (AL') is in the advanced position; the backstop head (ED') is in the advanced locked position; and the knock-down head (DD') is in the retracted position.

FIG. 42 shows the first discrete charge of compressible material (105') of FIG. 41 being compressed into a first plug (1P'). In embodiments, plugs (1P', 2P', 3P', 4P', 5P') or the leading plug (LP') or terminal plug (TP') may are described in FIG. 7 when referring to a plug (1D, 2D, 3D, 4D, 5D, 6D) of densified carbonaceous material (2D-02) that may be produced by a densification system (2D0).

FIG. 43

FIG. 43 elaborates upon the non-limiting embodiment of FIG. 42 showing the densification system (1000') again in a first mode of operation (state 1: loading state) and accepting a second discrete charge of compressible material (105') entering the compression chamber (00') via the inlet (04') while a first plug (1P') of compressed material remains in the compression region (09') of the compression chamber (00').

As shown in FIG. 43, the densification system (1000') is configured to selectively occupy a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04').

FIG. 43 shows a second discrete charge of compressible material (105') being introduced to the interior (02') of the compression chamber (00'). The compressible material (105') may be carbonaceous material (101').

FIG. 44

FIG. 44 elaborates upon the non-limiting embodiment of FIG. 43 showing the densification system (1000') again in a second mode of operation (state 2: compression state) but now compressing the second discrete charge of compressible material (105') into a second plug (2P') of compressed material.

As shown in FIG. 44, the densification system (1000') is configured to selectively occupy a compression state in which: the compression head (AL') is in the advanced position; the backstop head (ED') is in the advanced locked position; and the knock-down head (DD') is in the retracted position.

FIG. 44 shows the second discrete charge of compressible material (105') being compressed into a second plug (2P'). The second plug (2P') is compressed up against the first plug (1P'). Here, the second plug (2P') is the terminal plug (TP') and the first plug (1P') is the leading plug (LP').

FIG. 45

FIG. 45 elaborates upon the non-limiting embodiment of FIG. 44 showing the densification system (1000') again in a first mode of operation (state 1: loading state) and accepting a third discrete charge of compressible material (105') entering the compression chamber (00') via the inlet (04') while a first plug (1P') and second plug (2P') of compressed material remains in the compression region (09') of the compression chamber (00').

As shown in FIG. 45, the densification system (1000') is configured to selectively occupy a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04').

FIG. 46

FIG. 46 elaborates upon the non-limiting embodiment of FIG. 45 showing the densification system (1000') again in a second mode of operation (state 2: compression state) but now compressing the third discrete charge of compressible material (105') into a third plug (3P') of compressed material.

As shown in FIG. 46, the densification system (1000') is configured to selectively occupy a compression state in which: the compression head (AL') is in the advanced position; the backstop head (ED') is in the advanced locked position; and the knock-down head (DD') is in the retracted position.

FIG. 46 shows the third discrete charge of compressible material (105') being compressed into a third plug (3P'). The third plug (3P') is compressed up against the second plug (2P'). Here, the third plug (3P') is the terminal plug (TP') and the first plug (1P') is the leading plug (LP').

FIG. 47

FIG. 47 elaborates upon the non-limiting embodiment of FIG. 46 showing the densification system (1000') again in a first mode of operation (state 1: loading state) and accepting a fourth discrete charge of compressible material (105') entering the compression chamber (00') via the inlet (04') while a first plug (1P'), second plug (2P'), and third plug (3P') of compressed material remains in the compression region (09') of the compression chamber (00').

As shown in FIG. 47, the densification system (1000') is configured to selectively occupy a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04').

FIG. 48

FIG. 48 elaborates upon the non-limiting embodiment of FIG. 47 and displays one non-limiting embodiment of a densification system (1000') in a third mode of operation (state 3: unlocked backstop state).

As shown in FIG. 48, the densification system (1000') is configured to selectively occupy an unlocked backstop state in which: the compression head (AL') is in the advanced position; the backstop head (ED') is in the retracted position; and the knock-down head (DD') is in the retracted position.

FIG. 48 elaborates upon FIG. 47 and shows the fourth discrete charge of compressible material (105') being compressed into a fourth plug (4P'). The fourth plug (4P') is compressed up against the third plug (3P'). Here, the fourth plug (4P') is the terminal plug (TP') and the first plug (1P') is the leading plug (LP').

FIG. 49

FIG. 49 elaborates upon the non-limiting embodiment of FIG. 48 and displays one non-limiting embodiment of a densification system (1000') in a fourth mode of operation (state 4: ejection state).

As shown in FIG. 49, the densification system (1000') is configured to selectively occupy an ejection state in which: the compression head (AL') is in the retracted position; the backstop head (ED') is in the retracted position; and the knock-down head (DD') is in the advanced position.

FIG. 49 shows the first plug (1P') or leading plug (LP') (as shown in FIG. 48) being ejected from the interior (02') of the compression chamber (00'). The knock-down head (DD') is advanced to remove the first plug (1P') from the interior (02') of the compression chamber (00') via the outlet (06'). The first plug (1P') may then be provided to a Density Reduction (2F) as depicted in FIG. 9.

FIG. 50

FIG. 50 elaborates upon the non-limiting embodiment of FIG. 49 and displays one non-limiting embodiment of a densification system (1000') again in a first mode of operation (state 1: loading state) and accepting a fifth discrete charge of compressible material (105') entering the compression chamber (00') via the inlet (04') while a second plug (2P'), and third plug (3P'), and fourth plug (4P') of compressed material remain in the compression region (09') of the compression chamber (00').

As shown in FIG. 50, the densification system (1000') is configured to selectively occupy a loading state in which: the compression head (AL') is in the retracted position; the backstop head (ED') is in the advanced locked position; the knock-down head (DD') is in the retracted position; and a source of uncompressed material is in fluid communication with the chamber interior, via the chamber inlet (04').

FIG. 50 elaborates upon FIG. 49 and shows a fifth discrete charge of compressible material (105') being introduced to the interior (02') of the compression chamber (00') to be later compressed into a fifth plug. The fifth plug would then be compressed up against the fourth plug (4P'). FIG. 50 depicts the fourth plug (4P') being the terminal plug (TP') and the second plug (2P') is the leading plug (LP').

As shown in FIGS. 38-50, while operating in a steady state mode of operation, the controller is configured to cause the densification system (1000') to repeatedly cycle through the following states: (a) the loading state; (b) then the compression state; (c) then the unlocked backstop state; and (d) then the ejection state, thereby discharging a leading plug of compressed material from the compression chamber with each cycle.

In embodiments, the controller is configured to cause the system to operate such that at least three plugs of compressed material remain in the compression region (09'), as the leading plug is discharged.

In embodiments, in a startup mode of operation, the controller is configured to cause the system to occupy the following states to discharge an initial plug of compressed material from the compression chamber: (a) the loading state followed by the compression state, at least two times in a row; (b) then the unlocked backstop state; and (c) then the ejection state, thereby discharging the initial plug of compressed material from the compression chamber, while at least one plug of compressed material remains in the compression region.

In embodiments, in the startup mode of operation and prior to occupying the unlocked backstop state: the controller is configured to cause the system to occupy the loading state followed by the compression state, three times in a row, thereby discharging the initial plug of compressed material from the compression chamber, while two plugs of compressed material remain in the compression region.

In embodiments, in the startup mode of operation and prior to occupying the unlocked backstop state: the controller is configured to cause the system to occupy the loading state followed by the compression state, four times in a row, thereby discharging the initial plug of compressed material from the compression chamber, while three plugs of compressed material remain in the compression region.

In embodiments, this disclosure describes a method for converting carbonaceous material into Fischer-Tropsch products using a catalyst, the method comprising:
  (a) splitting a source of bulk carbonaceous material into a plurality of carbonaceous material streams;
  (b) providing a supply of pressurized carbon dioxide;
  (c) reducing a pressure of the pressurized carbon dioxide to form a reduced-pressure carbon dioxide;
  (d) mixing the reduced-pressure carbon dioxide with each of the plurality of carbonaceous material streams to form a plurality of CO2-laden carbonaceous material streams;
  (e) transferring said plurality of CO2-laden carbonaceous material streams to a first reactor via a plurality of inlets that are circumferentially spaced apart from one another;
  (f) reacting carbonaceous material with superheated steam, carbon dioxide and optionally an oxygen-containing gas, within the interior of the first reactor to produce a first reactor product gas containing H2, CO, CO2, and char;
  (g) reacting the char of step (f) with an oxygen-containing gas and superheated steam and optionally carbon dioxide, within the interior of the second reactor to produce a second reactor product gas containing $H_2$, $CO$, $CO_2$, and solids;
(h) combining a portion of the first reactor product gas of step (f) with a portion of the second reactor product gas of step (g) to form a combined product gas;
(i) compressing at least a portion of the combined product gas to thereby form a compressed product gas;
(j) removing carbon dioxide from the compressed product gas to provide as a supply of pressurized carbon dioxide for step (b);
(k) reacting the compressed product gas with a catalyst after removing carbon dioxide to generate Fischer-Tropsch products; and
(l) upgrading the Fischer-Tropsch products of step (k) into chemical compounds selected from the group consisting of diesel, jet fuel, and naphtha;
wherein:
the first reactor has a steam to carbonaceous material weight ratio in the range of 0.125:1 to 3:1; the first reactor has a carbon dioxide to carbonaceous material weight ratio less than 1:1; the first reactor has an oxygen-containing gas to carbonaceous material weight less than 0.5:1; the second reactor has a steam to char-carbon weight ratio less than 2.5:1; the second reactor has an oxygen-containing gas to char-carbon weight ratio less than 2:1; the second reactor has a carbon dioxide to char-carbon weight ratio less than 2.5:1; the first reactor product gas has a first $H_2$ to $CO$ ratio, the second reactor product gas has a second $H_2$ to $CO$ ratio; and the first $H_2$ to $CO$ ratio is greater than the second $H_2$ to $CO$ ratio; the first reactor product gas has a first $CO$ to $CO_2$ ratio, the second reactor product gas has a second $CO$ to $CO_2$ ratio, and the second $CO$ to $CO_2$ ratio is greater than the first $CO$ to $CO_2$ ratio; the carbon conversion rate in the first reactor is in the range from 75% to 95%; second reactor converts greater than 50% of the carbon contained within char transferred from the first reactor to the second reactor into said second reactor product gas; the char in the first reactor product gas has a carbon content of 10% carbon to 90% carbon on a weight basis; the char in the first reactor product gas has an ash content range from 90% ash to 10% ash on a weight basis; operating the second reactor at a temperature greater than the first reactor; and operating the second reactor at a pressure lower than the first reactor.

It will be appreciated that the foregoing examples, given for purposes of illustration, are not to be construed as limiting the scope of this disclosure. Although only a few exemplary embodiments of this disclosure have been described in detail above, those skilled in the art will readily appreciate that many variation of the theme are possible in the exemplary embodiments without materially departing from the novel teachings and advantages of this disclosure. Accordingly, all such modifications are intended to be included within the scope of this disclosure that is defined in the following claims and all equivalents thereto. Further, it is recognized that many embodiments may be conceived in the design of a given system that do not achieve all of the advantages of some embodiments, yet the absence of a particular advantage shall not be construed to necessarily mean that such an embodiment is outside the scope of the present disclosure.

Thus, specific systems and methods of a feedstock delivery system and a feed zone delivery system have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the foregoing text sets forth a detailed description of numerous different embodiments of the disclosure, it should be understood that the scope of the disclosure is defined by the words of the claims set forth at the end of this patent. The detailed description is to be construed as exemplary only and does not describe every possible embodiment of the disclosure because describing every possible embodiment would be impractical, if not impossible. Numerous alternative embodiments could be implemented, using either current technology or technology developed after the filing date of this patent, which would still fall within the scope of the claims defining the disclosure.

Thus, many modifications and variations may be made in the techniques and structures described and illustrated herein without departing from the spirit and scope of the present disclosure. Accordingly, it should be understood that the methods and apparatus described herein are illustrative only and are not limiting upon the scope of the disclosure.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

LISTING OF REFERENCE NUMERALS

Bulk Transfer (2A)
Bulk Transfer Control Volume (CV-2A)
input (2A-IN1)
output (2A-OUT1)
bulk carbonaceous material (2A-01)
bulk carbonaceous material (2A-02)
mass flow rate (2A-02MASS)
carbon content (2A-02CC)
energy content (2A-02BTU)
water content (2A-02H2O)
volatiles content (2A-02VOL)
bulk transfer system (2A1)
transport assembly (2A-03)
conveyor belt (2A-04)
motor (M2A)
controller (C-M2A)
signal (XM2A)
speed sensor (2A-05)
signal (X2A05)
input (2A-06)
output (2A-08)
first mass sensor (W2A-1)
signal (X2WA1)
second mass sensor (W2A-2)
signal (X2WA2)
carbon content measurement unit (2A-CC)
signal (X2ACC)
energy content measurement unit (2A-BTU)
signal (X2AE)
volatiles content measurement unit (2A-VOL)
signal (X2AVOL)
water content measurement unit (2AW)
signal (X2AH2O)
Flow Splitting (2B)
Flow Splitting Control Volume (CV-2B)
input (2B-IN1)
output (2B-OUT1)
first output (2B-OUT1A)
second output (2B-OUT1B)
third output (2B-OUT1C)
fourth output (2B-OUT1D)
fifth output (2B-OUT1E)
sixth output (2B-OUT1F)
bulk carbonaceous material (2B-01)
first split carbonaceous material stream (2B-02A)
second split carbonaceous material stream (2B-02B)
third split carbonaceous material stream (2B-02C)
fourth split carbonaceous material stream (2B-02D)
fifth split carbonaceous material stream (2B-02E)
sixth split carbonaceous material stream (2B-02F)
first split stream (2B-01A)
second split stream (2B-01B)
first splitter (2B1)
interior (2B1IN)
splitter input (2B-03)
top section (2B-04)
bottom section (2B-05)
side wall (WA)
first splitter level sensor (LB1)
signal (XB1)
first splitter first screw conveyor (2B-06)
first output (2B-07)
first splitter first screw conveyor motor (M2B1A)
controller (C2B1A)
signal (X2B1A)
first splitter second screw conveyor (2B-08)
second output (2B-09)
first splitter second screw conveyor motor (M2B1B)
controller (C2B1B)
signal (X2B1B)
first splitter third screw conveyor (2B-10)
third output (2B-11)
first splitter third screw conveyor motor (M2B1C)
controller (C2B1C)
signal (X2B1C)
second splitter (2B2)
interior (2B2IN)
splitter input (2B-12)
top section (2B-13)
bottom section (2B-14)
side wall (WB)
second splitter level sensor (LB2)
signal (XB2)
second splitter first screw conveyor (2B-15)
first output (2B-16)
second splitter first screw conveyor motor (M2B2A)
controller (C2B2A)
signal (X2B2A)
second splitter second screw conveyor (2B-17)
second output (2B-18)
second splitter second screw conveyor motor (M2B2B)
controller (C2B2B)
signal (X2B2B)
second splitter third screw conveyor (2B-19)
third output (2B-20)
second splitter third screw conveyor motor (M2B2C)
controller (C2B2C)
signal (X2B2C)
Mass Flow Regulation (2C)
Mass Flow Regulation Control Volume (CV-2C)
Mass Flow Regulation (2C')
Mass Flow Regulation Control Volume (CV-2C')
input (2C-IN1)
input (2C-IN1A)
input (2C-IN1B)
input (2C-IN1C)
input (2C-IN1D)
input (2C-IN1E)
input (2C-IN1F)
gas input (2C-IN2)
gas input (2C-IN2A)

gas input (2C-IN2B)
gas input (2C-IN2C)
gas input (2C-IN2D)
gas input (2C-IN2E)
gas input (2C-IN2F)
output (2C-OUT1)
output (2C-OUT1A)
output (2C-OUT1B)
output (2C-OUT1C)
output (2C-OUT1D)
output (2C-OUT1E)
output (2C-OUT1F)
carbonaceous material (2C-01)
carbonaceous material (2C-02)
gas (2C-03)
volumetric flow rate (2C-02VOL)
mass flow rate (2C-02MASS)
density (2C-02RHO)
carbon content (2C-02CC)
energy content (2C-02BTU)
water content (2C-02H2O)
volatiles content (2C-02VOL)
weigh feeder (2C1)
interior (2C1IN)
first feed zone delivery system input (FZ-IN1)
second feed zone delivery system input (FZ-IN2)
third feed zone delivery system input (FZ-IN3)
fourth feed zone delivery system input (FZ-IN4)
fifth feed zone delivery system input (FZ-IN5)
sixth feed zone delivery system input (FZ-IN6)
first feed zone delivery system input (FZ-IN1')
second feed zone delivery system input (FZ-IN2')
third feed zone delivery system input (FZ-IN3')
fourth feed zone delivery system input (FZ-IN4')
fifth feed zone delivery system input (FZ-IN5')
sixth feed zone delivery system input (FZ-IN6')
first feed zone delivery system output (FZ-OUT1)
second feed zone delivery system output (FZ-OUT2)
third feed zone delivery system output (FZ-OUT3)
fourth feed zone delivery system output (FZ-OUT4)
fifth feed zone delivery system output (FZ-OUT5)
sixth feed zone delivery system output (FZ-OUT6)
first feed zone delivery system output (FZ-OUT1')
second feed zone delivery system output (FZ-OUT2')
third feed zone delivery system output (FZ-OUT3')
fourth feed zone delivery system output (FZ-OUT4')
fifth feed zone delivery system output (FZ-OUT5')
sixth feed zone delivery system output (FZ-OUT6')
feeder input (2C-05)
feeder output (2C-06)
receiving unit (2C-07)
side wall (2C-08)
height (2C-08H)
first sensor height (2C-08Ha)
second sensor height (2C-08Hb)
third gas connection height (2C-08Hc)
fourth gas connection height (2C-08Hd)
width (2C-08W)
third gas connection width (2C-08Wa)
fourth gas connection width (2C-08Wb)
length (2C-08L)
first sensor length (2C-08La)
second sensor length (2C-08Lb)
volume (2C-V1) (not shown)
top section (2C-09)
bottom section (2C-10)
top opening (2C-11)
bottom opening (2C-12)
first proximity sensor (C-P1)
connection (C-P1C)
signal (XCP1)
first proximity sensor dust accumulation (C1D)
second proximity sensor (C-P2)
connection (C-P2C)
signal (XCP2)
second proximity sensor dust accumulation (C2D)
first gas supply (2C-14)
first gas nozzle (2C-15)
second gas supply (2C-16)
second gas nozzle (2C-17)
third gas supply (2C-18)
third gas connection (2C-19)
fourth gas supply (2C-20)
fourth gas connection (2C-21)
transport unit (2C-22)
height (2C-22H) (not shown)
width (2C-22W) (not shown)
diameter (2C-22D)
length (2C-22L)
volume (2C-V2) (not shown)
interior (2C-23)
side wall (2C-24)
screw conveyor (2C-25)
shaft (2C-26)
shaft rotation measurement unit (2C-27)
signal (X2C27)
motor (M2C)
controller (C-M2C)
signal (XM2C)
weight measurement unit (2C-30)
first mass sensor (W2C-1)
first signal (X2WC1)
first transport unit connection (CT1)
first receiving unit connection (CR1)
N carbonaceous material mass loss value (Cdelta1)
second mass sensor (W2C-2)
second signal (X2WC2)
second transport unit connection (CT2)
second receiving unit connection (CR2)
N+1 carbonaceous material mass loss value (Cdelta2)
difference value (Cdelta3)
carbon content measurement unit (2C-CC)
connection (2C-CCC)
signal (X2CCC)
energy content measurement unit (2C-BTU)
connection (2C-EC)
signal (X2CE)
volatiles content measurement unit (2C-VOL)
connection (2C-VC)
signal (X2CVOL)
water content measurement unit (2CW)
connection (2C-WC)
signal (X2CH2O)
pressure sensor (P-2C)
signal (XP2C)
Densification (2D)
Densification Control Volume (CV-2D)
Densification (2D')
Densification Control Volume (CV-2D')
input (2D-IN1)
input (2D-IN1A)
input (2D-IN1B)
input (2D-IN1C)
input (2D-IN1D)

input (2D-IN1E)
input (2D-IN1F)
output (2D-OUT1)
output (2D-OUT1A)
output (2D-OUT1B)
output (2D-OUT1C)
output (2D-OUT1D)
output (2D-OUT1E)
output (2D-OUT1F)
carbonaceous material (2D-01)
first lower density (2D-01$rho$)
densified carbonaceous material (2D-02)
second higher density (2D-02$rho$)
densification system (2D0)
first piston cylinder assembly (2D1)
second piston cylinder assembly (2D2)
third piston cylinder assembly (2D3)
first cylinder (D01)
first cylinder first flange (D02)
first cylinder second flange (D03)
first cylindrical pipe branch opening (D04)
first hydraulic cylinder (D05)
first hydraulic cylinder flange (D06)
first hydraulic cylinder front cylinder space (D07)
first hydraulic cylinder rear cylinder space (D08)
first hydraulic cylinder front connection port (D09)
first hydraulic cylinder rear connection port (D10)
first rod (D11)
first piston (D12)
densifier input (D13)
first ram (D14)
first piston rod linear transducer (2Z1)
signal (X2Z1)
second cylinder (D15)
second cylinder first flange (D16)
second cylinder second flange (D17)
second cylinder third flange (D18)
second cylindrical pipe branch opening (D19)
second hydraulic cylinder (D20)
second hydraulic cylinder flange (D21)
second hydraulic cylinder front cylinder space (D22)
second hydraulic cylinder rear cylinder space (D23)
second hydraulic cylinder front connection port (D24)
second hydraulic cylinder rear connection port (D25)
second rod (D26)
second piston (D27)
second ram (D28)
second piston rod linear transducer (2Z2)
signal (X2Z2)
third cylinder (D30)
third cylinder first flange (D31)
third cylinder second flange (D32)
third cylinder third flange (D33)
third hydraulic cylinder (D34)
third hydraulic cylinder flange (D35)
third hydraulic cylinder front cylinder space (D36)
third hydraulic cylinder rear cylinder space (D37)
third hydraulic cylinder front connection port (D38)
third hydraulic cylinder rear connection port (D39)
third rod (D40)
third piston (D41)
third ram (D42)
first ram particulate solids evacuation port (D43)
first flange support (D44)
second ram particulate solids evacuation port (D45)
second flange support (D46)
third ram particulate solids evacuation port (D47)
third flange support (D48)
first plug (1D)
second plug (2D)
third plug (3D)
fourth plug (4D)
fifth plug (5D)
sixth plug (6D)
second subsequent material (D+2)
first subsequent material (D+1)
densifier output (D45)
third piston rod linear transducer (2Z3)
signal (X2Z3)
first hydraulic cylinder pressure sensor (2P1)
signal (X2P1)
second hydraulic cylinder pressure sensor (2P2)
signal (X2P2)
third hydraulic cylinder pressure sensor (2P3)
signal (X2P3)
first piston cylinder assembly pump (2PU1)
suction line (2PU1A)
discharge line (2PU1B)
second piston cylinder assembly pump (2PU2)
suction line (2PU2A)
discharge line (2PU2B)
third piston cylinder assembly pump (2PU3)
suction line (2PU3A)
discharge line (2PU3B)
first hydraulic cylinder front connection port valve (VD1)
common port (VD1A)
supply port (VD1B)
drain port (VD1C)
controller (CD1)
signal (XD1)
first hydraulic cylinder rear connection port valve (VD2)
common port (VD2A)
supply port (VD2B)
drain port (VD2C)
controller (CD2)
signal (XD2)
second hydraulic cylinder front connection port valve (VD3)
common port (VD3A)
supply port (VD3B)
drain port (VD3C)
controller (CD3)
signal (XD3)
second hydraulic cylinder rear connection port valve (VD4)
common port (VD4A)
supply port (VD4B)
drain port (VD4C)
controller (CD4)
signal (XD4)
third hydraulic cylinder front connection port valve (VD5)
common port (VD5A)
supply port (VD5B)
drain port (VD5C)
controller (CD5)
signal (XD5)
third hydraulic cylinder rear connection port valve (VD6)
common port (VD6A)
supply port (VD6B)
drain port (VD6C)
controller (CD6)
signal (XD6)
plug control rear connection port valve (VD7)

controller (CD7)
signal (XD7)
plug control drain valve (VD8)
controller (CD8)
signal (XD8)
common drain line (D50)
primary tank drain connection (D52)
first hydraulic cylinder drain line (D54)
second hydraulic cylinder drain line (D56)
third hydraulic cylinder drain line (D58)
oil heat exchanger supply pump (D60)
suction line (D62)
discharge line (D64)
oil filter input (D66)
oil filter (D68)
oil filter output (D70)
oil heat exchanger transfer conduit (D72)
oil heat exchanger input (D74)
oil heat exchanger (HX-D)
oil heat exchanger output (D78)
heat transfer medium input (D80)
heat transfer medium (D83)
heat transfer medium output (D82)
filtered and cooled oil transfer conduit (D84)
primary tank (D2000)
secondary tank (D2100)
suction line (D85)
secondary tank transfer pump (D86)
discharge line (D88)
plug control transfer line (D90)
plug control drain line (D92)
first higher hydraulic oil inlet temperature (TD1)
second lower hydraulic oil inlet temperature (TD2)
Plug Control (2E)
Plug Control Control Volume (CV-2E)
Plug Control (2E')
Plug Control Control Volume (CV-2E')
input (2E-IN1)
input (2E-IN1A)
input (2E-IN1B)
input (2E-IN1C)
input (2E-IN1D)
input (2E-IN1E)
input (2E-IN1F)
output (2E-OUT1)
output (2E-OUT1A)
output (2E-OUT1B)
output (2E-OUT1C)
output (2E-OUT1D)
output (2E-OUT1E)
output (2E-OUT1F)
carbonaceous material (2E-01)
carbonaceous material (2E-02)
plug control system (2E1)
plug control cylinder (E02)
plug control input (E03)
plug control assembly first flange (E04)
plug control output (E05)
plug control assembly second flange (E06)
plug control assembly third flange (E08)
plug control hydraulic cylinder (E10)
plug control hydraulic cylinder rear cylinder space (E12)
plug control hydraulic cylinder rear connection port (E14)
plug control hydraulic cylinder drain port (E15)
plug control rod (E16)
plug control piston (E18)
ram (E20)
plug guide (E22)
plug guide support (E24)
particulate solids evacuation port (E25)
first pressure sensor (P-E1)
signal (XPE1)
second pressure sensor (P-E2)
signal (XPE2)
third pressure sensor (P-E3)
signal (XPE3)
carbon monoxide sensor (CO-E)
signal (XCOE)
plug control rod linear transducer (E28)
signal (X28)
plug control cross-sectional view (X2E)
first plug control assembly third flange (E08A)
first plug control hydraulic cylinder (E10A
first plug control hydraulic cylinder rear cylinder space (E12A)
first plug control hydraulic cylinder rear connection port (E14A)
first plug control hydraulic cylinder drain port (E15A)
first plug control rod (E16A)
first plug control piston (E18A)
first ram (E20A)
second plug control assembly third flange (E08B)
second plug control hydraulic cylinder (E10B)
second plug control hydraulic cylinder rear cylinder space (E12B)
second plug control hydraulic cylinder rear connection port (E14B)
second plug control hydraulic cylinder drain port (E15B)
second plug control rod (E16B)
second plug control piston (E18B)
second ram (E20B)
Density Reduction (2F)
Density Reduction Control Volume (CV-2F)
Density Reduction (2F')
Density Reduction Control Volume (CV-2F')
input (2F-IN1)
input (2F-IN1A)
input (2F-IN1B)
input (2F-IN1C)
input (2F-IN1D)
input (2F-IN1E)
input (2F-IN1F)
output (2F-OUT1)
output (2F-OUT1A)
output (2F-OUT1B)
output (2F-OUT1C)
output (2F-OUT1D)
output (2F-OUT1E)
output (2F-OUT1F)
densified carbonaceous material (2F-01)
reduced density carbonaceous material (2F-02)
first higher density (2F-01RHO)
second lower density (2F-02RHO)
motor (M2F)
shaft rotation measurement unit (2F-04)
signal X2F04
controller (C-M2F)
signal (XM2F)
density reduction system (2F1)
chamber (F00)
shredder (F01)
density reduction chamber pressure sensor (P-F)
signal (XPF)
density reduction chamber temperature sensor (T-F)

signal (XTF)
density reduction system first flange (F02)
density reduction input (F03)
density reduction chamber second flange (F04)
density reduction output (F05)
density reduction chamber third flange (F06)
density reduction chamber seal (F08)
density reduction system inlet conduit (F10)
side wall (F12)
interior (F14)
shaft (F16)
first seal (F18)
aperture (F19)
second seal (F20)
Gas Mixing (2G)
Gas Mixing Control Volume (CV-2G)
Gas Mixing (2G')
Gas Mixing Control Volume (CV-2G')
input (2G-IN1)
input (2G-IN1A)
input (2G-IN1B)
input (2G-IN1C)
input (2G-IN1D)
input (2G-IN1E)
input (2G-IN1F)
gas input (2G-IN2)
gas input (2G-IN2A)
gas input (2G-IN2B)
gas input (2G-IN2C)
gas input (2G-IN2D)
gas input (2G-IN2E)
gas input (2G-IN2F)
output (2G-OUT1)
output (2G-OUT1A)
output (2G-OUT1B)
output (2G-OUT1C)
output (2G-OUT1D)
output (2G-OUT1E)
output (2G-OUT1F)
gas output (2G-OUT2A)
gas and carbonaceous material mixing system (2G1)
first gas and carbonaceous material mixing system (2G1A)
second gas and carbonaceous material mixing system (2G1B)
third gas and carbonaceous material mixing system (2G1C)
fourth gas and carbonaceous material mixing system (2G1D)
fifth gas and carbonaceous material mixing system (2G1E)
sixth gas and carbonaceous material mixing system (2G1F)
carbonaceous material (2G-01)
first carbonaceous material (2G-01A)
second carbonaceous material (2G-01B)
third carbonaceous material (2G-01C)
fourth carbonaceous material (2G-01D)
fifth carbonaceous material (2G-01E)
sixth carbonaceous material (2G-01F)
carbonaceous material and gas mixture (2G-02)
first carbonaceous material and gas mixture (2G-02A)
second carbonaceous material and gas mixture (2G-02B)
third carbonaceous material and gas mixture (2G-02C)
fourth carbonaceous material and gas mixture (2G-02D)
fifth carbonaceous material and gas mixture (2G-02E)
sixth carbonaceous material and gas mixture (2G-02F)
mixing gas (2G-03)
first mixing gas (2G-03A)
second mixing gas (2G-03B)
third mixing gas (2G-03C)
fourth mixing gas (2G-03D)
fifth mixing gas (2G-03E)
sixth mixing gas (2G-03F)
gas (2G-04)
mixing chamber (G00)
first mixing chamber (G00A)
second mixing chamber (G00B)
third mixing chamber (G00C)
fourth mixing chamber (G00D)
fifth mixing chamber (G00E)
sixth mixing chamber (G00F)
interior (G01)
side wall (G02)
mixing chamber carbonaceous material stream input (G03)
first mixing chamber carbonaceous material stream input (G03A)
second mixing chamber carbonaceous material stream input (G03B)
third mixing chamber carbonaceous material stream input (G03C)
fourth mixing chamber carbonaceous material stream input (G03D)
fifth mixing chamber carbonaceous material stream input (G03E)
sixth mixing chamber carbonaceous material stream input (G03F)
chamber first flange (G04)
mixing output (G05)
first mixing output (G05A)
second mixing output (G05B)
third mixing output (G05C)
fourth mixing output (G05D)
fifth mixing output (G05E)
sixth mixing output (G05F)
chamber second flange (G06)
mixing gas flow sensor (G07)
signal (XG7)
mixing chamber gas input (G08)
first mixing chamber gas input (G08A)
second mixing chamber gas input (G08B)
third mixing chamber gas input (G08C)
fourth mixing chamber gas input (G08D)
fifth mixing chamber gas input (G08E)
sixth mixing chamber gas input (G08F)
entry gas connection (G09)
first gas supply (G10)
mixing chamber gas input (G12)
middle gas connection (G13)
second gas supply (G14)
exit gas connection (G15)
mixing chamber gas input (G16)
third gas supply (G18)
exit section (G19, G19A, G19B, G19C, G19D, G19E, G19F)
middle section (G20)
entry section (G21, G21A, G21B, G21C, G21D, G21E, G21F)
evacuation gas line (G22)
evacuation gas line (G24)
particulate filter (G26)
air (G30)
differential pressure sensor (DPG)

signal (XDPG)
connector impulse line (G1)
entry impulse line (G1A)
exit impulse line (G1B)
gas evacuation pressure sensor (P-G)
gas evacuation pressure sensor signal (XPG)
first gas supply pressure sensor (P-G1)
first gas supply pressure sensor signal (XPG1)
second gas supply pressure sensor (P-G2)
second gas supply pressure sensor signal (XPG2)
first isolation valve (VG1A, VG1B, VG1C, VG1D, VG1E, VG1F)
controller (CG1)
signal (XG1)
second isolation valve (VG2)
controller (CG2)
signal (XG2)
first mixing gas input valve (VG3, VG3A, VG3B, VG3C, VG3D, VG3E, VG3F)
controller (CG3)
signal (XG3)
middle section gas input valve (VG4)
controller (CG4)
signal (XG4)
exit section gas input valve (VG5)
controller (CG5)
signal (XG5)
gas evacuation valve (VG6)
controller (CG6)
signal (XG6)
restriction (RO-G)
Transport (2H)
Transport Control Volume (CV-2H)
Transport (2H')
Transport Control Volume (CV-2H')
input (2H-IN1)
input (2H-IN1A)
input (2H-IN1B)
input (2H-IN1C)
input (2H-IN1D)
input (2H-IN1E)
input (2H-IN1F)
output (2H-OUT1)
output (2H-OUT1A)
output (2H-OUT1B)
output (2H-OUT1C)
output (2H-OUT1D)
output (2H-OUT1E)
output (2H-OUT1F)
carbonaceous material and gas mixture (2H-01)
first carbonaceous material and gas mixture (2H-01A)
second carbonaceous material and gas mixture (2H-01B)
third carbonaceous material and gas mixture (2H-01C)
fourth carbonaceous material and gas mixture (2H-01D)
fifth carbonaceous material and gas mixture (2H-01E)
sixth carbonaceous material and gas mixture (2H-01F)
carbonaceous material and gas mixture (2H-02)
first carbonaceous material and gas mixture (2H-02A)
second carbonaceous material and gas mixture (2H-02B)
third carbonaceous material and gas mixture (2H-02C)
fourth carbonaceous material and gas mixture (2H-02D)
fifth carbonaceous material and gas mixture (2H-02E)
sixth carbonaceous material and gas mixture (2H-02F)
transport assembly (2H1)
first transport assembly (2H1A)
second transport assembly (2H1B)
third transport assembly (2H1C)
fourth transport assembly (2H1D)
fifth transport assembly (2H1E)
sixth transport assembly (2H1F)
transport assembly first flange (H02)
transport input (H03)
first transport input (H03A)
second transport input (H03B)
third transport input (H03C)
fourth transport input (H03D)
fifth transport input (H03E)
sixth transport input (H03F)
expansion joint (H04)
transport output (H05)
first transport output (H05A)
second transport output (H05B)
third transport output (H05C)
fourth transport output (H05D)
fifth transport output (H05E)
sixth transport output (H05F)
side wall (H06)
interior (H08)
screw conveyor (H10)
shaft (H11)
motor (M2H)
shaft rotation measurement unit (2H-04)
signal X2H04
controller (C-M2H)
signal XM2H
heat exchange auger (HX-H)
heat transfer medium input (H12)
heat transfer medium supply (H14)
heat transfer medium supply inlet temperature sensor (TH1)
signal (XH1)
heat transfer medium output (H16)
heat transfer medium return (H18)
heat transfer medium discharge output temperature sensor (TH2)
signal (XH2)
transport assembly second flange (H20)
feedstock delivery system output (H22)
first feedstock delivery system output (H22A)
second feedstock delivery system output (H22B)
third feedstock delivery system output (H22C)
fourth feedstock delivery system output (H22D)
fifth feedstock delivery system output (H22E)
sixth feedstock delivery system output (H22F)
feed zone delivery system control volume (CV-2050)
feed zone delivery system (2050)
first feed zone delivery system (2050A)
second feed zone delivery system (2050B)
third feed zone delivery system (2050C)
fourth feed zone delivery system (2050D)
fifth feed zone delivery system (2050E)
sixth feed zone delivery system (2050F)
first feed zone delivery system control volume (CV-2050A)
second feed zone delivery system control volume (CV-2050B)
third feed zone delivery system control volume (CV-2050C)
fourth feed zone delivery system control volume (CV-2050D)
fifth feed zone delivery system control volume (CV-2050E)
sixth feed zone delivery system control volume (CV-2050F)

hydraulic compression circuit (2065)
feedstock delivery and product gas generation system (2075)
feedstock delivery and product gas generation system (2075A)
feedstock delivery and product gas generation system (2075B)
feedstock delivery and product gas generation system (2075C)
feedstock delivery and product gas generation system (2075D)
bulk transfer system (2A1')
bulk carbonaceous material (2B-01')
first splitter (2B1')
second splitter (2B2')
first split stream (2B-01A)
second split stream (2B-01B')
split carbonaceous material stream (2B-02A')
split carbonaceous material stream (2B-02B')
split carbonaceous material stream (2B-02C')
split carbonaceous material stream (2B-02D')
split carbonaceous material stream (2B-02E')
split carbonaceous material stream (2B-02F')
first reactor first carbonaceous material input (104A')
first reactor second carbonaceous material input (104B)
first reactor third carbonaceous material input (104C')
first reactor fourth carbonaceous material input (104D')
first reactor fifth carbonaceous material input (104E')
first reactor sixth carbonaceous material input (104F')
first feed zone delivery system (2050A')
second feed zone delivery system (20503)
third feed zone delivery system (2050C')
fourth feed zone delivery system (2050D')
fifth feed zone delivery system (2050E')
sixth feed zone delivery system (2050F')
first reactor (100); steam reformer (100)
first reactor longitudinal axis (AX)
first reactor (100A)
first reactor (100B)
first reactor (100C)
first reactor (100D)
first interior (101)
carbonaceous material and gas mixture (102)
first carbonaceous material and gas mixture (102A)
second carbonaceous material and gas mixture (102B)
third carbonaceous material and gas mixture (102C)
fourth carbonaceous material and gas mixture (102D)
fifth carbonaceous material and gas mixture (102E)
sixth carbonaceous material and gas mixture (102F)
first reactor carbonaceous material and gas input (104)
first carbonaceous material and gas input (104A)
second carbonaceous material and gas input (104B)
third carbonaceous material and gas input (104C)
fourth carbonaceous material and gas input (104D)
fifth carbonaceous material and gas input (104E)
sixth carbonaceous material and gas input (104F)
first reactor particulate heat transfer material (105)
first reactor reactant (106)
first reactor dense bed zone reactant (106A)
first reactor feed zone reactant (106B)
first reactor splash zone reactant (106C)
first reactor reactant input (108)
first reactor dense bed zone reactant input (108A)
first reactor feed zone reactant input (108B)
first reactor splash zone reactant input (108C)
first reactor solids input (107)
first reactor reactant input (108)
first reactor heat exchanger fuel (110)
first reactor first heat exchanger fuel (110A)
first reactor second heat exchanger fuel (110B)
first reactor third heat exchanger fuel (110C)
first reactor fourth heat exchanger fuel (110D)
first reactor heat exchanger fuel inlet (112)
first reactor first heat exchanger fuel inlet (112A)
first reactor second heat exchanger fuel inlet (112B)
first reactor third heat exchanger fuel inlet (112C)
first reactor fourth heat exchanger fuel inlet (112D)
combined combustion stream (114)
first reactor first heat exchanger combustion stream (114A)
first reactor second heat exchanger combustion stream (114B)
first reactor third heat exchanger combustion stream (114C)
first reactor fourth heat exchanger combustion stream (114D)
heat exchanger combustion stream outlet (116)
first reactor first heat exchanger combustion stream outlet (116A)
first reactor second heat exchanger combustion stream outlet (116B)
first reactor third heat exchanger combustion stream outlet (116C)
first reactor fourth heat exchanger combustion stream outlet (116D)
first reactor oxygen-containing gas (118)
first reactor dense bed zone oxygen-containing gas (118A)
first reactor feed zone oxygen-containing gas (118B)
first reactor splash zone oxygen-containing gas (118C)
first reactor oxygen-containing gas input (120)
first reactor dense bed zone oxygen-containing gas input (120A)
first reactor feed zone oxygen-containing gas input (120B)
first reactor splash zone oxygen-containing gas input (120C)
first reactor product gas (122)
first reactor product gas (122A)
first reactor product gas (122A1)
first reactor product gas (122A2)
first reactor product gas (122B)
first reactor product gas (122C)
first reactor product gas (122D)
first reactor product gas output (124)
internal cyclone (125)
char depleted first reactor product gas (126)
char depleted first reactor product gas (126A)
char depleted first reactor product gas (126A1)
char depleted first reactor product gas (126A2)
char depleted first reactor product gas (126B)
char depleted first reactor product gas (126C)
char depleted first reactor product gas (126D)
char depleted first reactor product gas conduit (128)
char depleted first reactor product gas conduit (128A1)
char depleted first reactor product gas conduit (128A2)
riser (130)
distributor (145)
first solids separation device (150)
first solids separation device (150A)
first solids separation device (150A1)
first solids separation device (150A2)
first solids separation device (150B)
first solids separation device (150C)
first solids separation device (150D)

first separation input (152)
first separation input (152A1)
first separation input (152A2)
first separation char output (154)
first separation char output (154A1)
first separation char output (154A2)
first separation gas output (156)
first separation gas output (156A1)
first separation gas output (156A2)
second reactor (200); carbon trim cell (200)
second reactor longitudinal axis (BX)
second reactor (200A)
second reactor (200B)
second reactor (200C)
second reactor (200D)
second interior (201)
char (202)
char (202A)
char (202B)
char (202C)
char (202D)
second reactor char input (204)
second reactor first char input (204A)
second reactor second char input (204B)
second reactor third char input (204C)
second reactor fourth char input (204D)
second reactor particulate heat transfer material (205)
second reactor reactant (206)
second reactor dense bed zone reactant (206A)
second reactor feed zone reactant (206B)
second reactor splash zone reactant (206C)
second reactor solids output (207)
second reactor reactant input (208)
second reactor dense bed zone reactant input (208A)
second reactor feed zone reactant input (208B)
second reactor splash zone reactant input (208C)
second reactor heat transfer medium (210)
second reactor heat transfer medium inlet (212)
second reactor heat transfer medium outlet (216)
second reactor oxygen-containing gas (218)
second reactor dense bed zone oxygen-containing gas (218A)
second reactor feed zone oxygen-containing gas (218B)
second reactor splash zone oxygen-containing gas (218C)
second reactor oxygen-containing gas input (220)
second reactor dense bed zone oxygen-containing gas input (220A)
second reactor feed zone oxygen-containing gas input (220B)
second reactor splash zone oxygen-containing gas input (220C)
second reactor product gas (222)
second reactor product gas (222A)
second reactor product gas (222B)
second reactor product gas (222C)
second reactor product gas (222D)
second reactor product gas output (224)
second internal cyclone (225)
solids depleted second reactor product gas (226)
solids depleted second reactor product gas conduit (228)
combined reactor product gas conduit (230)
combined reactor product gas conduit (230A)
combined reactor product gas conduit (230B)
combined reactor product gas conduit (230C)
combined reactor product gas conduit (230D)
second reactor separated solids (232)
portion (233)
solids transfer conduit (234)
riser (236)
riser connection (238)
riser conveying fluid (240)
terminal portion (242)
dipleg (244)
dipleg (244A)
dipleg (244B)
solids flow regulator (245)
first solids flow regulator (245A)
second solids flow regulator (245B)
solids flow regulator solids input (246)
first solids flow regulator solids input (246A)
second solids flow regulator solids input (246B)
solids flow regulator solids output (247)
first solids flow regulator solids output (247A)
second solids flow regulator solids output (247B)
third solids flow regulator solids output (247C)
fourth solids flow regulator solids output (247D)
solids flow regulator gas input (248)
solids flow regulator gas (249)
second solids separation device (250)
second solids separation device (250A)
second solids separation device (250B)
second solids separation device (250C)
second solids separation device (250D)
second separation input (252)
second separation solids output (254)
second separation gas output (256)
fuel (262)
fuel input (264)
third reactor (300); hydrocarbon reformer (300)
third interior (301)
combined product gas (302)
combined product gas input (304)
third reactor heat transfer medium (310)
third reactor heat transfer medium inlet (312)
third reactor heat transfer medium outlet (316)
third reactor oxygen-containing gas (318)
third reactor oxygen-containing gas input (320)
first hydrocarbon stream (322)
first hydrocarbon stream input (324)
second hydrocarbon stream (326)
second hydrocarbon stream input (328)
third hydrocarbon stream (330)
third hydrocarbon stream input (332)
third reactor product gas (334)
third reactor product gas output (336)
third reactor slag (338)
third reactor slag output (340)
third reactor quench water (342)
third reactor quench water input (344)
impingement surface (345)
burner (346)
burner nozzle (347)
steam drum (350)
steam drum heat transfer medium supply inlet (352)
supply (353)
steam drum heat transfer medium reactor inlet (354)
steam drum heat transfer medium outlet (356)
steam outlet (358)
heat transfer medium conduit (360)
heat transfer medium conduit (362)
heat transfer medium conduit (364)
steam outlet conduit (365)
steam pressure control valve (366)
pressure sensor (370)

level sensor (372)
product gas inlet (373)
product gas outlet (375)
heat transfer medium inlet (376)
heat transfer medium outlet (377)
product gas outlet conduit (378)
product gas inlet (379)
venturi scrubber (380)
product gas outlet (381)
venturi scrubber product gas outlet conduit (382)
product gas inlet (383)
scrubber (384)
product gas outlet (385)
scrubber product gas outlet conduit (386)
downcomer (387)
separator (388)
level sensor (389)
solvent pump (390)
pump discharge (391)
scrubber transfer conduit (392)
venturi scrubber transfer conduit (393)
water pump (394)
pump discharge (395)
valve (396)
condensate discharge conduit (397)
separator (398)
heat exchanger (399)
cooling water supply (401)
cooling water return (402)
process fluid (403)
venturi scrubber transfer conduit (404)
scrubber transfer conduit (405)
second reactor carbon dioxide (406)
second reactor carbon dioxide input (407)
engine (410)
product gas inlet (412)
gas outlet (414)
shaft (416)
piston (417)
generator (418)
cylinder (419)
power output (420)
spark plug (421)
scrubber pressure (P-S)
carbonaceous material (500)
carbonaceous material and gas mixture (510)
first carbonaceous material and gas mixture (510A)
second carbonaceous material and gas mixture (510B)
third carbonaceous material and gas mixture (510C)
fourth carbonaceous material and gas mixture (510D)
fifth carbonaceous material and gas mixture (510E)
sixth carbonaceous material and gas mixture (510F)
HX-2000 heat transfer medium inlet (525)
HX-2000 heat transfer medium outlet (550)
entry conduit (563)
bulk transfer entry conduit (563A)
flow splitting entry conduit (563B)
flow splitting entry conduit (563BA)
mass flow regulation entry conduit (563C)
densification entry conduit (563D)
solids transfer entry conduit (563E)
airborne particulate solid evacuation system (565)
filter (566)
entry section (566A)
exit section (566B)
fan (567)
motor (568)
valve (569)
transport screw (570)
differential pressure sensor (571)
particulate solid laden gas (572)
particulate solid depleted gas (573)
particulate solids portion (574A)
gas portion (574B)
HX-2000 heat transfer medium (575)
entry section output (576)
transport unit (577)
reduced temperature gas (580)
water removal system (585)
water-depleted gas (590)
water (595)
Feedstock Preparation System (1000)
three-stage energy-integrated product gas generation system (1001)
product gas generation and particulate classification system (1002)
product gas generation system (1003)
product gas generation system (1003A)
product gas generation system (1003B)
product gas generation system (1003C)
product gas generation system (1003D)
upgraded product (1500)
Feedstock Delivery System (2000)
Product Gas Generation System (3000)
Primary Gas Clean Up System (4000)
Compression System (5000)
Secondary Gas Clean Up System (6000)
Synthesis System (7000)
Upgrading System (8000)
carbonaceous material input (1-IN1)
carbonaceous material output (1-OUT1)
feedstock input (2-IN1)
feedstock gas input (2-IN2)
mixture output (2-OUT1)
first mixture output (2-OUT1A)
second mixture output (2-OUT1B)
third mixture output (2-OUT1C)
fourth mixture output (2-OUT1D)
fifth mixture output (2-OUT1E)
sixth mixture output (2-OUT1F)
particulate solid output (2-OUT2)
First Stage Product Gas Generation System (3A)
reactor mixture input (3A-IN1)
first reactor mixture input (3A-IN1A)
second reactor mixture input (3A-IN1B)
third reactor mixture input (3A-IN1C)
fourth reactor mixture input (3A-IN1D)
fifth reactor mixture input (3A-IN1E)
sixth reactor mixture input (3A-IN1F)
first reactor reactant input (3A-IN2)
oxygen-containing gas input (3A-IN3)
fuel input (3A-IN4)
first stage gas input (3A-IN5)
first reactor gas output (3A-OUT1)
combustion products output (3A-OUT2)
solids (3A-OUT3)
vent (3A-OUT4)
Second Stage Product Gas Generation System (3B)
second reactor gas input (3B-IN1)
second reactor heat transfer medium input (3B-IN2)
oxygen-containing gas input (3B-IN3)
gas input (3B-IN4)
fuel input (3B-IN5)
second reactor gas output (3B-OUT1)

second reactor heat transfer medium output (3B-OUT2)
solids output (3B-OUT3)
Third Stage Product Gas Generation System (3C)
third reactor gas input (3C-IN1)
third reactor heat exchanger heat transfer medium input (3C-IN2)
oxygen-containing gas input (3C-IN3)
first hydrocarbon input (3C-IN4)
second hydrocarbon input (3C-IN5)
third hydrocarbon input (3C-IN6)
quench water input (3C-IN7)
third reactor output (3C-OUT1)
third reactor heat transfer medium output (3C-OUT2)
solids output (3C-OUT3)
carbonaceous material and gas mixture input (3-IN1)
product gas output (3-OUT1)
primary gas clean-up input (4-IN1)
primary gas clean-up output (4-OUT1)
fuel output (4-OUT2)
compression system input (5-IN1)
compression system output (5-OUT1)
secondary gas clean-up input (6-IN1)
secondary gas clean-up system output (6-OUT1)
carbon dioxide output (6-OUT2)
synthesis system input (7-IN1)
synthesis system output (7-OUT1)
first synthesis hydrocarbon output (7-OUT2)
synthesis product input (8-IN1)
upgraded product output (8-OUT1)
first hydrocarbon output (8-OUT2)
second hydrocarbon output (8-OUT3)
dense bed zone (AZ-A)
dense bed zone steam/oxygen connection (AZA0)
dense bed zone steam/oxygen (AZA1)
dense bed zone steam/oxygen input (AZA2)
feed zone (AZ-B)
feed zone steam/oxygen connection (AZB0)
feed zone steam/oxygen (AZB1)
first feed zone steam/oxygen input (AZB2)
second feed zone steam/oxygen input (AZB3)
third feed zone steam/oxygen input (AZB4)
fourth feed zone steam/oxygen input (AZB5)
fifth feed zone steam/oxygen input (AZB6)
sixth feed zone steam/oxygen input (AZB7)
splash zone (AZ-C)
splash zone steam/oxygen connection (AZC0)
splash zone steam/oxygen (AZC1)
first splash zone steam/oxygen input (AZC2)
second splash zone steam/oxygen input (AZC3)
third splash zone steam/oxygen input (AZC4)
fourth splash zone steam/oxygen input (AZC5)
fifth splash zone steam/oxygen input (AZC6)
sixth splash zone steam/oxygen input (AZC7)
seventh splash zone steam/oxygen input (AZC8)
eighth splash zone steam/oxygen input (AZC9)
dense bed zone (BZ-A)
dense bed zone steam/oxygen connection (BZA0)
dense bed zone steam/oxygen (BZA1)
dense bed zone steam/oxygen (BZA2)
feed zone (BZ-B)
feed zone steam/oxygen connection (BZB0)
feed zone steam/oxygen (BZB1)
feed zone steam/oxygen input (BZB2)
feed zone steam/oxygen input (BZB3)
feed zone steam/oxygen input (BZB4)
feed zone steam/oxygen input (BZB5)
splash zone (BZ-C)
splash zone steam/oxygen connection (BZC0)
splash zone steam/oxygen (BZC1)
splash zone steam/oxygen input (BZC2)
splash zone steam/oxygen input (BZC3)
splash zone steam/oxygen input (BZC4)
splash zone steam/oxygen input (BZC5)
Feedstock Preparation Control Volume (CV-1000)
Feedstock Delivery Control Volume (CV-2000)
Product Gas Generation Control Volume (CV-3000)
First Stage Product Gas Generation Control Volume (CV-3A)
Second Stage Product Gas Generation Control Volume (CV-3B)
Third Stage Product Gas Generation Control Volume (CV-3C)
Primary Gas Clean Up Control Volume (CV-4000)
Compression Control Volume (CV-5000)
Secondary Gas Clean Up Control Volume (CV-6000)
Synthesis Control Volume (CV-7000)
Upgrading Control Volume (CV-8000)
combustion zone (CZ-A)
combustion zone output (CZ-AP)
reaction zone (CZ-B)
reaction zone output (CZ-BP)
cooling zone (CZ-C)
cooling zone output (CZ-CP)
quench zone (CZ-D)
quench zone output (CZ-DP)
restriction orifice differential pressure sensor (DP-AB)
combined hydrocarbon connection (CZC0)
combined hydrocarbon (CZC1)
combined hydrocarbon input (CZC2)
freeboard zone (FB-A)
freeboard zone (FB-B)
auxiliary heat exchanger (HX-2)
Primary Gas Clean Up Heat Exchanger (HX-4)
first reactor heat exchanger (HX-A)
first reactor first heat exchanger (HX-A1)
first reactor second heat exchanger (HX-A2)
first reactor third heat exchanger (HX-A3)
first reactor fourth heat exchanger (HX-A4)
second reactor heat exchanger (HX-B)
third reactor heat exchanger (HX-C)
Feedstock Delivery System CO2 Heat Exchanger (HX-2000)
classifier interior (INA, INB)
fluid bed level (L-A)
fluid bed level (L-B)
first reactor pressure (P-A)
second reactor pressure (P-B)
third reactor pressure (P-C)
third reactor steam drum pressure (P-C1)
first quadrant (Q1)
second quadrant (Q2)
third quadrant (Q3)
fourth quadrant (Q4)
first quadrant (Q1')
second quadrant (Q2')
third quadrant (Q3')
fourth quadrant (Q4')
restriction orifice (RO-B)

Biorefinery Superstructure System (BSS)
third reactor heat transfer medium inlet temperature (T0)
second reactor heat transfer medium inlet temperature (T1)
second reactor heat transfer medium outlet temperature (T2)
first reactor heat exchanger fuel inlet temperature (T3)
first reactor first heat exchanger fuel inlet temperature (T3A)
first reactor second heat exchanger fuel inlet temperature (T3B)
first reactor third heat exchanger fuel inlet temperature (T3C)
first reactor fourth heat exchanger fuel inlet temperature (T3D)
first reactor heat exchanger combined combustion stream outlet temperature (T4)
first reactor first heat exchanger combustion stream outlet temperature (T4A)
first reactor second heat exchanger combustion stream outlet temperature (T4B)
first reactor third heat exchanger combustion stream outlet temperature (T4C)
first reactor fourth heat exchanger combustion stream outlet temperature (T4D)
gas output temperature (T5)
gas input temperature (T6)
first reactor temperature (T-A)
second reactor temperature (T-B)
third reactor temperature (T-C)
first reactor dense bed zone reactant valve (VA1)
first reactor dense bed zone reactant valve controller (CA1)
first reactor dense bed zone reactant valve signal (XA1)
first reactor dense bed zone oxygen-containing gas valve (VA2)
first reactor dense bed zone oxygen-containing gas valve controller (CA2)
first reactor dense bed zone oxygen-containing gas valve signal (XA2)
first reactor feed zone reactant valve (VA3)
first reactor feed zone reactant valve controller (CA3)
first reactor feed zone reactant valve signal (XA3)
first reactor feed zone oxygen-containing gas valve (VA4)
first reactor feed zone oxygen-containing gas valve controller (CA4)
first reactor feed zone oxygen-containing gas valve signal (XA4)
first reactor splash zone reactant valve (VA5)
first reactor splash zone reactant valve controller (CA5)
first reactor splash zone reactant valve signal (XA5)
first reactor splash zone oxygen-containing gas valve (VA6)
first reactor splash zone oxygen-containing gas valve controller (CA6)
first reactor splash zone oxygen-containing gas valve signal (XA6)
second reactor heat transfer medium supply valve (VB0)
second reactor heat transfer medium supply valve controller (CB0)
second reactor heat transfer medium supply valve signal (XB0)
second reactor dense bed zone reactant valve (VB1)
second reactor dense bed zone reactant valve controller (CB1)
second reactor dense bed zone reactant valve signal (XB1)
second reactor dense bed zone oxygen-containing gas valve (VB2)
second reactor dense bed zone oxygen-containing gas valve controller (CB2)
second reactor dense bed zone oxygen-containing gas valve signal (XB2)
second reactor feed zone reactant valve (VB3)
second reactor feed zone reactant valve controller (CB3)
second reactor feed zone reactant valve signal (XB3)
second reactor feed zone oxygen-containing gas valve (VB4)
second reactor feed zone oxygen-containing gas valve controller (CB4)
second reactor feed zone oxygen-containing gas valve signal (XB4)
second reactor splash zone reactant valve (VB5)
second reactor splash zone reactant valve controller (CB5)
second reactor splash zone reactant valve signal (XB5)
second reactor splash zone oxygen-containing gas valve (VB6)
second reactor splash zone oxygen-containing gas valve controller (CB6)
second reactor splash zone oxygen-containing gas valve signal (XB6)
second reactor hydrocarbon valve (VB7)
second reactor hydrocarbon valve controller (CB7)
second reactor hydrocarbon valve signal (XB7)
first hydrocarbon valve (VC1)
first hydrocarbon valve controller (CC1)
first hydrocarbon valve signal (XC1)
third reactor oxygen-containing gas valve (VC2)
third reactor oxygen-containing gas valve controller (CC2)
third reactor oxygen-containing gas valve signal (XC2)
second hydrocarbon valve (VC3)
second hydrocarbon valve controller (CC3)
second hydrocarbon valve signal (XC3)
third hydrocarbon valve (VC4)
third hydrocarbon valve controller (CC4)
third hydrocarbon valve signal (XC4)
third reactor heat transfer medium valve (VC5)
third reactor heat transfer medium valve controller (CC5)
third reactor heat transfer medium valve signal (XC5)
connection (X1)
connection (X2)
connection (X3)
connection (X4)
connection (X5)
connection (X6)
connection (X7)
first reactor feed zone cross-sectional view (XAZ-B)
first reactor splash zone cross-sectional view (XAZ-C)
second reactor feed zone cross-sectional view (XBZ-B)
second reactor splash zone cross-sectional view (XBZ-C)
particulate classification chamber (A1A, A1B)
particulate classification chamber (B1)
bed material and inert feedstock contaminant mixture output (A2A, A2AA)
bed material and inert feedstock contaminant mixture output (B2)
bed material and inert feedstock contaminant mixture transfer conduit (A3A, A3AA)
bed material and inert feedstock contaminant mixture transfer conduit (B3)
bed material and inert feedstock contaminant mixture (A4A, A4AA)

bed material and inert feedstock contaminant mixture (B4)
bed material and inert feedstock contaminant mixture input (A5A, A5AA)
bed material and inert feedstock contaminant mixture input (B5)
classifier gas input (A6A, A6AA)
classifier gas input (B6)
classified recycled bed material output (A7A, A7AA)
classified recycled bed material output (B7)
classifier depressurization gas output (A8A, A8AA)
classifier depressurization gas output (B8)
classifier inert feedstock contaminant output (A9A, A9AA)
classifier inert feedstock contaminant output (B9)
classifier gas (A16, A16A)
classifier gas (B16)
classifier riser (A17, A17A)
classifier riser (B17)
classifier depressurization gas (A18, A18A)
classifier depressurization gas (B18)
classified inert feedstock contaminants (A19, A19A)
classified inert feedstock contaminants (B19)
classified recycled bed material input (A27, A27A)
classified recycled bed material input (B27)
classified recycled bed material (A37, A37A)
classified recycled bed material (B37)
mixture transfer valve (V9, V9A, V9AA)
mixture transfer valve controller (C9A, C9AA)
mixture transfer valve (V9B)
classification gas transfer valve (V10, V10A, V10AA)
classification gas transfer valve controller (C10A, C10AA)
classification gas transfer valve (V10B)
bed material riser recycle transfer valve (V11, V11A, V11AA)
bed material riser recycle transfer valve controller (C11A, C11AA)
bed material riser recycle transfer valve (V11B)
depressurization vent valve (V12, V12A, V12AA)
depressurization vent valve controller (C12A, C12AA)
depressurization vent valve (V12B)
inert feedstock contaminant drain valve (V13, V13A, V13AA)
inert feedstock contaminant drain valve controller (C13A, C13AA)
inert feedstock contaminant drain valve (V13B)
computer (COMP)
processor (PROC)
memory (MEM)
input/output interface (I/O)
code (CODE)
first reactor product gas first quality sensor (AQ1)
signal (XAQ1)
combined product gas first quality sensor (BQ1)
signal (XBQ1)
third reactor product gas first quality sensor (CQ1)
signal (XCQ1)
densification system (1000')
carbonaceous material (101')
discrete charge of compressible material (105')
controller (500')
compression chamber (00')
forming tube (00A')
chamber extension (00B')
longitudinal axis (A')
interior (02')
side wall (03')
inlet (04')
first end (05')
outlet (06')
second end (07')
closed end (08')
compression region (09')
first rod opening (10')
first direction (11')
second direction (13')
press frame connection (14')
first press frame (PF1')
second press frame (PF2')
first compression column (1CL')
first tie rod (1R')
first tie rod first nut (1N1')
first tie rod second nut (1N2')
first wear plate (WP1')
first guide block (GB1')
second compression column (2CL')
second tie rod (2R')
second tie rod first nut (2N1')
second tie rod second nut (2N2')
connector (X1')
second wear plate (WP2')
second guide block (GB2')
third compression column (3CL')
third tie rod (3R')
third tie rod first nut (3N1')
third tie rod second nut (3N2')
third wear plate (WP3')
third guide block (GB3')
fourth compression column (4CL')
fourth tie rod (4R')
fourth tie rod first nut (4N1')
fourth tie rod second nut (4N2')
fourth wear plate (WP4')
fourth guide block (GB4')
primary piston cylinder assembly (A0')
primary cylinder (AA')
primary piston (AB')
primary rear cylinder space (AC')
primary first rear connection port (AD')
primary second rear connection port (AE')
primary frame connection (AF')
primary piston opening (AG')
primary piston platen connection (AH')
platen (AI')
primary compression rod (AJ')
compression rod connection (AK')
compression head (AL')
advanced position (A100')
retracted position (A200')
first ancillary piston cylinder assembly (B0')
first ancillary cylinder (BA')
first ancillary piston (BB')
first ancillary rod (BC')
first ancillary front cylinder space (BD')
first ancillary rear cylinder space (BE')
first ancillary front connection port (BF')
first ancillary rear connection port (BG')
first ancillary frame connection (BH')
first ancillary piston opening (BI')
first ancillary platen connection (BJ')
second ancillary piston cylinder assembly (C0')
second ancillary cylinder (CA')
second ancillary piston (CB')

second ancillary rod (CC')
second ancillary front cylinder space (CD')
second ancillary rear cylinder space (CE')
second ancillary front connection port (CF')
second ancillary rear connection port (CG')
second ancillary frame connection (CH')
second ancillary piston opening (CI')
second ancillary platen connection (CJ')
knock-down piston cylinder assembly (D0')
knock-down cylinder (DA')
knock-down piston (DB')
knock-down rod (DC')
knock-down head (DD')
knock-down front cylinder space (DE')
knock-down rear cylinder space (DF')
knock-down front connection port (DG')
knock-down rear connection port (DH')
knock-down piston opening (DI')
guide rod (DJ')
advanced ejection position (D100')
knock-down retracted position (D200')
backstop piston cylinder assembly (E0')
backstop cylinder (EA')
backstop piston (EB')
backstop rod (EC')
backstop head (ED')
backstop front cylinder space (EE')
backstop rear cylinder space (EF')
backstop front connection port (EG')
backstop rear connection port (EH')
backstop piston opening (EI')
backstop frame connection (EJ')
advanced locked position (E100')
backstop retracted position (E200')
first press frame (PF1')
second press frame (PF2')
plugs (PP')
first plug (1P')
second plug (2P')
third plug (3P')
fourth plug (4P')
fifth plug (5P')
leading plug (LP')
terminal plug (TP')

What is claimed is:

1. A system for using a recycled conditioned syngas, the system comprising:
a steam reformer connected to a first source of recycled conditioned syngas for combusting therein to provide heat and to produce a first reactor product gas;
a hydrocarbon reformer connected to a second source of recycled conditioned syngas and to a stream containing oxygen gas to form a combustion zone and/or a reaction zone of the hydrocarbon reformer, and further configured to receive a portion of the first reactor product gas, the hydrocarbon reformer configured to produce an improved syngas; and
at least one gas clean-up system configured to receive the improved syngas and remove at least one contaminant in the improved syngas to produce a new conditioned syngas, the at least one gas clean-up system comprising a gas clean-up system output through which the new conditioned syngas exits,
wherein the gas clean-up system output serves as the first source of recycled conditioned syngas connected to the steam reformer and as the second source of recycled conditioned syngas connected to the hydrocarbon reformer.

2. The system according to claim 1, wherein the steam reformer comprises a particulate heat transfer material.

3. The system according to claim 2, wherein the steam reformer comprises a plurality of pulse combustion heat exchangers in thermal contact with the particulate heat transfer material.

4. The system according to claim 3, wherein at least one of the plurality of pulse combustion heat exchangers is configured to combust at least a portion of the first source of recycled conditioned syngas to indirectly heat the particulate heat transfer material.

5. The system according to claim 1, wherein the hydrocarbon reformer is configured to receive a portion of the first reactor product gas and a portion of the second source of recycled conditioned syngas through separate inputs.

6. The system according to claim 1, comprising:
a carbon trim cell having a second reactor gas input and a second reactor gas output, the second reactor gas input connected to the steam reformer and configured to receive char from the steam reformer, the second reactor gas output configured to output a second reactor product gas,
wherein the hydrocarbon reformer is configured to receive a portion of the second reactor product gas to form the improved syngas.

7. The system according to claim 6, further comprising:
a combined reactor product gas conduit connected to both the steam reformer and the carbon trim cell, and configured to receive a portion of the first reactor product gas and a portion of the second reactor product gas,
wherein the hydrocarbon reformer is connected to the combined reactor product gas conduit and is configured to receive a portion of the first reactor product gas and a portion of the second reactor product gas to form the improved syngas.

8. The system according to claim 6, wherein the hydrocarbon reformer is configured to receive a portion of the second reactor product gas and a portion of the second source of recycled conditioned syngas through separate inputs.

9. The system according to claim 1, wherein the at least one gas cleanup system comprises:
a first gas clean-up system configured to receive the improved syngas from the hydrocarbon reformer and output a primary conditioned syngas in response thereto;
a compression system configured to compress the primary conditioned syngas; and
a second gas clean-up system configured to receive the compressed primary conditioned syngas from the compression system and output a second conditioned syngas in response thereto,
wherein the new conditioned syngas comprises at least one of the primary conditioned syngas and the second conditioned syngas.

10. The system according to claim 9, wherein the new conditioned syngas comprises only the second conditioned syngas.

11. The system according to claim 9, wherein the second gas clean-up system is further configured to remove one or more contaminants comprising carbonyl sulfide, hydrogen sulfide, mercury, arsenic, lead, cadmium, or a combination thereof.

12. The system according to claim 9, further comprising:
a hydrogen separation system connected to the gas clean-up system output and configured to receive a portion of the new conditioned syngas and to produce a first off-gas stream and hydrogen.

13. The system according to claim 12, wherein a portion of the first off-gas stream is transferred to the steam reformer, the hydrocarbon reformer, and/or a gas turbine system configured to receive a portion of the first off-gas stream to produce electricity.

14. The system according to claim 12, further comprising:
an upgrading system configured to receive a portion of the hydrogen to produce one or more of an upgraded liquid fuel, naphtha, and a second off-gas stream.

15. The system according to claim 14, wherein a portion of the naphtha is transferred to the steam reformer, the hydrocarbon reformer, and/or a gas turbine system configured to receive a portion of the naphtha to produce electricity.

16. The system according to claim 14, wherein a portion of the second off-gas stream is transferred to the steam reformer, the hydrocarbon reformer, and/or a gas turbine system configured to receive a portion of the second off-gas stream to produce electricity.

17. The system according to claim 1, comprising:
a synthesis system connected to the gas clean-up system output and configured to receive a first portion of the new conditioned syngas, wherein the synthesis system is configured to output one or more synthesis products.

18. The system according to claim 17, wherein a portion of the one or more synthesis products is transferred to the steam reformer, the hydrocarbon reformer, and/or a gas turbine system configured to receive a portion of one or more synthesis products to produce electricity.

19. The system according to claim 17, wherein at least one of the one or more synthesis products is selected from the group consisting of a hydrocarbon, a tail gas, a liquid fuel, and a chemical.

20. The system according to claim 17, wherein the synthesis system comprises at least one catalyst.

21. The system according to claim 17, wherein the synthesis system comprises a bioreactor containing microorganisms, and wherein the bioreactor is configured to produce ethanol.

22. The system according to claim 17, wherein the synthesis system comprises a bioreactor containing microorganisms, and wherein the bioreactor is configured to produce one or more of 3-hydroxypropionate; mevalonate; mevalonic acid; isoprene; aromatics; benzoate (p-hydroxyl, 2-amino, dihydroxy); salicylate; 1-propanol; 1,2-propanediol; (R)-1,2-propanediol; (S)-1,2-propanediol; mixed isomers of 1,2-propanediol; acetoin; methyl ethyl ketone; branched-chain amino acids; valine, leucine, isoleucine; succinate; lactate; 2,3-butanediol; (R,R)-2,3-butanediol; meso-2,3-butanediol; mixed isomers of 2,3-butanediol; citramalate; 1,3-butanediol; (R)-1,3-butanediol; (S)-1,3-butanediol; mixed isomers of 1,3-butanediol; 3-hydroxybutyrate; (R)-3-hydroxybutyrate; (S)-3-hydroxybutyrate; mixed isomers of 3-hydroxybutyrate; butyrate; acetone; isopropanol; acetate; 1,3-butadiene; biopolymers; isobutene; and long chain alcohols.

23. The system according to claim 17, further comprising:
a syngas compressor configured to compress a portion of the new conditioned syngas prior to exiting the at least one gas clean-up system output and entering the synthesis system.

24. The system according to claim 17, further comprising:
an upgrading system configured to receive a portion of the one or more synthesis products to produce one or more upgraded products.

25. The system according to claim 24, wherein at least one of the one or more upgraded products is selected from the group consisting of an upgraded liquid fuel and an upgraded chemical.

26. A method of producing liquid fuel and/or chemicals from a carbonaceous material, the method comprising:
combusting a first portion of conditioned syngas in a steam reformer, thereby causing a carbonaceous material to react with a superheated steam to produce a first reactor product gas;
reacting a second portion of conditioned syngas and a stream containing oxygen gas an with at least a portion of the first reactor product gas in a hydrocarbon reformer to produce an improved syngas;
performing clean-up of the improved syngas to produce new conditioned syngas;
transferring a first portion of the new conditioned syngas to a synthesis system to produce tail gas and at least one from the group consisting of liquid fuel and chemicals; and
recycling a second portion of the new conditioned syngas for use as the first portion of conditioned syngas and the second portion of conditioned syngas.

* * * * *